US009175291B2

(12) United States Patent
Macleod et al.

(10) Patent No.: US 9,175,291 B2
(45) Date of Patent: Nov. 3, 2015

(54) MODULATION OF ANDROGEN RECEPTOR EXPRESSION

(71) Applicant: ISIS Pharmaceuticals Inc., Carlsbad, CA (US)

(72) Inventors: Robert A. Macleod, Carlsbad, CA (US); Youngsoo Kim, Carlsbad, CA (US); Tianyuan Zhou, Carlsbad, CA (US); Susan M. Freier, Carlsband, CA (US); Brett Monia, Carlsbad, CA (US)

(73) Assignee: ISIS Pharmaceuticals Inc., Carlsbad, CA (US)

( * ) Notice: Subject to any disclaimer, the term of this patent is extended or adjusted under 35 U.S.C. 154(b) by 0 days.

(21) Appl. No.: 14/050,574

(22) Filed: Oct. 10, 2013

(65) Prior Publication Data

US 2014/0107180 A1 Apr. 17, 2014

Related U.S. Application Data

(60) Provisional application No. 61/712,756, filed on Oct. 11, 2012, provisional application No. 61/712,780, filed on Oct. 11, 2012, provisional application No. 61/723,701, filed on Nov. 7, 2012, provisional application No. 61/777,813, filed on Mar. 12, 2013, provisional application No. 61/777,851, filed on Mar. 12, 2013, provisional application No. 61/777,895, filed on Mar. 12, 2013.

(51) Int. Cl.

| | |
|---|---|
| ***C12N 15/11*** | (2006.01) |
| ***C12N 15/113*** | (2010.01) |
| ***A61K 31/7088*** | (2006.01) |
| ***A61K 31/4166*** | (2006.01) |

(52) U.S. Cl.

CPC ........ *C12N 15/1138* (2013.01); *A61K 31/4166* (2013.01); *A61K 31/7088* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01)

(58) Field of Classification Search

None

See application file for complete search history.

(56) References Cited

U.S. PATENT DOCUMENTS

| | | | |
|---|---|---|---|
| 4,981,957 | A | 1/1991 | Lebleu et al. |
| 5,034,506 | A | 7/1991 | Summerton et al. |
| 5,118,800 | A | 6/1992 | Smith et al. |
| 5,166,315 | A | 11/1992 | Summerton et al. |
| 5,185,444 | A | 2/1993 | Summerton et al. |
| 5,319,080 | A | 6/1994 | Leumann |
| 5,359,044 | A | 10/1994 | Cook et al. |
| 5,393,878 | A | 2/1995 | Leumann |
| 5,446,137 | A | 8/1995 | Maag et al. |
| 5,466,786 | A | 11/1995 | Buhr et al. |
| 5,514,785 | A | 5/1996 | Van Ness et al. |
| 5,519,134 | A | 5/1996 | Acevedo et al. |
| 5,556,956 | A | 9/1996 | Roy et al. |
| 5,567,811 | A | 10/1996 | Misiura et al. |
| 5,576,427 | A | 11/1996 | Cook et al. |
| 5,591,722 | A | 1/1997 | Montgomery et al. |
| 5,597,909 | A | 1/1997 | Urdea et al. |
| 5,610,300 | A | 3/1997 | Altmann et al. |
| 5,627,053 | A | 5/1997 | Usman et al. |
| 5,639,873 | A | 6/1997 | Barascut et al. |
| 5,646,265 | A | 7/1997 | McGee |
| 5,670,633 | A | 9/1997 | Cook et al. |
| 5,698,685 | A | 12/1997 | Summerton et al. |
| 5,700,920 | A | 12/1997 | Altmann et al. |
| 5,792,847 | A | 8/1998 | Buhr et al. |
| 5,801,154 | A | 9/1998 | Baracchini et al. |
| 5,877,160 | A | 3/1999 | Harper et al. |
| 5,994,076 | A | 11/1999 | Chenchik et al. |
| 6,255,110 | B1 | 7/2001 | Cowsert et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,600,032 | B1 | 7/2003 | Manoharan et al. |
| 6,670,461 | B1 | 12/2003 | Wengel et al. |
| 6,673,661 | B1 | 1/2004 | Liu et al. |
| 6,680,342 | B2 | 1/2004 | Young et al. |
| 6,770,748 | B2 | 8/2004 | Imanishi et al. |
| 6,794,499 | B2 | 9/2004 | Wengel et al. |
| 6,861,432 | B2 | 3/2005 | Cleve et al. |
| 6,960,474 | B2 | 11/2005 | Salvati et al. |
| 7,034,133 | B2 | 4/2006 | Wengel et al. |
| 7,053,207 | B2 | 5/2006 | Wengel |
| 7,064,207 | B2 | 6/2006 | Du et al. |
| 7,067,256 | B2 | 6/2006 | Roy et al. |

(Continued)

FOREIGN PATENT DOCUMENTS

| | | |
|---|---|---|
| EP | 1598421 | 1/2011 |
| JP | 2002247986 | 9/2002 |

(Continued)

OTHER PUBLICATIONS

Jepsen et al, LNA-Antisense rivals siRNA for gene silencing, 2004, Current Opinion in Drug Discovery and Development, 7(2):188-194.*

(Continued)

*Primary Examiner* — Tracy Vivlemore
*Assistant Examiner* — Kate Poliakova

(57) ABSTRACT

Certain embodiments are directed to compounds and compositions targeted to human androgen receptor (AR) for inhibiting androgen receptor levels in a cell, which can be useful for methods of treating cancer and inhibiting cancer cell growth or proliferation.

20 Claims, No Drawings

(56) References Cited

U.S. PATENT DOCUMENTS

| | | | |
|---|---|---|---|
| 7,268,232 | B2 | 9/2007 | Schlienger et al. |
| 7,371,735 | B2 | 5/2008 | Harel-Bellan et al. |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,601,748 | B2 | 10/2009 | Cleve et al. |
| 7,622,592 | B2 | 11/2009 | Kim et al. |
| 7,696,345 | B2 | 4/2010 | Alleson et al. |
| 7,709,517 | B2 | 5/2010 | Sawyers et al. |
| 7,732,480 | B2 | 6/2010 | Li et al. |
| 7,737,125 | B2 | 6/2010 | Worm |
| 7,960,435 | B2 | 6/2011 | Njar et al. |
| 7,989,429 | B2 | 8/2011 | Worm |
| 8,003,649 | B2 | 8/2011 | Bradbury et al. |
| 8,067,569 | B2 | 11/2011 | Iversen et al. |
| 8,133,724 | B2 | 3/2012 | Qiu et al. |
| 8,252,762 | B2 | 8/2012 | Dean et al. |
| 8,450,290 | B2 | 5/2013 | Worm et al. |
| 2001/0053519 | A1 | 12/2001 | Fodor et al. |
| 2002/0165381 | A1 | 11/2002 | Ahrens-Fath et al. |
| 2003/0228597 | A1 | 12/2003 | Cowsert et al. |
| 2004/0171570 | A1 | 9/2004 | Allerson et al. |
| 2004/0259085 | A1 | 12/2004 | Chang |
| 2005/0130923 | A1 | 6/2005 | Bhat et al. |
| 2005/0159376 | A1 | 7/2005 | McSwiggen et al. |
| 2005/0164970 | A1 | 7/2005 | Li |
| 2005/0202077 | A1 | 9/2005 | Watson et al. |
| 2005/0244851 | A1 | 11/2005 | Blume et al. |
| 2005/0246794 | A1* | 11/2005 | Khvorova et al. ............ 800/286 |
| 2006/0040263 | A1 | 2/2006 | Rousseau |
| 2007/0031844 | A1 | 2/2007 | Khvorova et al. |
| 2007/0111227 | A1 | 5/2007 | Green et al. |
| 2007/0141009 | A1 | 6/2007 | Khan |
| 2008/0039618 | A1 | 2/2008 | Allerson et al. |
| 2008/0311659 | A1 | 12/2008 | Huynh et al. |
| 2008/0311661 | A1 | 12/2008 | Huynh et al. |
| 2009/0012281 | A1 | 1/2009 | Swayze et al. |
| 2009/0181916 | A1 | 7/2009 | Worm |
| 2009/0282496 | A1 | 11/2009 | Chang |
| 2009/0311716 | A1 | 12/2009 | Buttyan et al. |
| 2010/0068802 | A1 | 3/2010 | Qiu et al. |
| 2010/0069471 | A1 | 3/2010 | Manoharan et al. |
| 2010/0136139 | A1 | 6/2010 | Tatsumi et al. |
| 2010/0144843 | A1 | 6/2010 | McSwiggen et al. |
| 2010/0167940 | A1 | 7/2010 | Feinberg |
| 2010/0172966 | A1 | 7/2010 | Smith |
| 2010/0172975 | A1 | 7/2010 | Sawyers et al. |
| 2010/0183703 | A1 | 7/2010 | Kerner et al. |
| 2010/0210665 | A1 | 8/2010 | Sawyers et al. |
| 2010/0215729 | A1 | 8/2010 | Phiasivongsa et al. |
| 2010/0234451 | A1 | 9/2010 | Worm |
| 2010/0261188 | A1 | 10/2010 | Bhatt et al. |
| 2010/0292140 | A1* | 11/2010 | Bhanot et al. .................. 514/6.5 |
| 2011/0054005 | A1 | 3/2011 | Naito et al. |
| 2011/0110923 | A1 | 5/2011 | Lee et al. |
| 2011/0110926 | A1 | 5/2011 | Luo et al. |
| 2011/0152348 | A1 | 6/2011 | Worm et al. |
| 2011/0178283 | A1 | 7/2011 | Rigoutsos et al. |
| 2011/0224283 | A1 | 9/2011 | Iversen |
| 2011/0319471 | A1 | 12/2011 | Worm |
| 2012/0040460 | A1 | 2/2012 | Rigoutsos et al. |
| 2012/0052487 | A9 | 3/2012 | Khvorova et al. |
| 2013/0116258 | A1 | 5/2013 | Smith et al. |

FOREIGN PATENT DOCUMENTS

| | | | |
|---|---|---|---|
| JP | 2004008140 | | 1/2004 |
| JP | 2004254600 | | 9/2004 |
| JP | 2004254601 | | 9/2004 |
| JP | 2007215481 | | 8/2007 |
| JP | 2007282598 | | 11/2007 |
| WO | WO 94/18835 | | 9/1994 |
| WO | WO 97/11170 | | 3/1997 |
| WO | WO 97/17469 | | 5/1997 |
| WO | WO 98/39352 | | 9/1998 |
| WO | WO 99/14226 | | 3/1999 |
| WO | WO 00/63364 | | 10/2000 |
| WO | WO 01/49687 | | 7/2001 |
| WO | WO 01/73116 | | 10/2001 |
| WO | WO 01/77384 | | 10/2001 |
| WO | WO 01/83740 | | 11/2001 |
| WO | WO 02/085308 | | 10/2002 |
| WO | WO 03/004602 | | 1/2003 |
| WO | WO 2004/011624 | | 2/2004 |
| WO | WO 2004/035765 | | 4/2004 |
| WO | WO 2004/063331 | | 7/2004 |
| WO | WO 2004/106356 | | 12/2004 |
| WO | WO 2005/021570 | | 3/2005 |
| WO | WO 2005/080410 | | 9/2005 |
| WO | WO 2005/121371 | | 12/2005 |
| WO | WO 2006/047842 | | 5/2006 |
| WO | WO 2007/126765 | | 11/2007 |
| WO | WO 2007/134181 | | 11/2007 |
| WO | WO 2008/101157 | | 8/2008 |
| WO | WO 2008/119015 | | 10/2008 |
| WO | WO 2008/150729 | | 12/2008 |
| WO | WO 2008/154401 | | 12/2008 |
| WO | WO 2009/006478 | | 1/2009 |
| WO | WO 2009/067647 | | 5/2009 |
| WO | WO 2009/068033 | | 6/2009 |
| WO | WO 2009/100320 | | 8/2009 |
| WO | WO 2009/144424 | | 12/2009 |
| WO | WO 2010/036696 | | 4/2010 |
| WO | WO 2010/036698 | | 4/2010 |
| WO | WO 2011/005793 | | 1/2011 |
| WO | WO 2011/112581 | | 9/2011 |
| WO | WO 2011/113015 | | 9/2011 |
| WO | WO 2011/150408 | | 12/2011 |
| WO | WO 2012/005898 | | 1/2012 |
| WO | WO 2012/006241 | | 1/2012 |
| WO | WO 2012/018881 | | 2/2012 |
| WO | WO 2012/065051 | | 5/2012 |
| WO | 2012109395 | A1 | 8/2012 |
| WO | WO 2012/106508 | | 8/2012 |
| WO | WO 2013/033230 | | 3/2013 |
| WO | WO 2013/120003 | | 8/2013 |

OTHER PUBLICATIONS

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71: 7731-7740.

Allshire, "RNAi and Heterochromatin—a Hushed-Up Affair" Science (2002) 297: 1818-1819.

Altmann et al., "Second-generation antisense oligonucleotides: structure-activity relationships and the design of improved signal-transduction inhibitors" Biochem. Soc. Trans. (1996) 24: 630-637.

Altmann et al., "Second Generation of Antisense Oligonucleotides: From Nuclease Resistance to Biological Efficacy in Animals" Chimia (1996) 50: 168-176.

Altmann et al., "Second generation antisense oligonucleotides—inhibition of PKC-a an c-RAF kinase expression by chimeric oligonucleotides incorporating 5'-substitute carbocyclic nucleosides and 2'-O-ethylene glycol substituted ribonucleosides." Nucleosides Nucleotides (1997) 16(7-9): 917-926.

Attard et al., "Steroid Hormone Receptors in Prostate Cancer: A Hard Habit to Break?" Cancer Cell (2009) 16:458-462.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem., (1997) 272(18): 11944-12000.

Bennett et al. "Molecular cell biology of androgen receptor signaling" Int J Biochem Cell Biol. (2010) 42:813-827.

Braasch et al., "Novel Antisense and Peptide Nucleic Acid Strategies for Controlling Gene Expression" Biochemistry (2002) 41(14): 4503-4510.

Braasch et al., "Locked nucleic acid (LNA): fine-tuning the recognition of DNA and RNA" Chem. Biol. (2001) 8: 1-7.

(56) References Cited

OTHER PUBLICATIONS

Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cochrane et al., "Preclinical Evaluation of Enzalutamide in Breast Cancer Models" Cancer Res (2012) 72 (24 Supplement): P2-14-02.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2): 923-937.
De Bono et al. "Abiraterone and Increased Survival in Metastatic Prostate Cancer" N Engl J Med (2011) 364(21): 1995-2005.
Elayadi et al., "Application of PNA and LNA oligomers to chemotherapy" Curr. Opinion Invest. Drugs (2001) 2: 558-561.
Freier et al., "The ups and downs of nucleic acid duplex stability: structure-stability studies on chemically-modified DNA:RNA duplexes" Nucleic Acids Research (1997) 25(22): 4429-4443.
Frieden et al., "Expanding the design horizon of antisense oligonucleotides with alpha-L-LNA" Nucleic Acids Research (2003) 31(21): 6365-6372.
Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.
Gregory et al., "Androgen Receptor Stabilization in Recurrent Prostate Cancer Is Associated with Hypersensitivity to Low Androgen" Cancer Res (2001) 61: 2892-2898.
Gu et al. "Base Pairing Properties of D- and L-Cyclohexene Nucleic Acids (CeNA)" Oligonucleotides (2003) 13(6): 479-489.
Gu et al., "Synthesis of enantiomeric-pure cyclohexenyl nucleoside building blocks for oligonucleotide synthesis" Tetrahedron (2004) 60(9): 2111-2123.
Gu et al., "Enzymatic Resolution and Base Pairing Properties of D- and L-Cyclohexenyl Nucleic Acids (CeNA)" Nucleosides, Nucleotides & Nucleic Acids (2005) 24(5-7): 993-998.
Guo et al., "A Novel Androgen Receptor Splice Variant Is Up-regulated during Prostate Cancer Progression and Promotes Androgen Depletion—Resistant Growth" Cancer Res. (2009) 69(6): 2305-2313.
Hall et al., "Establishment and Maintenance of a Heterochromatin Domain" Science (2002) 297: 2232-2237.
Hall et al., "MDA-MB-453, an androgen-responsive human breast carcinoma cell line with high level androgen receptor expression." Eur. J. Cancer (1994) 30A(4): 484-490.
Handratta et al., "Novel C-17-Heteroaryl Steroidal CYP17 Inhibitors/Antiandrogens: Synthesis, in Vitro Biological Activity, Pharmacokinetics, and Antitumor Activity in the LAPC4 Human Prostate Cancer Xenograft Model" Journal of Medicinal Chemistry (2005) 48(8): 2972-2984.
Hickey et al., "Minireview: The androgen receptor in breast tissues: growth inhibitor, tumor suppressor, oncogene?" Molecular Endocrinology (2012) 26(8): 1252-1267.
Hornberg et al., "Expression of Androgen Receptor Splice Variants in Prostate Cancer Bone Metastases is Associated with Castration-Resistance and Short Survival" PLoS One (2011) 6(4):e19059, 1-9.
Horvath et al., "Stereoselective synthesis of (-)-ara-cyclohexenyl-adenine" Tetrahedron Letters (2007) 48: 3621-3623.
Hu et al., "Distinct transcriptional programs mediated by the ligand-dependent full-length androgen receptor and its splice vaiants in castration-resistant prostate cancer" Cancer Research (2012) 72(14):3457-3462.
Hu et al., "Ligand-independent androgen receptor variants derived from splicing of cryptic exons signify hormone-refractory prostate cancer." Cancer Res (2009) 69(1):16-22.
Jenuwein "An RNA-Guided Pathway for the Epigenome" Science (2002) 5590: 2215-2218.
Kabanov et al., "A new class of antivirals: antisense oligonucleotides combined with a hydrophobic substituent effectively inhibit influenza virus reproduction and synthesis of virus-specific proteins in MOCK cells" FEBS Lett., (1990) 259: 327-330.
Kaku et al., "Discovery of orteronel (TAK-700), a naphthylmethylimidazole derivative, as a highly selective 17,20-lyase inhibitor with potential utility in the treatment of prostate cancer" Bioorganic and Medicinal Chemistry (2011) 19(21): 6383-6399.
Knudsen et al. "Partners in crime: deregulation of AR activity and androgen synthesis in prostate cancer." Trends Endocrinol Metab (2010) 21(5): 315-324.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54: 3607-3630.
Kumar et al., "The First Analogues of LNA (Locked Nucleic Acids):Phosphorothioate-LNA and 2'-TmO-LNA" Bioorg. Med. Chem. Lett. (1998) 8: 2219-2222.
Letsinger et al., "Cholesteryl-conjugated oligonucleotides: Synthesis, properties, and activity as inhibitors of replication of human immunodeficiency virus in cell culture" PNAS (1989) 86: 6553-6556.
Leumann, "DNA Analogues: From Supramolecular Principles to Biological Properties" Bioorg. Med. Chem. (2002) 10: 841-854.
Li et al., "Androgen receptor splice vaiants mediate enzalutamide resistance in castration-resisant prostate cancer cell lines" Cancer Research (2013) 73(2): 483-489.
Lin et al., "Prostate-localized and androgen-regulated expression of the membrane-bound serine protease TMPRSS2." Cancer Res. (1999) 59(17): 4180-4184.
Linja et al., "Amplification and Overexpression of Androgen Receptor Gene in Hormone-Refractory Prostate Cancer" Cancer Res (2001) 61: 3550-3555.
Maher et al., "Comparative bybrid arrest by tandem antisense oligodeoxyribonucleotides or oligodeoxyribonucleoside methylphosphonates in a cell-free system" Nuc. Acid. Res. (1988) 16(8):3341-3358.
Manoharan et al., "Chemical Modifications to Improve Uptake and Bioavailability of Antisense Oligonucleotides" Ann. N.Y. Acad. Sci. (1992) 660: 306-309.
Manoharan et al., "Inoduction of a lipophilic thioether tether in the minor groove of nucleic acids for antisense applications" Bioorg. Med. Chem. Let. (1993) 3(12): 2765-2770.
Manoharan et al., "Cholic Acid-Oligonucleotide Conjugates for Antisense Applications" Bioorg. Med. Chem. Let. (1994) 4(8): 1053-1060.
Manoharan et al., "Oligonucleotide Conjugates: Alteration of the Pharmacokinetic Properties of Antisense Agents" Nucleosides & Nucleotides (1995) 14(3-5): 969-973.
Manoharan et al., "Lipidic Nucleic Acids" Tetrahedron Lett. (1995) 36(21): 3651-3654.
Martin, "Ein neuer Zugang zu 2'-O-Alkylribonucleosiden and Eigenscbaften deren Oligonucleotide" Helv. Chim. Acta (1995)78: 486-504.
Meyer et al., "BRCA2 Mutations and Triple-Negative Breast Cancer" PLoS One (2012) 7(5): e38361, 1-5.
Mishra et al., "Improved leishmanicidal effect of phosphorotioate antisense oligonucleotides by LDL-mediated delivery" Biochim. Biophys. Acta (1995) 1264: 229-237.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
Nauwelaerts et al., "Cyclohexenyl nucleic acids: conformationally flexible oligonucleotides" Nucleic Acids Research (2005) 33(8): 2452-2463.
New England Biolabs 1998/99 Catalog (cover page and pp. 121 and 284).
Ni et al., "Targeting Androgen Receptor in Estrogen Receptor-Negative Breast Cancer" Cancer Cell (2011) 20: 119-131.
Oberhauser et al., "Effective incorporation of 2'-O-methyl-oligoribonucleotides into liposomes and enhanced cell association through modification with thiocholesterol" Nucl. Acids Res. (1992) 20(3): 533-538.

(56) References Cited

OTHER PUBLICATIONS

Orum et al., “Locked nucleic acids: A promising molecular family for gene-function analysis and antisense drug development” Curr. Opinion Mol. Ther. (2001) 3: 239-243.
Pal-Bhadra et al., “Heterochromatic Silencing and HP1 Localization in Drosophila Are Dependent on the RNAi Machinery” Science (2004) 303: 669-672.
Reynolds et al., “Rational siRNA design for RNA interference” Nature Biotechnology (2004) 22(3):326-330.
Robeyns et al., “Oligonucleotides with cyclohexene-nucleoside building blocks: crystallization and preliminary X-ray studies of a left-handed sequence GTGT ACAC” Acta Crystallographica, Section F: Structural Biology and Crystallization Communications (2005) F61(6): 585-586.
Robeyns et al., “Structure of the Fully Modified Left-Handed Cyclohexene Nucleic Acid Sequence GTGTACAC” J. Am. Chem. Soc. (2008) 130(6): 1979-1984.
Saison-Behmoaras et al., “Short modified antisense oligonucleotides directed against Ha-ras point mutation induce selective cleavage of the mRNA and inhibit T24 cells proliferation” EMBO J. (1991) 10: 1111-1118.
Sanghvi et al., “Heterocyclic Base Modifications in Nucleic Acids and Their Applications in Antisense Oligonucleotides” Antisense Research and Applications (1993) pp. 273-288.
Scher et al., “Biology of Progressive, Castration-Resistant Prostate Cancer: Directed Therapies Targeting the Androgen-Receptor Signaling Axis” J Clin Oncol (2005) 23(32): 8253-8261.
Scher et al., “Increased survival with enzalutamide in prostate cancer after chemotherapy.” N. Engl. J. Med. (2012) 367(13):1187-1197.
Shea et al., “Synthesis, hybridization properties and antiviral activity of lipid-oligodeoxynucleotide conjugates” Nucl. Acids Res. (1990) 18: 3777-3783.
Singh et al., “LNA (locked nucleic acids): synthesis and high-affinity nucleic acid recognition” Chem. Commun. (1998) 4: 455-456.
Singh et al., “Synthesis of 2'-Amino-LNA: A Novel Conformationally Restricted High-Affinity Oligonucleotide Analogue with a Handle” J. Org. Chem. (1998) 63: 10035-10039.
Srivastava et al., “Five- and Six-Membered Conformationally Locked 2',4'-Carbocyclic ribo-Thymidines: Synthesis, Structure, and Biochemical Studies” J. Am. Chem. Soc. (2007) 129(26): 8362-8379.
Svinarchuk et al., “Inhibition of HIV proliferation in MT-4 cells by antisense oligonucleotide conjugated to lipophilic groups” Biochimie (1993) 75: 49-54.
Thalmann et al., “Androgen-independent cancer progression and bone metastasis in the LNCaP model of human prostate cancer.” Cancer Res. (1994) 54(10): 2577-2581.
Verbeure et al., “RNase H mediated cleavage of RNA by cyclohexene nucleic acid (CeNA)” Nucleic Acids Research (2001) 29(24): 4941-4947.
Verdel et al., “RNAi-Mediated Targeting of Heterochromatin by the RITS Complex” Science (2004) 303: 672-676.
Volpe et al., “Regulation of heterochromatic silencing and histone H3 lysine-9 methylation by RNAi.” Science (2002) 297(5588): 1833-1837.
Wahlestedt et al., “Potent and nontoxic antisense oligonucleotides containing locked nucleic acids” PNAS (2000) 97: 5633-5638.
Wang et al., “Cyclohexene Nucleic Acids (CeNA): Serum Stable Oligonucleotides that Activate RNase H and Increase Duplex Stability with Complementary RNA” J. Am. Chem. (2000) 122: 8595-8602.
Wang et al., “A Straightforward Stereoselective Synthesis of D- and L-5-Hydroxy-4-hydroxymethyl-2-cyclohexenylguanine” J. Org. Chem. (2001) 66: 8478-8482.
Wang et al., “Stereocontrolled Synthesis of Ara-Type Cyclohexenyl Nucleosides” J. Org. Chem. (2003) 68: 4499-4505.
Wang et al., “Cyclohexene Nucleic Acids (CeNA) Form Stable Duplexes With RNA and Induce RNASE H Activity”Nucleosides, Nucleotides & Nucleic Acids (2001) 20(4-7) 785-788.
Woolf et al. “Specificity of antisense oligonucleotides in vivo”PNAS (1992) 89:7305-7309.
Yin et al., “Recent Progress in Pharmaceutical Therapies for Castration-Resistant Prostate Cancer” Int. J. Mol. Sci. (2013) 14(7):13958-13978.
Yingming et al., “Androgen Receptor Splice Variants Mediate Enzalutamide Resistance in Castration-Resistant Prostate Cancer Cell Lines” Cancer Res (2013) 73(2):483-489.
Zhou et al., “Fine Tuning of Electrostatics around the Internucleotidic Phosphate through Incorporation of Modified 2',4'-Carhocyclic-LNAs and -ENAs Leads to Significant Modulation of Antisense Properties” J. Org. Chem., 2009, 74, 118-134.
Seth et al., “Design, Synthesis and Evaluation of Constrained Methoxyethyl (cMOE) and Constrained Ethyl (cEt) Nucleoside Analogs” Nucleic Acids Symposium Series No. 52, pp. 553-553, Sep. 8, 2008.
International Search Report issued for PCT/US2013/064479 on Apr. 17, 2014.
Written Opinion issued for PCT/US2013/064479 on Apr. 17, 2014.

* cited by examiner

MODULATION OF ANDROGEN RECEPTOR EXPRESSION

CROSS-REFERENCE TO RELATED PATENT APPLICATIONS

This specification claims the benefit of priority to U.S. Provisional Patent Application No. 61/712,780 filed Oct. 11, 2012; U.S. Provisional Patent Application No. 61/712,756 filed Oct. 11, 2012; U.S. Provisional Patent Application No. 61/723,701 filed Nov. 7, 2012; U.S. Provisional Patent Application No. 61/777,813 filed Mar. 12, 2103; U.S. Provisional Patent Application No. 61/777,851 filed Mar. 12, 2103 and U.S. Provisional Patent Application No. 61/777,895 filed Mar. 12, 2103. The entire text of the above-referenced patent applications is incorporated herein by reference in their entirety.

SEQUENCE LISTING

The present application is being filed along with a Sequence Listing in electronic format. The Sequence Listing is provided as a file entitled BIOL0212WOSEQ.txt created Sep. 17, 2013, which is approximately 556 KB in size. The information in the electronic format of the sequence listing is incorporated herein by reference in its entirety.

FIELD

Certain embodiments are directed to compounds and compositions targeted to human androgen receptor (AR) for inhibiting androgen receptor levels in a cell, which can be useful for methods of treating cancer and inhibiting cancer cell growth or proliferation.

BACKGROUND

Androgen receptor (AR) belongs to the superfamily of nuclear receptors and is activated by binding to its hormone ligands: androgen, testosterone, or DHT. Upon binding hormone ligand in the cytoplasm, androgen receptor translocates to the nucleus where it binds DNA and functions as a transcription factor to regulate expression of a number of target genes, such as prostate specific antigen (PSA) and TMPRSS2. Knudsen et al. (Trends Endocrinol Metab 21: 315-24, 2010) Bennett et al. (Int J Biochem Cell Biol. 42:813-827, 201).

Androgen receptor (AR) signaling is a critical survival pathway for prostate cancer cells, and androgen-deprivation therapy (ADT), also known as "chemical castration", is a first-line treatment strategy against hormone-sensitive, androgen-dependent prostate cancer that reduces circulating androgen levels and thereby inhibits AR activity. Although a majority of patients initially respond to ADT, most will eventually develop castrate resistance in which the disease progresses despite castrate levels of testosterone. This type of cancer is known as castrate-resistant prostate cancer (CRPC). There are a number of mechanisms underlying the development of castrate (castration) resistance including an increase in the expression of AR protein which can sensitize cells to low levels of androgen, AR mutations that can alter transactivation or sensitize AR to alternative ligands and the emergence of alternatively spliced forms of AR, which lack the ligand binding domain but can nevertheless act to promote tumour growth in the absence of ligand stimulation. Additionally prostate tumors may also synthesize their own androgens thereby increasing the local intra-tumoral testosterone levels available to activate the AR.

Androgen receptor (AR) signaling is a critical survival pathway for prostate cancer cells, and androgen-deprivation therapy (ADT) remains the principal treatment for patients with locally advanced and metastatic disease. Although a majority of patients initially respond to ADT, most will eventually develop castrate resistance in which the disease progresses despite castrate levels of testosterone. This type of cancer is known as castrate-resistant prostate cancer (CRPC) (Karantos et al., Oncogene advance online: 1-13, 2013). There are a number of mechanisms underlying the development of castration resistance including an increase in the expression of AR protein which can sensitize cells to low levels of androgen (Gregory et al., Cancer Res 61: 2892-2898, 2001; Linja et al., Cancer Res 61: 3550-3555, 2001), AR mutations that can alter transactivation or sensitize AR to alternative ligands (Scher et al., J Clin Oncol 23: 8253-8261, 2005) and the emergence of alternatively spliced forms of AR, which lack the ligand binding domain but can nevertheless act to promote tumour growth in the absence of ligand stimulation (Yingming et al., Cancer Res 73:483-489, 2013). Additionally prostate tumors may also synthesize their own androgens thereby increasing the local intra-tumoral testosterone levels available to activate the AR (Attard et al., Cancer Cell 16:458-462, 2009).

The fact that the androgen receptor remains active in castrate resistant prostate cancer has led to the development of new agents that inhibit the production of androgen ligands or block the actions of these ligands on the AR. These new agents include abiraterone acetate which inhibits 17-α-hydroxylase/17,20-lyase (CYP17) activity resulting in a reduction in residual androgens synthesized by the adrenals and in the prostate tumour itself deBono et al. (N Engl J Med 364: 1995-2006, 2011) and enzalutamide which prevents androgen ligand from binding to AR, translocating to the nucleus, and binding to DNA (Scher et al., N Engl J Med 367:1187-1197, 2012). A number of other androgen synthesis inhibitors or androgen receptor blockers are under development either pre-clinically or clinically and include for example, ARN509, ODM201, TOK001, VT464.

Although the activity of agents such as enzalutamide and abiraterone in CRPC is very encouraging, neither works in all patients and both are associated with the development of additional resistance through re-activation of the AR by the mechanisms described above (Yingming et al., Cancer Res 73:483-489, 2013). Thus, there is a continued need to identify alternative therapies for the treatment of CRPC, and in particular those that can either remove and/or inhibit the activity of all forms of AR including for example, wildtype, mutated and splice variant ARs.

The present invention provides antisense oligonclueotides which by virtue of their design and mode of action (base-pair with the AR RNA target and mediate its destruction by RNase H, an enzyme that destroys the RNA in a DNA/RNA duplex) are aimed at inhibiting the major forms of AR By targeting an appropriate region of the AR mRNA the antisense oligonucleotide will result in inhibition of the major forms (full length, splice variant and mutated forms) of androgen receptor proteins and therefore be suitable for the treatment of patients with CRPC.

Aside from prostate cancer, AR is also implicated as a factor in the progression of other tumours such as breast cancer. In breast cancer AR is expressed in 70-80% of tumours which are also ER positive and in 12% cases which are known as triple negative (no expression of ER, PR and HER2) (Hickey et al., Molecular Endocrinology 26: 1252-

1267, 2012). In pre-clinical studies, the androgen receptor antagonist bicalutamide induces anti-proliferative responses in vitro in breast cancer cells and this is potentiated by addition of a Pi3K/mTOR inhibitor (Ni et al., Cancer Cell 20: 119-131, 2011). The 2nd generation anti-androgen, enzalutamide inhibits dihydrotestosterone (DHT) mediated proliferation in ER+/AR+ breast cancer cells and is as effective as tamoxifen at inhibiting estrogen-stimulated breast cancer tumour growth in pre-clinical models in vivo (Cochrane et al., Cancer Res 72(24 Supplement): P2-14-02, 2012). Enzalutamide also inhibits proliferation in HER2+ and triple-negative breast cancer cells. It appears that in situations where estrogen action is reduced (eg. long-term estrogen deprivation or absence of ER) AR levels increase and can become oncogenic. This would suggest that AR antagonists may be best positioned in triple negative or hormone resistant breast cancer settings (Hickey et al., Molecular Endocrinology 26: 1252-1267, 2012). AR targeted therapies are currently under investigation in clinical trials for breast cancer (NCT00468715, NCT01597193, NCT01381874, NCT00755886).

AR is also expressed in a variety of other tumours, including, but not limited to bladder, ovarian, gastric, lung and liver. Pre-clinical data support a similar role as in breast cancer, to promote tumour cell proliferation survival; thus blocking AR in these tumours could have therapeutic clinical benefit (Chang et al., Oncogene advance online: 1-10, 2013).

SUMMARY

Several embodiments provided herein relate to the discovery of compounds and compositions for inhibiting androgen receptor levels in a cell, which can be useful for methods of treating cancer and inhibiting proliferation or growth of cancer cells, such as prostate, breast, ovarian, gastric or bladder cancer or cancer cells.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification at the 2' position of a sugar ring, e.g. a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of Androgen Receptor", it is implied that Androgen Receptor levels are inhibited within a range of 63% and 77%.

"Administration" or "administering" refers to routes of introducing an antisense compound provided herein to a subject to perform its intended function. An example of a route of administration that can be used includes, but is not limited to parenteral administration, such as subcutaneous, intravenous, or intramuscular injection or infusion.

"Androgen-receptor positive" with respect to breast cancer or a breast cancer cell refers to a breast cancer or a breast cancer cell that expresses androgen receptor.

"Animal" refers to a human or non-human animal, including, but not limited to, mice, rats, rabbits, dogs, cats, pigs, and non-human primates, including, but not limited to, monkeys and chimpanzees.

"Anti-androgenic agent" refers to a therapeutic compound or drug which is an androgen synthesis inhibitor or an androgen receptor blocker.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

Also included within the definition of LNA according to the invention are LNAs in which the 2'-hydroxyl group of the ribosyl sugar ring is connected to the 4' carbon atom of the sugar ring, thereby forming a methyleneoxy ($4'-CH_2—O-2'$) bridge to form the bicyclic sugar moiety. The bridge can also be a methylene ($—CH_2—$) group connecting the 2' oxygen atom and the 4' carbon atom, for which the term methyleneoxy ($4'-CH_2—O-2'$) LNA is used. Furthermore; in the case of the bicylic sugar moiety having an ethylene bridging group in this position, the term ethyleneoxy ($4'-CH_2CH_2—O-2'$) LNA is used. α-L-methyleneoxy ($4'-CH_2—O-2'$), an isomer of methyleneoxy ($4'-CH_2—O-2'$) LNA is also encompassed within the definition of LNA, as used herein.

"Cap structure" or "terminal cap moiety" means chemical modifications, which have been incorporated at either terminus of an antisense compound.

"Castrate-resistant prostate cancer" or "Castration-resistant prostate cancer" and prostate cancer cells refer to the reduction of sensitivity of prostate cancer and prostate cancer cells to androgen deprivation therapy or an anti-androgenic agent.

"cEt" or "constrained ethyl" means a bicyclic sugar moiety comprising a bridge connecting the 4'-carbon and the 2'-carbon, wherein the bridge has the formula: $4'-CH(CH_3)—O-2'$.

"Constrained ethyl nucleoside" (also cEt nucleoside) means a nucleoside comprising a bicyclic sugar moiety comprising a $4'-CH(CH_3)—O-2'$ bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-β-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Downstream" refers to the relative direction toward the 3' end or C-terminal end of a nucleic acid.

"Efficacy" means the ability to produce a desired effect.

"Estrogen-receptor (ER) positive" with respect to breast cancer or a breast cancer cell refers to breast cancer or a breast cancer cell that expresses estrogen receptor (ER).

"Estrogen-receptor (ER) negative" with respect to breast cancer or a breast cancer cell refers to breast cancer or a breast cancer cell that does not express estrogen receptor (ER).

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Her2/neu negative" with respect to breast cancer or a breast cancer cell refers to breast cancer or a breast cancer cell that does not express Her2/neu.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease", upregulate", "downregulate", or the like, generally denote quantitative differences between two states.

"Inhibiting the expression or activity" refers to a reduction, blockade of the expression or activity and does not necessarily indicate a total elimination of expression or activity.

"Internucleoside linkage" refers to the chemical bond between nucleosides.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Progesterone receptor (PR) negative" with respect to breast cancer or a breast cancer cell refers to breast cancer or a breast cancer cell that does not express progesterone receptor (PR).

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Sites," as used herein, are defined as unique nucleobase positions within a target nucleic acid.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments. "Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Synergy" or "synergize" refers to an effect of a combination that is greater than additive of the effects of each component alone.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Treating cancer" refers to performing actions that lead to amelioration of cancer or of the symptoms accompanied therewith. The combination of said actions is encompassed by the term "treatment." Amelioration of cancer includes, but is not limited to, reducing the number of cancer cells in a subject or reducing the number of cancer cells in the subject. Said treatment as used herein also includes an entire restoration of the health with respect to cancer. It is to be understood that treatment as used in accordance with embodiments provided herein may not be effective in all subjects to be treated. However, a population of subjects suffering from cancer referred to herein can be successfully treated. In certain embodiments, "treating cancer" can be described by a number of different parameters including, but not limited to, reduction in the size of a tumor in a subject having cancer, reduction in the growth or proliferation of a tumor in a subject having cancer, preventing metastasis or reducing the extent of metastasis, and/or extending the survival of a subject having cancer compared to control. The cancer referred to in this definition can be any cancer including one selected from prostate cancer, breast cancer, ovarian cancer, gastric cancer and bladder cancer.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Upstream" refers to the relative direction toward the 5' end or N-terminal end of a nucleic acid.

Certain Embodiments

Certain embodiments provide methods, compounds, and compositions for inhibiting androgen receptor (AR) mRNA expression.

Certain embodiments provide antisense compounds or compositions targeted to an androgen receptor nucleic acid. In certain embodiments, the androgen receptor nucleic acid is the sequences set forth in GENBANK Accession No. NT_011669.17_TRUNC_5079000_5270000 (incorporated herein as SEQ ID NO: 1), GENBANK Accession No. NM_000044.3 (incorporated herein as SEQ ID NO: 2), GENBANK Accession No. NM_001011645.2 (incorporated herein as SEQ ID NO: 3), GENBANK Accession No. FJ235916.1 (incorporated herein as SEQ ID NO: 4), GENBANK Accession No. FJ235917.1 (incorporated herein as SEQ ID NO: 5), GENBANK Accession No. FJ235918.1 (incorporated herein as SEQ ID NO: 6), GENBANK Accession No. FJ235919.1 (incorporated herein as SEQ ID NO: 7), or GENBANK Accession No. FJ235920.1 (incorporated herein as SEQ ID NO: 8).

In certain embodiments, the compounds or compositions comprise a modified oligonucleotide 10 to 30 linked nucleosides in length targeted to AR. The AR target can have a sequence recited in any one of SEQ ID NOs: 1-8 or a portion thereof or a variant thereof. In certain embodiments, the AR target can have a sequence of known AR splicing variants including, but are not limited to, AR-V1, AR-V2, AR-V3, AR-V4, AR-V5, AR-V6, and AR-V7 (also referred to as AR3), which contain exons 1-3 but lack exons 4-8. AR-V1, AR-V2, AR-V3, AR-V4, AR-V5, AR-V6, AR-V7, and additional splicing variants targetable by compounds provided herein are described in Hu et al., *Cancer Res* 2009; 69:16-22 and US Patent Application Publication No. US 2010/0068802, each of which is incorporated herein by reference in its entirety.

In certain embodiments, the compounds or compositions comprise a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside.

In certain embodiments, the compounds or compositions comprise a modified oligonucleotide consisting of 10 to 30 linked nucleosides and having a nucleobase sequence consisting of a nucleobase sequence of any of SEQ ID NOs: 12-179. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside.

In certain embodiments, the compounds or compositions targeted to androgen receptor comprise a single-stranded modified oligonucleotide consisting of 16 linked nucleosides having a nucleobase sequence consisting of the sequence of SEQ ID NO: 35, 39, 43, 124, 150, 155, 169, or 175, or a pharmaceutically acceptable salt thereof. In certain embodiments, the antisense compound targeted to human AR is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 20 linked nucleosides, the gap segment consisting of 10 linked deoxynucleosides, the 5' wing segment consisting of five linked nucleosides, the 3' wing segment consisting of five linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 16 linked nucleosides, a gap segment consisting of 10 linked deoxynucleosides, a 5' wing segment consisting of three linked nucleosides, a 3' wing segment consisting of three linked nucleosides, each nucleoside of each wing segment comprises a constrained ethyl (cEt) sugar, each internucleoside linkage is a phosphorothioate linkage and each cytosine is a 5-methylcytosine.

In certain embodiments, the modified oligonucleotide consists of 16 linked nucleosides, a gap segment consisting of 9 linked deoxynucleosides, a 5' wing segment consisting of three linked nucleosides, a 3' wing segment consisting of four linked nucleosides; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are each a constrained ethyl (cEt) sugar; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of four linked nucleosides, a 3' wing segment consisting of four linked nucleosides; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 8 linked deoxynucleosides, a 5' wing segment consisting of five linked nucleosides, a 3' wing segment consisting of three linked nucleosides; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of seven linked nucleosides, a 3' wing segment consisting of two linked nucleosides; the seven linked nucleosides of the 5' wing segment are a 2'-O-methoxyethyl sugar, a constrained ethyl (cEt) sugar, a constrained ethyl (cEt) sugar, a 2'-O-methoxyethyl sugar, a 2'-O-methoxyethyl sugar, a constrained ethyl (cEt) sugar, and a constrained ethyl (cEt) sugar in the 5' to 3' direction; the two linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of six linked nucleosides, a 3' wing segment consisting of three linked nucleosides; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of five linked nucleosides, a 3' wing segment consisting of four linked nucleosides; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, a gap segment consisting of 7 linked deoxynucleosides, a 5' wing segment consisting of four linked nucleosides, a 3' wing segment consisting of five linked nucleosides; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

In certain embodiments, the compounds or compositions targeted to androgen receptor comprise a single-stranded modified oligonucleotide consisting of 16 linked nucleosides having a nucleobase sequence consisting of the sequence of SEQ ID NO: 35, 39, 43, 124, 150, 155, 169, or 175, or a pharmaceutically acceptable salt thereof, wherein the modified oligonucleotide comprises a gap segment consisting of deoxynucleosides; a 5' wing segment; and a 3' wing segment, wherein the gap segment is positioned between the 5' wing segment and the 3' wing segment and each nucleoside of each wing segment comprises a modified sugar. In certain embodiments, each internucleoside linkage of the modified oligonucleotide is a phosphorothioate linkage. In certain embodiments, each cytosine of the modified oligonucleotide is a 5'-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 8 linked deoxynucleosides;

a 5' wing segment consisting of four linked nucleosides; and a 3' wing segment consisting of four linked nucleosides;

wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 8 linked deoxynucleosides;

a 5' wing segment consisting of five linked nucleosides; and a 3' wing segment consisting of three linked nucleosides;

wherein the gap segment is positioned between the 5' wing segment and the 3' wing segment; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 7 linked deoxynucleosides;

a 5' wing segment consisting of four linked nucleosides; and a 3' wing segment consisting of five linked nucleosides;

wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 7 linked deoxynucleosides;

a 5' wing segment consisting of six linked nucleosides; and a 3' wing segment consisting of three linked nucleosides;

wherein the gap segment is positioned between the 5' wing segment and the 3' wing segment; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 43, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 124, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 150, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 155, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 169, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, a compound targeted to androgen receptor comprises a single-stranded modified oligonucleotide consisting of 16 linked nucleosides having a nucleobase sequence consisting of the sequence of SEQ ID NO: 175, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

In certain embodiments, an antisense compound or antisense oligonucleotide targeted to an androgen receptor nucleic acid is complementary within the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, 67454-67469, 102156-102171, 114874-114889, 115272-115287, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments, an antisense compound or antisense oligonucleotide targeted to an androgen receptor nucleic acid target the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, 67454-67469, 102156-102171, 114874-114889, 115272-115287, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments, antisense compounds or antisense oligonucleotides target a region of an androgen receptor nucleic acid. In certain embodiments, such compounds or oligonucleotides targeted to a region of an androgen receptor nucleic acid have a contiguous nucleobase portion that is complementary to an equal length nucleobase portion of the region. For example, the portion can be at least an 8, 9, 10, 11, 12, 13, 14, 15, or 16 contiguous nucleobases portion complementary to an equal length portion of a region recited herein. In certain embodiments, such compounds or oligonucleotide target the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, 67454-67469, 102156-102171, 114874-114889, 115272-115287, 115365-115380, 134971-134986, 139682-139697, 139762-139777, 139782-139797, 144856-144871, 144938-144953, 148406-148421, 148443-148458, 148520-148535, 181695-181710, 182958-182973, or 183049-183064.

In certain embodiments, an antisense compound or antisense oligonucleotide provided herein targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4047-4062, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536.

In certain embodiments, an antisense compound or antisense oligonucleotide provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170, 102156-102171, 139682-139697, 139762-139777, or 139782-139797.

In certain embodiments, an antisense compound or antisense oligonucleotide provided herein targets AR within exon 3, for example within nucleotide regions 144841-144957 (exon 3), 148380-148594 (exon 3b), or 153504-154908 (exon 3d) of SEQ ID NO: 1. In certain embodiments, an antisense compound provided herein targeted to exon 3 of AR is complementary within any of the following nucleotide regions of SEQ ID NO: 1: 144856-144871, 144938-144953, 148406-148421, 148443-148458, or 148520-148535.

In certain embodiments, an antisense compound or antisense oligonucleotide provided herein targets AR within exon 7, for example within nucleotide region 181658-181815 of SEQ ID NO: 1. In certain embodiments, an antisense compound provided herein targeted to exon 7 of AR is complementary within nucleotide region 181695-181710 of SEQ ID NO: 1.

In certain embodiments, an antisense compound or antisense oligonucleotide provided herein targets AR within exon 8, for example within nucleotide region 182517-189455 of SEQ ID NO: 1. In certain embodiments, an antisense compound provided herein targeted to exon 8 of AR is complementary within nucleotide regions 182958-182973 or 183049-183064 of SEQ ID NO: 1.

In certain embodiments, an antisense compound or antisense oligonucleotide provided herein targets AR within intron 1, for example within nucleotide regions 5594-27671 or 27854-102086 of SEQ ID NO: 1. In certain embodiments, an antisense compound provided herein targeted to intron 1 of AR is complementary within any of the following nucleotide regions of SEQ ID NO: 1: 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, or 67454-67469.

In certain embodiments, an antisense compound or antisense oligonucleotide provided herein targets AR within intron 2, for example within nucleotide regions 102239-139550 or 139835-144840 of SEQ ID NO: 1. In certain embodiments, an antisense compound provided herein targeted to intron 2 of AR is complementary within any of the following nucleotide regions of SEQ ID NO: 1: 114874-114889, 115272-115287, 115365-115380, or 134971-134986.

In certain embodiments, the following nucleotide regions of SEQ ID NO: 1, when targeted by antisense compounds or antisense oligonucleotides, display at least 50% inhibition: 3099-3114, 3120-3135, 3351-3366, 3353-3368, 3361-3376, 3513-3528, 3519-3534, 3768-3783, 3799-3814, 3851-3866, 3888-3903, 4059-4074, 4534-4549, 4555-4570, 4571-4586, 4578-4593, 4655-4670, 4699-4714, 4750-4765, 4755-4770, 4865-4880, 5054-5069, 5060-5075, 5061-5076, 5062-5077, 5155-5170, 5265-5280, 5392-5407, 5448-5463, 5483-5498, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58735, 58720-58739, 58721-58736, 58722-58737, 58723-58738, 58724-58739, 58725-58740, 58750-58765, 58750-58769, 58751-58766, 58752-58767, 58753-58768, 58754-58769, 58755-58770, 60902-60917, 67454-67469, 102156-102171, 114874-114889, 114874-114889, 115272-115287, 115365-115380, 134971-134986, 144856-144871, 181695-181710, 182958-182973, and 183049-183064.

In certain embodiments, the following nucleotide regions of SEQ ID NO: 1, when targeted by antisense compounds or antisense oligonucleotides, display at least 60% inhibition: 3799-3814, 3851-3866, 3888-3903, 4059-4074, 4534-4549, 4555-4570, 4571-4586, 4578-4593, 4655-4670, 4699-4714, 4755-4770, 4865-4880, 5060-5075, 5061-5076, 5062-5077, 5155-5170, 5265-5280, 5392-5407, 5448-5463, 5483-5498, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 42017-42032, 56050-56065, 58719-58734, 58720-58735, 58720-58739, 58721-58736, 58722-58737, 58723-58738, 58724-58739, 58725-58740, 58750-58765, 58750-58769, 58751-58766, 58752-58767, 58753-58768, 58754-58769, 58755-58770, 67454-67469, 102156-102171, 115272-115287, 115365-115380, 144856-144871, 181695-181710, 182958-182973, and 183049-183064.

In certain embodiments, the following nucleotide regions of SEQ ID NO: 1, when targeted by antisense compounds or antisense oligonucleotides, display at least 70% inhibition: 3799-3814, 3851-3866, 3888-3903, 4059-4074, 4534-4549, 4655-4670, 4699-4714, 4755-4770, 4865-4880, 5060-5075, 5062-5077, 5155-5170, 5265-5280, 5392-5407, 5448-5463, 5483-5498, 7543-7558, 8471-8486, 8638-8653, 9464-9479, 10865-10880, 11197-11212, 11855-11870, 13189-13204, 13321-13336, 13346-13361, 16555-16570, 16793-16808, 16968-16983, 17206-17221, 18865-18880, 33315-33330, 42017-42032, 58719-58734, 58720-58739, 58720-58735, 58721-58736, 58722-58737, 58723-58738, 58724-58739, 58725-58740, 58750-58769, 58750-58765, 58751-58766, 58752-58767, 58753-58768, 58754-58769, 58755-58770, 102156-102171, 115365-115380, 144856-144871, 181695-181710, 182958-182973, and 183049-183064.

In certain embodiments, the following nucleotide regions of SEQ ID NO: 1, when targeted by antisense compounds or antisense oligonucleotides, display at least 80% inhibition: 3799-3814, 3851-3866, 3888-3903, 4059-4074, 4534-4549, 4655-4670, 4699-4714, 4755-4770, 4865-4880, 5060-5075, 5062-5077, 5155-5170, 5265-5280, 5392-5407, 5448-5463, 5483-5498, 8471-8486, 8638-8653, 9464-9479, 10865-10880, 11197-11212, 13189-13204, 16793-16808, 58719-58734, 58720-58735, 58721-58736, 58722-58737, 58723-58738, 58724-58739, 58725-58740, 58750-58765, 58751-58766, 58752-58767, 58753-58768, 58754-58769, 58755-58770, 102156-102171, 144856-144871, 181695-181710, 182958-182973, and 183049-183064.

In certain embodiments, the following nucleotide regions of SEQ ID NO: 1, when targeted by antisense compounds or antisense oligonucleotides, display at least 90% inhibition: 4534-4549, 5060-5075, 5062-5077, 5155-5170, 5265-5280, 5448-5463, 58720-58735, 58721-58736, 58722-58737, 58723-58738, 58724-58739, 58725-58740, 58750-58765, 58751-58766, 58752-58767, 58753-58768, 58754-58769, 58755-58770, 182958-182973, and 183049-183064.

In certain embodiments, the following antisense compounds or antisense oligonucleotides target a region of an androgen receptor nucleic acid and effect at least a 50% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560132, 560133, 560137, 569213, 569215, 569216, 569220, 569222, 569223, 569227, 569228, 569229, 569236, 569238, 583559, 583567, 583608, 583609, 583613, 583635, 583638, 583662, 583795, 583796, 583799, 583834, 583919, 584145, 584148, 584149, 584152, 584157, 584158, 584162, 584163, 584165, 584166, 584167, 584168, 584179, 584180, 584183, 584184, 584192, 584233, 584242, 584245, 584263, 584269, 584274, 584312, 584329, 584361, 584465, 584465, 584468, 584469, 584469, 584495, 584495, 585233, 585259, 585262, 585263, 585264, 585265, 585268, 585269, 585271, 585274, 586124, 586224, 586224, 586225, 586225, 586227, and 586227.

In certain embodiments, the following antisense compounds or antisense oligonucleotides target a region of an androgen receptor nucleic acid and effect at least a 50% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 39, 40, 41, 42, 43, 46, 49, 53, 54, 55, 57, 59, 63, 92, 93, 95, 101, 125, 148, 149, 150, 151, 152, 153, 154, 155, 156, 157, 158, 159, 160, 161, 162, 163, 164, 165, 166, 167, 168, 169, 170, 171, 172, 173, 174, 175, 176, and 177.

In certain embodiments, the following antisense compounds or antisense oligonucleotides target a region of an androgen receptor nucleic acid and effect at least a 60% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560137, 569213, 569216, 569222, 569228, 569236, 583795, 583796, 583799, 584145, 584148, 584149, 584152, 584157, 584158, 584162, 584163, 584165, 584166, 584167, 584168, 584179, 584180, 584183, 584184, 584192, 584233, 584242, 584245, 584274, 584312, 584361, 584468, 584469, 585233, 585259, 585262, 585263, 585264, 585265, 585268, 585269, 585274, 586124, 586224, 586225, and 586227.

In certain embodiments, the following antisense compounds or antisense oligonucleotides target a region of an androgen receptor nucleic acid and effect at least a 60% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 38, 39, 40, 41, 42, 43, 92, 93, 95, 148, 149, 150, 151, 152, 153, 154, 155, 156, 157, 158, 159, 160, 161, 162, 163, 164, 165, 166, 167, 170, 171, 173, 175, and 176.

In certain embodiments, the following antisense compounds or antisense oligonucleotides target a region of an androgen receptor nucleic acid and effect at least a 70% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560071, 560098, 560099, 560100, 560131, 560137, 569222, 584145, 584148, 584149, 584152, 584162, 584163, 584165, 584166, 584167, 584168, 584179, 584180, 584183, 584184, 584192, 584245, 584274, 584469, 585259, 585262, 585268, 585269, 586124, 586224, 586225, and 586227.

In certain embodiments, the following antisense compounds or antisense oligonucleotides target a region of an androgen receptor nucleic acid and effect at least a 70% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 38, 39, 40, 41, 43, 148, 149, 150, 151, 154, 155, 156, 157, 158, 159, 160, 161, 162, 163, 164, 167, 170, and 176.

In certain embodiments, the following antisense compounds or antisense oligonucleotides target a region of an androgen receptor nucleic acid and effect at least a 80% inhibition of an androgen receptor mRNA, ISIS IDs: 549332, 549334, 549338, 549347, 549358, 549360, 549361, 549362, 549366, 549371, 549372, 549374, 549377, 549379, 549380, 549381, 549387, 549390, 549414, 549432, 549434, 549457, 549458, 549459, 560098, 560099, 560100, 560137, 584148, 584149, 584152, 584162, 584163, 584166, 584180, 586124, 586224, 586225, and 586227.

In certain embodiments, the following antisense compounds or antisense oligonucleotides target a region of an androgen receptor nucleic acid and effect at least a 80% inhibition of an androgen receptor mRNA, SEQ ID NOs: 12, 13, 14, 15, 16, 17, 18, 19, 20, 21, 22, 23, 24, 25, 26, 27, 29, 31, 32, 33, 34, 35, 36, 37, 39, 40, 41, 43, 149, 150, 151, 154, 155, 157, and 161.

In certain embodiments, the following antisense compounds or antisense oligonucleotides target a region of an androgen receptor nucleic acid and effect at least a 90% inhibition of an androgen receptor mRNA, ISIS IDs: 549358, 549371, 549372, 549374, 549377, 549380, 549432, 549434, 549457, 549458, 549459, 560098, 560099, 560100, 560137, and 586224.

In certain embodiments, the following antisense compounds or antisense oligonucleotides target a region of an androgen receptor nucleic acid and effect at least a 90% inhibition of an androgen receptor mRNA, SEQ ID NOs: 16, 21, 22, 23, 24, 26, 33, 34, 35, 36, 37, 39, 40, and 41.

Percent inhibition of androgen receptor mRNA can be determined using standard methods known to those of skill in the art, such as described in Example 1.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by ISIS number (ISIS #) indicate a combination of nucleobase sequence, chemical modification, and motif.

In certain embodiments, the compounds or compositions as described herein are efficacious by virtue of having at least one of an in vitro $IC_{50}$ of less than 250 nM, less than 200 nM, less than 150 nM, less than 100 nM, less than 90 nM, less than 80 nM, less than 70 nM, less than 65 nM, less than 60 nM, less than 55 nM, less than 50 nM, less than 45 nM, less than 40 nM, less than 35 nM, less than 30 nM, less than 25 nM, or less than 20 nM when delivered to HuVEC cells. In certain embodiments inhibition is measured with primer probe set RTS3559, as described herein.

In certain embodiments, the compounds or compositions as described herein are highly tolerable as demonstrated by having at least one of an increase an ALT or AST value of no more than 4 fold, 3 fold, or 2 fold over saline treated animals or an increase in liver, spleen, or kidney weight of no more than 30%, 20%, 15%, 12%, 10%, 5%, or 2%. In certain embodiments, the compounds or compositions as described herein are highly tolerable as demonstrated by having no increase of ALT or AST over saline treated animals. In certain embodiments, the compounds or compositions as described herein are highly tolerable as demonstrated by having no increase in liver, spleen, or kidney weight over saline treated animals.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain. An example of such an AR splicing variant includes, but is not limited to, AR-V7, which contains exons 1-3 but lacks exons 4-8. Additional examples of such AR splicing variants include, for example, AR3, AR4, AR4b, AR5, and AR6 (SEQ ID NOs: 4-8, respectively). In certain embodiments, an antisense compound targeted to AR upstream of the 3' end of exon 3 and/or upstream of the ligand binding domain is capable of inhibiting androgen receptor levels to a greater extent than an antisense compound targeted to the ligand binding domain, such as EZN-4176, which is targeted to exon 4 and corresponds to SEQ ID NO: 58 described in U.S. Pat. No. 7,737,125.

In certain embodiments, an antisense compound targets an AR splicing variant that has a functional DNA binding domain, but not a functional ligand binding domain. It will be understood that in certain embodiments an antisense compound can target an AR splicing variant that includes the entire or at least a functional portion of exon 1 encoding the N-terminal domain and the entire or at least a functional portion of exons 2 and 3 encoding the DNA binding domain, but does not include at least a functional portion of exon 4 encoding the short hinge region or at least a functional portion of exons 4-8 encoding the ligand binding domain. It is contemplated that certain AR splicing variants targeted by the antisense compounds provided herein substantially consisting of exons 1-3 may also include a non-functional portion of nucleic acid sequence from a genomic region or exons 4-8. It is contemplated that the splicing process may give rise to such AR splicing variants that retain DNA binding function but not ligand binding function. In certain embodiments, an antisense compound targeted to an AR splicing variant that has a functional DNA binding domain, but not a functional ligand binding domain, is capable of inhibiting growth or proliferation of prostate cancer cells that are castrate-resistant. In certain embodiments, an antisense compound targeted to an AR splicing variant that has a functional DNA binding domain, but not a functional ligand binding domain, is capable of inhibiting growth or proliferation of a prostate cancer cell resistant to a diarylhydantoin AR inhibitor of Formula XI to a greater extent than an antisense compound targeted to the ligand binding domain, such as EZN-4176, which is targeted to exon 4 and corresponds to SEQ ID NO: 58 described in U.S. Pat. No. 7,737,125. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, an antisense compound provided herein is capable of reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain. In certain embodiments, such an antisense compound targets human androgen receptor upstream of the ligand binding domain. In certain embodiments, such antisense compounds target human androgen receptor upstream of the 3' end of exon 3. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain. An example of such an AR splicing variant includes, but is not limited to, AR-V7, which contains exons 1-3 but lacks exons 4-8.

Certain embodiments are drawn to an antisense compound targeted to human androgen receptor (AR) upstream of the ligand binding domain that is capable of inhibiting growth or proliferation of the resistant prostate cancer cell to a greater extent than an antisense compound targeted to the ligand binding domain, such as EZN-4176, which is targeted to exon 4 and corresponds to SEQ ID NO: 58 described in U.S. Pat. No. 7,737,125. In certain embodiments, an antisense compound targeted to human androgen receptor (AR) upstream of the ligand binding domain is targeted to a region of AR upstream of the 3' end of exon 3. In certain embodiments, an antisense compound provided herein targets AR within exon 1, which is upstream of the 3' end of exon 3 and/or upstream of the ligand binding domain. In certain embodiments, an antisense compound provided herein targets AR within exon 2, which is upstream of the 3' end of exon 3 and/or upstream of the ligand binding domain. In certain embodiments, an antisense compound provided herein targets AR within intron 1, which is upstream of the 3' end of exon 3 and/or upstream of the ligand binding domain.

In certain embodiments, the nucleobase sequence of a modified oligonucleotide provided herein is at least 70%, 75%, 80%, 85%, 90%, 95% or 100% complementary to any one of SEQ ID NOs: 1-8, as measured over the entirety of the modified oligonucleotide.

In certain embodiments, an antisense compound is a modified oligonucleotide consisting of 12 to 30 linked nucleosides and having a nucleobase sequence at least 90% complementary to any of SEQ ID NOs: 1-8 as measured over the entirety of said modified oligonucleotide.

In certain embodiments, an antisense compound is a modified oligonucleotide consisting of 12 to 30 linked nucleosides and having a nucleobase sequence 100% complementary to any of SEQ ID NOs: 1-8 as measured over the entirety of said modified oligonucleotide. In certain embodiments, a compound or modified oligonucleotide provided herein is single-stranded.

In certain embodiments, a modified oligonucleotide provided herein consists of 8, 9, 10, 11, 12, 13, 14, 15, 16, 17, 18, 19, 20, 21, 22, 23, 24, 25, 26, 27, 28, 29 or 30 linked nucleosides. In certain embodiments, the modified oligonucleotide consists of 20 linked nucleosides. In certain embodiments, the modified oligonucleotide consists of 16 linked nucleosides.

In certain embodiments, at least one internucleoside linkage of a modified oligonucleotide provided herein is a modified internucleoside linkage. In certain embodiments, each internucleoside linkage is a phosphorothioate internucleoside linkage.

In certain embodiments, at least one nucleoside of the modified oligonucleotide comprises a modified sugar. In certain embodiments, at least one modified sugar comprises a 2'-O-methoxyethyl group ($2'-O(CH_2)_2—OCH_3$). In certain embodiments, the modified sugar comprises a $2'-O—CH_3$ group.

In certain embodiments, at least one modified sugar is a bicyclic sugar. In certain embodiments, the bicyclic sugar comprises a $4'-(CH_2)_n—O-2'$ bridge, wherein n is 1 or 2. In certain embodiments, the bicyclic sugar comprises a $4'-CH_2—O-2'$ bridge. In certain embodiments, the bicyclic sugar comprises a $4'-CH(CH_3)—O-2'$ bridge.

In certain embodiments, at least one nucleoside of a modified oligonucleotide provided herein comprises a modified nucleobase. In certain embodiments, the modified nucleobase is a 5-methylcytosine.

In certain embodiments, a modified oligonucleotide provided herein consists of a single-stranded modified oligonucleotide.

In certain embodiments, compounds or compositions provided herein comprise a salt of the modified oligonucleotide.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an androgen receptor nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to an androgen receptor nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, the compounds or compositions further comprise a pharmaceutically acceptable carrier or diluent.

Certain Indications

Certain aspects of the invention are directed to methods of treating cancer which comprises administering an antisense compound targeted to androgen receptor as provided herein. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects are directed to an antisense compound targeted to androgen receptor provided herein for use in treating cancer. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects are directed to use of an antisense compound targeted to androgen receptor provided herein for the manufacture of a medicament for treating cancer. In certain embodiments, the cancer is AR positive. In certain embodiments, the cancer is prostate cancer, breast cancer, ovarian cancer, bladder cancer or gastric cancer. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Certain aspects of the invention are directed to the use of an antisense compound targeted to human androgen receptor (AR) as described herein, for treating a cancer patient whose cancer has become resistant to treatment with an anti-androgenic agent (e.g. compound or drug). In certain embodiments, said cancer is prostate cancer. In certain embodiments, said patient is one that has, or whose cancer has, developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536. In certain embodiments, an antisense compound provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170, 102156-102171, 139682-139697, 139762-139777, or 139782-139797. In certain embodiments, an antisense compound provided herein targets AR within exon 3, for example within nucleotide regions 144841-144957 (exon 3), 148380-148594 (exon 3b), or 153504-154908 (exon 3d) of SEQ ID NO: 1. In certain embodiments, an antisense compound provided herein targeted to exon 3 of AR is complementary within any of the following nucleotide regions of SEQ ID NO: 1: 144856-144871, 144938-144953, 148406-148421, 148443-148458, or 148520-148535. In certain embodiments, an antisense compound provided herein targets AR within intron 1, for example within nucleotide regions 5594-27671 or 27854-102086 of SEQ ID NO: 1. In certain embodiments, an antisense compound provided herein targeted to intron 1 of AR is complementary within any of the following nucleotide regions of SEQ ID NO: 1: 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58720-58735, 58721-58736, 58722-58737, 58723-58738, 58724-58739, 58724-58739, 58725-58740, 58725-58740, 58725-58740, 58750-58769, 58750-58765, 58751-58766, 58752-58767, 58753-58768, 58754-58769, 58755-58770, 60902-60917, or 67454-67469. In certain embodiments, an antisense compound provided herein targets AR within intron 2, for example within nucleotide regions 102239-139550 or 139835-144840 of SEQ ID NO: 1. In certain embodiments, an antisense compound provided herein targeted to intron 2 of AR is complementary within any of the following nucleotide regions of SEQ ID NO: 1: 114874-114889, 115272-115287, 115365-115380, or 134971-134986. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

By resistant to treatment with a particular agent (e.g. compound or drug) is meant that the agent is less or no longer effective in halting the growth or spread of the cancer and so the patient, or their cancer, has become less responsive or sensitive to it over time. Typically such patient would be classed as resistant to said agent and would no longer be treated with such agent. A subject having prostate cancer resistant to an agent selected from: MDV3100, ARN-059, ODM-201, abiraterone acetate, TOK001, TAK700 and VT464 can include, for example, a patient who previously received said agent but whose prostate cancer has become less sensitive or responsive to a agent. For example, prostate cancer resistant to an anti-androgenic agent selected from: MDV3100, ARN-059, ODM-201, abiraterone acetate, TOK001, TAK700 and VT464, can include prostate cancer that has increased in tumor volume, metastasis, or progression despite treatment with the agent. In certain embodiments, prostate cancer resistant to an anti-androgenic agent selected from: MDV3100, ARN-059, ODM-201, abiraterone acetate, TOK001, TAK700 and VT464, can include prostate cancer that is refractory to the agent and is not decreasing in tumor volume, metastasis, or progression despite treatment. Several embodiments relate to a method of treating prostate cancer resistant to an anti-androgenic agent selected from: MDV3100, ARN-059, ODM-201, abiraterone acetate, TOK001, TAK700 and VT464, in a subject comprising identifying the subject as having prostate cancer resistant to the agent and administering to the subject an antisense compound targeted to human androgen receptor (AR) upstream of the 3' end of exon 3 and/or upstream of the ligand binding domain, as described herein. Several embodiments relate to a method of treating prostate cancer resistant to an anti-androgenic agent selected from: MDV3100, ARN-059, ODM-201, abiraterone acetate, TOK001, TAK700 and VT464, in a subject comprising administering to a subject identified or diagnosed as having prostate cancer resistant to said anti-androgenic agent an antisense compound targeted to human androgen receptor (AR) upstream of the 3' end of exon 3 and/or upstream of the ligand binding domain, as described herein. In certain embodiments, prostate cancer cells resistant to an anti-androgenic agent selected from: MDV3100, ARN-059, ODM-201, abiraterone acetate, TOK001, TAK700 and VT464, preferentially expresses an AR splicing variant over full-length AR.

Certain aspects of the invention are directed to a method of treating a patient suffering from prostate cancer wherein the patient has, or their cancer has, developed or become resistant to treatment with an anti-androgenic agent (compound or drug) comprising administering to said patient an antisense compound targeted to human androgen receptor (AR) as described herein. In certain embodiments, said patient is one that has developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

A prostate cancer that has developed or become resistant to treatment with an anti-androgenic agent is referred to as castrate-resistant prostate cancer (CRPC). Thus, in several embodiments, a prostate cancer cell resistant to an anti-androgenic agent, such as MDV3100, was previously exposed to the inhibitor and has become less responsive or sensitive to it over time. For example, MDV3100 might initially inhibit prostate cancer cell growth or proliferation in the patient, but over time such inhibitory effect may be diminished when the cells become resistant to the inhibitor.

Certain aspects of the invention are directed to the use of an antisense compound targeted to androgen receptor provided herein for the manufacture of a medicament for treating cancer in a patient whose cancer has become resistant to treatment with an anti-androgenic agent (compound or drug). In certain embodiments the cancer is prostate cancer. In certain embodiments, said patient is one that has, or whose cancer has, developed resistance to treatment with an agent selected from: MDV3100, ARN-059, ODM-201, abiraterone acetate, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound is single-stranded. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Enzalutamide:

MDV3100, also known as enzalutamide (Xtandi™) and by the IUPAC name 4-(3-(4-cyano-3-(trifluoromethyl)phenyl)-5,5-dimethyl-4-oxo-2-thioxoimidazolidin-1-yl)-2-fluoro-N-methylbenzamide, is an androgen receptor ligand binding inhibitor belonging to the diarylhydantoin class of androgen receptor inhibitors represented by Formula XI. MDV3100 has the following chemical formula:

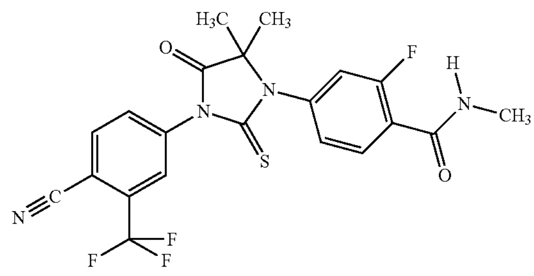 [SMILES: CNC(=O)c1ccc(N2C(=S)N(c3ccc(C#N)c(C(F)(F)F)c3)C(=O)C2(C)C)cc1F]

MDV3100 and additional diarylhydantoin androgen receptor inhibitors suitable for use in certain embodiments provided herein are described in U.S. Pat. No. 7,709,517, US Patent Application Publication No. US20100172975 and US Patent Application Publication No. US20100210665, which are incorporated herein by reference in their entireties.

ARN-509:

(XII)

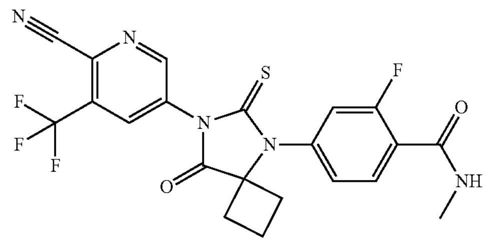

The compound of Formula XII, also known as ARN-509 and by the IUPAC name 4-(7-(6-Cyano-5-(trifluoromethyl)pyridin-3-yl)-6,8-dioxo-5,7-diazaspiro[3.4]octan-5-yl)-2-fluoro-N-methylbenzamide, is an androgen receptor ligand binding inhibitor. ARN-509 and additional androgen receptor inhibitors suitable for use in certain embodiments provided herein are described in WO 2007126765, WO 2008119015 and US Patent Application Publication No. 2013/0116258, which are incorporated herein by reference in their entirety.

Abiraterone Acetate

The compound of Formula XIII, which is also known as Abiraterone acetate and ZYTIGA® and by the IUPAC name [(3S,8R,9S,10R,13S,14 S)-10,13-dimethyl-17-(3-pyridyl)-2,3,4,7,8,9,11,12,14,15-decahydro-1H-cyclopenta[a] phenanthren-3-yl]acetate, is an androgen biosynthesis inhibitor and has the following chemical formula:

(XIII)

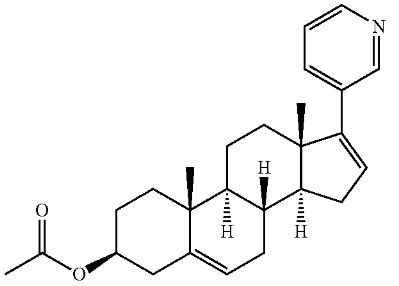

The structure and synthesis of Abiraterone acetate is described in Potter et al., Journal of Medicinal Chemistry (38(13), 2463-71, 1995), which is incorporated herein by reference in its entirety.

Galeterone:

The compound of Formula XIV, which is also known as TOK-001 and Galeterone, and by the IUPAC name (3S,10R,13S)-17-(1H-benzo[d]imidazol-1-yl)-10,13-dimethyl-2,3,4,7,8,9,10,11,12,13,14,15-dodecahydro-1H-cyclopenta[a] phenanthren-3-ol, has the following chemical formula:

(XIV)

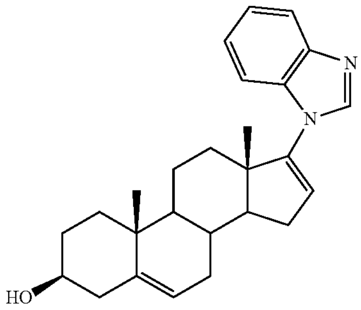

The structure and synthesis of TOK-001 is described in Handratta et al., (Journal of Medicinal Chemistry (2005), 48(8), 2972-84, 2005), which is incorporated herein by reference in its entirety:

Orteronel:

The compound of Formula XV, which is also known as TAK-700 and Orteronel and by the IUPAC name 6-[7(S)-hydroxy-6,7-dihydro-5H-pyrrolo[1,2-c]imidazol-7-yl]-N-methylnaphthalene-2-carboxamide, is an androgen biosynthesis inhibitor and has the following chemical formula:

(XV)

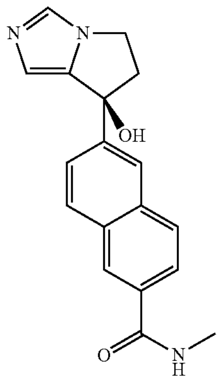

The structure and synthesis of TAK-700 is described in Kaku et al., Bioorganic and Medicinal Chemistry (19(21), 6383-99, 2011).

Yin et al., (*Int. J. Mol. Sci.,* 14(7):13958-13978, 2013) discusses recent progress with various pharmaceutical therapies, including ODM-21, VT464, ARN509, TAK700 and TOK-001, for castration-resistant prostate cancer.

Certain Combinations and Combination Therapies

In certain embodiments, a first agent comprising the compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compounds or compositions provided herein are co-administered with one or more anti-androgenic agents. In certain embodiments, one or more compounds or compositions provided herein and one or more anti-androgenic agents, are administered at different times. In certain embodiments, one or more compounds or compositions provided herein and one or more anti-androgenic agents, are prepared together in a single formulation. In certain embodiments, one or more compounds or compositions provided herein and one or more anti-androgenic agents, are prepared separately. In certain embodiments, an anti-androgenic agent is selected from MDV3100, ARN-059, ODM-201, abiraterone, TOK001, TAK700 and VT464.

Certain aspects of the invention are directed to the use of an antisense compound targeted to human androgen receptor (AR) as described herein in combination with an anti-androgenic agent. In particular embodiments such use is in a method of treating a patient suffering from cancer or in the manufacture of a medicament for treating cancer. In certain embodiments the cancer is selected from: prostate cancer, breast cancer, ovarian cancer, bladder cancer or gastric cancer. Particular classes of anti-androgenic agents are the second generation anti-hormonal agents such as: enzalutamide (MDV3100), ARN-059, ODM-201, abiraterone acetate, Galeterone (TOK001), orteronel (TAK700) and VT464 (see Yin et al. supra).

Certain aspects are drawn to a combination of an antisense compound targeted to human androgen receptor (AR) as described herein and an anti-androgenic agent, such as a second generation anti-hormonal agent selected from: MDV3100, ARN-059, ODM-201, abiraterone, TOK001, TAK700 and VT464.

In certain embodiments, such a combination of an antisense compound targeted to androgen receptor (AR) as described herein and an anti-androgenic agent, such as a second generation anti-hormonal agent selected from: MDV3100, ARN-059, ODM-201, abiraterone, TOK001, TAK700 and VT464, is useful for inhibiting cancer cell growth or proliferation and/or treating cancer. In certain embodiments the cancer is selected from: prostate cancer, breast cancer, ovarian cancer, bladder cancer or gastric cancer. In certain embodiments the cancer is prostate cancer. In certain embodiments the cancer is breast cancer. In certain embodiments, an antisense compound targeted to AR as described herein and an anti-androgenic agent, such as a second generation anti-hormonal agent selected from: MDV3100, ARN-059, ODM-201, abiraterone, TOK001, TAK700 and VT464, synergize in combination to inhibit growth or proliferation of a cancer cell. In several embodiments, the cancer cell is a prostate cancer cell which is or has become castration-resistant. In various embodiments, the cancer cell is a prostate cancer cell which is or has become resistant to a second generation anti-hormonal agent selected from: MDV3100, ARN-059, ODM-201, abiraterone, TOK001, TAK700 and VT464. In certain embodiments, the antisense compound targeted to androgen receptor comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, the antisense compound targeted to androgen receptor comprises a modified oligonucleotide consisting of 10 to 30 linked nucleosides and having a nucleobase sequence comprising any of SEQ ID NOs: 12-179. In certain embodiments, the antisense compound targeted to androgen receptor comprises a modified oligonucleotide consisting of the nucleobase sequence of any of SEQ ID NOs: 12-179. In certain embodiments, the antisense compound targeted to androgen receptor comprises a modified oligonucleotide consisting of 16 linked nucleosides and having a nucleobase sequence consisting of SEQ ID NO: 35, 39, 43, 124, 150, 155, 169, or 175. In certain embodiments, the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Several embodiments are drawn to a combination of an antisense compound targeted to human androgen receptor (AR) and a diarylhydantoin AR inhibitor of Formula XI, such as MDV3100. In several embodiments, a diarylhydantoin Androgen Receptor (AR) inhibitor is a compound of Formula XVI:

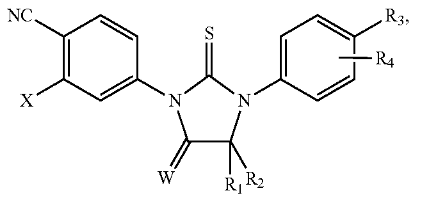

(XVI)

wherein X is selected from the group consisting of trifluoromethyl and iodo, wherein W is selected from the group consisting of O and NR5, wherein R5 is selected from the group consisting of H, methyl, and

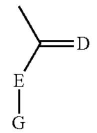

wherein D is S or O and E is N or O and G is alkyl, aryl, substituted alkyl or substituted aryl; or D is S or O and E-G together are C1-C4 lower alkyl, wherein R1 and R2 together comprise eight or fewer carbon atoms and are selected from the group consisting of alkyl, substituted alkyl including haloalkyl, and, together with the carbon to which they are linked, a cycloalkyl or substituted cycloalkyl group, wherein R3 is selected from the group consisting of hydrogen, halogen, methyl, C1-C4 alkoxy, formyl, haloacetoxy, trifluoromethyl, cyano, nitro, hydroxyl, phenyl, amino, methylcarbamoyl, methoxycarbonyl, acetamido, methanesulfonamino, methanesulfonyl, 4-methanesulfonyl-1-piperazinyl, piperazinyl, and C1-C6 alkyl or alkenyl optionally substituted with hydroxyl, methoxycarbonyl, cyano, amino, amido, nitro, carbamoyl, or substituted carbamoyl including methylcarbamoyl, dimethylcarbamoyl, and hydroxyethylcarbamoyl, wherein R4 is selected from the group consisting of hydrogen, halogen, alkyl, and haloalkyl, and wherein R3 is not methylaminomethyl or dimethylaminomethyl.

R5 may be

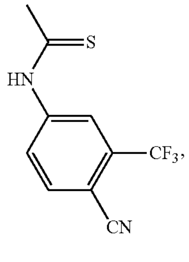

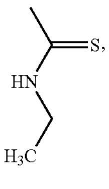

,

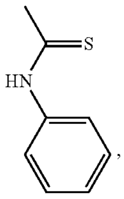

, or

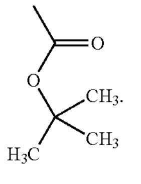

.

In certain embodiments, such a combination of an antisense compound targeted to androgen receptor (AR) and a diarylhydantoin AR inhibitor of Formula XVI, such as MDV3100, is useful for inhibiting prostate cancer cell growth or proliferation and/or treating prostate cancer. In certain embodiments, an antisense compound targeted to AR and a diarylhydantoin AR inhibitor of Formula XVI, such as MDV3100, synergize in combination to inhibit growth or proliferation of a prostate cancer cell. In several embodiments, the prostate cancer cell is castration-resistant. In various embodiments, the prostate cancer cell is resistant to a diarylhydantoin AR inhibitor of Formula XVI, such as MDV3100. In certain embodiments, the prostate cancer cell or castration-resistant prostate cancer cell preferentially expresses an AR splicing variant over full-length AR. In certain embodiments the antisense compound targeted to AR as described herein and the other anti-androgenic agent are used in combination treatment by administering the two agents simultaneously, separately or sequentially. In certain embodiments the two agents are formulated as a fixed dose combination product. In other embodiments the two agents are provided to the patient as separate units which can then either be taken simultaneously or serially (sequentially).

In certain embodiments, antisense compounds useful for inhibiting prostate cancer cell and/or castration-resistant prostate cancer cell growth or proliferation in combination with another anti-androgenic agent, such as a second generation anti-hormonal agent selected from: MDV3100, ARN-059, ODM-201, abiraterone, TOK001, TAK700 and VT464, target human androgen receptor upstream of the 3' end of exon 3 and/or upstream of the ligand binding domain. In certain embodiments, an antisense compound provided herein targets AR within exon 1, exon 2, exon 3, intron 1, or intron 2 as described herein.

In certain embodiments, an antisense compound provided herein targets an AR splicing variant that includes exon 1 encoding the N-terminal domain and exons 2 and 3 encoding the DNA binding domain, but does not include at least a portion of exon 4 encoding the short hinge region or at least a portion of exons 4-8 encoding the ligand binding domain. An example of such an AR splicing variant includes, but is not limited to, AR-V7, which contains exons 1-3 but lacks exons 4-8. Additional examples of such AR splicing variants include, for example, AR3, AR4, AR4b, AR5, and AR6 (SEQ ID NOs: 4-8, respectively). In certain embodiments, the prostate cancer cell, which may be castration-resistant, preferentially expresses an AR splicing variant over full-length AR. In particular embodiments the prostate cancer cell is castration-resistant to an anti-androgenic agent selected from: MDV3100, ARN-059, ODM-201, abiraterone, TOK001, TAK700 and VT464 In certain embodiments, an antisense compound targeted to AR upstream of the 3' end of exon 3 and/or upstream of the ligand binding domain is capable of inhibiting growth or proliferation of a prostate cancer cell, including a castration-resistant prostate cancer cell, in combination with an anti-androgenic agent selected from: MDV3100, ARN-059, ODM-201, abiraterone, TOK001, TAK700 and VT464, to a greater extent than an antisense compound targeted to the ligand binding domain, such as EZN-4176, which is targeted to exon 4 and corresponds to SEQ ID NO: 58 described in U.S. Pat. No. 7,737,125, in combination with the same anti-androgenic agent selected from: MDV3100, ARN-059, ODM-201, abiraterone, TOK001, TAK700 and VT464. In certain embodiments, the combination of an antisense compound as described herein and the anti-androgenic agent selected from: MDV3100, ARN-059, ODM-201, abiraterone, TOK001, TAK700 and VT464, provides a synergistic (e.g. greater-than-additive) effect in inhibiting the growth or proliferation of a prostate cancer cell, such as a castration-resistant prostate cancer cell, compared to the antisense compound alone or the anti-androgenic agent selected from: MDV3100, ARN-059, ODM-201, abiraterone, TOK001, TAK700 and VT464 alone. Accordingly, in certain embodiments the amounts of either or both of the antisense compound and/or anti-androgenic agent selected from: MDV3100, ARN-059, ODM-201, abiraterone, TOK001, TAK700 and VT464, when used in combination can be less than the corresponding amount of either the antisense compound alone or the anti-androgenic agent selected from: MDV3100, ARN-059, ODM-201, abiraterone, TOK001, TAK700 and VT464, alone necessary to achieve an equivalent level of prostate cancer cell growth or proliferation inhibition.

In certain embodiments, an antisense compound provided herein useful for inhibiting prostate cancer cell and/or castration-resistant prostate cancer cell growth or proliferation in combination with an anti-androgenic agent selected from: MDV3100, ARN-059, ODM-201, abiraterone, TOK001, TAK700 and VT464, targets an AR splicing variant that has a functional DNA binding domain, but not a functional ligand binding domain. It will be understood that in certain embodiments an antisense compound can target an AR splicing variant that includes the entire or at least a functional portion of exon 1 encoding the N-terminal domain and the entire or at least a functional portion of exons 2 and 3 encoding the DNA binding domain, but does not include at least a functional portion of exon 4 encoding the short hinge region or at least a functional portion of exons 4-8 encoding the ligand binding domain. It is contemplated that certain AR splicing variants targeted by the antisense compounds provided herein substantially consisting of exons 1-3 may also include a non-functional portion of nucleic acid sequence from a genomic region or exons 4-8. It is contemplated that the splicing process may give rise to such AR splicing variants that retain DNA binding function but not ligand binding function. In certain embodiments, the prostate cancer cell, which may be castrate-resistant, preferentially expresses an AR splicing variant over full-length AR. In certain embodiments the prostate cancer cell is castrate-resistant to an anti-androgenic agent selected from: MDV3100, ARN-059, ODM-201, abiraterone, TOK001, TAK700 and VT464. In certain embodiments, an antisense compound provided herein targets AR within exon 1, which is upstream of the 3' end of exon 3 and/or upstream of the ligand binding domain. In certain embodiments, an antisense compound provided herein targets AR within exon 1, exon 2, exon 3, intron 1, or intron 2 as described herein.

In certain embodiments, an antisense compound targeted to an AR splicing variant that has a functional DNA binding domain, but not a functional ligand binding domain, is capable of inhibiting growth or proliferation of a prostate cancer cell, including a castration-resistant prostate cancer cell, in combination with a an anti-androgenic agent selected from: MDV3100, ARN-059, ODM-201, abiraterone, TOK001, TAK700 and VT464, to a greater extent than an antisense compound targeted to the ligand binding domain, such as EZN-4176, which is targeted to exon 4 and corresponds to SEQ ID NO: 58 described in U.S. Pat. No. 7,737,125, in combination with a the same anti-androgenic agent selected from: MDV3100, ARN-059, ODM-201, abiraterone, TOK001, TAK700 and VT464. In certain embodiments, the combination of an antisense compound and anti-androgenic agent selected from: MDV3100, ARN-059, ODM-201, abiraterone, TOK001, TAK700 and VT464, provides a synergistic (e.g. greater-than-additive) effect in inhibiting the growth or proliferation of a prostate cancer cell, such as a castration-resistant prostate cancer cell, compared to the antisense compound alone or the anti-androgenic agent alone. Accordingly, in certain embodiments the amounts of either or both of the antisense compound and/or anti-androgenic agent selected from: MDV3100, ARN-059, ODM-201, abiraterone, TOK001, TAK700 and VT464, when used in combination can be less than the corresponding amount of either the antisense compound alone or anti-androgenic agent, alone necessary to achieve an equivalent level of prostate cancer cell growth or proliferation inhibition.

In certain embodiments, an antisense compound provided herein useful for inhibiting prostate cancer cell and/or castration-resistant prostate cancer cell growth or proliferation in combination with a anti-androgenic agent selected from: MDV3100, ARN-059, ODM-201, abiraterone, TOK001, TAK700 and VT464 is capable of reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain. In certain embodiments, such an antisense compound targets human androgen receptor upstream of the ligand binding domain. In certain embodiments, such antisense compounds target human androgen receptor upstream of the 3' end of exon 3. In certain embodiments, an antisense compound provided herein targets AR within exon 1, which is upstream of the 3' end of exon 3 and/or upstream of the ligand binding domain.

In certain embodiments, there is provided a combination of an antisense compound targeted to human androgen receptor (AR) as described herein and an anti-androgenic agent selected from: MDV3100, ARN-059, ODM-201, abiraterone, TOK001, TAK700 and VT464, wherein the antisense compound comprises a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 12-179. In certain embodiments, there is provided a combination of an antisense compound targeted to human androgen receptor (AR) and an anti-androgenic agent selected from: MDV3100, ARN-059, ODM-201, abiraterone, TOK001, TAK700 and VT464, wherein the antisense compound comprises a modified oligonucleotide consisting of 10 to 30 linked nucleosides and having a nucleobase sequence comprising any of SEQ ID NOs: 12-179. In certain embodiments, there is provided a combination of an antisense compound targeted to human androgen receptor (AR) and an anti-androgenic agent selected from: MDV3100, ARN-059, ODM-201, abiraterone, TOK001, TAK700 and VT464, wherein the antisense compound comprises a modified oligonucleotide consisting of the nucleobase sequence of any of SEQ ID NOs: 12-179. In certain embodiments, there is provided a combination of an antisense compound targeted to human androgen receptor (AR) and a diarylhydantoin AR inhibitor of Formula XI, such as MDV3100, wherein the antisense compound comprises a modified oligonucleotide consisting of 16 linked nucleosides and having a nucleobase sequence consisting of SEQ ID NO: 35, 39, 43, 124, 150, 155, 169, or 175. In certain embodiments, there is provided a combination of an antisense compound targeted to human androgen receptor (AR) and a diarylhydantoin AR inhibitor of Formula XI, such as MDV3100, wherein the antisense compound targeted to androgen receptor is ISIS 560131, ISIS 569213, ISIS 569216, ISIS 569221, ISIS 569236, ISIS 579671, ISIS 586124, ISIS 583918, ISIS 584149, ISIS 584163, ISIS 584269, or ISIS 584468.

Several embodiments are drawn to a method of inhibiting prostate cancer cell growth or proliferation comprising contacting the prostate cancer cell with an antisense compound targeted to human androgen receptor (AR) and an anti-androgenic agent selected from: MDV3100, ARN-059, ODM-201, abiraterone, TOK001, TAK700 and VT464. In certain embodiments, the antisense compound and an anti-androgenic agent selected from: MDV3100, ARN-059, ODM-201, abiraterone, TOK001, TAK700 and VT464, synergize in combination to inhibit the growth or proliferation of the prostate cancer cell. In several embodiments, the prostate cancer cell is castration-resistant. In various embodiments, the prostate cancer cell is castration-resistant by being resistant to an anti-androgenic agent selected from: MDV3100, ARN-059, ODM-201, abiraterone, TOK001, TAK700 and VT464. In certain embodiments, the prostate cancer cell or castration-resistant prostate cancer cell preferentially expresses an AR splicing variant over full-length AR.

In certain aspects of any of the foregoing embodiments, antisense compounds useful for inhibiting prostate cancer cell growth or proliferation in combination with a diarylhydantoin AR inhibitor of Formula XVI, such as MDV3100, can target (i) human androgen receptor upstream of the 3' end of exon 3 and/or upstream of the ligand binding domain or (ii) an AR splicing variant that has a functional DNA binding domain, but not a functional ligand binding domain; and/or is capable of (i) reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain; with the proviso that the antisense compounds do not have a nucleobase sequence consisting of any of SEQ ID NOs: 194-215 identified in Table A below.

TABLE A

| SEQ ID NO: | Sequence |
|---|---|
| 194 | GAGAACCATCCTCACC |
| 195 | GGACCAGGTAGCCTGT |
| 196 | CCCCTGGACTCAGATG |
| 197 | GCACAAGGAGTGGGAC |
| 198 | GCTGTGAAGAGAGTGT |
| 199 | TTTGACACAAGTGGGA |
| 200 | GTGACACCCAGAAGCT |
| 201 | CATCCCTGCTTCATAA |
| 202 | TGGGGAGAACCATCCTCACCCTGC |
| 203 | TCCAGGACCAGGTAGCCTGTGGGG |
| 204 | TGTTCCCCTGGACTCAGATGCTCC |
| 205 | TGGGGCACAAGGAGTGGGACGCAC |
| 206 | TTCGGCTGTGAAGAGAGTGTGCCA |
| 207 | CGCTTTTGACACAAGTGGGACTGG |
| 208 | CATAGTGACACCCAGAAGCTTCAT |

TABLE A-continued

| SEQ ID NO: | Sequence |
|---|---|
| 209 | GAGTCATCCCTGCTTCATAACATT |
| 210 | CTGTGAAGAGAGTG |
| 211 | TGTGAAGAGAGT |
| 212 | TTGACACAAGTGGG |
| 213 | TGACACAAGTGG |
| 214 | TGACACCCAGAAGC |
| 215 | GACACCCAGAAG |

In certain aspects of any of the foregoing embodiments, antisense compounds useful for inhibiting growth or proliferation of a prostate cancer cell resistant to anti-androgenic agent selected from: MDV3100, ARN-059, ODM-201, abiraterone, TOK001, TAK700 and VT464, can target (i) human androgen receptor upstream of the 3' end of exon 3 and/or upstream of the ligand binding domain or (ii) an AR splicing variant that has a functional DNA binding domain, but not a functional ligand binding domain; and/or is capable of (i) reducing expression of both full-length AR and an AR splicing variant that includes exon 1 encoding the N-terminal domain and exons 2 and 3 encoding the DNA binding domain, but does not include at least a portion of exon 4 encoding the short hinge region or at least a portion of any one of exons 4-8 encoding the ligand binding domain; or (ii) inhibiting growth or proliferation of the resistant prostate cancer cell to a greater extent than an antisense compound targeted to the ligand binding domain, such as EZN-4176; with the proviso that the antisense compounds do not have a nucleobase sequence consisting of any of SEQ ID NOs: 194-215 described in U.S. Pat. No. 7,737,125 as SEQ ID NOs: 2-9, 49-50, 52-53, 55-56, and 86-93 (herein incorporated by reference), and identified in Table A.

Certain aspects are directed to methods of treating breast cancer and methods of inhibiting breast cancer cell growth or proliferation with an antisense oligonucleotide targeted to human androgen receptor (AR) as described herein. In certain embodiments, the breast cancer has one or more of the following characteristics: Androgen Receptor positive, dependent on androgen for growth, Estrogen Receptor (ER) negative, independent of estrogen for growth, Progesterone Receptor (PR) negative, independent of progesterone for growth, or Her2/neu negative. In certain embodiments, the breast cancer or breast cancer cell is apocrine.

Certain embodiments are drawn to a method of treating breast cancer in a subject comprising administering to the subject an antisense compound targeted to human androgen receptor (AR). Certain embodiments are drawn to a method of treating breast cancer in a subject comprising identifying a subject having breast cancer and administering to the subject an antisense compound targeted to human androgen receptor (AR), thereby treating the subject's breast cancer. Certain embodiments are directed to a method of inhibiting growth or proliferation of a breast cancer cell comprising contacting the breast cancer cell with an antisense compound targeted to human androgen receptor (AR). Certain embodiments relate to a method of inhibiting AR expression in a subject having or at risk of having breast cancer comprising identifying a subject breast cancer, and administering to the subject an antisense compound targeted to human AR, wherein the antisense compound inhibits AR expression in the subject.

In certain embodiments, the breast cancer or breast cancer cell has one or more of the following characteristics: Androgen Receptor positive, dependent on androgen for growth, Estrogen Receptor (ER) negative, independent of estrogen for growth, Progesterone Receptor (PR) negative, independent of progesterone for growth, or Her2/neu negative. In certain embodiments, the breast cancer or breast cancer cell is ER, PR, and HER2 triple negative and AR positive (ER−, PR−, HER2−, AR+). In certain embodiments, the breast cancer or breast cancer cell is ER negative and AR positive (ER−, AR+). In certain embodiments, the breast cancer or breast cancer cell is ER positive and AR positive (ER+, AR+).

In certain embodiments, the breast cancer or breast cancer cell is apocrine. Apocrine breast cancers are often "triple negative", meaning that the cells do not express ER, PR, or HER2 receptors, and usually, but not necessarily, AR positive. In certain embodiments, an apocrine breast cancer or breast cancer cell is ER, PR, and HER2 triple negative and AR positive (ER−, PR−, HER2−, AR+). In certain embodiments, an apocrine breast cancer or breast cancer cell is ER negative and AR positive (ER−, AR+). In certain embodiments, an apocrine breast cancer or breast cancer cell originates from the sweat gland of the breast. In certain embodiments, an apocrine breast cancer or breast cancer cell is a ductal cancer or cancer cell of the breast. In certain embodiments, an apocrine breast cancer can have any one or more of the following features: a large amount of eosinophilic granular cytoplasm, well-defined margins, large vesicular nuclei, a nuclear to cytoplasmic ratio of about 1:2, and/or accumulations of secreted granules in the apical cytoplasm known as apical snouts.

In certain embodiments, the breast cancer or breast cancer cell is an ER negative and AR positive (ER−, AR+) molecular apocrine breast cancer or breast cancer cell. In certain aspects, an ER negative and AR positive (ER−, AR+) molecular apocrine breast cancer or breast cancer cell can further be PR positive, PR negative, HER2 negative, or HER2 positive.

Breast cancer can be identified as positive or negative with respect to hormone receptors, such as ER, PR, or HER2 by standard histological techniques. For example, histological breast cancer samples can be classified as "triple negative" (ER−, PR−, HER2−) when less than 1% of cells demonstrate nuclear staining for estrogen and progesterone receptors, and immunohistochemical staining for HER2 shows a 0, 1-fold, or a 2-fold positive score and a FISH ratio (HER2 gene signals to chromosome 17 signals) of less than 1.8 according to the relevant ASCO and CAP guidelines. (Meyer, P. et al., PLoS ONE 7(5): e38361 (2012)).

In certain embodiments, an antisense compound useful for treating breast cancer or inhibiting growth or proliferation of a breast cancer cell target provided herein targets AR within exon 1, which is upstream of the 3' end of exon 3 and/or upstream of the ligand binding domain. In certain embodiments, an antisense compound provided herein targets AR within exon 1, for example within nucleotide regions 2863-5593 (exon 1) or 27672-27853 (exon 1B) of SEQ ID NO: 1. In certain embodiments, an antisense compound provided herein targeted to exon 1 of AR is complementary within any of the following nucleotide regions of SEQ ID NO: 1: 3353-3368, 3361-3376, 3519-3534, 3735-3750, 3768-3783, 3798-3813, 3799-3814, 3851-3866, 3870-3885, 3874-3889, 3888-3903, 4047-4062, 4062-4077, 4109-4124, 4534-4549, 4537-4552, 4555-4570, 4571-4586, 4573-4588, 4578-4593, 4655-4670, 4750-4765, 4752-4767, 4833-4848, 4837-4852, 4839-4854, 4865-4880, 4872-4887, 4874-4889, 4876-4891, 4916-4931, 4918-4933, 5052-5067, 5054-5069, 5060-5075, 5061-

5076, 5061-5076, 5062-5077, 5155-5170, 5265-5280, 5293-5308, 5392-5407, 5448-5463, 5483-5498, 5486-5501, or 5494-5509.

In certain embodiments, an antisense compound provided herein targets AR within exon 2, which is upstream of the 3' end of exon 3 and/or upstream of the ligand binding domain. In certain embodiments, an antisense compound useful for treating breast cancer or inhibiting growth or proliferation of a breast cancer cell target provided herein targets AR within exon 2, for example within nucleotide regions 102087-102238 (exon 2) or 139551-139834 (exon 2c) of SEQ ID NO: 1. In certain embodiments, an antisense compound provided herein targeted to exon 2 of AR is complementary within any of the following nucleotide regions of SEQ ID NO: 1: 102155-102170 or 102156-107171.

In certain aspects, an antisense compound useful for treating breast cancer or inhibiting growth or proliferation of a breast cancer cell provided herein targets AR within intron 1, which is upstream of the 3' end of exon 3 and/or upstream of the ligand binding domain. In certain embodiments, an antisense compound provided herein targets AR within intron 1, for example within nucleotide regions 5594-27671 or 27854-102086 of SEQ ID NO: 1. In certain aspects, an antisense compound provided herein targeted to intron 1 of AR is complementary within any of the following nucleotide regions of SEQ ID NO: 1: 5666-5681, 6701-6716, 7543-7558, 8471-8486, 8638-8653, 9464-9479, 10865-10880, 11197-11212, 11855-11870, 13189-13204, 13321-13336, 13346-13361, 16793-16808, 16968-16983, 17206-17221, 18865-18880, 32290-32305, 33315-33330, 39055-39070, 40615-40630, 42017-42032, 56050-56065, 58719-58734, 58720-58735, 58721-58736, 58722-58737, 58723-58738, 58725-58740, 58750-58765, 58751-58766, 58752-58767, 58753-58768, 58754-58769, or 58755-58770.

In certain aspects of any of the foregoing embodiments, antisense compounds useful for treating breast cancer or inhibiting growth or proliferation of a breast cancer cell target human androgen receptor upstream of the 3' end of exon 3 and/or upstream of the ligand binding domain. In certain embodiments, antisense compounds provided herein, including but not limited to those that target human androgen receptor upstream of the 3' end of exon 3 and/or upstream of the ligand binding domain, can treat breast cancer or inhibiting growth or proliferation of a breast cancer cell to a greater extent than an antisense compound targeted to the ligand binding domain, such as EZN-4176; with the proviso that the antisense compounds do not have a nucleobase sequence consisting of any of SEQ ID NOs: 194-215 described in U.S. Pat. No. 7,737,125 as SEQ ID NOs: 2-9, 49-50, 52-53, 55-56, and 86-93 (herein incorporated by reference), and identified in Table A.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound is 10-30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compoun is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to an Androgen Receptor nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides."Y" may comprise 2'-deoxynucleosides. As used herein, a gapmer described as "X-Y-Z"

has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to an Androgen Receptor nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:

each A is independently a 2'-substituted nucleoside;

each B is independently a bicyclic nucleoside;

each J is independently either a 2'-substituted nucleoside or a 2'-deoxynucleoside;

each D is a 2'-deoxynucleoside;

m is 0-4; n is 0-2; p is 0-2; r is 0-2; t is 0-2; v is 0-2; w is 0-4; x is 0-2; y is 0-2; z is 0-4; g is 6-14; provided that:

at least one of m, n, and r is other than 0;

at least one of w and y is other than 0; the sum of m, n, p, r, and t is from 2 to 5; and the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

IIc

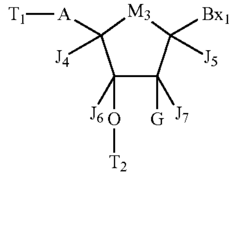

wherein:

$T_1$ is an optionally protected phosphorus moiety;

$T_2$ is an internucleoside linking group linking the compound of Formula IIc to the oligomeric compound;

A has one of the formulas:

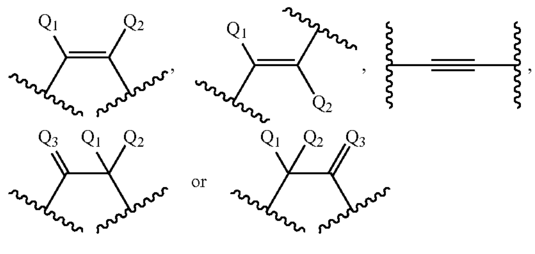

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15}){=}C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20}){=}C(R_{21})$, $C[{=}C(R_{20})(R_{21})]$ and $C({=}O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C{=}O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH═CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

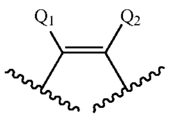

or

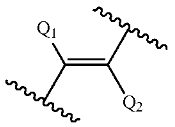

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

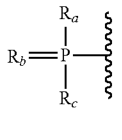

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH═$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH═$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—N(H)—$(CH_2)_2$—$N(CH_3)_2$ or $OCH_2$—N(H)—$C(=NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

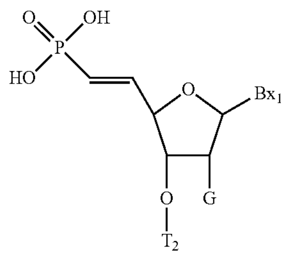

IIe

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$, wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

$-(A)_2-(B)_x-(A)_2-(C)_y(A)_3-$ wherein: A is a first type of modified nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

$5'-(O)-(AB)_xA_y-(D)_z$ wherein:

Q is a nucleoside comprising a stabilized phosphate moiety. In certain embodiments, Q is a nucleoside having Formula IIc or IIe;

A is a first type of modified nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

$5'-(O)-(A)_x-(D)_z$ wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS |

ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is Androgen Receptor. In certain embodiment, the degradation of the targeted Androgen Receptor is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target Androgen Receptor by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode human Androgen Receptor include, without limitation, the following: GENBANK Accession No. NT_011669.17_TRUNC_5079000_5270000 (incorporated herein as SEQ ID NO: 1), GENBANK Accession No. NM_000044.3 (incorporated herein as SEQ ID NO: 2), GENBANK Accession No. NM_001011645.2 (incorporated herein as SEQ ID NO: 3), GENBANK Accession No. FJ235916.1 (incorporated herein as SEQ ID NO: 4), GENBANK Accession No. FJ235917.1 (incorporated herein as SEQ ID NO: 5), GENBANK Accession No. FJ235918.1 (incorporated herein as SEQ ID NO: 6), GENBANK Accession No. FJ235919.1 (incorporated herein as SEQ ID NO: 7), and GENBANK Accession No. FJ235920.1 (incorporated herein as SEQ ID NO: 8).

Androgen Receptor mRNA encodes several functional domains. In certain embodiments, full-length Androgen Receptor mRNA includes exon 1 encoding the N-terminal domain, exons 2 and 3 encoding the DNA binding domain, exon 4 encoding the short hinge region, and exons 4-8 encoding the ligand binding domain.

In certain embodiments, Androgen Receptor splicing variants targetable by the antisense compounds provided herein include exon 1 encoding the N-terminal domain and exons 2 and 3 encoding the DNA binding domain, or functional portions thereof, but does not include at least a portion of exon 4 encoding the short hinge region or at least a portion of exons 4-8 encoding the ligand binding domain. Examples of such AR splicing variants include, but are not limited to, AR-V1, AR-V2, AR-V3, AR-V4, AR-V5, AR-V6, and AR-V7 (also referred to as AR3), which contain exons 1-3 but lack exons 4-8. AR-V1, AR-V2, AR-V3, AR-V4, AR-V5, AR-V6, AR-V7, and additional splicing variants targetable by the antisense compounds provided herein are described in Hu et al., *Cancer Res* 2009; 69:16-22 and US Patent Application Publication No. US 2010/0068802, each of which is incorporated herein by reference in its entirety. Further examples of such AR splicing variants targetable by the antisense compounds provided herein include, but are not limited to, AR3, AR4, AR4b, AR5, and AR6 (SEQ ID NOs: 4-8, respectively) as described in Guo et al., *Cancer Res.* 2009; 69: 2305-13, which is incorporated herein by reference in its entirety.

Hybridization

In some embodiments, hybridization occurs between an antisense compound disclosed herein and an Androgen Receptor. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with Androgen Receptor.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Androgen Receptor nucleic acid).

Non-complementary nucleobases between an antisense compound and an Androgen Receptor nucleic acid may be tolerated provided that the antisense compound remains able to specifically hybridize to a target nucleic acid. Moreover, an antisense compound may hybridize over one or more segments of an Androgen Receptor nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Androgen Receptor nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to an Androgen Receptor nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Androgen Receptor nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Androgen Receptor nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Androgen Receptor nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein 4'-$(CH_2)$—O-2' (LNA) is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'—$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_1)$—$(CH_2)_2$—$N(R_m)(R_n)$, where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2'(LNA); 4'-$(CH_2)$—S-2'; 4'-$(CH_2)_2$—O-2'(ENA); 4'-$CH(CH_3)$—O-2' (also referred to as constrained ethyl or cEt) and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—$N(OCH_3)$-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C—$(H)(CH_3)$-2' (see Chattopadhyaya et al., *J. Org. Chem.,* 2009, 74, 118-134); and 4'-$CH_2$—C(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2007, 129(26) 8362-8379; Elayadi et al., *Curr. Opinion Invest. Drugs,* 2001, 2, 558-561; Braasch et al., *Chem. Biol.,* 2001, 8, 1-7; and Orum et al., *Curr. Opinion Mol. Ther.,* 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —C(=O)—, —C(=$NR_a$)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$alicyclic radical, halogen, $OJ_1$, $NJ_1J_2$, $SJ_1$, $N_3$, $COOJ_1$, acyl (C(=O)—H), substituted acyl, CN, sulfonyl $(S(=O)_2$-$J_1)$, or sulfoxyl $(S(=O)$-$J_1)$; and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4'-$CH_2$-2',4'-$(CH_2)_2$-2',4'-$(CH_2)_3$-2',4'-$CH_2$—O-2',4'-$(CH_2)_2$—O-2',4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, (J) propylene carbocyclic (4'-$(CH_2)_3$-2') BNA and (K) vinyl BNA as depicted below:

(A)

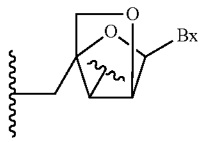

(B)

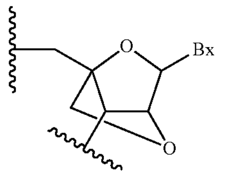

(C)

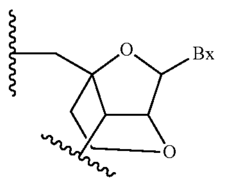

(D)

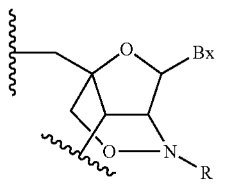

-continued (E)

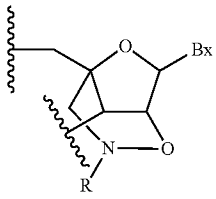

(F)

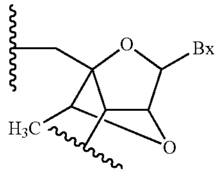

(G)

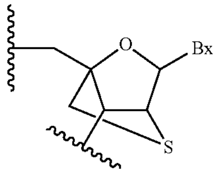

(H)

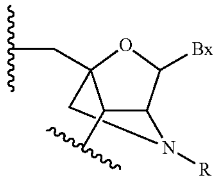

(I)

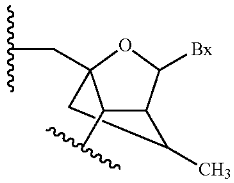

(J)

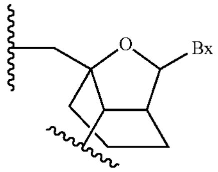

(K)

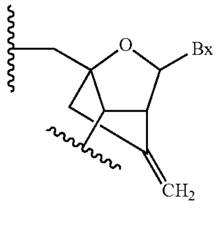

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

I

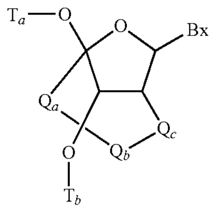

wherein:

Bx is a heterocyclic base moiety;

$-Q_a-Q_b-Q_c-$ is $—CH_2—N(R_c)—CH_2—$, $—C(=O)—N(R_c)—CH_2—$, $—CH_2—O—N(R_c)—$, $—CH_2—N(R_c)—O—$ or $—N(R_c)—O—CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

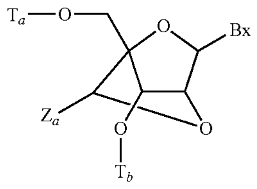

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

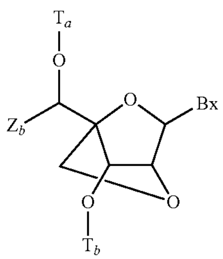

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

IV

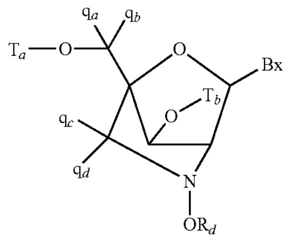

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

V

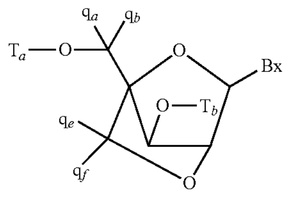

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)O$J_j$, C(=O)N$J_jJ_k$, C(=O)$J_j$, O—C(=O)—N$J_jJ_k$, N(H)C(=NH)N$J_jJ_k$, N(H)C(=O)N$J_jJ_k$ or N(H)C(=S)N$J_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). Bicyclic nucleic acids (BNAs) and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

VI

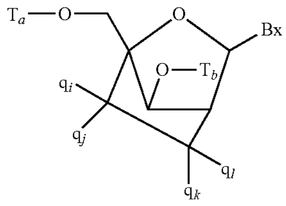

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)O$J_j$, C(=O)N$J_jJ_k$, C(=O)$J_j$, O—C(=O)N$J_jJ_k$, N(H)C(=NH)N$J_jJ_k$, N(H)C(=O)N$J_jJ_k$ or N(H)C(=S)N$J_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.,* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., Chimia, 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854) or fluoro HNA (F-HNA) having a tetrahydropyran ring system as illustrated below:

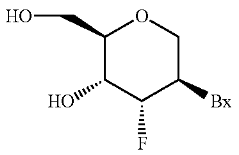

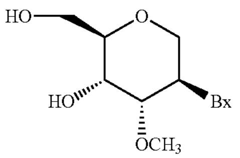

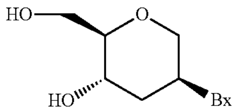

In certain embodiments, sugar surrogates are selected having Formula VII:

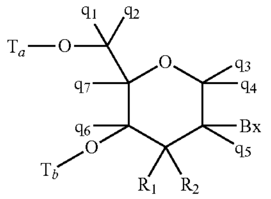

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry,* 2002, 41, 4503-4510; and U.S. Pat. Nos. 5,698,685; 5,166,315; 5,185,444; and 5,034,506). As used here, the term "morpholino" means a sugar surrogate having the following formula:

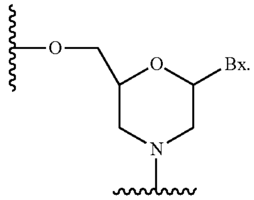

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.,* 2008, 130(6), 1979-1984; Horváth et al., *Tetrahedron Letters,* 2007, 48, 3621-3623; Nauwelaerts et al., *J. Am. Chem. Soc.,* 2007, 129(30), 9340-9348; Gu et al., *Nucleosides, Nucleotides & Nucleic Acids,* 2005, 24(5-7), 993-998; Nauwelaerts et al., *Nucleic Acids Research,* 2005, 33(8), 2452-2463; Robeyns et al., *Acta Crystallographica, Section F: Structural Biology and Crystallization Communications,* 2005, F61(6), 585-586; Gu et al., *Tetrahedron,* 2004, 60(9), 2111-2123; Gu et al., *Oligonucleotides,* 2003, 13(6), 479-489; Wang et al., *J. Org. Chem.,* 2003, 68, 4499-4505; Verbeure et al., *Nucleic Acids Research,* 2001, 29(24), 4941-4947; Wang et al., *J. Org. Chem.,* 2001, 66, 8478-82; Wang et al., *Nucleosides, Nucleotides & Nucleic Acids,* 2001, 20(4-7), 785-788; Wang et al., *J. Am. Chem.,* 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

X

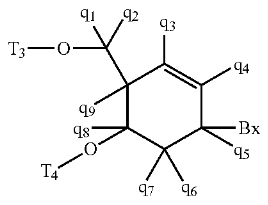

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $C_7$, $q_{18}$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—C(═O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.,* 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an androgen receptor nucleic acid comprise one or more modified nucleobases. In certain embodiments, shortened or gap-widened antisense oligonucleotides targeted to an androgen receptor nucleic acid comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

For additional conjugates including those useful for ssRNA and their placement within antisense compounds, see e.g., PCT Publication No.; WO2013/033230.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an androgen receptor nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to an androgen receptor nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Yet another technique used to introduce antisense oligonucleotides into cultured cells includes free uptake of the oligonucleotides by the cells.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Embodiments

E1. A compound comprising a modified oligonucleotide consisting of 10 to 30 linked nucleosides and having a nucleobase sequence comprising at least 8 contiguous nucleobases of any of the nucleobase sequences of SEQ ID NOs: 12-179.

E2. A compound comprising a modified oligonucleotide consisting of 16 to 30 linked nucleosides and having a nucleobase sequence comprising the nucleobase sequence of any one of SEQ ID NOs: 12-179.

E 3. A compound comprising a modified oligonucleotide consisting of the nucleobase sequence of any one of SEQ ID NOs: 12-179.

E 4. A compound comprising a modified oligonucleotide consisting of 10 to 30 linked nucleosides and having a nucleobase sequence comprising at least 8 contiguous nucleobases of any of the nucleobase sequences of SEQ ID NO: 35, 39, 43, 124, 150, 155, 169, or 175.

E 5. A compound comprising a modified oligonucleotide consisting of 16 to 30 linked nucleosides and having a nucleobase sequence comprising the nucleobase sequence of SEQ ID NO: 35, 39, 43, 124, 150, 155, 169, or 175.

E6. A compound comprising a modified oligonucleotide consisting of 16 linked nucleosides and having a nucleobase sequence consisting of the nucleobase sequence of SEQ ID NO: 35, 39, 43, 124, 150, 155, 169, or 175.

E7. A compound comprising a modified oligonucleotide consisting of 10 to 30 linked nucleosides complementary within nucleotides 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, 134971-134986, 102156-102171, 139682-139697, 139762-139777, 139782-139797, 144856-144871, 144938-144953, 148406-148421, 148443-148458, 148520-148535, 181695-181710, 182958-182973, or 183049-183064 of SEQ ID NO: 1, wherein said modified oligonucleotide is at least 90% complementary to SEQ ID NO: 1.

E8. A compound comprising a modified oligonucleotide consisting of 10 to 30 linked nucleosides having a nucleobase sequence comprising a portion of at least 8 contiguous nucleobases 100% complementary to an equal length portion of nucleobases 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-

4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, 5521-5536, 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, 134971-134986, 102156-102171, 139682-139697, 139762-139777, 139782-139797, 144856-144871, 144938-144953, 148406-148421, 148443-148458, 148520-148535, 181695-181710, 182958-182973, or 183049-183064 of SEQ ID NO: 1, wherein the nucleobase sequence of the modified oligonucleotide is complementary to SEQ ID NO: 1.

E9. The compound of any one of E1, E7, or E8, wherein the compound comprises a modified oligonucleotide consisting of 10 to 30 linked nucleosides complementary within exon 1 nucleotides 2957-2972, 3079-3094, 3099-3114, 3109-3124, 3113-3128, 3120-3135, 3133-3148, 3224-3239, 3226-3241, 3351-3366, 3353-3368, 3361-3376, 3388-3403, 3513-3528, 3517-3532, 3519-3534, 3641-3656, 3735-3750, 3764-3779, 3768-3783, 3798-3813, 3799-3814, 3851-3866, 3870-3885, 3874-3889, 3876-3891, 3878-3893, 3884-3899, 3886-3901, 3888-3903, 3901-3916, 3956-3971, 3962-3977, 3964-3979, 3967-3982, 4019-4034, 4038-4053, 4049-4064, 4056-4071, 4059-4074, 4062-4077, 4066-4081, 4070-4085, 4101-4116, 4103-4118, 4105-4120, 4109-4124, 4305-4320, 4405-4420, 4532-4547, 4534-4549, 4537-4552, 4539-4554, 4555-4570, 4571-4586, 4573-4588, 4578-4593, 4597-4612, 4632-4647, 4655-4670, 4656-4671, 4662-4677, 4699-4714, 4747-4762, 4750-4765, 4752-4767, 4754-4769, 4755-4770, 4769-4784, 4798-4813, 4804-4819, 4807-4822, 4833-4848, 4837-4852, 4839-4854, 4865-4880, 4868-4883, 4872-4887, 4874-4889, 4876-4891, 4887-4902, 4889-4904, 4916-4931, 4918-4933, 4938-4953, 4942-4957, 4944-4959, 4951-4966, 5050-5065, 5052-5067, 5054-5069, 5056-5071, 5060-5075, 5061-5076, 5062-5077, 5133-5148, 5141-5156, 5155-5170, 5265-5280, 5293-5308, 5308-5323, 5392-5407, 5448-5463, 5469-5484, 5481-5496, 5483-5498, 5486-5501, 5488-5503, 5494-5509, or 5521-5536 of SEQ ID NO:1.

E10. The compound of E9, wherein the compound comprises a modified oligonucleotide consisting of 10 to 30 linked nucleosides complementary within exon 1 nucleotides 5052-5067 of SEQ ID NO:1.

E11. The compound of any one of E1, E7, or E8, wherein the compound comprises a modified oligonucleotide consisting of 10 to 30 linked nucleosides complementary within intron 1 nucleotides 5666-5681, 6222-6237, 6701-6716, 7543-7558, 8471-8486, 8638-8653, 9464-9479, 10217-10232, 10250-10265, 10865-10880, 11197-11212, 11855-11870, 13189-13204, 13321-13336, 13346-13361, 16555-16570, 16793-16808, 16968-16983, 17206-17221, 18865-18880, 29329-29344, 32290-32305, 33315-33330, 39055-39070, 40615-40630, 42017-42032, 56050-56065, 58719-58734, 58720-58739, 58721-58736, 58722-58737, 58723-58738, 58724-58739, 58725-58740, 58750-58769, 58751-58766, 58752-58767, 58753-58768, 58754-58769, 58755-58770, 60902-60917, 67454-67469, 114874-114889, 115272-115287, 115365-115380, or 134971-134986 of SEQ ID NO:1.

E12. The compound of E11, wherein the compound comprises a modified oligonucleotide consisting of 10 to 30 linked nucleosides complementary within intron 1 nucleotides 8638-8653, 11197-11212, 40615-40630, 58719-58734, 58720-58735, or 58721-58736 of SEQ ID NO:1.

E13. The compound of any one of E1-12, wherein the modified oligonucleotide comprises at least one modified sugar.

E14. The compound of E13, wherein at least one modified sugar comprises a 2'-β-methoxyethyl group.

E15. The compound of E13, wherein the at least one modified sugar is a bicyclic sugar.

E16. The compound of E15, wherein the bicyclic sugar comprises a 4'-$CH(CH_3)$—O-2' group.

E17. The compound of E15, wherein the bicyclic sugar comprises a 4'-$CH_2$—O-2' or 4'-$(CH_2)_2$O-2' group.

E18. The compound of any one of E1-17, wherein the modified oligonucleotide comprises at least one modified internucleoside linkage.

E19. The compound of E18, wherein each internucleoside linkage of the antisense oligonucleotide is a phosphorothioate internucleoside linkage.

E20. The compound of any one of E1-19, wherein the modified oligonucleotide comprises at least one modified nucleobase.

E21. The compound of E20, wherein the modified nucleobase is a 5-methylcytosine.

E22. The compound of any one of E1-21, wherein the modified oligonucleotide comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

E23. The compound of E22, wherein the modified oligonucleotide comprises:

a gap segment consisting of ten linked deoxynucleosides;

a 5' wing segment consisting of 3 linked nucleosides; and a 3' wing segment consisting of 3 linked nucleosides;

wherein the gap segment is positioned between the 5' wing segment and the 3' wing segment, wherein each nucleoside of each wing segment comprises a 2'-O-methoxyethyl sugar or a constrained ethyl sugar; and wherein each internucleoside linkage is a phosphorothioate linkage.

E24. A compound comprising a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E25. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E26. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 8 linked deoxynucleosides;

a 5' wing segment consisting of four linked nucleosides; and a 3' wing segment consisting of four linked nucleosides;

wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

E27. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 8 linked deoxynucleosides;

a 5' wing segment consisting of five linked nucleosides; and a 3' wing segment consisting of three linked nucleosides;

wherein the gap segment is positioned between the 5' wing segment and the 3' wing segment; the five linked nucleosides of the 5' wing segment are a 2'-O-methoxyethyl sugar, a 2'-O-methoxyethyl sugar, a constrained ethyl (cEt) sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

E28. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 7 linked deoxynucleosides;

a 5' wing segment consisting of four linked nucleosides; and a 3' wing segment consisting of five linked nucleosides;

wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

E29. A compound comprising a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 7 linked deoxynucleosides;

a 5' wing segment consisting of six linked nucleosides; and a 3' wing segment consisting of three linked nucleosides;

wherein the gap segment is positioned between the 5' wing segment and the 3' wing segment; the six linked nucleosides of the 5' wing segment are a 2'-O-methoxyethyl sugar, a constrained ethyl (cEt) sugar, a constrained ethyl (cEt) sugar, a 2'-O-methoxyethyl sugar, a constrained ethyl (cEt) sugar, and a constrained ethyl (cEt) sugar in the 5' to 3' direction; the three linked nucleosides of the 3' wing segment are each a constrained ethyl (cEt) sugar; each internucleoside linkage is a phosphorothioate linkage; and each cytosine is a 5-methylcytosine.

E30. A compound comprising a single-stranded modified oligonucleotide consisting of 16 linked nucleosides having a nucleobase sequence consisting of the sequence of SEQ ID NO: 43, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E31. A compound comprising a single-stranded modified oligonucleotide consisting of 16 linked nucleosides having a nucleobase sequence consisting of the sequence of SEQ ID NO: 124, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E32. A compound comprising a single-stranded modified oligonucleotide consisting of 16 linked nucleosides having a nucleobase sequence consisting of the sequence of SEQ ID NO: 150, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E33. A compound comprising a single-stranded modified oligonucleotide consisting of 16 linked nucleosides having a nucleobase sequence consisting of the sequence of SEQ ID NO: 155, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E34. A compound comprising a single-stranded modified oligonucleotide consisting of 16 linked nucleosides having a nucleobase sequence consisting of the sequence of SEQ ID NO: 169, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E35. A compound comprising a single-stranded modified oligonucleotide consisting of 16 linked nucleosides having a nucleobase sequence consisting of the sequence of SEQ ID NO: 175, or a pharmaceutically acceptable salt thereof, wherein the modified oligonucleotide comprises:

a gap segment consisting of 10 linked deoxynucleosides;

a 5' wing segment consisting of three linked nucleosides; and a 3' wing segment consisting of three linked nucleosides;

wherein the gap segment is positioned between the 5' wing segment and the 3' wing segment; each nucleoside of each wing segment comprises a constrained ethyl (cEt) sugar; each internucleoside linkage is a phosphorothioate linkage; and each cytosine is a 5-methylcytosine.

E36. The compound of any one of E1-35, wherein the modified oligonucleotide is at least 90% complementary to a nucleic acid encoding androgen receptor.

E37. The compound of any one of E1-36, wherein the antisense oligonucleotide is 100% complementary to a nucleic acid encoding androgen receptor.

E38. The compound of E37, wherein the nucleic acid encoding androgen receptor comprises the nucleotide sequence of any one of SEQ ID NOs: 1-8.

E39. A composition comprising the compound of any one of E1-38, or pharmaceutically acceptable salt thereof, and a pharmaceutically acceptable diluent or carrier.

E40. A composition comprising the compound of any one of E1-38 and a diarylhydantoin Androgen Receptor (AR) inhibitor of Formula XVI:

(XVI)

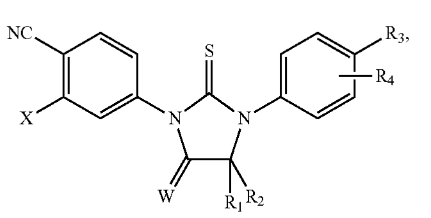

wherein X is selected from the group consisting of trifluoromethyl and iodo, wherein W is selected from the group consisting of O and NR5, wherein R5 is selected from the group consisting of H, methyl, and

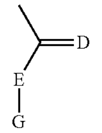

wherein D is S or O and E is N or O and G is alkyl, aryl, substituted alkyl or substituted aryl; or D is S or O and E-G together are C1-C4 lower alkyl, wherein R1 and R2 together comprise eight or fewer carbon atoms and are selected from the group consisting of alkyl, substituted alkyl including haloalkyl, and, together with the carbon to which they are linked, a cycloalkyl or substituted cycloalkyl group, wherein R3 is selected from the group consisting of hydrogen, halogen, methyl, C1-C4 alkoxy, formyl, haloacetoxy, trifluoromethyl, cyano, nitro, hydroxyl, phenyl, amino, methylcarbamoyl, methoxycarbonyl, acetamido, methanesulfonamino, methanesulfonyl, 4-methanesulfonyl-1-piperazinyl, piperazinyl, and C1-C6 alkyl or alkenyl optionally substituted with hydroxyl, methoxycarbonyl, cyano, amino, amido, nitro, carbamoyl, or substituted carbamoyl including methylcarbamoyl, dimethylcarbamoyl, and hydroxyethylcarbamoyl, wherein R4 is selected from the group consisting of hydrogen, halogen, alkyl, and haloalkyl, and wherein R3 is not methylaminomethyl or dimethylaminomethyl.

R5 may be

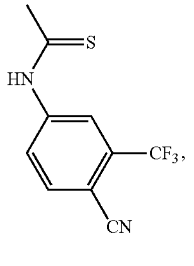 , 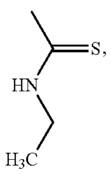 , 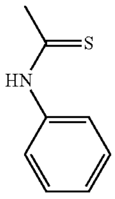 , or

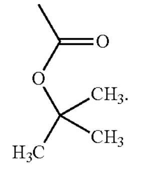 .

E41. The composition of E40, wherein the diarylhydantoin Androgen Receptor (AR) inhibitor is MDV3100.

E42. A composition comprising the compound of any one of E1-38 and an anti-androgenic agent selected from: MDV3100, ARN-059, ODM-201, abiraterone, TOK001, TAK700 and VT464.

E43. A method of treating cancer comprising administering to a subject having cancer the compound of any one of E1-38 or composition of any one of E39-42, thereby treating cancer in the subject.

E44. An antisense compound of any one of E1-38 or composition of any one of E39-42 for use in treating cancer E45. The compound or composition of E44, wherein the cancer is prostate cancer, breast cancer, ovarian cancer, gastric cancer or bladder cancer.

E46. The compound or composition of E45, wherein the cancer is castrate-resistant prostate cancer.

E47. The compound or composition of E46, wherein the castrate-resistant prostate cancer is resistant to an anti-androgenic agent selected from: MDV3100, ARN-059, ODM-201, abiraterone, TOK001, TAK700 and VT464.

E48. The method of E43, wherein the cancer is prostate cancer, breast cancer, ovarian cancer, gastric cancer or bladder cancer.

E49. The method of E48, wherein the cancer is castrate-resistant prostate cancer.

E50. The method of E49, wherein the castrate-resistant prostate cancer is resistant to an anti-androgenic agent selected from: MDV3100, ARN-059, ODM-201, abiraterone, TOK001, TAK700 and VT464.

E51. The compound of E44-47 or the method of E49 or E50, wherein the antisense compound targets an AR splicing variant.

E52. The compound or method of E51, wherein the AR splicing variant lacks a functional ligand binding domain.

E53. The compound of E44-47 or the method of any one of E49-52, wherein the antisense compound is capable of reducing expression of full-length AR and an AR splicing variant lacking any one of exons 4-8.

E54. The compound or method of E51, wherein the AR splicing variant consists of exons 1-3.

E55. The compound of E44-47 or the method of any one of E49-52, wherein the antisense compound is targeted to AR upstream of the 3' end of exon 3 and is capable of inhibiting growth or proliferation of the prostate cancer cell to a greater extent than an antisense compound targeted to a region of AR downstream of the 3' end of exon 3.

E56. The compound or method of E55, wherein the antisense compound targeted to a region of AR downstream of the 3' end of exon 3 is capable of reducing levels of full-length AR but not an AR splicing variant consisting of exons 1-3.

E57. The compound or method of E56, wherein the region downstream of the 3' end of exon 3 comprises exon 4.

E58. The compound of E44-47 or the method of any one of E49-52, wherein the prostate cancer cell preferentially expresses an AR splicing variant over full-length AR.

E59. The compound or method of E58, wherein the AR splicing variant lacks a functional ligand binding domain.

E60. A method of treating prostate cancer resistant to a anti-androgenic agent selected from: MDV3100, ARN-059, ODM-201, abiraterone, TOK001, TAK700 and VT464 in a subject comprising administering to the subject an antisense compound targeted to human androgen receptor (AR) upstream of the 3' end of exon 3, thereby treating the prostate cancer.

E61. The method of E60, wherein the subject is diagnosed as having prostate cancer resistant to the anti-androgenic agent selected from: MDV3100, ARN-059, ODM-201, abiraterone, TOK001, TAK700 and VT464.

E62. The method of E60 or E61, wherein the antisense compound targets an AR splicing variant.

E63. The method of E62, wherein the AR splicing variant lacks a functional ligand binding domain.

E64. The method of any one of E60-63, wherein the antisense compound is capable of reducing expression of full-length AR and an AR splicing variant lacking any one of exons 4-8.

E65. The method of E64, wherein the AR splicing variant consists of exons 1-3.

E66. The method of any one of E60-65, wherein the antisense compound is targeted to AR upstream of the 3' end of exon 3 and is capable of inhibiting growth or proliferation of a prostate cancer cell resistant to the diarylhydantoin Androgen Receptor (AR) inhibitor to a greater extent than an antisense compound targeted to a region of AR downstream of the 3' end exon 3.

E67. The method of E66, wherein the antisense compound targeted to a region of AR downstream of the 3' end of exon 3 is capable of reducing levels of full-length AR but not an AR splicing variant lacking any one of exons 4-8.

E68. The method of E67, wherein the AR splicing variant consists of exons 1-3.

E69. The method of E68, wherein the region downstream of the 3' end of exon 3 comprises exon 4.

E70. The method of any one of E60-69, wherein the prostate cancer is castration-resistant.

E71. The method of any one of E60-70, wherein the prostate cancer comprises cells that preferentially express an AR splicing variant over full-length AR.

E72. The method of E71, wherein the AR splicing variant lacks any one of exons 4-8.

E73. The method of E72, wherein the AR splicing variant consists of exons 1-3.

E74. The method of E72, wherein the AR splicing variant lacks a functional ligand binding domain.

E75. A method of inhibiting prostate cancer cell growth or proliferation comprising contacting the prostate cancer cell with an antisense compound targeted to human androgen receptor (AR) and anti-androgenic agent selected from: MDV3100, ARN-059, ODM-201, abiraterone, TOK001, TAK700 and VT464, wherein the antisense compound and the anti-androgenic agent synergize in combination to inhibit the growth or proliferation of the prostate cancer cell.

E76. The method of E75, wherein the antisense compound is targeted to AR upstream of the 3' end of exon 3.

E77. The method of E75 or E76, wherein the prostate cancer cell is contacted with an amount of the antisense compound and an amount of anti-androgenic agent that are each or both less in combination than the amount of either the antisense compound or anti-androgenic agent alone effective in inhibiting the growth or proliferation of said prostate cancer cell.

E78. The method of any one of E75-77, wherein the antisense compound and anti-androgenic agent provide a greater-than-additive effect compared to the antisense compound alone or anti-androgenic agent alone in inhibiting the growth or proliferation of said prostate cancer cell.

E79. The method of any one of E75-78, wherein the antisense compound targets an AR splicing variant.

E80. The method of E79, wherein the AR splicing variant lacks a functional ligand binding domain.

E81. The method of any one of E75-80, wherein the antisense compound is capable of reducing expression of full-length AR and an AR splicing variant consisting of exons 1-3.

E82. A method of inhibiting growth or proliferation of an androgen receptor (AR)-positive breast cancer cell comprising contacting the breast cancer cell with an antisense compound targeted to human androgen receptor (AR) wherein the growth or proliferation of the breast cancer cell is inhibited.

E83. A method of inhibiting AR expression in a subject having or at risk of having an androgen receptor (AR)-positive breast cancer comprising:

identifying a subject having or at risk of having AR-positive breast cancer, and administering to the subject an antisense compound targeted to human AR, wherein the antisense compound inhibits AR expression in the subject.

E84. A method of treating AR-positive breast cancer in a subject comprising administering to the subject an antisense compound targeted to human androgen receptor (AR), thereby treating the breast cancer in the subject.

E85. The method of any one of E82-84, wherein the AR-positive breast cancer or breast cancer cell is dependent on androgen expression for growth.

E86. The method of any one of E82-85, wherein the breast cancer or breast cancer cell is estrogen receptor (ER)-negative, progesterone receptor (PR)-negative, or Her2/neu-negative.

E87. The method of any one of E82-85, wherein the breast cancer or breast cancer cell is ER-positive and AR-positive.

E88. The method of any one of E82-85, wherein the breast cancer or breast cancer cell is ER-negative and AR-positive.

E89. The method of any one of E82-88, wherein the breast cancer or breast cancer cell is an apocrine breast cancer or breast cancer cell.

E90. The method of any one of E60-88, wherein the antisense compound is the compound of any one of E1-38, or pharmaceutically acceptable salt thereof.

E91. The method of any one of E60-88, wherein the antisense compound is the compound of any one of E24-35, or pharmaceutically acceptable salt thereof.

EXAMPLES

Non-limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human AR in HuVEC Cells

Antisense oligonucleotides were designed targeting an AR nucleic acid and were tested for their effects on AR mRNA in vitro. The antisense oligonucleotides were tested in a series of experiments that had similar culture conditions. The results for each experiment are presented in separate tables shown below. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 (forward sequence TCCTTCACCAATGTCAACTCC, designated herein as SEQ ID NO: 9; reverse sequence GAGCCATCCAAACTCTTGAGA, designated herein as SEQ ID NO: 10; probe sequence AGTACCGCATGCACAAGTCCCG, designated herein as SEQ ID NO: 11) was used to measure mRNA levels. AR mRNA levels were adjusted according to total RNA content, as measured by RIBOGREEN®. Results are presented as percent inhibition of AR, relative to untreated control cells. A total of 155 oligonucleotides were tested. Only those oligonucleotides which were selected for further study are shown in Tables 1 and 2.

The newly designed chimeric antisense oligonucleotides in Tables 1 and 2 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 1 and 2 is targeted to either the human AR genomic sequence, designated herein as SEQ ID NO: 1 (GENBANK Accession No. NT_011669.17 truncated from nucleotides 5079000 to 5270000) or the human AR mRNA sequence, designated herein as SEQ ID NO: 2 (GENBANK Accession No. NM_000044.3), or both. 'n/a' indicates that the oligonucleotide does not target that particular gene sequence.

TABLE 1

| Target Start Site for SEQ ID NO: 1 | Target Start Site for SEQ ID NO: 2 | ISIS No | Sequence | % inhibition | SEQ ID NO |
|---|---|---|---|---|---|
| 3799 | 937 | 549332 | GCGCTCTGACAGCCTC | 84 | 12 |
| 3851 | 989 | 549334 | CACCTGCGGGAAGCTC | 83 | 13 |
| 3888 | 1026 | 549338 | GGCTGTGATGATGCGG | 83 | 14 |
| 4047 | 1185 | 549345 | TCTGGAACAGATTCTG | 82 | 191 |
| 4059 | 1197 | 549347 | CTTCGCGCACGCTCTG | 84 | 15 |
| 4534 | 1672 | 549358 | ATGGTGCTGGCCTCGC | 91 | 16 |
| 4655 | 1793 | 549360 | GGTCGAAGTGCCCCCT | 89 | 17 |
| 4699 | 1837 | 549361 | GACACCGACACTGCCT | 84 | 18 |
| 4755 | 1893 | 549362 | CCCGAAGCTGTTCCCC | 85 | 19 |
| 4865 | 2003 | 549366 | CTTGCCTGCGCTGTCG | 84 | 20 |
| 5060 | 2198 | 549371 | GTTGTAGTAGTCGCGA | 93 | 21 |
| 5062 | 2200 | 549372 | AAGTTGTAGTAGTCGC | 92 | 22 |
| 5155 | 2293 | 549374 | GCGCTGCCGTAGTCCA | 93 | 23 |
| 5265 | 2403 | 549377 | AGGATGAGGAAGCGGC | 90 | 24 |
| 5392 | 2530 | 549379 | GCTCCCGCCTCGCCGC | 86 | 25 |
| 5448 | 2586 | 549380 | CGCTTTCCTGGCCCGC | 94 | 26 |
| 5483 | 2621 | 549381 | GCCGCCAGGGTACCAC | 89 | 27 |

TABLE 1-continued

| Target Start Site for SEQ ID NO: 1 | Target Start Site for SEQ ID NO: 2 | ISIS No | Sequence | % inhibition | SEQ ID NO |
|---|---|---|---|---|---|
| n/a | 2721 | 549383 | CCAAACGCATGTCCCC | 88 | 28 |
| 102155 | 2800 | 549386 | GCTTCATCTCCACAGA | 77 | 192 |
| 102156 | 2801 | 549387 | AGCTTCATCTCCACAG | 84 | 29 |
| n/a | 2871 | 549388 | TCCCTTCAGCGGCTCT | 88 | 30 |
| 144856 | 2801 | 549390 | TTTCTGCTGGCGCACA | 89 | 31 |

TABLE 2

| Target Start Site for SEQ ID NO: 1 | Target Start Site for SEQ ID NO: 2 | ISIS No | Sequence | % inhibition | SEQ ID NO |
|---|---|---|---|---|---|
| 181695 | 3602 | 549414 | GTTCATTCGAAGTTCA | 81 | 32 |
| 182958 | 4164 | 549432 | GAGGATCATCACAGAT | 90 | 33 |
| 183049 | 4255 | 549434 | CTAAACTTCCCGTGGC | 96 | 34 |
| 58721<br>58751 | n/a | 549457 | TTGATTTAATGGTTGC | 98 | 35 |
| 58722<br>58752 | n/a | 549458 | GTTGATTTAATGGTTG | 95 | 36 |
| 58725<br>58755 | n/a | 549459 | ATGGTTGATTTAATGG | 96 | 37 |

Example 2

Dose-dependent Antisense Inhibition of Human AR in HuVEC Cells

Gapmers from the study described above exhibiting significant in vitro inhibition of AR mRNA were selected and tested at various doses in HuVEC cells. Cells were plated at a density of 20,000 cells per well and transfected using electroporation with 18.5 nM, 55.6 nM, 166.7 nM, 500.0 nM and 1500.0 nM concentrations of antisense oligonucleotide, as specified in Tables 3 and 4. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Tables 3 and 4. As illustrated, AR mRNA levels were reduced in a dose-dependent manner in the antisense oligonucleotide treated cells.

TABLE 3

| ISIS No | 18.5 nM | 55.6 nM | 166.7 nM | 500.0 nM | 1500.0 nM | $IC_{50}$ (nM) |
|---|---|---|---|---|---|---|
| 549358 | 0 | 29 | 63 | 85 | 95 | 141 |
| 549360 | 2 | 44 | 58 | 79 | 83 | 116 |
| 549361 | 0 | 12 | 30 | 52 | 66 | 525 |
| 549362 | 0 | 10 | 23 | 57 | 74 | 447 |
| 549371 | 0 | 30 | 52 | 83 | 88 | 148 |
| 549372 | 0 | 22 | 51 | 85 | 89 | 150 |
| 549374 | 15 | 40 | 59 | 83 | 92 | 108 |
| 549377 | 0 | 13 | 52 | 72 | 93 | 216 |
| 549379 | 9 | 11 | 51 | 68 | 88 | 237 |
| 549380 | 14 | 50 | 87 | 94 | 98 | 62 |
| 549381 | 4 | 14 | 33 | 71 | 91 | 261 |
| 549383 | 2 | 10 | 34 | 75 | 88 | 270 |
| 549388 | 0 | 15 | 42 | 36 | 86 | 428 |
| 549390 | 12 | 0 | 35 | 55 | 91 | 369 |

TABLE 4

| ISIS No | 18.5 nM | 55.6 nM | 166.7 nM | 500.0 nM | 1500.0 nM | $IC_{50}$ (nM) |
|---|---|---|---|---|---|---|
| 549332 | 24 | 35 | 57 | 79 | 79 | 104 |
| 549334 | 9 | 29 | 46 | 63 | 72 | 253 |
| 549338 | 30 | 32 | 47 | 67 | 78 | 154 |
| 549347 | 5 | 15 | 37 | 62 | 71 | 357 |
| 549366 | 8 | 44 | 58 | 72 | 91 | 129 |
| 549387 | 2 | 9 | 41 | 68 | 92 | 261 |
| 549414 | 0 | 21 | 35 | 53 | 76 | 366 |
| 549432 | 10 | 15 | 46 | 80 | 92 | 179 |
| 549434 | 27 | 38 | 60 | 86 | 96 | 85 |
| 549457 | 50 | 70 | 95 | 99 | 99 | 18 |
| 549458 | 22 | 48 | 84 | 97 | 98 | 57 |
| 549459 | 51 | 61 | 90 | 94 | 97 | 18 |

Example 3

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 82 oligonucleotides were tested. Only those oligonucleotides which were selected for further study are shown in Table 5.

The newly designed chimeric antisense oligonucleotides in Table 5 were designed as 3-10-3 (S)-cET gapmers or 5-10-5 MOE gapmers. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The 5-10-5 MOE gapmer is 20 nucleosides in length, wherein the central gap segment comprises of ten 2'-deoxynucleosides and is flanked by wing segments on the 5' direction and the 3' direction comprising five nucleosides each.

Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 5 is targeted to the human AR genomic sequence, designated herein as SEQ ID NO: 1 (GENBANK Accession No. NT_011669.17 truncated from nucleotides 5079000 to 5270000)

TABLE 5

| Target Start Site | Target Stop Site | ISIS No | ISIS No | Motif | % inhibition | SEQ ID NO |
|---|---|---|---|---|---|---|
| 58721<br>58751 | 58736<br>58766 | 549457 | TTGATTTAATGGTTGC | 3-10-3 | 98 | 35 |
| 58722<br>58752 | 58737<br>58767 | 549458 | GTTGATTTAATGGTTG | 3-10-3 | 94 | 36 |
| 58725<br>58755 | 58740<br>58770 | 549459 | ATGGTTGATTTAATGG | 3-10-3 | 92 | 37 |
| 58720<br>58750 | 58739<br>58769 | 560071 | TGGTTGATTTAATGGTTGCA | 5-10-5 | 73 | 38 |
| 58720<br>58750 | 58735<br>58765 | 560098 | TGATTTAATGGTTGCA | 3-10-3 | 99 | 39 |
| 58723<br>58753 | 58738<br>58768 | 560099 | GGTTGATTTAATGGTT | 3-10-3 | 95 | 40 |
| 58724<br>58754 | 58739<br>58769 | 560100 | TGGTTGATTTAATGGT | 3-10-3 | 91 | 41 |
| 58721<br>58751 | 58736<br>58766 | 560137 | TTGATTTAATGGTTGC | 3-10-3 | 95 | 35 |

Example 4

Dose-dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 31.3 nM, 62.5 nM, 125.0 nM, 250.0 nM, 500.0 nM, and 1000.0 nM concentrations of antisense oligonucleotide, as specified in Table 6. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 6. As illustrated, AR mRNA levels were reduced in a dose-dependent manner in the antisense oligonucleotide treated cells.

TABLE 6

| ISIS No | 31.25 nM | 62.5 nM | 125.0 nM | 250.0 nM | 500.0 nM | 1000.0 nM | $IC_{50}$ (μM) |
|---|---|---|---|---|---|---|---|
| 549457 | 40 | 57 | 78 | 89 | 96 | 96 | 0.03 |
| 549458 | 15 | 25 | 47 | 70 | 88 | 93 | 0.1 |
| 549459 | 16 | 23 | 50 | 71 | 85 | 92 | 0.1 |
| 560071 | 7 | 0 | 19 | 40 | 57 | 76 | 0.4 |
| 560098 | 20 | 41 | 64 | 83 | 94 | 94 | 0.1 |
| 560099 | 13 | 29 | 58 | 72 | 89 | 94 | 0.1 |
| 560100 | 16 | 24 | 53 | 69 | 81 | 93 | 0.1 |
| 560137 | 27 | 49 | 61 | 82 | 91 | 96 | 0.1 |

Example 5

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 250 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 40 oligonucleotides were tested. Only those oligonucleotides which were selected for further study are shown in Table 7.

The newly designed chimeric antisense oligonucleotides in Table 7 were designed as 3-10-3 (S)-cET gapmers or deoxy, MOE and (S)-cEt oligonucleotides. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The deoxy, MOE and (S)- cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; and 'e' indicates a MOE modification. The internucleoside linkages throughout each gapmer are phosphorothioate linkages. All cytosine residues throughout each gapmer are 5-methylcytosines. The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 7 is targeted to the human AR genomic sequence, designated herein as SEQ ID NO: 1 (GENBANK Accession No. NT_011669.17 truncated from nucleotides 5079000 to 5270000).

TABLE 7

| Target Start Site | Target Stop Site | Sequence | ISIS No | Chemistry | % inhibition | SEQ ID NO |
|---|---|---|---|---|---|---|
| 58721<br>58751 | 58736<br>58766 | TTGATTTAATGGTTGC | 549457 | kkk-10-kkk | 67 | 35 |
| 58722<br>58752 | 58737<br>58767 | GTTGATTTAATGGTTG | 549458 | kkk-10-kkk | 71 | 36 |
| 58720<br>58750 | 58735<br>58765 | TGATTTAATGGTTGCA | 560098 | kkk-10-kkk | 69 | 39 |
| 58721<br>58751 | 58736<br>58766 | TTGATTTAATGGTTGC | 560131 | kkk-9-kkke | 74 | 35 |
| 58721<br>58751 | 58736<br>58766 | TTGATTTAATGGTTGC | 560137 | ekkk-8-kkke | 66 | 35 |
| 58720<br>58750 | 58735<br>58765 | TGATTTAATGGTTGCA | 569213 | kkk-9-kkke | 69 | 39 |
| 58720<br>58750 | 58735<br>58765 | TGATTTAATGGTTGCA | 569216 | ekkk-8-kkke | 68 | 39 |
| 58721<br>58751 | 58736<br>58766 | TTGATTTAATGGTTGC | 569222 | eekkk-8-kkk | 74 | 35 |
| 58721<br>58751 | 58736<br>58766 | TTGATTTAATGGTTGC | 569228 | eekkk-7-kkke | 67 | 35 |
| 58720<br>58750 | 58735<br>58765 | TGATTTAATGGTTGCA | 569236 | ekkk-7-kkkee | 66 | 39 |

Example 6

Dose-dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 31.3 nM, 62.5 nM, 125.0 nM, 250.0 nM, 500.0 nM, and 1000.0 nM concentrations of antisense oligonucleotide, as specified in Table 8. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 8. As illustrated, AR mRNA levels were reduced in a dose-dependent manner in the antisense oligonucleotide treated cells.

TABLE 8

| ISIS No | 31.25 nM | 62.5 nM | 125.0 nM | 250.0 nM | 500.0 nM | 1000.0 nM | $IC_{50}$ (μM) |
|---|---|---|---|---|---|---|---|
| 549457 | 34 | 44 | 75 | 82 | 93 | 96 | 0.06 |
| 549458 | 30 | 36 | 54 | 70 | 85 | 90 | 0.10 |
| 560098 | 30 | 54 | 65 | 78 | 89 | 97 | 0.07 |
| 560131 | 16 | 48 | 65 | 82 | 89 | 97 | 0.09 |

TABLE 8-continued

| ISIS No | 31.25 nM | 62.5 nM | 125.0 nM | 250.0 nM | 500.0 nM | 1000.0 nM | $IC_{50}$ (μM) |
|---|---|---|---|---|---|---|---|
| 560137 | 35 | 39 | 64 | 73 | 89 | 94 | 0.08 |
| 569213 | 35 | 53 | 65 | 83 | 94 | 96 | 0.06 |
| 569216 | 38 | 51 | 68 | 83 | 91 | 96 | 0.05 |
| 569222 | 36 | 48 | 67 | 83 | 91 | 98 | 0.06 |
| 569228 | 26 | 43 | 62 | 78 | 88 | 92 | 0.09 |
| 569236 | 17 | 39 | 54 | 79 | 84 | 92 | 0.11 |

Example 7

Dose-dependent Antisense Inhibition of Human AR in HuVEC Cells

Additional antisense oligonucleotides were designed as deoxy, MOE and (S)-cEt oligonucleotides targeting AR gene sequences and were tested at various doses in HuVEC cells. The oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise 'd' indicates deoxyribose; and 'e' indicates a MOE modification. The internucleoside linkages throughout each gapmer are phosphorothioate linkages. All cytosine residues throughout each gapmer are 5-methylcytosines. The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 9 is targeted to the human AR genomic sequence, designated herein as SEQ ID NO: 1 (GENBANK Accession No. NT_011669.17 truncated from nucleotides 5079000 to 5270000)

TABLE 9

| Target Start Site | Target Stop Site | Sequence | ISIS No | Chemistry | SEQ ID NO |
|---|---|---|---|---|---|
| 58720<br>58750 | 58735<br>58765 | TGATTTAATGGTTGCA | 569221 | eekkk-8-kkk | 39 |
| 58720<br>58750 | 58735<br>58765 | TGATTTAATGGTTGCA | 569227 | eekkk-7-kkke | 39 |
| 58720<br>58750 | 58735<br>58765 | TGATTTAATGGTTGCA | 569236 | ekkk-7-kkkee | 39 |
| 58720<br>58750 | 58735<br>58765 | TGATTTAATGGTTGCA | 579666 | ekkeekk-7-kk | 39 |
| 58721<br>58751 | 58736<br>58766 | TTGATTTAATGGTTGC | 579667 | ekkeekk-7-kk | 35 |
| 58720<br>58750 | 58735<br>58765 | TGATTTAATGGTTGCA | 579670 | ekkekk-7-kkk | 39 |
| 58721<br>58751 | 58736<br>58766 | TTGATTTAATGGTTGC | 579671 | ekkekk-7-kkk | 35 |
| 58721<br>58751 | 58736<br>58766 | TTGATTTAATGGTTGC | 569228 | eekkk-7-kkke | 35 |
| 58723<br>58753 | 58738<br>58768 | GGTTGATTTAATGGTT | 579669 | ekkeekk-7-kk | 40 |
| 58722<br>58752 | 58737<br>58767 | GTTGATTTAATGGTTG | 579672 | ekkekk-7-kkk | 36 |
| 58722<br>58752 | 58737<br>58767 | GTTGATTTAATGGTTG | 569217 | ekkk-8-kkke | 36 |
| 58723<br>58753 | 58738<br>58768 | GGTTGATTTAATGGTT | 569214 | kkk-9-kkke | 40 |
| 58723<br>58753 | 58738<br>58768 | GGTTGATTTAATGGTT | 560099 | kkk-10-kkk | 40 |

Cells were plated at a density of 20,000 cells per well and transfected using electroporation with 62.5 nM, 125.0 nM, 250.0 nM, 500.0 nM, and 1000.0 nM concentrations of antisense oligonucleotide, as specified in Tables 10-12. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Tables 10-12. As illustrated, AR mRNA levels were reduced in a dose-dependent manner in some of the antisense oligonucleotide treated cells.

TABLE 10

| ISIS No | 62.5 nM | 125.0 nM | 250.0 nM | 500.0 nM | 1000.0 nM | $IC_{50}$ (nM) |
|---|---|---|---|---|---|---|
| 549458 | 25 | 46 | 55 | 64 | 78 | 203 |
| 569227 | 8 | 40 | 33 | 51 | 73 | 388 |
| 569228 | 29 | 44 | 63 | 77 | 87 | 158 |
| 569236 | 4 | 35 | 54 | 68 | 88 | 252 |
| 579666 | 33 | 34 | 47 | 64 | 80 | 229 |
| 579667 | 30 | 29 | 44 | 36 | 76 | 411 |

TABLE 11

| ISIS No | 62.5 nM | 125.0 nM | 250.0 nM | 500.0 nM | 1000.0 nM | $IC_{50}$ (nM) |
|---|---|---|---|---|---|---|
| 549458 | 16 | 22 | 44 | 64 | 74 | 324 |
| 579669 | 24 | 39 | 45 | 74 | 91 | 207 |
| 579670 | 27 | 28 | 55 | 75 | 70 | 236 |
| 579671 | 6 | 40 | 54 | 57 | 77 | 288 |
| 579672 | 9 | 30 | 50 | 72 | 86 | 258 |

TABLE 12

| ISIS No | 62.5 nM | 125.0 nM | 250.0 nM | 500.0 nM | 1000.0 nM | $IC_{50}$ (nM) |
|---|---|---|---|---|---|---|
| 549458 | 19 | 22 | 45 | 38 | 71 | 470 |
| 569214 | 20 | 26 | 61 | 62 | 76 | 265 |
| 569217 | 34 | 39 | 49 | 64 | 64 | 247 |
| 569221 | 12 | 32 | 59 | 57 | 73 | 294 |

Example 8

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 1,000 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 75 oligonucleotides were tested. Only those oligonucleotides which were selected for further study are shown in Table 13.

The newly designed chimeric antisense oligonucleotides in Table 13 were designed as 3-10-3 (S)-cET gapmers, 3-9-4 (S)-cEt gapmers, 4-8-4 (S)-cEt gapmers, 4-9-3 (S)-cEt gapmers, 5-7-4 (S)-cEt gapmers, 5-8-3 (S)-cEt gapmers, 6-7-3 (S)-cEt gapmers, or deoxy, MOE and (S)-cEt oligonucleotides. The 3-10-3 (S)-cEt gapmers are 16 nucleosides in length, wherein the central gap segment comprises of ten 2'-deoxynucleosides and is flanked by wing segments on both the 5' direction and on the 3' direction comprising three nucleosides. The 3-9-4 (S)-cEt gapmers are 16 nucleosides in length, wherein the central gap segment comprises of nine 2'-deoxynucleosides and is flanked by a wing segment on the 5' direction comprising three nucleotides and on the 3' direction comprising four nucleosides. The 4-8-4 (S)-cEt gapmers are 16 nucleosides in length, wherein the central gap segment comprises of eight 2'-deoxynucleosides and is flanked by wing segments on both the 5' direction and on the 3' direction comprising four nucleosides. The 4-9-3 (S)-cEt gapmers are 16 nucleosides in length, wherein the central gap segment comprises of nine 2'-deoxynucleosides and is flanked by a wing segment on the 5' direction comprising four nucleotides and on the 3' direction comprising three nucleosides. The 5-7-4 (S)-cEt gapmers are 16 nucleosides in length, wherein the central gap segment comprises of seven 2'-deoxynucleosides and is flanked by a wing segment on the 5' direction comprising five nucleotides and on the 3' direction comprising four nucleotides. The 5-8-3 (S)-cEt gapmers are 16 nucleosides in length, wherein the central gap segment comprises of eight 2'-deoxynucleosides and is flanked by a wing segment on the 5' direction comprising five nucleotides and on the 3' direction comprising three nucleosides. The 6-7-3 (S)-cEt gapmers are 16 nucleosides in length, wherein the central gap segment comprises of seven 2'-deoxynucleosides and is flanked by a wing segment on the 5' direction comprising six nucleotides and on the 3' direction comprising three nucleosides. Each nucleoside in the 5' wing segment and each nucleoside in the 3' wing segment has an (S)-cEt modification. The deoxy, MOE and (S)-cEt oligonucleotides are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise 'd' indicates deoxyribose; and 'e' indicates a MOE modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 13 is targeted to the human AR genomic sequence, designated herein as SEQ ID NO: 1 (GENBANK Accession No. NT_011669.17 truncated from nucleotides 5079000 to 5270000).

TABLE 13

| Target Start Site | Target Stop Site | Sequence | ISIS No | Chemistry | % inhibition | SEQ ID NO |
|---|---|---|---|---|---|---|
| 5062 | 5077 | AAGTTGTAGTAGTCGC | 549372 | kkk-10-kkk | 64 | 22 |
| 5061 | 5076 | AGTTGTAGTAGTCGCG | 585233 | kkk-8-keeee | 69 | 42 |
| 5062 | 5077 | AAGTTGTAGTAGTCGC | 585259 | ekkk-9-kkk | 71 | 22 |
| 5062 | 5077 | AAGTTGTAGTAGTCGC | 585262 | kkk-9-kkke | 77 | 22 |
| 5062 | 5077 | AAGTTGTAGTAGTCGC | 585263 | kkk-8-kkkee | 69 | 22 |
| 5062 | 5077 | AAGTTGTAGTAGTCGC | 585264 | kkk-7-kkkeee | 62 | 22 |
| 5062 | 5077 | AAGTTGTAGTAGTCGC | 585265 | eekk-8-kkee | 69 | 22 |
| 5062 | 5077 | AAGTTGTAGTAGTCGC | 585268 | keke-8-ekek | 72 | 22 |
| 5062 | 5077 | AAGTTGTAGTAGTCGC | 585269 | ekek-8-ekek | 73 | 22 |
| 5062 | 5077 | AAGTTGTAGTAGTCGC | 585271 | ekk-10-kke | 57 | 22 |
| 5062 | 5077 | AAGTTGTAGTAGTCGC | 585274 | kkk-10-kke | 65 | 22 |
| 58719 | 58734 | GATTTAATGGTTGCAA | 586124 | kkk-10-kkk | 82 | 43 |
| 58720<br>58750 | 58735<br>58765 | TGATTTAATGGTTGCA | 569227 | eekkk-7-kkke | 51 | 39 |
| 58722<br>58752 | 58737<br>58767 | GTTGATTTAATGGTTG | 560132 | kkk-9-kkke | 58 | 36 |
| 58722<br>58752 | 58737<br>58767 | GTTGATTTAATGGTTG | 569229 | eekkk-7-kkke | 57 | 36 |
| 58722<br>58752 | 58737<br>58767 | GTTGATTTAATGGTTG | 569238 | ekkk-7-kkkee | 51 | 36 |
| 58722<br>58752 | 58737<br>58767 | GTTGATTTAATGGTTG | 549458 | kkk-10-kkk | 87 | 36 |
| 58722<br>58752 | 58737<br>58767 | GTTGATTTAATGGTTG | 569223 | eekkk-8-kkk | 59 | 36 |
| 58724<br>58754 | 58739<br>58769 | TGGTTGATTTAATGGT | 569215 | kkk-9-kkke | 59 | 41 |

TABLE 13-continued

| Target Start Site | Target Stop Site | Sequence | ISIS No | Chemistry | % inhibition | SEQ ID NO |
|---|---|---|---|---|---|---|
| 58725<br>58755 | 58740<br>58770 | ATGGTTGATTTAATGG | 560133 | kkk-9-kkke | 53 | 37 |
| 58725<br>58755 | 58740<br>58770 | ATGGTTGATTTAATGG | 569220 | ekkk-8-kkke | 58 | 37 |
| 58721<br>58751 | 58736<br>58766 | TTGATTTAATGGTTGC | 586224 | kkkkk-8-kkk | 90 | 35 |
| 58722<br>58752 | 58737<br>58767 | GTTGATTTAATGGTTG | 586225 | kkkkk-8-kkk | 88 | 36 |
| 58720<br>58750 | 58735<br>58765 | TGATTTAATGGTTGCA | 586227 | kkkkk-8-kkk | 87 | 39 |

Example 9

Dose-dependent Antisense Inhibition of Human AR in HuVEC Cells

Antisense oligonucleotides from the studies described above exhibiting significant in vitro inhibition of AR mRNA were selected and tested at various doses in HuVEC cells. Cells were plated at a density of 20,000 cells per well and transfected using electroporation with 31.25 nM, 62.5 nM, 125.0 nM, 250.0 nM, 500.0 nM, and 1000.0 nM concentrations of antisense oligonucleotide, as specified in Table 14. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells. The antisense oligonucleotides were tested in a series of experiments that had similar culture conditions. The results for each experiment are presented in separate tables shown below.

The half maximal inhibitory concentration ($IC_{50}$) of each oligonucleotide is also presented in Table 14. As illustrated, AR mRNA levels were reduced in a dose-dependent manner in the antisense oligonucleotide treated cells.

TABLE 14

| ISIS No | 31.25 nM | 62.5 nM | 125.0 nM | 250.0 nM | 500.0 nM | 1000.0 nM | $IC_{50}$ nM |
|---|---|---|---|---|---|---|---|
| 549372 | 2 | 17 | 31 | 51 | 61 | 80 | 271 |
| 549458 | 0 | 19 | 40 | 63 | 74 | 90 | 196 |
| 560132 | 8 | 19 | 21 | 53 | 65 | 85 | 252 |
| 560133 | 17 | 15 | 24 | 35 | 58 | 79 | 336 |
| 569215 | 12 | 2 | 26 | 55 | 71 | 90 | 234 |
| 569220 | 11 | 29 | 34 | 43 | 59 | 78 | 275 |
| 569223 | 21 | 20 | 30 | 59 | 73 | 87 | 191 |
| 569227 | 13 | 22 | 45 | 46 | 61 | 74 | 255 |
| 569229 | 16 | 14 | 36 | 47 | 74 | 84 | 220 |
| 569238 | 4 | 32 | 33 | 54 | 71 | 88 | 202 |

Example 10

Dose-dependent Antisense Inhibition of Human AR in HuVEC Cells

Gapmers from Example 8 exhibiting significant in vitro inhibition of AR mRNA were selected and tested at various doses in HuVEC cells. Cells were plated at a density of 20,000 cells per well and transfected using electroporation with 46.9 nM, 187.5 nM, 750.0 nM, and 3000.0 nM concentrations of antisense oligonucleotide, as specified in Table 15. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells.

The half maximal inhibitory concentration ($IC_{50}$) of each oligonucleotide is also presented in Table 15. As illustrated, AR mRNA levels were reduced in a dose-dependent manner in antisense oligonucleotide treated cells.

TABLE 15

| ISIS No | 46.9 nM | 187.5 nM | 750.0 nM | 3000.0 nM | $IC_{50}$ (μM) |
|---|---|---|---|---|---|
| 549372 | 9 | 41 | 66 | 87 | 0.29 |
| 549458 | 15 | 50 | 85 | 96 | 0.19 |
| 586124 | 28 | 47 | 84 | 94 | 0.13 |
| 586224 | 39 | 75 | 93 | 98 | 0.05 |
| 586225 | 17 | 61 | 89 | 97 | 0.13 |
| 586227 | 20 | 60 | 88 | 96 | 0.13 |

Example 11

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 500 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 616 oligonucleotides were tested. Only those oligonucleotides which were selected for further study are shown in Tables 16-23.

The newly designed chimeric antisense oligonucleotides in Tables 16-23 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines.

The SEQ ID NO listed in the table refers to the oligonucleotide sequence. "Start site" indicates the 5'-most nucleoside to which the gapmer is targeted in the human gene sequence. "Stop site" indicates the 3'-most nucleoside to which the gapmer is targeted human gene sequence. Each gapmer listed in Tables 16-23 is targeted to either the human AR genomic sequence, designated herein as SEQ ID NO: 1 (GENBANK Accession No. NT_011669.17 truncated from nucleotides 5079000 to 5270000) or the human AR mRNA sequence, designated herein as SEQ ID NO: 2 (GENBANK Accession No. NM_000044.3), or both. 'n/a' indicates that the oligonucleotide does not target that particular gene sequence.

TABLE 16

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 47 | 22 |
| 58722<br>58752 | 58737<br>58767 | GTTGATTTAATGGTTG | 549458 | 60 | 36 |
| 2957 | 2972 | ACAGCACTGGAGCGGC | 583542 | 45 | 44 |
| 3079 | 3094 | AACTTCACCGAAGAGG | 583556 | 43 | 45 |
| 3099 | 3114 | AGTCTTTAGCAGCTTT | 583559 | 52 | 46 |
| 3109 | 3124 | GCTTCCTCCGAGTCTT | 583564 | 45 | 47 |
| 3113 | 3128 | CCTTGCTTCCTCCGAG | 583566 | 47 | 48 |
| 3120 | 3135 | GCACTTTCCTTGCTTC | 583567 | 52 | 49 |
| 3133 | 3148 | TCAGTCCTACCAGGCA | 583571 | 43 | 50 |
| 3224 | 3239 | GACTGAGGCAGCTGCG | 583583 | 45 | 51 |
| 3226 | 3241 | CCGACTGAGGCAGCTG | 583584 | 44 | 52 |

TABLE 17

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 40 | 22 |
| 58722<br>58752 | 58737<br>58767 | GTTGATTTAATGGTTG | 549458 | 46 | 36 |
| 3351 | 3366 | GCTAGCTCGCCCGCTC | 583608 | 51 | 53 |
| 3353 | 3368 | CAGCTAGCTCGCCCGC | 583609 | 51 | 54 |
| 3361 | 3376 | GCAATGTGCAGCTAGC | 583613 | 51 | 55 |
| 3388 | 3403 | GTCGCCTGGCTCCTAA | 583620 | 41 | 56 |
| 3513 | 3528 | CTGGCTCCGCACTCGG | 583635 | 50 | 57 |

TABLE 17-continued

| Target Start Site | Target Stop Site | Sequence | ISIS No | % inhibition | SEQ ID NO |
|---|---|---|---|---|---|
| 3517 | 3532 | ATCTCTGGCTCCGCAC | 583637 | 43 | 58 |
| 3519 | 3534 | TGATCTCTGGCTCCGC | 583638 | 51 | 59 |
| 3641 | 3656 | AGTGTCCACTGAAGTA | 583642 | 42 | 60 |
| 3735 | 3750 | AGGCTCACAGTCTGTC | 583649 | 46 | 61 |
| 3764 | 3779 | GACACACGGTGGACAA | 583660 | 44 | 62 |
| 3768 | 3783 | AGAAGACACACGGTGG | 583662 | 51 | 63 |
| 3798 | 3813 | CGCTCTGACAGCCTCA | 583667 | 42 | 64 |

TABLE 18

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 26 | 22 |
| 58722<br>58752 | 58737<br>58767 | GTTGATTTAATGGTTG | 549458 | 48 | 36 |
| 3870 | 3885 | GTCGCTGCAGCTAGCT | 583685 | 47 | 65 |
| 3874 | 3889 | GGTAGTCGCTGCAGCT | 583687 | 41 | 66 |
| 3876 | 3891 | GCGGTAGTCGCTGCAG | 583688 | 38 | 67 |
| 3878 | 3893 | ATGCGGTAGTCGCTGC | 583689 | 39 | 68 |
| 3884 | 3899 | GTGATGATGCGGTAGT | 583692 | 41 | 69 |
| 3886 | 3901 | CTGTGATGATGCGGTA | 583693 | 36 | 70 |
| 3901 | 3916 | GAAGAGTTCAACAGGC | 583700 | 36 | 71 |
| 3956 | 3971 | GCTTGGCTGAATCTTC | 583709 | 39 | 72 |
| 3962 | 3977 | CCTTGAGCTTGGCTGA | 583712 | 37 | 73 |
| 3964 | 3979 | ATCCTTGAGCTTGGCT | 583713 | 36 | 74 |
| 3967 | 3982 | TCCATCCTTGAGCTTG | 583714 | 36 | 75 |
| 4019 | 4034 | GTAGGTCTTGGACGGC | 583719 | 36 | 76 |
| 4038 | 4053 | GATTCTGGAAAGCTCC | 583727 | 40 | 77 |
| 4049 | 4064 | GCTCTGGAACAGATTC | 583728 | 45 | 78 |
| 4056 | 4071 | CGCGCACGCTCTGGAA | 583731 | 34 | 79 |
| 4062 | 4077 | TCACTTCGCGCACGCT | 583734 | 46 | 80 |
| 4066 | 4081 | TGGATCACTTCGCGCA | 583736 | 47 | 81 |
| 4070 | 4085 | GTTCTGGATCACTTCG | 583738 | 36 | 82 |
| 4101 | 4116 | CGCTCGCGGCCTCTGG | 583745 | 40 | 83 |
| 4103 | 4118 | TGCGCTCGCGGCCTCT | 583746 | 32 | 84 |
| 4105 | 4120 | GCTGCGCTCGCGGCCT | 583747 | 35 | 85 |

TABLE 19

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 39 | 22 |
| 58722<br>58752 | 58737<br>58767 | GTTGATTTAATGGTTG | 549458 | 50 | 36 |
| 4109 | 4124 | AGGTGCTGCGCTCGCG | 583749 | 36 | 86 |
| 4305 | 4320 | GCTGTTCCTCATCCAG | 583759 | 38 | 87 |
| 4405 | 4420 | TGCTGCGGCAGCCCCT | 583771 | 40 | 88 |
| 4532 | 4547 | GGTGCTGGCCTCGCTC | 583787 | 37 | 89 |
| 4537 | 4552 | TGCATGGTGCTGGCCT | 583789 | 39 | 90 |
| 4539 | 4554 | GTTGCATGGTGCTGGC | 583790 | 39 | 91 |
| 4555 | 4570 | TGCTGTTGCTGAAGGA | 583795 | 63 | 92 |
| 4571 | 4586 | GGATACTGCTTCCTGC | 583796 | 65 | 93 |
| 4573 | 4588 | TCGGATACTGCTTCCT | 583797 | 35 | 94 |
| 4578 | 4593 | TGCCTTCGGATACTGC | 583799 | 65 | 95 |
| 4597 | 4612 | CTCGCTCTCCCGCTGC | 583802 | 37 | 96 |
| 4632 | 4647 | TGTCCTTGGAGGAAGT | 583809 | 45 | 97 |
| 4656 | 4671 | TGGTCGAAGTGCCCCC | 583818 | 42 | 98 |
| 4662 | 4677 | CAGAAATGGTCGAAGT | 583821 | 42 | 99 |

TABLE 20

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 23 | 22 |
| 58722<br>58752 | 58737<br>58767 | GTTGATTTAATGGTTG | 549458 | 54 | 36 |
| 4747 | 4762 | TGTTCCCCTGGACTCA | 583833 | 37 | 100 |
| 4750 | 4765 | AGCTGTTCCCCTGGAC | 583834 | 52 | 101 |
| 4752 | 4767 | GAAGCTGTTCCCCTGG | 583835 | 44 | 102 |
| 4754 | 4769 | CCGAAGCTGTTCCCCT | 583836 | 37 | 103 |
| 4769 | 4784 | GTACATGCAATCCCCC | 583843 | 35 | 104 |
| 4798 | 4813 | ACAGCGGGTGGAACTC | 583847 | 34 | 105 |
| 4804 | 4819 | GGACGCACAGCGGGTG | 583850 | 38 | 106 |
| 4807 | 4822 | GTGGGACGCACAGCGG | 583851 | 33 | 107 |
| 4833 | 4848 | TGCATTCGGCCAATGG | 583853 | 33 | 108 |
| 4837 | 4852 | CCTTTGCATTCGGCCA | 583855 | 44 | 109 |
| 4839 | 4854 | AACCTTTGCATTCGGC | 583856 | 45 | 110 |
| 4868 | 4883 | GCTCTTGCCTGCGCTG | 583862 | 32 | 111 |
| 4872 | 4887 | CAGTGCTCTTGCCTGC | 583864 | 46 | 112 |
| 4874 | 4889 | TTCAGTGCTCTTGCCT | 583865 | 45 | 113 |
| 4876 | 4891 | TCTTCAGTGCTCTTGC | 583866 | 32 | 114 |

TABLE 20-continued

| Target Start Site | Target Stop Site | Sequence | ISIS No | % inhibition | SEQ ID NO |
|---|---|---|---|---|---|
| 4887 | 4902 | ACTCAGCAGTATCTTC | 583868 | 34 | 115 |
| 4889 | 4904 | ATACTCAGCAGTATCT | 583871 | 47 | 116 |
| 4916 | 4931 | TTTGGTGTAACCTCCC | 583880 | 39 | 117 |
| 4918 | 4933 | CCTTTGGTGTAACCTC | 583881 | 47 | 118 |
| 4938 | 4953 | CTAGGCTCTCGCCTTC | 583890 | 32 | 119 |
| 4942 | 4957 | CAGCCTAGGCTCTCGC | 583892 | 35 | 120 |
| 4944 | 4959 | AGCAGCCTAGGCTCTC | 583893 | 34 | 121 |
| 4951 | 4966 | CTGCCAGAGCAGCCTA | 583896 | 37 | 122 |

TABLE 21

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 37 | 22 |
| 58722<br>58752 | 58737<br>58767 | GTTGATTTAATGGTTG | 549458 | 47 | 36 |
| 5050 | 5065 | TCGCGACTCTGGTACG | 583917 | 37 | 123 |
| 5052 | 5067 | AGTCGCGACTCTGGTA | 583918 | 47 | 124 |
| 5054 | 5069 | GTAGTCGCGACTCTGG | 583919 | 55 | 125 |
| 5056 | 5071 | TAGTAGTCGCGACTCT | 583920 | 42 | 126 |
| 5061 | 5076 | AGTTGTAGTAGTCGCG | 583922 | 37 | 42 |
| 5133 | 5148 | TCTCCAGCTTGATGCG | 583932 | 39 | 127 |
| 5141 | 5156 | CAGCGGGTTCTCCAGC | 583933 | 38 | 128 |
| 5293 | 5308 | CCTTCTTCGGCTGTGA | 583969 | 44 | 129 |
| 5308 | 5323 | GGTCCATACAACTGGC | 583975 | 42 | 130 |

TABLE 22

| Target Start Site on SEQ ID NO: 1 | Target Start Site on SEQ ID NO: 2 | Sequence | ISIS No | % inhibition | SEQ ID NO |
|---|---|---|---|---|---|
| 5062 | 2200 | AAGTTGTAGTAGTCGC | 549372 | 46 | 22 |
| 58722<br>58752 | n/a<br>n/a | GTTGATTTAATGGTTG | 549458 | 39 | 36 |
| 5469 | 2607 | ACACATCAGGTGCGGT | 583990 | 30 | 131 |
| 5481 | 2619 | CGCCAGGGTACCACAC | 583996 | 33 | 132 |
| 5486 | 2624 | CATGCCGCCAGGGTAC | 583998 | 45 | 133 |
| 5488 | 2626 | ACCATGCCGCCAGGGT | 583999 | 29 | 134 |
| 5494 | 2632 | CTGCTCACCATGCCGC | 584002 | 30 | 135 |

TABLE 22-continued

| Target Start Site on SEQ ID NO: 1 | Target Start Site on SEQ ID NO: 2 | Sequence | ISIS No | % inhibition | SEQ ID NO |
|---|---|---|---|---|---|
| 5521 | 2659 | ACACAAGTGGGACTGG | 584006 | 33 | 136 |
| n/a | 2870 | CCCTTCAGCGGCTCTT | 584044 | 29 | 137 |

TABLE 23

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 25 | 22 |
| 58722<br>58752 | 58737<br>58767 | GTTGATTTAATGGTTG | 549458 | 51 | 36 |
| 144938 | 144953 | CAGAGTCATCCCTGCT | 584069 | 36 | 138 |
| 148406 | 148421 | CACCCTCAAGATTCTT | 584100 | 36 | 139 |
| 148443 | 148458 | AAGGTAGTCTTTAAGG | 584106 | 30 | 140 |
| 148520 | 148535 | GTTTTCAAATGCAGCC | 584111 | 33 | 141 |
| 139682 | 139697 | GCCATGAGACAGCTTT | 584125 | 35 | 142 |
| 139762 | 139777 | ATTCTTGACTGTCTGA | 584128 | 38 | 143 |
| 139782 | 139797 | GCATGCCAGCTGGCTC | 584130 | 29 | 144 |
| 5666 | 5681 | CGCGCAGGTAGGAGCC | 584138 | 35 | 145 |
| 6222 | 6237 | TCTAAACATGACGGTT | 584139 | 37 | 146 |
| 6701 | 6716 | ATGCAATTGCCTGCCA | 584141 | 39 | 147 |

Example 12

Antisense Inhibition of Human AR in HuVEC Cells

Additional antisense oligonucleotides were designed targeting an AR nucleic acid and were tested for their effects on AR mRNA in vitro. Cultured HuVEC cells at a density of 20,000 cells per well were transfected using electroporation with 1,000 nM antisense oligonucleotide. After a treatment period of approximately 24 hours, RNA was isolated from the cells and AR mRNA levels were measured by quantitative real-time PCR. Human primer probe set RTS3559 was used to measure mRNA levels. AR mRNA levels were adjusted according to total RNA content, as measured by RIBOGREEN®. Results are presented as percent inhibition of AR, relative to untreated control cells. A total of 385 oligonucleotides were tested. Only those oligonucleotides which were selected for further study are shown in Tables 24-28.

The newly designed chimeric antisense oligonucleotides in Tables 24-28 were designed as 3-10-3 (S)-cET gapmers. The gapmers are 16 nucleosides in length, wherein the central gap segment comprises of ten 2'-deoxynucleosides and is flanked by wing segments on both the 5' direction and on the 3' direction comprising three nucleosides. Each nucleoside in the 5' wing segment and each nucleoside in the 3' wing segment has an (S)-cEt modification. The internucleoside linkages throughout each gapmer are phosphorothioate linkages. All cytosine residues throughout each gapmer are 5-methylcytosines.

The SEQ ID NO listed in the table refers to the oligonucleotide sequence. “Start site” indicates the 5'-most nucleoside to which the gapmer is targeted in the human gene sequence. “Stop site” indicates the 3'-most nucleoside to which the gapmer is targeted human gene sequence. Each gapmer listed in Tables 24-28 is targeted to the human AR genomic sequence, designated herein as SEQ ID NO: 1 (GENBANK Accession No. NT_011669.17 truncated from nucleotides 5079000 to 5270000)

TABLE 24

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 63 | 22 |
| 58722<br>58752 | 58737<br>58767 | GTTGATTTAATGGTTG | 549458 | 88 | 36 |
| 7543 | 7558 | ATGGGAGTAACTTTTG | 584145 | 76 | 148 |
| 8471 | 8486 | CATATTATTGTGCTGC | 584148 | 85 | 149 |
| 8638 | 8653 | GTCAATATCAAAGCAC | 584149 | 85 | 150 |
| 9464 | 9479 | GAGTTGTGATTTCAGG | 584152 | 88 | 151 |
| 10217 | 10232 | TTGATGGAATGCTGAT | 584157 | 69 | 152 |
| 10250 | 10265 | GGTTAACTTTCTCTGA | 584158 | 69 | 153 |
| 10865 | 10880 | TGGATTGTAAATTACG | 584162 | 82 | 154 |
| 11197 | 11212 | GAACATTATTAGGCTA | 584163 | 81 | 155 |
| 11855 | 11870 | TCAATCTAGATACCAT | 584165 | 70 | 156 |
| 13189 | 13204 | CACATCAGAAGGAGTA | 584166 | 89 | 157 |
| 13321 | 13336 | GAGTGTTAATGAAGAC | 584167 | 78 | 158 |
| 13346 | 13361 | CTGATTAGCTATGACC | 584168 | 70 | 159 |
| 16555 | 16570 | ATGAGTCCTCAGAATC | 584179 | 74 | 160 |
| 16793 | 16808 | GTAGATTCTAGCTTTG | 584180 | 81 | 161 |
| 16968 | 16983 | ACAGGCTCTGACTAGG | 584183 | 76 | 162 |
| 17206 | 17221 | TGTGTGACCCTTGGAC | 584184 | 78 | 163 |
| 18865 | 18880 | AAGTATGAGCATGGTT | 584192 | 73 | 164 |

TABLE 25

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 59 | 22 |
| 58722<br>58752 | 58737<br>58767 | GTTGATTTAATGGTTG | 549458 | 76 | 36 |
| 29329 | 29344 | GGATTCTCTACACACA | 584233 | 62 | 165 |
| 32290 | 32305 | CCATTTGTGCCAAACC | 584242 | 62 | 166 |
| 33315 | 33330 | AGGTTAGGGAGTAGGC | 584245 | 70 | 167 |
| 39055 | 39070 | TAGGGTTTGGTCAGAA | 584263 | 56 | 168 |

TABLE 25-continued

| Target Start Site | Target Stop Site | Sequence | ISIS No | % inhibition | SEQ ID NO |
|---|---|---|---|---|---|
| 40615 | 40630 | CCTTATGGATGCTGCT | 584269 | 57 | 169 |
| 42017 | 42032 | GTTATCTTACTCTCCC | 584274 | 70 | 170 |

TABLE 26

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 58 | 22 |
| 58722<br>58752 | 58737<br>58767 | GTTGATTTAATGGTTG | 549458 | 79 | 36 |
| 56050 | 56065 | GATTGTGTATAGCTGC | 584312 | 65 | 171 |
| 60902 | 60917 | GGTTATGGTTCTGTCT | 584329 | 58 | 172 |
| 67454 | 67469 | CTTCATTGCAGGTCTG | 584361 | 61 | 173 |

TABLE 27

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 70 | 22 |
| 58722<br>58752 | 58737<br>58767 | GTTGATTTAATGGTTG | 549458 | 76 | 36 |
| 114874 | 114889 | TAGCCAACTTTCTTTA | 584465 | 58 | 174 |
| 115272 | 115287 | CATTGTACTATGCCAG | 584468 | 64 | 175 |
| 115365 | 115380 | TTTGGTAACATTAGGC | 584469 | 74 | 176 |
| 134971 | 134986 | ATGGTTGTCCTGTACA | 584495 | 58 | 177 |

TABLE 28

| Target Start Site | Target Stop Site | Sequence | ISIS No | % inhibition | SEQ ID NO |
|---|---|---|---|---|---|
| 5062 | 5077 | AAGTTGTAGTAGTCGC | 549372 | 54 | 22 |
| 58722<br>58752 | 58737<br>58767 | GTTGATTTAATGGTTG | 549458 | 65 | 36 |
| 114874 | 114889 | TAGCCAACTTTCTTTA | 584465 | 54 | 174 |
| 115365 | 115380 | TTTGGTAACATTAGGC | 584469 | 63 | 176 |
| 134971 | 134986 | ATGGTTGTCCTGTACA | 584495 | 53 | 177 |

Example 13

Dose-dependent Antisense Inhibition of Human AR in HuVEC Cells

Gapmers from the studies described above exhibiting significant in vitro inhibition of AR mRNA were selected and tested at various doses in HuVEC cells. Cells were plated at a density of 20,000 cells per well and transfected using electroporation with 46.9 nM, 187.5 nM, 750.0 nM, and 3000.0 nM concentrations of antisense oligonucleotide, as specified in Tables 29-37. After a treatment period of approximately 16 hours, RNA was isolated from the cells and AR mRNA levels were measured by quantitative real-time PCR. Human AR primer probe set RTS3559 was used to measure mRNA levels. AR mRNA levels were adjusted according to total RNA content, as measured by RIBOGREEN®. Results are presented as percent inhibition of AR, relative to untreated control cells.

The half maximal inhibitory concentration ($IC_{50}$) of each oligonucleotide is also presented in Tables 29-37. As illustrated, AR mRNA levels were reduced in a dose-dependent manner in some of the antisense oligonucleotide treated cells.

TABLE 29

| ISIS No | 46.9 nM | 187.5 nM | 750.0 nM | 3000.0 nM | $IC_{50}$ (μM) |
|---|---|---|---|---|---|
| 549372 | 7 | 41 | 70 | 91 | 0.32 |
| 549458 | 21 | 72 | 91 | 97 | 0.11 |
| 583542 | 9 | 28 | 47 | 66 | 0.90 |
| 583556 | 19 | 47 | 68 | 66 | 0.34 |
| 583559 | 30 | 49 | 63 | 80 | 0.22 |
| 583564 | 16 | 33 | 55 | 74 | 0.52 |
| 583566 | 0 | 28 | 50 | 74 | 0.73 |
| 583567 | 17 | 34 | 60 | 79 | 0.43 |
| 583571 | 18 | 36 | 53 | 59 | 0.80 |
| 583583 | 21 | 31 | 49 | 64 | 0.79 |
| 583584 | 24 | 44 | 52 | 73 | 0.41 |
| 583608 | 12 | 46 | 67 | 76 | 0.35 |
| 583609 | 16 | 48 | 63 | 73 | 0.36 |
| 583613 | 24 | 60 | 70 | 75 | 0.19 |
| 583635 | 35 | 56 | 69 | 78 | 0.13 |
| 583638 | 33 | 64 | 79 | 85 | 0.11 |
| 583649 | 28 | 50 | 68 | 84 | 0.20 |
| 583660 | 21 | 39 | 61 | 72 | 0.42 |
| 583662 | 27 | 59 | 75 | 75 | 0.15 |

TABLE 30

| ISIS No | 46.9 nM | 187.5 nM | 750.0 nM | 3000.0 nM | $IC_{50}$ (μM) |
|---|---|---|---|---|---|
| 549372 | 13 | 29 | 69 | 90 | 0.37 |
| 549458 | 22 | 62 | 92 | 97 | 0.13 |
| 583620 | 0 | 17 | 44 | 54 | 1.85 |
| 583637 | 22 | 32 | 59 | 75 | 0.45 |
| 583642 | 18 | 35 | 67 | 74 | 0.46 |
| 583667 | 35 | 55 | 73 | 82 | 0.14 |
| 583685 | 32 | 53 | 73 | 81 | 0.16 |
| 583687 | 34 | 67 | 83 | 81 | 0.08 |
| 583688 | 3 | 26 | 50 | 60 | 1.05 |
| 583689 | 20 | 34 | 62 | 74 | 0.44 |
| 583692 | 8 | 47 | 61 | 71 | 0.44 |
| 583709 | 8 | 50 | 70 | 84 | 0.29 |
| 583712 | 15 | 47 | 72 | 78 | 0.29 |
| 583727 | 18 | 49 | 70 | 76 | 0.29 |
| 583728 | 9 | 48 | 67 | 70 | 0.40 |
| 583734 | 29 | 60 | 74 | 75 | 0.12 |
| 583736 | 21 | 38 | 60 | 63 | 0.51 |
| 583738 | 16 | 40 | 56 | 71 | 0.51 |
| 583745 | 19 | 51 | 68 | 77 | 0.27 |

TABLE 31

| ISIS No | 46.9 nM | 187.5 nM | 750.0 nM | 3000.0 nM | $IC_{50}$ (μM) |
|---|---|---|---|---|---|
| 549372 | 5 | 36 | 69 | 88 | 0.36 |
| 549458 | 24 | 59 | 92 | 98 | 0.13 |
| 583693 | 12 | 39 | 64 | 80 | 0.38 |
| 583700 | 14 | 34 | 57 | 71 | 0.55 |

TABLE 31-continued

| ISIS No | 46.9 nM | 187.5 nM | 750.0 nM | 3000.0 nM | $IC_{50}$ (μM) |
|---|---|---|---|---|---|
| 583713 | 29 | 51 | 67 | 74 | 0.22 |
| 583714 | 22 | 34 | 59 | 79 | 0.40 |
| 583719 | 22 | 46 | 65 | 72 | 0.32 |
| 583731 | 18 | 24 | 47 | 58 | 1.31 |
| 583746 | 24 | 44 | 65 | 67 | 0.35 |
| 583747 | 13 | 38 | 50 | 69 | 0.64 |
| 583771 | 17 | 27 | 47 | 69 | 0.77 |
| 583789 | 30 | 49 | 71 | 85 | 0.19 |
| 583790 | 17 | 42 | 65 | 81 | 0.32 |
| 583795 | 37 | 61 | 83 | 90 | 0.09 |
| 583796 | 38 | 69 | 83 | 90 | 0.07 |
| 583799 | 29 | 60 | 76 | 85 | 0.14 |
| 583809 | 13 | 37 | 68 | 81 | 0.36 |
| 583818 | 9 | 46 | 71 | 84 | 0.31 |
| 583821 | 11 | 35 | 61 | 77 | 0.46 |

TABLE 32

| ISIS No | 46.9 nM | 187.5 nM | 750.0 nM | 3000.0 nM | $IC_{50}$ (μM) |
|---|---|---|---|---|---|
| 549372 | 15 | 39 | 70 | 86 | 0.30 |
| 549458 | 19 | 58 | 89 | 96 | 0.15 |
| 583749 | 34 | 40 | 75 | 87 | 0.17 |
| 583759 | 5 | 28 | 61 | 67 | 0.63 |
| 583787 | 15 | 31 | 66 | 74 | 0.43 |
| 583797 | 21 | 50 | 74 | 82 | 0.22 |
| 583802 | 17 | 25 | 47 | 60 | 1.07 |
| 583834 | 34 | 54 | 73 | 84 | 0.13 |
| 583835 | 20 | 55 | 74 | 88 | 0.19 |
| 583836 | 11 | 27 | 67 | 86 | 0.39 |
| 583850 | 9 | 21 | 54 | 78 | 0.60 |
| 583855 | 22 | 50 | 81 | 91 | 0.18 |
| 583856 | 31 | 55 | 74 | 89 | 0.14 |
| 583864 | 30 | 49 | 72 | 85 | 0.17 |
| 583864 | 0 | 47 | 62 | 85 | 0.37 |
| 583865 | 33 | 42 | 68 | 85 | 0.19 |
| 583871 | 28 | 30 | 68 | 87 | 0.28 |
| 583880 | 13 | 52 | 78 | 92 | 0.22 |
| 583881 | 28 | 50 | 85 | 91 | 0.15 |

TABLE 33

| ISIS No | 46.9 nM | 187.5 nM | 750.0 nM | 3000.0 nM | $IC_{50}$ (μM) |
|---|---|---|---|---|---|
| 549372 | 14 | 33 | 64 | 90 | 0.34 |
| 549458 | 21 | 61 | 90 | 96 | 0.13 |
| 583833 | 26 | 43 | 70 | 74 | 0.26 |
| 583843 | 22 | 40 | 67 | 85 | 0.30 |
| 583847 | 8 | 30 | 60 | 84 | 0.46 |
| 583851 | 8 | 24 | 54 | 76 | 0.61 |
| 583853 | 24 | 51 | 70 | 80 | 0.21 |
| 583862 | 15 | 37 | 64 | 79 | 0.41 |
| 583866 | 17 | 48 | 71 | 91 | 0.24 |
| 583868 | 19 | 31 | 59 | 81 | 0.41 |
| 583890 | 0 | 0 | 17 | 33 | >30 |
| 583892 | 22 | 38 | 68 | 83 | 0.27 |
| 583893 | 15 | 35 | 62 | 79 | 0.42 |
| 583896 | 13 | 17 | 49 | 69 | 0.86 |
| 583918 | 16 | 47 | 68 | 86 | 0.30 |
| 583919 | 27 | 60 | 85 | 91 | 0.14 |
| 583920 | 11 | 16 | 50 | 72 | 0.76 |
| 583969 | 12 | 26 | 66 | 86 | 0.44 |
| 583975 | 19 | 49 | 55 | 88 | 0.36 |

TABLE 34

| ISIS No | 46.9 nM | 187.5 nM | 750.0 nM | 3000.0 nM | $IC_{50}$ (μM) |
|---|---|---|---|---|---|
| 549372 | 14 | 36 | 64 | 88 | 0.32 |
| 549458 | 14 | 53 | 84 | 95 | 0.18 |
| 583917 | 6 | 30 | 50 | 70 | 0.64 |
| 583922 | 16 | 43 | 76 | 92 | 0.23 |
| 583932 | 9 | 35 | 64 | 81 | 0.38 |
| 583933 | 22 | 25 | 56 | 81 | 0.41 |
| 583990 | 0 | 9 | 33 | 56 | 1.92 |
| 583996 | 26 | 12 | 50 | 70 | 0.71 |
| 583998 | 4 | 25 | 38 | 70 | 0.89 |
| 583999 | 13 | 12 | 30 | 64 | 1.53 |
| 584002 | 12 | 46 | 70 | 92 | 0.25 |
| 584006 | 21 | 26 | 59 | 88 | 0.35 |
| 584044 | 23 | 30 | 51 | 78 | 0.44 |
| 584069 | 18 | 40 | 63 | 82 | 0.30 |
| 584100 | 6 | 5 | 20 | 44 | 7.79 |
| 584125 | 12 | 12 | 47 | 76 | 0.72 |
| 584128 | 20 | 22 | 41 | 72 | 0.74 |
| 584139 | 13 | 33 | 56 | 85 | 0.4 |
| 584141 | 22 | 37 | 61 | 85 | 0.29 |

TABLE 35

| ISIS No | 46.9 nM | 187.5 nM | 750.0 nM | 3000.0 nM | $IC_{50}$ (μM) |
|---|---|---|---|---|---|
| 549372 | 0 | 28 | 64 | 88 | 0.42 |
| 549458 | 13 | 49 | 84 | 91 | 0.19 |
| 584106 | 3 | 13 | 12 | 32 | >30 |
| 584111 | 22 | 30 | 59 | 84 | 0.33 |
| 584130 | 0 | 10 | 11 | 37 | >30 |
| 584138 | 2 | 40 | 62 | 89 | 0.37 |
| 584145 | 6 | 32 | 63 | 88 | 0.36 |
| 584148 | 16 | 48 | 79 | 95 | 0.20 |
| 584149 | 11 | 37 | 68 | 89 | 0.31 |
| 584152 | 28 | 59 | 87 | 95 | 0.11 |
| 584162 | 24 | 45 | 80 | 92 | 0.18 |
| 584163 | 19 | 37 | 74 | 90 | 0.25 |
| 584166 | 34 | 52 | 84 | 92 | 0.10 |
| 584167 | 13 | 45 | 76 | 93 | 0.21 |
| 584179 | 1 | 25 | 62 | 87 | 0.44 |
| 584180 | 26 | 56 | 84 | 96 | 0.12 |
| 584183 | 3 | 41 | 64 | 87 | 0.31 |
| 584184 | 9 | 42 | 76 | 93 | 0.23 |
| 584192 | 1 | 34 | 73 | 95 | 0.30 |

TABLE 36

| ISIS No | 46.9 nM | 187.5 nM | 750.0 nM | 3000.0 nM | $IC_{50}$ (μM) |
|---|---|---|---|---|---|
| 549372 | 2 | 26 | 61 | 85 | 0.42 |
| 549458 | 1 | 51 | 83 | 96 | 0.23 |
| 584157 | 6 | 6 | 52 | 82 | 0.59 |
| 584158 | 14 | 37 | 70 | 89 | 0.26 |
| 584165 | 12 | 34 | 66 | 89 | 0.30 |
| 584168 | 5 | 32 | 70 | 91 | 0.32 |
| 584233 | 0 | 30 | 66 | 86 | 0.39 |
| 584242 | 12 | 38 | 66 | 93 | 0.27 |
| 584245 | 4 | 33 | 69 | 90 | 0.32 |
| 584263 | 9 | 24 | 67 | 90 | 0.34 |
| 584269 | 6 | 26 | 69 | 92 | 0.34 |
| 584274 | 17 | 36 | 74 | 93 | 0.23 |
| 584312 | 17 | 37 | 65 | 93 | 0.26 |
| 584329 | 0 | 17 | 67 | 86 | 0.46 |
| 584361 | 0 | 18 | 71 | 87 | 0.41 |
| 584465 | 0 | 0 | 32 | 51 | 2.5 |
| 584468 | 9 | 26 | 60 | 90 | 0.37 |
| 584469 | 13 | 46 | 73 | 89 | 0.22 |
| 584495 | 0 | 14 | 55 | 74 | 0.65 |

TABLE 37

| ISIS No | 46.9 nM | 187.5 nM | 750.0 nM | 3000.0 nM | $IC_{50}$ (μM) |
|---|---|---|---|---|---|
| 549372 | 9 | 41 | 66 | 87 | 0.29 |
| 549458 | 15 | 50 | 85 | 96 | 0.19 |
| 586124 | 28 | 47 | 84 | 94 | 0.13 |
| 586195 | 41 | 62 | 90 | 95 | 0.07 |
| 586197 | 27 | 47 | 77 | 94 | 0.14 |
| 586198 | 39 | 62 | 89 | 96 | 0.07 |
| 586199 | 25 | 56 | 89 | 97 | 0.13 |
| 586200 | 23 | 44 | 85 | 95 | 0.15 |
| 586205 | 34 | 67 | 89 | 95 | 0.07 |
| 586207 | 0 | 39 | 79 | 93 | 0.3 |
| 586208 | 32 | 70 | 88 | 93 | 0.08 |
| 586212 | 20 | 60 | 86 | 94 | 0.13 |
| 586221 | 39 | 72 | 94 | 98 | 0.04 |
| 586224 | 39 | 75 | 93 | 98 | 0.05 |
| 586225 | 17 | 61 | 89 | 97 | 0.13 |
| 586227 | 20 | 60 | 88 | 96 | 0.13 |
| 586232 | 24 | 45 | 82 | 91 | 0.17 |
| 586240 | 14 | 49 | 83 | 93 | 0.18 |
| 586570 | 16 | 44 | 81 | 91 | 0.21 |

Example 14

Selection of Antisense Oligonucleotides Targeting Human Androgen Receptor (AR) mRNA for Assays with Prostate Cancer Cell Lines Antisense oligonucleotides from those presented in the studies above, targeting different regions of the human AR genomic sequence, were selected for further studies in prostate cancer cell lines. AR-V7 and AR-V567es are major AR splice variants detected in cancer patients as described in Hornberg, E. et al., PLoS One 2011. Vol. 6.

The following ISIS oligonucleotides were selected for further studies: ISIS 549372, which targets the human AR genomic sequence at exon 1; ISIS 549434, which targets the human AR genomic sequence at the 3'-end of exon 8 beyond the stop codon of AR; ISIS 560131, which targets the human AR genomic sequence at intron 1; and ISIS 569236, which targets the human AR genomic sequence at intron 1. Another antisense oligonucleotide, ISIS 554221 (ACCAAGTTTCTTCAGC, designated herein as SEQ ID NO: 178), was designed as a 3-10-3 LNA gapmer with phosphorothioate backbone targeted to exon 4, (i.e. the ligand binding domain) of AR identical to an antisense oligonucleotide designated as SEQ ID NO: 58 of U.S. Pat. No. 7,737,125 for use as a benchmark.

Example 15

Effect of Antisense Inhibition of Human Androgen Receptor (AR) mRNA on Androgen Receptor Protein Levels in MDV3100-resistant C4-2B Cells C4-2B cells are androgen-independent human prostate adenocarcinoma cells commonly used in the field of oncology and have been established as clinically relevant cultured cells (Thalmann, G. N. et al., Cancer Res. 1994. 54: 2577). MDV3100 or Enzalutamide is an experimental androgen receptor antagonist drug developed by Medivation for the treatment of castration-resistant prostate cancer. ISIS 549372, ISIS 554221, and ISIS 549434 were tested in MDV3100-resistant (MR) C4-2B cells.

The cells were cultured in the presence of 5 μM concentration of MDV3100 over the course of 2 months to induce MDV3100 resistance. ISIS 549372, ISIS 549434, and ISIS 554221 at 1 μM concentration of antisense oligonucleotide were each added to the culture media at 1 μM concentration for free uptake by the cells. After a treatment period of 2 days, cells were harvested in RIPA buffer containing protease inhibitors. The presence of bands for full-length AR, as well as the variant form, AR-V7, was detected by western blot using AR antibody (N-20, Santa Cruz). Treatment of the cells with ISIS 549372 reduced full-length AR and AR-V7 more extensively than treatment with either ISIS 554221 or ISIS 549434.

Example 16

Effect of Antisense Inhibition of Human Androgen Receptor (AR) mRNA on AR-target Genes in MDV3100-resistant C4-2B Cells The effect of antisense inhibition of AR on AR target genes was analyzed. ISIS 549372, ISIS 549458, ISIS 554221, and ISIS 549434 were tested in C4-2B MR cells.

Cells were plated at a density of 40,000 cells per well in 96-well plates and cultured in RPMI1640 medium with 10% fetal bovine serum. The cells were cultured in the presence of 5 μM concentration of MDV3100 over the course of 2 months to induce MDV3100 resistance. ISIS 549372, ISIS 549458, ISIS 549434, and ISIS 554221 were each added at 0.04 μM, 0.20 μM, 1.00 μM, and 5.00 μM concentrations of antisense oligonucleotide to culture media for free uptake by the cells. A control oligonucleotide, ISIS 347526 (sequence TCTTATGTTTCCGAACCGTT (SEQ ID NO: 179) 5-10-5 MOE gapmer) with no known target region in human gene sequences, was included as a negative control. After a treatment period of 24 hrs, total AR mRNA levels were measured by quantitative real-time PCR using primer probe set RTS3559. Human AR primer probe set hAR_LTS00943 (forward sequence GCCCCTGGATGGATAGCTACT, designated herein as SEQ ID NO: 180; reverse sequence CCACAGATCAGGCAGGTCTTC, designated herein as SEQ ID NO: 181; probe sequence ACTGCCAGGGACCATGTTTTGCCC, designated herein as SEQ ID NO: 182) was used to measure AR-V7 mRNA levels. AR mRNA levels were adjusted to human actin mRNA levels. Results are presented in Table 38 as percent inhibition of total AR, relative to untreated control cells. Treatment of the cells with ISIS 549372, ISIS 549458, and ISIS 549434 reduced total AR transcript levels in a dose dependent manner more extensively than treatment with ISIS 554221.

Western analysis of full-length AR, as well as the AR-V7 variant, was also conducted in a manner similar to the assay described above. The assay demonstrated that treatment with ISIS 549372 and ISSI 549458 reduced levels of full-length AR and AR-V7. Treatment with ISIS 549434 reduced levels of full-length AR but not that of AR-V7. Treatment with ISIS 554221 reduced levels of full-length AR less extensively compared to ISIS 549372, and did not reduce levels of AR-V7. The control oligonucleotide ISIS 347526 did not reduce protein levels, as expected.

The mRNA level of the AR target gene, KLK2 was measured using the primer probe set hKLK2_LTS00963 (forward sequence CTTGCGCCCCAGGAGTCT, designated herein as SEQ ID NO: 183; reverse sequence CTCAGAGTAAGCTCTAGCACACATGTC, designated herein as SEQ ID NO: 184; probe sequence AGTGTGTGAGCCTCCATCTCCTGTCCAA, designated herein as SEQ ID NO: 185). The mRNA level of the AR target gene, KLK3 was measured using the primer probe set RTS1072 (forward sequence GCCAAGGAGGGAGGGTCTT, designated herein as SEQ ID NO: 186; reverse sequence CCCCCCAT-AGTGAATCAGCTT, designated herein as SEQ ID NO: 187; probe sequence ATGAAGTAAGGAGAGGGACTGGAC-CCCC, designated herein as SEQ ID NO: 188). As presented in Tables 39 and 40, treatment with I ISIS 549372, ISIS 549458, and ISIS 549434 reduced target gene levels in a dose dependent manner more extensively than treatment with ISIS 554221.

TABLE 38

| Percent inhibition of full-length AR mRNA in C4-2B MR cells | | | | |
|---|---|---|---|---|
| ISIS No | 0.04 μM | 0.20 μM | 1.00 μM | 5.00 μM |
| 549372 | 35 | 47 | 88 | 91 |
| 549434 | 9 | 36 | 66 | 88 |
| 549458 | 41 | 78 | 94 | 97 |
| 554221 | 0 | 0 | 0 | 23 |
| 347526 | 28 | 35 | 31 | 17 |

TABLE 39

| Percent inhibition of KLK3 mRNA in C4-2B MR cells | | | | |
|---|---|---|---|---|
| ISIS No | 0.04 μM | 0.20 μM | 1.00 μM | 5.00 μM |
| 549372 | 17 | 35 | 68 | 80 |
| 549434 | 10 | 47 | 42 | 64 |
| 549458 | 0 | 42 | 81 | 92 |
| 554221 | 0 | 0 | 47 | 56 |
| 347526 | 5 | 38 | 42 | 16 |

TABLE 40

| Percent inhibition of KLK2 mRNA in C4-2B MR cells | | | | |
|---|---|---|---|---|
| ISIS No | 0.04 μM | 0.20 μM | 1.00 μM | 5.00 μM |
| 549372 | 14 | 16 | 57 | 87 |
| 549434 | 5 | 27 | 49 | 68 |
| 549458 | 35 | 47 | 87 | 93 |
| 554221 | 24 | 25 | 56 | 66 |
| 347526 | 28 | 29 | 23 | 22 |

Example 17

Effect of Antisense Inhibition of Human Androgen Receptor (AR) mRNA on the Proliferative Ability of MDV3100-resistant C4-2B Cells The effect of antisense inhibition of AR on the proliferative ability of cancer cells was analyzed. ISIS 549372, ISIS 549458, ISIS 554221, and ISIS 549434 were tested in C4-2B MR cells.

ISIS 549372, ISIS 549434, ISIS 549458, and ISIS 554221 were each added to the culture media at 0.04 μM, 0.20 μM, 1.00 μM, and 5.00 μM concentration of antisense oligonucleotide. ISIS 347526 was included as a negative control. After a treatment period of 6 days, the proliferative capacity of the cancer cells was measured with using CellTiter 96® AQueous One Solution Cell Proliferation kit (Promega), following the manufacturer's instructions. Results are presented in Table 41 as percent inhibition of proliferation, relative to non-treated cells. Treatment of the cells with ISIS 549372, ISIS 549434, and ISIS 549458 reduced proliferation of the cells in a dose dependent manner more extensively than treatment with ISIS 554221.

TABLE 41

| Percent inhibition of C4-2B MR cell proliferation | | | | |
|---|---|---|---|---|
| ISIS No | 0.04 μM | 0.20 μM | 1.00 μM | 5.00 μM |
| 549372 | 0 | 4 | 25 | 43 |
| 549434 | 0 | 0 | 21 | 22 |
| 549458 | 8 | 16 | 41 | 56 |
| 554221 | 11 | 12 | 0 | 24 |
| 347526 | 11 | 22 | 7 | 16 |

Example 18

Effect of Antisense Inhibition of Human Androgen Receptor (AR) mRNA on MDV3100-resistant LMR20 Cells An MDV3100-resistant cell line, designated as LMR20, was created. The effect of antisense inhibition of AR on the proliferative ability and AR mRNA levels of LMR20 cells was analyzed. ISIS 560131, ISIS 549458, and ISIS 569236 were tested along with the LNA gapmer, ISIS 554221.

LnCaP cells were incubated with increasing concentrations of MDV3100 for approximately 6 months. A single clone was selected after extensive culturing in the presence of 20 μM MDV3100. The clone, LMR20, maintained the ability to allow free uptake of antisense oligonucleotides without lipid-mediated transfection, while demonstrating an approximately ten-fold increase in $IC_{50}$ when treated with MDV3100, compared to parental LnCaP cells.

Study 1

LMR20 cells were plated at 1,500 cells per well in phenol red-free medium with charcoal-stripped fetal bovine serum (CSS), to remove any androgens from the medium (Life Technologies). ISIS 560131, ISIS 549458, ISIS 569236, and ISIS 554221 were individually added to the culture media at 0.04 μM, 0.2 μM, 1.0 μM, or 5.0 μM concentration. ISIS 549148, which has no known human target sequence, was included as a control. The synthetic androgen agonist, R1881, (Takeda, A. N. et al., Mol. Pharmacol. 2007. 71: 473-82) was added on day 1 at 1 nM dose to a set of cells also treated with each of the antisense oligonucleotides. DHT was added on day 1 at a dose of 10 nM to another set of cells also treated with each of the antisense oligonucleotides. MDV3100 was added on day 1 at a dose of 10 nM to another set of cells untreated with antisense oligonucleotide, which served as a control. After a treatment period of 5 days, the proliferative ability of the cancer cells was measured by the standard MTT assay. Results are presented in Table 42 as percent inhibition of proliferation, relative to non-treated cells.

As presented in Table 42, in the presence of androgen agonists R1881 or DHT, ISIS 560131, ISIS 549458, and ISIS 569236 significantly inhibited MDV3100-resistant prostate cancer cell proliferation in a dose dependent manner more extensively than ISIS 554221. Inhibition of proliferation by the antisense oligonucleotides was also either comparable or more potent than with treatment with MDV3100.

TABLE 42

| Percent inhibition of LMR20 cell proliferation | | | | | | |
|---|---|---|---|---|---|---|
| Treatment | ASO (μM) | ISIS 560131 | ISIS 569236 | ISIS 549458 | ISIS 554221 | MDV3100 |
| CSS | 0.04 | 0 | 0 | 0 | 0 | 0 |
| | 0.20 | 0 | 10 | 0 | 1 | 5 |

TABLE 42-continued

| Percent inhibition of LMR20 cell proliferation | | | | | | |
|---|---|---|---|---|---|---|
| Treatment | ASO (μM) | ISIS 560131 | ISIS 569236 | ISIS 549458 | ISIS 554221 | MDV3100 |
| | 1.0 | 9 | 0 | 0 | 2 | 0 |
| | 5.0 | 16 | 12 | 5 | 16 | 11 |
| CSS + | 0.04 | 0 | 0 | 0 | 1 | 0 |
| R1881 | 0.20 | 13 | 2 | 22 | 10 | 5 |
| | 1.0 | 55 | 34 | 59 | 19 | 31 |
| | 5.0 | 70 | 61 | 74 | 54 | 67 |
| CSS + | 0.04 | 0 | 0 | 0 | 0 | 0 |
| DHT | 0.20 | 13 | 10 | 25 | 0 | 1 |
| | 1.0 | 57 | 32 | 60 | 10 | 13 |
| | 5.0 | 71 | 57 | 70 | 36 | 41 |

Study 2

LMR20 cells were plated at 1,500 cells per well in phenol red-free medium with CSS. ISIS 560131, ISIS 549458, ISIS 569236, and the LNA gapmer ISIS 554221 were individually added to the culture media at 0.04 μM, 0.2 μM, 1.0 μM, or 5.0 μM concentration. ISIS 549148, which has no known human target sequence, was included as a control. MDV3100 was added on day 1 at a dose of 10 nM to a set of cells, and served as a control. DHT was added on day 1 at a dose of 10 nM for 72 hrs to one set of cells also treated with each of the antisense oligonucleotides or MDV3100. R1881 was added on day 1 at a dose of 10 nM for 72 hrs to another set of cells also treated with each of the antisense oligonucleotides or MDV3100. mRNA levels of AR, prostate-specific antigen (PSA) and TMPRSS2, an androgen-regulated gene (Lin, B., et al., Cancer Res. 1999. 59: 4180), were measured. Results are presented in Tables 43-45 as mRNA levels expressed as a percentage of the baseline values. mRNA levels may be lowered or increased after treatment.

As presented in Tables 43-45, ISIS 560131, ISIS 549458, and ISIS 569236 reduced AR mRNA levels in LMR20 cells, treated with or without either AR agonist, in a dose dependent manner relative to the baseline. Treatment with the LNA gapmer ISIS 554221 did not alter AR mRNA levels. ISIS 560131, ISIS 549458, and ISIS 569236 reduced PSA levels and TMPRSS2 more extensively than the LNA gapmer ISIS 554221 or MDV3100. Treatment with MDV3100 increased the levels of AR mRNA in cells treated with AR agonist, and did not reduce either PSA or TMPRSS2 mRNA levels.

TABLE 43

| mRNA levels (% baseline value) of cells without AR agonist treatment | | | | | | |
|---|---|---|---|---|---|---|
| Gene | ASO (μM) | 560131 | 569236 | 549458 | 554221 | MDV3100 |
| AR | 0.04 | 107 | 104 | 101 | 124 | 106 |
| | 0.20 | 74 | 87 | 75 | 140 | 101 |
| | 1.0 | 29 | 42 | 30 | 132 | 99 |
| | 5.0 | 17 | 27 | 25 | 98 | 92 |
| PSA | 0.04 | 113 | 122 | 135 | 106 | 98 |
| | 0.20 | 83 | 90 | 85 | 118 | 93 |
| | 1.0 | 75 | 78 | 50 | 58 | 90 |
| | 5.0 | 71 | 73 | 72 | 87 | 113 |
| TMPRSS2 | 0.04 | 92 | 96 | 110 | 95 | 101 |
| | 0.20 | 67 | 81 | 85 | 117 | 119 |
| | 1.0 | 52 | 59 | 54 | 77 | 119 |
| | 5.0 | 45 | 48 | 62 | 73 | 141 |

TABLE 44

| mRNA levels (% baseline value) after treatment with DHT | | | | | | |
|---|---|---|---|---|---|---|
| Gene | ASO (μM) | 560131 | 569236 | 549458 | 554221 | MDV3100 |
| AR | 0.04 | 89 | 94 | 91 | 137 | 105 |
| | 0.20 | 55 | 77 | 66 | 135 | 124 |
| | 1.0 | 25 | 44 | 34 | 136 | 110 |
| | 5.0 | 20 | 34 | 31 | 100 | 143 |
| PSA | 0.04 | 74 | 108 | 93 | 97 | 124 |
| | 0.20 | 61 | 79 | 71 | 86 | 108 |
| | 1.0 | 35 | 46 | 47 | 64 | 95 |
| | 5.0 | 35 | 46 | 47 | 64 | 95 |
| TMPRSS2 | 0.04 | 112 | 113 | 127 | 121 | 134 |
| | 0.20 | 108 | 123 | 119 | 118 | 144 |
| | 1.0 | 93 | 111 | 106 | 122 | 132 |
| | 5.0 | 71 | 110 | 91 | 114 | 124 |

TABLE 45

| mRNA levels (% baseline value) after treatment with R1881 | | | | | | |
|---|---|---|---|---|---|---|
| Gene | ASO (μM) | 560131 | 569236 | 549458 | 554221 | MDV3100 |
| AR | 0.04 | 87 | 89 | 88 | 131 | 94 |
| | 0.20 | 65 | 80 | 56 | 133 | 107 |
| | 1.0 | 30 | 44 | 25 | 124 | 115 |
| | 5.0 | 26 | 37 | 32 | 99 | 136 |
| PSA | 0.04 | 92 | 90 | 93 | 100 | 84 |
| | 0.20 | 77 | 90 | 67 | 93 | 101 |
| | 1.0 | 44 | 57 | 50 | 80 | 92 |
| | 5.0 | 35 | 41 | 44 | 57 | 87 |
| TMPRSS2 | 0.04 | 132 | 126 | 137 | 136 | 114 |
| | 0.20 | 117 | 131 | 119 | 134 | 125 |
| | 1.0 | 88 | 98 | 96 | 125 | 133 |
| | 5.0 | 76 | 95 | 96 | 122 | 139 |

Example 19

Effect of Antisense Inhibition of Human Androgen Receptor (AR) mRNA in Combination with MDV3100 on the Proliferative Ability of C4-2B Cells The effect of antisense inhibition of AR in combination with different doses of MDV3100 on the proliferative ability of cancer cells was analyzed. ISIS 549372, ISIS 549434, ISIS 549458, and ISIS 554221 were tested in C4-2B cells.

C4-2B cells were plated at 1,500 cells per well. ISIS 549372, ISIS 549434, ISIS 549458, or ISIS 554221 were individually added to the culture media at 0.1 μM concentration. ISIS 347526 was included as a negative control. MDV3100 was also added on day 1 at doses of 0.25 μM or 1.00 μM. After a treatment period of 6 days, the proliferative capacity of the cancer cells was measured with CellTiter 96® AQueous One Solution Cell Proliferation kit (Promega), following the manufacturer's instructions. Results are presented in Table 46 as percent inhibition of proliferation, relative to non-treated cells. Treatment of the cells with ISIS 549372 or ISIS 549458 reduced proliferation of the cells more extensively than treatment with ISIS 554221. For instance, as presented in Table 46, treatment with ISIS 549372 alone reduced cell proliferation by 59% and treatment with ISIS 549458 reduced cell proliferation by 74% compared to ISIS 554221 alone, which reduced cell proliferation by 23%.

As presented in Tables 46 and 47, ISIS 549372 or ISIS 549458 in combination with MDV3100 inhibited prostate cancer cell proliferation to a greater extent than an equal molar concentration of ISIS 554221 in combination of MDV3100.

To find out whether treatment of the cells with ISIS 549372 or ISIS 549458 was synergistic with MDV3100, the assay was repeated at 0.1 μM ASO. As presented in Table 46, treatment with ISIS 549372 or ISIS 549458 was synergistic with MDV3100. For instance, MDV3100 alone at 0.25 μM inhibited proliferation by 4%; ISIS 549372 alone at 0.1 μM inhibited cell proliferation by 23%; in combination, cell proliferation was inhibited by 66%. Similarly, ISIS 549458 alone at 0.1 μM inhibited cell proliferation by 39%; in combination, cell proliferation was inhibited by 75%. Hence, the combination of ISIS 549372 or ISIS 549458 and MDV3100 was synergistic (i.e. greater than additive) in terms of inhibition of prostate cancer cell proliferation.

TABLE 46

Percent inhibition of C4-2B cell proliferation with 0.1 μM ASO

| | MDV3100 | | |
|---|---|---|---|
| | 0 μM | 0.25 μM | 1 μM |
| PBS | 0 | 9 | 38 |
| ISIS 549372 | 23 | 44 | 66 |
| ISIS 549458 | 39 | 59 | 75 |
| ISIS 554221 | 9 | 29 | 59 |
| ISIS 141923 | 0 | 4 | 38 |

TABLE 47

Percent inhibition of C4-2B cell proliferation with 0.2 μM ASO

| | MDV3100 | | |
|---|---|---|---|
| | 0 μM | 0.25 μM | 1 μM |
| PBS | 0 | 20 | 46 |
| ISIS 549372 | 59 | 69 | 77 |
| ISIS 549458 | 74 | 75 | 79 |
| ISIS 554221 | 23 | 45 | 67 |
| ISIS 141923 | 0 | 5 | 50 |

Example 20

Effect of Antisense Inhibition of Human Androgen Receptor (AR) mRNA in Combination with MDV3100 on the Proliferative Ability of LNCaP Cells The effect of antisense inhibition of AR in combination with different doses of MDV3100 on the proliferative ability of cancer cells was analyzed. ISIS 560131 and ISIS 569236 were tested in LNCaP cells.

LNCaP cells were plated at 1,000 cells per well. ISIS 560131 or ISIS 569236 was individually added to the culture media at 0.08 μM, 0.04 μM, 0.2 μM, or 1.0 μM concentration. ISIS 549148 was included as a negative control. MDV3100 was added to the ISIS oligonucleotide-treated cells on day 2 at doses of 0.016 μM, 0.08 μM, 0.4 μM, or 2.0 μM. After a treatment period of 5 days, the proliferative capacity of the cancer cells was measured with CellTiter 96® AQueous One or CellTiter-Glo® Solution Cell Proliferation kit (Promega), following the manufacturer's instructions. Results are presented in Tables 48-52 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 0.08 μM inhibited proliferation by an average of 7%; ISIS 560131 alone at 0.04 μM inhibited cell proliferation by 24%; in combination, cell proliferation was inhibited by 41%. Similarly, ISIS 569236 alone at 0.04 μM inhibited cell proliferation by 9%; in combination, cell proliferation was inhibited by 26%. Hence, the combination of ISIS 560131 or ISIS 569236 and MDV3100 was synergistic (i.e. greater than additive) in terms of inhibition of prostate cancer cell proliferation.

TABLE 48

Proliferation (% untreated control) in LNCaP without MDV-3100

| | ASO Dose | | | |
|---|---|---|---|---|
| | 0.08 μM | 0.04 μM | 0.2 μM | 1.0 μM |
| ISIS 560131 | 106 | 76 | 50 | 26 |
| ISIS 569236 | 106 | 91 | 60 | 35 |
| ISIS 549148 | 104 | 101 | 91 | 82 |

TABLE 49

Proliferation (% untreated control) in LNCaP with 0.016 μM MDV-3100

| | ASO Dose | | | |
|---|---|---|---|---|
| | 0.08 μM | 0.04 μM | 0.2 μM | 1.0 μM |
| ISIS 560131 | 103 | 71 | 49 | 25 |
| ISIS 569236 | 104 | 92 | 58 | 29 |
| ISIS 549148 | 106 | 86 | 83 | 59 |

TABLE 50

Proliferation (% untreated control) in LNCaP with 0.08 μM MDV-3100

| | ASO Dose | | | |
|---|---|---|---|---|
| | 0.08 μM | 0.04 μM | 0.2 μM | 1.0 μM |
| ISIS 560131 | 99 | 59 | 48 | 27 |
| ISIS 569236 | 98 | 74 | 51 | 31 |
| ISIS 549148 | 93 | 101 | 89 | 90 |

TABLE 51

Proliferation (% untreated control) in LNCaP with 0.4 μM MDV-3100

| | ASO Dose | | | |
|---|---|---|---|---|
| | 0.08 μM | 0.04 μM | 0.2 μM | 1.0 μM |
| ISIS 560131 | 68 | 50 | 40 | 26 |
| ISIS 569236 | 61 | 48 | 41 | 27 |
| ISIS 549148 | 65 | 57 | 50 | 48 |

TABLE 52

Proliferation (% untreated control) in LNCaP with 2.0 μM MDV-3100

| | ASO Dose | | | |
|---|---|---|---|---|
| | 0.08 μM | 0.04 μM | 0.2 μM | 1.0 μM |
| ISIS 560131 | 45 | 42 | 38 | 23 |
| ISIS 569236 | 44 | 41 | 35 | 23 |
| ISIS 549148 | 39 | 42 | 41 | 32 |

Example 21

Effect of Antisense Inhibition of Human Androgen Receptor (AR) mRNA in Combination with MDV3100 on the Proliferative Ability of C4-2B Cells The effect of antisense inhibition of AR in combination with different doses of MDV3100 on the proliferative ability of cancer cells was analyzed. ISIS 560131 and ISIS 569236 were tested in C4-2B cells.

C4-2B cells were plated at 1,000 cells per well. ISIS 560131 or ISIS 569236 was individually added to the culture media at 0.08 µM, 0.04 µM, 0.2 µM, or 1.0 µM concentration. ISIS 549148 was included as a negative control. MDV3100 was added to the ISIS oligonucleotide-treated cells on day 2 at doses of 0.016 µM, 0.08 µM, 0.4 µM, or 2.0 µM. After a treatment period of 5 days, the proliferative capacity of the cancer cells was measured with CellTiter 96® AQueous One Solution Cell Proliferation kit (Promega), following the manufacturer's instructions. Results are presented in Tables 53-57 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 0.4 µM inhibited proliferation by an average of 6%; ISIS 560131 alone at 0.08 µM inhibited cell proliferation by 16%; in combination, cell proliferation was inhibited by 31%. Similarly, MDV3100 with control oligonucleotide, ISIS 549148, at 0.08 µM did not inhibit proliferation (0%); ISIS 569236 alone at 0.2 µM inhibited cell proliferation by 37%; in combination, cell proliferation was inhibited by 52%. Hence, the combination of ISIS 560131 or ISIS 569236 and MDV3100 was synergistic (i.e. greater than additive) in terms of inhibition of prostate cancer cell proliferation.

TABLE 53

Proliferation (% untreated control) in C4-2B without MDV-3100

| | ASO Dose | | | |
|---|---|---|---|---|
| | 0.08 µM | 0.04 µM | 0.2 µM | 1.0 µM |
| ISIS 560131 | 84 | 59 | 47 | 41 |
| ISIS 569236 | 100 | 72 | 63 | 51 |
| ISIS 549148 | 111 | 117 | 118 | 126 |

TABLE 54

Proliferation (% untreated control) in C4-2B with 0.016 µM MDV-3100

| | ASO Dose | | | |
|---|---|---|---|---|
| | 0.08 µM | 0.04 µM | 0.2 µM | 1.0 µM |
| ISIS 560131 | 104 | 71 | 53 | 39 |
| ISIS 569236 | 107 | 74 | 65 | 55 |
| ISIS 549148 | 110 | 107 | 124 | 103 |

TABLE 55

Proliferation (% untreated control) in C4-2B with 0.08 µM MDV-3100

| | ASO Dose | | | |
|---|---|---|---|---|
| | 0.08 µM | 0.04 µM | 0.2 µM | 1.0 µM |
| ISIS 560131 | 66 | 73 | 56 | 42 |
| ISIS 569236 | 89 | 79 | 51 | 43 |
| ISIS 549148 | 84 | 125 | 123 | 114 |

TABLE 56

Proliferation (% untreated control) in C4-2B with 0.4 µM MDV-3100

| | ASO Dose | | | |
|---|---|---|---|---|
| | 0.08 µM | 0.04 µM | 0.2 µM | 1.0 µM |
| ISIS 560131 | 69 | 69 | 48 | 48 |
| ISIS 569236 | 90 | 63 | 48 | 39 |
| ISIS 549148 | 89 | 110 | 88 | 88 |

TABLE 57

Proliferation (% untreated control) in C4-2B with 2.0 µM MDV-3100

| | ASO Dose | | | |
|---|---|---|---|---|
| | 0.08 µM | 0.04 µM | 0.2 µM | 1.0 µM |
| ISIS 560131 | 37 | 42 | 49 | 43 |
| ISIS 569236 | 44 | 45 | 48 | 46 |
| ISIS 549148 | 47 | 40 | 52 | 59 |

Example 22

Effect of Antisense Inhibition of Human Androgen Receptor (AR) mRNA in Combination with MDV3100 on the Proliferative Ability of 22RV1 Cells The effect of antisense inhibition of AR in combination with different doses of MDV3100 on the proliferative ability of cancer cells was analyzed. ISIS 560131 and ISIS 569236 were tested in 22RV1 cells.

22RV1 cells were plated at 2,000 cells per well in 5% CSS medium for 48 hours. Cells were transfected using RNAiMAX reagent with ISIS 560131 or ISIS 569236 at 0.4 nM, 1.34 nM, 4 nM, or 13.4 nM concentrations. ISIS 549148 was included as a negative control. DHT at 1 nM and/or MDV3100 at doses of 0.04 µM, 0.2 µM, 1.0 µM, or 5.0 µM were added after 4 hours. After a treatment period of 3 days, the proliferative capacity of the cancer cells was measured with CellTiter 96® AQueous One Solution Cell Proliferation kit (Promega), following the manufacturer's instructions. Results are presented in Tables 58-62 as percent inhibition of proliferation, relative to non-treated cells.

As presented in the Tables, treatment with ISIS 560131 or ISIS 569236 was synergistic with MDV3100. For instance, MDV3100 with control oligonucleotide, ISIS 549148, at 1.0 µM inhibited proliferation by an average of 5%; ISIS 560131 alone at 1.34 nM inhibited cell proliferation by 3%; in combination, cell proliferation was inhibited by 23%. Similarly, MDV3100 with control oligonucleotide, ISIS 549148, at 1.0 µM inhibited proliferation by 5%; ISIS 569236 alone at 1.0 µM inhibited cell proliferation by 17%; in combination, cell proliferation was inhibited by 30%. Hence, the combination of ISIS 560131 or ISIS 569236 and MDV3100 was synergistic (i.e. greater than additive) in terms of inhibition of prostate cancer cell proliferation.

TABLE 58

| Proliferation (% untreated control) in 22RV1 without MDV-3100 | | | | |
|---|---|---|---|---|
| | ASO Dose | | | |
| | 0.4 nM | 1.34 nM | 4.0 nM | 13.4 nM |
| ISIS 560131 | 103 | 97 | 77 | 57 |
| ISIS 569236 | 97 | 83 | 69 | 37 |
| ISIS 549148 | 109 | 109 | 109 | 99 |

TABLE 59

| Proliferation (% untreated control) in 22RV1 cells with 0.04 µM MDV-3100 | | | | |
|---|---|---|---|---|
| | ASO Dose | | | |
| | 0.4 nM | 1.34 nM | 4.0 nM | 13.4 nM |
| ISIS 560131 | 96 | 80 | 65 | 39 |
| ISIS 569236 | 83 | 70 | 61 | 24 |
| ISIS 549148 | 106 | 106 | 100 | 85 |

TABLE 60

| Proliferation (% untreated control) in 22RV1 cells with 0.2 µM MDV-3100 | | | | |
|---|---|---|---|---|
| | ASO Dose | | | |
| | 0.4 nM | 1.34 nM | 4.0 nM | 13.4 nM |
| ISIS 560131 | 95 | 90 | 76 | 51 |
| ISIS 569236 | 93 | 77 | 60 | 20 |
| ISIS 549148 | 101 | 115 | 110 | 96 |

TABLE 61

| Proliferation (% untreated control) in 22RV1 cells with 1.0 µM MDV-3100 | | | | |
|---|---|---|---|---|
| | ASO Dose | | | |
| | 0.4 nM | 1.34 nM | 4.0 nM | 13.4 nM |
| ISIS 560131 | 96 | 77 | 63 | 40 |
| ISIS 569236 | 79 | 70 | 52 | 18 |
| ISIS 549148 | 106 | 95 | 98 | 82 |

TABLE 62

| Proliferation (% untreated control) in 22RV1 cells with 5.0 µM MDV-3100 | | | | |
|---|---|---|---|---|
| | ASO Dose | | | |
| | 0.4 nM | 1.34 nM | 4.0 nM | 13.4 nM |
| ISIS 560131 | 91 | 76 | 63 | 41 |
| ISIS 569236 | 82 | 72 | 52 | 24 |
| ISIS 549148 | 96 | 102 | 98 | 85 |

Example 23

Effect of Antisense Inhibition of Human Androgen Receptor (AR) mRNA on CWR22-RV1 Cells The effect of antisense inhibition of AR on the proliferative ability of cancer cells was analyzed. ISIS 549372, ISIS 549434, ISIS 549458, and ISIS 554221 were tested in CWR22-RV1 cells.

CWR22-RV1 cells were plated and transfected using RNAiMax reagent (Life Technologies) with ISIS oligonucleotides at 1.7 nM, 5.0 nM, 16.7 nM, or 50 nM concentrations. ISIS 347526 was included as a negative control. After a treatment period of 6 days, the target reduction and proliferative capacity of the cancer cells was measured.

Antisense inhibition of AR full-length mRNA was measured with the RTS3559 primer probe set. The results are presented in Table 63 as percent inhibition relative to non-treated cells. The reduction in V7 splice variant of the AR mRNA was also measured by RT-PCR using SYBR Green staining (Hu, R. et al., Cancer Res. 2009. 69: 16-22). The results are presented in Table 64, as percent reduction, relative to non-treated cells. Cell proliferation was measured with CellTiter 96® AQueous One Solution Cell Proliferation kit (Promega), following the manufacturer's instructions. Results are presented in Table 65 as percent inhibition of proliferation, relative to non-treated cells.

TABLE 63

| Percent inhibition of AR full-length mRNA | | | | | |
|---|---|---|---|---|---|
| Dose (nM) | ISIS 549372 | ISIS 549434 | ISIS 549458 | ISIS 554221 | ISIS 347526 |
| 1.7 | 24 | 27 | 28 | 24 | 0 |
| 5.0 | 53 | 46 | 41 | 41 | 3 |
| 16.7 | 64 | 69 | 61 | 67 | 4 |
| 50.0 | 78 | 86 | 78 | 72 | 0 |

TABLE 64

| Percent inhibition of AR splice variant, V7 | | | | | |
|---|---|---|---|---|---|
| Dose (nM) | ISIS 549372 | ISIS 549434 | ISIS 549458 | ISIS 554221 | ISIS 347526 |
| 1.7 | 23 | 0 | 18 | 25 | 17 |
| 5.0 | 35 | 20 | 34 | 1 | 0 |
| 16.7 | 56 | 4 | 58 | 7 | 0 |
| 50.0 | 82 | 23 | 82 | 35 | 10 |

TABLE 65

| Percent inhibition of cell proliferation | | | | | |
|---|---|---|---|---|---|
| Dose (nM) | ISIS 549372 | ISIS 549434 | ISIS 549458 | ISIS 554221 | ISIS 347526 |
| 1.7 | 0 | 8 | 0 | 17 | 0 |
| 5.0 | 0 | 15 | 0 | 11 | 0 |
| 16.7 | 25 | 13 | 17 | 27 | 0 |
| 50.0 | 53 | 38 | 40 | 47 | 0 |

Example 24

Effect of Antisense Inhibition of Human Androgen Receptor (AR) mRNA by Free Uptake of Antisense Oligonucleotide by C4-2B Cells The effect of free uptake of antisense oligonucleotides on AR mRNA levels was investigated. ISIS 549372, ISIS 549434, ISIS 549458, and ISIS 554221 were tested.

Cells were plated at a concentration of 1,000 cells/well in 96-well plates to measure cell proliferation, and at 4,000 cells/well to measure target reduction. ISIS 549458, ISIS 549372, ISIS 549434, and ISIS 554221 were added individually at 0.04 μM, 0.20 μM, 1.00 μM, or 5.00 μM. After an incubation period of 24 hrs, mRNA levels were measured using hAR_LTS00943. The data is presented in Table 66. The results indicate that ISIS 549458, ISIS 549372, and ISIS 549434 inhibited AR mRNA expression more potently than ISIS 554221.

On day 6, cells plated for measuring proliferation were incubated with MTT reagent until the development of color. Color intensity was measured using a spectrophotometer at 490 nm. The data is presented in Table 67.

TABLE 66

| Percent inhibition of AR full-length mRNA | | | | |
|---|---|---|---|---|
| Dose (μM) | ISIS 549372 | ISIS 549434 | ISIS 549458 | ISIS 554221 |
| 0.04 | 10 | 10 | 16 | 0 |
| 0.20 | 36 | 35 | 48 | 0 |
| 1.00 | 73 | 52 | 80 | 0 |
| 5.00 | 80 | 55 | 86 | 0 |

TABLE 67

| Percent inhibition of cell proliferation | | | | |
|---|---|---|---|---|
| Dose (μM) | ISIS 549372 | ISIS 549434 | ISIS 549458 | ISIS 554221 |
| 0.04 | 8 | 0 | 7 | 0 |
| 0.20 | 34 | 14 | 31 | 10 |
| 1.00 | 44 | 35 | 45 | 21 |
| 5.00 | 45 | 37 | 41 | 30 |

Example 25

Effect of Antisense Inhibition of Human Androgen Receptor (AR) mRNA by Free Uptake of Antisense Oligonucleotide by LnCaP Cells The effect of free uptake of antisense oligonucleotides on AR mRNA levels was investigated.

Cells were plated at a concentration of 4,000 cells/well in 96-well plates. ISIS oligonucleotides, specified in Table 68, were added individually at 0.02 μM, 0.10 μM, 0.50 μM, 2.50 μM, or 10.00 μM. After an incubation period of 24 hrs, mRNA levels were measured using primer probe set hAR_LTS00943. The data is presented in Table 68. The results indicate that most of the ISIS oligonucleotides inhibited AR mRNA expression more potently than ISIS 554221 at each concentration.

TABLE 68

| Percent inhibition of AR mRNA | | | | | |
|---|---|---|---|---|---|
| ISIS No | 0.02 μM | 0.1 μM | 0.5 μM | 2.5 μM | 10 μM |
| 554221 | 0 | 0 | 0 | 0 | 17 |
| 549372 | 0 | 0 | 21 | 63 | 78 |
| 549458 | 4 | 14 | 67 | 86 | 89 |
| 560131 | 0 | 0 | 13 | 31 | 57 |
| 569213 | 3 | 0 | 31 | 59 | 78 |
| 569216 | 15 | 17 | 49 | 66 | 82 |
| 569221 | 18 | 31 | 49 | 78 | 91 |
| 569227 | 0 | 0 | 4 | 33 | 55 |
| 569236 | 3 | 2 | 21 | 43 | 70 |
| 579666 | 0 | 8 | 30 | 49 | 68 |
| 579667 | 0 | 0 | 8 | 12 | 40 |
| 579671 | 15 | 0 | 19 | 54 | 71 |
| 583918 | 8 | 0 | 0 | 0 | 13 |
| 584149 | 0 | 0 | 0 | 14 | 39 |
| 584163 | 0 | 0 | 19 | 41 | 70 |
| 584269 | 0 | 0 | 0 | 12 | 23 |
| 584468 | 0 | 0 | 10 | 44 | 73 |
| 586124 | 0 | 0 | 19 | 64 | 82 |
| 586227 | 0 | 0 | 14 | 44 | 59 |

Example 26

Effect of Antisense Inhibition of Human Androgen Receptor (AR) mRNA in the Presence of DHT on the Proliferative Ability of 22RV1 Cells Dihydrotestosterone (DHT) is an androgen hormone and AR activator. The effect of antisense inhibition of AR on the proliferative ability of cancer cells treated with DHT was analyzed. ISIS 560131 and ISIS 569236 were tested in the human prostate carcinoma cell line, 22RV1.

22RV1 cells were plated at 1,500 cells per well. ISIS 560131 and ISIS 569236 were individually transfected into the cells using RNAiMAX™ reagent (Life Technologies) at 1.34 nM, 4.00 nM, 13.4 nM, or 40.0 nM concentration. ISIS 549148, which has no known human target sequence, was included as a control. Separate sets of cells, also treated with each of the antisense oligonucleotides, were treated with DHT added on day 1 at a final concentration of 1 nM. After a treatment period of 5 days, the proliferative ability of the cancer cells was measured using the standard MTT assay. Results are presented in Table 69 as percent inhibition of proliferation, relative to non-treated cells.

As presented in Table 69, both ISIS 560131 and ISIS 569236 significantly inhibited prostate cancer cell proliferation even in the presence of AR activator, DHT, compared to the control. The control oligonucleotide did not show any effect on proliferation, as expected.

TABLE 69

| Percent inhibition of 22RV1cell proliferation | | | | |
|---|---|---|---|---|
| | ASO (nM) | ISIS 560131 | ISIS 569236 | ISIS 549148 |
| −DHT | 1.34 | 0 | 0 | 0 |
| | 4.0 | 2 | 18 | 0 |
| | 13.4 | 29 | 47 | 4 |
| | 40.0 | 54 | 64 | 0 |
| +DHT | 1.34 | 0 | 0 | 0 |
| | 4.0 | 1 | 6 | 0 |
| | 13.4 | 13 | 32 | 3 |
| | 40.0 | 34 | 56 | 0 |

Example 27

Time-course Study of Treatment C4-2B Cells with ISIS Oligonucleotides Targeting AR The effect of antisense inhibition of on C4-2B cancer cells on gene expression was analyzed. ISIS 560131 and ISIS 569236 were tested.

AR mRNA Analysis

C4-2B cells were plated at 1,000 cells per well in complete medium. ISIS 560131 or ISIS 569236 was individually added to the culture media to the final concentrations of 0.04 μM, 0.2 μM, 1.0 μM, or 5.0 μM concentrations without using transfection reagent. ISIS 549148 was included as a negative control. MDV3100 was added at dose of 0.04 μM, 0.2 μM, 1.0 μM, or 5.0 μM in a separate set of cells. After a treatment period of 8 hours, 24 hours, and 48 hours, AR expression was measured with primer probe set hAR-LTS00943. Results are presented in Tables 70-72 as percent expression of AR, relative to non-treated cells. Treatment of the cells with ISIS 560131 or ISIS 569236 reduced AR expression in the cells relative to the control set. Treatment with MDV-3100 increased AR expression at the 48 hour time-point.

TABLE 70

Percent expression of AR compared to the control group in 8 hours

| | 0.04 μM | 0.2 μM | 1 μM | 5.0 μM |
|---|---|---|---|---|
| ISIS 560131 | 110 | 85 | 68 | 45 |
| ISIS 569236 | 100 | 87 | 84 | 58 |
| ISIS 549148 | 116 | 105 | 111 | 110 |
| MDV-3100 | 99 | 100 | 92 | 103 |

TABLE 71

Percent expression of AR compared to the control group in 24 hours

| | 0.04 μM | 0.2 μM | 1 μM | 5.0 μM |
|---|---|---|---|---|
| ISIS 560131 | 47 | 18 | 5 | 4 |
| ISIS 569236 | 103 | 35 | 15 | 5 |
| ISIS 549148 | 87 | 85 | 87 | 107 |
| MDV-3100 | 88 | 99 | 96 | 84 |

TABLE 72

Percent expression of AR compared to the control group in 48 hours

| | 0.04 μM | 0.2 μM | 1 μM | 5.0 μM |
|---|---|---|---|---|
| ISIS 560131 | 33 | 5 | 6 | 4 |
| ISIS 569236 | 80 | 19 | 7 | 2 |
| ISIS 549148 | 98 | 90 | 87 | 99 |
| MDV-3100 | 94 | 94 | 113 | 126 |

AR Protein Analysis

Protein levels in the cells were also analyzed. The cells were harvested in RIPA buffer containing protease inhibitors. The presence of bands for full-length AR was detected by western blot using AR antibody (N-20, SC-816, Santa Cruz Biotechnology). Full-length AR was significantly reduced in cells treated with ISIS 560131 or ISIS 569236 for 24 hours and 48 hours, normalized to the levels of the house-keeping gene, GAPDH.

mRNA Expression Analysis of Downstream Genes

Expression analysis of prostate-specific antigen (PSA) and TMPRSS2 were also analyzed. Results are presented in Tables 73-75 as percent inhibition of PSA expression and Tables 76-78 as percent inhibition of TMPRSS2 expression, relative to non-treated cells. Treatment of the cells with ISIS 560131 or ISIS 569236 reduced PSA and TMPRSS2 expression in the cells relative to the control set at the 24 hr and 48 hr time points. Treatment with MDV-3100 also reduced downstream gene expressions but not as potently as that with the ISIS oligonucleotides.

TABLE 73

Percent inhibition of PSA expression compared to the control group in 8 hours

| | 0.04 μM | 0.2 μM | 1 μM | 5.0 μM |
|---|---|---|---|---|
| ISIS 560131 | 12 | 0 | 3 | 1 |
| ISIS 569236 | 18 | 3 | 0 | 0 |
| ISIS 549148 | 1 | 8 | 8 | 0 |
| MDV-3100 | 0 | 3 | 23 | 33 |

TABLE 74

Percent inhibition of PSA expression compared to the control group in 24 hours

| | 0.04 μM | 0.2 μM | 1 μM | 5.0 μM |
|---|---|---|---|---|
| ISIS 560131 | 27 | 46 | 56 | 60 |
| ISIS 569236 | 10 | 34 | 44 | 54 |
| ISIS 549148 | 22 | 13 | 16 | 6 |
| MDV-3100 | 24 | 24 | 53 | 65 |

TABLE 75

Percent inhibition of PSA expression compared to the control group in 48 hours

| | 0.04 μM | 0.2 μM | 1 μM | 5.0 μM |
|---|---|---|---|---|
| ISIS 560131 | 20 | 61 | 71 | 80 |
| ISIS 569236 | 4 | 45 | 68 | 76 |
| ISIS 549148 | 2 | 0 | 18 | 10 |
| MDV-3100 | 5 | 5 | 32 | 63 |

TABLE 76

Percent inhibition of TMPRSS2 expression compared to the control group in 8 hours

| | 0.04 μM | 0.2 μM | 1 μM | 5.0 μM |
|---|---|---|---|---|
| ISIS 560131 | 0 | 0 | 6 | 0 |
| ISIS 569236 | 0 | 0 | 0 | 0 |
| ISIS 549148 | 5 | 0 | 0 | 0 |
| MDV-3100 | 0 | 6 | 45 | 52 |

TABLE 77

Percent inhibition of TMPRSS2 expression compared to the control group in 24 hours

| | 0.04 μM | 0.2 μM | 1 μM | 5.0 μM |
|---|---|---|---|---|
| ISIS 560131 | 35 | 57 | 66 | 67 |
| ISIS 569236 | 10 | 32 | 57 | 66 |
| ISIS 549148 | 29 | 10 | 29 | 10 |
| MDV-3100 | 23 | 31 | 63 | 72 |

TABLE 78

| Percent inhibition of TMPRSS2 expression compared to the control group in 48 hours | | | | |
|---|---|---|---|---|
| | 0.04 µM | 0.2 µM | 1 µM | 5.0 µM |
| ISIS 560131 | 46 | 71 | 77 | 76 |
| ISIS 569236 | 22 | 57 | 70 | 75 |
| ISIS 549148 | 0 | 4 | 0 | 0 |
| MDV-3100 | 5 | 16 | 46 | 59 |

Example 28

Antisense Inhibition of AR mRNA in LNCaP Cells Cultured in Complete Media and CSS Media The effect of antisense inhibition of AR in LNCaP cells cultured in complete medium, as well as CSS medium with DHT, was investigated.

Gene Expression in Complete Medium

Cells were plated at 1,000 cells per well. ISIS 560131 or ISIS 569236 was added individually at 0.04 µM, 0.2 µM, 1.0 µM, or 5.0 µM. ISIS 549148 was included as a negative control. MDV3100 was added a dose of 0.04 µM, 0.2 µM, 1.0 µM, or 5.0 µM. µM in a separate set of cells. After an incubation period of 48 hours, RNA levels of AR, PSA and TMPRSS2 were measured. The data is presented in Tables 79-81.

Protein analysis of full-length AR also demonstrated a dose-dependent decrease of expression, normalized to levels of the house-keeping gene, GAPDH.

TABLE 79

| Percent expression of AR in LNCaP cells cultured in complete medium | | | | |
|---|---|---|---|---|
| | 0.04 µM | 0.2 µM | 1 µM | 5.0 µM |
| ISIS 560131 | 101 | 53 | 17 | 7 |
| ISIS 569236 | 98 | 90 | 47 | 20 |
| ISIS 549148 | 102 | 111 | 109 | 109 |
| MDV-3100 | 111 | 133 | 121 | 139 |

TABLE 80

| Percent inhibition of PSA expression in LNCaP cells cultured in complete medium | | | | |
|---|---|---|---|---|
| | 0.04 µM | 0.2 µM | 1 µM | 5.0 µM |
| ISIS 560131 | 0 | 60 | 87 | 90 |
| ISIS 569236 | 0 | 19 | 63 | 81 |
| ISIS 549148 | 0 | 0 | 0 | 0 |
| MDV-3100 | 0 | 35 | 84 | 87 |

TABLE 81

| Percent inhibition of TMPRSS2 expression in LNCaP cells cultured in complete medium | | | | |
|---|---|---|---|---|
| | 0.04 µM | 0.2 µM | 1 µM | 5.0 µM |
| ISIS 560131 | 0 | 25 | 50 | 51 |
| ISIS 569236 | 0 | 5 | 40 | 48 |
| ISIS 549148 | 0 | 0 | 0 | 0 |
| MDV-3100 | 0 | 0 | 34 | 39 |

Gene Expression in CSS Medium and CSS+DHT Media

Cells were plated at 2,000 cells per well and cultured in phenol red-free RPMI supplemented with 5% charcoal stripped serum (Gibco) media for 16 hours. ISIS 560131 or ISIS 569236 was added individually at 0.04 µM, 0.2 µM, 1.0 µM, or 5.0 µM to each cell set. ISIS 549148 was included as a negative control. MDV3100 was added at 0.04 µM, 0.2 µM, 1.0 µM, or 5.0 µM in a separate set of cells. After an incubation period of 4 hrs, DHT was added to the medium to a final concentration of 1 nM as indicated. RNAs were collected 48 hrs later and levels of AR, PSA and TMPRSS2 were measured. The data is presented in Table 82-85. In the absence of DHT, AR expression in LNCaP cells was 95%, PSA expression was 7% and TMPRSS2 expression was 24% compared to the untreated control.

TABLE 82

| Percent expression of AR in LNCaP cells cultured in CSS medium | | | | |
|---|---|---|---|---|
| | 0.04 µM | 0.2 µM | 1 µM | 5.0 µM |
| ISIS 560131 | 81 | 46 | 16 | 5 |
| ISIS 569236 | 94 | 66 | 35 | 13 |
| ISIS 549148 | 106 | 97 | 96 | 104 |
| MDV-3100 | 91 | 67 | 64 | 77 |

TABLE 83

| Percent expression of AR in LNCaP cells cultured in CSS + DHT medium | | | | |
|---|---|---|---|---|
| | 0.04 µM | 0.2 µM | 1 µM | 5.0 µM |
| ISIS 560131 | 101 | 71 | 27 | 10 |
| ISIS 569236 | 104 | 86 | 55 | 21 |
| ISIS 549148 | 98 | 102 | 96 | 111 |
| MDV-3100 | 107 | 121 | 110 | 113 |

TABLE 84

| Percent inhibition of PSA expression in LNCaP cells cultured in CSS + DHT medium | | | | |
|---|---|---|---|---|
| | 0.04 µM | 0.2 µM | 1 µM | 5.0 µM |
| ISIS 560131 | 10 | 21 | 21 | 72 |
| ISIS 569236 | 4 | 11 | 45 | 59 |
| ISIS 549148 | 0 | 8 | 0 | 9 |
| MDV-3100 | 15 | 38 | 81 | 82 |

TABLE 85

| Percent inhibition of TMPRSS2 expression in LNCaP cells cultured in CSS + DHT medium | | | | |
|---|---|---|---|---|
| | 0.04 µM | 0.2 µM | 1 µM | 5.0 µM |
| ISIS 560131 | 6 | 11 | 26 | 64 |
| ISIS 569236 | 6 | 8 | 40 | 50 |
| ISIS 549148 | 0 | 0 | 1 | 10 |
| MDV-3100 | 8 | 24 | 60 | 69 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One Solution or CellTiter-Glo® solution Cell Proliferation kit (Promega), following the manufacturer's instructions. Results are presented in Tables 86 and 87 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 17% of untreated control levels.

TABLE 86

Proliferation (% untreated control) in LNCaP cells cultured in complete medium

| | 0.04 μM | 0.2 μM | 1 μM | 5.0 μM |
|---|---|---|---|---|
| ISIS 560131 | 96 | 70 | 48 | 45 |
| ISIS 569236 | 100 | 85 | 68 | 54 |
| ISIS 549148 | 101 | 95 | 94 | 110 |
| MDV-3100 | 107 | 88 | 65 | 45 |

TABLE 87

Proliferation (% untreated control) in LNCaP cells cultured in CSS + DHT medium

| | 0.04 μM | 0.2 μM | 1 μM | 5.0 μM |
|---|---|---|---|---|
| ISIS 560131 | 97 | 81 | 46 | 8 |
| ISIS 569236 | 95 | 99 | 54 | 17 |
| ISIS 549148 | 112 | 96 | 95 | 89 |
| MDV-3100 | 112 | 95 | 74 | 33 |

Example 29

Antisense Inhibition of AR mRNA in C4-2 Cells Cultured in Complete Media and CSS Media The effect of antisense inhibition of AR mRNA levels in C4-2 cells cultured in complete medium, as well as CSS medium with DHT, was investigated.

Gene Expression in Complete Medium

Cells were plated at 1,000 cells per well. ISIS 560131 or ISIS 569236 was added individually at 0.04 μM, 0.2 μM, 1.0 μM, or 5.0 μM. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Tables 88-90. Treatment with ISIS oligonucleotide inhibited AR expression, whereas treatment with MDV-3100 increased AR expression in the cells.

Protein analysis of full-length AR and PSA also demonstrated a dose-dependent decrease of expression, normalized to levels of the house-keeping gene, GAPDH.

TABLE 88

Percent expression of AR in C4-2 cells cultured in complete medium

| | 0.04 μM | 0.2 μM | 1 μM | 5.0 μM |
|---|---|---|---|---|
| ISIS 560131 | 48 | 13 | 8 | 8 |
| ISIS 569236 | 72 | 27 | 11 | 9 |
| ISIS 549148 | 89 | 90 | 84 | 86 |
| MDV-3100 | 95 | 99 | 132 | 137 |

TABLE 89

Percent inhibition of PSA expression in C4-2 cells cultured in complete medium

| | 0.04 μM | 0.2 μM | 1 μM | 5.0 μM |
|---|---|---|---|---|
| ISIS 560131 | 48 | 78 | 88 | 89 |
| ISIS 569236 | 35 | 62 | 83 | 88 |
| ISIS 549148 | 15 | 24 | 24 | 23 |
| MDV-3100 | 28 | 40 | 72 | 89 |

TABLE 90

Percent inhibition of TMPRSS2 expression in C4-2 cells cultured in complete medium

| | 0.04 μM | 0.2 μM | 1 μM | 5.0 μM |
|---|---|---|---|---|
| ISIS 560131 | 29 | 62 | 76 | 71 |
| ISIS 569236 | 17 | 54 | 67 | 67 |
| ISIS 549148 | 2 | 7 | 10 | 0 |
| MDV-3100 | 10 | 20 | 44 | 67 |

Gene Expression in CSS+DHT Media

Cells were plated at 2,000 cells per well and cultured in CSS media with 1 nM DHT. ISIS 560131 or ISIS 569236 was added individually at 0.04 μM, 0.2 μM, 1.0 μM, or 5.0 μM to each cell set. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Table 91-93. In the absence of DHT, AR expression in C4-2 cells was 153%, PSA expression was 42% and TMPRSS2 expression was 23% compared to the untreated control. Treatment with ISIS oligonucleotide inhibited AR expression, whereas treatment with MDV-3100 increased AR expression in the cells.

TABLE 91

Percent expression of AR in C4-2 cells cultured in CSS + DHT medium

| | 0.04 μM | 0.2 μM | 1 μM | 5.0 μM |
|---|---|---|---|---|
| ISIS 560131 | 88 | 57 | 20 | 15 |
| ISIS 569236 | 89 | 82 | 52 | 23 |
| ISIS 549148 | 101 | 101 | 118 | 111 |
| MDV-3100 | 101 | 109 | 156 | 148 |

TABLE 92

Percent inhibition of PSA expression in C4-2 cells cultured in CSS + DHT medium

| | 0.04 μM | 0.2 μM | 1 μM | 5.0 μM |
|---|---|---|---|---|
| ISIS 560131 | 10 | 24 | 49 | 74 |
| ISIS 569236 | 0 | 4 | 57 | 64 |
| ISIS 549148 | 0 | 8 | 21 | 22 |
| MDV-3100 | 9 | 8 | 51 | 73 |

TABLE 93

| Percent inhibition of TMPRSS2 expression in C4-2 cells cultured in CSS + DHT medium | | | | |
|---|---|---|---|---|
| | 0.04 μM | 0.2 μM | 1 μM | 5.0 μM |
| ISIS 560131 | 10 | 17 | 51 | 78 |
| ISIS 569236 | 0 | 11 | 61 | 67 |
| ISIS 549148 | 3 | 0 | 22 | 28 |
| MDV-3100 | 9 | 0 | 44 | 78 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One Solution or CellTiter-Glo® Cell Proliferation kit (Promega), following the manufacturer's instructions. Results are presented in Tables 94 and 95 as percent inhibition of proliferation, relative to non-treated cells. Treatment of the cells with ISIS 560131, ISIS 569236, and MDV-3100 reduced proliferation of the cells in a dose dependent manner compared to the control. The proliferative capacity of cells cultured in CSS medium without DHT is 17% of untreated control levels.

TABLE 94

| Proliferation (% untreated control) in C4-2 cells cultured in complete medium | | | | |
|---|---|---|---|---|
| | 0.04 μM | 0.2 μM | 1 μM | 5.0 μM |
| ISIS 560131 | 104 | 82 | 70 | 51 |
| ISIS 569236 | 103 | 81 | 57 | 58 |
| ISIS 549148 | 106 | 112 | 91 | 94 |
| MDV-3100 | 105 | 108 | 71 | 67 |

TABLE 95

| Proliferation (% untreated control) in C4-2 cells cultured in CSS + DHT medium | | | | |
|---|---|---|---|---|
| | 0.04 μM | 0.2 μM | 1 μM | 5.0 μM |
| ISIS 560131 | 106 | 94 | 47 | 31 |
| ISIS 569236 | 99 | 99 | 88 | 51 |
| ISIS 549148 | 102 | 82 | 82 | 91 |
| MDV-3100 | 122 | 124 | 87 | 22 |

Example 30

Antisense Inhibition of AR mRNA in C4-2B Cells Cultured in Complete Media and CSS Media The effect of antisense inhibition of AR mRNA levels in C4-2B cells cultured in complete medium, as well as CSS medium with DHT, was investigated.

Gene Expression in Complete Medium

Cells were plated at 1,000 cells per well. ISIS 560131 or ISIS 569236 was added individually at 0.04 μM, 0.2 μM, 1.0 μM, or 5.0 μM. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Tables 96-98. Treatment with ISIS oligonucleotide inhibited AR expression, whereas treatment with MDV-3100 increased AR expression in the cells.

Protein analysis of full-length AR also demonstrated a dose-dependent decrease of expression, normalized to levels of the house-keeping gene, GAPDH.

TABLE 96

| Percent expression of AR in C4-2B cells cultured in complete medium | | | | |
|---|---|---|---|---|
| | 0.04 μM | 0.2 μM | 1 μM | 5.0 μM |
| ISIS 560131 | 34 | 15 | 14 | 14 |
| ISIS 569236 | 61 | 23 | 20 | 16 |
| ISIS 549148 | 101 | 91 | 88 | 87 |
| MDV-3100 | 108 | 121 | 157 | 182 |

TABLE 97

| Percent inhibition of PSA expression in C4-2B cells cultured in complete medium | | | | |
|---|---|---|---|---|
| | 0.04 μM | 0.2 μM | 1 μM | 5.0 μM |
| ISIS 560131 | 56 | 84 | 89 | 92 |
| ISIS 569236 | 30 | 72 | 81 | 89 |
| ISIS 549148 | 3 | 11 | 18 | 14 |
| MDV-3100 | 8 | 27 | 73 | 88 |

TABLE 98

| Percent inhibition of TMPRSS2 expression in C4-2B cells cultured in complete medium | | | | |
|---|---|---|---|---|
| | 0.04 μM | 0.2 μM | 1 μM | 5.0 μM |
| ISIS 560131 | 46 | 71 | 72 | 75 |
| ISIS 569236 | 33 | 59 | 69 | 73 |
| ISIS 549148 | 0 | 2 | 4 | 0 |
| MDV-3100 | 3 | 24 | 55 | 71 |

Gene Expression in CSS+DHT Media

Cells were plated at 2,000 cells per well and cultured in CSS media with 1 nM DHT. ISIS 560131 or ISIS 569236 was added individually at 0.04 μM, 0.2 μM, 1.0 μM, or 5.0 μM to each cell set. ISIS 549148 was included as a negative control. MDV3100 was added at 0.04 μM, 0.2 μM, 1.0 μM, or 5.0 μM in a separate set of cells. After an incubation period of 48 hrs, RNA levels of AR, PSA and TMPRSS2 were measured. The data is presented in Tables 99-101. In the absence of DHT, AR expression in C4-2 cells was 188%, PSA expression was 43% and TMPRSS2 expression was 27% compared to the untreated control. Treatment with ISIS oligonucleotide inhibited AR expression, whereas treatment with MDV-3100 increased AR expression in the cells.

TABLE 99

| Percent expression of AR in C4-2B cells cultured in CSS + DHT medium | | | | |
|---|---|---|---|---|
| | 0.04 μM | 0.2 μM | 1 μM | 5.0 μM |
| ISIS 560131 | 55 | 31 | 15 | 13 |
| ISIS 569236 | 67 | 49 | 24 | 19 |
| ISIS 549148 | 91 | 104 | 101 | 95 |
| MDV-3100 | 112 | 144 | 165 | 173 |

TABLE 100

| Percent inhibition of PSA expression in C4-2B cells cultured in CSS + DHT medium | | | | |
|---|---|---|---|---|
| | 0.04 μM | 0.2 μM | 1 μM | 5.0 μM |
| ISIS 560131 | 0 | 17 | 50 | 61 |
| ISIS 569236 | 0 | 5 | 33 | 46 |
| ISIS 549148 | 0 | 0 | 0 | 0 |
| MDV-3100 | 0 | 0 | 37 | 45 |

TABLE 101

| Percent inhibition of TMPRSS2 expression in C4-2B cells cultured in CSS + DHT medium | | | | |
|---|---|---|---|---|
| | 0.04 μM | 0.2 μM | 1 μM | 5.0 μM |
| ISIS 560131 | 0 | 34 | 60 | 76 |
| ISIS 569236 | 0 | 6 | 43 | 59 |
| ISIS 549148 | 0 | 0 | 0 | 3 |
| MDV-3100 | 0 | 11 | 48 | 66 |

Effect on Proliferation in CSS Medium and CSS+DHT Media

After a treatment period of 5 days in complete medium or CSS+1 nM DHT medium, the proliferative capacity of the cancer cells was measured with using CellTiter 96® AQueous One or CellTiter-Glo® Solution Cell Proliferation kit (Promega), following the manufacturer's instructions. Results are presented in Tables 102 and 103 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 12% of untreated control levels.

TABLE 102

| Proliferation (% untreated control) in C4-2B cells cultured in complete medium | | | | |
|---|---|---|---|---|
| | 0.04 μM | 0.2 μM | 1 μM | 5.0 μM |
| ISIS 560131 | 93 | 50 | 50 | 41 |
| ISIS 569236 | 98 | 64 | 55 | 48 |
| ISIS 549148 | 119 | 97 | 103 | 98 |
| MDV-3100 | 131 | 105 | 72 | 60 |

TABLE 103

| Proliferation (% untreated control) in C4-2B cells cultured in CSS + DHT medium | | | | |
|---|---|---|---|---|
| | 0.04 μM | 0.2 μM | 1 μM | 5.0 μM |
| ISIS 560131 | 111 | 75 | 49 | 40 |
| ISIS 569236 | 109 | 109 | 67 | 39 |
| ISIS 549148 | 109 | 131 | 119 | 114 |
| MDV-3100 | 125 | 100 | 83 | 17 |

Example 31

Antisense Inhibition of AR mRNA in VCaP Cells Cultured in Complete Media and CSS Media The effect of antisense inhibition of AR in VCaP prostate cancer cells (Korenchuk, S. et al., In Vivo. 2001. 15: 163-168)

cultured in complete medium, as well as CSS medium with DHT, was investigated. VCaP cells express both full length AR, as well as the V7 variant.

Gene Expression in Complete Medium

Cells were plated at 10,000 cells per well. ISIS 560131 or ISIS 569236 was added individually at 1.34 nM, 4 nM, 13.4 nM, or 40 nM using RNAiMax transfection reagent. ISIS 549148 was included as a negative control. After an incubation period of 48 hrs, RNA levels of full length AR, the V7 variant, PSA and TMPRSS2 were measured. The data is presented in Tables 104-107.

Protein analysis of full-length AR and the V7 variant also demonstrated a dose-dependent decrease of expression of both compared to levels of the house-keeping gene, GAPDH.

TABLE 104

| Percent inhibition of full-length AR in VCaP cells cultured in complete medium | | | | |
|---|---|---|---|---|
| | 1.34 nM | 4.0 nM | 13.4 nM | 40 nM |
| ISIS 560131 | 0 | 59 | 77 | 84 |
| ISIS 569236 | 0 | 41 | 49 | 74 |
| ISIS 549148 | 0 | 8 | 5 | 17 |

TABLE 105

| Percent inhibition of AR V7 variant in VCaP cells cultured in complete medium | | | | |
|---|---|---|---|---|
| | 1.34 nM | 4.0 nM | 13.4 nM | 40 nM |
| ISIS 560131 | 0 | 57 | 78 | 84 |
| ISIS 569236 | 0 | 40 | 53 | 80 |
| ISIS 549148 | 0 | 8 | 0 | 14 |

TABLE 106

| Percent inhibition of PSA expression in VCaP cells cultured in complete medium | | | | |
|---|---|---|---|---|
| | 1.34 nM | 4.0 nM | 13.4 nM | 40 nM |
| ISIS 560131 | 2 | 24 | 35 | 46 |
| ISIS 569236 | 7 | 19 | 40 | 52 |
| ISIS 549148 | 2 | 0 | 0 | 20 |

TABLE 107

| Percent inhibition of TMPRSS2 expression in VCaP cells cultured in complete medium | | | | |
|---|---|---|---|---|
| | 1.34 nM | 4.0 nM | 13.4 nM | 40 nM |
| ISIS 560131 | 0 | 0 | 0 | 4 |
| ISIS 569236 | 0 | 0 | 0 | 36 |
| ISIS 549148 | 0 | 0 | 0 | 0 |

A separate set of cells was treated with MDV-3100 at 0.04 μM, 0.2 μM, 1.0 μM, or 5.0 μM. After an incubation period of 48 hrs, RNA levels of full length AR, the V7 variant, PSA and TMPRSS2 were measured. The data is presented in Tables 108 expressed as percent expression of gene levels compared to the untreated control.

TABLE 108

| Percent of gene expression in VCaP cells treated with MDV-3100 and cultured in complete medium | | | | |
|---|---|---|---|---|
| | 0.04 μM | 0.2 μM | 1.0 μM | 5.0 μM |
| Full length AR | 136 | 135 | 160 | 178 |
| AR V7 variant | 172 | 179 | 244 | 237 |
| PSA | 105 | 76 | 75 | 61 |
| TMPRSS2 | 131 | 121 | 135 | 141 |

Gene Expression in CSS+DHT Media

Cells were plated at 15,000 cells per well and cultured in CSS media for 16 hours. Cells were then transfected using RNAiMax reagent with ISIS 560131 or ISIS 569236 at 1.34 nM, 4 nM, 13.4 nM, or 40 nM to each cell set. ISIS 549148 was included as a negative control. After 4 hrs, 1 nM DHT was added. MDV3100 was added in a separate set of cells at doses of 0.04 μM, 0.2 μM, 1.0 μM, or 5.0 μM. After an incubation period of 48 hrs, RNA levels of AR, PSA and TMPRSS2 were measured. The data is presented in Tables 109-113. In the absence of DHT, AR expression in VCaP cells was 555%, V7 variant expression was 656%, PSA expression was 11%, and TMPRSS2 expression was 22% compared to the untreated control.

TABLE 109

| Percent inhibition of full-length AR in VCaP cells cultured in CSS + DHT medium | | | | |
|---|---|---|---|---|
| | 1.34 nM | 4.0 nM | 13.4 nM | 40 nM |
| ISIS 560131 | 12 | 16 | 37 | 38 |
| ISIS 569236 | 23 | 21 | 38 | 35 |
| ISIS 549148 | 0 | 0 | 0 | 0 |

TABLE 110

| Percent inhibition of AR V7 variant in VCaP cells cultured in CSS + DHT medium | | | | |
|---|---|---|---|---|
| | 1.34 nM | 4.0 nM | 13.4 nM | 40 nM |
| ISIS 560131 | 27 | 31 | 39 | 41 |
| ISIS 569236 | 37 | 33 | 48 | 39 |
| ISIS 549148 | 12 | 0 | 0 | 5 |

TABLE 111

| Percent inhibition of PSA expression in VCaP cells cultured in CSS + DHT medium | | | | |
|---|---|---|---|---|
| | 1.34 nM | 4.0 nM | 13.4 nM | 40 nM |
| ISIS 560131 | 0 | 35 | 69 | 73 |
| ISIS 569236 | 8 | 25 | 62 | 74 |
| ISIS 549148 | 0 | 3 | 9 | 0 |

TABLE 112

| Percent inhibition of TMPRSS2 expression in VCaP cells cultured in CSS + DHT medium | | | | |
|---|---|---|---|---|
| | 1.34 nM | 4.0 nM | 13.4 nM | 40 nM |
| ISIS 560131 | 0 | 21 | 49 | 57 |
| ISIS 569236 | 6 | 19 | 40 | 54 |
| ISIS 549148 | 0 | 0 | 0 | 0 |

TABLE 113

| Percent of gene expression in VCaP cells treated with MDV-3100 and cultured in CSS + DHT medium | | | | |
|---|---|---|---|---|
| | 0.04 μM | 0.2 μM | 1.0 μM | 5.0 μM |
| Full length AR | 114 | 94 | 142 | 233 |
| AR V7 variant | 82 | 65 | 101 | 181 |
| PSA | 90 | 72 | 57 | 30 |
| TMPRSS2 | 115 | 96 | 70 | 42 |

Effect on Proliferation

After a treatment period of 5 days in complete medium or CSS+1 nM DHT medium, the proliferative capacity of the cancer cells was measured with using CellTiter 96® AQueous One or CellTiter-Glo® Solution Cell Proliferation kit (Promega), following the manufacturer's instructions. Results are presented in Tables 114-116 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 12% of untreated control levels.

TABLE 114

| Proliferation (% untreated control) in VCaP cells cultured in complete medium | | | | |
|---|---|---|---|---|
| | 1.34 nM | 4.0 nM | 13.4 nM | 40 nM |
| ISIS 560131 | 98 | 66 | 53 | 48 |
| ISIS 569236 | 98 | 76 | 68 | 59 |
| ISIS 549148 | 98 | 98 | 113 | 106 |

TABLE 115

| Proliferation (% untreated control) in VCaP cells cultured in CSS + DHT medium | | | | |
|---|---|---|---|---|
| | 1.34 nM | 4.0 nM | 13.4 nM | 40 nM |
| ISIS 560131 | 95 | 65 | 42 | 37 |
| ISIS 569236 | 83 | 68 | 61 | 45 |
| ISIS 549148 | 114 | 123 | 104 | 92 |

TABLE 116

| Proliferation (% untreated control) in VCaP cells treated with MDV-3100 | | |
|---|---|---|
| | Complete medium | CSS + DHT medium |
| 0.04 μM | 49 | 117 |
| 0.2 μM | 44 | 119 |
| 1.0 μM | 27 | 71 |
| 5.0 μM | 17 | 65 |

Effect on Apoptosis

After a treatment period of 72 hours in complete medium, apoptosis of the cancer cells was measured with Caspase-Glo 3/7 assay (Promega). Results are presented in Tables 117 and 118 as percent apoptosis of the cells, relative to non-treated cells. Treatment of the cells with ISIS 560131, ISIS 569236, and MDV-3100 increased apoptosis of the cells in a dose dependent compared to the control.

Apoptosis was also measured by protein western blot analysis of cleaved PARP levels, which were shown to be increased in a dose-dependent manner in cells treated with ISIS 560131, ISIS 569236, and MDV-3100.

TABLE 117

Apoptosis (% untreated control) in VCaP cells cultured in complete medium

| | 1.34 nM | 4.0 nM | 13.4 nM | 40 nM |
|---|---|---|---|---|
| ISIS 560131 | 189 | 253 | 356 | 262 |
| ISIS 569236 | 176 | 293 | 402 | 581 |
| ISIS 549148 | 131 | 108 | 103 | 146 |

TABLE 118

Apoptosis (% untreated control) in VCaP cells treated with MDV-3100

| | % |
|---|---|
| 0.04 µM | 186 |
| 0.2 µM | 210 |
| 1.0 µM | 612 |
| 5.0 µM | 528 |

Example 32

Antisense Inhibition of AR mRNA in 22RV1 Cells Cultured in Complete Media and CSS Media The effect of antisense inhibition of AR in 22RV1 cells cultured in complete medium, as well as CSS medium with DHT, was investigated.

Gene Expression in Complete Medium

Cells were plated at 1,000 cells per well. ISIS 560131 or ISIS 569236 was added individually at 1.34 nM, 4 nM, 13.4 nM, or 40 nM using RNAiMax transfection reagent. ISIS 549148 was included as a negative control. After an incubation period of 48 hrs, RNA levels of full length AR, the V7 variant, PSA and TMPRSS2 were measured. The data is presented in Tables 119-122.

Protein analysis of full-length AR and the V7 variant also demonstrated a dose-dependent decrease of expression compared to levels of the house-keeping gene, GAPDH.

TABLE 119

Percent inhibition of full-length AR in 22RV1 cells cultured in complete medium

| | 1.34 nM | 4.0 nM | 13.4 nM | 40 nM |
|---|---|---|---|---|
| ISIS 560131 | 7 | 19 | 49 | 76 |
| ISIS 569236 | 17 | 15 | 37 | 71 |
| ISIS 549148 | 6 | 0 | 11 | 17 |

TABLE 120

Percent inhibition of AR V7 variant in 22RV1 cells cultured in complete medium

| | 1.34 nM | 4.0 nM | 13.4 nM | 40 nM |
|---|---|---|---|---|
| ISIS 560131 | 12 | 29 | 57 | 81 |
| ISIS 569236 | 30 | 2 | 46 | 81 |
| ISIS 549148 | 0 | 0 | 22 | 26 |

TABLE 121

Percent inhibition of PSA expression in 22RV1 cells cultured in complete medium

| | 1.34 nM | 4.0 nM | 13.4 nM | 40 nM |
|---|---|---|---|---|
| ISIS 560131 | 10 | 20 | 27 | 36 |
| ISIS 569236 | 0 | 17 | 25 | 7 |
| ISIS 549148 | 9 | 11 | 17 | 27 |

TABLE 122

Percent inhibition of TMPRSS2 expression in 22RV1 cells cultured in complete medium

| | 1.34 nM | 4.0 nM | 13.4 nM | 40 nM |
|---|---|---|---|---|
| ISIS 560131 | 7 | 3 | 19 | 32 |
| ISIS 569236 | 0 | 13 | 21 | 36 |
| ISIS 549148 | 15 | 9 | 14 | 4 |

A separate set of cells was treated with MDV-3100 at 0.04 µM, 0.2 µM, 1.0 µM, or 5.0 µM. After an incubation period of 48 hrs, RNA levels of full length AR, the V7 variant, PSA and TMPRSS2 were measured. The data is presented in Tables 123 expressed as percent expression of gene levels compared to the untreated control.

TABLE 123

Percent of gene expression in 22RV1 cells treated with MDV-3100 and cultured in complete medium

| | 0.04 µM | 0.2 µM | 1.0 µM | 5.0 µM |
|---|---|---|---|---|
| Full length AR | 103 | 93 | 81 | 83 |
| AR V7 variant | 106 | 98 | 87 | 77 |
| PSA | 83 | 70 | 71 | 86 |
| TMPRSS2 | 101 | 80 | 82 | 93 |

Gene Expression in CSS+DHT Media

Cells were plated at 2,000 cells per well and cultured in CSS media for 16 hours. Cells were then transfected using RNAiMax reagent with ISIS 560131 or ISIS 569236 at 1.34 nM, 4 nM, or 13.4 nM to each cell set. ISIS 549148 was included as a negative control. After 4 hrs, 1 nM DHT was added. MDV3100 was added in a separate set of cells at doses of 0.04 µM, 0.2 µM, 1.0 µM, or 5.0 µM. After an incubation period of 48 hrs, RNA levels of AR, AR V7 variant, PSA and TMPRSS2 were measured. The data is presented in Tables 124-128. In the absence of DHT, AR expression in VCaP cells was 555%, V7 variant expression was 656%, PSA expression was 11%, and TMPRSS2 expression was 22% compared to the untreated control.

Treatment with ISIS oligonucleotides resulted in significant inhibition of full length AR and the V7 variant, as well as downstream gene expression. Treatment with ISIS oligonucleotides resulted in inhibition of gene expression to a greater extent than treatment with MVD-3100.

TABLE 124

| Percent inhibition of full-length AR in 22RV1 cells cultured in CSS + DHT medium | | | |
|---|---|---|---|
| | 1.34 nM | 4.0 nM | 13.4 nM |
| ISIS 560131 | 65 | 85 | 93 |
| ISIS 569236 | 59 | 89 | 97 |
| ISIS 549148 | 2 | 13 | 22 |

TABLE 125

| Percent inhibition of AR V7 variant in 22RV1 cells cultured in CSS + DHT medium | | | |
|---|---|---|---|
| | 1.34 nM | 4.0 nM | 13.4 nM |
| ISIS 560131 | 63 | 83 | 93 |
| ISIS 569236 | 54 | 88 | 97 |
| ISIS 549148 | 19 | 19 | 32 |

TABLE 126

| Percent inhibition of PSA expression in 22RV1 cells cultured in CSS + DHT medium | | | |
|---|---|---|---|
| | 1.34 nM | 4.0 nM | 13.4 nM |
| ISIS 560131 | 3 | 50 | 66 |
| ISIS 569236 | 28 | 49 | 70 |
| ISIS 549148 | 8 | 23 | 29 |

TABLE 127

| Percent inhibition of TMPRSS2 expression in 22RV1 cells cultured in CSS + DHT medium | | | |
|---|---|---|---|
| | 1.34 nM | 4.0 nM | 13.4 nM |
| ISIS 560131 | 39 | 50 | 59 |
| ISIS 569236 | 27 | 50 | 75 |
| ISIS 549148 | 0 | 3 | 1 |

TABLE 128

| Percent of gene expression in 22RV1 cells treated with MDV-3100 and cultured in CSS + DHT medium | | | | |
|---|---|---|---|---|
| | 0.04 μM | 0.2 μM | 1.0 μM | 5.0 μM |
| Full length AR | 5 | 11 | 6 | 18 |
| AR V7 variant | 16 | 17 | 19 | 12 |
| PSA | 15 | 19 | 18 | 16 |
| TMPRSS2 | 17 | 9 | 26 | 18 |

Effect on Proliferation

After a treatment period of 5 days in complete medium, the proliferative capacity of the cancer cells was measured with using CellTiter 96® AQueous One or CellTiter-Glo® Solution Cell Proliferation kit (Promega), following the manufacturer's instructions. Results are presented in Tables 129 and 130 as percent inhibition of proliferation, relative to non-treated cells. Treatment of the cells with ISIS 560131, ISIS 569236, and MDV-3100 reduced proliferation of the cells in a dose dependent compared to the control. Treatment with ISIS oligonucleotides in CSS+DHT medium reduced the proliferative capacity to a greater extent than treatment with MVD-3100. The proliferative capacity of cells cultured in CSS medium without DHT is 12% of untreated control levels.

TABLE 129

| Proliferation (% untreated control) in 22RV1 cells cultured in complete medium | | | | |
|---|---|---|---|---|
| | 1.34 nM | 4.0 nM | 13.4 nM | 40 nM |
| ISIS 560131 | 94 | 72 | 50 | 17 |
| ISIS 569236 | 92 | 53 | 20 | 7 |
| ISIS 549148 | 97 | 97 | 101 | 83 |

TABLE 130

| Proliferation (% untreated control) in 22RV1 cells treated with MDV-3100 | |
|---|---|
| | % |
| 0.04 μM | 87 |
| 0.2 μM | 83 |
| 1.0 μM | 81 |
| 5.0 μM | 74 |

Effect on Apoptosis

After a treatment period of 72 hours in complete medium or CSS+DHT medium, apoptosis of the cancer cells was measured with Caspase-glo 3/7 assay kit (Promega). Results are presented in Tables 131 and 132 as percent apoptosis of the cells, relative to non-treated cells. Treatment of the cells with ISIS 560131 and ISIS 569236 increased apoptosis of the cells in a dose dependent compared to the control.

TABLE 131

| Apoptosis (% untreated control) in 22RV1 cells cultured in complete medium | | | | |
|---|---|---|---|---|
| | 1.34 nM | 4.0 nM | 13.4 nM | 40 nM |
| ISIS 560131 | 99 | 127 | 131 | 566 |
| ISIS 569236 | 91 | 141 | 333 | 1452 |
| ISIS 549148 | 81 | 76 | 72 | 123 |

TABLE 132

| Apoptosis (% untreated control) in 22RV1 cells cultured in CSS + DHT medium | | | | |
|---|---|---|---|---|
| | 1.34 nM | 4.0 nM | 13.4 nM | 40 nM |
| ISIS 560131 | 121 | 113 | 172 | 518 |
| ISIS 569236 | 127 | 106 | 257 | 1136 |
| ISIS 549148 | 113 | 94 | 102 | 108 |

Example 33

Effect of ISIS Antisense Oligonucleotides Targeting Human Androgen Receptor in Cynomolgus Monkeys Cynomolgus monkeys were treated with ISIS antisense oligonucleotides selected from studies described above. Antisense oligonucleotide efficacy and tolerability were evaluated. The human antisense oligonucleotides tested are cross-reactive with the rhesus genomic sequence (GENBANK Accession No. NW_001218131.1 truncated from nucleotides 134001 to 308000 and designated herein as SEQ ID NO: 189). The target start site and target region of each oligonucleotide to SEQ ID NO: 189, as well as the details of their chemistry and sequence, is presented in Table 133.

TABLE 133

| Antisense oligonucleotides complementary to SEQ ID NO: 189 | | | | | |
|---|---|---|---|---|---|
| ISIS No | Target Start Site | Target Region | Sequence | Chemistry | SEQ ID NO |
| 560131 | 59450 | Intron | TTGATTTAATGGTTGC | Deoxy, MOE, and (S)-cEt | 35 |
| 569213 | 59449<br>59479 | Intron | TGATTTAATGGTTGCA<br>TGATTTAATGGTTGCA | Deoxy, MOE, and (S)-cEt | 39<br>39 |
| 569216 | 59449<br>59479 | Intron | TGATTTAATGGTTGCA<br>TGATTTAATGGTTGCA | Deoxy, MOE, and (S)-cEt | 39<br>39 |
| 569221 | 59449<br>59479 | Intron | TGATTTAATGGTTGCA<br>TGATTTAATGGTTGCA | Deoxy, MOE, and (S)-cEt | 39<br>39 |
| 569236 | 59449<br>59479 | Intron | TGATTTAATGGTTGCA<br>TGATTTAATGGTTGCA | Deoxy, MOE, and (S)-cEt | 39<br>39 |
| 579671 | 59450 | Intron | TTGATTTAATGGTTGC | Deoxy, MOE, and (S)-cEt | 35 |
| 586124 | 59448 | Intron | GATTTAATGGTTGCAA | 3-10-3 (S)-cEt | 43 |
| 583918 | 3754 | Exon | AGTCGCGACTCTGGTA | 3-10-3 (S)-cEt | 124 |
| 584149 | 7260 | Intron | GTCAATATCAAAGCAC | 3-10-3 (S)-cEt | 150 |
| 584163 | 9811 | Intron | GAACATTATTAGGCTA | 3-10-3 (S)-cEt | 155 |
| 584269 | 41322 | Intron | CCTTATGGATGCTGCT | 3-10-3 (S)-cEt | 169 |
| 584468 | 109552 | Intron | CATTGTACTATGCCAG | 3-10-3 (S)-cEt | 175 |

Treatment

Prior to the study, the monkeys were kept in quarantine for a 30-day period, during which the animals were observed daily for general health. The monkeys were 2-4 years old and weighed between 2 and 4 kg. Thirteen groups of four randomly assigned male cynomolgus monkeys each were injected subcutaneously with ISIS oligonucleotide or PBS. PBS solution or ISIS oligonucleotides, at a dose of 40 mg/kg, were administered with a loading regimen consisting of four doses on the first week of the study (days 1, 3, 5, and 7), followed by a maintenance regimen consisting of once weekly administration starting on Day 14 (weeks 2 to 6). Subcutaneous injections were performed in clock-wise rotations at 4 sites on the back; one site per dose. The injection sites were delineated by tattoo, while sedated using ketamine, and were separated by a minimum of 3 cm.

During the study period, the monkeys were observed a minimum of once daily for signs of illness or distress. The protocols described in the Example were approved by the Institutional Animal Care and Use Committee (IACUC).

Target Reduction

RNA Analysis

RNA was extracted from liver, heart, skeletal muscle, kidney, and prostate tissues for real-time PCR analysis of AR using primer probe set RTS3559. The results were normalized to RIBOGREEN®. Results are presented as percent inhibition of AR mRNA, relative to PBS control. As shown in Table 134, treatment with ISIS antisense oligonucleotides resulted in significant reduction of AR mRNA, relative to the PBS control. 'n/a' indicates that mRNA levels were not measured in that organ.

TABLE 134

| Percent Inhibition of AR mRNA in the cynomolgus monkey relative to the PBS control | | | | | |
|---|---|---|---|---|---|
| ISIS No | Heart | Skeletal Muscle | Kidney | Liver | Prostate |
| 560131 | 32 | 30 | 19 | 65 | 27 |
| 569221 | 52 | 35 | 31 | 60 | n/a |
| 569236 | 42 | 47 | 42 | 33 | 32 |
| 579671 | 24 | 31 | 53 | 33 | n/a |
| 583918 | 76 | 74 | 73 | 88 | 58 |
| 584149 | 33 | 63 | 77 | 93 | 45 |
| 584163 | 53 | 73 | 90 | 98 | 58 |
| 584269 | 72 | 76 | 92 | 96 | 41 |
| 584468 | 33 | 53 | 88 | 97 | 50 |

Protein Analysis

Serum testosterone protein levels were measured in the plasma with an ELISA kit (Enzo Life Sciences), following the manufacturer's instructions. The results are presented in Table 135, expressed in ng/mL. The results indicate that some of the ISIS oligonucleotides reduced testosterone protein levels.

TABLE 135

| Testosterone protein levels in the cynomolgus monkey | |
|---|---|
| | ng/mL |
| PBS | 12.6 |
| ISIS 560131 | 14.7 |
| ISIS 569221 | 8.8 |
| ISIS 569236 | 12.7 |
| ISIS 579671 | 7.3 |
| ISIS 584269 | 14.1 |
| ISIS 584468 | 13.6 |

Tolerability Studies

Body and Organ Weight Measurements

To evaluate the effect of ISIS oligonucleotides on the overall health of the animals, body and organ weights were measured. Body weights were measured on day 42 and are presented in Table 136. Organ weights were measured at the time of euthanasia and the data is also presented in Table 136. Specifically, treatment with ISIS 560131 was well tolerated in terms of the body and organ weights of the monkeys.

TABLE 136

Final body and organ weights in cynomolgus monkeys

| Treatment | Body Wt (kg) | Spleen (g) | Heart (g) | Kidney (g) | Mesenteric lymph nodes (g) | Liver (g) |
|---|---|---|---|---|---|---|
| PBS | 2.5 | 2.6 | 8.5 | 13 | 1.4 | 58 |
| ISIS 560131 | 2.4 | 2.5 | 9.8 | 12 | 2.0 | 58 |
| ISIS 569213 | 2.4 | 5.3 | 8.3 | 16 | 2.4 | 69 |
| ISIS 569216 | 2.6 | 4.9 | 9.3 | 15 | 2.7 | 71 |
| ISIS 569221 | 2.5 | 3.3 | 8.5 | 14 | 3.5 | 68 |
| ISIS 569236 | 2.4 | 3.2 | 8.4 | 12 | 2.4 | 56 |
| ISIS 579671 | 2.4 | 3.2 | 8.8 | 14 | 2.5 | 62 |
| ISIS 586124 | 2.5 | 3.3 | 9.4 | 14 | 2.8 | 58 |
| ISIS 583918 | 2.5 | 4.6 | 8.9 | 12 | 3.5 | 60 |
| ISIS 584149 | 2.5 | 2.2 | 9.3 | 13 | 2.1 | 60 |
| ISIS 584163 | 2.5 | 3.2 | 8.4 | 15 | 3.3 | 54 |
| ISIS 584269 | 2.5 | 4.7 | 8.7 | 13 | 3.6 | 60 |
| ISIS 584468 | 2.5 | 4.1 | 8.3 | 13 | 3.8 | 60 |

Liver Function

To evaluate the effect of ISIS oligonucleotides on hepatic function, the monkeys were fasted overnight. Approximately, 1.5 mL of blood samples were collected on day 44 from all the study groups. Blood was collected in tubes without anticoagulant for serum separation. The tubes were kept at room temperature for a minimum of 90 min and then centrifuged at 3,000 rpm for 10 min. Levels of various liver function markers were measured using a Toshiba 120FR NEO chemistry analyzer (Toshiba Co., Japan). The results are presented in Table 137. Specifically, treatment with ISIS 560131 was well tolerated in terms of the liver function markers.

TABLE 137

Liver function markers in cynomolgus monkey plasma

| Treatment | Albumin (g/dL) | AST (IU/L) | ALT (IU/L) |
|---|---|---|---|
| PBS | 4.2 | 37 | 39 |
| ISIS 560131 | 4.0 | 87 | 68 |
| ISIS 569213 | 3.7 | 80 | 47 |
| ISIS 569216 | 3.7 | 93 | 75 |
| ISIS 569221 | 4.0 | 73 | 48 |
| ISIS 569236 | 4.1 | 45 | 35 |
| ISIS 579671 | 4.0 | 53 | 56 |
| ISIS 586124 | 3.9 | 94 | 56 |
| ISIS 583918 | 4.1 | 73 | 75 |
| ISIS 584149 | 4.5 | 58 | 57 |
| ISIS 584163 | 4.2 | 68 | 50 |
| ISIS 584269 | 4.0 | 81 | 75 |
| ISIS 584468 | 4.0 | 52 | 46 |

Hematology

To evaluate any effect of ISIS oligonucleotides in cynomolgus monkeys on hematologic parameters, blood samples of approximately 0.5 mL of blood was collected day 44 from each of the available study animals in tubes containing $K_2$-EDTA. Samples were analyzed for red blood cell (RBC) count, white blood cells (WBC) count, platelet count, hemoglobin content and hematocrit, using an ADVIA2120i hematology analyzer (SIEMENS, USA). The data is presented in Table 138.

The data indicate treatment with most of the oligonucleotides did not cause any changes in hematologic parameters outside the expected range for antisense oligonucleotides at this dose. Specifically, treatment with ISIS 560131 was well tolerated in terms of the hematology of the monkeys.

TABLE 138

Hematological parameters in cynomolgus monkeys

| Treatment | RBC ($\times 10^6/\mu L$) | Platelets ($\times 10^3/\mu L$) | WBC ($\times 10^3/\mu L$) | Hemoglobin (g/dL) | HCT (%) |
|---|---|---|---|---|---|
| PBS | 5.3 | 426 | 13.6 | 13.2 | 43 |
| ISIS 560131 | 5.8 | 392 | 11.3 | 13.1 | 44 |
| ISIS 569213 | 5.6 | 426 | 12.9 | 12.5 | 42 |
| ISIS 569216 | 5.6 | 504 | 12.2 | 12.8 | 43 |
| ISIS 569221 | 5.6 | 406 | 11.1 | 12.9 | 45 |
| ISIS 569236 | 5.7 | 358 | 14.4 | 13.1 | 44 |
| ISIS 579671 | 5.4 | 438 | 10.0 | 12.5 | 42 |
| ISIS 586124 | 5.8 | 391 | 10.4 | 13.6 | 45 |
| ISIS 583918 | 5.8 | 435 | 12.7 | 13.3 | 46 |
| ISIS 584149 | 5.7 | 478 | 11.3 | 13.7 | 45 |
| ISIS 584163 | 5.5 | 461 | 9.1 | 12.8 | 44 |
| ISIS 584269 | 5.2 | 522 | 9.8 | 12.4 | 41 |
| ISIS 584468 | 5.9 | 408 | 11.1 | 13.5 | 45 |

Kidney Function

To evaluate the effect of ISIS oligonucleotides on kidney function, the monkeys were fasted overnight. Approximately, 1.5 mL of blood samples were collected from all the study groups on day 44. Blood was collected in tubes without anticoagulant for serum separation. The tubes were kept at room temperature for a minimum of 90 min and then centrifuged at 3,000 rpm for 10 min. Levels of BUN and creatinine were measured using a Toshiba 120FR NEO chemistry analyzer (Toshiba Co., Japan). Results are presented in Table 139, expressed in mg/dL. The plasma chemistry data indicate that most of the ISIS oligonucleotides did not have any effect on the kidney function outside the expected range for antisense oligonucleotides. Specifically, treatment with ISIS 560131 was well tolerated in terms of the kidney function of the monkeys.

Kidney function was also assessed by urinalysis. Fresh urine from all animals was collected on day 44 using a clean cage pan on wet ice. Food was removed overnight the day before fresh urine collection was done but water was supplied. The total protein and creatinine levels were measured using a Toshiba 120FR NEO automated chemistry analyzer (Toshiba Co., Japan) and the protein to creatinine ratio was calculated. The results are presented in Table 140.

TABLE 139

Plasma BUN and creatinine levels (mg/dL) in cynomolgus monkeys

| Treatment | BUN | Creatinine |
|---|---|---|
| PBS | 30.5 | 0.78 |
| ISIS 560131 | 23.7 | 0.84 |
| ISIS 569213 | 29.4 | 0.91 |
| ISIS 569216 | 28.4 | 0.81 |
| ISIS 569221 | 20.2 | 0.86 |
| ISIS 569236 | 24.9 | 0.87 |
| ISIS 579671 | 22.7 | 0.74 |
| ISIS 586124 | 23.8 | 0.87 |
| ISIS 583918 | 24.5 | 0.87 |
| ISIS 584149 | 26.4 | 0.85 |
| ISIS 584163 | 22.4 | 0.82 |
| ISIS 584269 | 21.8 | 0.89 |
| ISIS 584468 | 22.2 | 0.78 |

TABLE 140

| Urine protein/creatinine ratio in cynomolgus monkeys | |
|---|---|
| Treatment | Ratio |
| PBS | 0.00 |
| ISIS 560131 | 0.02 |
| ISIS 569213 | 0.02 |
| ISIS 569216 | 0.08 |
| ISIS 569221 | 0.00 |
| ISIS 569236 | 0.02 |
| ISIS 579671 | 0.00 |
| ISIS 586124 | 0.01 |
| ISIS 583918 | 0.01 |
| ISIS 584149 | 0.01 |
| ISIS 584163 | 0.01 |
| ISIS 584269 | 0.00 |
| ISIS 584468 | 0.00 |

C-reactive Protein Level Analysis

To evaluate any inflammatory effect of ISIS oligonucleotides in cynomolgus monkeys, the monkeys were fasted overnight. Approximately, 1.5 mL of blood samples were collected from all the study groups on day 44. Blood was collected in tubes without anticoagulant for serum separation. The tubes were kept at room temperature for a minimum of 90 min and then centrifuged at 3,000 rpm for 10 min. C-reactive protein (CRP), which is synthesized in the liver and which serves as a marker of inflammation, was measured on day 43 using a Toshiba 120FR NEO chemistry analyzer (Toshiba Co., Japan). Complement C3 was also measured similarly, and the data is presented as a percentage of baseline values. The results are presented in Table 141 and indicate that treatment with most of the ISIS oligonucleotides did not cause any inflammation in monkeys.

TABLE 141

| C-reactive protein and C3 levels in cynomolgus monkey plasma | | |
|---|---|---|
| Treatment | CRP (mg/dL) | C3 (% of baseline) |
| PBS | 2.5 | 118 |
| ISIS 560131 | 1.7 | 100 |
| ISIS 569213 | 2.8 | 60 |
| ISIS 569216 | 3.6 | 94 |
| ISIS 569221 | 4.9 | 91 |
| ISIS 569236 | 2.6 | 103 |
| ISIS 579671 | 4.5 | 101 |
| ISIS 586124 | 4.0 | 93 |
| ISIS 583918 | 3.5 | 89 |
| ISIS 584149 | 1.7 | 110 |
| ISIS 584163 | 1.0 | 102 |
| ISIS 584269 | 4.9 | 102 |
| ISIS 584468 | 1.3 | 111 |

Pharmacokinetics Studies

The concentrations of the full-length oligonucleotide in the kidney and the liver of select treatment groups were measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 190) was added prior to extraction. Tissue sample concentrations were calculated using calibration curves, with a lower limit of quantitation (LLOQ) of approximately 1.14 µg/g.

The results are presented in Table 142, expressed as µg/g tissue. The kidney to liver ratio was also calculated and is presented in Table 142.

TABLE 142

| Oligonucleotide concentration of in cynomolgous monkeys | | | |
|---|---|---|---|
| Treatment | Liver | Kidney | K/L ratio |
| ISIS 560131 | 793 | 2029 | 2.6 |
| ISIS 569221 | 966 | 1372 | 1.4 |
| ISIS 569236 | 898 | 1282 | 1.4 |
| ISIS 579671 | 871 | 2576 | 3.0 |
| ISIS 584269 | 698 | 2823 | 4.0 |
| ISIS 584468 | 474 | 2441 | 5.2 |

Example 34

Effect of Antisense Inhibition of Androgen Receptor (AR) on an Androgen Receptor-dependent Breast Cancer Orthotopic Model MDA-MB-453 cells express AR in the absence of estrogen receptors and progesterone receptor (Hall, R. E. et al., Eur. J. Cancer 1994. 30: 484-490). The effect of inhibition of AR mRNA expression with antisense oligonucleotides was examined in MDA-MB-453 tumor-bearing mice.

Study 1

ISIS 569216 (TGATTTAATGGTTGCA; SEQ ID NO: 39), which is the antisense oligonucleotide tested in the assay, was designed as a deoxy, MOE and (S)cEt oligonucleotide, and is 16 nucleosides in length. The chemistry of the oligonucleotide is 5'-Te Gk Ak Tk Td Td Ad Ad Td Gd Gd Td Tk Gk Ck A, where 'e' denotes a 2'-O-methoxyethyl ribose; 'k' denotes an (S)-cEt; denotes a 2'-deoxyribose. The internucleoside linkages throughout the oligonucleotide are phosphorothioate (P═S) linkages. All cytosine residues throughout the oligonucleotide are 5-methylcytosines. ISIS 569216 has two target start sites, 58720 and 58750, on the human AR genomic sequence (GENBANK Accession No. NT_011669.17 truncated from nucleosides 5079000 to 5270000, SEQ ID NO: 1).

Treatment

MDA-MB-453 breast carcinoma cells ($5\times10^6$), mixed with 50% Matrigel, were injected into the mammary fat pad of 10 female NSG mice. Dihydrotestosterone (DHT) pellets, the active form of the major circulating androgen, testosterone, were implanted subcutaneously at the same time. Once the tumor reached a size of 100 $mm^3$, the mice were randomly divided into two treatment groups. The first treatment group was injected with ISIS 569216 administered by subcutaneous injection at a dose of 50 mg/kg five times a week for 4 weeks. The second treatment group was injected with vehicle only, administered by subcutaneous injection five times a week for 4 weeks, and served as the control group. Tumor growth was monitored once a week and mice were sacrificed on day 32 after treatment. Tumor tissue and TB-interface samples were collected and processed for further analysis.

RNA Analysis

Tumors were excised and the tissue was processed for RNA extraction and qPCR analyses. AR mRNA expression was assessed at the TB-interface and normalized to actin mRNA expression. AR mRNA expression in mice treated with ISIS 569216 was inhibited by 48% compared to the control group.

Measurement of Tumor Volume

Tumor volumes were measured on a regular basis throughout the study period, using Vernier calipers. As shown in Table 143, tumor volumes were significantly decreased in mice treated with ISIS 569216 compared to the control group.

TABLE 143

| Tumor volume on different days in the MDA_MB-453 cancer orthotopic model | | | | | | |
|---|---|---|---|---|---|---|
| | Day 16 | Day 23 | Day 30 | Day 37 | Day 44 | Day 51 |
| ISIS 569216 | 134 | 142 | 173 | 125 | 92 | 73 |
| Control | 111 | 141 | 155 | 195 | 287 | 347 |

Study 2.

Treatment

MDA-MB-453 cells obtained from ATCC were maintained in Leibovitz's L-15 media with 10% FBS. Female NSG mice (Jackson Laboratories) were implanted in the mammary fat pad with $5\times10^6$ tumor cells in growth-factor-reduced matrigel (1:1). DHT pellets were also implanted at the same time in the mice between the shoulder blades.

After 20 days, the mice were then randomly divided into treatment groups. Groups of mice were injected with 50 mg/kg of ISIS 569236 or ISIS 560131 administered subcutaneously 5 days per week for 2 weeks. A group of mice were similarly treated with control oligonucleotide, ISIS 549148 (a 3-10-3 (S)-cEt gapmer with sequence GGCTACTACGCCGTCA, designated herein as SEQ ID NO: 193, with no known human sequence). Another control group of mice was similarly treated with PBS.

Measurement of Tumor Growth

Tumor volumes were measured on a regular basis throughout the study period, using Vernier calipers. As shown in Table 144, tumor volumes were decreased in mice treated with antisense oligonucleotides targeting AR compared to the control group.

TABLE 144

| Tumor volumes in the MDA-MB-453 model | | | | | | | |
|---|---|---|---|---|---|---|---|
| | Day 0 | Day 8 | Day 13 | Day 20 | Day 23 | Day 27 | Day 29 |
| PBS | 136 | 336 | 331 | 358 | 338 | 417 | 481 |
| ISIS 549148 | 148 | 303 | 312 | 365 | 413 | 490 | 550 |
| ISIS 560131 | 144 | 261 | 243 | 204 | 232 | 233 | 258 |
| ISIS 569236 | 134 | 283 | 260 | 230 | 264 | 329 | 323 |

RNA Analysis

RNA extraction was performed using an RNA extraction kit from Qiagen. AR RNA expression was measured using primer probe set LTS00943 and normalized to human actin mRNA expression. Human AR RNA expression was assessed in tumor tissue. AR RNA expression in mice treated with ISIS 560131 was inhibited by 35% and AR expression in mice treated with ISIS 569236 was inhibited by 19% compared to the control group.

What is claimed:

1. A compound comprising a single-stranded modified oligonucleotide consisting of 16 linked nucleosides having a nucleobase sequence consisting of the sequence of SEQ ID NO: 35, or a pharmaceutically acceptable salt thereof, wherein the modified oligonucleotide comprises:

a gap segment consisting of 9 linked deoxynucleosides;

a 5' wing segment consisting of three linked nucleosides; and a 3' wing segment consisting of four linked nucleosides;

wherein the gap segment is positioned between the 5' wing segment and the 3' wing segment; the three linked nucleosides of the 5' wing segment are each a constrained ethyl (cEt) sugar; the four linked nucleosides of the 3' wing segment are a constrained ethyl (cEt) sugar, a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine is a 5-methylcytosine.

2. A compound comprising a single-stranded modified oligonucleotide consisting of 16 linked nucleosides having a nucleobase sequence consisting of the sequence of SEQ ID NO: 39, or a pharmaceutically acceptable salt thereof, wherein the modified oligonucleotide comprises:

a gap segment consisting of 7 linked deoxynucleosides;

a 5' wing segment consisting of four linked nucleosides; and a 3' wing segment consisting of five linked nucleosides;

wherein the gap segment is positioned between the 5' wing segment and the 3' wing segment; the four linked nucleosides of the 5' wing segment are a 2'-O-methoxyethyl sugar, a constrained ethyl (cEt) sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a constrained ethyl (cEt) sugar, a 2'-O-methoxyethyl sugar, and a 2'-O-methoxyethyl sugar in the 5' to 3' direction; each internucleoside linkage is a phosphorothioate linkage; and each cytosine is a 5-methylcytosine.

3. A composition comprising the compound of claim 1 or claim 2, or a pharmaceutically acceptable salt thereof, and a pharmaceutically acceptable diluent or carrier.

4. A combination comprising the compound of claim 1 or claim 2, or a pharmaceutically acceptable salt thereof, and an anti-androgenic agent selected from: MDV3100, ARN-059, ODM-201, abiraterone, TOK001, TAK700 and VT464.

5. The combination of claim 4, wherein the anti-androgenic agent is MDV3100.

6. A method of treating cancer comprising administering to a subject having cancer a compound or salt of claim 1 or claim 2, thereby treating cancer in the subject.

7. The method of claim 6, wherein the cancer is prostate cancer, breast cancer, ovarian cancer, gastric cancer or bladder cancer.

8. The method of claim 6, wherein the cancer is castrate-resistant prostate cancer.

9. The method of claim 8, wherein the castrate-resistant prostate cancer is resistant to an anti-androgenic agent selected from: MDV3100, ARN-059, ODM-201, abiraterone, TOK001, TAK700 and VT464.

10. A method of treating prostate cancer in a patient in need thereof, comprising administering to the patient a compound or salt of claim 1 or claim 2 and an anti-androgenic agent.

11. The method of claim 10, wherein the anti-androgenic agent is selected from: MDV3100, ARN-059, ODM-201, abiraterone, TOK001, TAK700 and VT464.

12. The method of claim 10, wherein the compound and the anti-androgenic agent synergize in combination to inhibit the growth or proliferation of the prostate cancer cell.

13. The method of claim 10, wherein the patient is administered an amount of the compound and an amount of anti-androgenic agent that are each or both less in combination than the amount of either the compound or anti-androgenic agent alone effective in inhibiting the growth or proliferation of said prostate cancer cell.

14. A method of inhibiting growth or proliferation of an androgen receptor (AR)-positive breast cancer cell comprising contacting the breast cancer cell with a compound or salt of claim 1 or claim 2 wherein the growth or proliferation of the breast cancer cell is inhibited.

15. A method of treating prostate cancer in a patient in need thereof, comprising administering to the patient a composition of claim 3 and an anti-androgenic agent.

16. The method of claim 15, wherein the anti-androgenic agent is selected from: MDV3100, ARN-059, ODM-201, abiraterone, TOK001, TAK700 and VT464.

17. The method of claim 11, wherein the anti-androgenic agent is MDV3100.

18. The method of claim 17, wherein the compound and the anti-androgenic agent synergize in combination to inhibit the growth or proliferation of the prostatge cancer cell.

19. The method of claim 16, wherein the anti-androgenic agent is MDV3100.

20. The method of claim 19, wherein the compound and the anti-androgenic agent synergize in combination to inhibit the growth or proliferation of the prostate cancer cell.

* * * * *

SEQUENCE LISTING

```
<160> NUMBER OF SEQ ID NOS: 215

<210> SEQ ID NO 1
<211> LENGTH: 191001
<212> TYPE: DNA
<213> ORGANISM: Homo sapiens

<400> SEQUENCE: 1

ctgacagaaa gcagatcatt ggttgcctga ggaggaggag tataggagag gtggagggaa      60

aatgtacaaa gtggcacaat aaaaactttt ggaatcatag atatattcac tatcttgatt     120

gagtgatgat ttcatgagtg cacgcgtgtg tcaaaaatga tcaatttatg caactttaaa     180

tatgtgcagt ttattgtata tatcaattat acctcagtac ggctattaaa aagaaaccct     240

ctggctgcac aatgcagaac tgattctagg aaagagtgga gggaggatga ccatttacag     300

tgctccaggt ggaagagaac ggtgccttct ggaagtgaac taggttggca acaacagaga     360

tgaaataaat gggcagatgt gtgagatact taggaaataa aacccgatgg tcaccatttt     420

ccaaaggtca gctcatcctg gctttccaga gcaaagagct agggaagact ttattaataa     480

atccctcttg aagttgcaga ggaagcttat agcagaaact tactctcaac ctgactaatc     540

tgagagaaca cctctggttc catttgatta ctaaaaaact gcaaagaaca ggaggagaaa     600

gaagaagaaa gctggtacaa acagtgaact tatataatat taatcaataa ttgtctcttg     660

ttcttaaaag caatgggaag aaaatgagat ttgagctgga agatcagagt tcaaaatcca     720

aataaagtat atggccctaa tatgcttata gtagttaacc tttcctgata atgatataat     780

tgttgacagc accatcttta aaaataaaaa taacatagta atccttcaga tttgtagaat     840

gctttcctgt ttacaagttt gttctataca cattatgtct tttaaatgac acactagcct     900

tctgagggta acttatattg gcaacagttt tcagatgtgg aaactgtgaa gacaatgttg     960

gtgatgtgga agcaacataa actttggagt ctttcagacc caggtttgaa tgtcagactg    1020

ctttttattc agagtaactt cagagcatta tttctcacct taattttttt tcaggcctct    1080
```

```
ttgtgtctat gtgtcctctt cactcctgtc cattgttcat tcagtgattt ttgcaccttc   1140
cttcactgtt agtgtgtaga cacatagttc tcctggctct gagacctatg ttaattccat   1200
tctaccatcc tgccagccca ctcaattcct attgagcaat gctagttgaa agttgtggtg   1260
ggattaaatg ttgcaatgag tattcaaatg aggttgaagt atctacgcat tctacttaca   1320
tatggtgagg tatattcaag gaaggctgta gccattaaaa tctcaggaaa taatttttca   1380
cctcctcagg tgaaagggtc ttcaggcctt tgtgttctgg aaggttcatt tatagccatt   1440
tcccaaatga caatgcgatt gatgagtcta gagtctagct caaatagcaa tggactggaa   1500
gactagttta ggttttacta atgtggaaca tagaacaaat tatgtccttg tttcagcctg   1560
ttcatctgtg aaatagagcc tatcatatcc agtcttcctt gcctttaggt ttgagttacc   1620
ttctttggtc aaggtaagta aatgcctatg atgtttggct gtgcacaaga taaagctaca   1680
acaaagctac aacccatctt ttctctgtag aagactgcaa aaagcaaaag agacccaggc   1740
aaaaatctcg gaatgacttt tggaacagag agcctcccca gaatcagaag tcaaaggaat   1800
ttaaaacata gggaggccca gggtctctac tgacataaag gaaagatgtt ttccttatag   1860
gtttacgttt acattttctc tctctttcca ttcccacttg catctccacc tttacacagg   1920
gcttatggga cctcctccac aaaagagcag ttgcagtaac ccacatcatc ctctacgcct   1980
ggctgtccat caagaggcga aaagcagccc tatataggtt ctatccttgg atagttccag   2040
ttgtaaagtt taaaatatgc gaaggcaact tggaaaagca agcggctgca tacaaagcaa   2100
acgtttacag agctctggac aaaattgagc gcctatgtgt acatggcaag tgtttttagt   2160
gtttgtgtgt ttacctgctt gtctgggtga ttttgccttt gagagtctgg atgagaaatg   2220
catggttaaa ggcaattcca gacaggaaga aaggcagaga agagggtaga aatgacctct   2280
gattcttggg gctgagggtt cctagagcaa atggcacaat gccacgaggc ccgatctatc   2340
cctatgacgg aatctaaggt ttcagcaagt atctgctggc ttggtcatgg cttgctcctc   2400
agtttgtagg agactctccc actctcccat ctgcgcgctc ttatcagtcc tgaaaagaac   2460
ccctggcagc caggagcagg tattcctatc gtccttttcc tccctccctc gcctccaccc   2520
tgttggtttt ttagattggg ctttggaacc aaatttggtg agtgctggcc tccaggaaat   2580
ctggagccct ggcgcctaaa ccttggttta ggaaagcagg agctattcag gaagcagggg   2640
tcctccaggg ctagagctag cctctcctgc cctcgcccac gctgcgccag cacttgtttc   2700
tccaaagcca ctaggcaggc gttagcgcgc ggtgagggga ggggagaaaa ggaaagggga   2760
ggggagggaa aaggaggtgg gaaggcaagg aggccggccc ggtgggggcg ggacccgact   2820
cgcaaactgt tgcatttgct ctccacctcc cagcgccccc tccgagatcc cggggagcca   2880
gcttgctggg agagcgggac ggtccggagc aagcccagag gcagaggagg cgacagaggg   2940
aaaaagggcc gagctagccg ctccagtgct gtacaggagc cgaagggacg caccacgcca   3000
gccccagccc ggctccagcg acagccaacg cctcttgcag cgcggcggct tcgaagccgc   3060
cgcccggagc tgccctttcc tcttcggtga agtttttaaa agctgctaaa gactcggagg   3120
aagcaaggaa agtgcctggt aggactgacg gctgcctttg tcctcctcct ctccaccccg   3180
cctcccccca ccctgccttc ccccctccc ccgtcttctc tcccgcagct gcctcagtcg   3240
gctactctca gccaaccccc ctcaccaccc ttctccccac ccgccccccc gcccccgtcg   3300
gcccagcgct gccagcccga gtttgcagag aggtaactcc ctttggctgc gagcgggcga   3360
gctagctgca cattgcaaag aaggctctta ggagccaggc gactggggag cggcttcagc   3420
```

-continued

```
actgcagcca cgacccgcct ggttaggctg cacgcggaga gaaccctctg ttttccccca   3480
ctctctctcc acctcctcct gccttcccca ccccgagtgc ggagccagag atcaaaagat   3540
gaaaaggcag tcaggtcttc agtagccaaa aaacaaaaca aacaaaaaca aaaaagccga   3600
aataaaagaa aaagataata actcagttct tatttgcacc tacttcagtg gacactgaat   3660
ttggaaggtg gaggattttg tttttttctt ttaagatctg ggcatctttt gaatctaccc   3720
ttcaagtatt aagagacaga ctgtgagcct agcagggcag atcttgtcca ccgtgtgtct   3780
tcttctgcac gagactttga ggctgtcaga gcgctttttg cgtggttgct cccgcaagtt   3840
tccttctctg gagcttcccg caggtgggca gctagctgca gcgactaccg catcatcaca   3900
gcctgttgaa ctcttctgag caagagaagg ggaggcgggg taagggaagt aggtggaaga   3960
ttcagccaag ctcaaggatg gaagtgcagt tagggctggg aagggtctac cctcggccgc   4020
cgtccaagac ctaccgagga gctttccaga atctgttcca gagcgtgcgc gaagtgatcc   4080
agaacccggg ccccaggcac ccagaggccg cgagcgcagc acctcccggc gccagtttgc   4140
tgctgctgca gcagcagcag cagcagcagc agcagcagca gcagcagcag cagcagcagc   4200
agcagcagca gcagcaagag actagcccca ggcagcagca gcagcagcag ggtgaggatg   4260
gttctcccca agcccatcgt agaggcccca caggctacct ggtcctggat gaggaacagc   4320
aaccttcaca gccgcagtcg gccctggagt gccaccccga gagaggttgc gtcccagagc   4380
ctggagccgc cgtggccgcc agcaagggc tgccgcagca gctgccagca cctccggacg   4440
aggatgactc agctgcccca tccacgttgt ccctgctggg ccccactttc cccggcttaa   4500
gcagctgctc cgctgacctt aaagacatcc tgagcgaggc cagcaccatg caactccttc   4560
agcaacagca gcaggaagca gtatccgaag gcagcagcag cgggagagcg agggaggcct   4620
cgggggctcc cacttcctcc aaggacaatt acttaggggg cacttcgacc atttctgaca   4680
acgccaagga gttgtgtaag gcagtgtcgg tgtccatggg cctgggtgtg gaggcgttgg   4740
agcatctgag tccaggggaa cagcttcggg gggattgcat gtacgcccca cttttgggag   4800
ttccacccgc tgtgcgtccc actccttgtg ccccattggc cgaatgcaaa ggttctctgc   4860
tagacgacag cgcaggcaag agcactgaag atactgctga gtattcccct ttcaagggag   4920
gttacaccaa agggctagaa ggcgagagcc taggctgctc tggcagcgct gcagcaggga   4980
gctccgggac acttgaactg ccgtctaccc tgtctctcta caagtccgga gcactggacg   5040
aggcagctgc gtaccagagt cgcgactact acaactttcc actggctctg gccggaccgc   5100
cgccccctcc gccgcctccc catccccacg ctcgcatcaa gctggagaac ccgctggact   5160
acggcagcgc ctgggcggct gcggcggcgc agtgccgcta tggggacctg gcgagcctgc   5220
atggcgcggg tgcagcggga cccggttctg ggtcaccctc agccgccgct tcctcatcct   5280
ggcacactct cttcacagcc gaagaaggcc agttgtatgg accgtgtggt ggtggtgggg   5340
gtggtggcgg cggcggcggc ggcggcggcg gcggcggcgg cggcggcggc ggcggcgagg   5400
cgggagctgt agccccctac ggctacactc ggccccctca ggggctggcg ggccaggaaa   5460
gcgacttcac cgcacctgat gtgtggtacc ctggcggcat ggtgagcaga gtgccctatc   5520
ccagtcccac ttgtgtcaaa agcgaaatgg gcccctggat ggatagctac tccggacctt   5580
acggggacat gcggtaagtt tttccttcca gaaatgtcgc ctttcggccc agggcagagt   5640
cactctgtgt tctggggtat ctagcggctc ctacctgcgc gaacactcag attgcccctg   5700
ggagagctca gcagggtaaa cctagagctc tcccgtggac tcccggcctg ccagaggttt   5760
aacctgagct ctcctaattt ctgctgcgtg ccctgggtgc tgattcctgc cctcccagat   5820
```

-continued

```
tcttcaactc ccccaaccgc cccaaattct cactacctcc tggtactcga ggtcccaaac   5880
agaaatccta ttgcacgggc caccttcaga gataaagctc ccaagccctc cactcttcct   5940
ttcctcctgt cctcaaagtc tgagaacctc aacaggaatt tggcaattt ctcctcttca   6000
ggtctgttag gatttcactt tcagcctgcg cagattagag tcaaaaagac cggcccaata   6060
gcttctcagc gggtatcctc cagagaggta aagtgaaatt ctcggttagg gaaagaaagt   6120
ggtctctggg tgctgaggtc tgctgtgtga aagggtgaac ttctttctcc tgaagcaact   6180
ggggacttgc tccagggctg gaggtcagta gagataatcc aaaccgtcat gtttagagta   6240
ggcagagggg caactttctt ggtaaagact tcacaggatt tgcactcaca gtttctcaac   6300
gttggttgac tatgttgaaa gtagttgctt gggtcggttt tctcttgtaa agtgtttatt   6360
ttctctgtgg attataacag atccacagcc ccctacttca ggtttgcatc agatctataa   6420
agaggagaat attcttttaa tgtacaattt aattaggctt gactctgact tacaaaactg   6480
ttggaaaaca tttttttgta aagcatttcc tgctatttca gtgtgctcca aaatctccac   6540
tggggagggt ggagtgaggt tttttattat attcctttat ttttaggaca tgtttgcatt   6600
ttagaatatg tgcagttagc tctaacaaat tgagtaagaa ctcttaatga cctatgagcc   6660
gtaatcttac cccaaagttt taattagcat atgagaaaag tggcaggcaa ttgcatcgtg   6720
cttattaaaa attattcctc accgcagttg ttgagcttct tggagaccat gctgaagatt   6780
ttctccccca gcaaattaag atattagttt atctgctgag ggaggacaga ctgaattggg   6840
gaattaactc ctcaggtagg ccaggtgctg atgtccctgt ggacttttgt cttattcttt   6900
gtttctatgg ctgttttctt ttacctgtga cttctccgaa atttctttgt tagccttaac   6960
atctttgttt ggggacttaa atccagcaat ttgccttctt tcactgatgc tttccttctt   7020
acaaggtaga tagcacagtg ttagtaaaga aagaaagagg agggtaggat ttcatattat   7080
ttcgtgggct gttgaagaaa cagcttctta ccaggcttta cattccatta ggtttttaat   7140
gtttgactta caagattttc agagggttca tttgatattg tcaaagtctt ttccagttaa   7200
tttagactct tcatttttgt aatgggttta tgctatggga caaaaaaagt attcttcatt   7260
ttataagaac aaatttactt ggtagggtta atttttttc tagggctgtc actagacggt   7320
ggagcccctc ttctactgta aacttttctt gggggaaaat gtctaaggtg cattttgacc   7380
tgccatgata ctaaacccag acactggaac cttccatctt ctgcatgcct cccccacaac   7440
ttacttactt aacagggaaa aaactgatgg ttccacatat ttgctaaaaa atgtgtgcct   7500
tcaaagacaa aaccaaaatt tttagggaat aactatagag agcaaaagtt actcccatca   7560
agtagacaac gagcttggtg attttatttc aggtcttaat gaaaaaagct tctttatgag   7620
gaaggttatc atatcttggt gcctccttga cagtccgctt aaattaatga cataaactaa   7680
tgagaattta gcagttcctg cagaaagtac aagtttattt tttttttctg gtttgtgatt   7740
gctgcactga atatgaggag tctagttaaa gggacaactg gtgttcctgt cttgtgagtt   7800
gacgaagact ttccatttct aggatataga aaatccttaa gccggtttat tgaaaattaa   7860
tcaatttaat cagaatgcaa tcaattccaa tacaaaagtt agtattttct ttctttttat   7920
tgaaaattaa tttaatcaga atacaatcaa ttccaatcca aaagttgata ttttcttact   7980
ttctcttttt ttccctcatt ttgtagggat acaatttggt gaaaggcaag agatttctta   8040
agccaaagca agagtgtctt ccctctctgt gttgcatgca ttatgtgcca tgtttgagct   8100
aaaaatctca aaattgggca ggcttccaat gacctgttgg gtccctccct ttaccattca   8160
```

-continued

```
tgtgtgtgtt tatgtacata attttgtgga ggggtttttt taaaccttag taacatctgc   8220

actcactctg tgttcttata catttacagt gtttctgctg agaggaggga agatgcaaag   8280

gtggtctctt ttacttaatt tagcatgtgg tttgaacaga aggaaaaata aaaagtgatg   8340

gggcttgtgt gcaaccctga tgatatttta tggagctgtc tgtcttctct ctgagatcaa   8400

acaggactac aactttgtta attgaccact ggctcccttg gcaaaagtag ggcttcttat   8460

attccagcaa gcagcacaat aatatgacaa aaatttattc ttgggagttg ggttctaaga   8520

gagtgcatgc cagaattaga gtttggggtt tagagaaatt atccagatgc caaaagaaca   8580

ttttaatttt tctcttggta atttgttctg gtctccatag taggtagtat tttagtagtg   8640

ctttgatatt gacaagtctt gctccctttc tctattagat ttttcaaaat aaggcatttt   8700

attaattcct ctttccttct cctctctcct ctcagttatc aagcattttt atgactatct   8760

tacaagcaac agtttgtctt gtaaagcaga attttccttt gaaaccaaga cagattattt   8820

ctgcccatag gcttcaggaa ccaatatttt ggcaagaagc atcttttctt tgtggtcagc   8880

aaataggtgg tgagttctgt ctggatccca acaatcaaca cctgaggacc aaatagccac   8940

actgggtggc accccattcg gaagtataca caggaagtag ccctcttgct tgttcacagc   9000

tcaagtcagc caaagattaa cactggtgag agatattttc aaagaagttt gcaggcttcc   9060

aattgcaggg tcattttggg gtgctttctt gcctgtacta attttatctc atcaagcttc   9120

cattctttga gctgtaaact ttgaaataat atactggatt tgctggtacg tttaattttc   9180

tttgttaagt gttttcattc ccatagtaat ttttcatcta gtgtacatat atgcatttaa   9240

aacaaaaatt ctttggtctc cttatgcgta tatgcactgc ggcttgtaca cgtacaagct   9300

acttggtggg attatgtgaa ctggagttag aaatgtggac aattttatta tgattatttt   9360

taatggtgat atcaagatca ccagtttcat tcggaacctt gcataagcag ggagcagaat   9420

gcggactggg tgtggcaaag caagggctta ttttatagcc aaacctgaaa tcacaactct   9480

gaaaaataaa aaaaaaaaaa accaaacaaa aaaatcaagt tttgtgagct tggtcagaga   9540

aggaaaagga aatctctccc tacccccac ctccaccatt ttctctttgt ctgcagcttc   9600

ctcaagtgct gcctgtcccc gattttcttt tattccactc ctttcatgtt tttgacattg   9660

aaatacagac tcttctttcc acttctcagg gtatttttct tattacacct gtggcatgct   9720

cctaaagaat ttcttttta aaaaaaatct gtagagtagt agattagatt aaccccagta   9780

tctctccctt aagactagat gacatgaggg gattgcaaaa tgaatagctg ggtttttttt   9840

tttttttttt tttttacctt gaggttaaag cctggttcaa cagttgctga gagagttaac   9900

tagattgctt gaggacttgg caatttcata aagtattttg tcttatgctg tctctgtctc   9960

tgtcttgatc tctgtctctc tctgtctact gtaatgttgg ctactttctc tcagagcctg  10020

agagacagct ctgagacact tcccaggtct gttcggttca gacctcagta gctggatcac  10080

aagcagtacc caatatgcat atgagggtgc gtgctgcaag tgtccggctg ggctaatctg  10140

cttaagcttc ataaaaatta atcatttgaa aacaaagaaa gatattaaag aaattattct  10200

atctccgact tcccctatca gcattccatc aagttctggg atgttaaatt cagagaaagt  10260

taaccttatc ttaaacacaa agttgacttt taaacaaaat tgcttataaa gttctgtaca  10320

gttaccagca ttggttgccc tttgtcgtac ggaagagaat tatgaaatct catatttaca  10380

tagcattctt ccaaaaaaag agacggtgtt ttccagttta ttcactgcat tcgtgtaagt  10440

gtgagtaggc caggaggggt gcttagtgat taccctttg ctaggtaaca aagtagaaag  10500

ttagatttc tatgatattt gtttaccacg taggggaacc tctctagagc aatactccca  10560
```

-continued

```
agctttttct tcttgaaatt tcccacctga cagataatac tttagattgt tgctcttaag  10620
gacttctctc agtagctgct acatagagat gattgtccgt gaattattgc ttgcacactc  10680
atgggtgatg ctactccctc tctctcatgg caattcttgc tgccaacctg caggccacac  10740
caggattgag ggcagctcat ctcgataaat ttatagcatt aaagtgctgg gtcatttgag  10800
aatgttgtca atttaggtta cttagtacct aagttttatt ctttaaataa cagctttatt  10860
gagacgtaat ttacaatcca tacaattcac tcatctaaag tgtacagttt catgcttttt  10920
agaatattca gagttgtgca accattattg caatcaattt tagaacattt taatcacccc  10980
caaaggaaac cctatgcacc tttgtgttca tccccctata ttccctcagt ccttagcaac  11040
caataatcta cttctatcta tggatgtgct tattctaaca ttttgtatga atgaaatcat  11100
gtaatatgtg gtcttttgtg actagcttct ttcacataaa atatgttttc aaggtcatcc  11160
atgttgaagc acatatcagt acttcactat tttttatagc ctaataatgt tccactatat  11220
ggatatacca cattctatct atccatttat caggtgatga gcattacggt tgtttccacc  11280
ttttggctat tatgaataat actgctgtga acattcacgt gcaagtttat tgtggacata  11340
ttcagtccac atattttgga cattttcagt tcttttggat acatacatag gattgaaatc  11400
tctgagtcat atgatacctc tgtgtttatc cttttgaaga actgtcaaac tgtttctaa  11460
agtgtctgca ctgttttaca atcccatcag caacctatgg gggtccattt cttccacatc  11520
cttgccaaca cttgttattc tctgtctttt tcattatagc tatattagtg ggtgtgaagt  11580
ggtacctcat tgtggctttt atttccattt ccctaataac aaataatgtt cagtatccat  11640
gttcttattg gccatttgta tatcttcttt tttgagaaat atctatttgg atcctttgct  11700
cagtttttag ttgggttttt tattattgag ttttaagatt tttaaaaaat atattctgga  11760
tacatgtcct ttaatagatt gtgatttgta gatatttttt cacattctgt gagttgtctt  11820
ttttactttc cttttttttc tttttacgtt cttaatggta tctagattga agcacaaaaa  11880
tgtttttaag tttgatgaag tccaattcat ctatttattt tctgttttgg cttatgattt  11940
tggcgtcgta tctaagaagt ctttgcctaa tccaagatca caaagattta catatgtttc  12000
cttctaagag ttttatagtt ttcgctattt acatttaggt ctttcatcag ttttgatgta  12060
atgtttatat atgactgagg taggggtcca acttcattct tttgcatgta gatattcagt  12120
tctcacaata ttgttgttga atctttcctc acttaactgt cttggcaccc tttgtgtaaa  12180
atcagttgac cgtaaatgtg agggtttaat tgtggactct caactatatt cagttgatct  12240
atatgtttat tcctatgccg gtaccacgtt atcttgatta ttgtaggttt ttagtgagtt  12300
ttgaaattag gaattttgaa ctcttcaact ttggtcttct ttttcaagat tgctttggct  12360
cttgtgggtc ccttgaattt tcaaatgaat tgggataagc ttgtcaattt ctacgaagaa  12420
gtcagctagg attctcacag gaactatatt aaatctgtaa accaatttgg ggagcattgt  12480
catctcaaca acgttaagtt attttcatcc ataaatatgc gatgtcttcc catttattta  12540
ggtcttcctt ttgtcaacaa tttttattgt tttcagatta taagttttgc agttcttttt  12600
aaaatttatt cctaagtgat ttattttttg atactataaa ttgaactgtc ttattgattt  12660
tattttcaga ttattcgctg ccaatgtatg gaaatataat tgttttgtat attgatcttg  12720
tatcctgcaa ccttgctgaa aatacctgag ttttgaatgc ttctgggact tatggggaag  12780
agggcttctg ctgctgcact gaaagttaaa gcttacttca tttcatcctg tatgaaggct  12840
gcatggggac attcttctca gttttactca gctataaatt cgaactggta atcccatccc  12900
```

-continued

```
ctttcgggat gaataggaga gtgtttttaa atgttcatct ctttagagaa cagcaggaaa  12960
gaagcctagt aaggtttggg tagtttataa tcccttttt agaatttgga tttgggaact  13020
attagcaagg cagtgagtaa taataataat ttctatatag aaaactaaca tgtagaggtg  13080
acaaatgaaa tcactagcta tattaggctt atgtttaggt tatcgtaagc agctaaaatc  13140
ataattttat gtttttatat gttgtccttt ggacaaagta aattccagta ctccttctga  13200
tgtgcatttc tagatgggga aaggattcat ttactctcat ataatttaag cttcttttta  13260
gggatgtact ccatagccat gaagcaaaga taaaattcat ctatacacag actgaacttt  13320
gtcttcatta acactctagg ctaagggtca tagctaatca gctacaactg taatgtcctg  13380
ataattgtga attaactgca gggcacccag caaaaggttt agttataatc taatagctgt  13440
ctgtagagat tagcctaata aagggatttt ttaaaaaaga atctggccgg gcatggtggc  13500
tcaatcctgt aatcccagca ctttgggagg ccgaggtggg tggatcacct gagatcggga  13560
gtccaagacc agcctggcca acatggtgaa accccatgtc tactaaaaat acaaaaatta  13620
tccaggcgtt ttggtgagca cccacaatcc cagctacttg tgaggctgag gcaggaggat  13680
cacttaagcc taagaggcag aggttgcagt gagccgagat catgccactg cactccaggc  13740
tccgtcaaaa aaaaaaaaaa aaaagaatct atcaatcaac cacttttcat taagcacctg  13800
ctatgtgccc agcatgtgct aggaagagat aaggtgaaag gggacacaat tcagacagaa  13860
tcttcttgag gtaactgctt acgaggagct tatagccact aaaaacaaaa acaaacaaaa  13920
accaaacaac caaaaaccaa acagaaatgc agtatcatca tgccatgatg cctgtatgag  13980
atcctggatt gtacggtatg gatttcttaa aatgtagata ttttaaaaaa aaagaggaat  14040
gaatcaatag aggctgaagt ggtcagcaat gttacctgtg gctgctttta atccttcgtg  14100
gaagtaagta ggagcatgtc taaactcaag caatagatta aagatcttga tgtatatttt  14160
aaataacaga agttagtacc actggaaaga atgaactgga ggaatgggtt gaaatctatt  14220
tctgcttatt caatagtgca ccccagtcaa gttagttgcc aatttcttct tcagtttctt  14280
tggctatatc attgcacttg gtgggtacat gtttatgatg tctttatctg aacaagtcag  14340
caataatatg agtaataaat taaaattgaa ggtgattaat ggctctgaat ttgacataag  14400
agttgttttc ctgccttcta agtttccatt gatcctgatg aattgcacaa accaaacaat  14460
tcggggagta agggggcaca tgatgatctt ataagagctt tgctgtatta gacaacgtaa  14520
cattctgaaa tggcctacca cctaacatgg gctctgttct ctgcaggttg agtaggttcc  14580
ttgcttgtgg aactgtagtc ccgctatttg gccgctaggg ggactgcaag tgccccgtgg  14640
caggatttcc ctgggaatgg tgagcctcca ttgatggttt caacacacag ccaaggccct  14700
atcgcaggat aacttgaacc agaactgcct agcaccagac aataaataag ctactatggt  14760
acttactgtt tcatttggga tgttgtttct cgaagtggca agcatttttt agtaatattt  14820
tgacttttta ataccttttct ttgcatatgg agcagaaaac agtgacactg gatatattca  14880
agtagcactg tccagtttat agagaagttt catattccat tattgcattt cattcttgtt  14940
tctacctttt acaagtaact agagtttgga gtattataat agtattcata ctattacagt  15000
actattattc ccattataaa aattgtgcaa agagtggtta agttacatgt ttacaatcaa  15060
acagcttcaa agtgactgat ctggaatttc agtcccattc tttcttctcc agatcatgtg  15120
ttccctgctt ttatctcaca gctcttttta ccttatagat gggaaacatg agagtcagag  15180
aggcaaaaga accacaagtg gtatcaatac tagaaattta tgaatttctt aaggcttcta  15240
ggtttgttac ccatccacca gactgatgga tttggttgtg tgagagttct gggtgccaat  15300
```

-continued

```
aaccttgcca ttctacttta cagactgcat atattcaata aatgcttatt aagcatctac  15360
tatatgccaa attctgtact aggcaccaat gatgtagtgg tgaacagaac agacaaaaat  15420
ctcttcgtgg agcagacagt ttaatgagag gagacatgta gtgtacatct gagcatgaaa  15480
agtgccatgc agaataactt cacagagtgt agggtataga gattgatggt gagagggaat  15540
attttatatt tgctggccag ggaaaacctt actggaaaag taaattttga gtagtgacct  15600
gaaggaaatt aggaaatgag ctgctatttg gacatctgga gttagaatat tccaggccca  15660
gggaaccaca ggcgcaaagg gcctgaggca ggagcacact tgctgtgatg gaggacaaag  15720
aggcccatat ggctggttta aataagtgaa ggatggtaga caatgagatc agagttaatg  15780
aggttgcatg gtaggtcttc cttaggactt tgaattttac tcctaagcag gttgtattgg  15840
acggttttga gcagggtaac atgacctgac ttacatttta acaggctccc tcctcttcat  15900
aacatctgtc actctgatat attatacgtt tgtttgttta cttactgtat gtggggggaa  15960
gagactgtgg gagcaagggg ggaagcaggg aaacaagtac actgcagtga tctgggtgag  16020
aggtgaccgt gtctcagact aaggtggtat tggtggagaa ggtaggaagt ggctgaattc  16080
tggatgagtt ttgatggtat agccaacagc atttactgac agattggata ttcactgtga  16140
aaaaaataga gatgaggatg attgccaagt ttttggtctg agtaactgga aaaatgagat  16200
tgccatttac tgaaatggtg aagactgtat gtagagcagg tgcatgggca gggtagaaat  16260
caagagtttg atttttgact tataaagttt gaattatctg atgaacatcc tgatggcttc  16320
ttctcagtta gttctcatgc agtgccttca gctttgctgt tcttcaagaa aattaaaaag  16380
gaacttagag atcgcctagg ctgtaggtac cctctcccct ctttcctttt actttataga  16440
ggtctataga agggtaggga cttatccaag gtgaaacagt gagctggcga cagaactagg  16500
gcacaaaccc agttctcttg aattctgaat cagtagattt tcttttttta gtgtgattct  16560
gaggactcat ttgggcaaga gtgagttttt tgttattgtt ttttgtttgt ttctttgccc  16620
aaacctaaaa ccaggtaatt aaactaaata gtgaataaaa ctgggaaact atacaaattg  16680
gttgctctcc ccaatcacac tgaaatatta ttatttttac tgaaccacat accaaaatat  16740
ttttcctgta aaaacacagt aagtgaactt ttaaaggcaa ttgagctttt aacaaagcta  16800
gaatctacag aggacctgga cagaaatggc cttaaatcct aggaaattag agttcatgga  16860
acctgggaga ccatcttgtc cagctagctc attttatggg tgaggtgcct gaggcaccaa  16920
gatggaaagg gacctggcta agctcataca gcaagctagt gcctgagcct agtcagagcc  16980
tgttttaagg gttagtcgta tgttgttttc ttgaaaaaag ttacattgga aaagtgaaaa  17040
ttctttggtc catactgaga acaaagaatt atacataatc atatataata ataatgatag  17100
cacttcctga atgtttgctg tgtaaacttt ggcaccttgc atgaattgat tcatttaatt  17160
ctcatgtcaa ctttaggaag caggcctaga gaggttaagg aacatgtcca agggtcacac  17220
agctaggaag tagcagaact tgtgtgcact cccaggaagt ctggcttcta accacaaggt  17280
tctaactact gtgcaatacc aggagcttct cagattaccc ttcaccttta ccaacccaaa  17340
tgactggtga cgtaggtgac ttcattatgc tctgccccta ttatagtcca ctgatcctca  17400
ccaaataggt gggtggccta gaggttaaag tagaggcaga gtgatggaaa ggggtggtta  17460
gaagaagttg atgactcatg atagggattg gaaaacagga ctacaggaat tattgaaaag  17520
ggcctagaga tcccaaggag gttgatctcc gactgctaca aacctgggca attcaatgcc  17580
tgcttaaata ggagagttaa gataagaaaa ataaaattgc caatttttac agtcagacat  17640
```

-continued

```
tgttttattt attttacatg tattaattca tttaatcctc aaaatactcc atgaggtagc  17700
tacaattatc atttctatgt tgtagatgaa gaaacaggca cagagcaatt aaataacatg  17760
cacaagatta gagaacaagt aagtggaagt gccaatatta gaatctaggt agttcagctc  17820
cacaacttat gttattttcc actatattta tggaatgagg taattttctt ataacagaaa  17880
gtttttaaaa tgcaaaaaca ttgtgcctga acttcaaaca ctgaacaact catatcctta  17940
atatgcacca gtttctttta agcactctta gaaggaagga tacttaacct aatgtcacat  18000
ggtgagtaag tagcagaacc ggaacttgaa tttgagactc cggactgcca gacctctttc  18060
cactctatca cttgggctcc cttctaacat tgacttgtct ccctccattc ctcctccgta  18120
ttgttctgcc cttcaccttt taattacctg tctccatcaa caagattgga cagagaattg  18180
ggagagtgag cagagtccat ttccttccag agactggaca aaaggaacaa aatgttagga  18240
aaaaatgtca gcatgtggga tttgtgggat ttacactaaa taagaaggga cacttcccag  18300
gactgacaag atgctacctc cgtccctcta ggccccaatg tgttgtgcag gatcccatag  18360
gaagtcatga atgtggttgt cagataacct ttttgttact gtggaaatgg aagcaggcta  18420
ctgcaaaaat ctgtctctcc aggttttctt ttaaagaagg tagtcttgct aaatgataac  18480
tatttcagca tttatttgaa aatgggcagt gcaggagaga aagaattttt ccaagcttgt  18540
cacattgggc cacctctctg aagcattgtc caacttctaa ttagatgagg agactgcata  18600
aaccaagagt tgagagtaaa gatggaaaca cttgatgttt ggtgtttggg tgcagaaagg  18660
attccagaac atgttttggg tctctttact ctgtccatcc ctccttccct ttcatctttg  18720
tttaaaaacc acagttagca aatgtgtagt ctgtttgcaa ttgttcatct gaaaaatttg  18780
tttgatcagc cttttgaata aaaaagacca aattagactg agatatttca gtcaccaact  18840
atctaataat agaccaaaaa ttttaaccat gctcatactt tcatatggta tgtagtttgc  18900
tttagacatt ttctgggctt cagtgaggtg ctagattgac tcaaaatatg gcaggtcaga  18960
tgtgggattg agcagggtgg actcttctct acccttccca attcagagtt ccccatcaaa  19020
gatgatctca tagtgtttga aaaaccaagc tgaaggcttt gggaattagg gtgctgaagg  19080
gatatgctgt ttcccaaagc cttctcagtc attccttctc cccccagttc agattcttaa  19140
cacctctttc caggattagt gcagtgatcc cacgtccttt ctctctagct ctctctgcta  19200
ctctctaatt cctattgtat ttgtgccacc agatctttcc aaagtttagc tccaatcttg  19260
tctgtatact gctttaaatg tctattagtc tttaagctcc ttaagggtgg gagtcctgtc  19320
ttattttttc cctattcttc gtgcttaatg caaaggaagc cttgctgtat agttgtgtaa  19380
tgcatgatta caatttcagc ttctccccat tggcttatgg gttaaagtcc aaattattta  19440
aatctggtgt tcaagtcctt ttatgatctg cttatttttc cagcctgaat tcctggagtt  19500
cccttacaaa actcttaaaa cccagccaaa aggatctagt cactgtcact ttaaaccatc  19560
ctcactctct tgttttttga acatgttatt tttcttataa tccctttgac cttgaaggct  19620
atcccaattt caatactatc cattcttcta tgacagcccc ctacaaaatg aatattctca  19680
acctcccaac ccaaggagaa gtgatctata tgacacaata tggttgaaag aatgttggct  19740
tcacttcttt atctgtaaac caggggctag aaatctctag tttataagat tttgtggaga  19800
ggggatcata tgtgattatg gatgttaggc acaagtcaag agtgcataag accttttgga  19860
tttatccctt ttttctttct ccatcaatat ggtacttagt cccttaaatc agaagtactt  19920
gtgttaatgt ctgataacgt ccttctaaat atacctctaa acatctgtct ctctttaggg  19980
caaaggttgg atatatctgc aaagattctc tttggatata agatatccac agcacataac  20040
```

-continued ttaacagtgg tgtacacagt aggtattcca taagtatttc tttatgaaat gattcagagt 20100
caatagtagt aagtaactgc caaaaacaac tgatggattg taagttccat taacataaat 20160
acagtcagcc ctccatatcc atggattcca tatccacaga tttaagcaac tgcagatgga 20220
aaatatattt tagagacaca gtaaaaataa caattcgaca gtaaaaaaat acaaataaaa 20280
ttatgtaaaa caactattta cataacattg tattagctat tacaagtaat ctagatataa 20340
atgaaatata tgggggatgt atataggtta aatacaaata tgacaccatt ttatatgttt 20400
tagttaagga acatgaatat ttttggattt tggtattcat gggagtgggg gaatggaacc 20460
atgccccttc aaataccaag ggactattat atgggacaca gaataaagga gttgattgtc 20520
ttgctctgtt aaattctggt cagacacatt tgcaatgtat tgttcagccc cagtattcat 20580
ggagcatctc cttttgtaaa gcatggagga gctgtgagag agacatggag cagtgaacat 20640
aactattgtt tcaacgtacc tgaaggatta tcatggaata aagaagttag atgtttttct 20700
gtagtacccc aaagggcaaa agcaatgagg acagattaca gttcagtaaa cgaaagaggt 20760 ttttttttt ttttttttt tttttgaga tgggagtctt cactcttgtc gcccaggctg 20820
gagtgcaatg gcgcaatctt ggctcactgc aacctcgcct cccgggttca agtgattctc 20880
ctgccttagc ctctggagta gctgggatta caggtgtata ccaccactcc tgggtaattt 20940
tatttattat ttatttattt ctttatttat tttagtagag acggagattt catcatgttg 21000
gccaagctgg tctcaaactc ctgactgcag gtgatccgcc tgcctcggcc tcccaaattg 21060
ttgagattac aggcgtgaat caatgtgccc agcctgaaag atattttctt agaatagctt 21120
ctttcaccct tcatcagaag ttgtcaacat ggaccatatg agttttgttt ggtctatatg 21180
gtgtatatgt gtgtgtgtgt gtgtgtgtgt gtgtgtgtgt gtgtgtatgt gtgtgtgttt 21240
attgaattac ttgctaacat tttacttcaa aattcagatt tccaccatag ggaatgaaga 21300
tctggcaata caggactttc attcctacat ggtaatgacc agctgtaggt gaaaagcagc 21360
tgatcctctg gatgggccat gcactttgca gtttgcccag gcagcactga tccgctttat 21420
tcatttaagt tacctgcttg actcttctag tcattcgagt atgtcatccc catcagatca 21480
gagacctaag caaatcttgg gtcccttgct tactccaagg gctttcactc ctcgtatagg 21540
aggagctaaa gaaatgtaca agcagcacca caataggatc agacctggct ttcaattcta 21600
gcacggccac ataacatagt tggatgacct caggacagta acataacccc tctgagcctc 21660
tagatcttca ttatctgtag agcactcttc ttatagagtt attataagaa tgaaataaaa 21720
caactaggat aaagggcatg gcacttagta ggtgctgaaa tattagttcc cttcttctaa 21780
ttcaccacac catatctgtc tatctattgg ctgaatcaca taaatagtaa attcacattc 21840
actgaagaca ttcaagaaga gtctggaccc tttgggaacc atgtataggg caaaggtttg 21900
aactcatagt agatgatttt tacagtcact ttttaacaat ttaaaagcct atagatgact 21960
ccaaaatgcc catttggatg atatgaggca tactttgtgt agttaaggat tttaaataca 22020
taacagagag gctgaagggc cttcgggaaa gaagctgggg taagagtcaa agtgtagtat 22080
gttgaccgat gttcaggaat aggctttggc atctgacaga ttttgtttta aatactggct 22140
ctgggtctta ctagcttcca gttctgggct gcttcacctc tcttgagttt cagtttcttc 22200
atttctaaaa tgaagatact aatgcttcct ttgttgggtt tttgtgaata taagtgagat 22260
aataaatgta aatatctagc ccagggcctg gtgcatagta caagcttcat aaattgtacc 22320
tattattatt agtagtagta gtagtccaga caaacagagc ttgggaaaac gctagactct 22380

-continued

```
ggctgacata catgggcttt tccccaggcc actgctgcct ggcttcccct tccacaaagc  22440
tttgagtctc caaaatgctt tggctggaat gtaagcgtga ggtcattgca gataacaggg  22500
gagcatgatt tgcttcggta atgcaagtta ttaagttact tccctcagcc cagctgaaat  22560
ctcttattgg ttgatgtgtg cttcaaagtg tgagacagag ctagtctgag gagagaggga  22620
gagtgagaag attcctcttc ttggccagag gtcatggtct tccacaagga acagaatgac  22680
tcaatgcaaa ttatgggacc tctttgagtt tggggcccct acatttaaac tagtaactcc  22740
gttgcacata ttggcaccct tcccccaaca aaattactgg gcaggaattt tcttgaatcc  22800
ttccgtggcc tggaatgatc tcccttctca tccttgtgat ccacacagct ggcaaatggc  22860
aggcagcaga acaaaaacaa gcctcttagc atatagggag agaaagagtc acagcagtac  22920
tgaatttgct tgggaaccta atgttaacaa aggaccttcc tctcaacacc ccaaacagat  22980
taaaacattt ttttaacagc aagttgtgtc tcggagcagc tctttgcttg ggtatattta  23040
aagatctgct gagtcattta agagcaggct ggcatatcct aagaggcaag gactataccc  23100
cagtctatgg gggagtaagt tgagaggtga aatctgtttg gctttctccc atggaaacaa  23160
acaaggtgat ccacttccat ctcccacgac tctggagagc atctactaag ccttcttatt  23220
ctatcaactt tgaactcctc agtgtataat agagtaaggg tgagagggaa ggagcagtcg  23280
taccagtgtc attattggta tgttcaggag ttcaatttct tcctgattca gtcttggcgg  23340
gatgtatttg tttgggaatt tatccatttt ttctagattt ttctagtttg tgtgcataga  23400
ggtgttcata ataccttctg atagttattt ttatttctgt ggtgtcagtg gtaataaccc  23460
ctgctgtctg aaattgtaat ggccctgcta ttggtagctg agagtagcat ggaagtgtca  23520
ggttgatggg ttcatttaat tcttttcttt tcagtttcag tcacatgcat tgttaccatg  23580
gcatatgaca gttgctagaa agtgaaataa ttttttttct actttattct ccactgcact  23640
tctaaattta ttagtggaga aattagcagt taccaactgt tcattatagg tacacattgg  23700
ggtttcctta gagccaattt tccccctggt tttcatcttg taaatctgta atcctaaaaa  23760
ttagcaaaac ctagagcttc tctttggtcc tggcctgttt gaaccctgtt ccacagaccc  23820
caatcttctt tcttgtttga ggcaactatc cttctctttg cccaccgcca ttttccttca  23880
tctactttc ccttctctag cacctcagac tgtcttccca cagtggcaca gcctcccact  23940
ccactttcac tgtgccatct ccttgccatc aaaaccatcc tcacagaccc ttctgaaacc  24000
acttctagga agggaaatca caatggatcc atgaaggatg ctttctggat gactttaaaa  24060
gattggtatt aagatatttt atcagtggta gcaacactga cttattcagg cagccatgcc  24120
ccggatctat aagaaatcag gtaagctaaa agttgcttga gctggcagga gacctagttc  24180
tctttttcc tttccctctt gcattttgtt tatcgatggt tttcaaagga cttagaggct  24240
ggctttgtta tagttagttg gtaagagaaa tggtggagga ccggaaaatg ggagtggaac  24300
gaatgagcat gtttgagact aagttattac aattcctagg atgtataaat tgcttgaaat  24360
ctaccaagta ctttcagaca cattatcttt tttactcttc aaaatcaact tggaggtagg  24420
cacaacaggg atcaaatcct tagttcacag atgagtaaac tgagactgga ggaaattaaa  24480
ggagattcca aggtaactca gacaataagc aacagaacca ggatttggtg aattttttgg  24540
ggggtgggag gtacagagtc tcactcaggc tggagtgcag tggcaaggtc tcgtctcact  24600
gcaacctctg cctcctgagt tcaagtgatt ctcgtgcctc aacctcctga gtagctggga  24660
ttacagacat gtgctacaat gcctggctaa tttttgtatt tttagtagag atgaggtttt  24720
gtcatgttgc ccaggccggt cctgaattct tggtctcaag tgatccacct ccattggcct  24780
```

-continued

```
tccaaagtgc agggattata agcatgagcc actgctccca gccccagacc attaattttt  24840
gacagtaagt ccaacttttt tcaagttcac agctcagatt tgctattgaa tgaatgagta  24900
tatatgtcat ttgggaacat tctttccaac ttttggttga agatttgttt tatcacttgt  24960
gaaaattttt tttcattctt agcaatgtca gtttagttaa atgagcattt catttgcgaa  25020
ttcactaatt aattatttta ttcatcaata catttcctga gtaccaactt tctatcaaac  25080
cctgtgctgg attctgaggc tacaaagaga aataagatac catctcaggc ctctaaaatc  25140
tcacagactg gggactgaca tctcagtagt aaacatatga acagcaactt gtgaaacgcc  25200
attagcaaaa tctcaagtta tattcttcag tgactatggc catcctaaaa atggggtgtc  25260
ttttatttgg ggtaaatgaa gatgaagcct tatgagaaat tgcattttaa tctaatcttg  25320
tcttgctaag aacagaagtg gaatgtttca gcctctgtgt gtgtatttgt gtgtgtgaag  25380
gttgagtgtg tgatgatgga tggggctgcg agattgttaa gtaggatcta tggggggcct  25440
taaatggtcc tggtgagtcc caactttctg gttatgtatt tgagtagagt atgggggtga  25500
caaagattgt tgtttaagag ttgattttag attttttcca agtaaatggt cagctgactt  25560
ggagcatcat cattccactt gctttgaaaa cctgccactt aaggctcctt ccagtcatag  25620
gttaactctt tctggtcaag tattactctt tttgagcatt tacctgtcag tgacaggtac  25680
aatgttagat gttgtctctc tgttttcttg tttaatcttt actttgatcc taggtagctc  25740
ttattagttc cactttatag gtaagaaact gaatttcaga gacttgaatg acttgttcaa  25800
gatcacatag tatagtaact tggtagtttg ggacttgaat tttgattgtt cagtttttttg  25860
tttgtttgtt tcctggcctc cctgctgttt tcactattcc acaccacttc agctttattt  25920
ttcatagagg ccattaaatg taccctccat cagccaaagc ctcttgcctc ccttcaacgt  25980
aactcttctc tagcgtcctc ttaataatct tctgaaaagg ttttacagcc tttctgggta  26040
ctgggaccca gagtcttaat ccaggctctt aagtgcctta tttaactgta atatggaaaa  26100
tcaaagtcac agctaattca ggaaaaatga gtttgggatg tgaatttcct aggcaacttg  26160
tcatctcttt tttacttcct tagcttcata aacttaccca caatgttccc tgaggactaa  26220
gagtaatgga gggtgatgag gaaaggcttt cctcccttcc tttccgagag tcctttagcc  26280
aaatgccaca cctcctcctg tttccctagt ctccgtgcag agatggaagt gggagataga  26340
catgggttcc tttcagccct gagttcatgc cagggttttc tttccctcta gctggactga  26400
ggtaggagga gaggttgaag tccaccaata agaccatgag tgaagaagac taaagtactt  26460
gaaagagcag cagacctacg cttaaaatac tagggtttgt gtccagactt tgtgggttac  26520
tatctgtata attttgggca agtcaacagt tctgagtcag agttccctta tcagcagatt  26580
ggaagataaa ttctaattat atagatgaaa cattaagtct agaagtaatt tgtaaattca  26640
gaaagggctt atagatttaa agtgtagccg ttttgattac cacaaactaa atcctatact  26700
tcagggataa aatcttctcc tgttttttct aaaagcctgt gcatgtgtgg tgtaaggggt  26760
gggttttccc ttgtaccagc aacttagcaa ttgtagtaac ggggctgagg gcagtggcat  26820
gcttcttcat tgagcaagtg tgaaaagagg gttatgcatt caggggtcag cagatggcag  26880
gcagagtagc ccctccaaat ctccctccca taccacaaag ccctcttatt tattcaaact  26940
taacattaga agctcatttc aagtaggcac gtctgtgtct gggcgtctat tttccttctt  27000
tgtatatagc aggcatttgt caacttggtg aaaagcatta ctcttctttc catttctgag  27060
gactaattgt gcttcttcgc tagacacgag ttcaaaacag tgggttgaaa gagggcaagt  27120
```

```
ttatgccaaa gaatcagaaa tagtcataat ttagagagaa ttctagaggt cagttccctt  27180
tcgtatggac tgggcaactg aaacccagac agggaaggga attagaccaa gttcacaagc  27240
acaaacactt tactggcaca ttcagattgg aaatcgaggg cttctgctcc caggtcagaa  27300
ctaaatgccc tttctagcta gggtgttctt tgatctcagt gattttgact ctttctactg  27360
cactctgggg acagtgggtt ctgcggtacc aactccaatt aaagtgggaa tatgtaccag  27420
cccctcccct tggtttttat ttttcagagg cctggcagtc agagggattc tgatctctat  27480
atgcaatatt ttcacactac tgtacttatt gaaatcacat ttgaatcttg gcaattaaca  27540
aggcagtaat tggcatcagg agggtatgtt agtttgctta tctgcgccgt ccctcctctt  27600
cccaacccac tgtgtattgc agaatgtttt atcagctctg atttgccaag ttgctctctt  27660
ctccagtagg tgctgcgagc agagagggat tcctcggagg tcatctgttc catcttcttg  27720
cctatgcaaa tgcctgcctg aagctgctgg aggctggctt tgtaccggac tttgtacagg  27780
gaaccaggga aacgaatgca gagtgctcct gacattgcct gtcacttttt cccatgatac  27840
tctggcttca caggtgggag gttcttcaat tgaaaactta gaactcagtt tctagggtag  27900
tgagtgttgt aaggtttgga ctgtgaccta atattacgca gccatgacat tatctattag  27960
gcatctagac tagcttgctt gaatatctta gcatgttgac taatttgggg cagaatatag  28020
tgtgggtggg ggattttgtg tgtggggggg ggttgggggt tgagcaattc attattatta  28080
aaatgcaaaa agcacttaat tcgctatgat aagattgcct ttttcatgca tactggccta  28140
cctgcaagac ccctagagac agtaagcagc atacatggtg tcttccagtt ttcagccttt  28200
gtgcaaggaa caactgtggg tttctgcaca tgtgttgtgg tttgatgttt gtatgtgatt  28260
gtgtaccagg gtatgtgtgt ctgttattgt gagttcattt ctgagcagtt gtgacacaca  28320
gagatccaga aacagtgtct taccctgtgt gctttgctag tgggaacgtg tcttttcttt  28380
tgtgctcgta tctctgtgta atcgagtgtc ttgctaagtc aatgtgcctc tgtctctttt  28440
taccagttct gtctttgtgt ctctgtgcct tcatgtattt tttcccctga gtttgcacgt  28500
ctctgtctat gtggatatct ctcactccag gccactgtat cactgtgtct gtattacagc  28560
tgtttatttc tgtcggtgtg tggatttcta tgtctgtttt catcttaatt tgtgtgtcta  28620
agcaagactg ttttggggtg actatttcag tttatgtcat agccattctt tgtgtgactg  28680
cttctaggta tgtctttttc tatgccccta ttgtccccat ctccatgtgt ctctgtgtgt  28740
atatgttcta atgtatctgc ctacttatct tagtttgtat ttctctgggt gtatatccct  28800
ctcttgcagt tctgggcctt tgcagttttt ggcttatgtt tttgtatata tccactagaa  28860
ttggcttctt atcttttttg tgcatgtttt agtttgtatg agtgagcata tccaactctg  28920
tctttgagaa gcagaactgt ctgtgtttgc agtcagttgt gttggctgtc cctgtgtttg  28980
tccctgtgtg tgcatttcat tgtatgtgta cgcatccatg tatctttctg cttctctgtg  29040
accagatatt tctgtgtagc tgtctatgta tattggcttc tgtctgtgtc tgtgttgttg  29100
gctctacgtc tgtgcatatg cacccaccgg gttcataaaa agctcacctg ctctccaagg  29160
aatctaccag attattttgt gaaataactc acgtttcgtt tttttacttg ccagctgcta  29220
tggtacttaa aagtgtgttg gtacgtaggt gtgcataatt tattcatgta ggatgtcaaa  29280
agagtcagtt aaaaattatg cacagtgtgt ctttattaac aggacacttg tgtgtagaga  29340
atccttgaga aatgagtggt tagatgataa atcttttcat attaatttca tgatgtcagt  29400
gaagtaaatt tgcaagatat gggctgcata agaactatgt tctttttaaa actcagcata  29460
ttgatggtgg agaaagcatt tatttgtact gcaaagtctt atttctgata agacatcaca  29520
```

aataagaatt attgtgatga gacttatcac aaataagaat tattgtgata attcttattt 29580
gtgataagaa ttactgggtt agaaggtgtt acttttctgg ttttgtttgg gtttttgttt 29640
tgaagtgtta ctacagatgg tgtcttaggg acaaagagct ctgaggttga cttagaacac 29700
atggagtaca gataaaaagg agaatgaaaa gtaacagaga gatgggcata ttccttgttt 29760
gaatggagtc atccaggggc tcaggatgga gtgcacagga aatggagagg tgaaggtcat 29820
agagagaagt ttagcaggac cagatctttc cttgtcctgg gctgctgtga ccatataagg 29880
aaggcagtaa ggggaggggt agggatgagg aagagaccag ctctcctctt tctttctgat 29940
ggaaggttac cacctctatt taaaacttct gttcttttgg tttctctttc tttctttgat 30000
tatattattt tctggacttg ttctgccaaa gcaagaagga aattccacat gtggctcact 30060
catttattat acttgtttct ttgcacgata ttaaagacag cttgttaagt gtcactgcaa 30120
acatcataca cactgatcca ctgatatggg caggggggttc tttatgccag ttctgctctc 30180
ttcccagtgt atctgtggtg cttaatgggc gcaaccatga tttttctgat gtcagtctgt 30240
gatgtcagtt gtccagtgtg tatgcaggct gcttaagagt acatacagtt ccttcacaat 30300
tatggtagtc cctgagaagg aagtggtcat taataaaaga ctaggttcag tagaaacatg 30360
taagttgtct aggtgttgga aattaataca gtactgtgct aagggaacat atatctagaa 30420
gttaactgaa ttatgctcaa taaaaagagt acaaatgttt cataaatatt ttgacctaat 30480
cctcctgtaa gattaggaga gggatatttc cgatattcaa ataatttttt taattggcaa 30540
acaccttaga catactattt acataaaatt gacatgacaa aattaagtca ttgtgtctgt 30600
tttatgataa aacaggctct tttgatttag ttagaattat tgaatgtaaa ataatgaaaa 30660
ttaaaaaaaa aacaaggagg aggaatctat cctattttat aattcagacc gttgaattga 30720
gtttttcttt tgttgtattg atttaaatgc agagaagtct atgatgctgg attccagtca 30780
gaagataaac atttgtatgt gggctctaca ttgcagccaa ccttgataat ttcaaacctc 30840
gattttctca tctgtataat ggtaataata aagcctgtct cagtagctac caaatgattg 30900
catatgacaa acttctcact tatttaaggg aaaaaaataag aaaaagaagg acaatagggt 30960
ggatttttca tatagtaaaa tttattcagt tagggtaata ttctgagatt gtcttctgaa 31020
gcaaaccctg caaaccctgg ccattctgtt ttgtttagga aagaattcat cagttctgat 31080
tctgcctttt ctggggaggg aggctgagta ttggattgaa gaggagtcac tacttttctg 31140
agatgatata tccgtggtaa aaattattaa tgctttgcac atgcaacata gagtgttcaa 31200
ttttgttagt caacaaatat ttaagtggca gctgttatga cctcaggggt gtagtgactt 31260
ccttattgtc ctttaattat taaaaaagaa atctatatca gaatatcagg taaactctta 31320
ttacatcaaa tattataata aagatacttt ttatattctc taaacaaagt agagatctca 31380
gatgttggtt catttatcaa tataatatta gatttgaaaa ttccagtata caaaaggaaa 31440
aggacagctt cttaaagttt atagtgattt tctatgaact atcaattccg ttttttctg 31500
ttttactggt atgatggaaa ctaaatttcg agttgtaagt agtagataat tagactgcag 31560
ggtaagcctt gagattactt cttttcaggt aggaaactct actgtgtatt tggctagttc 31620
aacctatcat gggtagtcaa aaatagttac atatacaagt cagcattttt taaattgttc 31680
agttgtgctt aagattggtc ctttccagga acaatccagc tttatcaaaa aattattgcg 31740
tacatgtaaa gtgttctgac attttaatgc tcacaatagc cgaatgacgt gggtaagaat 31800
cttcgtcttc attttataga tgaagaaatg aagacacaga gacataaatt aactgggcca 31860
gggtcctacc actagaatgt gatagatgat aatttgagct cagcacatag ttatttccct 31920
ataatatttg ttttatgatt gtatagatgt ctgctgacca accttaatct ctgctcccta 31980
agattaacca ttctacaaag cagaaactgg aggtcattca aatgaaagct ctacactttt 32040
agagggccat taacaatgct caagttaaag aaaagcaatc aaagacaact aaaatactgg 32100
taccttcaaa cagtacttat gaattattta accttagata atttggcttt gagttagaaa 32160
gatagagtaa gatggaggaa ccaattcttc cctgggttga tatttattta tcttgctctt 32220
ttgaagtcta ggccaatcat cctatttatt ctgaatggcc cgttaacgtt tatccattta 32280
gggacagcag gtttggcaca aatggattgg ttttctgagg tcttatgtag agggctgcac 32340
tgactgactt ctgaaagtcc cccctaaccc ttcaaatctc agggtcatct ggtctcaagc 32400
cttcaattat gaatacattt ctattgcctt tttgagtaac agcacaacac tgcaagctga 32460
cccactgggt ggatggaatg gggctcttgc cctaccaccc tttggcaaac aatttgaggg 32520
tggcattgtc actacctcat tgtatatagg gtctcttgag gcccagaatg gcaaaataat 32580
tttcccagtg tcacacagcg agttattgtc agagtaaata tcaattttga atttgtagac 32640
cacgtggttt tacctcatca tttctgtttg ttatgaaagt tttacaaata attagaagta 32700
gaaataatga ttaaaataaa gcataactac taaaaaatag tttattgcag caccacctaa 32760
attcatctca ccactctacc agtagcatac atttcacaat tgggttaaca ttgctctgga 32820
tcttatagct gttgaagaag acaaaattct ttccattctc cagcttatat tttccccatt 32880
tgtaaaacat aatggaagtg tacggaaaat aggagttgat aatttttaag gcccttgcca 32940
gcacattagt acataggatt cttgcaagtg gtggtttact tcacttcaac tatagaaggc 33000
ctatgcgaca ccacccatag agggtagttt gaaagaaaat gctagtgact acgtgtgttt 33060
ccttcctgac atattttata gaaggtgatg agttccagca ttttttcaga cttggatctg 33120
gctttcattc cccttctcct cccaccctct aaaacaacag aggcagcaac catttacaca 33180
ctttccagaa gtaagtaagt aagactgtat tccagaaaca ccctatatca aaatggaaat 33240
atactcaagt gccccaatga cccattgggc tagtttgaac gtgtgcagtc tctgtgctcc 33300
ccgttttagc ttaagcctac tccctaacct gtcatatgtc acccagccat ggagcctagg 33360
gcaatgactg ccatcatatc tgactttatg gcctctcagc tttcaatgac tagctttgta 33420
gcagaagttt agcctctcat ccccataact ttggaagtag tgttgagata aagaaacgtt 33480
gaattgaagg ttgtgttttc tagatttctt tcaattgctc cttaggcttt agaagataaa 33540
ttctcctaaa agagaggtgc tacaattaat ccaagcaaag ggaaagatgt cagtaaaact 33600
gccccttttc atagaggtgt ggcaactgct gggaaggaag aaattagcct gaggccatgt 33660
gattactaat aaactcaaag cggcattttt ttacttctca atatgaggtt gaaactataa 33720
gcttaaattg ctgactttct ggcagcacca aacagtaagg aaaccacaaa gataaaccca 33780
aataatagag ccaattttct ttttttccgg gggggatgac ttctaactag tgatatgagg 33840
aaggataaga aaatgtttct ttgtaggaca tatgatcttt gctaagtgca ctgaatgtat 33900
gtagaggaga caagtctgct gagggtatga gaattgggcc aagatttaac acattttcaa 33960
agctccatga agaagcctac tgagcagtgg gagtggagca ggttggggat agtgaagtat 34020
ttgtaattca tttttaaaaa ggagagggag agagaaaagg aaaaactggg ccacccatcc 34080
tttgaaaaga aaccttgaaa gaggtccaaa tatccttaga aatccttgac ttcttaaaag 34140
tgatgtttgt tttttccccc tgacaattat agaggtcaga gagtttttct tttctattac 34200
aaaacattga gagtgtgtag aaataattgt aggtagctta gccttggctg tagtcagaac 34260

```
ttttgtactg tgactttagg atctgtatgg aatcgtatga tatgcggata caccaaaaac  34320
tctatgggtt atcaaaatgg gatagcatta aaagaaatag tgcttttgtt tagaagaaga  34380
aatgaaatgc ttgtgtccag atgcttaaag gaaggcagtg cagactttca gaaactagac  34440
tttaagagct gtactcagat actgagaagg gctgatggct gaaggaggaa caatttaaaa  34500
gaataaccgt ctctcctctc cctgtatatt ggacataaaa gaatatccca ttcttttcag  34560
aaatgtaata caacagttta gcttgctagt aacttcacat gctatttcct ttacctctta  34620
tatttgaggt gtctatttgg agtgggctgt gtttctagct attctgttta tctggtttgt  34680
ttttgttggt gtaggaaact ggtataaatt ttatttgggt aaatatcacc tcaattttca  34740
actaaagctt tatttaagtt tcacatgaaa aagacaaatg aggcaaagga agagaaaaat  34800
gcattgtcag aatcagaatt atgagaaaaa aagtcaaaca aacatatttg aaatgtccag  34860
aaaacctgtg agtttttatg tatactatac aggaaagata ttctgtcatc tggttgccaa  34920
actatggagg gtgggagact tcgaattttt gtcaaaaagt attctttcat tagaaagata  34980
catgggtgtg cttccatgtc agcaacatga ctgcagacca ggaagtcctc acggagagct  35040
ggaatatggg tattttggac tctctggtta gatgcagctt ttacttcaca tcctcagtgg  35100
tactactgta aattttcatt ttcctgtgga ataccctatt tggttccatt gtatatagtt  35160
gacaactaga attcgttcgc tgttgcttga gcccaactat aacttcttgg cactatacct  35220
atcttctgat gtgcctgtgg aagagctacc ataatgaatg tgtacatgga caaaaaaaaa  35280
gagagagaga gagagaatta aatcatgagt ttgtgccttg ggagctacag tttaaacatt  35340
tgctgttttt ctcacttaat gaaaaattta tttgaaaata acagcacaga aaggaagaaa  35400
gacaggctgg caagcatcct cctcctaata cacttatcca cgtttggata ccttggtctc  35460
agcctcagag gtcatatttt tagtaaaatg gccaccagaa ataaaggatt ttattttcca  35520
gactttggtg tttggagctg gtgtgctgag agctagcaga gaaagcccta ctcaggtaga  35580
tgtaccagag caggatggtt gctggtggat atggtggaat accttttatg tggttatctc  35640
ctccttgtaa ctcttggctg cataaccctt attttctttt ctatttttat tctctctctt  35700
ggaaaaaaaa ttggtggtaa attttcatgt gagccatatt gtctttttaa atagttttat  35760
taatataaaa tgtacgtacc ataaagcata cccatttaaa ctgtaaatgt caatgggttt  35820
ctctctctct ctctcttttt tttttttttt ttggatgctc agagttgtgc aacaattatc  35880
aaaatcaatt ttggaacaat ttcattgccc caaaaggaaa ccctctgccc attagcagtt  35940
actccccatt tcccccaccc cctgaccctt caaccctagg caagcacaaa tgtactttct  36000
gtctctatag atttagccat tctggacatt tcatgtaaac agaatcatgc aatatgtcac  36060
cctttgtatc tggcttcttt cacttagcat gatgtttcca aggttcatct gcattgtagc  36120
atctgccaat acttcattcc ttatttatgg ctgaataata ttccattgta ttaatgtatc  36180
atatttgttt tttccaatca tcagttgatg gacatttggg ttgttttcat cctttttta   36240
gctattttaa ataatgctgc tatgaacgtt cgtgtacaag tttttgtatg aacatctgtt  36300
tttatttctc cttggtatac acctaggagt ggaattgctg ggtaatatgg tagcttaaca  36360
tttaatcttt tgaggaactg ccagattttt ccaaagcagc agaatcattt tacattttga  36420
ccagaagtat atgagagttt tagtttctcc acatcctcaa caacactcat tattgtcatt  36480
gtccttttca gctttttga taatagtaat ctcaatgggt gtgaattggg accccatcat  36540
gcttttgatt tgcatttcct tgaagagtaa ggatattgat catcttttca tgtgcttatt  36600
```

-continued ggccgtttgt atattttttg atcctttgct catttccaaa ttgggttatt tgtctttgca 36660
ttattgagtt gtaagatctt acaatatatt ttggatgttt gtcattttag ggatgatact 36720
tcacagttat atgatgtttt ctagcaagca tttgcgttgt tctactggtg ttacatatct 36780
tagctgcatt agccactttg ctgggtatga atgccagcag aatctaagtg accttggctt 36840
cactactgag aatgcaaccc aagaacagaa atttgtcaga aatttagcac tgaagccccc 36900
cacttcccaa acttatctgg gacaaggaga atctacattt aaagctctat actttgtgtt 36960
gtgttttttt tactttagct tggttggatt taggatcttt tctttttgtt ttgccttatg 37020
catacctaag cagaggcaag ggaggaaagg gatatgaacc tggtagaaaa gtaagtaagc 37080
tttattcaga ttggcatatc catcttaata tggttcaatt ggctgaagaa gtatctcaac 37140
taaaactctg gaatactttg aagtaccagc aatatgtacc aaatgtactt tttatttatg 37200
tttggtctct atgtacttgt gtgtgaaaca atgagcacaa ataataccct ccttgttttt 37260
aagcaattta tattggtgat ttaaaaataa aataaactca agtgggaaat catgaaaccc 37320
catgtaaaaa caataagagc atgttttaaa atcccacaga ctttagtttc aaatagtggt 37380
tttgctattt cttagctgtg tgtcactgtg caagttactt tgtttctctg agtctttatt 37440
ggtgatatat gtaaaaaccc accttctcaa attattgtga ggacaaaatg aagtaattaa 37500
cataaagttc ctggtgtata ataagtgttc atattttgta tttgagcaca gggcaactgg 37560
gtttttgaaa ctgcacatta ctgttgcagt caaatctggc atgaaattag tgcatagaca 37620
gaatgggctg ggaaaatgaa aggactttga acatttatat tctgctttat ttaggcataa 37680
gtgcttaata attattgata gtttcttctg gttatctgac attttgaaga tactattacc 37740
tagcagaaat ttcttgtaat aataatctct tacacttata tactgttttg tgcctttaga 37800
agtacttaat gctctttatt tcactatctg ttcataaaca ttctctgaag caagcataca 37860
gtcagtatga attccatttt tcagatgaga cagctgaggc tgaaagacat agagttactt 37920
gtctcaattc acaaagtaaa gtgccagagt ttgaaccaga gcccaggtct tctctctcaa 37980
cgtagctctt tttctccttc attatatcag gcatagtagc aacgtattct tttactagct 38040
ttttatcttg aatatccttt tagcgacttg cctttggtgt tagtgtgcct ataacattgt 38100
cgttgaatat cttaatacat ttagtggtct tggcaagcag ttttgtcttc agaaggacac 38160
tgaaatctgt ggaaaggact gcagaagatt gggtgggcag acacctatca ctttcggggc 38220
tggtagactt tctattgaag caatttgcaa ggctactttg tattgtctaa aagcactact 38280
tcagaaaagg gttgtgatgt caaaataggc actttgagtg aagaaagggc tgtaagcatg 38340
ggtggaaaat gtggtagatg attgtcttga gttattttct ttaatgtcaa acaggcagtc 38400
cttggaatgc tacttcaaaa agtgttgtat aatgttgaag atacagttac agatttccaa 38460
cacgaaactc ataaatatgc aattccctgt cctcctaggc acatgaagga aaatttatga 38520
gcttcaggtt tctatgcagc tattaaagca tatttaatct gctttgagct caagctcact 38580
ctcgttggct ctcttcgttt cttcctctta catgagcaaa ctgcctttct ttttgtttaa 38640
aaatagtaag taggtttgtt ttcctccagg tgtcatgaat gcaaacattg taatttctca 38700
tctgttcagc ctttttgcac aacaaaatgg cagcacccag gaggttgaaa gggttaaatt 38760
gttccttctc tgagtagtac cataagttgt tagtctgcta ctctttctcc cagttggcac 38820
atgaccctaa catccaatcg ctagtggtgt ggccattttt tggtcttatt ttggcctttc 38880
ctcagccacc actcatcagt tctcatgcgt atttgtcaga tcctgctccc caactccaca 38940
gttcttagtt catcttaagc atatggctgt ctgtcttttc tctaaagatc ctcaagggaa 39000
aaaaaaaaaa gcatctccag ggggaattta ctgcctcata gccctgacag agatttctga 39060
ccaaacccta acgaaaaaat ttcttccctc catttgtctt ttattgtttt tacaggggag 39120
atatgtaaca taataacaat tatattgcac ataataatta cttctacaaa taataatctg 39180
ttgtcaaaaa tatacacagc tttggatttc cttattatgg cccttcatta agttgtggtt 39240
taagaatagc tatgattatt acttttgtga taattataat ccataaatatg gaaacttata 39300
aaattacctt taaagtgtta ctattattct ggccacagga tggaaagttg ttcgctagtt 39360
actcatttat aacctgaatg tactttttac tgaatctaaa ggtatcatct ttgcttggca 39420
attcccatga cttgtctttc tgactcttca gatctcagct taaaagctct cccttcaaag 39480
aagccttccc tgaccactct ggttttttct tcttttttta cctctactcc ttttcccatt 39540
acttgctgtc atagcattct gtttgtttcc tttgaagtgc ctattccaat ttgtcattat 39600
gaatgagttt ttttgttctg ttgcttatta tccattttcc ccactagatt gtcaactctg 39660
tgagggcaga gaccatgata ctctgttcac tcctatatac attcccagca ctatcagact 39720
ttttggcaca tagaagatac tcagtaaata tttgttgaat gaataagtca taaagaagag 39780
tttatatttt aactcttagt tgaataatct aagccaagaa ttatcaacct gggttggacg 39840
tgagaatcat taatgaatct ttaaaacaat gacaaggcaa tctatttatt aattatctcc 39900
aggtctaaac tttagcacgt atatacattt taaaagccca taagtgattc ttacgtatag 39960
ccagtgctat ctgtctcttc tcctgtcctt tcccctcctc tccttactcc tctctcatag 40020
ttttaggatt agcatggccc cacaacaaat ctttaattca catggcaatt tctaggattt 40080
atcatggaaa atgagccaaa ttgccttcaa gaagttttta cgtacctctt atatagaatg 40140
tgatgtttta tatgtacctc ttatagaatg tgagctttta agaggcatat cttattgcaa 40200
gaaatttcaa tgttgaaaaa aatattgaat atttataaag tcaaaaatgc aaacttttat 40260
atgattttca aacctatgaa gttatatcat gttcaggcct tctttccagc atgtggctct 40320
cagccctggt actgtcctta accataaacc tcatctttgc cctctatagg gagaggttta 40380
tggttataat tactcatttt aaatagtgta tattagtaat gtacactatt tgtatatttg 40440
ttgactgcct cctatatgcc aaccactatg ctagaaattt tgtaatattc ttcacgatat 40500
tcaagatatt aacatatccg cattttataa atgaggaaac tgctctcaaa gaggttagtt 40560
tacacagcca gtaagccgct aagcctagat tggatggaag gtatgtgaga aaaaagcagc 40620
atccataagg ttttcattct cctaccctgt acgacagagg taatagaaat tattagttaa 40680
agaaataata gaattttaca agactctagg aagggagaat gtgaaggata cagttctcag 40740
ttactggaat gagtgccaga gtaccagtac atggcttgcc ttggggtttg gactacctat 40800
cttaactcct ttgctcctcc caatcttgat ctcatttgtt tgaaagatca tctgcccaac 40860
ataaaaatgc atttctaatt ctgtaattta agtcagtggc aagatcagat tcagttaaag 40920
tttactttcc tgacagcttt ttagtatcat atctattttg caaaactcta gtgataaatg 40980
tatgcacatt tacacataca gcatctcttc tgattctgac taagatatta ctgggttgtg 41040
tagaagtgat gggctcttta gaagaaaggt ttgatatact actaatctaa ggactgaatt 41100
ttctcatctt tgtctttgcc ccttttgact gatgaccaga gcaggagcac ataacattct 41160
tttgtgctaa cagtatctct gcatcacatt gatcaggaga attggcatct ccagagccct 41220
gggatggtaa cttctctgtt gattttcagg aaagattagg tgatattttc tccatgggaa 41280
gaggatgttt gatgtgtgtt ggctttagca aaaggaagct tgtggagtca actgtaagta 41340
gacagaattg cctttgactt aatctgtttc agtcgttgtt catactcagg tcctccagag 41400
gacctttaag catttttatt gactttgtgg tctattacac gaaactaaag atactgattc 41460
tcagtcatga gtctgctcca aaattgccta gggaatcaaa aataattgta ccagttccta 41520
ttcctggaca ttatgattca tttggtctgg tatgaaggcc aggaatctgt atttttaaaa 41580
ttcactcaag caattttcat atatagctat aattgaaaat ctgtggctga acttctccac 41640
tcccgtatcc atcgcaatac ttccccaagg tggcatttaa gatgggccta gagggttata 41700
taagatttca atattaaaac atggattaaa agtgaagact tttcacatgg agataatttg 41760
gaagaaaaac ttgcaaaaat gtgagagcat tgagaacttt tctttcccaa ggaaagaagt 41820
ggcagcttca tttttggtca ttgcaaacag cagtgccata catgaaagga aagtggtggt 41880
gctcatcaac tttgaataac tttgtacaga acccttgaga ctcctctctg cttataaaga 41940
aaaagtgtca actgtaaagt tgatttattt atgaaccata ggctactatg aaatctctgt 42000
tcccagctag aggcctggga gagtaagata actacttgtt tattccacgg agccacttat 42060
tagctttttc tatagcacat acctcaaatg aagcatttca ataaaagaac cacattctat 42120
tcacatgctt cattttattc tgatttatgt aaaaattccc aaactcctca agcagtgttt 42180
ctttgtaagg caataatctt cagttctgtt gcaaaggtca ggagtgatag aatgaaaatg 42240
gtactagata caacagctct ttggtatttg catggccatt acattgccat ggggctgcaa 42300
gacttgtgag tgcttgatat tttgcttgtt gatgaatgag tctgtgtttg tgctaatgga 42360
gtgatttgag aggtagttct ccactgtcag tcaagaggtt ggttttgaaa gctgattgcc 42420
aatggtcatt ctgctaacca ctctggttct cctttagata gagacttatt cagattcaag 42480
tcttcatgta ctttgtggca taaacattgt acacaccaga tgtattcaac aaccataaaa 42540
aaaaacaatt aggactcaag tagtatgtca gagtgtagtc actgatgata tataattctc 42600
cactaccaag aagatggaag cacactgttg agtagctaca tcctacatat gttggccaga 42660
atttaggaat acacatgtga tctatacatt ttgaggtatt gtctgacccc tagaaaatcc 42720
tggtgaagtt tttctggtgt cagtttggtc ttaatgttta ggaaatgccc acagactact 42780
cctgctttct gcttattcac atagtaaacg caaagcacag gactagtttg tcatctggat 42840
caaggagaaa tgagttagca gatataaaat aaatcagaaa ggaggtagtt ctcaaatatt 42900
tactccatga atagttgctg gatgttcatt aactctatag catttgttac tacttattgg 42960
ggatcctgga aagaaaatat attgtctata tccactgttc actgaggccc tctccctacc 43020
cagaaactcc ctgtctccat cactcactct ccacattcat tgacccaggg gaacagttca 43080
tggatgagtg aacttgagct ctatcttaaa ggatggagtt cgatttcaag gcaagaggta 43140
taagagaaag ttcagagaca acactggcta tggtctttgt gaagaaaagt gaattgaata 43200
ggctcctgtg gagatcttaa gtaagtactt ctggagataa ggttgaggaa aagtaggttt 43260
gaatcttcat ccagaggtag cccctaaatg tgttgagttt attgaaagag tacttgactt 43320
ggattcagac agatctgcat ttgactcctg ttttgccatt tataagaatt tgagtaatta 43380
ttgtttctaa ataagagttt attgagccaa gcactcagta aatgtttgaa tgggaaaatt 43440
aactgccctg tttttctatt gtcagatggt cctcttcgtt ggataacttg gtaactgttg 43500
ataacctttt ctcaggaatc agaaggtaga aaggttggga aaatataaga aacaaaaagg 43560
catattccta tttttatttt catattgtct tccaactctc ccaggcttct ttgtttgcaa 43620
ggctgacttt tataatactt tttgggtaga gcaggtcctt ctttggtttg gggttaaacc 43680
gtgagtaacc ttattttcta ggtctcagcc aactttgaag ggcatgaact cacagtagcc 43740

-continued

```
tcactaggat cacttcagca gtgagaattt atctttcttg tataaaagtg taagagttga  43800
tggcggccag gcgcagtggc tcacgactgt aatcccagca ctttaggagg ttgagatggg  43860
tggatcacct gaggtcagga gttcaagacc agcctgacca acatggtgaa accccatgtc  43920
tactaaaaat acaaaaatta gttgggtgtg gtggcacatg cctgtaatcc cagctactca  43980
ggaggctgag acagaagaat tgcttgaacc tggaaagcag aggttggaga ttgcagtgag  44040
ccgagattgc accactgcac tccagcctgg gtgacagagt gagactgtca aaaaaaaaaa  44100
aaaaaaagag ttgatagcaa aataactatc tgtagcataa acctcagtat tctttatcat  44160
tcagtatcaa cattattact gaaaacaata agcaatatgg actgagtttc tgtggggtgg  44220
aaatgtgaag tggatcatag catgatataa cttgtcattt ggcttccttt ataaacatta  44280
tcaactacct cagctctatc aatcacttgg cagtccgtag tgaacattat aactcaaatg  44340
actagtcagg tctgttcatt gcccatgtaa aggcatatac ctgaagtgag aagtctgagg  44400
taacttagca ataagcttgc agtacagtgt ttagtgaagc cgaggaattc aaggatttga  44460
gtcatgccag attgctccat aaccatagcc tatctttgtc acaagtaaga aggtttaaaa  44520
atcaccatac cattattggt cacaacgttt ggagataggg aagagtttgt ggatggatca  44580
tggcagtgca tggacagtga ttagcccata acacaaccag tgaacactgt tgtacccaaa  44640
gcacataaat caccacatat actattaata tatttatgga tgacaacaga cactataatt  44700
ttatgtcagt gctttctgct gtgaaaaaca aagaaagtta agggtacctt ttttatattt  44760
gcatcatatc tccagacctt ttcctttatc tccttcttgc aagttcttct ttctttcagc  44820
tgactatctg ctgttcctgc tatggctccc agtggctttt caagagggta cttgtttttt  44880
aagagaagac ccttgaagga cagagagagc ctgaatcatt caaaataatg aattactcag  44940
gatgaaattt caataatttg caagtgtgtg gagatagata ttttgaggaa gcataatttt  45000
ctatgtaccc ctcaaatcgt ggctggagat gacagcctct tccacctcca tataagacca  45060
tttcatttcc ttctactttt ttctccctcc ttcccccaaa cacacaaaca tacacatatc  45120
ctgtgcttca gtcacacaga acttcttact atttcatttc aattctctat ggctttgcat  45180
gttctgctcc ttctgcctag aatgctcctt tcctttttc acctggaaac atcccaattc  45240
aaatgtcacc tcccttattt ataccaactt tgtctgtaac tcctttatca cacttcttcc  45300
tgtgattagt caattcactt gtctgctgtt acacctctat gagagatgaa aattccttct  45360
ccatctctgg aactcatgcc cttcgcatat agtaggcaat ctgtaaatgt ttgaaggttg  45420
agtgaattaa tgaatgacct tcaacctttc aggcttccaa ttttctctct gaaaaggaca  45480
gccaaatgaa aactcataat tttagaagat gaggttagac ggttggtagg tgcatgcaga  45540
gaccagttat tatttaggta ttatggaagt ttatagttct tgtatgttga gttcagtgta  45600
agagtggccc caaacatagt taatgaccac tccagaccca gttgttatag agttggcccc  45660
agctgtattg cttctattta agactaggat aagaaatgac actttcctac tttttacctt  45720
attgaaaggg tagaggctca ctgttatcaa tctcagttca cttgttgatt gcactggctt  45780
gccaagtgag aatattagca cctctgcaca tttctatagc tctgccactt atgagatctt  45840
tccttcccat tgtcatattt aataatcagg atagccctat aaaatatgca ttctcatttc  45900
ccagatgagg atactaaggc tcaagtagga gaacttactt gtttagtaag atcatacagc  45960
taggaagtgg gagaggcaag agttgaaccc agatcttcct agctcctagt ccattgttct  46020
gtctactggg tcacactgga ccagccagga ggcaggaaaa tcagctgggg aatgtggtgc  46080
```

-continued

```
caacgtgtga tgtttgccta aatgtgtgca tccttgctgg aagccagcca tgattcatgc  46140
tgcataagta ttcattaatg ttcatttcat ttatttggct atccatatgc tttccagggc  46200
gaaggcaagc taggacaagg gcagacaagc agccttaaag tttgggtgct ttccttcgaa  46260
gttgagctgc ctgtttgaaa atcacacttt ttggtgatag aagatggttc cagtacagat  46320
tttatttatt actgcatcta catggataga cattttccaa agcatagctg aaaatatgtg  46380
taagtcccag aatattttct gatttagaca cagactttga gcatgataac cacatttagc  46440
atgttaggaa attctgtcag aatgcttctg gaaaggctac ctttccagaa tgaaatgaaa  46500
aaagaaaagg atggactttg aaactggcta gatttgggtt atacttactc atagtgtgac  46560
cctggcaaat gatttaactt ctccgaattt cacttttctt attctttgaa gtgaaatttt  46620
aaaatgccat cttgcctgat ttttgtgaga atgaaaatga gatcccacac caggaattta  46680
gaagctactc agtaaatatt gcttctctcc tttccccttc cccagtcctg tcccccgaga  46740
cattcagtag ttattcacag gcatgcattc tgaagtctgc ctactgctcc atgttgaaat  46800
gcactgctct tgcaaggact gattatctat ttttctgtct tccaaggccc cctgtgttcc  46860
actccaccct cccaattctg gggcttcca aagtgggcag gtacagaatg ttctgtggag  46920
catcggaggc tgttactcaa tatcttggcc agcactctca actgctcttt gcacacactc  46980
catatgaagg caaactccag atcttggagc ccatgtgtgt gtcatgcatt gtactgcttc  47040
ttgtacccaa atccatctca agggtgagta gaccaggctc agacttgtcc tgggagcaga  47100
tttctcaagc tgcccatgtc cccacactgt ttgattaaaa ggaggtgctt caaactcttt  47160
ggctttatat agactagaat cagaatgatt ggtggtgcct ctgttctcaa ggtatcccaa  47220
agcactttgt aaggaaatat gacaagcgct gaggccatgc aggccagtac aacagccgcc  47280
acccagcact tcacaattag tcatgcccag cctgggatca tcaagcctgt ttttattgga  47340
agagcaagag agagagggaa tgctagctgg caatttcccc aggtaccctt tatgaaagtg  47400
cccttggctc ttccaatttc atctgaataa ccagctcagg caaattttcc tctatcaaaa  47460
agcagaatgt gatagtgaca agctgatgcc cggctgatgc cccaggacat tgactaaata  47520
gacttggcct cacaattggt ttttattctc tatctccttt cttccctttt gttcttttc  47580
tgtgtttctt tccccattgc catctgcaga gtgttctcag tcagaagtca gctgtggggt  47640
ggacagtttg tcattttaag atcatcccta ttctgtctac ctttcttatc cctcatatca  47700
ttgcttttag agcaaggaca attctggaag tgaaactaca ataacactct gggctccttt  47760
ccctctagta gtactcaaca cacttgtaat tacatgttca aatttgtctt tcttatttct  47820
acttaggttc atgaaggcaa gggacatgcc tgtgttgctt actttctctt ggcaggcaca  47880
tacagcaagt cttcaaaaaa tgcttgttaa ctacaaatta agtgtttaag aagtccactg  47940
ttaattagcc gggcgcggtg gcgggcgcct gtagtcccag ctactcggga ggctgaggca  48000
ggagaatggc gtgaacccgg gaagcggagc ttgcagtgag ccgagattgc gccactgcag  48060
tccgcagtcc ggcctgggcg acagagcgag actccgtctc aaaaaaaaaa aaaaaaaaga  48120
agtccactgt tagtatcttt tcccctgcct agtttgtaag caactggcct cttctatttg  48180
taagttacct gttttcattt ccatatgccc caaagcaaac tttagctcac ggccttacag  48240
agtgtgtatg ttagtatgtt aaaatgaaat caactttcct ctcccaggcc ttctaattga  48300
catgaatttg ggagtagact tgcattggcc tttgtcctga cagccaacag agtcctcttc  48360
tgttgtattc actgttgcct tccatgagga tcccatggag aaagtttgtc attgatatac  48420
attttgaggg cagactcaac ttgagtaaac ctgattgagc tttccccatc tgcctcccag  48480
```

agatcactgc ctgtgctttg ttaaaaagag aattatagga gtcctctcaa ggcagagagg 48540
cctaaaatta gacatggcag ccatgccttt ggtgtgcatg gaggttggat acaggcagcc 48600
agtttcccct ctgttttctc ccttgcttac acagccaagg agtggagcca agcctcaagg 48660
ggaggagctg tatactcgag catgccctgt ggttcctggc cctgactgag ggactatttt 48720
atatatccca atagagaagc gtggaagaca tctaggttgc cactgtcatt tgaaattgga 48780
atttttaaaa gagaaacctg aagacttgaa gaaagctttc ttttgcctcc ccttacagtt 48840
gatttttgag cttcttaaag ctacctagtc caaagtaccc acactcttat tcttttgtct 48900
ttcctactgg ttttattttt ttttcatctt cccaggtgtt tgatgatcac taagagcttc 48960
aacattgctc accctgacca ggtatgaagc caagagtttg gtttagggca taaaagaatg 49020
tcggaactca aggactaggt tgaggtgggg aagggggatg aaggcttctt tttttcttgg 49080
gttaagcaga aataacttag atctcagagt gaaagccttg aattatcaca tatatcactg 49140
gaaaagacta gttctttgct atgataacaa ttgttcatca tctctcccct gaggatttgg 49200
ggtcaaggcc tggctacacc ttttaatgat ttcagtcatg tgacttaacc tctttaaact 49260
tggattttct tcatctttac aatggaaatg atgacaataa tcactacctc acagatattg 49320
ataataatga tatctcacta ggaagagaat taagtaatat gagggataaa aaggcatttg 49380
taaatggtaa aatgagatta tgattttgaa agctattatt attttccttt cactgtctat 49440
tatctcaact cttctatttt cttgcctttt gtacagcatg gataatttag atgtgactct 49500
ggacagaggg atggatcaga tgacttctta agttatcttc cagtttagga gttcgtaaac 49560
tatactttct cctttccaga ctatcctagt aagaaaattc tcttttaaga cagagtagaa 49620
ctctggaatt catcagtttt gatgtttctt aaagtgtaat ctaagatagt gctcctgtat 49680
taagttctga tgtctgacca ttgttcaaat aaagagtaaa atgcaaatga caggaaattg 49740
gctgcgttct gaatcctatt tttatttggg ataacaataa gcctgtatgg tcactgtgac 49800
ctttgatttg ctgtttctgc aacctcacac ttgtctcagg attcttcttc cacttctgca 49860
ctttatattg ggtttcttcc aggcatcata ttaaacttta agccaggtat gtgtatatgc 49920
atgggctgtg ggcctgaaaa aaattagccc gagagagaaa aaaatttaag tagtgggcta 49980
gaagtaagca tgctactaga aacagaattt gggaacacag ctctgggcct agaaaagcga 50040
cctgtcaact tgttacagtt aacatcaata actataggat gggtttggtg gaaaattatg 50100
ctgaccaaca gggtgggaga gaatagggtc agaatatata tcgctgtaag gttgagaaaa 50160
aaagaagtga aaaaaaaaga aatgcataga gagaaaaagg agtttagagg taacatgtta 50220
aagtgtgaga aataaactgg agagcttgac ttctcttgaa tatattttta aataaagtac 50280
tcctttcaac tccaaatgca gcaggcttgg ttcccttctc ctacctccat tgcggatgaa 50340
agcttaatct ttaagatggg cttgggtggg tagagtacgc cccttggtga gcactgtgct 50400
ctctgcaacc ccaataaggc ccaacagggc tctccaagga ggcaaaattc tgatgataca 50460
tttctgttta gtggaaaatg ggtagggaaa attatgtctt agaatcaatt aaccaaacat 50520
aaaatcctcc aaggggcttg gtaggatgcc tagggaagag ccacgagata aaaactccag 50580
gctggaaggg cattgttgca gcactgtcat tctccagttt ctcttggagt tgtcaccacc 50640
ctctcctttg ttctcactgc tgacatcatt tgtaaaataa tttcttccct taaataaaca 50700
agacatacaa tcctctaaat gactaaagaa cagttaccta gaagaaacct tagtggaaag 50760
tattttcttc atctaacgga tgattgtctt tacagaggtg gagtaaagga tgtgcgaggg 50820
agcataatca agctaagaga tgcatgctga cttaaaaggc atgatatatg tgaaactaag 50880
ataatgtgtt caagagtgat gctttgttga tgcagaacca ctgaattcct tactattatg 50940
tttgcctgac tatcggcctc ttaataaaga acttgtggtt tgagtgttca ttgaaattag 51000
ccatattagg tttatgtggg gatgtgagga tctatgtcta ccaattgcag cctctgctgc 51060
aaattggagg cagaaatctg ggctgaacaa taggtaagag tgtcaactct acagatctct 51120
cacatgctaa gcaagcacaa tatagggcaa tccaggttta cacaaaggat taatttggga 51180
acaattatcc tcattttcac ttcctaaaaa gattttgaat aagatgtctt ttaagtaaga 51240
agctccctga atgcatttaa aatatgattt gattatgtac atttcagatt tttctacctt 51300
tctaggagta tctctgttgt ataaaaacac aaaattctgg aacttttgaa aggaagatgt 51360
gcctctcttc atacatttgt cattcttgaa cgattgtaaa atgaagtgac tgcatatcac 51420
gtcatgtgcc ctattgattt cttttcttgt tttaggaata ttcccagaaa aaaaaaaaac 51480 ttttttttt ttaaaatcta ctaagcatgc taggtaagac tgaagatgaa tctatttaag 51540
ttatgtcaat atctatttat aaagattttt gtgatattct tttcactgta gaacttcaag 51600
catatcctaa aaggaacggt tagatacctc tacaaactgt ggcaatgact tactgagtaa 51660
ttgctggcaa ctgatttttg gtgcttcttg ttttgatagt atagcagtgc gagtaggttt 51720
cagaagagca aaactaagac aatccaggga aatgccattt gagaatttct aactttaaaa 51780
aaacaagtaa aatagtgcca agaatattat ctaactaacc ccaaagtcta caatgtaact 51840
cttttatttt gataatgctg ttctaaccct atctacttca gtcctttccc acccagctgg 51900
tttaggaatc aaattcccaa tgtttcatca ctgttaacat tactgtttta ctcttcactt 51960
tagttcttaa atggcatagt gtcttaaatt ccctcagcct ctttcacatt tgatttcttt 52020
ggaaactttt taccttttca ttgaagccca tatgatcttt tccgaaacag acccttatct 52080
ttacctcctt ctttggagtc tttctcctac ttgaatttct gaacttctta aaatggccgc 52140
tttgggttgg tgtcagtaat tcagtaataa gttttctttt cttttttttt ttttcttttt 52200
ttttgagaca gagtcttgct ctgtcaccag gctgcaggct gtagtgcagt ggagtgatct 52260
tggctcactg caacctccac ctcccgggtt caagcgattc ccttgcctca gactcccaag 52320
tagcaagtag cagcaccatg cccagctaat gtttgtattt ttagtagagt cggggtttcg 52380
ccatgttggc caggatggtc tcgatctctt gacctcatga tctgcccgcc ttgccctccc 52440
aaagtgctgg gattacaggc gtgtgccagt atgcccagcc agtaataagt tttcttaagt 52500
gctttcttaa tattctgata tttttaaaaa agatctggac tattttgtca tacaggcaac 52560
agaatgttaa accatttcat aaaacaatga caaatataca tgaatttttc atcagttata 52620
aatgcatttc ctttataaca ttgaacatgt ttttgcaact gaaataagta cggttttcat 52680
ttttagaagg cacatgataa agttaaggca gtggttaatt aattttttca gattaatttt 52740
tcagaaaagt gactgtttct gtctattgtc ttaaccccag gcatcaaagg attttaatca 52800
gaaagaaccg aggaataatt tggttatttt agtgcctttt tttgagacaa agtcttattc 52860
tgtctcccag gctggagtac agtagtgcgc tcatggctta ctacagcctc gatctcctgg 52920
ttcaagtgat cctccaactt cactttccca gctaactggg accacaagtg ggcaccacac 52980
tctctgcaat ttattttaat ttttcataga aatggggtct cactatgttg ccctggctgg 53040
tctcagaatc ctaggttcaa gcaatccttc cacctcagcc tcctaaagtg ctgtgatttc 53100
aggcataagc cactacactc accctatttt agagctttgt caagctttgg aaagaaaacc 53160
atttataata taatagataa attatggata tttgaggcag tttttatcat agtatacatg 53220
gtaaaccaca gccccccttt ataatatttg tatttaataa aaatgaaaat attactttta 53280
tcttaaacat gttttaacaa agcaagcata tgtagattag cactaattaa aacaaaaacc 53340
tttgtaatga tagctgtttt ttatatgatt acaaaaaatt tactatacaa atttttatcc 53400
taatcagtgt gaaaaactgc aaatattagc ttatagggct agtcttcaga gtcctcttcc 53460
tacctactac tgctaataag ccaatgaaaa actctctgat gtgtgtggtg gctcaggcct 53520
gtaatcccag cactttggga ggccaaggtg ggtggatcac ttgcactcag gagtttaaga 53580
ccagcctggg caacatggtg aaaccctgtc tctactaaaa atacaaaaaa ttagctaggc 53640
gttgtggtac gcacctgtag tcccagctac tcaggaggct gaggtgggag gatcacttga 53700
gcccaggagg ttgaggttgc agtgagccaa gatcacagga ctgcactcca gcctgagcta 53760
caaagtgaaa ccttgtcaaa aagaaagaaa gaagagagag agagagagac aggctcctcc 53820
gctttttcag ttcctaaata attttccaat ctagaatgca aaagattctg aaggaagaca 53880
gttaccattt cagatcggca gaagttgtgg ctttaatcta gactcgaata tgttttacat 53940
caaagggttg cctcaacagt gctcaaacct gcctctctga aaacatgctg agcacgaagg 54000
ttacttgaag tcttagcttg agtacttaag agagtgctat ggagggattg ttgatgagag 54060
ctgtgtcaca gctaattttt ctttagtaat taaaggttta taaaaatctt acactgtata 54120
ttgacaaatt tagcaacaaa atgagcttga gaaaaaaatc aaggcctgcc atggcatctt 54180
tgcttttttt tcttaaaaaa aaaacttttt agaaagatta tgcgactgta ttatctgtaa 54240
ctactgcaat ggtgtaaatc ctgatggtat aatttgcttt ttaaagctat ctttacttca 54300
gtataactta gattaaattt attttaaatt taaatgatat ttttctcttt gtttattatt 54360
ttataatgtt tcccatagaa ttcacaaaat tcattagaaa gatttttttt tacttcctta 54420
ggtcattaag attctgattt gtcaatggat ttcacataaa ccctgtcttt ccaaaaatat 54480
acaaaaaaaa aaaaaatagc caggcgtgat ggtgcgtgcc tatagtccca gctactcaga 54540
aggccgagtt gggaggattg cttgaaccca ggaagttatg gctgcagtga gctatggtca 54600
caccactgca ctccagcctg ggcaacaaag tgagacccca tctccaataa ataaataaac 54660
aaataagtaa ataattttca ccttgaaaag cttataaatg tatgaaatca caatgagggt 54720
cgctgatata gtttggatgt gtgtccctgc ccaaatttgg ttttgaattg taatccccag 54780
tgttggagat ggggcctgga gggaggtgat tggatcatga gggcagtttt ttcatgaatg 54840
gctcagcacc atccccttgg tgctgttgtg gtgatagtaa gttctcatga gatctggttg 54900
tatagcacct cccccccttgc tctcttgttc ctgctttcac catgtgacat gcctgctccc 54960
ccttcacctt ctgccataat tttaagttgc ctgaggcctc accagaagcc gaacagatgc 55020
cggcaccatg ctttctgcac agcttgcaaa gccatgagcc aattaaacct cttttttttt 55080
tttttataaa ttacccagtc tcaagtattc tttatagcaa ggcaagaatg gacttacaca 55140
gtctcttttg tatcagggag agggtcttct tggtgactcc acttcttttc tttgtttatg 55200
tatccttcca gatgatgtat ttatttcctt tgtttttcaa ttgatattta ctcttaaatt 55260
aaactaatta tttaaaaaag cattttaaag tctcatttta gattattttg actatctgat 55320
ttttaaaatg gtttaaaaaa tctatcttgg cctccatatg caatcaaata agaaacacat 55380
tttaagcata ttatttacct tgtggattct gccttcctca gtgtgttcag tctgtgtata 55440
ttcatttctc ccacactgta agaagctagt cagatgtata attggattat catgctacat 55500
aatcttagca cactcatttt aagcatacat agactagtga gcaccactca ttacatgtca 55560

-continued

```
tttctctaga gaaactagtt gggccatggc tgcaggactc tcacttgaaa agacatgtgt  55620
ggtgatgttt tctcaggcag ttaagcaata aagtgtaccc tgatttgcac tgaaaataaa  55680
gattccttta aagggagcag ttctagttat ctctctcttt aggtaccata tgctgaacgt  55740
ttttctatgc actaaaacag caactaggtt ttatactctg ccttacagcc tacttcacac  55800
ccatttcaca gggagaggaa cagagaggta agtgatttgc cccaaattac ataactagga  55860
agttatttgc tcagtgtgga aacttgttca gaaggtcatt tcattgaaat gtaggaagag  55920
tttctggcac ttctcttgag caggagtcaa aaaccttttt ttgcactagc ccagatagta  55980
aacattttag gctttgtggg ccatatgatc tctgtcaaaa ctcctctact tcgttgttgt  56040
agtgcaaaag cagctataca caatcctgaa atgaatgggt gtggccgtgt tccagtacaa  56100
ccttacagaa aaggcaatag gctggatttg gctctgagac tgtagtttgc tgacctcagc  56160
tcttgaactg agctctttaa ctgacctcag ctcttgaact atggtacaag atcccatggt  56220
cctgtttggt acctccattt gccctccttt tcactctctg ggagcatagc taagttcaaa  56280
attgaattag gtacttgtag taagagcata cttataatcc tgggatcttc atgttgccag  56340
atattaacct cttgaagttt ttcaccacaa cctgggcact tttctgattt gctcacttct  56400
agccccacct ttgggcccct tcataagcaa acatgcaggt tttccagaga gctgtatgct  56460
actgaatgca gaaaatttgg ctcatactgg cctatggact atctgctcac tgccctgata  56520
actattttcc aagggagtgg gtgccctacc tttcctacat gaagtttttt gctagtcttg  56580
ccctaaaaat tctaggtatc ccttgctttt aggataaata tgtttcactg ggaccagctg  56640
gaaaacgaaa aatagaatta tccaactacc actttaaaat tggacaaaga cttttgttgt  56700
tgttgttgga gggggtggta aacatcattt tagcagacca aatatacttt tggtgaaagg  56760
cagcctgttg caaagacaca acacttggac aagattttga agccctggtt gcctttacta  56820
ctgacttaac tacagtattt gcggacttga gcaagttgct tcccttctgt gagcctcagg  56880
ttattcatct ttgaaatgag tataatacct gtgattataa ttacttatct ggattctgca  56940
gagaattgaa ggagataatg ggtgtaaaag tactttagcg cccagcactg ctccttatga  57000
aaatgaggaa ataattgaga tgagtgagcc attgaggcaa cagtacaaaa agtgctgaaa  57060
actcactgct taaataagca cctcttactg cttttgtggc actttgtagc aatgtttttt  57120
ttttttttt tgagacggag tcttgctgtc ttgcccaggc tggagttcag tggcacgatc  57180
tcggctcact gcaacctccg cctcacaggt tcaagcattc tctgacttca gcctcctgaa  57240
tagctggatt agaggtgcgt gccaccacgc ccagctaatt tttgtatttt tagtagagac  57300
ggggtttcac catgttgatc aggttggtct cgaactcctg acctcatgat ctgcccgcct  57360
tggcctccca aaatgctagg attacagatg tgagccaccg caccccacct cagcaatgtg  57420
tttttattct gactagaaaa gtaatgtttg gttttgtttg gctctttgct taatataccc  57480
ataataaggg tacctatttg cctttggacc attagttcaa atattatttt attaatatgg  57540
aattactggg ctccagaagc catagtcttc ttagctgctc cctatcccca ctctcacctc  57600
aattttttt tttcactttt gtttttcttc tcagggaaag gtttgaggca aagaatgtct  57660
tcttatgatc caaaaccaag catggtggtg atttattcac caagagattc ctaagtacct  57720
gtgtgatgga catggtagaa tctttgtcct gagggagcta tctagatcca ttccttctga  57780
tatgcagcca gtagccactt gtggtaatgg agcaatagaa acaacactag ttcaagtgga  57840
aacgtgagat gagaagtagg aggtggagag aactaaccag aagagggtac ccaaataaac  57900
cagaaatatg tatgtgttag agaaggggcc tattgagcgg gtggcagtgg catgtgtggc  57960
```

```
attacttgct cctgtattct ctgcttttta cttagttgtg gctttggtgg tatagtctca  58020
aatctaagtt acgtaggtaa tattgttatg tatcatgttt tggcaatgta gactaaatac  58080
ttgctcataa gagtacagga caatgaggat agtttggttt tgtttactgc atggaaaatg  58140
caggatgttt agtaaataga ttcatggcgt agtgagttca ctactaaaat cagactctga  58200
gaatgggttt gatttaaatg gctagtttag aagactgaat ttaggccact tgattgagaa  58260
aggccatttt gggtaattat aaaccaccaa cattgtgttt tgaatgttaa agcttatatt  58320
tgtcttccag ttaccagaat gtaagcttct tgaggaggga gagaggagtt ttcttaatct  58380
ctgaacctgc acctttcttc tgtgcctagc ccagtgcctg gcaccaaaca ggtgctcaat  58440
caatgttgat tctatgctac caacaaaaat gagtccatga tgtttactat tcaacaaatg  58500
aatacaattt tagagtaaat ttttactgct tacactacat gtagattttc tttttagaga  58560
tttcgcaatg ctgatttatt tcaaaataag cttgaagcta agcgacaaag ctgaatgatg  58620
atttgttttt tatttatttt taaatccaaa cttacaattt tacatgtcat tgccagaaaa  58680
atcattaaat aaattatgat atgcgcatat ggaatacttt gcaaccatta aatcaaccat  58740
taaatactat gcaaccatta aatcaaccat taaatatgtt ggtatatgca aatgtgcata  58800
taccaacata ttatatagtt gagtaagaaa agctagtttc aaatgagtat gttaatatca  58860
tctgactctt gcaaaaggaa aaccatacat ttgaatgtac atatatgcat atgtttatat  58920
gtgcatagaa aaagctatga ggggatatac ctcaagttgc taaaagtggc tccacctgga  58980
gagggacatg gaaaggagtt ggctaaaaac tgaggtttgt tatggtatac acccctgcac  59040
agtttgattt tttaaaaaca atgattataa attactttta ttatttataa aaatattatt  59100
taaaattttg gtactaaaaa cagagctcca tcaacaggtc aatggataaa gaaaatgtgg  59160
tacatatata caaccgagta ctattcgtca taaaaaaatg agaccctgtc atttttgcaa  59220
caaaatggat ggaactggaa attattatat taagtgaaat aaggcaggca cagaaaggca  59280
aacattgcat gttctcattt aatctgtgga atctaaaaat caaaacaatt gaactaatgg  59340
atatagaaag tagaaggatg gtaaccaaag gctagaaagg atagttggtg gggcagggga  59400
gggtgaggtg agcatgttta atgggcacaa aaaaatagaa acaatgaata agacctatta  59460
tgtgatagca caataaggtg actatagtta ataataattt aattgtacat tttaaaataa  59520
ctaaagaggt ataataggat tgattgtaac acaaagaata aatgcttgag ggatgtatac  59580
ctcattctct ataatgtgat tagtacacat tgcatgcttc tatcaaaaat tttcatatac  59640
cccataaata tatacatcca ttgtgtactc acaaaattaa aaaaaactgt gcattaaaga  59700
aaaacaaaaa taaaaaccat agttcaagtt ataaacaaaa taaaggtaat ttggaggaaa  59760
actgtcttca gttatattgg atatttgggg gacatttttg tatgttagtt agcaaagatc  59820
acttgaaaaa gaagattctt ccttctatga ttcaagggag cctagcaaaa aataaatgaa  59880
atgaaataaa ataatacaaa gagaaaagat tattccataa attctgctta cttatttctg  59940
gcaaacttgt tgacagcaca tgtgaccttt tggtaaaaag acatttttat atttttagtt  60000
aagtttcaaa tataaattgt ttgtgttttt aaaataaatt aaatggatga tttcagccag  60060
atcattatga aaacacatga gatattgggt tatgcaatga ctaacagtgt gtacctttttc 60120
ttgatattta ttcataaact ggggaataaa agtacatttt ggcccattta ctccttaaat  60180
aattttatgt ctcccaagga gagttgtaag ttgcttgata gtaaatgcta tgtattttgt  60240
accttagtgt atatattatg ggatttcagc gttagaagag ctcttaaatg ccgtgttcat  60300
```

-continued agtccaacct gtcttctgat gcttgaaatc cccttgcagt aggaaatgca aagtagagag 60360
cagacactca ataatgtagt tagtgaatta tttagaaaga ggcattttga gcccataatg 60420
tatgataggt acttctacat ttattatttt attctttgca gacctgcaga aaactgtaag 60480
aaaaaagttt atttcagatt catgtgttta tttgattaat ctcttcatag gtttcatttt 60540
tcagctcctg tcagaaaata cagattctta taaggttcac cttttaccca taagaataat 60600
agtataaagg ggataatgtg aaatacaatc acttcacaga ctgtttcaat taaataagag 60660
ctcgtagata attcagtcca ccacacccca ttttacagat gttgaaattg aagcccccac 60720
caaaaggaaa agacttgttc aaagtcacac agcaagtcag tggtgaacct aattaggccc 60780
cctgccttcc attttagtga gattcctgtg ctgatagtca tacccatatc aaatcctctt 60840
tggcagttat agcttgccca cagtaatgtg tcctgaaaaa tatgacaatt aattaagttg 60900
gagacagaac cataacctct ttataaaaat tttctggaaa gtttacatga cagtaagtaa 60960
tatataatta gaaaggataa ttcttatttc atatttatct ttttgtttca gaataataaa 61020
ctaagctatc tctactcagt ccattttaat acaaaaatat ttttacccgg actgagtttt 61080
tatgcttttt aggaactttg tatctgcctc acttagttaa aatcctagct gcactaatca 61140
cttactgtgg tgggcagaat tctagaatga ccctgaatac cttgtccttg tatgattcct 61200
tcctctttaa gtaaggataa aaactgtgaa tatgatatca ctcccttgat taggctttgt 61260
tatatggcac agttaacttt aagaaaggac caatcacaca agccatttga aagcagaggg 61320
tttgggtatt ttttaactgg tggcagaaag ccacgcagag atttgaacat tgaggggaat 61380
ttgaatttga tgtgccagta ctaacttgaa gatagaggag gctgcatgga aagtggcctt 61440
taggagtgat ccctggctga cagccagtaa gaaaatgagg gcctcagacc tacagccata 61500
aagaattctg tcagtgaact tgaacttgga agtggattct tcctctagaa cttccatata 61560
agagtccagc ctgattgaca ccttgatttt ggacttgtga gaccctgagc agagaatcca 61620
gttgacttct gacctaaaaa aaaagtcaga taataaatga gtattgtttt aaactgctaa 61680
ttttgtgata atttgttatg cagcaataaa aaactaatat atttaccatg caaggcaagg 61740
catttatcct ctcatgattc agtttctttt tacctgacat aatggaatta atttatactg 61800
ctgtgaagtt gtagttgaga aacatgactt ctaaagtaat agaggacatg tattattaat 61860
tttagtagta ttaatagtaa tgatactgat tctcccaggc ctatacaaat cctttgatac 61920
acaaatgaat agtaaaggaa cataaattgt ctctaggtag actttcccac aatgcaattt 61980
taggatacag aggtcatatg cctgttattc tactgtggca gagaaaatat ggagcctgga 62040
aaactgttca tttgcatcac atacatcttg ggagctcact ctgaacctgg taccataata 62100
agctctgtag acagtataaa gaggaaagga atcagacatg gtgtctgacc tcaagtgtct 62160
cataacgtag tagaagaggt aaaatatggg tcacactaac tctactgcaa agtaggaagt 62220
gcttgtcgcc ttgagattga caaaatttgg taagagttca gaggagattg tctgtgaact 62280
gggccttgaa gaatagttag gatttgaata ggagaaggtg aagaaggaag gcattccagc 62340
tagggagaag agcacaaaca aaagcataga taaccttgaa catcatcata tgggataatt 62400
caatagttca gtataatgga agtataagat gcataaaaat aagtgtagta ggaaacaagt 62460
ttaaaagtat agattggggt tagtcataca aggccttgaa tttcaggcta aggagtttag 62520
acattaacat ttgtttttga acaaaggggt gaactgatca catctgtgat ttagaaagaa 62580
aattctagca atagtgtaga taagggttga tggtaaagtt tggaaggtgg tgaggcagag 62640
gctggagaca gggagcacat ttaggataga aagatgataa agagatgatt tagaagagtt 62700

```
gttttggaaa aggagaagac agaaaatgtt ttagaggtgt catagagata aaattggcat  62760
ggcatggtgc aaggaggtaa agcccaatag ctttgtaagg tgctgagata gattgaaatc  62820
acagagttag gaagttttag agtcaggatt agtaccaaga cagcttggct ctagatctca  62880
tacttaacac ttacagtata attctgagag ggtgggtaac agcaatagtc agaggaaaga  62940
acccttttat acatgatggt acaggaacaa cactggcttc caaccccaca gctgctcttt  63000
aacagaaggt cagaagctgg ggagaaatat gtgtgtgtgt gtgtgtgtgt gtgtgtgtgt  63060
gtgtgtgtgt gtgtgtatgt gccatttctg ggactaagga tgggaagtag attagttgag  63120
gccactgcag tggggtctgc aagttgctag cactcacccg ttccaagagg ccttaaaggt  63180
gttgatctgt tccctgggca tcaccacatt ccacaaatta atgttcctct gagagaatag  63240
ggtgattcaa tttcactgtg cccgaaggtt acttttgggg ttcatgtttg ttctaagtct  63300
atgctaatga tctgccaact gtctgtttgt cactttctct aacccttagc atgtataaac  63360
tgatctgttg ggaaatgtgt agcatttata ggatggtagg atttgtaaca tgcgatcaca  63420
ggactgttta tatagagtcc ctgggaaggg gagagaagag tatttctgtt acaaatgtgg  63480
attctttggc ccctcctcaa acttactgag gttcaagaat tgacatttat aataagcaca  63540
tatccatttt caataaacat gaaagtttca taccctcttt taatgtttga aatcctcaaa  63600
taaattagtc attggtgcca gagtatcaaa taattatggt acagaatgta tttctctgaa  63660
tgacaccttc tcccagagat tctgatatat attcctctgc actcaccctg tttgataatt  63720
accagtatat ggaccattta cctgaagaat aagagtaggg tttcctactg ttgttgaaaa  63780
tttgcttgac tcttaacaac ttgtgtgtga ctgtaacaag atcacacagg gtaaacaata  63840
ttagcttatt caaccactgg ctgaagaaat ttaggaaagt gaacacattt ttctttacat  63900
ttctctttgt tctgtgagcc ttttatgctg gaatagtttt cactgcaggc tgttattgtc  63960
tgcctccaga ggagggagtt gacctagcag tggtaactgg agagtgtttt ttgaaacctc  64020
tttccaaggt tagttgccaa tggcatcttt ggaacagtgt ccttcacttt tgtccctcag  64080
ggaccagtgt gagaatggga actttatgat ctggagctgg ttaagtgaag tccaaaaata  64140
attaagaaag tgtttccttc cctgggaatg agttcagtag gaatctcaat gtattgtaga  64200
gcactaagga ctcagcctca ggcatttgca aaggattctt ccagttgcct gtgttacaga  64260
ggacacagtt ggcatttcct tttggtgttg aggggagatg tgtacatggt tgtgagatga  64320
ctcacccttt ttgcttagat agttccactt tcattgtgga cagactcttt ggagggccag  64380
tttggcatgc acgtgtgtgt tcattccatc ctggagcatt ctttatgaga aagccatttg  64440
ttgagtggtt tgccattttg ttttacagcc actctgtggg ctatgaaatg gtcatccggc  64500
cgctttattt gtccctaaaa aaagcagttt ttccctttct tatcttcatg gctgccaagc  64560
agcagaaaga gtaactcagg gaagccatgt gatagccttt tatctgtctg ttcagaaact  64620
gatgatgtat tggatttgat aattcatcaa atctgaggtt tactggtttg tatttgcctc  64680
aaaatgggca tataatattt tgtcaggtaa cataatagac agatcattgg cattgcttta  64740
ttgaagtgaa ttaattcaat aagcctgtaa gtgcctgaca tgtgccaggc actgtgctag  64800
gcattctgtt aacagatgag acaaatctct gtcttttagg tgttttcagt cgaacagggg  64860
agacaaatat atgagcaaat tgctattttt tttaaatttc atagtgtaca tgagtataag  64920
gtgctgaata tgtgattgat tctgagggaa aagagagata agggaaagtt ctcagagaaa  64980
gtcaagctga gggaagaaaa gcaccccaga cagagggact agcatagagc tatgctagta  65040
```

-continued

```
cattgagttt aagggaatgg cacatacttc actgttgctt cagcagacag caggcctgtt  65100
aggttacaaa gggccttgga tgacatgctg aggggtttta aaattttatt taaattttaa  65160
ttgacaaaat ataattgtat atttctgtga ggtacaatgt gacgttatga tatatgtatg  65220
caatgtagaa tgattaaatc aagctaattt gtatatctac cacctcacat acttattttt  65280
tggttagaac atttaaaatt tattctctta acaactttga aatagacaac acattattat  65340
caactgtagt caccatgttg tgcagatctc aaaaacttct aacaaaaact ttttaccctt  65400
tgaagatatt gaactgtttt atgaacacaa tcttagaagg atttaaaaaa taatttgcta  65460
ttcaccaagt acttcttacg tacactgtgc atgaaatgat tattactttt tctaatatta  65520
gttttcttga ttgaggcttg gcaattatta gtttgtatgc ctttagaagg atcataagca  65580
gaggtttatc ccagtaggat ttgcatttta gaatgatgac tttgggagta aaatacagag  65640
aagtgaaacc agagatagtg ggatcattct ggagtctgtt gcctacactg aacagtagtt  65700
gagcgaaaaa ggatgggcag aatgtgttgg ttctgggtat tgcaaattca tggcacttga  65760
gtgaaaaagt ttaagccttc tattggctct ttgtgaatat cttcaacatg catgactaca  65820
aatagaacac atggttttgt tgttattgtt gttgtgtttt tgtttttttt tttatttgag  65880
atggagtttt gctcttcttg cccagactgg agtgcaatgg cacgaatttg gctcaccaca  65940
acctccgcct cccaggttca agcgattctc ctgcctcagc ctcctgagta gctgggatta  66000
gaatcatgcg ccaccacacc cggctaattt tgtattttta gtagaaacag ggtttctcca  66060
tgttggtcag gctgtcttga actcccgacc tcagatgatc ctcccacctc ggcctcccaa  66120
agtactgaga ttacgggcat gagccaccgc gcccggccca cacggtattt ttgaaagaac  66180
agtgagcttg gattagaaca ctagtgtcca ggccctgctg ctactacata agtaattatg  66240
aatccatagc catcttgttg ctcttcttct ctgagccttg gtttctttag ctataaaatg  66300
ggaagttgaa actttctagc tacttctttg agttatgagt aacaagttag gtaatacact  66360
taaaagagaa tgtgctatac aaatactggt tcttaagaca gctgttgtta atgtactgag  66420
tattatgctt acctcacagg gttattgtga gcatcaaatg ggataatgga tttgtaagca  66480
ttttgtttaa agtgtgattc aaatgttaag aattagtaaa aatagtaaaa gaacaattca  66540
ttctccatcc agatgttctg tccccactgt gacttatgtg ctcattcaga gttgtacaga  66600
aaaacctcca cttaattttc acaagctgga gttccacatg taacagaatc atatgggacc  66660
aaaaaattct ctgtattggc ttcttccctg ccgtattttg gctctgggac caacaagaca  66720
cccattttgc atgagctgcc tgccaccaac tttgcgctca catctagttc tgttgcccat  66780
gtgcaagctg aatttgggcc cgggccccca gatctaacat gaaactcaag tttccttctg  66840
ttcaaactgt ccaggcataa tagtcttaaa gtccgatgcc cagcagagcc gtagattttt  66900
cactggccaa aaatcaacat gaaaccagat gtatctgtaa atctagtttc ataacacttt  66960
gtagtcaatg gaaatacagt agcaggcaga ccagaccaga gtttactatt tgcagtggaa  67020
ttaataacca catggaaact ttgcctttgg tatctgcgag atggaagata aaggtgcgaa  67080
ttcaaagcag ttcccacctt accctctaaa ttccaacata aagaggcctt gaatgtcctt  67140
ctatcttatt gtatatttca ttaacagaag tatgttccta gctacttagt cattctatct  67200
ctattctcct ttgttttaac ttcagtggtg ccagcttaag atgctctggc tttcagcttt  67260
catggagcac gtcatgtttt taaacttatc tttagggaca gaaatgttag gaagatccta  67320
gttcctcatc tctttgctcc tgacaaggaa atttagaatt gcctaaagaa aggatgtatt  67380
ggccaaccta ataataaatc agtattagtg aatctaaagc atatttgaaa aatttgtaac  67440
```

atgagttgaa attcagacct gcaatgaagt gtttttaaaa gatttaaaat cgaaataata 67500
taaaagaatg ttaaaaacaa gtaaaacata tcactagtta atcactctac caaaattcat 67560
ttttatgttt gcatatttaa ccattttat tttctatatt tgtccatgaa catgtgtttt 67620
tatatattgt ttatattaaa catggtttta atcatggctt atttctttta tgttttactt 67680
cttttccttt gacataaaat attgtatttt ttaaatttta attgcttctt ggcataccct 67740
tccaatattg gtggctatat agattgaagt taaaactaat tacaatcaga gaaaattaac 67800
aattcatccc ttcaatctca ttagtcacaa gttaaatact caatagccac atctatctag 67860
ttgctactgt tttgaatagt acagatataa gacattttca tcaacacaga aaattcactt 67920
ggaaagcatt gccctggagt aaatgtgcca gactgtacta tatcattttt ctcttgttgg 67980
acatctaagt tatttcttat tttttaaata ttttatataa cttgacggtg aatataccta 68040
tgtacatagc tatttgcttt ggctgaatta tttcttagaa tcaatttcaa aagtggagtt 68100
attaggtcaa agagcatgag aagatttttt ggaacctgca gtgtattgcc atagtcctct 68160
caaaaaagtt tatgtcaact taaagtactt ctagcagcat atgattgtac taatttcgct 68220
gcaatctcaa caacactgga cattataagt ttttattcta ccctattttc cattaaaaga 68280
tagcttatgc ttgattgact ttgcatttta ttttattatt aataatgatg tggtttcctt 68340
ttttctagat tttattttta tttaaggcat cctttgattt taacctgatt ttttttctct 68400
aaaaattatt ctaagaaaag acaaaggtga tacgaaatat atcctgagtt tttatttttt 68460
tcttgcatgg gatttgtata tttgcacctt tgcccattta tactatgatt tcttagtgtc 68520
ttccctggca attttaatga agacttcatg tatatcaatt tttccacaaa tataatcttt 68580
ctaaaaatat gtttttttcca caatataatt cagacgtatt ctccgaaatg ttggaaaaac 68640
ttaagtaggc atcaaagcat ttgaagattt gtttaaaggt tgtttttata ccagttttaa 68700
attgtaattt aagggtcata aaataggtga aaattaaatc atttttcagt aagggggcaa 68760
gaccacttaa ctcttggaaa atacaggaaa cgtagatttc tagaggccaa gaaggaggta 68820
gggattattt tgtaactgcc cccaaccttc taacctgtaa tgaaacaaac actgaaggcc 68880
cttaaacatt tttaggctta attggctgtc cttgtactta gggcacatct aaaaatcctg 68940
aggcaaccac tcaagagaac atgcttttgt taattcaaag ggagctgtcc tacgagtgtc 69000
cagaatcctc tgtagtcttg ggcctggtgc ttgagagacc caaaggaaag gtcaatggaa 69060
ttacagctta gtgttagagc tttcatgcat cacactaatt aattaatgtc ataaaggtct 69120
ctctcctgtt atgggaaaaa gcagcaaata ggaacttctg gtagggtgct taaagttggt 69180
ttgatatttt ttattagcat ttttaactaa tacaagtaat acatgcttat ggtagaatga 69240
taaaactgaa aaaaaaggta tgaaaattta gaagttctcc tactcatgac ctcacccctt 69300
ctttcactcc cagtttcact cctcagaggg taaccacagt gactagcttc ttgtgtttgg 69360
ttcctgagat tttctatgta tatatattgt tagatatatg catggtatgt tttcaaaatt 69420
cctgttacac tataattact gttctacaac ttaatttttt cacttaatta atagacctta 69480
tatatgcttt tccatatcgg tatatataga tctatataag ttttcttaaa ggttgcacaa 69540
ctttcaattg tatggctgtc ttgtaattta ctttttgttt cccttactaa tggatatttc 69600
atgtttccct aactcttttg atattaagag tagtgctgca attaacatcc ttgagaggca 69660
gtatatatgg tgtttaagat gaatggttct ggagccagac tactttggat tgaatattgg 69720
tgccaccaat tccttgctgt atgaccttag gcaagttgct taatttcttt gcctcagtgt 69780

```
ccttgtgtga aaaaatggag gcaataatgg tcactatcca gtagggcttt tatgaggatt  69840
tagtaagtta ataatgcact ttaagaactt agttattttt agattaagta gtgaaggact  69900
atataattgt tagtataatt gtataccttt attatcatac ttttgcatgt atagcaataa  69960
gacaaattct tagatgttta accattggac ataaggaatg tacgcatttt aagtactggt  70020
agatattacc ttttccctgc caaaaattgc aaatattgga tattaacttt ttaaatctta  70080
gtaaatctga taagtataaa taacagttta tcatcatttt aagttgccta tcttaatttt  70140
gtgtgaaaat gattatcttt tcacatgttt ttttggccat ttatgtttct ttccatgtga  70200
actaactgtt cctggccatt gcctatttgt tgttgctgtt actatatggc ttttcatctg  70260
tttcttattg gtttatggag ctctttgtat atacaggaat ttagcctcta tttatatgtg  70320
tgacaaatac tttttccaat ttatctttaa aatttgttta tgttttccta ttcatcagtc  70380
taaaattatg tagttaaatt catcattgtt ttttcttatg actttagagt ttggagatca  70440
tgcttcaaag gtctttctag gtggggatga tttaaatcat gtactggaag tatttttgcc  70500
aaaaagactc acgaattatg gatgttagag ctaaaaggga ccttagagat ttcctagttc  70560
aaccaccttt tcttcatacc tttttaattt ttctctgcag atgaaaagaa gtttagtcct  70620
aaagaaagaa aagagtctaa aggttctcca gtaagctaat ggcaaaaatg tagactggaa  70680
cttctagctc ctgatgtgta tttcagtgat cattcaattt aaccagatgg tttcacaaaa  70740
agagctttct actaaaaaat aaaatacata cttaagcaac tcagagaatt ttttttttat  70800
ttttcagatt aattttcact tagagattca tcagcatatg tactatacat gtacaaatca  70860
cctgtgtgtt ttggatattt agttaaacaa atgtgcaaat attttaacca aaggagcata  70920
ttcatttgtg ttttattttc ttaatggttt tcgttatgaa tgtgaaatgt gtatttacct  70980
taacagaaat taagtatatt tttggtctga catatatgag aactgaaaag cattggcttg  71040
gctgctaact gcattctcat ctttctttct ctgctttggc aaagtctggg attaaatcta  71100
ataccttttta aactgtttgg gacttcagcc agagtgacct gtcttgaatt cagaactgcg  71160
cagatcattc cccattctaa ggccctctca tgcctcctca ttgcctgtag gatgagatcc  71220
aagtacctta gcatagctta tgcactgtag tcacttgacc tctagcacct atgcagtctt  71280
ccagtcttat ttacacattc ctttgcacat gctgtttccc cgtgtggggc aactttttc  71340
ttgcctgtct gcctgcctaa gccaacttaa ataaacatca tttctgtaac ttctgtgaag  71400
ccttttccaa tctctccact ccaagacgaa ggtgtttcta taggcatgac ttctggaatg  71460
gcagatcaag gatctggtgg accctctact cagtgaaaca accgtttaac tagtaaaaat  71520
gatcaatcaa ccatttaaaa tcttcagaaa atatcctaag ggcacatagc aaaaagagaa  71580
acatttattc aagaaaagct attaagcctc agtaaaaaca gcaagagtct atggcatttg  71640
agtcatgacc tgttcctaat ccttccctta tctccattct tcaggcaagt gcaaccaaga  71700
agatggaggc ttcctctctc tcaaaatctt actccatagt tataatttca cccacaatgg  71760
ggcagaccac aagcatctct tttttttccc ccagccctat attacagaat cactgttcta  71820
ggaaggcata gcttagagga ttggagattc cttccacacc cactttctac gtatgagggc  71880
tttgccccag ggatggtaag tcaagaatac agggatcctg cttgtgcctg cctcagctca  71940
tatataaggt aaagcttcca cactaggaaa ggcaaattaa gaggactagg gaatataccg  72000
ttatccccag ggtccacttg tagaacaggg gtgtcattct gggagaagca ggtcactgcc  72060
ccacttgtgg aacaggggag tcactcgtca ctgtccctgg ttcaaattct attgcagtga  72120
cagaggttct gtcccaggga aaggcaggtt gttaggatgg agaactccac agttctccct  72180
```

gaggtgactg actttatttg gaacagagca tgaagaagtt catgcctaag ggcactgtca 72240
aaaataatgg agatcttggt ggtgagcaat taagagtgga ttggtagctc catgatacta 72300
gtaacaacaa gcaaaacagc agaccagcat ggaggatacc agagaaccag acaaaggaat 72360
cactaagaag agcccttgtg gaattgcact cactgctggg tgtgtggaaa gttatgcatg 72420
tgtgctttac tgtaccctct caaaagcaac ctaaacagga tgtggggtag gctctaaagc 72480
attcctcaag ccacacatgg atccatcagt aaaatgtgga gggcttaagg ataaaaaggc 72540
ttaagtacaa tctctggccc tacattttct aaatgttatg ccaccctgac caaggggcaa 72600
ctcctacaaa gccaggcaaa ataataaaat catatttgtc tctagtggaa tggataacta 72660
tgcctaaaac tgtgcccttt gaaaagcaac tagagagata atttctgaag tgtttgtccc 72720
tacctgaatg tgtggcaaaa ttctaaactc cctgaagtgt gaaagtggtt tccaagccac 72780
atgcacatcc agtagtggta aagggtgaaa atctaactgg ctaagagggc ttcatagcaa 72840
cattaaccaa aaagtggttt atgtagtctt tgcctgcttc ataattccct aggcattcta 72900
tgctattctg tactcagaag gcttaaagtc aggttaggga aaggaggcct atgaggttac 72960
tgtgcagagg cagtgctggg aaataaatga agttaaataa atttaggcca tcgtggttta 73020
aagaatggat tgtggagata agaaggataa aggaaaccca gagtcaagaa aaataaaact 73080
tttcattggt gccatgccaa cccatatccg agcctgaggc aaaaggaaaa atgtgctccc 73140
tgatatacac ttatacaaaa tatcaactaa ttttatttgt tggactgaat agaaaaagtc 73200
aacaaaaatt aaaaataaaa aaatcatgac tatattttta ataagtggtt tatgtaaacc 73260
cagagttgac caatgggatg ccagtctcaa ccataaaaac aaacaaaaca ttgtgagtaa 73320
caacaccaga agtctcaaag tgtcagggaa accaatttca cagaagcagt tcagccaagt 73380
cactaaacaa acaaacgact aagcaaaaaa caagaatgag tctcagaaag ggtcaagtca 73440
gtatccagag ttgttacaat atagtatcta aaatattgtt ttgaactaaa aattttgagg 73500
catgcaaaga atgaggaaag tatgactcat acatggtatt atatgaaaaa atcaacaaaa 73560
aactatccat gaggaaacaa agatgttgaa attcactagg gaaagacttt aaaaaccagc 73620
tatttaaata tattcaaaga actgaaggaa ctatgtctaa aatactaaaa taaagtataa 73680
taacaatttc ttgtcaagta gagaatgcca ataaagagat agaagttata aaaaaagaaa 73740
aaaatggaaa atctggagtt gaaaattata ataactgaaa tgaaaaattc actagaaaag 73800
gtcacaagaa gatataactt ggcagaagaa acaatcagca aattagaaca tagatcaata 73860
tagattattc attttgaagg gtagaaagaa aaaaagaatg aagaaaactg aagattccca 73920
aagaaatgta ggacatctta aagacacatc attaggagaa gaaaagaagg gaaagaaaag 73980
agcagaaaga atatttttta aaaaatggat aaaatcttcc aaaatttaat gaaaaacatc 74040
aacctacaca tcaaagaaaa tttttttaaa acttcaagca ggaaaatgta acgatattga 74100
tacttagata catcatagtc aaaatattgg agtcaaatat aaagagaaaa ttttgaaatt 74160
agcaagagaa aaatgaaatg gaaccacaat aagattaaca gctgattctc atcagaaata 74220
acagagagca gaaggcagtg caatcccata ttctaaacgt tgaaagaata aaaaaactgt 74280
cagtcaagaa tcatatattc aacaaaacta tctttaaagg taaaaatgaa atgaagacat 74340
tcctaggtaa acaaaggctg agagaatttt tcattagctg acatgccttg caagaaatac 74400
taaaagcttc ctagacagta gctttaatct gcatgaaaaa aaattccaat aaagggaaat 74460
ttgtaaataa taaaaataca tcattatata ttcttttcca cttaacttat ttaaaatcaa 74520
tttcttaaag cactatctgt aaaattgtat tgttatttga caataaaatg taaaagaggg 74580
gagtgggaat taagctaaat tggagtaagg aaatggtatc acatggtaaa ttgaatttac 74640
agaaagaaat gaaaaaatta agtggcaaat atgaagagta acattaaaaa cttctataaa 74700
ttaattgtgg cctcctttct tcccttagct tctgtaaaag acataagact attaaaaatg 74760
acaataatta taaacacatt gttttattag taataaacat agacaaatta tctacaacaa 74820
ttattattat acaaggagag ggaatggagc tgtagaggag taaagttttt ataacctact 74880
ggaactaagt cagtataaat atgatgtcga ttctgttaat ttgagatata tgttagaagc 74940
cccaaagtaa tcactgagaa aatgatgcaa aaatacagtt ttaaaaagtt aaaaacatag 75000
tttagcttat gtgtgcctag tactccatta ttattttttt attatatttt aagttctggg 75060
gtacatgtgc agaatgtgca ggtttgttac ataggcatac atgtgccatg gtggtttgct 75120
gcacccatca atccgtcata tacattaggt atttctccta atactatccc tccccctgtc 75180
ccctaacccc ctcaacaggc cctggtgtgt gatgttcccc tccctgtgtc catgtgttct 75240
cattgttcaa ctcccactta tgagtgagaa catgcggtgt ttcgttttct gttcttgtgt 75300
tagtttgctg agaatgatgg tttccagctt catccatgtc cttgcagagg acatgaactc 75360
atccttttta tggctgcata gtagtccatc gtgtatatgt gccacatttt ctttctgctt 75420
gttcccagga gaaagtggct gaagattcca gagagaagct gaatgcagtt taattctttt 75480
tgccataaac acgacaaccc attttcctgc aagctgtgtt agtttgctct cttcttggtt 75540
cattcattca tttattcata gcttccataa atatttaaca aacactaatt aggggccaag 75600
ccatgtgcta ggcacagggg ataaaactgt gaacaaaaca agccccagct actcttaagg 75660
aactgataga caaatggacc agcaaacacg ctggtcctgt tttgaaggca aagcgcctgg 75720
tgctcctgat ctcatgagca cagagcattt agcctaagtc tcatcctcct aaggcctcag 75780
aaataaggcc ttattttaat aagtgcaagt cagtcatttg aagactaaat catagaatcc 75840
tagaaaacta gtaccgggag caaggcaaaa gaatgggatg agcatgaaac atatattcag 75900
aagttgtggt gtgtaggtat ataagccaag ctcttttctt cacttgcttg ctaagtcact 75960
tagcttttct gccttttgt ttgctctgtc tggaaatgga gttaatgaaa tatatctaca 76020
tgatagggat attgagacga ttaaataaga tgctgctgtc acccagtatg cccttaccct 76080
gctgtactta gaagtatatg aaattcattt tctaaatttt tgtatgagtg tttcatgcat 76140
gcccaccacc atggaagcta ccttaagaca gtgagggact ttgtttaact tgtttgtact 76200
acatcctcag tctaatggtg tctggcttat ggtaggcacc aaatataatt ttattgacag 76260
aaaggatgat aatgaatgtg aaggcatttt taagtttatg aagtgttgtg catattgttg 76320
ttaattttaa gctgttacgt taaagaaccc ctaatccaac tctcttgagt tttatagata 76380
tcatagaaga tatatcttcc cttgacatag aagcttccct tgaaggttcc cttgactcat 76440
gtatttgcct cacagtgatt gtgcagatcc cacaagataa atttatgtga atgtgcttta 76500
tgtgcttgaa gtgctccaca aatatgggtt ttataagatg agaaaataga gtcagggaga 76560
aaggtgactg atccaaggtc atgcaaagag ttagtgtcag aatttataat ggaatttcag 76620
gctcccaact cccactccag tatactaagg cagattccag agaagaaaca gtggagagca 76680
ggcactgatg agggacaaag aaaagcaggc tccgtctggc tgcaacttgt ctcttcatgg 76740
caaaaagaaa ctaggaaagt gctatgccag agacgacatg ataactttgc agaatggaaa 76800
gagcttgttt accacattga atactttatc tgtgtttatc taacgacagt tccaccagct 76860
ctttaccact tgacttttgc ctaattcaaa aatataccaa ctatgaaaca ttttccttct 76920

```
cagtttttat tctagattac attttgttca actttatctt aatgtgtagt gtagaaagag  76980
taaggtaaga gtatagcaag tggttatttt ccatttctac tgaggacaga gaaataatct  77040
aagggatttg tattagagat gaagaagtgc atggccagga catgagagat actgtgatag  77100
aatggatatt gtgaagtctt tggtagtttt tgaggggaaa aaagagaagg ttttctttgt  77160
ctgatatagt ttagcaacgt cttaatttag gattcaaaag ttgttcaggg tccatcttgg  77220
ccttcaaatt aagatgccct ttgagagata acattgttgt tttcaaactc tgttctgtga  77280
cttaagaatg agaggagaag gaagaaaaga ggagaaaatt tgagggaaaa gtgcccaagc  77340
agcgtcaagg ctagacactg gaaatttatc aatgaaagcc acatggtgga tgggaatcag  77400
atatgtgcat caattatttg tgttccaatc catatagaag taccgtataa tgcaccaagc  77460
taataggtgc tttgaaagaa gaccatacaa gtggagatgt gttcctattc tatctaggga  77520
tagagtcagg aagggcttca ttgaataagt ggtagcctct tgggctgaga cctgagttat  77580
gagatgatgt ggcaaaggag acagatggct gggggcaagg tggggtcatt gaaattggag  77640
gcagtagcaa tataagcaaa gctacagggg catgaaaaag caaggttaga ttagtgaatt  77700
gcaacagggt ggtactgctg gaaggtcaca tggaaaagat tgtgaaggta ttgagataag  77760
aagctagaaa taagctttga atgccatcct agtactttga atttgcatgc tgtaagccaa  77820
gtggttttca cttggtcatt taataaaatt acagattctc aggtctcacc tgtaacttca  77880
gattcagaag agtctgctaa ctgaaggtgg aatcagtgtt ccatattgct aattagctcc  77940
tcagaggatt ctaatatatc agtgagttat gaccactgct gtaagccata ggtagttatt  78000
gaaagctgct atggagagga gccacagaag cagatgtttt agataggatt cctctggggt  78060
cctgtgtaat ttatggactg gagaggatca gacaggaagc agaaagactt gaataagaca  78120
gttgcagtta ttttggaggc aaagattctc tctctctctc tctgtgtgtg tgtgtgtgtg  78180
tgtaattgta ggaactattt aggcagtaaa attaacagat attagtcact gattgactga  78240
gtggatggca gtgataggtg gggtgcgttg agggaagtgt attacattaa gtccaggatg  78300
actcatggtt ttctaagttg agtcattggg gattgccatc caatgtgaga aactatatag  78360
tcttatcata gttgatcttg gaggtagact tgaattaaaa tcttgaagcc atcaattgct  78420
gtatgtgggt cttgggcaga acacttaagg tttctggacc tcagttattt cttctgtaaa  78480
atgaggaaaa taatgcatac ctcatgcatt tgttgtaaag actaaatgag gttaaagtat  78540
gtagagtgta gtttagtaac tgggacgtat agtggtccag taaacatcag ctgttattat  78600
tgtgctatat gttgtgatgt gtactggagt gagatggggt aggggatttt ttagtctctg  78660
ccaatgactc ctctccccat gatcaaaatc agaaaatcag tctcttatgt gttgaggagt  78720
gagacacttc tcccaagtgt ttaaggctaa taccttgcct tgttttgcct tgggccagac  78780
ctcactacac atctgtttaa gagatcaggg taagctctgt tcttggtgag tatctcaatg  78840
gggctgtttt tctagttctt gtagtttctt tgggccaaca tgaaatgtct aaccttggct  78900
tcttggttgt ggattctcgt caacatttca ctgctaccca agttgtgtct gcttacatga  78960
tgctatcttc cttcttttgg gtttctgaag ccctcagaca cttggctgaa catttttcac  79020
atttcttaag ctatatcatc tgtgttttcc ctgccacaga caaagtcaca aaaggacttt  79080
aagataggtt ttggtttttt ttttccccag ggtttttata cattttgggt aagggcaagt  79140
ggtaaatgct gcttttctgc cttaaccagt agtgtctgac agaggaggta gcatgatgat  79200
tgcagagctc actggactga aagtcagatg ctttacccgc ctagactcta gtaccaaggg  79260
```

-continued gaagatggag tgagatgggg taaatgggga gaaattacca tttattttga gtgtgccagg 79320
ccttttctca tgtattgtct aatgcatttg tcacaattct ctttgggttt gaaatgtgat 79380
tttcttcatt ttatagataa ggaaacttat gggaagggag gttaggttca tcttgtgccc 79440
aactttacat ggctagtgat caataatagt gagattcaaa ctcagatttc tctgccccaa 79500
agcctttgct ttttcctctt ttgacactgt aactaatgag aagatgtatt taactctgag 79560
tctcatttgc ctcaactgta aaatggagct ctgtaactct tgctctgtat gacagtaaat 79620
ctcctcagac cagacttatg ataggggata aggatatttg tatctttggg cccctaatgt 79680
attgaaagtg cttctaagtg cctggcacat agaagggcac tcaataaata tttaccacat 79740
tttccagaaa gagggtagct ccataatggg tgagatacat tttggtggct actgtagtgt 79800
ttaatgcttt taccatctgt taaaatgatt ttggagtata gctagataac tgatgatggt 79860
tgttatatag attttttcat aggttgcctg ttccaaattc tatgccgtgg aagaagttaa 79920
atatccagaa tttgacagga aatattattc tacaacagat ccctggcgta agaatgataa 79980
cacctgtgtt ctagtctcag acttgcctct gaataactgt ttctcctggt caattctctg 80040
tctctatcta ggcttgaaat ttcccccaaa tgatgaagga gttggactag tttagtgggg 80100
ttcagcctcg agtggccatt aaaattattt ggggatcttt gaaaaaaatt agatgcccag 80160
atttttgtcg ttgttgttgt tgtttttgtt tgtttgtttt ttaattatac tttaagttct 80220
gggatacatg tgcagaacat gcaggtttgt tacataggta tacacgtgcc atggtggttt 80280
gctgcaccca tcaacccgtc atctacatta ggtatttctc ctaatgctat ccctccctag 80340
tcccctaacc ccagacaggc cctggtgtgt gatgttcccc tccctgtgtc tatgtgctct 80400
cattgttcag ctcccccctta tgagtgagaa cgtgcagtgt ttggttttct gttcctgtgt 80460
tagtttgctg agaatgatgg tttccagttt catccatgtt ctttcaaagg acatgaaccc 80520
atcctttttt atggtggcct gatattccat ggtgtattga actgctcact ccagttcaat 80580
taaatcagaa tacagaatgt tgagaggagc atcagtattt taagaaggcc ccctagtgaa 80640
gttcaatgtg cagccaaggg tgagaaacac tggactagat gattgataag ggccatccaa 80700
ctttgatagt caacaagaga caatgctata gagtatggtg gacagagcat gggctttaga 80760
gttagccagg tatgcattca gaccctggct ctgttactta ctagttgtgt gatcttgaag 80820
aaatcaaaat ggagatacac tatgtacctg gcagtaatag ttgtggggat taagcacctt 80880
caccagagct taggacataa taagccccca gtaaatagct tctttaatat cagaagttca 80940
gatggaagat gtgagaaaaa tattggttca gtaagattta acaggtaaat taaaatcaag 81000
tatttgaaaa cattttcctg tttctttagc aatggattcc agaaacataa tgtggaaata 81060
gctctcagtc cttagatttg atgacattgc agaaagaaat ctggctagtc gtcccatggc 81120
tgattggcta tgatggctag aaagccattg gaaaaaaaaa attggctcac agaagacagc 81180
agatgtggct tgggaaatgc aaggacatga ctgtaataag gatttgtcta tccagcccca 81240
tttatgagag tgattccagg agaaaaggac agatttgtat tgtcagtggg atacgctgtt 81300
aaaaaacact tttgctacta ccactccagc tgtcttggca tgtttgttgg tgatgtaagc 81360
tacagaaaat ggaaatcacc aatagggcta tagcaacctg atgcatagtg acaagtaatt 81420
gttctattca tggttatgtg ttgtacagag cacttgctgc atgtcaggtt tgagacttga 81480
gtatgcatta gggccatgga cacccccatc ttatctttaa gtagatttca aagtaaatat 81540
ttgatgaata tgtaaaatat ttagtttggt cagtcatagg gctgagaaca tggtggcagt 81600
tacctcctag tatctgcaag caaaaaaagt tttttcttcc tatagcaatt gccatctcag 81660

-continued

```
ccacttttgc agcatttctt tttgctacac tttgcattaa ccatttgtgc acttgtctta  81720
gcctcaaaca ggccatgaaa gctccttgag gataggggct atgtcttttt catctttata  81780
tatgcatcat ttagcagagc tgtcccttta taatgtacta attactgaat gaagggatgc  81840
atagatgaat aaatgaatga aaagtaggag tgacctgtct tctctctttc ttcacgatgg  81900
ggactagtgt gtgtatataa ggggataatt tttgtgtcac ataaaatata accttactta  81960
gaaggcaaga cttccagaat ggtggaatga gaaccacccc cccgcccccca taaatccgcc  82020
ctttcatgaa agcagtgaaa acgctagcaa acgttgtgaa aattaacttt tccagaactc  82080
tggaaaggaa acagaggctt ccaacaatct gagaagaatg tattcaagaa aaacttcggt  82140
aagctctctg atcacagtgg aaataataaa caattagtaa tagaaggata gttgggaaat  82200
tcaccatttg tgggatataa acagtggatc aaagaagaaa tcataaggga aatgagaaaa  82260
tactttgaga ttaatgaaaa tgaaaataca ttgttccaaa acttacagga tacagccaag  82320
ctaaagcagt acttaaaggg aaatttgtaa ctgcgaaggc ctatatcaac aaagacaaat  82380
gatctcaaat caagaaccta accttccacc ttagactagg aaaggaacag caaactacaa  82440
agaaagcagg aagaaagact aataaagact aaaagggaaa taaatgaaat aatagagtag  82500
aaaaacacta gaatcaatga aattaaacat tgattctttg aagagatcaa caaaactgaa  82560
aaaaacttta gtcagattga ataagaaaaa aagagagaaa attcaaatta tcaaaatgag  82620
caatgaaaat ggggccatca ctacctacct taaaaagaat tttcaaagga ttaaaagaaa  82680
atgccattgc attagttcat tctcacacaa ctataaaaaa gctacctgag atggggtagt  82740
ttatgaagaa aagcgcttta attgactcac agttccacag tctgtacagc aggcatggat  82800
catgaggcct taggaaattt acatcaggtg aaaggctaag gggcatggaa gacatgtctt  82860
cacacggcag caggagagag agcaaagagg gaagtgccac acacttttaa accatcagct  82920
ctcatgacaa ctcactcact atcatgagaa cagcaagggg aaaatctgcc ctcatgatcc  82980
aattacttcc taccaggtcc cttccccaac actggaaatt acaattcaac gtgcgatttg  83040
gatggtgtga cacagagcaa aaccatatca accatactgt atgccaaaaa attagatgac  83100
ctagatgaaa tggacaaata ctcagaaaaa cacaaactat ctaaagtgac cagtgaagaa  83160
acagaaaatc tgagtagtcc tgtaacaagt cctgtaacaa aactggatta gtaattaaga  83220
aacttcccac aaagaaaagc ccaggttcag tcttcactgg tgaatactat caaatattta  83280
aggaagattt aatccttcac aaattatttc aaaacttgga agaggctgga accctttcca  83340
actaattctg caaagtcagc attaccctga tgccaaaacc aaagatatga cacaaaaata  83400
aaactgcagg ctaatatcac atttgaatat agataacttt ctaaaaatct caacaaaatg  83460
ctagcaaaca gaattcagca acaaataaaa agggttataa agggtgacca agtaggattt  83520
atctctggaa tgtaaattaa cattcaaaaa cctaagaata ggaggaaact ttcttaactt  83580
tgtaatggac atctctgaaa aacacacagc taacatcata ctaaataggg aaagattgaa  83640
atttttcctt gtaagatcag gaacaagaca aggatgactg ttctcaccat ttcaatttac  83700
cattgtattg tagattcaag tcaaggcaat taggcaaaaa aaaaaaaaaa aaaaaaaaaa  83760
aaaaagaaag aggtaaaagg cacccatatt ggaaaggaag aggtgaaaat atctatattc  83820
acagatgaca tgatcttata caaagaaaac cttaaggaat ccatgataaa ctattaaaac  83880
gagtaaacga gttcagcaag gtttcagaat acaagattaa tgtgcaaaaa tcaattgtat  83940
ttctgtacac tagcaatgag caatctgaaa atgagattaa gaaaacagtt cactcacaat  84000
```

-continued

```
ataatcaaaa taccagaata cttaaaaata aatttaacaa aagaagcgta agacttgtat  84060
gctgcaaacc acaaaacact gtggaaagta attaaaaatc taaataaata gaaaaacatc  84120
ccttgttcat gtactagagg actcaatatt gtcaagatgg aaatactccc caaagattga  84180
aggaaatccc tatcaaaata ctggctgttt tcttagcaga aaatgaaaat ctgaccctaa  84240
aattaatatt taaatacatg gaacctagga taaccaaaat aatattgaga aagaaaaaca  84300
aagtcggcgt acccatgctt cctgattcca aaccttatta caaagcagtg gtaatcaaga  84360
gtgtatggta ttggcataag gacaaacaga tcaataaatg gaatactatt gagaatccaa  84420
aagttaactc ttacatttaa gaccaattga ctttcaaaag tgttgctaag acatttcaat  84480
gaggaaagaa tagtcttttc aataaattgt actggaaaaa ttggatatcc acatgaaaat  84540
aaaagatttt ggaccacttc aaacctgcaa aaaaaataaa atgatctcat ggtgtatcat  84600
ggatctaaat gctatagagc taagatgata aatctcagaa gaaaatatca aagtaaatct  84660
ttatgacctt gaagtaggca atggtttttt ggctataaca ccaaaagcac aagcaataag  84720
agaaaaaaaa tttttttaaa aaaacccttg attattttat taaaattttg ttgtgggtac  84780
aaagtaggtg tgtatattta tggggtatat gagatatttt gatacaggca tacaatgttc  84840
aatgatcata ttaggataaa tgaagtatcc agtacctcaa gcatttatca tttgtgttac  84900
aaacaatcca attatactct tttagttatt tttaaatgta cagtacatta ttattgtagt  84960
cattcccttg tgctatcaaa tactatatgt tattcattct atctaactat attattgtac  85020
ccattaacca tccccactcc cctgcctccc agctacactt cgtagcatct ggtaaccatg  85080
atttcctctt atctccatga gttcagtagt ttcagctcat ggagatagac agaactaatt  85140
ttattagctc ccacaaatta gctcccatgt cagaacatgt aaagtttgtc tttctgtgcc  85200
aggtttattt cacataacat aacgaactct agttccaacc atgttggtgc aaatgacagg  85260
ctctctcttt tttttttttt tttttttttt tgagatggag tctggctgtc tcccaggctg  85320
gactgcagtg gtgcaatctc agctcactgc aagctccgcc tcccaggttc atgccattct  85380
cctgcctcag cctcctgagt agctgggact acaggcaccc gccaccatgc ccgactaatt  85440
ttatatatat atatatatat atatatttat tattattata ctttaagttt tagggtacat  85500
gtgcacaatg tgcaggttag ttacatatgt atacatgtgc catgcaggtg cgctgcaccc  85560
actaactcat catctagcat taggtatatc tcccaatgct atccctcccc cctcccccac  85620
cccacaacat tccccagagt gtgatgttcc ccttcctctg tccatgtgtt ctcattgttc  85680
aattcccacc tatgagtgag aacatgcggt gtttggtttt ttgttcttgc gatagtttac  85740
tgagaatgat gatttccaat ttcatccatg tccctacaaa ggacatgaac tcatcctttt  85800
ttatggctgc atagtattcc atggtgtata tgtgccacat tttcttaatc cagtctatca  85860
ttgttggaca tttgggttgg ttccaagtct ttgctattgt gaataatgcc gcaatgaaca  85920
tacgtgtgca tgtgtcttta tagcagcatg atttatagtc ctttgggtat atacccagta  85980
atgggatggc tggttcaaat ggtatttcta gttctagatc cctgaggaat caccacactg  86040
acttccacaa gggttgaact agtttacagt cccaccaaca gtgtcaaagt gttcctattt  86100
ctccacatcc tctccagcac ctgttgtttc ctgacttttt aatgattgcc attctaactg  86160
gcgtgagatg atatctcatt gtggttttga tttgcatttc tctgatggcc agtgatggtg  86220
agcatttttt catgtgtttt ttgggtgcat aaatgtcttc tttttagaag tgtctgttca  86280
tatccttcgc ccactttttg atggggtcgt ttgttttttt cttgtaaatt tgtttgagtt  86340
cattgtagat tctggatatt agccctttgt cagatgagta cgttgcgaaa attttctctc  86400
```

```
attttgtagg ttgcctgttc aatctgatgg tagtttcttt tgctgtgcag aagctcttta  86460
gttgaattag atcccatttg tcaattttga cttttggtgt tttagacatg cttttggtgt  86520
tttagacatg aagtccttgc ccatgcctat gtcctgaatg gtaatgccta ggtttcttc   86580
tagggttttt atggttttag gtctaacgtt taagtcttta atccatctcg aattgatttt  86640
tgtataaggt gtaaggaagg gatccagttt cagctttcta catatggcta gccagttttt  86700
ccagcaccat ttattaaata gggaatcctt gccccattgc ttattttgt caggtttgtc   86760
aaagatcaga tagttgtaga tatgcggcat tatttctgag ggctctgttc tgtttcattg  86820
atctatatct ctcttttggt accagtacca tgctgttttg attactgtag ccttgtagta  86880
tagttagaag tcagggagtg tgatgcctcc agctttgttc ttttggctta ggattgactt  86940
ggggatgtgg gctctttttt ggttccatat gaactttaaa gtagtttttt ccaattctgt  87000
gaagaaagtc atcagtagct tgatggggat ggcattgaat ctataaatta ccttgggcag  87060
tatggccatt ttcacgatat tgattcttcc tacccatgag catggaatgt tcttccattt  87120
gtttgtatcc tcttttattt ccttgagcag tggtttgtag ttctccttga agaggtcctt  87180
cacatccctt gaaagttgga ttcctaggta ttttattctc tttgaagcaa ttgtgaatgg  87240
gagttcactc atgatttggc tctctgtttg tctgttattg gtgtataaga atgctgtgat  87300
ttttgtacat tgattttgta tcctgagact ttgctgaagt tgcttatcag cttaaggaga  87360
ttttgggctg agacaacggg gtttctaga tatacaatca tgtcatctgc aaacagggac   87420
aatttgactt cctcttttcc taattgaata ccctttattt ccttcttctg cctaattgcc  87480
ctggccagaa cttccaacac tatgttgaat aggagtggtg agagagggca tccctgtctt  87540
gtgccagttt tcaaagagaa tgcttccagt tttgaccat tcagtatgtt attggctgtg   87600
ggtttgtcat agatagctct tattatttta aaatacggcc catcaatacc taatttattg  87660
agagttttta gcatgaagcg ttattgaatt ttgtcaaagg ccttttctgc atctattgag  87720
ataatcatgt ggtttttgtc tttggttctg tttatatgct ggattacatt tattgatttg  87780
cgtatattga accagccttg catcccaagg atgaagccca cttgatcatg gtggataagc  87840
tttttgatgt gctgctggat tccgtttgcc agtattttat tgaggatttt tgcatcaatg  87900
ttcatcaagc atattggtct aaaattctct tttttggttg tgtctctgcc cgtctttggt  87960
atcaggatga tgctggcctc ataaaatgag ttagggagga ttccctcttt ttctattgat  88020
tggaatagtt tcagaaggaa tggtaccagt tcctccttgt acctctgata gaattcggct  88080
gtgaatccat ctggtcctgg actctttttg gttggtaagc tattgattat tgccacaatt  88140
tcagatcctg ttattggtct attcagagat tcaacttctt cctggtttag tcttgggagg  88200
gtgtatgtgt caaggaattt atccatttct tctagatttt ctagtttatt tgcgtagagg  88260
tgtttgtagt attctctgat ggtagtttgt atttctgtgg gatcggtggt gatatcccct  88320
ttatcatttt ttattgtgtc tatttgattc ttctctcttt ttttctttat tagtcttgct  88380
agcagtctat caattttgtt gatcctttca aaaaaccacc tcctggattc attaattttt  88440
tgaagggttt tttgtgtctc tatttccttt agttctgctc tgattttagt tatttcttgc  88500
cttctgctag cttttgaatg tgtttgctct tgcttttcta gttcttttaa ttgtgatgtt  88560
agggtgtcaa ttttggatct ttcctgcttt ctcttgcggg catttagtgc tataaatttc  88620
cctctacaca ctgctttgaa tgtgtcccag agattctggt atgttgtgtc tttgttctct  88680
ttggtttcaa agaacatctt tatttctgcc ttcatttcgt tatgtaccca gtagtcattc  88740
```

-continued

```
aggagcaggt tgttcagttt ccatgtagtt gagcggtttt gagtgagatt cttaatactg  88800
agttctagtt tgattgcacg gtggtctgag agatagtttg ttataatttc tgttctttta  88860
catttgctga ggagagcttt acttccaact atgtggtcaa ttttggaata ggtgtggtgt  88920
ggtgctgaaa aaaatgtata ttctgttgat ttggggtaga gagttctgta gatgtctatt  88980
aggtctgctt ggtgcagagc tgagttcaat tcctgggtat ccttgttaac tttctgtctc  89040
gttgatctgt ctaatgttga cagtggggtg ttaaagtctc ccattattaa tgtgtgagag  89100
tctaagtctc tttgtaggtc actaaggact tgctttatga atctgggtgc tcctgtattg  89160
ggtgcatata tatttaggat acttagctct tcttgttgaa ttgatccctt taccattatg  89220
taatggcctt ctttgtctct tttgatcttt gttggtttaa agtctgtttt atcagagact  89280
agaattgtaa cccctgcctt ttttttgttt tccatttgct tggtagatct tcctccatcc  89340
ttttattttg agcctatgtg tgtctctgca tatgagatgg gtttcctgaa tacagcacac  89400
tgatgggtct tgactcttta tccaatttgc cagtctgtgt cttttaattg gagcatttag  89460
tccatttaca tttaaagtta atattgttat gtgtgaattt tatcctgtca ttatgatttt  89520
agctggttat tttgctcgtt agttgatgca gtttcttcct agtctcgatg gtctttacat  89580
tttggcatga ttttgcagcg gctggtaccg gtcgttcctt tccatgttta gtgcttcctt  89640
caggacctct tttagggcag gcctggtggt gacaaaatct ctcggcattt gcttgtctgt  89700
aaaggatttt atttctcctt cacttatgaa gcttagtttg gctggatatg aaattctggg  89760
ttgaaaattc ttttctttat gaatgttgaa tattggcccc tactctcttc tggcttgtaa  89820
agtttctgcc gagagatctg ctgttagtct gatgggcttc cctttgaggg taacctgacc  89880
tttctctctg gctgccctta acattttttc cttcatttca actttttga atctgacaat  89940
tatgtgtctt ggagttgctc ttctcaagga gtatctttgt ggcattctct gtatttcctg  90000
aatctgaatg ttggcctgcc ttgctagact ggggaggttc tcctggataa tatcctgcag  90060
agtgttttcc aacttggttc cattctcccc gtcactttca ggtacaccaa tcagacatag  90120
atttggtctt ttcccatagt cccatatttc ttggaggctt tgctcgtttc tttttattct  90180
tttttctcta aagttccctt ctcacttcat ttcattcatt tcatcttcca tcgctgatac  90240
cctttcttcc agttgatcgc attggctcct gaggtttctg cattcttcac gtagttctcg  90300
agccttagtt ttcagctcca tcagctcctt taagcacttc tctgtattgg ttattctagt  90360
tatacattct tctaaatttt tttcaaagtt ttcaacttct ttgcctttgg tttgaatgtc  90420
ctcccatagc ttggagtaat ttgattgtct gaagccttct tctctcatct catcaaagtc  90480
attctctgtc cagctttgtt ccgttgctgg tgaggaactg cgttcctttg gaggaggaga  90540
ggcgctctgc tttttagtgt ttccagtttt tctgctctgt ttttccccat ctttgtggtt  90600
ttatctactt ttggtgtttg atgatggtga tgtacagatg ggtttttggt gtggatgtcc  90660
tttctgtttt ttagttttcc ttctaagaga caggaccctc agctgcaggt ctgttggagt  90720
acccggccgt gtgaggtgtc agtctgcccc tgctgggggg tgcctcccag ttaggctgct  90780
caggggtcag gggtcaggga cccacttgag gaggcagtct gcccattctc agatctccag  90840
ctgcgtgctg ggagaaccac tgctctcttc aaagctgtcc aacagggaca tttaagtctg  90900
cagaggttac tgctgtcttt ttgtttgtct atgccctgcc cccagaggtg aagcctatag  90960
aggcaggcag gcctccttga gctgtggtgg gctccaccca gttcgagctt cccagctgct  91020
ttgtttacct aagcaagcct gggcaatggc aggtgcccct cccccagcct cgctgccacc  91080
ttgcagtttg atctcagact gctgtgctag caataagcaa gactccatgg gcgtaggacc  91140
```

-continued ctctgagcca tgtgcgggat ataatctcct ggtgcgccgt tttttaagcc cgtcagaaaa 91200
acgcagtatt tgggtgggag tgacccaatt ttccaggtgc cgtctgtcac ccctttcttt 91260
gactaggaat gggaactccc tgaccccttg cgcttcccga gtgaggcaat gcctcgccct 91320
gcttcggctc acacacggtg cgctgcaccc actgacctgc gcccactgtc tggcactccc 91380
tagtgagatg agcccgctac ctcagatgga aatgcagaaa tcacccgtct tctgcttcgc 91440
tcatgctggg agctgtagac ctgagctgtt cctattcggc catcttggct ccagaaaaaa 91500
aaattgttaa attggacttc atcaaatttg aaatttttgt gctgcaaatg ataccatcaa 91560
gaaagtgaaa atctcaccca cagaatgaga gaaagtattt gcaaatcata tatctgataa 91620
gggtattgaa tttagaatat ataaagaact cttgcaactc aatataaaaa gacaacccaa 91680
ttttaaaatg ggcaaagtat ttgaatagaa atttcttgat agaagatata caaatttaaa 91740
aatgctcaac atcattagtc attagggaaa tgcagatcaa aaccaaattg agataccggt 91800
ttacacctat taagatggct atagaataaa agaacaaata acaagtattg gctttaatgt 91860
ggaggagcca gaacccttat atattgctgg taaaatgtaa agtcatgcag ccctttgaaa 91920
tacagtctgc aagtctttaa aaaattacta tttgttattt ggtttttctt cacttttaat 91980
ttaggttcag aggtacatat gcaggtttgc tatatagcta aattgtgtgt cacaggagtt 92040
tagtgtacac attatttcat cacccaggta ataagcatgg tacccaatag gtagtttttc 92100
tatcctcacc ctcctcctac cctccaccat caagtaggcc ctggtgcctc ttgttctttt 92160
ctttgtgttc atatgtactc aatatttagc ttccacttat cagtgagaac atgtggtatt 92220
tggttttctg ttcctgcttt agtttgctta ggatactggc ctccagattc atccacgttg 92280
ctgcaaagga catgatctca ttctttttgc atagtatact atggtgtaca tgtatcaaaa 92340
atgttactgt ttgacctagt aattctattc caaggtaaat actcaagaga aatgaaaaca 92400
tgtccacaca aatacttgta cacaaatgtt cattgcagca ttatttataa tagccaaaga 92460
gtggacgaca aatgtcttcc aaatgtgggc tccaaatgtc caccaactga taaatggaaa 92520
aacaaaatgt ggtatatcca tgccatggtt tatctgtcaa taataagaaa tgaagtactc 92580
atacatgctc caacatggat gaaccttgaa aacattatgc taggtgaaaa aagcaactca 92640
caaaagacta cactgtatga ttttatttgt attaaatgtc cataaaagaa aaatatttag 92700
agatagaaag gaaattagtt tttccagggt ctgggaggag acagtatgag gagtggctgc 92760
taatgggtac aggatttctt tttggagtga tataattgct ctaaaattag tttgcagtaa 92820
tagatgtgag tatgctaaaa tgggtgaatt ttatagtatg tgaaatataa ctcagtaagc 92880
ccattaaaaa caacctaatt aaattaaaac caagctataa cagaaatatt atatggcttt 92940
ggcagtttag aatagtggga aaatatggag taagggtggg gaaatagtcc caagtataat 93000
tctggttttg tcactactag tgtatggact tggacaagtc atttgctttc tctaagtatc 93060
agtttgcata tatgcaaaat agaggtaatg atacctacct cagtggtacc ttttcaaaac 93120
cttgttcttc ctcatctctc ctctaccact ttctcataat attattacag taataaccat 93180
ttattaagca ctgtgtccgc agtggtgtgg ggctgcttta cctccacaac ttcactgaat 93240
cctcactgca gtcttgtggg atctttattt ctttgcccat tttacatgta aataaattga 93300
agtcaaatga gttgttcaag gtccttctgt tagcaagtgg cagagatgga catgaaaact 93360
agatcttcta cctatgtgtc tttccacttc aactaaagaa tttattaaag agaattgaaa 93420
agctatgaac taaatttcgg taatactttt aatagtaaac attgctgccc tcgtgaatga 93480
acacacacta aatttcaaat ctcacggtgg cagggaataa agatgctacc tatcttaagc 93540
cattacttca ccaacttctc caccaaaata ttccttgtaa ccacaaataa gtaagcacaa 93600
tagatctata aggagagaat aattgtgaac tctgatttta tcttaaaaag tcatgtaggg 93660
atgtcatgtt ccacaatgtg attaataaaa tatattttgt tactaaacac aaggaaaaat 93720
attatgttcc ataaagatgt ttggtggttg cctcgacctc ttttagtttg aaaagtaggt 93780
atgtatgaga aagatatgtg tttacatgtt taccettgcc ttctctctgt ctcttcccct 93840
ctctctccct ccctccccaa ccctatgcc ctacaccccc gcaaccccca catgtattta 93900
cctttctcta aaagctctgc atagccaaga aaagtgctct tttttatttt taggatatta 93960
gatatttcat tttcttatgg taagacaaaa gattaaggca accaagactt acaatgtgcc 94020
taccatgtgg caggcacaga ggcaagggct tttacatgtt atttaatgta attgtaattc 94080
tcacaaaagc cgtctagagt tgaaaatatt tccaactcta aatgaggcaa atggagcaca 94140
gagagcctta attatttcac ccaaagttca gtggtagagg caggattcca acccaggtct 94200
ggtgggctcc aaatccttgt tgggttgcca ttcctcttgc taacaaataa aactggtctg 94260
tgacttttgc atttcacccc gcttccacag tcactggtgg gacttactta agttaatcag 94320
attcttcaaa gtatccccaa gtcctccttt gaaaagaaag ttgggggaca ggaggaggag 94380
cagaggagag gagataaaaa ggaaaggagt cagggagaga gagagagaga gagaaacctg 94440
gtgatctcag ctgggtgcca aggtttccta agcccaagtt ccccatggtt gagcctgtat 94500
tgtcaggcca acagcttcta gtaatccact tttatttaat taatagtgaa actgttgaag 94560
aattgcaagt ggtgttctgg ttcagaaacc ttccgttcta tggggcactg cttttgcttc 94620
agattcataa aaccaaatgc tctgcctcaa gataataagt gaacgtgtaa ccctcgggag 94680
gtaagaaaaa acacaatgtc acgtgcaaat tctgcacttg ttctcaaagc aaacctctcc 94740
tgtgtttgca attaggatgt tatctaggag catattcaaa acttttgagg tttttatttt 94800
agtttttctt tcattatgtg ctgttttagt aatatcaaag aatacatgta atatataatt 94860
tatatgtcat aacaataaaa ttaatgttga tgagcccaga ttaaagaatc aacaacatta 94920
acatcatgat tgcatcaacc ctattagaat ggaagctctg tgaaggcatg gatttttgtc 94980
cattttgttc actgctatat ccccaggacc tagaggagtg tcagccacat aataggagct 95040
tagtcaatat tttaaaaata agagcataaa tctacttata tcctctttcc tcttaccatc 95100
actcccagcc tcccctcaga ggtaaccact atcctatatt tgggctttat tattcccttg 95160
cattttgata agtttcaca tgtatattcc caaataatat attgcttgct tttgcttctt 95220
tttaaacttt atataatgga atcatattgt atgtatccta ttgtgaatta tgtcttttac 95280
acaacattag tatttgagat tcaactatgt gtagctcgat tccattcctt ttcattgctg 95340
attgtagttt attggatatg tgtgccataa attatttttc tcctgtcagt taatgtttat 95400
catttatgct ttaataaaca aaactgctat gactgttcct gcatgtgcct cctagtacat 95460
atgtgaccaa ctttctctag gatataagcc tgagagaggg actgcagttg gaatttacat 95520
ttccaaagcc caaagtttag ctcatgagtc agagctgcaa tgtgcccttt gtccacacta 95580
ggtcaggatc agtgggagtg ctacccaaaa tattttgcta gctggggagt cagggagaag 95640
cagagactga cctagtgagg ccaggaggca ctatctcagg tctctagtca aaatgggttg 95700
caattagtaa aagtccagat tctgaatccc cttcactatt tatcttcctc ttcctccttt 95760
acagttattt ttgttcaagg tgcactttat taaactcatg cctaacaaac aaaactctaa 95820
tgaatatttt gtctttcatt gattgtaaat tcaattaatt agattgcttg aaaaaatttt 95880
aactgtattt tcactttagt atggatgaaa atttcgattt ctttaaaaaa catttttttaa 95940
taataacaca acataaagtc taccctcata acaaaattta agggcacaac accatattgt 96000
ttttttttta ttttattatt attatacttt aagttttagg gtacatgtgc acaacgtgca 96060
ggtttgttgc atatgtatac atgtgccatg ttggtgtgct gcacccatta actcgtcatt 96120
tagcattagg tatatctcct aatgctatcc ctccccccctc cccccacccc acaacagtcc 96180
ccagtgtgtg atgttcccct tcctgtgtcc atgtgttctc aatgttcagt tcccacctat 96240
gagtgagaac atgtggtgtt tggttttttg tccttgccat agtttgctga ggatgatggt 96300
ttccagcttc atccatgtcc ctacaaagga catgaactca tcctttttta tggctgcata 96360
gtattccacg gtgtatatgt gccacatttt cttaatccag tctatcattg ttggacattt 96420
gggttggttc caagtctttg ctattgtgaa tagtgccgca ataaacatac gtgtgcatga 96480
caacaccata ttgttaactg taggcacaat gttgtacagc agacgtctag aactttttct 96540
tcaggcttaa ctgaaacttt atagccattg aacagcaaca ctccatttcc gtttcttaaa 96600
ggtcctttac aaaatgagct ttctgcgtgt ttccattttg tttatctgat aactttttttt 96660
tctttttttta ttatacttta agttctgggg tacatgtgca gaatgtacag gtttgttaca 96720
taggtacaca catgccaggg tgtttggctg cacctatcaa cctgtcatct acattagata 96780
tttctcctaa tgctattccc tcccttgccc ctcacccctc actggcccca gtgtgtgatg 96840
ttccctagcc tgtgtccaag tgttctcatt gttcaactcc cacttttgag tgagaacatg 96900
cagtgtttga ttttcttttc ttgtgttagt ttgctgagaa tgatggtttc cagcttcatc 96960
catgtccctg caaaggacat gaactcttcc ttttatatgg ctgcacaata ttccatggtg 97020
tatatgtgcc acaatttctt tatccaatct atcattgatg ggcatttcag ttgttccaag 97080
tctttgctat tgtgaatagt gccacagtag acataagtgt gcatgtgtct ttatggtaga 97140
atgatttata atcctttgtt tatataccca gtaatagaaa tgcttggtca aatggtattt 97200
ctagttctag atccttgagg aattgccaca ctgtcttcca caatggttga actaatttac 97260
actcccacca acaatgtaaa agcgttccta tttcttcaca tcctctccag cacctgttgt 97320
ttcctgactt tttaatgatc acgattctaa ctggcgtgag atggtatttc attgtggttt 97380
tgatttgcat ttctctaatg accagtgatg atgagctttt tttcatgttt gttgaccgca 97440
taaatgtctt cttttgagaa gtgcctgttc atttccttca cccacttttt gatggggttg 97500
tttgtctttt tcttgtaaat ttgtttaagt tcattgcaca ttctggatat taattaacct 97560
ttcgtcagat ggatagactg cagaaatttt ctcccattct gtaggttgct tgttcactct 97620
gatgatcgtt tcttttgctg tgcagaagct cttgagttta attagatcac atttgtcaat 97680
cttggctctt gttgccattg cttttggtgt tttagtcatg tagtctttgc ccatgcctat 97740
gtcctgaatg gtattgccta ggttttcttc tagggttttc atggttttag gtcttacgtg 97800
actcatcttg atttaatttt tgtgtaaggt gtaaggaagg ggtccagttt cagttttctg 97860
catatggcta gctagtttcc ccaacaccat ttattaaata gggaatcctt tccccattgc 97920
ttgtctttgt caggtttgtc aaagattaga tggttgtaga tgtgtggtat tatttctgag 97980
acctctgttc tgttccattg gtctatatat ctgttttggt accagtaccg tgctattttg 98040
gttactgtag ccttgtagta tagtttgaag tcaggtagca tgatgcctcc agctttgtgc 98100
ttttggctta gaattgcctt ggctatgcag gctctttatt ggttccatat gaaatttaaa 98160
gtagtttttt tataattctg cgaagaaagt cattggcagc ttgatggggt tagtattgaa 98220

```
tctgtaaaac actttgggca gtttggccat tttcatgata atgattcttc ctatccatga  98280
gcatggaatg gttttccatt tatttttgtc ttctcttatt tccttgagca gtggtttgta  98340
attctccttg aagaggtcct tcacatccct tgtaagttgg attcctacat attttattct  98400
gtttgtagca attgtgaatg ggagttcact catgatttgg ctctctgttt gtctgttatt  98460
ggtgtatagg aatgcttgtg attttcgcac actgattttg tatcctgaga ctttgctgaa  98520
gttgcttgtc agcttaaggt gattttgggc tgagagaatg ggttttctg aatatacatt  98580
catgtcatct gcaaacagag acaatttgac ttcctgtttt cctatttgaa tatcctttat  98640
tgctttctct ttcctgattg ccctggccag aacttccaat actatgttga atagggtgg  98700
tgagagacgg catccttgtc ttgttctggt tttcaaaggg agtgcttcca gtttttgacc  98760
attcagtatg atattgggtg tgggtttgtc ataaatagct cttattattt tgagatatat  98820
tccatcaata cctagtttat tgagagtttg agcatgaagc agtgttgtat tttgtcgaag  98880
gccttttctg catctattga gataatcata tggttttgtc attggttctg ttgatgtgat  98940
ggattatgtt tattgatttg tgtatgttga accagccttg catcccaggg gtgaagcgga  99000
cttgatcgtg gtggataagc tttttgatgt gctgctggat tgggtttgcc agtatttttt  99060
tattgaggat ttttgcactg atgttcatca gggttattgg cctgacgttt tcttttttg  99120
ttgtgtctct gccaggtttt ggtatcagga tgatgctggc ccataaaatg agttagggag  99180
gattccttct ttttctgttg tttggaatag tttcggaagg aatggtacca gctcctcttt  99240
gtacatctgg tagaattcat ctgtgaatcc ttctggttct ggactttttt tggttggtag  99300
gctattaatt acttcctcaa tttcagaact tgttatagtt ctattcaggt atttgacttc  99360
ctgctttagg cttgggaggg tatatgcgtt caggaattta tctatttctt ctagattttc  99420
tattttattt gccccagagg tgtttatagt attctctgat ggtaatttgt atttctgtgg  99480
gatccgtggt gatatcccct ttatcatttt ttattgcatc tgtgattctt ctctcttttc  99540
ttctttagta gtctggctag tggtctatct acaaaataga ctgtttatct gatatttatt  99600
ttgtaattat ctaataataa ccatcattat catcatcagc attatcatta tcatctcctt  99660
tacccataca tacatttgtg tctttcaaat aataatccca tctttgaagt gcatcctcat  99720
ctttagcagt ctgcactctg ctttcttata tcatttatta tcttatttta taattattta  99780
tttccagtcc ttcttctcta acagatagta gtttcttagg gccaaggaaa tatctcgatc  99840
accactatat ccccagcacc taaccctgtg cctggtccat agggccagat gctaagagtt  99900
gagttgaacc attgtaccta atcttaacct tcattagcac aacatggttt gtcagtggtt  99960
aagaatctac actttggagt cagactcacc caggatggaa tcctggcatt gccacttatt 100020
attaatagat gcgtgatctt gaacaagttt acttaattgt tctgagcatc agtttcctct 100080
tctgcaatat agggatgata cacagctacc tggtaggttg ttgggaaaat taaatgggat 100140
gatatgtatg aaatggcctg gcatatagag tgcctaaata catgttcttc tgattctatt 100200
tggacagttt gtgttagtaa cagaagtcaa aaaggtggag aaaggagaaa ggtacttgtg 100260
aaaatttcct atttcttctc catgtttcat tcaggactga ggaagggggc acagttttta 100320
cccaaggaaa tgacattttt agccaaaaga aatgatctta gcatttagct gaattatata 100380
ttggaagtaa gctccttcca tgtggaactt atggccttgc tagccttggt ttgttggaag 100440
tgctcttgct ggctttctag ttagggtagg gaaaggaagg cttgtgggga atgaagatag 100500
gccatgatat caagccactg ggtttgcaaa tcagtagaat tttttattgc tttctgttgt 100560
acttgggact tgaataaagg ctgatatttg tgtcttgctg gtaaagtgct tgtaaagtga 100620
```

gtgaaagttt tctttgctct tgtcctgaca tagctgttca cttggggttg aggggaggat 100680
aacctttcat gttttttttt tttcttcatt ctgatgactg tgctgaacat tcaaaccaaa 100740
aggccattgg tggaaagtaa aggtgagtgg tgagaagaca atagggtaat ggaaactgtg 100800
ttggacttgt aatcaaattg tcctgcactt cccctctcca agtcttaacg tttttcatct 100860
gtacagtgga tattaaaatg agaaaataag cttgtcttca cagagttttc gttaggtgtt 100920
gacacaacaa acaggctccc attagggctc attttccttc attccttagt aaggaagaag 100980
tgcttataaa atatagcagt tgtgctcttg tgaatgatag catgggcagt tgtcatctcc 101040
ctgaagcaga tgtaacccag aatgtcactt gagttttgtt taatgcttag gcataagaca 101100
taggaatgac aaaagctgac ctttgggtag tgagaacaat gttccatttt gttcaaactt 101160
gaatttttta ctataggaga ctgagaatta accttccatg aaggttttag gattggcttt 101220
ctggcccttc tccttcatat ccacctgaaa gagcttgggc gcagaagttc ttgcagaaag 101280
gcagttagac aaggtgactt ctgaagctcc agtggccaag tattttgatg gtagcctaaa 101340
agatgtccag aatcattgta catcattttt tcaacagaag cttcaggcat agggattatg 101400
cttggtactt tatgttgtgg aatggaatct ggcggatgtc catgtgatct atagaaacac 101460
ctaaggaaag tgaagaaatg agggaaaaaa aagaacaaga cttttatgat aatactaatc 101520
acgatccttg tgtatttatt ccaatggcat tttatccatt atctgattta tattaccact 101580
cacagcagca gctcaatagg atgggagata ttatctctat tttatagatg agatttgagg 101640
ctcacgaagc taaagcaagg aacatcaaat cactttgata tttggtctgg ttttgttata 101700
ggtctccctt tggatgaggt aaagttacaa acctgggttc atatcattta attagtctga 101760
aaatgttgcc tggacaccac cttcagttag atatcttaac ctcaggcttc ctgccttcat 101820
tgctcccgca tatagacata gactatgaga ttggctaatc ccagagaact tccctaatcc 101880
cttggcaaga tccaaaaagg ctcagtcaca ccctacaacc atcatcttta ggagaagtct 101940
cagaaaattc agcttcacac taactaactt gagcaatgaa taatagtcat ttatgcctgc 102000
aggttaatgc tgaagacctg agacttcact tgcctatttc tgccattcag tgacatgtgt 102060
tgcattggtt ttttgtgtct ttccagtttg gagactgcca gggaccatgt tttgcccatt 102120
gactattact ttccacccca gaagacctgc ctgatctgtg gagatgaagc ttctgggtgt 102180
cactatggag ctctcacatg tggaagctgc aaggtcttct tcaaaagagc cgctgaaggt 102240
aaagggtctt gcacatgcac ttctctttcc ctttctcctt taccttccag agagagacac 102300
taacctttca gggcccagga ttttatcatc tcagaaatag agtcattggc aaggccctat 102360
caaataactt aggagcctaa ggaagcaaat ttttgtactt gctagttccc tggtttcagc 102420
agccttgttt gtacaggcaa tttaggcagt gaaggtggtc ccagctgggg cttggggctc 102480
agtgggtcct agaaatgaaa gaaaaattaa tgatttgaaa agatttaatt tcctcccttc 102540
ttgttttcta ctctgctggc tagtaaagga aaaatttgtc cttattagag aggttagaag 102600
tggagaaacc ccaactgagt ccccagcctg ttccttggga tgaatatgag actgttcctt 102660
agcaaaggct tcctggcctc ggccccagaa agggagtgtt ctcactcttc agcagactat 102720
cagtctctgc acctgctccc tcctgttgtg gcctccttgg gacctgtctt tgcattaata 102780
gttcctaggt aggtaagaac tcagagtgaa gaaacacatt tattctcctc tccagagacc 102840
tgatctcaaa gcctgtccat tagtccctaa ccttaatcta aggtagcatc ttatatctgg 102900
ctaaattggc tcaagcccta gctccttagt tttatttagc ttagaacaac tcatgtctgc 102960

-continued tcaacctcta gaggcgctca gcccacattc tgcagtagaa actcccattt tcaggcctct 103020
tatatacggt aatgtctcct tcctctaacc acccagggct taagcttcct gcttatccac 103080
ttcaccctgt attgagggct ttcttctcaa agagacattg atgaggagcc cctagagaga 103140
gatgctgtgc tctgggacca gaccccttgt taaacaccag tattcacctc tgccccaact 103200
ttccccaaag aggtacttcc tgccaaggcc tttctctttc ctctcactgg ctggaagtgt 103260
tgagttccac ttcagaacca gaacagagaa cctttccttc tataagagct ataaaccttg 103320
agaacagtct taaaacatag gtatgtaggc cacaccattc accacgaatg tactgatact 103380
catcagaata tggaagaagc accagagagt ttgaagcatc tagagaaaag gtagaaagag 103440
aatgcccttt aactgacctc ctcagtgata gccaatcaca atgatgagtg ttgattcatc 103500
attttggcta ggtggcagaa atatctataa aacagaagct gccatgttgt tttcttccag 103560
tcctcagggc ctacaagaag gcagctatca tttggtatta ctgaaaacat gccccatgtt 103620
cagctcatac ccccaaatta cccattgcta ctgtttatgc tgggctaata tgaagcccag 103680
ggccctaatg tctaggtcta ggcagtaagg cctagagcag tgcctaaaga gcctgagagc 103740
agtgccttcc tttcttcaga gtactcatga aaggatggct gtcagaaaag gaaatgagga 103800
tgggttccag agacttcaga ccaccccaac ttccccagtg agaccctggc acctccccat 103860
accctctcac ctagcgggcc ctgtctatag agcagagaat gaaacagagc actcatctag 103920
aggtagtgtg tcagcaagcc caggcactgc accacagtaa tagcagccat atcagatggg 103980
aaaggagttc aagtgaacaa acaagcaaat tcaatagtca gatagattag attatacttg 104040
atgcttcctc tgagttttac aaatatgggt cactaaattg ttattttcag aaaacagggg 104100
aaatgctcaa tcacattgtg aaagggaaga ttttgctgtc atatcataca tcccacatgg 104160
gagctttctg cagaagttag agctgaagga gggaggcagg cagaagggca actggcaggg 104220
ctgcctggga ggagctctgc aatgaggtgg atcctgtgcc atttgagaac agggaagaaa 104280
agaaatgagg ttttggggag ggaatcaccc aactcacaga acacacagaa atccagcaag 104340
gtttcaaaac gctctacacc ttagagtctg ttaagttagg gaaactctgt gagctcatag 104400
ggccaaatgc acttgcctgc ttgaaatatg aaaaatcagc aatggattcc ttgaaaaaca 104460
atgaaaaggg aaccttctga gccccttggt tattttgaca tatggaccat agatttcagt 104520
cctgagccct ttgaaggtag gagaaggtgg tttagaaaac acacacacac acgcacacaa 104580
acacacacca gaatgaagca aaaaaaaaat tactggtgtt ttctttctcc tcccatctgt 104640
gaagctgttg gattgatttt actgccatca ttatccctgt ttgaaggcag ggggctgtct 104700
tattacccaa agaggacatt tattgatttg gttttctttt tccattttta caatgcatct 104760
ttatcgccca tatggccttt ctggaggtgg ttttcagtct ggcttgttga aacatcaaat 104820
tatacctgtc ttagagaaaa tagaaacaaa aatctttctc ttccttactt gcttgttgta 104880
gtcagttaac tcggactgag tattcagagt cttgattatc acttaattca tagtttcata 104940
aatctctgga atgggcatag gtacaggact taaaagcctg gcatctcaga cagaaatatg 105000
tttttagctt tggtggttta taacagatgg gacttttagg ctgtcattgg tgcagggctc 105060
agcacagagt cagttgtaat ctggacaggt tttgttgttg aggaagagtg ggaagaggga 105120
gtcctacatt ttctccttgt cagtaatgtt ggagaattgg ggtgagggtg aggctgggca 105180
gggagggtct gcatagaaaa aagggtgcgg tgagaaaaaa taatgctact aagccatgag 105240
ggtaaaatga ccaaattctg gttgagagaa acttggtcaa agtgtgtatg gggagagaaa 105300
gttggtcaaa gtctgtgtct gagtgcttgg tgggatgaac tctgggttag aaacaggcat 105360
ggagggaaat agttggttta tggagtgggt aggatgagtg gggtggtgaa agggaaggca 105420
ttttggatgc taagagacca ggaagtcaaa gcaaggcaat acacataaac agaggtaagg 105480
gctcagagag gttttagttg tgtagacttg gataagaaat tttccctttt ggacctcagt 105540
tttccttgtt tgtaaaacaa cggacttgaa ctagatattt taaaatgtgc ttccagctta 105600
gacattttgt gaccgttcta caaattacaa acataatcat catcatttca gcaaactcac 105660
atgtatttat acctgcataa gtttttggtc ttgctttcct agaaggtgac taatcccaga 105720
tcctaatcaa ttaaagaagc aatcttcaga tggggataga gccagctgag agagtgtact 105780
atggatggag tgagttaaaa ctcaggactc agattttctc cttgtgatca ttgctgggta 105840
acttcctttc ttttctattt tctcatctgg aaaatcagga tatgaatccc catctctacc 105900
tcattatgtt tcaaagaggg ttaattaatc catcatgtgc attatgtgct caagaattta 105960
ctatttttca gacattttct agtaaaacat tgaagattat atgtccattt gttttgtaca 106020
catggagtgc tgtttggtac acatcataaa attgaaactg tagtttacat tctgaactca 106080
aagaattaca ccatcctcac tgatgtttac aataggtccc aatttagttt ctttagcaaa 106140
ttttatgtaa gtatggcttt gattctctct ctcactccag gtttttgtta gggaagaaat 106200
gcaagtgaac cctcattgaa ctctttctgt cctttaaatc cattctttcc cacctcaact 106260
catgtggaat tgaatgttgc ctctagtttg gagtctagca gagagttttt ggtgcatatc 106320
agtgtcccct tcactccctg acttttcaag taacatttcc cagaggcaaa ttaactctgc 106380
taagaggatc tgcttgcagc ttcaacagag ccttcatcag gtatctttgg ccaaggagtt 106440
gactgatcct gactttgcga gtcctagaga tcttttcaca aagctcctct catgtttctg 106500
cctctgattt tcttaaatgt cacagacaga ctttagattt aggggttggt taactttttt 106560
tgtaaagggc catgtagtaa atattttagg ctttgtagat catatggtct ctgtgtcaac 106620
tactcaactc tgcctttgta ggatgaaagc agccatagac aatactggaa ctaatgggag 106680
tagctgtgtt ccaataaaac tttatgggca ctgaaatttg aatttcactt aattttcaca 106740
tgtcgtttaa tattattttt ctttttacc atttaaaaat ttagaaatca ttcttagctc 106800
tttgggcctc acaaaaacag atggtagagt ggatttggtt tatgggctgc agtttgttga 106860
cctgtgcttt agctaatcac ttctgtactt ataaatctgc ataggtttta tgtttttcca 106920
tctcttggta tcttagtagg ccagtcaaag tttgaacaac ttgttagcac agaatacctg 106980
gcctagtggc ttcttggtcc tgagcttatt tactaaacaa gagaaaaaat aaataagtct 107040
agaaatgcta gaagaggata cttttttgtt ttaatgatct agtagatcac tcctccttgc 107100
aatacccaga ggagaaactg aaaatatttc aaacattttc tagacttctg tgttgtaaat 107160
ttgtggataa ctatgaacta tatatgaatg aacttttctg gatgacacat atattccaga 107220
tggtaaaaag gaagggcttt ggggactctc tggtaccaag tgtcatggaa aaactgtgtg 107280
tctcatagaa agtagatccc aggaggccag cagagttgtg gatctgccat atattacctc 107340
atgattctgt cttcgcacac tcaccggctt aattctgggc ctccccataa cacgactaga 107400
ccacaggctt gcagaagaaa taatttagct ctgtaactca ttgaagttgg tgcccaccca 107460
agtctctgtc agtgcccaat tcgggagcca tgccaagaat ttgccattgc tgcttcatgg 107520
tggccttgtg cctgcttatt tatagcctgt gcattttatg aaacagggat taataagaag 107580
ttgccatagc acttgcacca ttatgtaaat atctgtaatg cttacataac ttttgtcact 107640
tgcaagacct tttgagtcca ttgccttctg ctaccatgcc ttaccaattt cctagtccct 107700
tattattatt tttcaattca ttatatttaa cttctgtgat acacgttcag aatatgcagg 107760
tttcttatat aggtatacac gtgccgtggt ggtgtgctgc aaccaacaac ccgtcatcta 107820
cattaggtat ttctcctaat gctatccctc cactagccca ccaccccta ataagcccca 107880 gtgtgtgatg ttcccctccc tgtgtccatg tgttctcatt gttcaactcc cacttatgag 107940
tgagaacatg cagtgtttgg ttttctgttc ctgtgtttgt ttctgagaa tgatggtttc 108000 cagcttcatc cgtgtccctg caaaggacat gaactcatcc tttttatga ctgcatagta 108060 ttccatggtg tatatgtgcc acattttctt tatccagtat atcattgatg ggcatttcgg 108120
ttggttccaa gtctgtgcta ttgtgaatag tgctgcaata aacatacgta tgcatgcgtc 108180
tttatagaag aatgacttat aatcctttgg gtatataccc agtaatggga tggctgggtc 108240
aaatggcatt tcaggttcta gatccttgag gaatctccac actgtcttcc acaatggttg 108300
aactgattta cacccccacc aacaatgtaa aagtgttcct atttctccat attctctcca 108360
gcatctgttg tttcctgact ttttaatgat cgccattcta actggcattg acatggtatc 108420
tcactgtggt tttgatttgc atttccctaa tgaccagtga tgataagctt tttttcatat 108480
gtttgttggc cgcataaatg tcttcttttg agaagtgtct gttcatatcc ttcacccact 108540
ttctggtgtg gttggttatt tttttcttgt aaatttgttt aagttccttg tagattctgg 108600
atattagccc tttgtcagat ggatagattg cgaaaatttt ctctcattct gtaggttggt 108660
tgttcactct gatgatagtt tcttttgctg tgcagaagct ctttagttta attagatttc 108720
atttgtcaat tttggctttt gttgccattg cttttggtgt tttagccatg aagactttgc 108780
ccattcacaa ttgctacaaa gagaataaaa tacctaggaa tacaactcac aagggatgtg 108840
aaggacctct tcaaggagaa ctacaaacca ctgctcaagg caataagaga ggacacaaac 108900
aaaaggagaa acattccatg ctcatggata ggaacaatca atatcgtgaa aattgccata 108960
ctgcccaaag taaattatag attcaatgct atccccatta agctaccatt gactttcttc 109020
acagaattag aaaatactac tttaaatttc atatggaacc aaaaagagcc catataccca 109080
agacaattct aagcaaaaag aataaagctg gaggtatcaa gctacctgac ttcaaactat 109140
actacaaggc tacagtaacc cttatcaatt ttttatgtgc ctctccatat tctgcagtca 109200
gaagcttctt cagtcctttc agggaattgc tgggtgacta tcaaactctg gtagttcatt 109260
tttgcagttg gctgctgttg tgaggataag agttagactc actttctctt cagagataga 109320
aattatgtat taattctctg ggttctagac ccacagcaag gagcatactg ctcctcaaaa 109380
taactgaatt ctgcgagaag ccatcattgt aaaacaacaa tatcttcagt tatagtagcc 109440
atgtgtgcaa cttctggaaa ctgttattca gattttcatg ttccttccct gtctcttcat 109500
agctaggcag ctgctttcag ccttgtacag atgctagtga gctttctacc tacaaacctg 109560
cagaaaattg aactgagatt tggaggtgaa agactcttga taaagggaac aaggtttaga 109620
attctcagtc cctttgctcc caggctgtgt tgtgactact gaggcactcc agtgaaatca 109680
ctattcctcc tatctagact aatgcctgtc tctgcagagc acctcataag aacaggcctg 109740
gtagtaatat cctcatgcat tcagtcagta aatatttaca gagtgcttac tacatatagg 109800
gtattgggct gacatatgca agatacaggg cctgcttcca ggaggttata gcttattgat 109860
cataaatgtg gcattttttt tttttgagac ggagtcttgc tctgtctgtc acccaggctg 109920
gagtgcagtg gcacgatctc ggctcactgc aacctccacc tcccaggttc atgtgatttt 109980
cctgcctcac cctcctgagc agctgagact acaggggctc atcaccacac ccagcttttt 110040
tttttttttc tgtattttta gtagagacag ggtttcacca tattggccag gctggtctcg 110100

-continued aactcctgac ctcgtgatcc acccacctca gcctcccaaa gtgctgggat tacaggcgtg 110160
aaaatgtggc aatctttaaa gctcttcagt ggatgaaagg ccaccctatc tgctgtcctt 110220
ttgaacttcg caactttctt ggtacagagt gagaggttat tctcttggtt ttccatataa 110280
gtaaactgag gctttgccag ttcatcaaca ggtagtaaat aatatatttg gaatttgaac 110340
ccaagtcttc tggggtcaaa ggcagcattc actctgctct gtcacagcag ctcctcaaat 110400
aagccaacat agaaaccaag tactatgcct aggcaacaag aaaggcagca atgaagagca 110460
acagcagagt caaatatgag agaaggaagt taagaaagat gttaagtact gtggggagta 110520
actgagaaac caccaagtat cgctaacatc acagggaact tgtcttccta agaaaattcc 110580
aagcacttaa aaccgctggt agttcatcag caactctctt cattagatgt gcgagggaca 110640
tgtgggccat agtccttcta ctaacttata ttcttcaggg gaaagttctg attctgatga 110700
gacccagcat ggtagctctt aattcactgt tgtcacacga ctatagaaca ggaagcacaa 110760
cttaacacct gtgctcatga gaattttgct ccttatgacc aagctaaaga aagagcttag 110820
acaggatgtg tggctataaa tgtagattaa tggttccttg gctctttggt ttgagccttc 110880
tcagcagagc atcccacgga gtgttttcca tggggccacg agcaagagaa atccacttcc 110940
ctcctcctca atgtcagaaa atagagaata ttgtctttca ggatagaatt aaaaagtcat 111000
agaggcagca acttgttttc ctatattagg gttttaaaat tctgtttttc cttcctctcc 111060
tgggtcagat cattgtgtgg atggaccttg atttcattgt ggtatctgta tgtggaccct 111120
gaagaccatg gacttctaac aattccttaa gttacataag cacattccta caggtcacaa 111180
gctcatttac ttacaggatg gttgatttgg tcacaggtta tttcatgaaa atacttaaaa 111240
gatttgcagt gttcaaaact gcagtatctt taaacactaa aacttgaagg aagggaattt 111300
agaaatcaaa aaatctggtc aaaccatttc atggaaaagg aaagtgaggc tcagagagag 111360
gaaattactt tcctgggttt gtatagccta taaatggcag aaatgagagc ctccctgcca 111420
tttctagttt tctgtctgag agactctcct gcctaatagc taattagcag agtcacagag 111480
gtcattacct tgcaattctc aagaattatg tgaggcagca tagtaagcat ttatggccct 111540
tggttcctag aaggagctta gtccctgata gtcatctctg cctttgccat tgtgtgagac 111600
tgtcttctgt aactgtatgt cttcctccct agtaagttaa tgagtaataa aggtattcta 111660
tagtgagagg actctgtaag acatttcttg gtgtgaggat tgttccaagg ttgttttgtg 111720
tgtatgtgca tgtataaact tttttaggga gcatattcat agcttttaca tggatctcag 111780
aggctctata acccagagaa gattacagaa taccagtctt gtctttggta aggattttat 111840
agacccatcc tgactacagt gatatccaac atggctatgt aatgactggc actttcccca 111900
cataacatat atttattcca cactcagtgc ctactgtgta catgagacct ataccgggca 111960
ctgggataag agacatgaaa taacagctaa aattgtttat tgagcagtca gtatgcatta 112020
gatgctttgt agtcattttc ttattcaatc tgtataccct caatttacaa atgaggaaac 112080
tgaggcacag aagagttgag tgatttgccc aaagtcatac aaatagtcag tggctatgtg 112140
atgaatagtt accaacataa aagagtgaga ttactgctgt actaaaagta ggtacataat 112200
cccctgagca gacagtatga gagaatgatt tattttacct ggaaagttta ggaaggcttc 112260
acagaggagt taagggttga tctgggtctt gagggatgga taagagtttg ccagatacaa 112320
aaaggtagga agagaacttc aggaggaggg aacaggctga gcaaagacac ggcgatgtga 112380
aagtgggagg cttgtttggg gaacattatg gaatctggag gttattgtgg ggaatctcat 112440
cagatgcagc aagctgtttg acaggccttc agttggctct ttgtaccttg ctccctccgc 112500
atgctgagct gtccatagct gccctaggct ggtgtctggg attttcggaa gaaggttact 112560
atccaggtag tgtaacaaga tgcagtgcaa aagcaccaga ttggggctct ggctctgctg 112620
ctgacttacc acctggcctt aagcatgtct agttccctct ttgtacatta aaatctccat 112680
tggaacagta acatggttgt attaaatgat cttgaagatt ttacctgcac gttttgcaca 112740
tgtaccctaa aacttaaagt ataataaaaa aattaaaata aaaaataaaa atataacaat 112800
ataaatcttt aacaataatt ttagtagtaa atctctacaa ttttacagat aatccagatg 112860
catccattgg ccaatggttc actttgtatg cataatattt gggaaacagg cagacccaat 112920
ttcaatcctt agttgtaaga cttaatacat atgtgatctc gagcaaatca cttttgtatg 112980
cctctataag gataataata gctcacagaa ttattttaag aactaaatga tgtgtaataa 113040
agctactggt actcagtaag ttttgtatcc ttttcctaga gtgagtcttg gtcataggca 113100
tgcgtatact tgcagcgtcc ctgggtaggc cgaaagagca aataagagat ggtatctatg 113160
gtattcccca ggtaaaggag gccttgggtt ggcataagat ttcacttctc tttagagtta 113220
cttaattagg gaccagaaag gccatcagca tttgtatgag aatataacaa aggtcaatct 113280
cttcctcttt actttttacc tcccagtaca ctgtgagtaa cattccccag ccagcccagc 113340
cagcacgtgt tcattgcctc tcttgacttc cagactttgg acttgaaggt gtcagagctc 113400
tctgtgtatc tttgtcccca acaagataag tctgacctcc ccagcaaatt caagtcctaa 113460
gccactgtcc aggagaaaag ctagcaaggt cataaattat tctccatatt ttccagccat 113520
tggtttccct tgtccagcca gaggtgtgtc tcaaagtatg ctgaggccag attcaataga 113580
aacctgagcc agcacctgtg taaataattt ttaaagctcc ttttcctgaa gctggatgaa 113640
tatttttaaa aactaagctg gattgtcttt tatctagcat gccgtctcct acattcctag 113700
tgctatggac ctcttggagg aatgtggttt ggttatagtg gtattgtctt gtctgttgtg 113760
ggggagggag acatttcttt cagaagcaag gtaatacttt ggtctggtct atgactctat 113820
tttgtttaaa atgaaactat ggcagtatag tggtattcat tctgcttccc ataggttaac 113880
tttacatccc tctgtcttca cccactcttc agttctgatt cttttaaaag cagccaacca 113940
aaaccagcaa gtacatactg cttatctctg acttccacca gaatcaactt cagatcttgt 114000
ccaaagctcc atctgaagag aggggaataa cacccagcca agagccctca gggcccatca 114060
gtaagtagac atcctgtcct tgaggttcct taactctgct cagcttcaga atacagaagg 114120
ggttggttct tcatttgtgt tgtttataac taaaagcctc ctactcccca ctttttgca 114180
tagcttcttc tgccatccca cctgtgtagc ctcttcaact cccccaaaac tcctctgtag 114240
cccatgtcac ttggaaagag ttttctttgt ctcttttgca acttgacaat gactagccag 114300
caagtttaag ttcaaattat tgttccatgg gagcagagat agatatagga aacaaaaaaa 114360
agggatatgg aggtatagag tgatttccca cctacctagt gagcactact gagatattca 114420
agtactctct acccaagaat tctattgata taaaggtaaa aaacttgatc ttaggtctaa 114480
tatccgttag tagtgtgacc ttgggaaaat gataccaccc ccaaaggctt agttttctta 114540
actgtaaaat aggcatacag atgaccaccc ccagaggatt cataaggata acatgagata 114600
aggcaacttg aaatttccta gcatagtgat agactttcga aaataaaatg aatcaaacac 114660
tgataacagt acttcctagt acacaaatga gaaatcagtc cctcatcaaa ttacagcaca 114720
ttttcaatgc tccaattatg tcactgtaga aatgctaatg tggattaaat aatttgtctg 114780
ttgctattta tacggataat ttgatagtag ttatttttgg acatggatag ctttgaagcc 114840
ttacagatga gtccatcccc aagtacccaa aactaaagaa agttggctag agtgatgaca 114900
aggtggcagc acagagctcc ctgcgttctg ggccctgtcc cctagctaga gagaactcca 114960
ggctataagc atttgtattc tcatagtcca atggcaggga agaagggctg gaggtgagta 115020
gttttcactc atttattttt tcaacaagca tgtatggtat caggccttgt atgcatccag 115080
agacaaatgt gaactagccg tgtcctcaag gagattccag tctggtgggc ctgccttcca 115140
aggtcagttg cagctttagc actataaaga gcacctacct gcggcagata caatgtgatg 115200
ggacatgaca gagaaaaaat ctataagcag agcctcccca ttcccaggca ttgaaacaat 115260
cctaaccaag actggcatag tacaatgagc ctgtccctat cagcaggttt ggaagcctta 115320
acaacaacaa caaaaacaat aataatggtg atgataatca tagagcctaa tgttaccaaa 115380
cattttccat gtgttaagta ctatactaag tgcatactta atcctcacaa caatgctata 115440
agatagtaga tactcttact actaccctga ttttacaaat gtggaaactg aggcacagaa 115500
gactaagaga acaggaatac acctaattca cctcagttca acaaacatca agcatctgtt 115560
ttatgtcagg cctcgtgctg gatggcaggg agagagagat gagtaaagca tagtttcagt 115620
ccagtgggag caaatgacag cacacagtgg ggcaggtata ttgcagccct tctgcttgat 115680
gctaagaact cagtgtcagt gatgaatgaa acacagtcat tctctcaaag atcttaaagc 115740
ttagtaggag atatctgtgt ggaaacaaaa attaaatact gctgtgataa gtgtcataag 115800
agataagtgg aaaatgagag agagagatca ctgtagcaat tgattggttt aaatcaaagc 115860
ccccaaaaaa atgttattga gaattataaa acaactaatt gatttaaatc aaagcccaaa 115920
cagaagtgtt tgctaatttt atttcaattt ggttgataat ttggttgaaa tgaatttatt 115980
tcatttttta ttccatcctt acaatggaag attagtgctt gtttcccacc caaggatacc 116040
aggatatttc aggggctgta ttacaatata gttaaattat tcctttatct caaagcacat 116100
ccacactttc ccctatcctt acctttactc agggtatctc ttctgcctca ggtgcttttt 116160
ctccacattt ccatattctt aagtcctacc ttccttcagg gcctcactca aatgcctcct 116220
cctccatgaa gcattcaccc gactgaaagg taccccgccc tctcctgtac tccacatcac 116280
ttcatgggtg tctccacttc ctgctttatc tttcagtaat acacttacag ttctctttcc 116340
tccactagac tgagctcttc agaggaagac tcacttggct gaaaccatga ttttacttta 116400
aacacattga aaacctctac tggagtgcat tgtgtctggt gggcttcaac cttaattctt 116460
aagtatgtga aaacacatca cctatctgga ggtttacact ttctgctaat gactttattt 116520
ttaagcccac caccctaaca caacaaatac ttaaaacttg tcttcatttc ctttaggtct 116580
ggccctcatg catgcatata atttatagag tcactgtttt gctcggttgt cctcatgcct 116640
ctatattatt ggaggtttag attgtttcca tatactcagg ttgtattcat gtcctttttt 116700
tctttttaaa tttccttagc atccatttcc accattggaa attcagggtc aaaacagggg 116760
tttgggattg gagcatgtct atcacagata accaatcatg tgttatgact taagaattta 116820
tgaaagggcc ctctacctga agatatcttg ctactgatgc tgtctcacag tgtctgaaac 116880
tcccatcata tgtggaattg ttttggaagg ctttgcctcc tgggacacat tcagccataa 116940
tcaagaaata gtattgagca ttagactgtc agtatgtcca ttagcaagac tgtggaggaa 117000
tggaatcacc aatattatat tttatagggg atacagaata caagagaagt tctgaagaga 117060
aaattcttat gtagaatagg aaggcttaga tacagcatga aagctgcagg ctttgaggag 117120
ccagaggtca aatgaaagca ttgagtattt gtttagatga aagaacagaa agggaaaaag 117180

-continued aagcagagga agggatagta gagagaaatg tataagtttt atccatttaa cttgtaattg 117240
tgtttggcta tgggcacaat agaagcagtg agatcacttt attttatttt attctttata 117300
gacagggtct tgctatgttg cccaggctgc agtgtgcagc tcttcacaag tgtgatcata 117360
gcgtactaca ccctcaaact cctggactca agcaatcctc ccatctcagc ctcctgagta 117420
gctgggacta caagtgcaca ccaccacgcc cagtgagatc acttgaaact agggagagat 117480
gtgtgagttc tgggcaacca gtagttggct ttacatagaa ctgtaggggt caaggccaaa 117540
ggggacgtcc tgttccaagt caccttcttt ggacattaga aaaccacgag gggtttggaa 117600
atcagaaaac cagcagaggc aggaaaactc agggcagcat gggagattca gtatatacaa 117660
aaaggttcac accagtaatc aaacagaatt ttaactgctg atgtggagta gaggcagctt 117720
tgtctgctgt gtgataacca aacctttacg aatagtaggt gtatatgggg aattggaggg 117780
agataggtgg ctgtgtttag taattggttg acttcactga gatggtttgg ggattgtggc 117840
ttccagatga tcagattttc ttttttaggt agagactcca acatcattac agaactataa 117900
attacatgtg gaaaagaaag gcctcctatg ttagaataga aaataaaatg ctgtggggtt 117960
gagggacaga ggtgctgtct aggaagtcag atagcgtttt ccagttctgt ccctcagagt 118020
tccttgtcct cattgagact caatttctct tacttttttt tttatacttt aagttttagg 118080
gtacatgtgc acaacatgca ggtttgttac atatgtatac atgtgccatg ttggtgtgct 118140
gcacccatta actcatcatt taacattagg tatatctcct aatgctatcc ttcccctctc 118200
ccctctcccc accacaggcc ctagtgtgtg atgttcccct tcctgtgtcc atgtgttctc 118260
attgttcaat tctcacctgt gagtgagaac atgcggtgtt tggttttttg tccttgtgat 118320
agtttgctga gaatgatggt ttccagcttc atccatgtcc ctacaaagga catgaactct 118380
tcatttttta tggctgcgta gtattccatg gtatatatgt gccacatttt cttaatccag 118440
tttatcattg atggacattt gggttggttc caaggctttg ctattgtgaa tagtgccatg 118500
ataaacatac gtgtgcatgt gtctttatag cagcatgatt tataatcctt agggtatata 118560
cccagtaatg ggatggctgg gtcaaatggt atttctagtt ctagatccct gaggaatcgc 118620
cacactgact tccacaatgg ttcaactagt ttacagtccc accaacagtg taaaagggtt 118680
cctatttctc cacgtcctct ccagcacctg ttgtttcctg actttttaat gatcaccatt 118740
ctaattggtg tgagatggta tctcgtggtt ttgatttgca tttctctgat ggccagtgat 118800
gatgagcatt ttttcatgtg tctgttggct gtgtaaatgt cttctttgag acgtgtctgt 118860
tcatatcctt tgcccacttt ttgatagggt tgtttgtttt tttcttgtaa atttgtttga 118920
gttctttgta gattctggat attacccttt gtcagatgag tagattgcaa aagttttctc 118980
ccattctgta ggttgcctgt tcactctgat ggtagtttct tttgctatgc agaagttctt 119040
tagttgaatt agatcccatt tgtcaatttt ggcttttgtt gccattgctt ttggtgtttt 119100
agacatgaag tccttgccca tgcctatgtc ctgaatggta ttgcgtaggt tttcttctag 119160
ggtttttatg gttttaggtc taacatgtaa gtctttaatc catcttgaat taattttagt 119220
ataaggtgta aggaagggat ccagtttcag ctgtctacat atggctagcc agttttccca 119280
acaccattta ttaaataggg aatcctttcc ccatttcttg tttttgtcag gtttgtcaaa 119340
gatcagatgg ttgtatatat gcggcattat ttctcagggc tctgttctgt tccattggtc 119400
tatatctctg ttttggtacc agtaccatgc tgttttggct actgtagcct tgtagtatag 119460
tttgaagtca gatagcgtga tgcctccagc tctgttcttt tggcttaggg ttgacttggc 119520
gattcaggct ctttttttggt tccatatgaa ctttaaagta gtttttttcca tttctgtgaa 119580 gaaagtcatg ggtagcttga tgaggatggc attgaatcta taaattacct tgggcagtat 119640
ggccattttc acaatattga ttcttcctac ccatgagcat ggaatgttct tccatttgtt 119700
tgtatcttct tttatttcat tgagcagtgg tttgtagttc tccttgaaga ggtccttcaa 119760
gtcccttgta agttggattc ctaggtattt tattctctta gaagcaattg caaatgggag 119820
ttcactcatg atttggctct ctgttttctg ttattggtgc ataagaatgc ttgtgatttt 119880
tgcacattga ttttgtatcc tgagactttg ctgaagttgc ttatcagctt aaggagattt 119940
tgggttgaga cgatggggtt ttctaggtat acaatcatgt catctgcaaa cagagacaat 120000
ttgacttcct cttttcctaa ttgaatgccc tttatttcct tctcctgcct gattgccctg 120060
gccagaactt ccaacagtat gttgaatagg agtggtgaga gagggcatcc ctgtcttgtg 120120
ccagttttca aagggaatgc ttccagtttt tgcccattca gtatgatatt ggctgtgggt 120180
ttgtcataga tagctcttat tattttgaga tacgtcccat caataactaa tttattgaga 120240
gtttttagca tgaagcgctg ttgaattttg ttaaaggcct tttctgcatc tattgagata 120300
atcatgtggt tttgtcgtt ggttctgttt atatgctgga ttatgtttat tgatttgcgt 120360
atattgaacc agccttgcat cccagggatg aagcccactt gatcatagtg gatacgcttt 120420
ttgctggtat tttattgagg atttttgcat caatgtttat cagggatatc ggtctaaaat 120480
tctctttttt gttgtgtctc tgcctggctt tggtatcagg atgatgttgg cctcctaaaa 120540
tgagttaggg aggattccct ctttttctat ttattggaat agtttcagaa ggaagggtac 120600
cagctcctcc ttgtacctct ggtaggattc agctgtgaat ccatctggtt ctggactttt 120660
tttgattggt aagctattag ttatatcctc aatttcagag cctgttattg gtctattcag 120720
agattcaact tcttcctggt ttagtcttgg gatggtgtat gtgtcgagga atttatccat 120780
ttcttctaga ttttctagtt tatttgcata caggtgttta tagtatgctc tgatggtagt 120840
ttgtacttct gtgggatcgg tgattatatc ccctttatca ttttttattg cgtctatttg 120900
attcttctcc cttttcttct ttattagtct tgctagtggt ctatcaattt tgttgatctt 120960
ttcaaaaaac cagttcctgg attcattgat tttttgaagg gtttttttaca tctctatttc 121020
cttcagttct gctctgatct tagttatttc ttgccttctg ctagcttttg aatgtgtttg 121080
cccttgcttc tctagttctt ttaattgtga tgttagggtt tcaattttgg atctttcctg 121140
ctttctcttg tgggcattta gtgctataaa tttccctctc cacactgctt tgaatgtgtc 121200
ccagagattc tggtatgttg tgtctttgtt ctcattggtt tcaaagaaca tctttatttc 121260
tgccttcatt tcattatgta cctagtagtc attaaggagt aggttgttca gtttccatgt 121320
agttgagcgg ttttgagtga gtttcttaat cctgagttct agtttgattg cactgtagtc 121380
tgagagacag tttgttataa tttctgttct tttacatttg ctgaggagtg ctttacttcc 121440
aactatgtgg tcaattttgg aataggtgtg gtgtggtgct gaaaagaatg tatattctgt 121500
tgatttgggg tggagagttc tgtagatgtc tgttaggtct gcttgacagt ggagtgttaa 121560
agtctcccat tattattgtg tgggagtcta agtctctttg taggtctcta aggacttgct 121620
ttatgaatct gggtgctcct gtattggttg catatatatt taggatagtt agctcttctt 121680
gttgaattga tccctttacc attatgtaat ggccttcttt gtctcttttg atctttgttg 121740
gtttaaagtc tgttttatct gagactagga ttgcaatccc tgcctttttg tgttttccgt 121800
ttgcttgata aatcttcttc catcccttta ttttgagcct atgtgtgtct ctgcatgtta 121860
gacgggtttc ctgaatacag cacactgatg ggtcttgtct ctttatccaa tttgccagtc 121920

```
tgtgtctttt aattggagca tttagcccat ttacatttaa ggttaatatt gttatgtgtg 121980
aatttgatcc tgtcattatg atgttagctg gttattttgc tcgttagttg atgcagtttc 122040
ttcctagcct cgacggtctt tacaatttgg tatgtttttg cagtggctgg taccggttgt 122100
tcctttccat gtttagtgct tccttcagga gctcctgcag tgcaggcctg gtggtgacaa 122160
aatttctcag catttgcttg tctgtaaagg attttatttc tccttcacct atgaaggtta 122220
gtttggctgg atatgaaatt ctggttttaa aattcttttc tttaagaatg ttgaatattg 122280
gcccccactc tcttctggct tgtagagttt ctgctgagag atcagctctt aatctgatgg 122340
gcttcccttt gtggggaacc tgacctgttt ctctggctgc ctttaacatt ttttccttca 122400
tttcaacttt ggtgaatctg acaattatgt gtcttggagt tgctcttctc aaggagtatc 122460
tttgtggtgt tctctgtatt tcctgaattt gaatattggc ctgccttgct agattgggga 122520
agttgtcctg gataatatcc tacagagtgt tttccaactt ggttccattc tccccatcac 122580
tttcaggtac accaatcaga catagatttg gtcttttcac atagtcccat atttcttgga 122640
ggctttgttc atttcttttt attctttttc ctctgaactt ctcgcttcat ttcattcatt 122700
tgatcttcaa tcactgatac cctttcttcc agttgatcta atcggctact gaggcttgtg 122760
catttgtcac gtagttctcg tgctgtgttt ttcagctcca tcaggtcctt taaggacttc 122820
tctgcattgg ttattctagt tagccatttg tctaattttt tttcaaggtt tttaacttct 122880
ttgccatgcg ttcgaacttc ctcctttagc tcagagtagt ttgattgtct gaagccttct 122940
tctctcaact cgtcaaagtc attctccatc cagctttgtt ccattgctgg tgaggagctg 123000
cattcctttg gaggaagaaa ggcactctga tttttagagt ttccggtttt tctgctctgt 123060
tttttcccca tctttgtggt tttatctccc tttggtcttt gaagatggtg atgtacagat 123120
gagcgtttgg tgtggatgtc ctttctgttt gttagttttc cttctgtcag gaccctcagc 123180
tgcaggtctg ttggagtttg ctgcaggtcc actccagacc ctgtttgcct ggttatcagc 123240
agcagaggct gcagaacagt ggatattggt gaacagaaaa tgttgctggt tgatcattcc 123300
tctggaagtt ttgtctcaga ggaataccg gatgtgtgag gtgtcagtct gcccctactt 123360
gggggtgcct cccagttagg ctactcgggg ttcagggaac cacttgagga ggcagtctgt 123420
ccgttctcag atctccagct gcatactggg agaaccacta ctctcttcaa agctgtcaga 123480
cagggacatt taagtctgca gaggtttctg ctgccttttg ttcggctatg ccctgccccc 123540
agaggtggag tctacagagg caggcaggcc tccttgagct gtggtgggct ccacccagtt 123600
cgagcttccc agctgctttg tttacctact caagcttcag caatggcggg cacccctccc 123660
ccagcctcgc tgctgccttg cagtttggtc tcagactgct atactagcaa tgagcgaggc 123720
tctgtgggcg taggaccctc tgagccaggc acaggatata atctcctggt gtgccgtttg 123780
tgaagaccat tgaaaaagtg cagtattatg gtgggagtga cccgattttc caggtgccat 123840
ctgtcacccc tttctttgac taggaaaggg aattctctga tcccttgtgc ttcctgggtg 123900
aggcgatgtc tcgccctgct ttggctcatg ctcggtgcgc tgcacccact gtcctgcacc 123960
caccatttga cactcccctg tgagatgaac ccggtacctc agttggaaat gcagaaatca 124020
cccatcttct gtgttgctca cgctgggagc tgtagactgg agctgttcct attcggccat 124080
cttcacaaaa atcttacttt ggtttctagt gttaccaccc actgttcttt ctcatctcaa 124140
ccctgagtat aagtacagat cacattcctt gggttcttag aaaataatag aaatgaactc 124200
tcattcatca aaatgcccat tagtaaatac tgagggagaa caaactagaa atccagtata 124260
gaaaataaaa ataggattat attccttgga atctcagaaa aaaacaatga agagctttct 124320
```

ttgggcatta gacactttcc cataaggtgg ctgactctct tttagtcatg tcagcttggc 124380
ccaatcttca cttggtagcc cttctttctt cttcattaat ccatctccta tgctcctatg 124440
gggtcctaga gaaatgccca tcatgtacac acacatctaa taacacaaag atcactctcg 124500
actagcaagc ccttttatga tggtgtgagc atttgacacc cttgttgcta gtaacatcag 124560
tgagtgacct gacccatttt tggaacagaa tatgatcagt atgttgcctc aaggaggccc 124620
tcactgttct aggaaatata attccagagt ttgctgactc acaccatgga atatatgcat 124680
aaaatggatc ctgcagataa gcctttctct gactagtttc agacattttt ttctgggtaa 124740
ttttaaagtt attttttatt tttgtgggta caaagtaggt gtatatatgt atgaggtacc 124800
tgaggcattt tgatacaagc atacagtgta taataatcac cagagttaat ggggtatccc 124860
tcaccacaag catttatcct ttctttgtga tacaaacaat ccaattatat tcttttagtt 124920
attttaagat gtataataaa ttattgttga ctgcagtcac cctgttgagc tatcaaatac 124980
tagatcttat tcattctaac tatactttg tacccagtag ccatcccact tcctcccctc 125040
ccactaccct tcccagcctc tgataaccat cattccactc tctatctcta tgagctcaat 125100
tgttttaagt tttagctccc acaaatatgt gagaaaatgc caagtttgtc tttctgtgcc 125160
tggcttattt cacataatat aatgtcctct agttccatcc atgttattgc aaatgacagg 125220
atctctttct tttttatggc ttaatagtac tttattgtat gtatgtacca cattttcttc 125280
atccatttgt ctgttgatag acaagagttg cttccaaata ttgactattg tgaatagtgc 125340
tgcaataaac gtgggaatgc agatctcttt gatatactga ttttctttct ttagggtgta 125400
tacccagcag tgggattgct gggtcatatg atagctctat ttttagtatt ttgtggaacc 125460
tcaaatctat tctacataat ggttttactg acttacatat ccaccaacag tgtatgagga 125520
tactcttttc tccacatcct caccagcatt cattactgcc tgttctttgg atgaaagcca 125580
ttttaactgt ggtgaaatga gatctcattg ttgttttgat gtgcacttct ctgatgatca 125640
gtgaggttga ggaccttgtc atatatctgt ttgtcatttg tatgttttat tttgagagat 125700
gtctacccag atcttttgcc catttttttaa tcagattgtt agattttttt tttcctacag 125760
agtgcttgag ctctttatat gccctagtta ctagtccctg gtcagatggg tagtttgcaa 125820
atagttgctc tcattctgtg ggttgtctct tcactttgtt gatcgaatca cttgctgtgc 125880
agaaggtttt taacttgatg tgacctcatt tgtccatttt tagttgcctg tgctggtgcg 125940
gtattactca agaaattttt gcccagatta atgttctgga gagtttcccc aatgttttct 126000
tgaagtagtt tcatggattg atgtcttaga tttaagtctt taatatgttt tgattttatt 126060
tttgtatttg ctgagagata gggctctagt ttccttctgc atatggatat ccagtttttc 126120
tagcaccttt tgttaaagag actattcatt ctctaatata cgttcttggc acctttgttg 126180
aaaataagtt cactgtagat gtatggactt gtttctgggt tctctgttct gttccattgg 126240
tctatgtgtc tgcttttatg tgaataccat gttgttttgg ttgcaaaagc tctgtagtat 126300
aatttgaaat caggtaatgt gattcttcca gttttgctct gttcttttttc ctcaagatag 126360
ctttgcctat cctgggtctc ttgtggttct atataaattt taggattatt ttttctattt 126420
atgtcaagaa tgtcattgat attttgatat aaattgcgtt gaatctgtag atagcttcag 126480
gtagtgtgga cattttaaca atatcaattc ttgaaatcca cgaacatgga atatccttct 126540
attatttgga tgtcttcttc aatttcttat attaattttt ttttagtttt cattgtagag 126600
atatttcatt tatttgacta agtttattgc taggtatttt attttatttt tacctattga 126660

-continued

```
caatgggatt gctttcttga tttctttttt agattgttca ctgttggcat acagaaatgc 126720
tactgatttt tatgtgatga ttttgtatcc cgcaacttta ctgaatttgt ttatcagttc 126780
taataggctt ttggtgcaga ctttaggctt ttccaaatat aagatcatat tatctgcaaa 126840
caagaataat ttgacttctt tcttttcaat ttggatgcct ttcatttctt tctcttgtct 126900
gattgctcta actaggactt ccagtactct gttgaataac agtggggaaa gttaacatcc 126960
ttgttttgtt tcagatctta tagccaaggc cttcagtttt tctgaattta gtatgatact 127020
agctatgggt ctgtcatata tggcttttat tatgttgaag tatgttccct agtttttga 127080
aggtttttat attttaagga agataaaaat tgaactttat caaatgcttt tcatgcaaca 127140
attgaaatga tcaagtgctt tttgtctttc attctgttga tacgatgtat cacactgatt 127200
gacttgtgta tttagaacca tccttgcatc ccgtggtaaa tcccacttag tcatggtgaa 127260
tgaacttttt aatgtgttgt tgaattcagt ttgctagtat tttgttgggg atttttgcat 127320
cagtgtttat cagggatatt ggcctatagt tttccttttt tttatgtgtc ttttgggttt 127380
tgttatcagg gtaatactgg ccttgtagaa tgagtttgga atgattctct cctctatttt 127440
ttgaaatact ttgaatagga ttgatgttac ttctttaaat gtttggtaaa attctgcact 127500
gaagccattg ggtcctgggc tttttactgc tggggagact tttcattaca gcttcaatct 127560
tattacttgt tattggtctg ttcaggcttt agattttttt catgaatcaa tcttcacaag 127620
ttgtctgttt ctcaaaattt atcaatttct tctaggtttt ccaatgtatt gtcatccagt 127680
tgctcataat gccctctaat gatgccttga atttttgcag taaccactgt aatgtttcct 127740
tttttaatct ctgattttat ttgagctttc tcttttttc ttagtctagc taaatatttg 127800
tcaatgttgt ttgttcatcc acaaaaccaa cttttcattt cactgatctt ttgtattatt 127860
ttttcctttt aattttattt atttctattc tgatatttat catttcattt cttccagtta 127920
tttgagtttg gtttgctctt gcttttccag ttctttaaga tgcattgtta ggttatttat 127980
ttgaactttt ttgatatagg tgcatattgc tataaacttt caccataata ttgcttttgc 128040
tgtatcccat aggttttagt atgttgttta gtatgtttcc aatttggtac atttcaataa 128100
atttttaaat tttcttcttt atttattgac atagtcattc cagagtatac tgtttaattt 128160
ccatgtggtt tgtatagttt ccaaaattcc tcttgttatt gatttctagt tttattccat 128220
tgtggtcaga gaagaagctt gatatgaatg caattgttaa taattttttt aaaacttgtt 128280
ttgtgaccta agatatgatc tgtcattgag aatgatccat atgctgagga aagaatgtat 128340
attctgcagc cattggataa aattgtcttt aaatatctat taggtccatt taagacataa 128400
tgcagattaa agccgatgtt tcattgttca tttttctgtc tggatgatct cttcagtgct 128460
gaaagtggtg tgttaaaatc tctaaatatt attgttttgg gatctttctc ttctttcaac 128520
tctgataata tttgctttag atacctgggt gctccagtgt tgggtgcata tatacttaaa 128580
attgttgtat cctcctgatg aattgacccc tttatcatta tataatgacc ttctttttct 128640
ctttgtgtag tgtttgtctt gaaatctatt ttgtcggata ttagtattgc tgctaatttt 128700
tttggtttcc atttgcatga aatatctttt tcattccttt attttcaggc agcgtgtttc 128760
tttatattta ataggtgaaa tatgtttctt gtaaataaaa attattattt taaaatattt 128820
ttaaaataat actatttttt aataagaaca attattattt tttaaaaaat ttcattagtt 128880
ttgggggcac aagtggattt tggttaaatg ggtgagttct ttagtagtgg attttgagat 128940
tttagtgcag cagccacctg agaagtgtac attacccata tattatatat atactatata 129000
tgctttatat atatagtgtg tatatataat atatatacaa ctacatattg ggtaatgtac 129060
```

acttctcagg tgactgctgc actaaaatct caaaatccac tactaaagaa ctcacccatt 129120
taaccaaaat ccacttgtgc ccccaaaact aatgaaattt tttaaaaaat aataattgtt 129180
cttattaaaa aatagtatta ttttaaaaat attttaaaat aataattttt atttacaaga 129240
aacataattc acctattaaa tataaagaaa cacgctgcct gaaagtaaag gaatgaaaaa 129300
gatatttcat gcaaatggaa accaaaaaaa ttagcagcta tactaatata ttatatatat 129360
actacataaa gcatatatat agtatagtat atatataata catttataaa gcatatatat 129420
agtatgtaga taatatatgt ttatatactt taagttctgg gatacatgtg cagaacgtgc 129480
aggtttctta cataggtata ctcgtgccat ggtggtttgc tgcacccatc aacctgccat 129540
atacattaag tatttctcct aatgctatct ttcccctagc cctaccccac tccctgacag 129600
gccctggtgt atgatgttcc cctccctgtg tccatgtgtt ctcattgttc aactgccact 129660
tatgagtgag aacatgtggt gtttggtttt ctgttcttgt gttttagttt gctgaggatg 129720
atggtttcca gcttcatcca tgtccctgca aaggacatga actcatcctt tttgatggct 129780
gcatagtatt ccatggtgta tatgtgccac gttttcttta tccagtatat cattgatggg 129840
cattttggtt ggttccaagt ctttgctatt gtgaatagtg ctgcaataaa catacgtgtg 129900
catttgtctt tatagaagaa tgatttataa tcttttgggt atatacccag taatgggatt 129960
gctgagtcaa atgatatttc tggttctaga tccttaatga attgccacac tgtcttccac 130020
aatggttgaa ctaatttatg ctcccaccaa cagtgtaaaa gcgttcctat ttcttcaaat 130080
cctcaccagc atctgttgtt tcctgacttt ttaatcgcca ttctaactgg catgagatgg 130140
tatctcattg tggttttgat ttgcatttct ctaatgacca gtgatgatga gctttttttc 130200
atgtttgttg gcagcataaa tgtcttcttt tgagaagtgt ctgttcatat tcttcaccca 130260
ctttttgatg gagttatttg ttttcttctt gtaaatttgt ttaagttcct tgtcgattct 130320
ggatattagc tctttgtcag atgaatagat tgcaaaaatt ttctcccatt ctgtaagttg 130380
cctgttccct ctgctgatag tttcttctgc tgtgcagaag ctctttagtt taattagatc 130440
ccatttgtca attttggctt ttgttgccat tgcttctggt gttttagtca tgaagtctct 130500
acccatgcct atgtcctgga tggtattgcc ttggttttct tctacagttt ttatggtttt 130560
aggtcttgca tttaagtctt taatccatct tgagttaatt ttgtataacg tgtaaggaag 130620
aggtccactt tcagttttct gcatgaggct aacgagtttt cccaacacca tttattaaat 130680
agggaatcct ttccccattg tttgtttttg tcaagtttgt caaagatcag gtggttgtag 130740
atgtgtggtg ttatttctga ggcctctgct ctgttccacg tgtctatatc tctgttttgg 130800
taccagtacc atgctgtttt gggtactgta ccacttgatt ggtgagagag ggaatccttg 130860
tcttgcactg gttttcaaag ggaatgcttc agcttttgcc tattcagtat gaccaatatg 130920
tagtctttta ttcctcaccc tctctcaaca ccccaccccc acggagtcct caaagtccat 130980
tatatcactc tgtatgtttt tgcgttctca tagcttagct cccacttata aatgagaaaa 131040
tacagtattt ggttttccat tctttggtta cttaattagt ataatggcct ccagctccat 131100
ccaggtgtct tgtttttcat ccattcagcc agtctataac ttttgcttgg agagtttcgt 131160
ccatttagat tcagcgttat gattgataac taagggctta ctcctgccat ttggttgttt 131220
tctggttatt ctgtggtctt ctcttccttt tttccttctt tcctgtctcc cttttagtga 131280
aagtggtttt ctctggtggt gtattttatt ttcttccttt ttattttttt ttgtgtgtat 131340
ttgttgcatg ttattgattt gaggttacca tgaggcttgt acataatatt ttctaactca 131400
ttatttcaaa ctgatgacaa cactctatcg cataaaaaaa catggaaaga gaaaactaat 131460
aaaaactcta cattttaact tcatctctct gcttgttgtc actttgtcgt ttctatttac 131520
atcttattgt actgtttatg tcttgaaaag tagtttcagt tattactttt gattggttca 131580
tctcatagtc tttctactca agatatgagt agttcacaca ccacaattac agtgttacaa 131640
tattctgtgt ttttctgtgt actttcaatt acccatgagt tttgtatttt cagataattt 131700
gttattgctc actaacatcc tattctttca gattaaagag ctccctttag catttcttgt 131760
aggaaaagtc tggtgttaat gaattccttc agctcttgtt gatctgtgaa agtctttatt 131820
tttccttcat gtttcaagga tattttcact ggatagtcta ttctagggta aaagtttttt 131880
tttttttttt cttcagccct tcaggtaagt catgccactc tctcctggcc tataaggcta 131940
ccactgaaaa gtctgctgcc agacatatat gagttccatt ctatgttact tgtttatttt 132000
ctcttgttac ttttaggatc ctttctttat ctttgacctt tgggagtttg attattaaat 132060
gccttgaggt ggtctttttt ggattaaatc ttcttcgtgt tcttgtactt ggatattaat 132120
atctttctct aggtttggga agttctctgt tattatccct ttgaataaac tttctaccaa 132180
gatctctctt tctctctctg tctctctctc tctctctctc tccttcttaa ggccaataac 132240
ttttagattt gccctttttga ggctgttttc tagatctcgt aggtgtgctt cattgtttgc 132300
tatttttttt tttttttttgt ctcttctgac tacattttca aatagcctgt tttaaaactc 132360
actaattctt tcttttgcct ggtcaattat gctgttaaga gactctgagg cattcttcag 132420
tgtgtcagtt gcatttttca gcaccagaat gtctgcttat tttttttttag attatttcca 132480
tctctttgtt aaatatatct gatagaattc tgaattcttt cttagtgtta tctttaattt 132540
ccttgaattt cctcaacaca actattttga attatctgtc tgaaaggtca catatctcta 132600
tttttccagg attgctatct ggtgctttat ttagttcatt ttgtgaggtc atgttttcct 132660
ggatggtgtt aatgctagta gatgtttttc agtgtctgag cattgaaaag ttagatgttt 132720
attgtagtct tcacagtctg ggcttgttca tacctgccct ccttgggaga ctttccaagt 132780
attcgaaggg atttggatgc tgtgatctta gtctttggtc actgcagcca tatctgcttt 132840
atggagcatc ccatgctcag taatgctgtg gctctttcag actcatagag ttactgcctg 132900
catgctcttg ggtaagagcc aggaaaattc cctggattac caagcagaga ctcttgttct 132960
cttctctcac tttcccccaa acaaatagag tctctctctc tctctctctt tctctctctc 133020
tctctccctc tcattctctg ccgacctgcc tgaatctggg gtagggatga cacaatcaca 133080
tttgtagtca acaccattgg gactgtgcta ggtcagaccc aaagctggca cagcactgag 133140
tctcgcccaa cgcccacaga gaccactccc tgggtaatgt ctgtgtttgc tcaaagccta 133200
agggctatac aatcagtcag tggtgaagcc agcctgtctt atgtccttcc cttcagggtg 133260
atgagttcct caagcaggtc cagggatggt gtccaggagc caaggcctcg agctgtgact 133320
gagctggcac ccaatccata agacaaagat tttttccaca ctttccttcc ttgtcctcaa 133380
gcaaaggagt ctctccctgt ggccaccacc acccccatgt tcatggcaag tattgtctgg 133440
ctaccaccaa tcttcactca aggcccaggg gttctttagt tagcttatgg tgaatgctac 133500
caaggctgag tctctccctt caaggaagtg ggctcctctc tggcccaggg caggtccgga 133560
aatactatcc aagagccaag gcctggaatc agtttcccca agagtccatt tggtgctcta 133620
cacccactgt ggcagaacca gtacccaagc tgcaagacaa agtcctcttt actcttcctt 133680
ctcctttaca gagactctcc ctatagccac cacagctggg aatatgctgg gtcactcttg 133740
aagcaagaac agctctgagt ctcactcaaa actcctggca agtactgcct ggctatcaca 133800

-continued ctgattattc agggcccaag ggctctttag tcagcaggag atgaatcctg ccagtactga 133860
ttccttccct tcaaggcagc cggtttcttt ctggcccagt gtgtatctag aaatatcatt 133920
tgggagctag ggcctggcat ggtgacctca ggactctgcc tggtgccctg ttctactgtg 133980
gctgatgtag tatccaaatt gcaagaccaa gtcctcttta ctctcccctc tcctgtcttc 134040
aagcagaagg aatgagtccg ccctggagtt gggagctgca ttgcctggga ttggaggagg 134100
ggtggcacaa gcactctctt ggtcacccca gctggtgtct tactaggtcg catgttcccc 134160
aagtccactg gctctgaggc tagcacacca ggatttgacc aagaattgca attcttgtgg 134220
cttacactgc ctttcaagtt tatttgagat cccagagcac tttagcccac agtgacaggg 134280
cttgccagaa tttagtttct gactgctgag atggacaatt tgcgtctgat tagggctggt 134340
ctaagtgctc cttctgtggg cactggctga gttctgctcc atgttgcttt ctgctgtgac 134400
agggcaacat tgagtttcaa tgcaagtccc acagtcactg caatcttcct ctcccaagcc 134460
tgctctgaac accatgtggt tgctgctggg ggctggggga gggatgttgt aggcaattca 134520
agaatgtctt tcctaccctt ttcggtgctt ctttccttgg tatgatatta aaaccagtta 134580
ctgtgattgc tcacctgatt tttggttctt atgaaggtgc ttttttgtgt ggatcactgt 134640
tcaatttgtg cctgcaagcg gggatggggg acaattgctg gaggcttctc tttggccatc 134700
ttgctccacc tctaccctag tattagcaat ttcaaagcag ttgggatgga ggtagaagga 134760
aagggcgctt ggaatcagaa aatccatgtc ttagctttga gccttagaaa attcatttga 134820
cccttgtaag cctcagttgc ttcatctgta aaagagaaat aatataatgg ctgaaaagat 134880
caaaggtgat aatgcttttg aaaacactat agaaaatgac aaaatatcac atgagtatta 134940
ttttctagtt tctaggagtc tccttaccat tgtacaggac aaccatgtct atttttaaat 135000
aaattattat ttgcctctga gcaaccctgc aaagagttgc ctgtaggaga aacagcttta 135060
cttgcaaatc actccactgt tttctttgtg cacagcttat taatacataa ggcacatgtc 135120
ctccagcctg cagtaacatt ggaatcatta cctctttgga gtacctacca gagcttctca 135180
aagtgaattt tgtttatcac cacaaaaaat agtctgttgc agagataacc tccaaattca 135240
atgacaatat ttccaatcac ttttgcatga tgcagaaata gacaaatata taattttgct 135300
tatagagaca attattgtct cccaacaagt gatcagtagt cagaaaatgg ccaagaaata 135360
ccatggggtg tgccttccca taacagctta tctttgtgtt ttagttgcaa ggttactaaa 135420
agcctgtgca gggtttatgg caaaagtaaa acttgctcca ggagcaagcc cttgtttcat 135480
tgtctaatgt tcttaatccc cagcagacag gatttggatc tggcatttgg taacagggca 135540
gtttccaaag ttgctgtacg caacttgagg aagagaggtg atattatcgg aatgaatttc 135600
tttgttgtaa gttataaatg tatgggcttt tccaatccca tcacccttaa aactttattt 135660
gttttctgca gtgagggtgt ctccgttgtc tttaatatgc ttgctttgag ttcatggatg 135720
aacattcctg cctggctgac atgtggactc tctgaaattg ttataaggtc tttttctttg 135780
ttttttcttt gatgcccaag ctgccaaggg tagtactggc agtggtgggc agacaaggag 135840
gtgatagcaa actttgtcct ctggcctccc ttgacccatt ccattcatta tctaagggac 135900
tccaagccag cattccacag agtgccctca ccaaactcac taagactgaa ggcgaaccag 135960
gattccaaac agccattatg aaaggaaaga gagagagact tagggtttgc aaaataagat 136020
accctgttga ttctttttat tccatacaga tactactatt ctttaggaaa acgttaaaat 136080
cacatgatct tccaggacct gggctgcttc tttaagaagc atgttacaga aagctttatt 136140

-continued ggccaacaac atattgaaag atagattaat caatcattca ttcaaataag gtatattcag 136200
aattgaggta tattgtagcc agacagtgag actacaaaaa aagaatgcac cgtaccctta 136260
tctcttgcac aatctaacga gggagataac cactctttca atttatagtg acctataaca 136320
tttcgtacac tgctgaatat ctttacatgg taataacaca atggaaagct tgcaaaatag 136380
acagaggcta ggggaagaag gattgagtgt gaatatagcc tcttataaat cgagaggaat 136440
ggtctgtgtc ttctgatcat acagagataa taaatatgga aatgatttca aactaacaaa 136500
gcaaatgtgc agaaaatact gagaatatag tgggcaggat acctgagttt tggttccatc 136560
tctgttattg actcattgtg taatctgagt caggtctgtt ctgctctctg gatctcaccc 136620
tttcctatct gtaaaatgag attgttggat tagatgatct ccatagaggt tctcacctat 136680
tctgacattc aaaaggactc ctaatttttc ttatataata ataatatata tgatctgtag 136740
agtgctttac actttatatg atatttttgc atctgttatc tcatgtgaga aaagcactgg 136800
actgctggac tggcaatgag gacacctgga ttcttgtctc tgttttgaca ctgattcatg 136860
gtgtgatctt caagcaaatt ctctgagttt cagtttctca atctgtaaaa tagggggggta 136920
tgaagattgg actaaatcag taggtctcta aaatgttcca caaagccctg gggtgggggg 136980
ctcctacaga gtttcgctaa ggcaaaccac aacgctaagc ctgcatggaa gaggagaaaa 137040
agagtggcct gacaagagaa gttcccagtt tcctatgcca accccaggca gattacattt 137100
aattttatct gatttatata gagagtttct atgtaatgtt ttattcttaa aaatagttta 137160
ctataaaaaa ctcaactggt ttgattttta aagattgcac atataagtga gatcatgcag 137220
tcagtatttg tctttctatg cctggcttat ttcacttagc ataatgtctt ccagcatcat 137280
ctatgttgct gcaaatgaca gacttttctt ttcattaaag gctatatagt attccatcgt 137340
gtatgtacac cacattttct cttttgtaac tttcatttta ggttcagggg ttcatgtgca 137400
tgtttgatat ataggtaaac tgcatgtcag agaggtttct tgtacagatt atttcatcac 137460
ccaggtaata agcatagtat ctaatcaatt tttttctgat cctctccctt ctcccaccct 137520
acaacctcaa gtaggccctg gtgtctattg ttccccctctt tgtgtccatt acaccacatt 137580
ttctttatcc acttatccat ccatggacac ttagtttgct tccatatgtt ggctattgtg 137640
aataatgctg aaaaaagtca aactcataga agcagagagt agaatggtgg ttaccaggga 137700
ctgggaggca gttgactgag ctaggaaaag agagataata aaagggtaca atgtgtcagt 137760
tatatagaag gaataagtta tattgaacta ttgcacagca tggtgaccat agttaataat 137820
aatgtattat atgtctcagt attgctaaaa gagtaaattt aaatattcta accacaaaaa 137880
attattagta ggcaaggtga tggatatgtt aatttgcttg atttaatctt tctagaatgc 137940
atacatatat caaaacatcc cactgtaccc cataaatata tacaattatt atttgtcaat 138000
ttagaaattt aaaaacttga tttagatgag ctctaaggcc ttaagtatta aagtattaag 138060
tattaaagtg atatgtaacc aagtatattg tttggtaact tcatttttgt tattatttta 138120
acaaaccaat atattgtgaa tatacttcca agtgaaaaga aaaaagacat tgcagtcatc 138180
actaataact gcaaaacatt cctttgcaag aatatggaat aattcattta atcattcccc 138240
taatgttaga cattcaaatg tttccaactt tttctattta aataatgcta caataaactt 138300
ctattttgtg cttattgtat tattttctta caacacatcc ctagaagtgg aattcctaga 138360
agtttataca catttccaat ttttttccaa atatatggca aaatttctct ctaaagtatt 138420
tttattccta ccagaaatac ctcttcacca acacgtagta tttaatctgt accaatctgg 138480
cttaagacaa tgatatttaa tttgtatttc tgtgatttct agctaaatta aataatcttc 138540
atatgcttat tggtcatttg tacttctaac tgctttctcc tgtctgttgc ccatttttct 138600
attgtgctgt ttatttttat atatcgaata tattgaccat tggttttaca tacttgatgc 138660
taataattat tcttagttta tggtttgtct ttgagtttta taatggtgtt tatttcacat 138720
aagaaattat aaatgttttc taatgaaatt tatcaagtct gtcttcactt atgttttctt 138780
cattgtcaat aacttaaaat gaccttttct acctttaaaa attttgaaat tttcctctgt 138840
attgtctaat agtacttaca tgatttcctc ttttaaattg acatatttaa tccatttgga 138900
atttattttg attttaacta gtaatttaac tttattttct tctccaaatg attcactagt 138960
tgttctgaca ttatttagtg aataattcat cctttcttca ctgaattgga atggcatatt 139020
ccatatactg tgtctggttt tggcttttct gatctcttcc actgatcaac ctaagctgga 139080
gccagtatca aactgttgta atcattatgc ctttagatac tttaaatgta cagcagggaa 139140
tgtcttatta ctcttatttt tcacaaatat cttggcattg tctcatgttt tattccttca 139200
gataaatttt gggattattt tgtcaagatt ttgtttgagt tgttttaaat ttttagattt 139260
cattgggaaa gaactgaaat ccttgaaata ttgcttcttc ttagccagga atatggtaca 139320
actttgcatt taattcagtt ctttccttaa ataccaccat gaagtttttt gttttgttca 139380
tataggtcct gcattaacac catatatata aagtgtgaga aatactacat tcttcaggat 139440
tctctgtagg ttaacaatga agatgatgac tcaacccttt ctttgtttgc ataatgtgat 139500
gccactaata gtgggtaact tctctgcctt acctcctctg ttccaaacag gatttttcag 139560
aatgaacaaa ttaaaagaat cataatcaga cactaacccc aagccatact gcatggcagc 139620
accaatggga ctgacagaaa acaacagaaa taggaagaaa tcctacagag aaacaaactt 139680
gaaagctgtc tcatggcctt tgaatcatac ttaagtttta tgatggaagg atacgactat 139740
gaagaaagac acagagcaac atcagacagt caagaatttc agagccagct ggcatgcagt 139800
ggacctcatg ccagcccatt ttatgactat ttaggtagtc aagggtttaa gatttttcta 139860
ataagacagt tattatgcat ttcaatgagt gatttctttg cagctctaga gtgtggcctt 139920
acctacttca acatgagaag atttttgtat tttgtcagtc atttcacaat gacttttagt 139980
gagcccttca ttatagactg tggatacaac tttgctgttg gaaattaaca gtgtcaaaca 140040
actgggtata atgtttgtaa tatctgagga gggggagctg cctaggaagt tgtattccct 140100
gtgttaattt ttcagtctct taggttatag aggaccttct agaaccacct tacagcagga 140160
ttacatccca tttacacagt tctctgtcac ttgaatacag agaagggatc cacaaggcca 140220
tatgcttcct agacaaagag aaaagatttc tgccacactc agaacgcttt gtcttcagac 140280
tataatcacc cacaccatat ttcctttgga tccactttcc agatttttgt gctggcacta 140340
acaccaactt gctgtggctt ggggcatgta atttcaatac tttgtgccca ttttcataag 140400
tgaagtgtca ggcatcacat tggacatttt aagattcttt acagcccaat gattctgtgt 140460
ttctaattag gcccaatggg ttagagctaa aaggaaacag tgagtttcct ggaaggaaag 140520
gacatataac acagtccaga ggtaaaatgg gctgtattca agaaaagata ggacaatact 140580
ttgcagggat gctgcagaga ggattcaagc cttgtatgga ggaatggatg tgatacaacc 140640
aaaaagtctt taaaaattct ttccaactaa tctgagattt gtaaccttat ggactgtgat 140700
ttgcagcaaa ccaaggatgt gataaagact agtattgttt ctagaatgca aggatggttc 140760
aacatatgca aatcaatagt attaacagaa tgaaggacaa aaactatatg atcatctcaa 140820
tagatgcaga aaaataattt gacaaaattc aacatcattt tatgataaaa tctttcaaga 140880
aattgggtat tagaaggaat gtttctcaac acaataaagg ccatatcaga caagcccaca 140940
gctaacatta tattcaatga ccaggaatga gataaggatg ctcactctca ccacttctgt 141000
ttaacatagt actggaagtc ctagccaatt tcatattaat gagcctcatt ttcttcatca 141060
tagaatgaag tatataataa tccctgttat acttactttg cacagattat tattattatt 141120
taattattat tttgagacag ggtctcactc tgtcacccag gctggagtgc agtaccacaa 141180
tcacagctta cttcagccac gacctcccag gcataaagga tcctagcccc tcagcctcct 141240
gagtagctgg gagtacaggt gcacaccacc acacctagct aatttttttt tttcattttt 141300
ttatagagac ggagtctcac tatgctgccc aggctggtct caaactcctg tgctcaagca 141360
atctttccac cttggccttc caaagtgctg ggattacagg agtgagccac tgcacctggc 141420
cttgcagatt attattaaac tttgtaaact aatcaaatga gagtgattat tgttactgtt 141480
aagaactctg atagcctcat ccatatattt ggagaaattg aataaataat aggaaagaaa 141540
taatagcatc ccaatgattt taccttggct ctaccatcat ttggggaagt gataattcag 141600
ataggagaag tgacttggaa gcagtcttga gagattgcct gttccatccc ctatctttgt 141660
ccttaaacca aattgtacag ataaataagg tcttattttt aggacttaca gaaaaaagat 141720
tcctttcata tccatctttg caatcctcaa ccacttctgt cactattatg tgtcatttca 141780
aacattaaat tcctcattct gctttgaagg aacacatgtg tcatgtgtac ccatttgtat 141840
gttttggtgt gttttatgct ttatgtgatc acccacatat gcacagataa ttccaaaatc 141900
cagtgtgtgg gtgttgtatt ccctgtgtta attattcagt cacactcaaa cacctatgca 141960
ctcacacata catgaataca cacatgtaca ttagcatgtt tatgcttatg ttgcatgtga 142020
ctggcaacat cagtgccttt ctaaggcaat gttaactacc ttgagttttg ggagagcttt 142080
agagaacaaa gacaagagac taaatgattc tagatgtaag agacaatgtt gcaataagtt 142140
actatcctaa aaagacagaa tacagggaca agagactatt attttggata gtttcttgct 142200
taccagtaat acttaagtcc tttacattaa aaaaaaaaaa ctctgtaaat atattgcaga 142260
agaaatccag acatccttca agattcttag agctggaaaa gattttaatg actttccagt 142320
ccaatctatc tcatgtaatc aatggggccc agagaggcaa aaggtcttgt ccaaggtcat 142380
atagtgagtt agtgataagg ctgaacaagg attcagatgt tggggcttcc agcccactgc 142440
tctttctctc atctgggatt tgtgtatttt tgttcattag agattttcct ctgtaacctc 142500
aatatccaat gcagggcctt gcacataata gattatcagt aaatgttaaa ttaatatgtc 142560
atggctttgg ttgtactggg cttttgcact tactcctgag taaattgtaa agaatatcta 142620
cgttttaggt tgccttgttt tagaccaaga ggtacccaga gaaaaggtgt gaactatgct 142680
aaggaaatta tccgagttcc aaattgaaaa aaaaaaaaaa tcatgctttt ccgctataac 142740
ctctctcatt cacagagtga ttctctttca gaagggcaat ctagaactat tatgggagcc 142800
atattccatt ggtggtgcaa ccatttcttg acaaactagg gtccaagaaa gtattttcct 142860
ggggaagatg agatttctca aagaaggcac gcactttcta acctaagctt atttcagtaa 142920
tcaatgtaac aagctggtct tgatgattgc agcagtacca atactgtggg agtgtaccag 142980
ttctagaaca gctacaacat tggaattgaa cgcactagaa ttggatacag gacctgtttt 143040
tgaggagcta acacccaaag gctgaacagc actcgtagca ccgtcctttc tgtgcacata 143100
tggtagtcct cagtttgcaa cagaaataaa gctgttagca aattatgtgt tctatttatg 143160
caaataaaat cttgtggtat gctagaaaga gcactggcct ggagacctta gttttctcat 143220
atgttaaaaa cccctaacac aggcctggtt catagtaggc acccaataaa tagtagtttt 143280
cttcctttgg gggcctccga ttcagtgtgc ttcttcaggt aagtcacttc cctggaactc 143340
ctccttggaa tgagagttgt actgttgtga tttttaacag ttccttcaag ccaagcattt 143400
tggaatcctt tcataaaggg agaaaggaag gaaagaagaa aggaaaatta aaggaaaaag 143460
aacaaataaa acgttaaaaa ggaggaaagg aaaaaggatc ctttactaca ataaaactaa 143520
tcttatgttc ttgcaagtag cactttaagt aaaagaagtt ctttgctgac ctggttacta 143580
ctgaacctac tacataaaat agcctactat aatagatgca tttatgtgcc taatcttcac 143640
tttttaggct tagtaaaggg agaggaaagc tgatgtatag ttaaatttat gtttttagtt 143700
gttttttttt ctactctcaa atatcaatca ctctttagtt tctctttctt tttccgacca 143760
caagcattct tcctctgctt aaagaagctt ccctaaaatc ccagtctatc cagtaagcca 143820
aagcacagca ataaatttga ggaaaaaata ccagggactt agagacagaa aggagtgagg 143880
ggatgcagaa gctgaagctg gagcacggtt gcaagcatga gaagttctgc gtgtttcaga 143940
gcagccaagg atgtattttt gcctattcct gctggtgact ctgtgtgtct atgcatccat 144000
ctgctatatt tacatgttta gtcagtcaat ccacgtttgc tgagagcctg ctgtgtgcca 144060
ggattgtgct agcgtaaagg agcaaagtat tgagcaaaat atgtttgagc agctgtaatt 144120
ctgaggatct ctaggtctga gcatgtgtat gtgtgtgcgc ttctatgtat ctgtgacaac 144180
tccaggtgtt catgacagtg atctttgtta ctctgttggc ttcatcgaac ttccttttac 144240
ttgctgtgat tcactacata gagtgggctt tatctctgat ttttataacc tgcaagactg 144300
ggggtatgat caccagcaat ctaaaaacag ttagaaatcc catggagtta tcttttgtag 144360
aaattttcct ctactaatat tatgaaaaat aagcatctta ttagctcgag tgtaattcta 144420
tgcatgatta caggtatcaa taggaagaaa cattgactga gttcaaatct cttctacgcc 144480
atgctaaagg ggtgacaagt tccacaatgg atcattttct catgggcatt tctgactttt 144540
ggtaaaagta gagcacctta ttttaaaaac cattgagtag tcctaatagt ggagatatca 144600
tcaggatctg aattgttcat ccctaaaaaa aacaccaatg gaaatcaaac aatatagtgc 144660
caaattaaac tgtttgaata tttaggttct gtatgatcaa attgtttggt gccatactct 144720
gtccactttt ttcatgtggt aggatataat ttcatatctt ttctgttcta gaaataccg 144780
aagaaagaga ctctggaaac tcattatcag gtctatcaac tcttgtattt gttctcccag 144840
ggaaacagaa gtacctgtgc gccagcagaa atgattgcac tattgataaa ttccgaagga 144900
aaaattgtcc atcttgtcgt cttcggaaat gttatgaagc agggatgact ctgggaggta 144960
agatactttt ctttctcttc ctcctccttc ctctctcccc cttctccctc attttctagt 145020
ctctctttag accagatttt cttctttgat gcttccaagg ggaccagcca tgctctagac 145080
acaggctgac cctttcatag gcaacgtggc catcagccag ctggtgcctt ttttttaatc 145140
cttatctata ccaatcccca ttccggggct cagcattaga gcaggcggtg tgaagcaggg 145200
atcaggagcc aacagaaggt gagtgaggat gcatctgact gggcagggcc cccaggggac 145260
ttaatgatac tggcctgatg ttgttcagtg gtagctagga tgagagaact aagaaatcca 145320
gaacagtcag aggtgcagga tgacccaggc ataggcgcag gatgacccag gcacaggctg 145380
atcctgaaca cctgggaata tcccttagct aactgctgcc tatgttgtag ggccagccac 145440
ctcgaatgag aagctacttc tctttggagc ctgtgactag gctgccacac agagccaatt 145500
tcctatccta tctctcccaa agatgagcag gtgttttaat aatttccttt tctttgcaaa 145560
gctattgacc atttccaaaa gcattttttt tcagtagcac agtaacgtga tagatggaag 145620

-continued atacagctct ttcaagggcg ttcctctatc ataaggctct ctgtcccaca aacctgtcta 145680
ccatgagtgt tgtcaccatt ccagaaaggc ttgacatcag ttgattgaga cttatatttt 145740
ccctctccaa actcccccat ctcttcatgt ttacatctgc ccaatgccag ggtcctcgct 145800
gctgcctgct acttccaaaa agatgtgtct ttcatgagaa aaacaagatc attaatccac 145860
ttcgatttgg aaatggaatt tgaagaaagg caagcctatt tctgagtgcc tgcaactgta 145920
gcctcatacc caattattca ttattagcct ggaaaaccca agtgcctaga atccaaccct 145980
ctcccctctc ctcttaagtc taatttagac cagttgtcta tctctggctt tctgtgaggt 146040
gttcaatacc ttgtctgcct atgtgcacat ttatagacaa caactagttc tcttatcctg 146100
gagcagggcc atgtgtggat cttcatatag ataactatat cctccccatc ctcacagggc 146160
agtagtatta tttaaacaga acaaagtacc tcacatgaat tgacccaggc tggatgagag 146220
acaatttcaa aagaatcatc tcaagtagcg tccagtactc ccaaacatca caggtagatg 146280
ttctgtgagt ggctttccaa gcatccacat caaatgagac tcagatatct gagaaaactc 146340
aaccttgttt tggtttgctt ggtgcacccc aaagaaatcc aacaattgag gtctacagtg 146400
gagaagaagt aggactgggg tcagggagta cagaggcaaa ggcaggaagg gtgacaaagt 146460
gattgacaag aaaaaatgtt ctccatatga atgttgcagc cccatgttga gggttcttat 146520
acactcaact gtcaattatt tagccttctg tgaattatgt atagtataaa agatagggac 146580
tctcaagtag ggaacctctt ggcttgccat ctggcaatat gaattgcaag tccactttga 146640
tgcaggtaaa gtttaatggt aacaaaagtc ctcataacat ttggatgcaa atcttaacat 146700
taattccatg tctcagccaa cattctccat tattaagcag cctgtgatgt gattacagtg 146760
aaccactttt gaaaaggagc ctgtgtataa cagatagttt cactatacta tataaccgtc 146820
agatgcaggc ttgtaaatta atttgttggt gacaatgttt cagtacattt tcaaattgat 146880
tcattggtat agtactcaaa tttgagtggg cttggtgaac acaatgaaga caagctgaga 146940
agtgctgtga ctggccttca tttcagttgc aggcccatga tattttgagt gtcttccatg 147000
tacaaggcac catgctaggc attagagctt gaggctggca aacttcagga agtgttcaca 147060
agataccagg attcttgatg ttgtgtaaat ggccttgcct ttagagtcag gcagatctag 147120
tttaaaggct cagctccttt atttactgtg tgcccctctg agcctcaatt tcctcatctc 147180
tgatttagaa ataccatcct catagagtta taatgagtat cagatgacat gatgaatgtg 147240
aacatccttg ataaatagca aaatgctaga caaatatggg ggcttaatat gacattgagg 147300
tcactagtaa tttagctgga aagtctgtaa cacagcactt cccgatggct tttaccctaa 147360
gtaacttggt atgccatata atatgtaaca gcaccaacag gcagagaatc gccagaaaac 147420
actcttgatt acctcaaacg aaaaagtacc accaggatcc tgttcagaag ctaattttag 147480
taattaaggg aatcatatgc tatgttcaaa taccatgcca gtaaaaaccc aattgtttac 147540
cttcttaaat cactgcttga agagcaaatc tttccatttt gctgaatgaa cttatctcca 147600
cgttccctgc cctactgaca caaccccctc ccaagtttat tgttaactta cacattcaat 147660
gcacagcaca cctttactca aacaatggaa aagaaagaaa gtgtcaattc aaagtggccc 147720
ttgtctattc cttaaggagt agacttccat tttcatcaga tttggattta gcatagacat 147780
attgattacc ttgaagaaga attcatataa ttttatcttc tgattcccat cactcaaatc 147840
aaaattacat aatatattcc aaaatggcaa ctaggaatgt ggccttgggc aagtcccttc 147900
tctcctctga tgcttggttt tcccatcata gaactggaat tgtggcttca ccgaggacct 147960
ttctggtgct aacattttgt gattctatgt aaaaagccac acagaaagga ttgtttttca 148020
gccctttctt agattgtctg ttccctgctc ccagaagtat agatagtgag acttgagtgc 148080
tttgatacat cgtaattgta tctacctcca ttcacaccta cttaagatat ctgtctaaaa 148140
gtagactaga cagattattc agagagtgga gggcagaagg gctgtctctg tatcttaaag 148200
aagctggcac tcttcagctg atggctgctt ggtcttgagg cctcaagatc tttaatctgg 148260
ctttctctat agtgtttcat tcactgtttg gtgatggaat ctcttcagtt cagagatact 148320
taatagatat agctttttct ttcctgcttc caggcctacc tacctgtttc ttgctttttt 148380
ttctagcagc tgttgttgtt tctgaaagaa tcttgagggt gtttggagtc tcagaatggc 148440
ttccttaaag actaccttca gactctcagc tgctcatcca caacagagat cagcctttct 148500
ttgtagatga ttcattcctg gctgcatttg aaaaccacat attgttaatt gcttgacgaa 148560
tttaaatccc ttgactactt ttcatttcag aaaacactta caaaaaaagt ccaaatgagg 148620
accttccctc cagtgaatta gctgtggctt tctcacagtc catagttagg ataaatgtaa 148680
agccatttct catttttctc cgcactttcc aagggtacac tccttgtttc caagatggaa 148740
tgagaaataa agaagtgccc ttcctgccat cttctcccct gaccctttcc tccttcccac 148800
tttcctccta ttcctcccca aacatgattt atttctgcgt tttgcaactc ttgagttctc 148860
agcatttagt aaatggtgtt ggtccctgtt gattccttcc tctcctggac catggaaggt 148920
agtaggcctt tcagaaattt caggtagcag ccaaacccca gaagaagaga aggaacacag 148980
agacctagac catgtgagaa cctgaggtgt gcagcattta cttcacagat tcgtctagca 149040
tatttgagag gtgtctttcc tactaggaga ctgaactctg catctgagaa taaaaactta 149100
acatatctac aggttttgac aacctctgtg aattatctag ttgagaggat ggctcaagga 149160
gcctattgcc atggtctgat gtcgttatgg acgctatgaa catccttgca gtttccattg 149220
ttgaagacag ccctgatgcc agctgtctca tcattcccca tgttcaagag catcccagca 149280
ttgctacctc aggatcccat gtcctgaatg caacagagtg atttcgctgc tgaattacta 149340
ttcatggcat ggctcttcac agcatttatt catccatgta tctatccatt catccttcca 149400
gccagccaag aagttcacgc tttcatcttt tcatccattt actcacctat ttattcattt 149460
agcaaatatt tattgagtac caactatgtg ccagacactc tgctaggcat tttggggaag 149520
cagaactgaa taagatacta ttcctttcct caaaaatttg agcaagagga gaaaggaagt 149580
aatgaggaat attccttagc cataaaggaa aaataagaaa tcacttggaa gaagttaggt 149640
gagatggaag gaaaaggaca tctaaggtaa agcgtacagt ttgaataaag gcacagagac 149700
atgaacaaaa tgcattgagg gtttgaggaa cagcaattgg tttaacatgg ccagagctgg 149760
ggaaatggta agggcaagct gaaaccacat tgaaagcaaa cttggttatt atactaggta 149820
gtttagactt caagcagttg aaaatctttg agcatgggat aggcatgatg acattgtgtt 149880
tatttgcatg tttctttaaa gaaaactggc agcagcacaa atgttttgtt gatgagggtt 149940
taaattgtag aaagtgagac aattttagga aggccagcta gagagaaatt tctagcatca 150000
aattttgcta aacacctagg atttgtagtt acctccattt gggttgttac ctgcaagtac 150060
tgaccacgta tatgaagaag tactggttta gaccaaggca attggcttgt ataagaggcc 150120
taccctcata ccaaaagcca gtttccttgg tctaggccag tgtttactgg tatgtgtcct 150180
gagaaaacta gttccatgac atgttccatg aaaaatatga tttctattgt caaataagtg 150240
agggaaactt gcatatcatg gtcctgctca ggaagattta caatccttat tagcatatca 150300
caggtcctgg tgaatactgc ggtaaagtaa ccgaggagct ttgtaactca ggattcccga 150360
agttgattca accacaggac ctcatttatt cacataacac ctgttatcct acaaaaccac 150420
tgttctctgg aatacacttt cgaaaacatg ggtatagaca aaaactctat cctataggca 150480
gagaatacct atacctctag ctcaggtcat cattttgcag atgtgtgtgt cattaagaat 150540
cagtcaataa tgcattaatg atcaaaagca gaccatcctt accacatggt gcataagatt 150600
atgctattat gctattagct actaatgcca ctaaagttaa ttatgttggg tctgcaacgt 150660
tgtcatacac aaaggatagg atgcaaaact gtcctaggcc aaagcatggt tattgcccaa 150720
gttatctaat gtctgcaggt acatattcct ggcctaagga ttgtgctaaa gaagttattt 150780
ctaagaaata tagtgacttc cagcatcatg cagaatgacc atttaatatt ttgaatatct 150840
agacattctg ctgtagaatt taatagtcct tttatacact gtctgaccaa cattttgaca 150900
tttactcaga accccatcac agtgctacca cataacctca ttgctaaagt gggaggccta 150960
gaaatcacag atttgtagaa accatccaat gattgaatcc cctctacttc ctgttcagca 151020
ggcagcagag tgtcataaag aattaacaac gtggaactca gttactggga tttcttccat 151080
tctcctttga ttctctagac tagaattcca aagaccctca ggctggtgat gcaagtggga 151140
agtctcattt ctgagaagtg ctgcttccta cccacaattc tttgatagct gagtgcttta 151200
gctgatctgc ataactgagg tgtgcaccaa ggagcagaat tactctataa attttggcat 151260
caacatgtgc aacttgtgac tcagcacttt gaaactctgg ggattttttt gtttggttgg 151320
tttttgtttt aagatgtcct gtggtatagt ggaaatagta caatagactc agatacagag 151380
aggccttgtt tctagtcttg gttctgtcac ttactatctt gatgtccttg cacaaatcac 151440
cagacctctc tgagcctcag tttctccaac cacactgtgg gaataataaa atctttttta 151500
cggcattgtt gtaagtatgt agagaaactg gtacacagta ggcacacaat caatgtcacc 151560
gtacccttca gcccttcttt tgtggatgaa aaatggtctt tgtgctccca gtcaccactg 151620
gggtctgttc tctctctctc tgctgttaca gtgtggcttt tggttcttgt ttctttgttc 151680
tttggtctgt aaattaccct tgaaacaacc cttgaaattt ccactccatg acctaaatcg 151740
tcatccctaa attggttaca tacatatttg gtgacacttt ggaggggaaa agctttatgt 151800
ctctctaact gtagttctta agggaatttg catatggaaa aaacagagac tgcgtctctt 151860
aattcctcca aaccaaatta tctgggatag cacatatatg ttgtactctg tctctgagca 151920
tttgctctta gagaactatg gttagagcga agtaaatttt tctaatcata aaaattaatg 151980
ataccgcata tctgatactt gaatgagtac ctccttgtaa aatttatact taaatccttg 152040
agtttttaaa gtgtaatagc aatagaaaga ttttattgtt gtttactttt actgtgagtg 152100
ctccaaaatc cctcagttgc tcttgaaaga gcaagatgat gccataggca atattttcca 152160
aaggtagtag gcagaaaact gagtacacag cacacaatag gccatatata caaaagcaag 152220
tattttgcaa ataataataa ttcaggaaaa aagcttcact ttcgttggta acctgtttgt 152280
ttaaaaccat tttattattt attatttaaa aagagtgtca cttgttacag attgtgggat 152340
gtgttcctta agatcacaaa aatgtaaaat attttctttt tatactgaac acatgcatag 152400
acaacttacc tgagcaagct gctttttgga gacatttgca catcttttgg gatcacgttg 152460
ttaagaagta gaactaaggg aaaaacacgc agccacccag aaatcggtag agccttcagc 152520
tcatctgtta ttaatatttc tgtgacaaca gatatctagg aagtaaacag gaaattgcat 152580
cgctatcctg catcaccttt tttggaatca ggttccattc ttctcagtcc agttcaacct 152640
tgtgatactt tttagatctc aaccaaggca tagaaatata ttttcccttg cttaataccc 152700
catggaacca atgcccctgt ggttgaagta aaaattgatt gttgagggac atttcagccc 152760
tctagcagtc aacaattaaa aacatgtaag caccgagcac ctgcagaaaa cttggactgg 152820
catttggatc taagaagaaa atctgcatct tgaccaagat gaaaagtcac cagcccaagc 152880
ttgtgcagtg aagtgtcatg ttggccacaa tgaaactgaa agagactgat gactctcctc 152940
agggtggaaa atgaggcatg gaagctttga ttagtgagct gttaggcaca cagacattaa 153000
tttcaaagca ttctcatctc cagtctgagt aataatgctt atagtattat gcaattgttt 153060
ggctgctgca agaaattcag cagactccaa caagtagtct ttcttggtct ctgagtgact 153120
gtaacttaaa ttctacctcc cttctcttct cctacatctt ctcactcccc accccacccc 153180
cacatacaca caattcttgt ccactatgtt cagagagatg cacgcacaca tatatatgta 153240
tatatatagt atatttgtca ataaagcaga aaagaagaaa aaactccaag taaacaattt 153300
tccatttccc catctcactt ctgtcttaca agtggatagg aaaagaaaaa cccccagtaa 153360
aaaatggcaa ccgcccacct ccccaacttt acatgctgct tcctatgtta gaggatctgt 153420
cttaggcatc tgattatgga gcctgctaga tacaagcccg tatttagact gctacagtca 153480
acaatgtctc tctttcatac tagaaaaatt ccgggttggc aattgcaagc atctcaaaat 153540
gaccagaccc tgaagaaagg ctgacttgcc tcattcaaaa tgagggctct agagggctct 153600
agtggatagt ctggagaaac ctggcgtctg aggcttagga gcttaggttt ttgctcctca 153660
acacagactt tgacgttggg gttgggggct actctcttga ttgctgactc cctccagcgg 153720
gaccaatagt gttttcctac ctcacaggga tgttgtgagg acgggctgta gaagtaatag 153780
tggttaccat tcatgtagtt gtgagtatca tgattattgt ttcctgtaat gtggcttggc 153840
attggcaaag tgctttttga ttgttcttga tcacatatga tgggggccag gcactgactc 153900
aggcggatgc agtgaagctc tggctcagtc gcttgctttt cgtggtgtgc tgccaggaag 153960
aaactttgct gatgggactc aaggtgtcac cttggacaag aagcaactgt gtctgtctga 154020
ggttcctgtg gccatcttta tttgtgtatt aggcaattcg tatttccccc ttaggttcta 154080
gccttctgga tcccagccag tgacctagat cttagcctca ggccctgtca ctgagctgaa 154140
ggtagtagct gatccacaga agttcagtaa acaaggacca gatttctgct tctccaggag 154200
aagaagccag ccaacccctc tcttcaaaca cactgagaga ctacagtccg actttccctc 154260
ttacatctag ccttactgta gccacactcc ttgattgctc tctcacatca catgcttctc 154320
ttcatcagtt gtaagcctct cattcttctc ccaagccaga ctcaaatatt gtattgatgt 154380
caaagaagaa tcacttagag tttggaatat cttgttctct ctctgctcca tagcttccat 154440
attgacacca gtttctttct agtggagaag tggagtctgt gaagccaggg aaacacacat 154500
gtgagagtca gaaggactct ccctgacttg cctggggcct gtctttccca ccttctccag 154560
tctgtctaaa cacacacaca cacacacaca cacacacaca cacgctctct ctctctctcc 154620
ccccccaaca cacacacact ctctctctct ctcacacaca cacacataca cacacacttc 154680
tttctctttc ccctgactca gcaacattct ggagaaaagc caaggaagga cttcaggagg 154740
ggagtttccc ccttctcagg gcagaatttt aatctccaga ccaacaagaa gttccctaat 154800
gtggattgaa aggctaatga ggtttatttt taactacttt ctatttgttt gaatgttgca 154860
tatttctact agtgaaattt tcccttaata aagccattaa tacaccaatc gtattttctt 154920
atttacaaca gactgagaga attaatgctg ttaacattgg atcttttttc tttttttttt 154980
ttcctttttt ttctctctcg tttgctttcc aggtcatgct gacctgttca gcttggactg 155040
tttcacattt gtttttaatg tcagtttaaa tgtaattgta aaagcatgta tgctctaaaa 155100

-continued tcatgtagtt actttttca gtggaaaagc ctggtattcg aaagcatttc caggctctgc 155160
aatttcatat gagcaggttt ttggtaaaat cttttgtccc tcactcaggg tggtatctgg 155220
acagtgagcc cctttcttct ggctcagtag tcagagagag gagacttgga gacagtttct 155280
gctggatcct gtgctttggc aaggatgtgc agcattgcat atcattctat cattaattat 155340
gtttactcct ccatgaacta aaaaccatta gactaaatag tccaacataa accttgaaag 155400
ataaaatttg atattctttt gcctggccat ttctctgacc cagaattggg gctgggaggg 155460
gattggagac ttgggggaaa gaatcaagga gccttcttgc ctgggggaat ttggcatgca 155520
cttattaatc ccatttggtt gcactcccta ctaatccctc actccatacc tgccaaggat 155580
tggctctgct ccctgcttct catccctgtc ctagttcttc ctcacctatc tccatttccc 155640
actactgatc cttctctcca gtaagatgct attcaacccg atgaaatata aagagtagca 155700
ccaccctgga agtcaggata ccttagtttt agctcctgct ctaccattat ctagctgtgt 155760
gacctggggc atgacttaac ctttgctctt cagtctgaac agtctttaag aattggtttg 155820
gaggaggaag gaagggatag acaagatcca aggcctttga actcttttt ggaaatgggt 155880 ccttttcttc aaacaaaatt tgatgcagag tcccaaattt acctacagaa taaaatactg 155940
ctgttcttgt ttgaaaggaa gtggggtgct tggagccaca tgctcaggcc cactttgccc 156000
cctctcagga accctcgaaa aaacttatag gacttatagg actgttgggg atctgccaag 156060
tctctcttat gttacatttc agtccttgtg aaactctata tgtttcatca gttcactttt 156120
tcagaaagtt cacctgcttg gggtaaaggt catgaagtgg agaatgtggg gctcagtaac 156180
tagcaatagt aaaaaacatc attgattggc ttgcagaatt tactctgttc taagcatctt 156240
acacacatac tcatccgaaa actcacaaca accttgtgag gtagatctgt tattatctta 156300
agattctgaa acctgccagc atgactctca atctttgact tgagaccagt tgcccaacat 156360
ggaaggttat acttttcaca gtttaccacc ataagcagtc tttcagagtg atttctagct 156420
agagatccat tcttagaaaa agtcagaacc tgcccattag catacactgt cacatggtgc 156480
agagtacctt cactgggttc atctcatttc ctcctaaaaa tagtcctatg cagtagtcca 156540
gtcatatcat caccattata tagatgagaa aaactgaggt gtaggagaaa tcaagagatc 156600
tgttcaaggt cacacattcc ataagactct gaataccacc atcaagaata ataaaccttt 156660
tatgtgaaaa gcattttaga acttcagtgt cattattgca ttctgcctcc tggagttcag 156720
tgcacttttt caccatgctt taatcttgga gtcctggtgg tacagaatct gccttctact 156780
ctcagacaac accacagtgt ctttatccct cataacaaac ttatgaatta agtaatgata 156840
ttatccccat tttacaaatt agttaactga gataccaaga ggctaagtct tgcccaaagt 156900
cacacagcta gtcagtgata gagccggagt tacaaatgag gcatcctgac tccagaatat 156960
ttgctcttaa ctactactct ttatacatat gtaaggaaac taaaagcaaa agagggaaag 157020
atgtccctga ggccccacag tgagctcccc tgactcacaa tccagtattc ctctgacctt 157080
ctaatcctaa agttatacag taaggtccct tgactctaat cctagtagat ggaaagatgg 157140
ctggcatgat ttaagccaga ggccacaaac tggcttcccc agagccagaa ttcacctgca 157200
gaattctgtt tgtccagcac agtgtttgtt tagaaaattg acgtagactg cccctaggca 157260
gggcatcaat cactgtcatt gtccccagcc ctccttattt atgtttgcca ggctttttta 157320
ctcatttatg tgtctgcctg acttgtgaag gtatttgagt ttatgacttt tagatttaag 157380
cattgcaata tataagcact gcacacatgc attcacaaaa gtatagccta gtctagcttc 157440
acaaagaatt tgtagcccta caccaaacac acctttatgt ttacttagtg tttagaatta 157500
gatttaagat cagaatttag tttcacaggc attcatgtgt ggaagaacct cagttattgt 157560
tttttgtttc atactgtctc acccttgctt tccctgctgt gtctggaccc ctgtcaatcc 157620
tgctttctgc cattcttcat gcctgagtta gggcccctgc aagccattca ctggttaatc 157680
tttaggaatg aatggagagt gaaaaccagt ttggagggtt cactgtgtcc caagcatcct 157740
ctcatttagt tctcataagt gtcctaagag acaggtagca gcacattcgt tttataaatg 157800
aggaaactaa atctcagaga agctgaacaa agacctcaaa gtcattaagg tagtaattaa 157860
cggagccggg atttgaacgc aagactgttg gactccagag cctattcttt tgccctacac 157920
cacagttcct tacaaggaag atgtattcat tttctattac tgcataacac attgccacaa 157980
atttagcagc ttcaaacatt tatcagctca ctgttttgta agtcagaagt ctggcacagc 158040
atggctagat tctcagttca gggtctctga aggatgaaac tgatgtgttt accaggatgc 158100
attctaatct gaagctcagg gttctcttcc aagctcatgt aattattgca ggattcagtt 158160
atttgtggtt gtaggactaa ggctccctct tcctttctgg ctaccagcca agggccattc 158220
tcagctcttg gaggctgccc tctttcctta tcatgtggac cccaacgcct tcaaagccaa 158280
caacagagac tcttccttgt gttgaatgtt tctcactcta cggatgtctt tcctggagga 158340
tcccagtccc gtaagggctc acctgatgag gtcaggtaca tcaagaatag ccacccttca 158400
aattcaactg aattagcacc ttcattacat ctacctagcc tttttacaac agcatctagg 158460
ttagtgcttg actgaatgac tggaaactaa ggtctcagaa tctcggggac cgtcttagaa 158520
gtcagcctac tacagatgtt gattcttttc atgtgtcaaa tttcatagtg agatagggag 158580
aacagaaaca tcacatcctt gaccttaggt aaagggattc aaacttccta agactttgga 158640
aacttcacgc cactttcacc ttttccttaa tcatggttga gaaggcctat atcttggagt 158700
ggccaggagt gagactggaa cagtacctaa aggttaagga cgctaaagaa gttacagatt 158760
ggttacatct gctcctccct aggaatgatc catggaacct gatttgaaat ttttttctct 158820
ggtgctatag atagctccca caggggtcta atgccccagg gctgaaaagt tagttcccca 158880
taggatccat ccaggcatga tatcaggcca ggtgttacaa tctcctaaag aggaggtatg 158940
gactggaaag ccccttgcca atggcccttt cttgtcactg ctctgaccca agactaacag 159000
ggcagagata gtgaactcac atactattaa aactatccac ttatacttcc ccctttctct 159060
ttgctttatc actccattta agtaaaccaa tgagtctctg ccttgacaca gtggcaagct 159120
gacctgtatc ttatatgaaa gaattagatt tgactctggg gctcaggtgc agagggcagg 159180
aggggcataa ggatggcctt catggaagaa aagaagtcct tggatactga gtaacagctg 159240
agactagcaa gcctcattgt ccaggattcc aagtcgtcta gcaacatcct ggtctctgct 159300
gcagacagaa cagaggatcc cccggcagaa tgaatggagt ctgatttcaa ttacgttcag 159360
tatagtcact ctctttaggc agagaagcca gaacacctgg tgcagctagg gccactgtgg 159420
tcacagggac aagcacacta cctgggtcct ggaggcaagt gggaatgcag tttttcttcc 159480
ttaagcagat gccatatagg cctggggagg aggatgtgag aataccagcc aagttctcat 159540
tggcactata cagagaaagg ggaattattt catcttgatg gattctcccc acagtctctg 159600
cacatattga tcttacttgt aatgagtttg cttaggttca cgagtcatca tcccagggag 159660
atctgagtca ttggtgggaa agtcgaggcg acagattata tctcactgat ctcactgtca 159720
ccaattgctc tgtgtgtccc tccacctttt gaaaaagtcc atggattcat ttgtgtgtaa 159780
ttcatttgga tttatttctt ctttatcaat agctttagtg gggtattgca aatgggaaag 159840

-continued ttgccccaga gaacagtgta cattcacagc attattcagt agaactttct gagatgatga 159900
aaatcttcta tatcttatgt tgtacaatat aatacagcca ctaactacat gtagcttttg 159960
aacactggaa atgtggcagg tgagactgag ggattatatt tttaattttt taatgttgta 160020
attaatttaa tttttttaaaa tttttgcttt ctattttata gtttaataat taaactaaac 160080
ttacgtagcc cacatgtggc tagttggcta ctatactgga cagtacaagt ctagaaggat 160140
ctcagagaga cacatgctga gatacagcag gaataagtca aaaagagagc caatgtaaca 160200
tagggaattc tggattggga attagagccc tggctctaat ctcagctctg ccactaggtg 160260
accttgccct ctctggcttc agcctcccca tctttgactt gaaaggttaa actaactaac 160320
gtcgaaagtc ccaaaatggt ggctatggac tgaattcaat tttgggatac acaagtttca 160380
ggaatttttt aaaaatctat taatgccttc taggtgtgtg tatgcacgct tgcagacatg 160440
tgcccatgca caagcatggg aaggcagtaa ggcattcatt tcaattcacc agtgtactaa 160500
ccattcacac acacacacac acacacacac acacacacac atgcacacac accctactgt 160560
attgcctatg tagagcctga agatctttta atctgtcacc attggataag ataatttcta 160620
aggacccttc ctgttttgtc atgctgaaaa tctttaagcc actatagtgt cccaaatcta 160680
ttccagtttg ggcagatgac tggagtattc tcatagcctc ctgtctattc ccttctggat 160740
ttgatactag ttatgaagtt tggagtcaag ggtgaagaag ggaggcaggg atgatataac 160800
cccagcccca ctcctcaact ctgcttttga gttagaagta gggttcaggg cttcagattc 160860
cttggggagg cagtagagag aatatgggct ttataatcag aagatgaggt tcagatgatt 160920
gggttctcac ctttttttata gctgtgttac ctcagtttat tcatttgtaa aatagggata 160980
agaaatatct ttaacctcct aagatcatgt ggaattaagt gatgtaatgt gatgaagcga 161040
ggcacgcaga aggccctgaa aaaattagta gttaccctta aggggactaa atggtctggc 161100
aactcccgag ctcaaagcta gaaaggtcca gtaatgggga agatggggtc tttctgtagg 161160
aactgtagca ggggagcaga tcctgtaggc caccagtctg tggagctgtg tccaagaact 161220
catgtttgca ataagcccac caaatgacaa gttattgtgg ggttcaggcc tctaactcaa 161280
gaagatggtc ttggcccaga tcataccttg cagcctgtgc ctttggtggg atgtgggtgt 161340
tggcagtggc tatgcatatc tccttattac tggctgtgcc aaagccccgc agaaatgatt 161400
gttggacaaa gtcatcttgc actcagggct ggttttccag gcttccttgt tattttcccc 161460
tgagttcttc tgtgttcctc ttgcaacacc aaccccacta ttttcctctt ccctacccta 161520
gttgttggtc caaacatgta atccattctt gcagtgattt attgggtgac accatgactg 161580
gagtttgcat tgaaggactt ctttttctaa ttagaactaa aagtcagttc caggctgggt 161640
gtggtggctc acgcctataa tcccagcact ttgggaggcc gagatgggag gattgcttaa 161700
ggccaggagt ttgagtccag cctggacaac atagtgagat cccatctcta caaaaaaatgt 161760 taaccaggag tggtagtgta caactctggt cccagctact tgggagactg aggagggaga 161820
attgcttgag cccaggaagt tgaggctaca gtgagctttg atcgtgccac tgctctccag 161880
ctgggtgaca gaggaagatc ctccttcaaa aaataaataa aaactaaaaa aaaagtcagt 161940
tccaggttgt atctttttttc acaggggcca gacacagatg agagcaggtt ttgttgtatt 162000
tatccattta aattgagcaa taaaattctc tctttggttt ctacctttct tatttattat 162060
tattatgtta aagggattaa agtggttcat ggtctttctc agtgcaactg cttatgctag 162120
acctcagaat tatgaccttt tcaattattt atatttctgt ctatataaat actggaaaaa 162180
atagtacaaa gtaagcatcg gaatgcctaa ggacctctaa attgtgtgtg tgagcacatg 162240
gggaagatgg ttcttaaggt ttgagttttg gattattgtg gttgtcttaa ataatgttat 162300
ttctatcatt ctttccaatg actgtctcct agcatagttc ccattttaca gactgatggc 162360
agaggcagaa agattctctc acttctttga tactattgag gacttcagcc tttcaccgct 162420
cttctcccct ttgctaaaaa agaaaaaaat caatatgtat gttacagtgc attttttaa 162480
atatttttta ttatacttta agttctaggg tacgtgtgca caacttgcag gtttgttaca 162540
tatgtataca tgtgccaagt tggtgtgctg cacccattaa ctccttattt acattaagta 162600
tatctcctaa tgctatccct ccacccttcc ccaaccccac aacaggcccc agtgtgtgat 162660
gttccccttc ctgtgtccag gtgttctcat tgttcaattc ccacctgtga gtgagaacat 162720
gcagtgtttg gctttttgtc cttgagatag tttgctgaga atgatggttt ccagcttcat 162780
ccatgtccct acaaaggaca tgaactcatc atttttatg gctgcatagt attccatggt 162840
gtatatatgc cacattttct taatccagtc tatcattgat ggacatttgg gttggttcca 162900
aggctttgct attgtgaata gtgccacaat aaacatatgt gtgcatgtac ctttagagca 162960
gcatgacata taatcctttg ggtatatacc caataatggg atggctgggt gcaatggtat 163020
ttctagttct agatccctga ggaatcacca cactgacttc cacaatggtt gaactagttt 163080
acagtcccac caacagtgta aaagtgttcc tatttctcca catcctttcc agcacctgtt 163140
gtttcctgac tttttaatga tcgccattct aactggtgtg agatggtatc tcattgtggt 163200
tttgatttgc atttctctga tggccagtga tgatgagcat tttttcatgt gtctgttggc 163260
tgcataaatg tctttttttg agaagtatct gttaatatcc tctgcccact tttgatggg 163320
gttgtttgtt tttttcttgt aaatttgttt gagttctttg tagattctgg gtatttgccc 163380
tttgtcagat gagtagatgg aaaaaatttt ctcccattct gtaggttgcc tgttcactct 163440
gatggtagtt tcttttgctg tgtagaagct ctttagttta attagatccc atttgtcaat 163500
tttggctttt gttgccattg cttttggtgt tttagacatg aagtccttgc cggtgcctat 163560
gtcatgaatg gtattgccta ggttttcttc tagggtttta tggttttagg tctaacattt 163620
aagtcttgaa tccatcttga attaattttt ctataaggtg taaggaaggg atccagtttc 163680
agctttctac atatggctaa ccagttttca cagcaccatt tgttaaatag ggaatctttt 163740
cccaatttct tgtttttgtc aggtttgtca aagatcagat ggttgtagat acgcagcatt 163800
atttctgagg gctctgttct gttccattga tctatatctc tgttttggta ccagtatcat 163860
gctgttttgg ttactgtagc cttgtagtat agtttgaagt caggtagcgt gatacctcca 163920
gctttgttct tttggcttag gattgtcttg gcaatgcagg ctcttttttg gttccatatg 163980
aactttaaag tagttttctc caattctgtg gagaaagtca ttgatagctt gatggggatg 164040
gcattgaatc tatgaattac cttgggcagt atggccattt tcacgatatt gattcttcct 164100
acccatgagc atggaatgtt cttccatttc tttgtatcct cttttatttc attgagcagt 164160
ggtttgtagt tctccttgaa gaggtccttc acgtcccttg taagttggat tcctaggtat 164220
tttattctct tagaagcagt tgtgaatggg agttcactca tgatttggct tctgtttgtg 164280
tgttattggt gtataagaat gcttgtgatt tttgcacatt gattttgtat cctgagactt 164340
tgctgaagtt gcttatcagc ttaaggagat tttgggctga gacaatgggg ttttctagat 164400
atacaatcat gtcatcggca aacagggaca atttgacttc ctcttttcct aattgaatac 164460
cctttatttc tttctgctgc ctgattgtcc tagccagaac ttccaacact atgttgaata 164520
ggaatggtga gagagggcat ccctgtcttg tgccagtttt caaagggagt gcttccagtt 164580

-continued tttgcctatt cagtatgata ttggctgtgg gtttgtcata aatagctctt attattttga 164640
gatacgtccc atcaatacct aatttattga gagtttttag catgaagggc tgttgaattt 164700
tgtcaaaggc cttttctgca tctattgaga taatcatgtg gtttttgtct ttggttctgt 164760
ttgtatgctc aattacattt attgatttgc atatgtggaa ccagtcttgc atcccaggga 164820
tgaagcccac ttgatcatgg tggataagct ttttgatgtg ctgctggatt cagtttgcca 164880
gtattgtatt gaggtttttt gcatcgatat tcatcaggga tattggtgta aaattctctt 164940
tttttgttgt gtctctgcca ggctttggta tcaggatgat gctggcctca taaaatgagt 165000
tagggaggat tccctctttt tctagtgatt ggaatggttt cagaaggaat ggtaccagct 165060
cctccttgta cctctggtag aattcagctg tgaaatccat ctagtcctgg actttttttg 165120
gctggtaagc tattaattat tgcctcaatt tcagaacctg ttattggtct attaagagat 165180
tcaacttcct cctagtttag tcttgggagg gtgtatgtgt cgaggaattt atccatttct 165240
tctagatttt ctagtttatt tgcatagagg tatttatagt attctctgat ggtagtttgt 165300
atttctgtgg gatcggtggt gatctcccct ttatcatttt ttattgcatc tatttgattt 165360
ttctctcttt tcttctttat tagtcttgcc agcagtctat caattttgtt gatcttttca 165420
aaaaaccagc tcctggattc attgattttt tgaagggttt cccatgtctc tatctccttc 165480
agttcttctc tgatcttggt tatttcttgc cttctgctag cttttgaatg tgtttgctct 165540
tccttctcta gttcttttaa ttgtgatgtt agggtgtcaa ttttagatct ttcctgcttt 165600
ctcttgtggg aatttggtgc tataaatttc cctctacaca ctactttaaa tgtgtcccag 165660
agattctggt atgttgtgtc tttgttctca ttggtttcaa ggaacatctt tatttctgcc 165720
ttcatttcat tatgtaccca gtagtcattc aggagcaggt tgttcagttt ccatgtagta 165780
gagtggtttt gagtgagttt cttaatcctg agttccagtt tgattgcact gtggtctgag 165840
agacagtttg ttataatttc tgttctttta catttgctga ggagtgtttt acttccaact 165900
cagtggtcaa ttttggaata ggtgtggtgt ggtgctgaga agaatgtata ttctgttgat 165960
ttggggtgga gagttctgta taagtctatt aggtccactt ggtacagagc tgagttcaat 166020
tcctggatat cctttgtgtc ttgttgatct gtctaatgtt gacagtgggg tgttaaagtc 166080
tcccttgatt attgtgtggg agtctaagtc tctttgtagg tctctaagta atcactttat 166140
gaatctggtt gttcctgtat tggtgcatat atatttagga tagttagttc ttcttgttga 166200
actgatccct ttaccattat gtaatggcct tctttgtctc ttttgatctt tgttggttta 166260
aagtctgttt tatcagagac tagcattgca atccctgcct cttttggttt tccatttgct 166320
tggtagatct tcctccatcc ctttgttttg agcctatatg tgtctctgca catgagatgg 166380
gtttcctgaa tacagcacac tgatgggtct tgactcttta tccaatttgc cagtctgtgt 166440
cttttaattg gagcatttag gttaatattt acgtttaagg ttaatattgt tatatgtgaa 166500
tttgatcctg tcattgtgat gttagctggt tcttttgctc gttggttgat gcagtttctt 166560
cctagcctcg atggtcttta caatttggca tgtttttgca gtggctggta ccggttgttc 166620
ctttccatgt ttagtgcttc cttcaggagc tcctgtagtg caggcctggt ggtgacaaaa 166680
tctctcagca tttgcttgtt tttaaagtat tttatttctc cttcacttat gaagcttagt 166740
ttggctggat atgaaattct gggttgaaaa ttcttttctt taagaatgat gaatattggc 166800
ccccactctc ttctggcttg tagagtttct gccaagaaat ccactgttag tctgatggct 166860
tccctttgtg ggtaacccga cctttctctc tggctgccct taacattgta tccttcattt 166920
caactttggc gaatctgata attatgtgtc ttggagttgc tcttctcgag gagtatcttt 166980
gtggcgttct ctgtatttcc tgaatgtgaa tgttggcctg tcttgctagg ttgggtaagt 167040
tctcctgggg aatatcctgc agagtgtttt ccaacttggt tccattctcc ctgtcacttt 167100
caggtacacc aatcagatgt agatttggtc ttttcacata gtcccatatt tcttggaggc 167160
tttgttcgtt tctttttact cttttttct ctaaacttct cttctcgctt catttcattc 167220
atttgatctt caatcactga taccettttt tccagttgat cgaatcagct actgaagctt 167280
gtgcattcgt catatagttc tcgtgccatg gttttcagct ccatcaggtc atttaaggcc 167340
gtctctacat tgattattct agttagccat tcgtctaatc ttttttcaag gtttttaact 167400
tctttgcgat gggttcaaac ttcctccttt agcttggaga aatttggtca tctgaagcct 167460
tctctcaact catcaaagtc attctccgtc caggtttgtt ctgttgctgg tgaggagctg 167520
tgttcctttg gaggagaaga ggggctctga tttttagaat gtttcagttt ttctgctctg 167580
ttttttcccc atctttgtgg ttttatctac ctttggtctt tgatgatggt gacatacaga 167640
tgggattttg gtgtggatgt cctttctgtt tgttagtttt ccttctaaca gtcaggaccc 167700
tcagctgcag gtctgttgga gtttgctgga ggtccactct agaccctgtt tgcctgggtg 167760
tcggcagcag aggctcagaa cagcgaatat tgctgaacag caaatgttgc tgcctactca 167820
ttcttctgga agtttcgtct cagaggggta cctagccatg tgaggtatca gtctgcccct 167880
actggtgggt gtctcccagt taggctactc gggggtcagg gagccacttg aggaggcagt 167940
ctgtccgttc tcagatctcc agctgtgtgc tgggagaacc actactctct tcaaagctgt 168000
cagacaggga catttaagtc tgcagaggtt tctgctgcct tttgttcggc tatgccctgc 168060
ccccagaggt ggagtctaca gaggcatgca ggcctccttg agttgcggta ggctccaccc 168120
agttcgagct tcccagctgc tttgtttacc tactcaagcc tcagcaatgg cgggtgcccc 168180
tcccccagcc tcactgctgc cttgcagttc gatttcagac tgctctgcta gcagtgagcg 168240
atgctccatg ggcgtgggac cctccgagcc aggtgtggga tataatctcc tggtgtgccg 168300
tttgctaaga ccattggaaa agtgcagtat tagggtggga gtgacccaat tttccaggtg 168360
ccatctgtca cagctttgct tggctaggaa agggaatttc ctgacccttt gcacttcccg 168420
ggtgaggcga tgcctctccc tgctttggct cacacttggt gcactgcacc cactgtcctg 168480
tacccactgt ccaacaagcc ccagtgagat gaacccggta cctcagtcgg aaatgcagaa 168540
atcactcatc ttctgcgtca ctcacgctgg gagctgtaga ctggagctgt tcctattcgg 168600
ccatcttatg aatcatgcat gttcaactat gagcaactat gtgtattcaa tgggaaatgg 168660
aataccataa aattgtcata tgttgagccc aaaatgatag gatagaattt gatagtctga 168720
ggatggaaag gaccttcaag gccactttta aaaaccccat tcccatatga tgcttgaatt 168780
cttaaccact gtgtgtctag tattttctca tttccagtga tatgtgtgcc tgccaacctt 168840
tccgtctcca agagctttaa ctatcaaaat gtatgtgtgt gtgtttttgt gtgtgcatgt 168900
gtgtgtgagt gtgcgtgtgt gtgtgtgtgt gtttagagag agagagagag acagaaagag 168960
aaggagagac taaaatccaa ttcactgttc tttctgggac ccaaagaaca agtctagtca 169020
ttctccattt ctagtctctt tccctagcaa tcggctagac atgctagaca tagacacatg 169080
tacatcactc ctttgaatta caacattcag tatttgtcta tcacttatat gataaaatac 169140
aaacttagct tttattttta tttttttaga gacagtgttt tactatgtca cccaggctag 169200
agcatcagtg gcacaatcat agcccactgc agcctggaac ccctgggctc aaggaatcct 169260
tccacctctg cctcctgagt agcagagact acagatgtgc accaccagac ccagctaatt 169320
tggtttttta ctatttttg tggagatggt gtattgtctt gtggtgttgc tcaggctgat 169380
cttgagctcc tggcctcaag cactcctccc atctcagcct cccaaaatgc tgggattaca 169440
ggcatgaacc accttaccca gccaaatttc ttaatatgat atacatgctc ctttaaaatc 169500
aagcaccatc tttgctttca acctcattat taaccacttt cccatatatg caacatatgt 169560
ttcagccata ctagtgtcta gtttttccct gaacactcct tggtgctttt gtttatgccc 169620
tttctgccca cctttgcctg gtgaaatcct catcaatctt caaattctat caaatactat 169680
cttccatata aagcattttc taaacccacc tatgtaaaaa gattagtgtt ttcctatttt 169740
gttgatgcct ccattgcagc attttccagt ccaacgtttt ctagaattga ttgtggccag 169800
gctaccagac tgggccaggg cctgtgtctt ttctgtcacc cagaagcaaa ggtctaacaa 169860
tggatatctg ctgaatgaat gaacgaaaat gaatcattaa tatattagta aatacgttaa 169920
ttaaagttcc aggtatgaat actgaaggct gcattcaggc agagctggat ccaaggatat 169980
gctaggttgg tctagcacaa gaatcagagt tttcctctgc aagctatgaa aaatttgggt 170040
ttagcaggta tttgggatga tgaattatac atttaaccag tgttgaatga gcacttgtcc 170100
ttaaggagtt tagagtctgt gaccagggag aatggtgatt ttcttagcta gggcagtttt 170160
tctaaaaagg tagttgcatt gtgtgttttt gaccactgat gataaattca agtctctctt 170220
ccttcccaat agcccggaag ctgaagaaac ttggtaatct gaaactacag gaggaaggag 170280
aggcttccag caccaccagc cccactgagg agacaaccca gaagctgaca gtgtcacaca 170340
ttgaaggcta tgaatgtcag cccatctttc tgaatgtcct ggaagccatt gagccaggtg 170400
tagtgtgtgc tggacacgac aacaaccagc ccgactcctt tgcagccttg ctctctagcc 170460
tcaatgaact gggagagaga cagcttgtac acgtggtcaa gtgggccaag gccttgcctg 170520
gtaaggaaaa gggaagtggg agcatgagat aagggggatc atatttagtg aacgctccta 170580
tggaccagcc accatgtctg gtgcttttct gcccattaac tcaggcagtc ttcatcataa 170640
ccctgtggga gagggattgt tacaagtctc aatttaaaca tacagggatc gaaactcaga 170700
aagcaaagag aaagatagta ttatcgggtg tcttatgtgg cccacattga tgcacagcag 170760
tcatgctttc atattcaact cacaaaaatg gtcagcaaat tttccattaa tcacaaatca 170820
catagacata cccatatatg ccttaggatg ctcttctata tttgcacaca caggctcacc 170880
ccaaagataa tctctagttt gactgacatt ctgtcttcaa tgtcatcttt aggagctata 170940
tcatgggaac tctcataata tggtatggtg gaaagaacat gaggttggga atcagaacac 171000
ttcgggtctg ctcttagctc tgctagtaac ttattgtgtg atcccttccc cttctgggtc 171060
tcaatttctc tatctgtata atgtataaag cgtggtttgt atcaaattga tggtttccag 171120
tttttgaaaa aaggaacgct ttttgcacct taaactacct aaggaatcat aatgagagga 171180
aagattaggt aatagtgaaa gaattaccaa gtgttggtct aacagaagtt ggataacaga 171240
agttcctcag tgatggggaa ctcacttctt tcttatgtca tctgttgttt aaacaagtct 171300
ggttattaaa atattacagc ttaaggaatt cttagagatc ctctatccaa tgattcacaa 171360
actttccttt agcagccaag tgctttattt ctcaaaagaa ttgtacacag atacaagtgg 171420
agctagttta tttaaagcca gagcctgtag cttgggcctc accagttcag cctctttctc 171480
tctatcccag ggaagcccta ggtcactctt gcaaaatctt agggctccaa ggaacacagt 171540
ttgaaaacca gtgaagtata tgccctttaa aggttctcct aatcctgcaa ttatgattca 171600
aagattcttt tgaaataaca acaaccaaac cttctcttgt ggagtcaaag attaacctgc 171660
ctttcaataa taactgccat tcaggtagaa atttatagtg aacagagcaa ttttgtatgt 171720
attacctgaa ttgattctta taggaatcct ataacatgag attctttctc ttattttaca 171780
gaccaaatag ggaagctgtg agaatgatgt gattggccta tagttacata gtcagaaaat 171840
agcaggacca gaacttgagc ccaggttctc tcctgattcc aaattctctc tattccactc 171900
cacctgtagg ctgtagcacc actgcagttc tgtagctctg ggctttacag tgaggggcca 171960
aggcttcatt gaaggccact tgggtcatag tatgggcttg ttgcatttga agacatttca 172020
tgttggctgt caagtcttag atttgtattt ccaactcaca gggcctggtc acagccctaa 172080
ccatctctta taccttctca gcttgggaag ctgaggtcga ctagccaata agaacactgg 172140
gaaggaaacc caaggactct gactggatat gctctgtgcc aaaacagagg gttcactcag 172200
agaggaaaaa tataaaaaag aaaaaggaga aggttgcttt aattcttatc actttttcat 172260
ctggatattt tgatatcatg tgtttgacag agattcaaag tttaatcttc ccaagcagtt 172320
tccaaacact tatctcattt tataggctac agagcttttt catatatatg atcccactta 172380
atctttacaa caattctatg aatcatagag actattattt ccatttcaca tgccaaggct 172440
caaagaggtt aactaacttg ctccatttgg tcacttaaca catggaacca gaacttgacc 172500
tagaccttcg ggtttctaaa ttggttatct tgacaataac ctagtgcaaa acactatagc 172560
agaatttgta tgacttggga tcactggggc tttccttggc ccaaccacca agatggaaag 172620
ccccctcccc ttacattaac aaatctgcaa gccaatatca gttcaccatc tagcttgcca 172680
gactaaatga tttctgaccc caagtctttt aaaagaatag cttcaaaaga aagccaatta 172740
ccacattcac aagaactgtt cttcatatta tctataatta cctacaagta caagtaattt 172800
gctaattcaa tagattgagt tcttgacctg taagatgaac tgtgctaggc ccctaataag 172860
ataaattttg ttttaagttt tctgtgacag taaagatgta tgaaaattgc ctagtagagt 172920
acctggcaca ttaataaatg ataactgtta atttggagtg ggtgagtaga ctgggtgtgc 172980
acagtatatt tagaatcaaa tttatctggt ttggaatcct agctatggac tagttctgtg 173040
accttgagca aatcacatgt cttctctgtg cttctgtgtc ctcatttgta agatgataga 173100
ataatcacta cctttcaaat tgttgtcaac aaaaagatta tgtataaaga gcacctagta 173160
acgtagcctg aaacatagtc aatgctctgt aaatggtggt ttattattat gagacttgaa 173220
tgctaagcca ctgctttcac gaaactcaat tttagctacc acttgccttg cctagaagct 173280
catgcatgga ccccaaggtg aaattgtgtt ctctgaagac ctcggctggc agatgtacta 173340
cagcagcaaa gatttccaaa ctggcctttc tttgagccca ttctcccaga ctagacagga 173400
gactacaagt ttctgctgca catgaaaaaa atatgatgtc aatcggattc tagtgagaaa 173460
acagagtctc aaagaaactg cttctgctcc ctagcgtgtt taatgtgttt cagaacctga 173520
gaatgactcc tctctgtttc tccagaacag cctaacacag tggcaaatgg gtgttgagtg 173580
aatgcatact taaggaaatc tgtagggttg cagctactct ttcctcaagt aatcccttga 173640
tagtcatgta ggctacttca gagattgggc attagagaac agagtcaggt attataatca 173700
gattagactc tagggaggtt agccagccat attgctgata tgtgcacagt tactgggttt 173760
gagtgctaag cagctctcat taaggacggt taattaatat tatggccaaa ttaagctttc 173820
ccttttctct cctctttgtt agttcggtgg cattttaggg agaaaaaaat aagcatcagt 173880
atggacaatt tgcttgatac ctgtacaatt taattctcat ccttccatgt gccttcacat 173940
tcacacattc caccagaaga ccaaggttca ccagccaaaa gcttttcttg ctccccactg 174000
cctcctaccc aagatattca gggtcaacct cccaggcctc ttctctaaga gatccttggt 174060

-continued tgctacatgc ttagaccctg cttcttattt cctgctgaga agggtcagtc caaggcattc 174120
tgtgctacag aagggttcca agcaggaact actctgggat ctgaggctcc agccggtctg 174180
tcagcgtgtc attacagtga aggtgggaag cacaggcctg ggagctaaga ctgctaagat 174240
gagggactct agaatccctg atacctggaa ggcctaggat ctaaaagaaa agaacaggga 174300
aatggggcta tatgagtgga cagggaccaa ccaagcagaa caatgtgtct ggataatgta 174360
gacttcagac ctgatcctat ggctgacaaa agctggtgac cttggtagtt cctgagctgt 174420
aaccttcatt agtggagtag aaaaaacact ggagaagaga atcagaacac ctgggttcta 174480
gtattagttc agccacatat aaaccatatg accttgggta agtcagttta tttctctggc 174540
cctcatgttc cttgttggta aaataagtgc cacatcacct aacctctggg attattgtga 174600
gagttaaatt aggtcatcaa caggaaagtg agaagtttga tctaaatttg gggaagcatt 174660
cctaatgagg tatgatgaca aaatttcaga taattctgga tttgttggtg agaagagaga 174720
gtgttggtag ggacgagctc tgaggtgatg cctttataac tttaagcatc caactgtttc 174780
aaaaactcca ggagaacatg gccatgtctg ttctacctgt gtattattgt agacgtagct 174840
tctgggagcc tctgctctct gagcttaagg gaggtaattt ggagatcatt taattctcat 174900
tttacaaaag gaaaaaaaat tgagggtctt taggccattt gtttaggtaa tatttcttaa 174960
gtgcccactc aaatacgtgg actgtactaa gtactaggga ggtaaagata aataagaaga 175020
tatggtccct gtcttcaaga agctccaagt cttgtggggg agacagacat gtatatacat 175080
agacttcaat gctgtgtaat gactgctata attgggtgag gctacacaag gtgcaatgag 175140
aatgtaaaag aagaatcttt aagccttctt cttggatgag ttgggaaagc cttcacagaa 175200
gaggtagcct ttgagtgaag acttgaaaga tgagtagtgt ttaccggatg aaaggcctga 175260
gaaggaggaa tgcattctag gcaaaagtaa ctgcctgtgc agagataaca gagatataga 175320
ggcatgtgag agcgcaagtg gcaagagatc agtctaggta ggcaggtcat aaagggccta 175380
ttcatgtata atgatggcag taagatgagg atggcagtag ggtgggaaat tagtagggcc 175440
agggtaccta ttgagtagaa aagaatggag aggaaatgcc aggcagaaag aggatggacg 175500
caagagaggg aacatgaaag tggtgaacag gtggcagtgg ctgtcaagac atctctccat 175560
accctgtaca ctgtatgtaa tatccatctc ccagggttgt tagaagggtc aaaccagatc 175620
gtagctggaa aacagctttg tgaagtgaaa actgctgttt atgtgggggga aatgattgtt 175680 aaactgcatc tttggaaagg tgaagtgatc aagagcacag accttggaat ctgactgctt 175740
tgctttgtaa cttggtctgc caattactag ctgtatgatc ttggacaagt tccttaacct 175800
ctctctgact cacttgtact ggttcacaga atggagataa taatagtact taccttactc 175860
attgttgtga atgttaaatg agataaatata agtaaagtgc ttagaaaaga gttaaatgta 175920
ccccataaat acatacaact atcatgtacc caaaattatt tttaattttt ttaaaaaaga 175980
gcaatccaat agcaaaagaa aaaaagagtt cactcatata agcagtcaat aagtgttaga 176040
ttatttttct cttacaactg acaatgccct ttttgtctcc atcatcatct catttgagca 176100
gctcagggaa gtagggagga taaggaatat tatcctcacc atatagtttg tgcttttccc 176160
caccacccct taatggccag cctggatggt ccctggggat ccttagggga tgcccgaata 176220
ccagagcatc tctgcccaac agggactcag acttagctca acccgtcagt acccagactg 176280
accactgcct ctgcctcttc ttctccaggc ttccgcaact tacacgtgga cgaccagatg 176340
gctgtcattc agtactcctg gatggggctc atggtgtttg ccatgggctg gcgatccttc 176400
accaatgtca actccaggat gctctacttc gcccctgatc tggttttcaa tgagtaagtg 176460
ctcctggggc ccagacctca ctaaaataca gcagcttggc cagacctggt tggtggtgat 176520
ggtgatgggg tgacagtgaa gcttagctca tttgatctgc agttgtcgca gcggatgccc 176580
cagccagcca atccagtatg aggcggcttt gccctggctt tcagccaact ggcaggagcc 176640
caggaggatg gtgctgagac cacccctttc acacccaaga accaatccta gtcatatttc 176700
tggtctgctt tgcagcttat ctcaaaacca catggaaaga ttcctcccct tcacatataa 176760
aagaggcaga aagactctgg ctttaagggc tggagtttct tgggttcttt tgctaccacc 176820
aaaggctact tctagtcacc atttgctgag caactagttt gtgccaagac tatgctagat 176880
actttctaaa tcctagctca ttgagtcctc atggtgacct gacctcacct ttttatagat 176940
aacactattt ttttatggat ggggaaaatc aggctcagca aaataaagtg actcacccaa 177000
agtcacagag ctagtgcctg ttggagacaa gattcaaacg tatgtccctg tcgatctcag 177060
ctcttctgcg tcatggtggt aactgatggg aaggagtacc tctaccgctc tctggctgtg 177120
tgaccttggt actgccattt tccttccctt aaacagcttt aattaatacc tgccctgcca 177180
ccagctccat ataacatcat gaatttggcc agtggctcag attttggaat tacatttttc 177240
tccactaaaa tctcagttct actattttct tagtcagcat ctttgggaaa gacctttaac 177300
ttttccgacc ctcaatttct tcatccatta atgataacag aaccttcata agtaatttct 177360
tatgataact aaatgggaat tgacagatgt ggaatgtctg gcccatagta ggcaagaagg 177420
aaaaaaaaag tccctttctg attcaccctt tccctaatag tgatacattt tttttccccg 177480
agatggggtt ttgctctgcc acccaggctg gagggcagtg gcgcaatgat ctcagcccag 177540
tgcaacctcc acctccctgg ttcaagcaat tctcctgcct cagcttcccg agtagctggg 177600
attatagatg cccgccaccg tgtccatcta atttttgtat ttttggtaga gacgggattt 177660
caccatgtta gccaggctgg tctcaaactc ctgacctcat gatctgcccg cctcagccgg 177720
gcatgataat cttttctatg tctgctgtat gaggtccctc gatggcattg tgaatggagc 177780
tggccagaga aatcttccca aggaccttga gctagtctca ccacagagaa tccttccagt 177840
caggacagga attgaccttc ccccctcttc agccctctaa cccagaagag tcttaaaata 177900
aaatctacag gccaatggtt ccttccagta cagcactgca atgcgaggga gagtgagcgt 177960
ccccagctgc cctctcccaa ccctgccagc ctggtagcca aaagctaaga ataaccacta 178020
ggcttttggc acaaactgct ttgtggtttt cagatctccg caaagttgcc tatgatgcca 178080
tcttctgggg caggccttga aaagccccct aactgttcat ctcccatcct taaacccctg 178140
ctgcccttaa gcagttgaat caactccatg agcacctgct ctaccttccc cagagccctg 178200
agacctttgg agctttgaaa agtgataatt ggttgttctc taaatcctca tttccttctc 178260
tgcctctaag taagcatgtg gcatcccacc tcggcttcct ggtccagtct tgttcatctt 178320
ataaaaaggc ctccctacgg ggtcagaggc ctagacccat caaacccagg gctcctgaaa 178380
caataggacc cctattcctc ctgtaggaag ccactgtgtt agagctctca gggtgtctac 178440
aaacatctag ataagtgttt ctcaacatgg attctgttga catattggga aaaataattt 178500
tgtcattatg tagaatatgg ttaacatacc tggcaccagc ctactctata ccaaatagga 178560
ttccagtcat tctgacagcc caaactgctc ccacacattt ctgacaccca ctgaagaggc 178620
agtactctcc agttgagtgc aactaatccc tgccagcctt cctaaggtgc taatggggag 178680
cctcagaccc aaagagagag agaagaactt gtccaatgta ggtcaaccca tttgctgatc 178740
tcttcaacac caagctctat tatcagccct gtttttttct ttctttctct ctttgtagag 178800
atcacatgtt gtgaggataa tgagcttgaa ccttagctgt gtgaccttgg gcaaattact 178860
gaacttctat gtgccgcaaa ttttatctgg agactgctga agagtattat aatagcacct 178920
ttctatatgt catttattga acacctgcta tgtgtcaggc actgtgctca gtgttttcca 178980
atcttcattt ctcctcttat tttctctctt gcactcccac caaccttgtt ctcttcctaa 179040
attccattcc tgcctcattt ttctaccctc cattctcctc tctcttcctt cctttaactg 179100
tctccctagt atttttcccc ttttccccct ttcttttccc cttcccccat gaatttcttc 179160
tctttccttt ccccttctct ttcctccatt ccccactttt tctgcccctg aggcctgcag 179220
caatgttaaa ggaatcctca ttccagcatt gtgatttcaa tggtaaaaag attgcagcat 179280
tgtcatcaac agaggtggga aagtacattg gagactggag cagagccaga cctcagggtc 179340
agccaatctt actaaaaaat tctctacagt gaaagagctt ggagcaacac tgttctgctc 179400
aattgatttg tgataccatc taaacacttc ctctttctag ttgggcttca gcctgagttg 179460
aataattcta caccatctgc cctcttctct ctttctccag gacagccaag atctctctga 179520
gataggatgc tgagcttcca cccagacaat accaggcctg ctcatcctat ggagtaggct 179580
agtggcttgg aaaccaaaat gtcaaaccat agcctttagg ctccatctgg gaggtctttg 179640
tcctcaccac ttaagtgggt gtcaaatttc cttccctttc tgcacacgct gcacaatcaa 179700
tttctgtctt acacacacac acacacacac acacacacac gatttttgaa gtgctgaaaa 179760
ctggaaggcc tactagcatg aggatgctgt gtcttctctt agaggtatgc catggtcagc 179820
catggaaccg agaggttgct cttccttgaa aagctggcca agcattggcc acttccccat 179880
ataatttata ggtgataatg tggtgatctg ttcagaagtg actataataa atgcaactca 179940
catatgtcta cagtttccaa actgtggtaa ggagcagcca gcatatgagg gaatgggctc 180000
cccttcagca ggggacattt aaactagaca ttcaaaaaca ctccctggca gatttaacat 180060
tggaactcgt tttgaaagaa caatgtggaa tctccttcac tgggagtttt tgaataagta 180120
tgaaatttct agtattccag gccagaggca aaggggtcaa caggatgacc aaacacttcg 180180
ggtcatttgc aaatcttgat gtcctgatgt taagagctga ctactggggc ttctcctaaa 180240
aatccttcat gttgagctgc ctggaaggca ggttctcatt ctggctgtag ctgagatgtt 180300
agaactgtag tcagggagac catgtgcctc ccccattgtg ttcatttggt taggctttcc 180360
tgtccctgac tcagaaaaca gaaggggcac agagacctgg aaattccatg tgctaaccca 180420
tatcctggcc agagaagatg agtagttatc agggtgtcag gattttggaa aacagagaga 180480
gaaaaaaaac aaacaaacag acaaacaaac aaaaaaacct tttcctggtc cctggagcac 180540
cagcaggaga aacagcaagc tcttcttgga aaacctggcg agggatggca atcagagaca 180600
ttccctctgg gcttattgta aacttcccct cattcctttt tcctctgtgt atctccttcc 180660
caggtaccgc atgcacaagt cccggatgta cagccagtgt gtccgaatga ggcacctctc 180720
tcaagagttt ggatggctcc aaatcacccc ccaggaattc ctgtgcatga aagcactgct 180780
actcttcagc attagtaagt gcctagaagt gcagggaatg ccccctgagg gcacagagat 180840
tcagagagga ccacttttgc cattaaaaca ttattaggga aaagccagct cctggacatt 180900
tcccttcttc attccccctc cccatcccca ctctactctc tctcagcatc attttcctaa 180960
caagaaacaa tttcatgact agaagccaat ttatttgcta gaagtcaacc tccatcagat 181020
tccccaccta tccccagtct gtctttggga caaggccttt ttgactggtt acagcaggtc 181080
tctgaatttt tccatagctt ctgctataga aacagacatg ggccaccttg tattctttgc 181140
agggcagtag agcaggaggc atttcctcct ggaaagattt cctcttctgc caacaggagg 181200

-continued agatctatgt aagcaactca gataggattt gtatggcagc caaggaactt ttctttaata 181260
tcttttctaa gagccctctc ttagcccta cggagggaga agggcaaaat ttgatattca 181320
aagctatgtg ttttggttat ctaaatcagg gttttactgt gaatgacata aaagcttagg 181380
tcctaaaaaa tgagtatctg agaagagtag aaaaagaaaa ggttcaggaa atttgattta 181440
cttgactcct ttcagatcgg atccagctat cctttcccct gagatctccc tgacagactg 181500
aaggccccaa gcacacagac ttcaactaac aggaagccaa gtagatggtt ccctgtgggg 181560
gtgggggtca agtctgtggt cagaaaactt ggtgctttgt ctaatgctcc ttcgtgggca 181620
tgcttcccct ccccattctg tcttcatccc acatcagttc cagtggatgg gctgaaaaat 181680
caaaaattct ttgatgaact tcgaatgaac tacatcaagg aactcgatcg tatcattgca 181740
tgcaaaagaa aaaatcccac atcctgctca agacgcttct accagctcac caagctcctg 181800
gactccgtgc agcctgtaag caaacgatgg agggtgcttt atcagggaga acagcctgat 181860
agagccaatg ataatatgct tctctagagt ctggcaccac ctgttgggag gtgcttccat 181920
tcccctctgg ctttgagtgt ggtccaggaa gaaaatgtgg tgaagaaaag aacacgggtc 181980
acagtgtccc agctggatat tgtgaaaggg gtggaggagt tgagaacaga gcagttggga 182040
ctcagggaag ggacttgcag cagatgaatt ctctaggcag acaaaacaga cctggatgtt 182100
tttcccctct tctttgagtc atgttcatgt gagtttgtct gtctgtgtgt gtgtgtgtgt 182160
gtgtgtgtgt gtgtgtgtgt gtgtcagaga gagagagaga gagagagaga tggagtgcgg 182220
aggcttgggt gagagcacaa gctggagaag tcttgagtca gagagcttac aatggtataa 182280
gacatctctt gggagccctc agtgactcca tggagaccat ttctttctct ctctctcgct 182340
gtctctctct aacacacaca cacacacaca cgacctcatg ggggaggacc aaggaagtac 182400
ggggaagggg gaggaaacaa aaggctgaaa gaccaaaaat cagaggttgg ggaagaggct 182460
agcagaggcc acctccttgt caaccctgtt tttctccctc ttattgttcc ctacagattg 182520
cgagagagct gcatcagttc acttttgacc tgctaatcaa gtcacacatg gtgagcgtgg 182580
actttccgga aatgatggca gagatcatct ctgtgcaagt gcccaagatc ctttctggga 182640
aagtcaagcc catctatttc cacacccagt gaagcattgg aaaccctatt tccccacccc 182700
agctcatgcc ccctttcaga tgtcttctgc ctgttataac tctgcactac tcctctgcag 182760
tgccttgggg aatttcctct attgatgtac agtctgtcat gaacatgttc ctgaattcta 182820
tttgctgggc tttttttttc tctttctctc ctttcttttt cttcttccct ccctatctaa 182880
ccctcccatg gcaccttcag actttgcttc ccattgtggc tcctatctgt gttttgaatg 182940
gtgttgtatg cctttaaatc tgtgatgatc ctcatatggc ccagtgtcaa gttgtgcttg 183000
tttacagcac tactctgtgc cagccacaca aacgtttact tatcttatgc cacgggaagt 183060
ttagagagct aagattatct ggggaaatca aaacaaaaac aagcaaacaa aaaaaaaaag 183120
caaaaacaaa acaaaaaata agccaaaaaa ccttgctagt gttttttcct caaaaataaa 183180
taaataaata aataaatacg tacatacata cacacataca tacaaacata tagaaatccc 183240
caaagaggcc aatagtgacg agaaggtgaa aattgcaggc ccatggggag ttactgattt 183300
tttcatctcc tccctccacg ggagacttta ttttctgcca atggctattg ccattagagg 183360
gcagagtgac cccagagctg agttgggcag gggggtggac agagaggaga ggacaaggag 183420
ggcaatggag catcagtacc tgcccacagc cttggtccct gggggctaga ctgctcaact 183480
gtggagcaat tcattatact gaaaatgtgc ttgttgttga aaatttgtct gcatgttaat 183540
gcctcacccc caaacccttt tctctctcac tctctgcctc caacttcaga ttgactttca 183600
atagtttttc taagaccttt gaactgaatg ttctcttcag ccaaaacttg gcgacttcca 183660
cagaaaagtc tgaccactga gaagaaggag agcagagatt taaccctttg taaggcccca 183720
tttggatcca ggtctgcttt ctcatgtgtg agtcagggag gagctggagc cagaggagaa 183780
gaaaatgata gcttggctgt tctcctgctt aggacactga ctgaatagtt aaactctcac 183840
tgccactacc ttttccccac ctttaaaaga cctgaatgaa gttttctgcc aaactccgtg 183900
aagccacaag caccttatgt cctcccttca gtgttttgtg ggcctgaatt tcatcacact 183960
gcatttcagc catggtcatc aagcctgttt gcttcttttg ggcatgttca cagattctct 184020
gttaagagcc cccaccacca agaaggttag caggccaaca gctctgacat ctatctgtag 184080
atgccagtag tcacaaagat ttcttaccaa ctctcagatc gctggagccc ttagacaaac 184140
tggaaagaag gcatcaaagg gatcaggcaa gctgggcgtc ttgcccttgt cccccagaga 184200
tgataccctc ccagcaagtg gagaagttct cacttccttc tttagagcag ctaaaggggc 184260
tacccagatc agggttgaag agaaaactca attaccaggg tgggaagaat gaaggcacta 184320
gaaccagaaa ccctgcaaat gctcttcttg tcacccagca tatccacctg cagaagtcat 184380
gagaagagag aaggaacaaa gaggagactc tgactactga attaaaatct tcagcggcaa 184440
agcctaaagc cagatggaca ccatctggtg agtttactca tcatcctcct ctgctgctga 184500
ttctgggctc tgacattgcc catactcact cagattcccc acctttgttg ctgcctctta 184560
gtcagaggga ggccaaacca ttgagacttt ctacagaacc atggcttctt tcggaaaggt 184620
ctggttggtg tggctccaat actttgccac ccatgaactc agggtgtgcc ctgggacact 184680
ggttttatat agtcttttgg cacacctgtg ttctgttgac ttcgttcttc aagcccaagt 184740
gcaagggaaa atgtccacct actttctcat cttggcctct gcctccttac ttagctctta 184800
atctcatctg ttgaactcaa gaaatcaagg gccagtcatc aagctgccca ttttaattga 184860
ttcactctgt ttgttgagag gatagtttct gagtgacatg atatgatcca caagggtttc 184920
cttccctgat ttctgcattg atattaatag ccaaacgaac ttcaaaacag ctttaaataa 184980
caagggagag gggaacctaa gatgagtaat atgccaatcc aagactgctg gagaaaacta 185040
aagctgacag gttccctttt tggggtggga tagacatgtt ctggttttct ttattattac 185100
acaatctggc tcatgtacag gatcactttt agctgtttta aacagaaaaa aatatccacc 185160
actcttttca gttacactag gttacatttt aataggtcct ttacatctgt tttggaatga 185220
ttttcatctt ttgtgataca cagattgaat tatatcattt tcatatctct ccttgtaaat 185280
actagaagct ctcctttaca tttctctatc aaatttttca tctttatggg tttcccaatt 185340
gtgactcttg tcttcatgaa tatatgtttt tcatttgcaa aagccaaaaa tcagtgaaac 185400
agcagtgtaa ttaaaagcaa caactggatt actccaaatt tccaaatgac aaaactaggg 185460
aaaaatagcc tacacaagcc tttaggccta ctctttctgt gcttgggttt gagtgaacaa 185520
aggagatttt agcttggctc tgttctccca tggatgaaag gaggaggatt tttttttct 185580 tttggccatt gatgttctag ccaatgtaat tgacagaagt ctcattttgc atgcgctctg 185640
ctctacaaac agagttggta tggttggtat actgtactca cctgtgaggg actggccact 185700
cagacccact tagctggtga gctagaagat gaggatcact cactggaaaa gtcacaagga 185760
ccatctccaa acaagttggc agtgctcgat gtggacgaag agtgaggaag agaaaaagaa 185820
ggagcaccag ggagaaggct ccgtctgtgc tgggcagcag acagctgcca ggatcacgaa 185880
ctctgtagtc aaagaaaaga gtcgtgtggc agtttcagct ctcgttcatt gggcagctcg 185940
cctaggccca gcctctgagc tgacatggga gttgttggat tctttgtttc atagcttttt 186000
ctatgccata ggcaatattg ttgttcttgg aaagtttatt attttttaa ctcccttact 186060 ctgagaaagg gatattttga aggactgtca tatatctttg aaaaaagaaa atctgtaata 186120
catatatttt tatgtatgtt cactggcact aaaaaatata gagagcttca ttctgtcctt 186180
tgggtagttg ctgaggtaat tgtccaggtt gaaaaataat gtgctgatgc tagagtccct 186240
ctctgtccat actctacttc taaatacata taggcataca tagcaagttt tatttgactt 186300
gtactttaag agaaaatatg tccaccatcc acatgatgca caaatgagct aacattgagc 186360
ttcaagtagc ttctaagtgt ttgtttcatt aggcacagca cagatgtggc ctttcccccc 186420
ttctctccct tgatatctgg cagggcataa aggcccaggc cacttcctct gccccttccc 186480
agccctgcac caaagctgca tttcaggaga ctctctccag acagcccagt aactacccga 186540
gcatggcccc tgcatagccc tggaaaaata agaggctgac tgtctacgaa ttatcttgtg 186600
ccagttgccc aggtgagagg gcactgggcc aagggagtgg ttttcatgtt tgacccacta 186660
caaggggtca tgggaatcag gaatgccaaa gcaccagatc aaatccaaaa cttaaagtca 186720
aaataagcca ttcagcatgt tcagtttctt ggaaaaggaa gtttctaccc ctgatgcctt 186780
tgtaggcaga tctgttctca ccattaatct ttttgaaaat cttttaaagc agtttttaaa 186840
aagagagatg aaagcatcac attatataac caaagattac attgtacctg ctaagatacc 186900
aaaattcata agggcagggg gggagcaagc attagtgcct ctttgataag ctgtccaaag 186960
acagactaaa ggactctgct ggtgactgac ttataagagc tttgtgggtt tttttttccc 187020
taataatata catgtttaga agaattgaaa ataatttcgg gaaaatggga ttatgggtcc 187080
ttcactaagt gattttataa gcagaactgg ctttcctttt ctctagtagt tgctgagcaa 187140
attgttgaag ctccatcatt gcatggttgg aaatggagct gttcttagcc actgtgtttg 187200
ctagtgccca tgttagctta tctgaagatg tgaaaccctt gctgataagg gagcatttaa 187260
agtactagat tttgcactag agggacagca ggcagaaatc cttatttctg cccactttgg 187320
atggcacaaa aagttatctg cagttgaagg cagaaagttg aaatacattg taaatgaata 187380
tttgtatcca tgtttcaaaa ttgaaatata tatatatata tatatatata tatatatata 187440
tatatagtgt gtgtgtgtgt tctgatagct ttaactttct ctgcatcttt atatttggtt 187500
ccagatcaca cctgatgcca tgtacttgtg agagaggatg cagttttgtt ttggaagctc 187560
tctcagaaca aacaagacac ctggattgat cagttaacta aaagttttct cccctattgg 187620
gtttgaccca caggtcctgt gaaggagcag agggataaaa agagtagagg acatgataca 187680
ttgtacttta ctagttcaag acagatgaat gtggaaagca taaaaactca atggaactga 187740
ctgagattta ccacagggaa ggcccaaact tggggccaaa agcctaccca agtgattgac 187800
cagtggcccc ctaatgggac ctgagctgtt ggaagaagag aactgttcct tggtcttcac 187860
catccttgtg agagaagggc agtttcctgc attggaacct ggagcaagcg ctctatcttt 187920
cacacaaatt ccctcacctg agattgaggt gctcttgtta ctgggtgtct gtgtgctgta 187980
attctggttt tggatatgtt ctgtaaagat tttgacaaat gaaaatgtgt ttttctctgt 188040
taaaacttgt cagagtacta gaagttgtat ctctgtaggt gcaggtccat ttctgcccac 188100
aggtagggtg tttttctttg attaagagat tgacacttct gttgcctagg acctcccaac 188160
tcaaccattt ctaggtgaag gcagaaaaat ccacattagt tactcctctt cagacatttc 188220
agctgagata acaaatcttt tggaattttt tcacccatag aaagagtggt agatatttga 188280

-continued atttagcagg tggagtttca tagtaaaaac agcttttgac tcagctttga tttatcctca 188340
tttgatttgg ccagaaagta ggtaatatgc attgattggc ttctgattcc aattcagtat 188400
agcaaggtgc taggtttttt cctttcccca cctgtctctt agcctgggga attaaatgag 188460
aagccttaga atgggtggcc cttgtgacct gaaacacttc ccacataagc tacttaacaa 188520
gattgtcatg gagctgcaga ttccattgcc caccaaagac tagaacacac acatatccat 188580
acaccaaagg aaagacaatt ctgaaatgct gtttctctgg tggttccctc tctggctgct 188640
gcctcacagt atgggaacct gtactctgca gaggtgacag gccagatttg cattatctca 188700
caaccttagc ccttggtgct aactgtccta cagtgaagtg cctggggggt tgtcctatcc 188760
cataagccac ttggatgctg acagcagcca ccatcagaat gacccacgca aaaaaaagaa 188820
aaaaaaaatt aaaaagtccc ctcacaaccc agtgacacct ttctgctttc ctctagactg 188880
gaacattgat tagggagtgc ctcagacatg acattcttgt gctgtccttg gaattaatct 188940
ggcagcagga gggagcagac tatgtaaaca gagataaaaa ttaattttca atattgaagg 189000
aaaaaagaaa taagaagaga gagagaaaga aagcatcaca caaagatttt cttaaaagaa 189060
acaattttgc ttgaaatctc tttagatggg gctcatttct cacggtggca cttggcctcc 189120
actgggcagc aggaccagct ccaagcgcta gtgttctgtt ctctttttgt aatcttggaa 189180
tcttttgttg ctctaaatac aattaaaaat ggcagaaact tgtttgttgg actacatgtg 189240
tgactttggg tctgtctctg cctctgcttt cagaaatgtc atccattgtg taaaatattg 189300
gcttactggt ctgccagcta aaacttggcc acatcccctg ttatggctgc aggatcgagt 189360
tattgttaac aaagagaccc aagaaaagct gctaatgtcc tcttatcatt gttgttaatt 189420
tgttaaaaca taaagaaatc taaaatttca gatgaatgtc atcagagttc ttttaattag 189480
ctctttttat tggctgtttt tattgaagtc aagagttggt atcatgcccg gttgcgtttt 189540
atgctatttt gattttcata tatttttaaa agtctttgca caagggttac aaatttgccc 189600
tgtggtggcc ttagcataag ctgacctggg accaccaaaa taacaaggaa tttgggctag 189660
aaagcacaga tggacactgg tgacccatca caacttctct tgaaaaaccc caaacttgtc 189720
agctggggaa aagccacaca aagcccagct gcccaccttc acatccttat ccttgtagga 189780
gcataaaatg gtgtcatcac tgcccagttc taaccaagct tcagttaaag aatgggtacc 189840
ttcacatctt cactattttt caggggcctt accgtccttg accacccaag taaaatctaa 189900
atcagccttc ttttgggttc ttcagttcaa gcaaggcctc ttcttgtggc ctctcagtat 189960
taatatttat gaggttgcag attgaatttt tgggcctgag atacaagcca tcaatgaggt 190020
gtgacaaagc atgtcaatga ataataagaa aattatctat tcttccatat cctcccctgt 190080
aataagggtt gtcagaatgc cttctttctg ggctgggttg aggattcagt gagaacatat 190140
gtgacacagc tggtgggcta ttaagctctg gctttgctcc ctgttaaaat gccagaaccc 190200
ttgagaggga tcccacattg agccatgttt atcactgacc accttagaat ggatggattt 190260
ctcagatttt tcctgagatc aatgcttgat ggagaggaga ggagaacaat agattcttgg 190320
gatgtgtgtt atgcatgtgt ttaagtaaga gacagagagt atgtttattt gcaggttgtg 190380
tgtgtaaagt cagagcctgc ctccagagga tcttctctaa ccaccattgc ttaggtcctg 190440
ttcgtttgca tctacagcga atgaccttac agccatctga cttggcttca ctcaccactc 190500
agctcctgcc taaacagacg aggtggttag catccaccat aagttttcca aggagtagca 190560
aagcacaaag gacacctatt gggttgaaaa gagcctagag gcatgagtcc tgtgtgtgac 190620
ttgttcatag tcatgcagct agtgtatagc taggattctc ccctgctgat ttactatgtg 190680
acactaggca gcaatctgcc cttgctggac ctcggttttc taatctgtaa aatgtgtgga 190740
gtaaaactac atgagatggg aagtcccttc tagtgcagat gccatggtta ttgaaaactg 190800
cagcaacatc tttcttaatc gtaaggggaa agaaaaagac catttactac tcctagaaca 190860
gttttggagc tagaatattc acatttgcac tcaataatta tttacaaaac aactagtgtg 190920
gagagggtca aaacaacagc tgagtcctgt gtaatagata ttgtcaaccc cttgatggat 190980
gaggaagggg ctcaaaggga a 191001

<210> SEQ ID NO 2
<211> LENGTH: 10661
<212> TYPE: DNA
<213> ORGANISM: Homo sapiens
<220> FEATURE:
<221> NAME/KEY: CDS
<222> LOCATION: (1116)...(3878)

<400> SEQUENCE: 2
cgagatcccg gggagccagc ttgctgggag agcgggacgg tccggagcaa gcccagaggc 60
agaggaggcg acagagggaa aaagggccga gctagccgct ccagtgctgt acaggagccg 120
aagggacgca ccacgccagc cccagcccgg ctccagcgac agccaacgcc tcttgcagcg 180
cggcggcttc gaagccgccg cccggagctg ccctttcctc ttcggtgaag tttttaaaag 240
ctgctaaaga ctcggaggaa gcaaggaaag tgcctggtag gactgacggc tgcctttgtc 300
ctcctcctct ccaccccgcc tccccccacc ctgccttccc cccctccccc gtcttctctc 360
ccgcagctgc ctcagtcggc tactctcagc caaccccccct caccaccctt ctccccaccc 420
gcccccccgc ccccgtcggc ccagcgctgc cagcccgagt ttgcagagag gtaactccct 480
ttggctgcga gcgggcgagc tagctgcaca ttgcaaagaa ggctcttagg agccaggcga 540
ctggggagcg gcttcagcac tgcagccacg acccgcctgg ttaggctgca cgcggagaga 600
accctctgtt ttcccccact ctctctccac ctcctcctgc cttccccacc ccgagtgcgg 660
agccagagat caaaagatga aaaggcagtc aggtcttcag tagccaaaaa acaaaacaaa 720
caaaaacaaa aaagccgaaa taaaagaaaa agataataac tcagttctta tttgcaccta 780
cttcagtgga cactgaattt ggaaggtgga ggattttgtt tttttctttt aagatctggg 840
catcttttga atctaccctt caagtattaa gagacagact gtgagcctag cagggcagat 900
cttgtccacc gtgtgtcttc ttctgcacga gactttgagg ctgtcagagc gctttttgcg 960
tggttgctcc cgcaagtttc cttctctgga gcttcccgca ggtgggcagc tagctgcagc 1020
gactaccgca tcatcacagc ctgttgaact cttctgagca agagaagggg aggcggggta 1080
agggaagtag gtggaagatt cagccaagct caagg atg gaa gtg cag tta ggg 1133
Met Glu Val Gln Leu Gly
1 5 ctg gga agg gtc tac cct cgg ccg ccg tcc aag acc tac cga gga gct 1181
Leu Gly Arg Val Tyr Pro Arg Pro Pro Ser Lys Thr Tyr Arg Gly Ala
10 15 20 ttc cag aat ctg ttc cag agc gtg cgc gaa gtg atc cag aac ccg ggc 1229
Phe Gln Asn Leu Phe Gln Ser Val Arg Glu Val Ile Gln Asn Pro Gly
25 30 35 ccc agg cac cca gag gcc gcg agc gca gca cct ccc ggc gcc agt ttg 1277
Pro Arg His Pro Glu Ala Ala Ser Ala Ala Pro Pro Gly Ala Ser Leu
40 45 50 ctg ctg ctg cag cag cag cag cag cag cag cag cag cag cag cag cag 1325
Leu Leu Leu Gln Gln Gln Gln Gln Gln Gln Gln Gln Gln Gln Gln Gln
55 60 65 70

-continued

```
cag cag cag cag cag cag cag cag cag caa gag act agc ccc agg cag      1373
Gln Gln Gln Gln Gln Gln Gln Gln Gln Gln Glu Thr Ser Pro Arg Gln
                75                   80                   85

cag cag cag cag cag ggt gag gat ggt tct ccc caa gcc cat cgt aga      1421
Gln Gln Gln Gln Gln Gly Glu Asp Gly Ser Pro Gln Ala His Arg Arg
            90                   95                  100

ggc ccc aca ggc tac ctg gtc ctg gat gag gaa cag caa cct tca cag      1469
Gly Pro Thr Gly Tyr Leu Val Leu Asp Glu Glu Gln Gln Pro Ser Gln
        105                 110                 115

ccg cag tcg gcc ctg gag tgc cac ccc gag aga ggt tgc gtc cca gag      1517
Pro Gln Ser Ala Leu Glu Cys His Pro Glu Arg Gly Cys Val Pro Glu
    120                 125                 130

cct gga gcc gcc gtg gcc gcc agc aag ggg ctg ccg cag cag ctg cca      1565
Pro Gly Ala Ala Val Ala Ala Ser Lys Gly Leu Pro Gln Gln Leu Pro
135                 140                 145                 150

gca cct ccg gac gag gat gac tca gct gcc cca tcc acg ttg tcc ctg      1613
Ala Pro Pro Asp Glu Asp Asp Ser Ala Ala Pro Ser Thr Leu Ser Leu
                155                 160                 165

ctg ggc ccc act ttc ccc ggc tta agc agc tgc tcc gct gac ctt aaa      1661
Leu Gly Pro Thr Phe Pro Gly Leu Ser Ser Cys Ser Ala Asp Leu Lys
            170                 175                 180

gac atc ctg agc gag gcc agc acc atg caa ctc ctt cag caa cag cag      1709
Asp Ile Leu Ser Glu Ala Ser Thr Met Gln Leu Leu Gln Gln Gln Gln
        185                 190                 195

cag gaa gca gta tcc gaa ggc agc agc agc ggg aga gcg agg gag gcc      1757
Gln Glu Ala Val Ser Glu Gly Ser Ser Ser Gly Arg Ala Arg Glu Ala
    200                 205                 210

tcg ggg gct ccc act tcc tcc aag gac aat tac tta ggg ggc act tcg      1805
Ser Gly Ala Pro Thr Ser Ser Lys Asp Asn Tyr Leu Gly Gly Thr Ser
215                 220                 225                 230

acc att tct gac aac gcc aag gag ttg tgt aag gca gtg tcg gtg tcc      1853
Thr Ile Ser Asp Asn Ala Lys Glu Leu Cys Lys Ala Val Ser Val Ser
                235                 240                 245

atg ggc ctg ggt gtg gag gcg ttg gag cat ctg agt cca ggg gaa cag      1901
Met Gly Leu Gly Val Glu Ala Leu Glu His Leu Ser Pro Gly Glu Gln
            250                 255                 260

ctt cgg ggg gat tgc atg tac gcc cca ctt ttg gga gtt cca ccc gct      1949
Leu Arg Gly Asp Cys Met Tyr Ala Pro Leu Leu Gly Val Pro Pro Ala
        265                 270                 275

gtg cgt ccc act cct tgt gcc cca ttg gcc gaa tgc aaa ggt tct ctg      1997
Val Arg Pro Thr Pro Cys Ala Pro Leu Ala Glu Cys Lys Gly Ser Leu
    280                 285                 290

cta gac gac agc gca ggc aag agc act gaa gat act gct gag tat tcc      2045
Leu Asp Asp Ser Ala Gly Lys Ser Thr Glu Asp Thr Ala Glu Tyr Ser
295                 300                 305                 310

cct ttc aag gga ggt tac acc aaa ggg cta gaa ggc gag agc cta ggc      2093
Pro Phe Lys Gly Gly Tyr Thr Lys Gly Leu Glu Gly Glu Ser Leu Gly
                315                 320                 325

tgc tct ggc agc gct gca gca ggg agc tcc ggg aca ctt gaa ctg ccg      2141
Cys Ser Gly Ser Ala Ala Ala Gly Ser Ser Gly Thr Leu Glu Leu Pro
            330                 335                 340

tct acc ctg tct ctc tac aag tcc gga gca ctg gac gag gca gct gcg      2189
Ser Thr Leu Ser Leu Tyr Lys Ser Gly Ala Leu Asp Glu Ala Ala Ala
        345                 350                 355

tac cag agt cgc gac tac tac aac ttt cca ctg gct ctg gcc gga ccg      2237
Tyr Gln Ser Arg Asp Tyr Tyr Asn Phe Pro Leu Ala Leu Ala Gly Pro
    360                 365                 370

ccg ccc cct ccg ccg cct ccc cat ccc cac gct cgc atc aag ctg gag      2285
Pro Pro Pro Pro Pro Pro Pro His Pro His Ala Arg Ile Lys Leu Glu
```

```
375                 380                 385                 390

aac ccg ctg gac tac ggc agc gcc tgg gcg gct gcg gcg gcg cag tgc      2333
Asn Pro Leu Asp Tyr Gly Ser Ala Trp Ala Ala Ala Ala Ala Gln Cys
                395                 400                 405

cgc tat ggg gac ctg gcg agc ctg cat ggc gcg ggt gca gcg gga ccc      2381
Arg Tyr Gly Asp Leu Ala Ser Leu His Gly Ala Gly Ala Ala Gly Pro
            410                 415                 420

ggt tct ggg tca ccc tca gcc gcc gct tcc tca tcc tgg cac act ctc      2429
Gly Ser Gly Ser Pro Ser Ala Ala Ala Ser Ser Ser Trp His Thr Leu
        425                 430                 435

ttc aca gcc gaa gaa ggc cag ttg tat gga ccg tgt ggt ggt ggt ggg      2477
Phe Thr Ala Glu Glu Gly Gln Leu Tyr Gly Pro Cys Gly Gly Gly Gly
    440                 445                 450

ggt ggt ggc ggc ggc ggc ggc ggc ggc ggc ggc ggc ggc ggc ggc ggc      2525
Gly Gly Gly Gly Gly Gly Gly Gly Gly Gly Gly Gly Gly Gly Gly Gly
455                 460                 465                 470

ggc ggc ggc gag gcg gga gct gta gcc ccc tac ggc tac act cgg ccc      2573
Gly Gly Gly Glu Ala Gly Ala Val Ala Pro Tyr Gly Tyr Thr Arg Pro
                475                 480                 485

cct cag ggg ctg gcg ggc cag gaa agc gac ttc acc gca cct gat gtg      2621
Pro Gln Gly Leu Ala Gly Gln Glu Ser Asp Phe Thr Ala Pro Asp Val
            490                 495                 500

tgg tac cct ggc ggc atg gtg agc aga gtg ccc tat ccc agt ccc act      2669
Trp Tyr Pro Gly Gly Met Val Ser Arg Val Pro Tyr Pro Ser Pro Thr
        505                 510                 515

tgt gtc aaa agc gaa atg ggc ccc tgg atg gat agc tac tcc gga cct      2717
Cys Val Lys Ser Glu Met Gly Pro Trp Met Asp Ser Tyr Ser Gly Pro
    520                 525                 530

tac ggg gac atg cgt ttg gag act gcc agg gac cat gtt ttg ccc att      2765
Tyr Gly Asp Met Arg Leu Glu Thr Ala Arg Asp His Val Leu Pro Ile
535                 540                 545                 550

gac tat tac ttt cca ccc cag aag acc tgc ctg atc tgt gga gat gaa      2813
Asp Tyr Tyr Phe Pro Pro Gln Lys Thr Cys Leu Ile Cys Gly Asp Glu
                555                 560                 565

gct tct ggg tgt cac tat gga gct ctc aca tgt gga agc tgc aag gtc      2861
Ala Ser Gly Cys His Tyr Gly Ala Leu Thr Cys Gly Ser Cys Lys Val
            570                 575                 580

ttc ttc aaa aga gcc gct gaa ggg aaa cag aag tac ctg tgc gcc agc      2909
Phe Phe Lys Arg Ala Ala Glu Gly Lys Gln Lys Tyr Leu Cys Ala Ser
        585                 590                 595

aga aat gat tgc act att gat aaa ttc cga agg aaa aat tgt cca tct      2957
Arg Asn Asp Cys Thr Ile Asp Lys Phe Arg Arg Lys Asn Cys Pro Ser
    600                 605                 610

tgt cgt ctt cgg aaa tgt tat gaa gca ggg atg act ctg gga gcc cgg      3005
Cys Arg Leu Arg Lys Cys Tyr Glu Ala Gly Met Thr Leu Gly Ala Arg
615                 620                 625                 630

aag ctg aag aaa ctt ggt aat ctg aaa cta cag gag gaa gga gag gct      3053
Lys Leu Lys Lys Leu Gly Asn Leu Lys Leu Gln Glu Glu Gly Glu Ala
                635                 640                 645

tcc agc acc acc agc ccc act gag gag aca acc cag aag ctg aca gtg      3101
Ser Ser Thr Thr Ser Pro Thr Glu Glu Thr Thr Gln Lys Leu Thr Val
            650                 655                 660

tca cac att gaa ggc tat gaa tgt cag ccc atc ttt ctg aat gtc ctg      3149
Ser His Ile Glu Gly Tyr Glu Cys Gln Pro Ile Phe Leu Asn Val Leu
        665                 670                 675

gaa gcc att gag cca ggt gta gtg tgt gct gga cac gac aac aac cag      3197
Glu Ala Ile Glu Pro Gly Val Val Cys Ala Gly His Asp Asn Asn Gln
    680                 685                 690

ccc gac tcc ttt gca gcc ttg ctc tct agc ctc aat gaa ctg gga gag      3245
```

```
Pro Asp Ser Phe Ala Ala Leu Leu Ser Ser Leu Asn Glu Leu Gly Glu
695                 700                 705                 710

aga cag ctt gta cac gtg gtc aag tgg gcc aag gcc ttg cct ggc ttc      3293
Arg Gln Leu Val His Val Val Lys Trp Ala Lys Ala Leu Pro Gly Phe
                715                 720                 725

cgc aac tta cac gtg gac gac cag atg gct gtc att cag tac tcc tgg      3341
Arg Asn Leu His Val Asp Asp Gln Met Ala Val Ile Gln Tyr Ser Trp
            730                 735                 740

atg ggg ctc atg gtg ttt gcc atg ggc tgg cga tcc ttc acc aat gtc      3389
Met Gly Leu Met Val Phe Ala Met Gly Trp Arg Ser Phe Thr Asn Val
        745                 750                 755

aac tcc agg atg ctc tac ttc gcc cct gat ctg gtt ttc aat gag tac      3437
Asn Ser Arg Met Leu Tyr Phe Ala Pro Asp Leu Val Phe Asn Glu Tyr
    760                 765                 770

cgc atg cac aag tcc cgg atg tac agc cag tgt gtc cga atg agg cac      3485
Arg Met His Lys Ser Arg Met Tyr Ser Gln Cys Val Arg Met Arg His
775                 780                 785                 790

ctc tct caa gag ttt gga tgg ctc caa atc acc ccc cag gaa ttc ctg      3533
Leu Ser Gln Glu Phe Gly Trp Leu Gln Ile Thr Pro Gln Glu Phe Leu
                795                 800                 805

tgc atg aaa gca ctg cta ctc ttc agc att att cca gtg gat ggg ctg      3581
Cys Met Lys Ala Leu Leu Leu Phe Ser Ile Ile Pro Val Asp Gly Leu
            810                 815                 820

aaa aat caa aaa ttc ttt gat gaa ctt cga atg aac tac atc aag gaa      3629
Lys Asn Gln Lys Phe Phe Asp Glu Leu Arg Met Asn Tyr Ile Lys Glu
        825                 830                 835

ctc gat cgt atc att gca tgc aaa aga aaa aat ccc aca tcc tgc tca      3677
Leu Asp Arg Ile Ile Ala Cys Lys Arg Lys Asn Pro Thr Ser Cys Ser
    840                 845                 850

aga cgc ttc tac cag ctc acc aag ctc ctg gac tcc gtg cag cct att      3725
Arg Arg Phe Tyr Gln Leu Thr Lys Leu Leu Asp Ser Val Gln Pro Ile
855                 860                 865                 870

gcg aga gag ctg cat cag ttc act ttt gac ctg cta atc aag tca cac      3773
Ala Arg Glu Leu His Gln Phe Thr Phe Asp Leu Leu Ile Lys Ser His
                875                 880                 885

atg gtg agc gtg gac ttt ccg gaa atg atg gca gag atc atc tct gtg      3821
Met Val Ser Val Asp Phe Pro Glu Met Met Ala Glu Ile Ile Ser Val
            890                 895                 900

caa gtg ccc aag atc ctt tct ggg aaa gtc aag ccc atc tat ttc cac      3869
Gln Val Pro Lys Ile Leu Ser Gly Lys Val Lys Pro Ile Tyr Phe His
        905                 910                 915

acc cag tga agcattggaa accctatttc cccaccccag ctcatgcccc              3918
Thr Gln
    920

ctttcagatg tcttctgcct gttataactc tgcactactc ctctgcagtg ccttggggaa   3978

tttcctctat tgatgtacag tctgtcatga acatgttcct gaattctatt tgctgggctt   4038

tttttttctc tttctctcct ttctttttct tcttccctcc ctatctaacc ctcccatggc   4098

accttcagac tttgcttccc attgtggctc ctatctgtgt tttgaatggt gttgtatgcc   4158

tttaaatctg tgatgatcct catatggccc agtgtcaagt tgtgcttgtt tacagcacta   4218

ctctgtgcca gccacacaaa cgtttactta tcttatgcca cgggaagttt agagagctaa   4278

gattatctgg ggaaatcaaa acaaaaacaa gcaaacaaaa aaaaaaagca aaaacaaaac   4338

aaaaaataag ccaaaaaacc ttgctagtgt tttttcctca aaaataaata aataaataaa   4398

taaatacgta catacataca cacatacata caaacatata gaaatcccca aagaggccaa   4458

tagtgacgag aaggtgaaaa ttgcaggccc atggggagtt actgattttt tcatctcctc   4518
```

-continued cctccacggg agactttatt ttctgccaat ggctattgcc attagagggc agagtgaccc 4578 cagagctgag ttgggcaggg gggtggacag agaggagagg acaaggaggg caatggagca 4638 tcagtacctg cccacagcct tggtccctgg gggctagact gctcaactgt ggagcaattc 4698 attatactga aaatgtgctt gttgttgaaa atttgtctgc atgttaatgc ctcaccccca 4758 aaccctttc tctctcactc tctgcctcca acttcagatt gactttcaat agtttttcta 4818 agacctttga actgaatgtt ctcttcagcc aaaacttggc gacttccaca gaaaagtctg 4878 accactgaga agaaggagag cagagattta accctttgta aggccccatt tggatccagg 4938 tctgctttct catgtgtgag tcagggagga gctggagcca gaggagaaga aaatgatagc 4998 ttggctgttc tcctgcttag gacactgact gaatagttaa actctcactg ccactacctt 5058 ttccccacct ttaaaagacc tgaatgaagt tttctgccaa actccgtgaa gccacaagca 5118 ccttatgtcc tcccttcagt gttttgtggg cctgaatttc atcacactgc atttcagcca 5178 tggtcatcaa gcctgtttgc ttcttttggg catgttcaca gattctctgt taagagcccc 5238 caccaccaag aaggttagca ggccaacagc tctgacatct atctgtagat gccagtagtc 5298 acaaagattt cttaccaact ctcagatcgc tggagccctt agacaaactg gaaagaaggc 5358 atcaaaggga tcaggcaagc tggcgtctt gcccttgtcc cccagagatg ataccctccc 5418 agcaagtgga gaagttctca cttccttctt tagagcagct aaaggggcta cccagatcag 5478 ggttgaagag aaaactcaat taccagggtg ggaagaatga aggcactaga accagaaacc 5538 ctgcaaatgc tcttcttgtc acccagcata tccacctgca gaagtcatga gaagagagaa 5598 ggaacaaaga ggagactctg actactgaat taaaatcttc agcggcaaag cctaaagcca 5658 gatggacacc atctggtgag tttactcatc atcctcctct gctgctgatt ctgggctctg 5718 acattgccca tactcactca gattccccac ctttgttgct gcctcttagt cagagggagg 5778 ccaaaccatt gagactttct acagaaccat ggcttctttc ggaaaggtct ggttggtgtg 5838 gctccaatac tttgccaccc atgaactcag ggtgtgccct gggacactgg ttttatatag 5898 tcttttggca cacctgtgtt ctgttgactt cgttcttcaa gcccaagtgc aagggaaaat 5958 gtccacctac tttctcatct tggcctctgc ctccttactt agctcttaat ctcatctgtt 6018 gaactcaaga aatcaagggc cagtcatcaa gctgcccatt ttaattgatt cactctgttt 6078 gttgagagga tagtttctga gtgacatgat atgatccaca agggtttcct tccctgattt 6138 ctgcattgat attaatagcc aaacgaactt caaaacagct ttaaataaca agggagaggg 6198 gaacctaaga tgagtaatat gccaatccaa gactgctgga gaaaactaaa gctgacaggt 6258 tcccttttg ggtgggata gacatgttct ggttttcttt attattacac aatctggctc 6318 atgtacagga tcactttag ctgttttaaa cagaaaaaaa tatccaccac tcttttcagt 6378 tacactaggt tacattttaa taggtccttt acatctgttt tggaatgatt ttcatctttt 6438 gtgatacaca gattgaatta tatcattttc atatctctcc ttgtaaatac tagaagctct 6498 cctttacatt tctctatcaa atttttcatc tttatgggtt tcccaattgt gactcttgtc 6558 ttcatgaata tatgttttc atttgcaaaa gccaaaaatc agtgaaacag cagtgtaatt 6618 aaaagcaaca actggattac tccaaatttc caaatgacaa aactagggaa aaatagccta 6678 cacaagcctt taggcctact ctttctgtgc ttgggtttga gtgaacaaag gagattttag 6738 cttggctctg ttctcccatg gatgaaagga ggaggatttt ttttttcttt tggccattga 6798 tgttctagcc aatgtaattg acagaagtct cattttgcat gcgctctgct ctacaaacag 6858 agttggtatg gttggtatac tgtactcacc tgtgagggac tggccactca gacccactta 6918

```
gctggtgagc tagaagatga ggatcactca ctggaaaagt cacaaggacc atctccaaac   6978
aagttggcag tgctcgatgt ggacgaagag tgaggaagag aaaaagaagg agcaccaggg   7038
agaaggctcc gtctgtgctg ggcagcagac agctgccagg atcacgaact ctgtagtcaa   7098
agaaaagagt cgtgtggcag tttcagctct cgttcattgg gcagctcgcc taggcccagc   7158
ctctgagctg acatgggagt tgttggattc tttgtttcat agctttttct atgccatagg   7218
caatattgtt gttcttggaa agtttattat ttttttaact ccccttactct gagaaaggga   7278
tattttgaag gactgtcata tatctttgaa aaaagaaaat ctgtaataca tatattttta   7338
tgtatgttca ctggcactaa aaaatataga gagcttcatt ctgtcctttg ggtagttgct   7398
gaggtaattg tccaggttga aaaataatgt gctgatgcta gagtccctct ctgtccatac   7458
tctacttcta aatacatata ggcatacata gcaagtttta tttgacttgt actttaagag   7518
aaaatatgtc caccatccac atgatgcaca aatgagctaa cattgagctt caagtagctt   7578
ctaagtgttt gtttcattag gcacagcaca gatgtggcct ttccccccctt ctctcccttg   7638
atatctggca gggcataaag gcccaggcca cttcctctgc cccttcccag ccctgcacca   7698
aagctgcatt tcaggagact ctctccagac agcccagtaa ctacccgagc atggcccctg   7758
catagccctg gaaaaataag aggctgactg tctacgaatt atcttgtgcc agttgcccag   7818
gtgagagggc actgggccaa gggagtggtt ttcatgtttg acccactaca aggggtcatg   7878
ggaatcagga atgccaaagc accagatcaa atccaaaact taaagtcaaa ataagccatt   7938
cagcatgttc agtttcttgg aaaaggaagt ttctacccct gatgcctttg taggcagatc   7998
tgttctcacc attaatcttt ttgaaaatct tttaaagcag tttttaaaaa gagagatgaa   8058
agcatcacat tatataacca aagattacat tgtacctgct aagataccaa aattcataag   8118
ggcagggggg gagcaagcat tagtgcctct ttgataagct gtccaaagac agactaaagg   8178
actctgctgg tgactgactt ataagagctt tgtgggtttt tttttcccta ataatataca   8238
tgtttagaag aattgaaaat aatttcggga aaatgggatt atgggtcctt cactaagtga   8298
ttttataagc agaactggct ttccttttct ctagtagttg ctgagcaaat tgttgaagct   8358
ccatcattgc atggttggaa atggagctgt tcttagccac tgtgtttgct agtgcccatg   8418
ttagcttatc tgaagatgtg aaacccttgc tgataaggga gcatttaaag tactagattt   8478
tgcactagag ggacagcagg cagaaatcct tatttctgcc cactttggat ggcacaaaaa   8538
gttatctgca gttgaaggca gaaagttgaa atacattgta aatgaatatt tgtatccatg   8598
tttcaaaatt gaaatatata tatatatata tatatatata tatatatata tatagtgtgt   8658
gtgtgtgttc tgatagcttt aactttctct gcatctttat atttggttcc agatcacacc   8718
tgatgccatg tacttgtgag agaggatgca gttttgtttt ggaagctctc tcagaacaaa   8778
caagacacct ggattgatca gttaactaaa agttttctcc cctattgggt ttgacccaca   8838
ggtcctgtga aggagcagag ggataaaaag agtagaggac atgatacatt gtactttact   8898
agttcaagac agatgaatgt ggaaagcata aaaactcaat ggaactgact gagatttacc   8958
acagggaagg cccaaacttg gggccaaaag cctacccaag tgattgacca gtggcccccct   9018
aatgggacct gagctgttgg aagaagagaa ctgttccttg gtcttcacca tccttgtgag   9078
agaagggcag tttcctgcat tggaacctgg agcaagcgct ctatctttca cacaaattcc   9138
ctcacctgag attgaggtgc tcttgttact gggtgtctgt gtgctgtaat tctggttttg   9198
gatatgttct gtaaagattt tgacaaatga aaatgtgttt ttctctgtta aaacttgtca   9258
```

```
gagtactaga agttgtatct ctgtaggtgc aggtccattt ctgcccacag gtagggtgtt   9318

tttctttgat taagagattg acacttctgt tgcctaggac ctcccaactc aaccatttct   9378

aggtgaaggc agaaaaatcc acattagtta ctcctcttca gacatttcag ctgagataac   9438

aaatcttttg gaatttttttc acccatagaa agagtggtag atatttgaat ttagcaggtg   9498

gagtttcata gtaaaaacag cttttgactc agctttgatt tatcctcatt tgatttggcc   9558

agaaagtagg taatatgcat tgattggctt ctgattccaa ttcagtatag caaggtgcta   9618

ggttttttcc tttccccacc tgtctcttag cctggggaat taaatgagaa gccttagaat   9678

gggtggccct tgtgacctga aacacttccc acataagcta cttaacaaga ttgtcatgga   9738

gctgcagatt ccattgccca ccaaagacta gaacacacac atatccatac accaaaggaa   9798

agacaattct gaaatgctgt ttctctggtg gttccctctc tggctgctgc ctcacagtat   9858

gggaacctgt actctgcaga ggtgacaggc cagatttgca ttatctcaca accttagccc   9918

ttggtgctaa ctgtcctaca gtgaagtgcc tggggggttg tcctatccca taagccactt   9978

ggatgctgac agcagccacc atcagaatga cccacgcaaa aaaaagaaaa aaaaaattaa  10038

aaagtcccct cacaacccag tgacaccttt ctgctttcct ctagactgga acattgatta  10098

gggagtgcct cagacatgac attcttgtgc tgtccttgga attaatctgg cagcaggagg  10158

gagcagacta tgtaaacaga gataaaaatt aattttcaat attgaaggaa aaaagaaata  10218

agaagagaga gagaaagaaa gcatcacaca aagattttct taaaagaaac aattttgctt  10278

gaaatctctt tagatggggc tcatttctca cggtggcact tggcctccac tgggcagcag  10338

gaccagctcc aagcgctagt gttctgttct ctttttgtaa tcttggaatc ttttgttgct  10398

ctaaatacaa ttaaaaatgg cagaaacttg tttgttggac tacatgtgtg actttgggtc  10458

tgtctctgcc tctgctttca gaaatgtcat ccattgtgta aaatattggc ttactggtct  10518

gccagctaaa acttggccac atcccctgtt atggctgcag gatcgagtta ttgttaacaa  10578

agagacccaa gaaaagctgc taatgtcctc ttatcattgt tgttaatttg ttaaaacata  10638

aagaaatcta aaatttcaaa aaa                                          10661
```

<210> SEQ ID NO 3
<211> LENGTH: 8112
<212> TYPE: DNA
<213> ORGANISM: Homo sapiens
<220> FEATURE:
<221> NAME/KEY: CDS
<222> LOCATION: (163)...(1329)

<400> SEQUENCE: 3

```
gctgcgagca gagagggatt cctcggaggt catctgttcc atcttcttgc ctatgcaaat     60

gcctgcctga agctgctgga ggctggcttt gtaccggact ttgtacaggg aaccagggaa    120

acgaatgcag agtgctcctg acattgcctg tcactttttc cc atg ata ctc tgg       174
                                               Met Ile Leu Trp
                                                1

ctt cac agt ttg gag act gcc agg gac cat gtt ttg ccc att gac tat      222
Leu His Ser Leu Glu Thr Ala Arg Asp His Val Leu Pro Ile Asp Tyr
 5                  10                  15                  20

tac ttt cca ccc cag aag acc tgc ctg atc tgt gga gat gaa gct tct      270
Tyr Phe Pro Pro Gln Lys Thr Cys Leu Ile Cys Gly Asp Glu Ala Ser
                25                  30                  35

ggg tgt cac tat gga gct ctc aca tgt gga agc tgc aag gtc ttc ttc      318
Gly Cys His Tyr Gly Ala Leu Thr Cys Gly Ser Cys Lys Val Phe Phe
            40                  45                  50
```

-continued

```
aaa aga gcc gct gaa ggg aaa cag aag tac ctg tgc gcc agc aga aat      366
Lys Arg Ala Ala Glu Gly Lys Gln Lys Tyr Leu Cys Ala Ser Arg Asn
        55                  60                  65

gat tgc act att gat aaa ttc cga agg aaa aat tgt cca tct tgt cgt      414
Asp Cys Thr Ile Asp Lys Phe Arg Arg Lys Asn Cys Pro Ser Cys Arg
    70                  75                  80

ctt cgg aaa tgt tat gaa gca ggg atg act ctg gga gcc cgg aag ctg      462
Leu Arg Lys Cys Tyr Glu Ala Gly Met Thr Leu Gly Ala Arg Lys Leu
 85                  90                  95                 100

aag aaa ctt ggt aat ctg aaa cta cag gag gaa gga gag gct tcc agc      510
Lys Lys Leu Gly Asn Leu Lys Leu Gln Glu Glu Gly Glu Ala Ser Ser
                105                 110                 115

acc acc agc ccc act gag gag aca acc cag aag ctg aca gtg tca cac      558
Thr Thr Ser Pro Thr Glu Glu Thr Thr Gln Lys Leu Thr Val Ser His
            120                 125                 130

att gaa ggc tat gaa tgt cag ccc atc ttt ctg aat gtc ctg gaa gcc      606
Ile Glu Gly Tyr Glu Cys Gln Pro Ile Phe Leu Asn Val Leu Glu Ala
        135                 140                 145

att gag cca ggt gta gtg tgt gct gga cac gac aac aac cag ccc gac      654
Ile Glu Pro Gly Val Val Cys Ala Gly His Asp Asn Asn Gln Pro Asp
    150                 155                 160

tcc ttt gca gcc ttg ctc tct agc ctc aat gaa ctg gga gag aga cag      702
Ser Phe Ala Ala Leu Leu Ser Ser Leu Asn Glu Leu Gly Glu Arg Gln
165                 170                 175                 180

ctt gta cac gtg gtc aag tgg gcc aag gcc ttg cct ggc ttc cgc aac      750
Leu Val His Val Val Lys Trp Ala Lys Ala Leu Pro Gly Phe Arg Asn
                185                 190                 195

tta cac gtg gac gac cag atg gct gtc att cag tac tcc tgg atg ggg      798
Leu His Val Asp Asp Gln Met Ala Val Ile Gln Tyr Ser Trp Met Gly
            200                 205                 210

ctc atg gtg ttt gcc atg ggc tgg cga tcc ttc acc aat gtc aac tcc      846
Leu Met Val Phe Ala Met Gly Trp Arg Ser Phe Thr Asn Val Asn Ser
        215                 220                 225

agg atg ctc tac ttc gcc cct gat ctg gtt ttc aat gag tac cgc atg      894
Arg Met Leu Tyr Phe Ala Pro Asp Leu Val Phe Asn Glu Tyr Arg Met
    230                 235                 240

cac aag tcc cgg atg tac agc cag tgt gtc cga atg agg cac ctc tct      942
His Lys Ser Arg Met Tyr Ser Gln Cys Val Arg Met Arg His Leu Ser
245                 250                 255                 260

caa gag ttt gga tgg ctc caa atc acc ccc cag gaa ttc ctg tgc atg      990
Gln Glu Phe Gly Trp Leu Gln Ile Thr Pro Gln Glu Phe Leu Cys Met
                265                 270                 275

aaa gca ctg cta ctc ttc agc att att cca gtg gat ggg ctg aaa aat     1038
Lys Ala Leu Leu Leu Phe Ser Ile Ile Pro Val Asp Gly Leu Lys Asn
            280                 285                 290

caa aaa ttc ttt gat gaa ctt cga atg aac tac atc aag gaa ctc gat     1086
Gln Lys Phe Phe Asp Glu Leu Arg Met Asn Tyr Ile Lys Glu Leu Asp
        295                 300                 305

cgt atc att gca tgc aaa aga aaa aat ccc aca tcc tgc tca aga cgc     1134
Arg Ile Ile Ala Cys Lys Arg Lys Asn Pro Thr Ser Cys Ser Arg Arg
    310                 315                 320

ttc tac cag ctc acc aag ctc ctg gac tcc gtg cag cct att gcg aga     1182
Phe Tyr Gln Leu Thr Lys Leu Leu Asp Ser Val Gln Pro Ile Ala Arg
325                 330                 335                 340

gag ctg cat cag ttc act ttt gac ctg cta atc aag tca cac atg gtg     1230
Glu Leu His Gln Phe Thr Phe Asp Leu Leu Ile Lys Ser His Met Val
                345                 350                 355

agc gtg gac ttt ccg gaa atg atg gca gag atc atc tct gtg caa gtg     1278
Ser Val Asp Phe Pro Glu Met Met Ala Glu Ile Ile Ser Val Gln Val
            360                 365                 370
```

-continued

```
ccc aag atc ctt tct ggg aaa gtc aag ccc atc tat ttc cac acc cag     1326
Pro Lys Ile Leu Ser Gly Lys Val Lys Pro Ile Tyr Phe His Thr Gln
        375                 380                 385

tga agcattggaa accctatttc cccaccccag ctcatgcccc ctttcagatg         1379

tcttctgcct gttataactc tgcactactc ctctgcagtg ccttggggaa tttcctctat   1439

tgatgtacag tctgtcatga acatgttcct gaattctatt tgctgggctt tttttttctc   1499

tttctctcct ttctttttct tcttccctcc ctatctaacc ctcccatggc accttcagac   1559

tttgcttccc attgtggctc ctatctgtgt tttgaatggt gttgtatgcc tttaaatctg   1619

tgatgatcct catatggccc agtgtcaagt tgtgcttgtt tacagcacta ctctgtgcca   1679

gccacacaaa cgtttactta tcttatgcca cgggaagttt agagagctaa gattatctgg   1739

ggaaatcaaa acaaaaacaa gcaaacaaaa aaaaaaagca aaaacaaaac aaaaaataag   1799

ccaaaaaacc ttgctagtgt tttttcctca aaaataaata aataaataaa taaatacgta   1859

catacataca cacatacata caaacatata gaaatcccca aagaggccaa tagtgacgag   1919

aaggtgaaaa ttgcaggccc atggggagtt actgattttt tcatctcctc cctccacggg   1979

agactttatt ttctgccaat ggctattgcc attagagggc agagtgaccc cagagctgag   2039

ttgggcaggg gggtggacag agaggagagg acaaggaggg caatggagca tcagtacctg   2099

cccacagcct tggtccctgg gggctagact gctcaactgt ggagcaattc attatactga   2159

aaatgtgctt gttgttgaaa atttgtctgc atgttaatgc ctcaccccca aacccttttc   2219

tctctcactc tctgcctcca acttcagatt gactttcaat agtttttcta agacctttga   2279

actgaatgtt ctcttcagcc aaaacttggc gacttccaca gaaaagtctg accactgaga   2339

agaaggagag cagagattta accctttgta aggccccatt tggatccagg tctgctttct   2399

catgtgtgag tcagggagga gctggagcca gaggagaaga aaatgatagc ttggctgttc   2459

tcctgcttag gacactgact gaatagttaa actctcactg ccactacctt ttccccacct   2519

ttaaaagacc tgaatgaagt tttctgccaa actccgtgaa gccacaagca ccttatgtcc   2579

tcccttcagt gttttgtggg cctgaatttc atcacactgc atttcagcca tggtcatcaa   2639

gcctgtttgc ttcttttggg catgttcaca gattctctgt taagagcccc caccaccaag   2699

aaggttagca ggccaacagc tctgacatct atctgtagat gccagtagtc acaaagattt   2759

cttaccaact ctcagatcgc tggagccctt agacaaactg gaaagaaggc atcaaaggga   2819

tcaggcaagc tgggcgtctt gcccttgtcc cccagagatg ataccctccc agcaagtgga   2879

gaagttctca cttccttctt tagagcagct aaaggggcta cccagatcag ggttgaagag   2939

aaaactcaat taccagggtg ggaagaatga aggcactaga accagaaacc ctgcaaatgc   2999

tcttcttgtc acccagcata tccacctgca gaagtcatga gaagagagaa ggaacaaaga   3059

ggagactctg actactgaat taaaatcttc agcggcaaag cctaaagcca gatggacacc   3119

atctggtgag tttactcatc atcctcctct gctgctgatt ctgggctctg acattgccca   3179

tactcactca gattccccac ctttgttgct gcctcttagt cagagggagg ccaaaccatt   3239

gagactttct acagaaccat ggcttctttc ggaaaggtct ggttggtgtg gctccaatac   3299

tttgccaccc atgaactcag ggtgtgccct gggacactgg ttttatatag tcttttggca   3359

cacctgtgtt ctgttgactt cgttcttcaa gcccaagtgc aagggaaaat gtccacctac   3419

tttctcatct tggcctctgc ctccttactt agctcttaat ctcatctgtt gaactcaaga   3479

aatcaagggc cagtcatcaa gctgcccatt ttaattgatt cactctgttt gttgagagga   3539
```

-continued

```
tagtttctga gtgacatgat atgatccaca agggtttcct tccctgattt ctgcattgat   3599
attaatagcc aaacgaactt caaaacagct ttaaataaca agggagaggg gaacctaaga   3659
tgagtaatat gccaatccaa gactgctgga gaaaactaaa gctgacaggt tccctttttg   3719
gggtgggata gacatgttct ggttttcttt attattacac aatctggctc atgtacagga   3779
tcacttttag ctgttttaaa cagaaaaaaa tatccaccac tcttttcagt tacactaggt   3839
tacattttaa taggtccttt acatctgttt tggaatgatt ttcatctttt gtgatacaca   3899
gattgaatta tatcattttc atatctctcc ttgtaaatac tagaagctct cctttacatt   3959
tctctatcaa atttttcatc tttatgggtt tcccaattgt gactcttgtc ttcatgaata   4019
tatgtttttc atttgcaaaa gccaaaaatc agtgaaacag cagtgtaatt aaaagcaaca   4079
actggattac tccaaatttc caaatgacaa aactagggaa aaatagccta cacaagcctt   4139
taggcctact ctttctgtgc ttgggtttga gtgaacaaag gagattttag cttggctctg   4199
ttctcccatg gatgaaagga ggaggatttt tttttctttt tggccattga tgttctagcc   4259
aatgtaattg acagaagtct cattttgcat gcgctctgct ctacaaacag agttggtatg   4319
gttggtatac tgtactcacc tgtgagggac tggccactca gacccactta gctggtgagc   4379
tagaagatga ggatcactca ctggaaaagt cacaaggacc atctccaaac aagttggcag   4439
tgctcgatgt ggacgaagag tgaggaagag aaaaagaagg agcaccaggg agaaggctcc   4499
gtctgtgctg ggcagcagac agctgccagg atcacgaact ctgtagtcaa agaaaagagt   4559
cgtgtggcag tttcagctct cgttcattgg gcagctcgcc taggcccagc ctctgagctg   4619
acatgggagt tgttggattc tttgtttcat agctttttct atgccatagg caatattgtt   4679
gttcttggaa agtttattat ttttttaact cccttactct gagaaaggga tattttgaag   4739
gactgtcata tatctttgaa aaaagaaaat ctgtaataca tatattttta tgtatgttca   4799
ctggcactaa aaaatataga gagcttcatt ctgtcctttg ggtagttgct gaggtaattg   4859
tccaggttga aaaataatgt gctgatgcta gagtccctct ctgtccatac tctacttcta   4919
aatacatata ggcatacata gcaagtttta tttgacttgt actttaagag aaaatatgtc   4979
caccatccac atgatgcaca aatgagctaa cattgagctt caagtagctt ctaagtgttt   5039
gtttcattag gcacagcaca gatgtggcct ttcccccctt ctctcccttg atatctggca   5099
gggcataaag gcccaggcca cttcctctgc cccttcccag ccctgcacca aagctgcatt   5159
tcaggagact ctctccagac agcccagtaa ctacccgagc atggcccctg catagccctg   5219
gaaaaataag aggctgactg tctacgaatt atcttgtgcc agttgcccag gtgagagggc   5279
actgggccaa gggagtggtt ttcatgtttg acccactaca aggggtcatg ggaatcagga   5339
atgccaaagc accagatcaa atccaaaact taaagtcaaa ataagccatt cagcatgttc   5399
agtttcttgg aaaaggaagt ttctacccct gatgcctttg taggcagatc tgttctcacc   5459
attaatcttt ttgaaaatct tttaaagcag tttttaaaaa gagagatgaa agcatcacat   5519
tatataacca aagattacat tgtacctgct aagataccaa aattcataag ggcagggggg   5579
gagcaagcat tagtgcctct ttgataagct gtccaaagac agactaaagg actctgctgg   5639
tgactgactt ataagagctt tgtgggtttt tttttcccta ataatataca tgtttagaag   5699
aattgaaaat aatttcggga aaatgggatt atgggtcctt cactaagtga ttttataagc   5759
agaactggct ttccttttct ctagtagttg ctgagcaaat tgttgaagct ccatcattgc   5819
atggttggaa atggagctgt tcttagccac tgtgtttgct agtgcccatg ttagcttatc   5879
tgaagatgtg aaacccttgc tgataaggga gcatttaaag tactagattt tgcactagag   5939
```

ggacagcagg cagaaatcct tatttctgcc cactttggat ggcacaaaaa gttatctgca 5999 gttgaaggca gaaagttgaa atacattgta aatgaatatt tgtatccatg tttcaaaatt 6059 gaaatatata tatatatata tatatatata tatatatata tatagtgtgt gtgtgtgttc 6119 tgatagcttt aactttctct gcatctttat atttggttcc agatcacacc tgatgccatg 6179 tacttgtgag agaggatgca gttttgtttt ggaagctctc tcagaacaaa caagacacct 6239 ggattgatca gttaactaaa agttttctcc cctattgggt ttgacccaca ggtcctgtga 6299 aggagcagag ggataaaaag agtagaggac atgatacatt gtactttact agttcaagac 6359 agatgaatgt ggaaagcata aaaactcaat ggaactgact gagatttacc acagggaagg 6419 cccaaacttg gggccaaaag cctacccaag tgattgacca gtggccccct aatgggacct 6479 gagctgttgg aagaagagaa ctgttccttg gtcttcacca tccttgtgag agaagggcag 6539 tttcctgcat tggaacctgg agcaagcgct ctatctttca cacaaattcc ctcacctgag 6599 attgaggtgc tcttgttact gggtgtctgt gtgctgtaat tctggttttg gatatgttct 6659 gtaaagattt tgacaaatga aaatgtgttt ttctctgtta aaacttgtca gagtactaga 6719 agttgtatct ctgtaggtgc aggtccattt ctgcccacag gtagggtgtt tttctttgat 6779 taagagattg acacttctgt tgcctaggac ctcccaactc aaccatttct aggtgaaggc 6839 agaaaaatcc acattagtta ctcctcttca gacatttcag ctgagataac aaatcttttg 6899 gaatttttc acccatagaa agagtggtag atatttgaat ttagcaggtg gagtttcata 6959 gtaaaaacag cttttgactc agctttgatt tatcctcatt tgatttggcc agaaagtagg 7019 taatatgcat tgattggctt ctgattccaa ttcagtatag caaggtgcta ggttttttcc 7079 tttccccacc tgtctcttag cctggggaat taaatgagaa gccttagaat gggtggccct 7139 tgtgacctga aacacttccc acataagcta cttaacaaga ttgtcatgga gctgcagatt 7199 ccattgccca ccaaagacta gaacacacac atatccatac accaaaggaa agacaattct 7259 gaaatgctgt ttctctggtg gttccctctc tggctgctgc ctcacagtat gggaacctgt 7319 actctgcaga ggtgacaggc cagatttgca ttatctcaca accttagccc ttggtgctaa 7379 ctgtcctaca gtgaagtgcc tggggggttg tcctatccca taagccactt ggatgctgac 7439 agcagccacc atcagaatga cccacgcaaa aaaaagaaaa aaaaaattaa aaagtcccct 7499 cacaacccag tgacaccttt ctgctttcct ctagactgga acattgatta gggagtgcct 7559 cagacatgac attcttgtgc tgtccttgga attaatctgg cagcaggagg gagcagacta 7619 tgtaaacaga gataaaaatt aattttcaat attgaaggaa aaaagaaata agaagagaga 7679 gagaaagaaa gcatcacaca aagattttct taaaagaaac aattttgctt gaaatctctt 7739 tagatggggc tcatttctca cggtggcact tggcctccac tgggcagcag gaccagctcc 7799 aagcgctagt gttctgttct ctttttgtaa tcttggaatc ttttgttgct ctaaatacaa 7859 ttaaaaatgg cagaaacttg tttgttggac tacatgtgtg actttgggtc tgtctctgcc 7919 tctgctttca gaaatgtcat ccattgtgta aaatattggc ttactggtct gccagctaaa 7979 acttggccac atcccctgtt atggctgcag gatcgagtta ttgttaacaa agagacccaa 8039 gaaaagctgc taatgtcctc ttatcattgt tgttaatttg ttaaaacata aagaaatcta 8099 aaatttcaaa aaa 8112

<210> SEQ ID NO 4
<211> LENGTH: 3641
<212> TYPE: DNA

```
<213> ORGANISM: Homo sapiens
<220> FEATURE:
<221> NAME/KEY: CDS
<222> LOCATION: (328)...(2265)

<400> SEQUENCE: 4

gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
                               1               5

gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55

cag cag cag cag cag cag cag cag cag cag cag cag cag cag cag cag      546
Gln Gln Gln Gln Gln Gln Gln Gln Gln Gln Gln Gln Gln Gln Gln Gln
         60                  65                  70

cag cag cag cag cag cag cag cag cag cag cag caa gag act agc ccc      594
Gln Gln Gln Gln Gln Gln Gln Gln Gln Gln Gln Gln Glu Thr Ser Pro
     75                  80                  85

agg cag cag cag cag cag cag ggt gag gat ggt tct ccc caa gcc cat      642
Arg Gln Gln Gln Gln Gln Gln Gly Glu Asp Gly Ser Pro Gln Ala His
 90                  95                 100                 105

cgt aga ggc ccc aca ggc tac ctg gtc ctg gat gag gaa cag caa cct      690
Arg Arg Gly Pro Thr Gly Tyr Leu Val Leu Asp Glu Glu Gln Gln Pro
                110                 115                 120

tca cag ccg cag tcg gcc ctg gag tgc cac ccc gag aga ggt tgc gtc      738
Ser Gln Pro Gln Ser Ala Leu Glu Cys His Pro Glu Arg Gly Cys Val
            125                 130                 135

cca gag cct gga gcc gcc gtg gcc gcc agc aag ggg ctg ccg cag cag      786
Pro Glu Pro Gly Ala Ala Val Ala Ala Ser Lys Gly Leu Pro Gln Gln
        140                 145                 150

ctg cca gca cct ccg gac gag gat gac tca gct gcc cca tcc acg ttg      834
Leu Pro Ala Pro Pro Asp Glu Asp Asp Ser Ala Ala Pro Ser Thr Leu
    155                 160                 165

tcc ctg ctg ggc ccc act ttc ccc ggc tta agc agc tgc tcc gct gac      882
Ser Leu Leu Gly Pro Thr Phe Pro Gly Leu Ser Ser Cys Ser Ala Asp
170                 175                 180                 185

ctt aaa gac atc ctg agc gag gcc agc acc atg caa ctc ctt cag caa      930
Leu Lys Asp Ile Leu Ser Glu Ala Ser Thr Met Gln Leu Leu Gln Gln
                190                 195                 200

cag cag cag gaa gca gta tcc gaa ggc agc agc agc ggg aga gcg agg      978
Gln Gln Gln Glu Ala Val Ser Glu Gly Ser Ser Ser Gly Arg Ala Arg
            205                 210                 215

gag gcc tcg ggg gct ccc act tcc tcc aag gac aat tac tta ggg ggc     1026
Glu Ala Ser Gly Ala Pro Thr Ser Ser Lys Asp Asn Tyr Leu Gly Gly
        220                 225                 230

act tcg acc att tct gac aac gcc aag gag ttg tgt aag gca gtg tcg     1074
Thr Ser Thr Ile Ser Asp Asn Ala Lys Glu Leu Cys Lys Ala Val Ser
```

```
    235                 240                 245

gtg tcc atg ggc ctg ggt gtg gag gcg ttg gag cat ctg agt cca ggg     1122
Val Ser Met Gly Leu Gly Val Glu Ala Leu Glu His Leu Ser Pro Gly
250                 255                 260                 265

gaa cag ctt cgg ggg gat tgc atg tac gcc cca ctt ttg gga gtt cca     1170
Glu Gln Leu Arg Gly Asp Cys Met Tyr Ala Pro Leu Leu Gly Val Pro
                270                 275                 280

ccc gct gtg cgt ccc act cct tgt gcc cca ttg gcc gaa tgc aaa ggt     1218
Pro Ala Val Arg Pro Thr Pro Cys Ala Pro Leu Ala Glu Cys Lys Gly
            285                 290                 295

tct ctg cta gac gac agc gca ggc aag agc act gaa gat act gct gag     1266
Ser Leu Leu Asp Asp Ser Ala Gly Lys Ser Thr Glu Asp Thr Ala Glu
        300                 305                 310

tat tcc cct ttc aag gga ggt tac acc aaa ggg cta gaa ggc gag agc     1314
Tyr Ser Pro Phe Lys Gly Gly Tyr Thr Lys Gly Leu Glu Gly Glu Ser
    315                 320                 325

cta ggc tgc tct ggc agc gct gca gca ggg agc tcc ggg aca ctt gaa     1362
Leu Gly Cys Ser Gly Ser Ala Ala Ala Gly Ser Ser Gly Thr Leu Glu
330                 335                 340                 345

ctg ccg tct acc ctg tct ctc tac aag tcc gga gca ctg gac gag gca     1410
Leu Pro Ser Thr Leu Ser Leu Tyr Lys Ser Gly Ala Leu Asp Glu Ala
                350                 355                 360

gct gcg tac cag agt cgc gac tac tac aac ttt cca ctg gct ctg gcc     1458
Ala Ala Tyr Gln Ser Arg Asp Tyr Tyr Asn Phe Pro Leu Ala Leu Ala
            365                 370                 375

gga ccg ccg ccc cct ccg ccg cct ccc cat ccc cac gct cgc atc aag     1506
Gly Pro Pro Pro Pro Pro Pro Pro Pro His Pro His Ala Arg Ile Lys
        380                 385                 390

ctg gag aac ccg ctg gac tac ggc agc gcc tgg gcg gct gcg gcg gcg     1554
Leu Glu Asn Pro Leu Asp Tyr Gly Ser Ala Trp Ala Ala Ala Ala Ala
    395                 400                 405

cag tgc cgc tat ggg gac ctg gcg agc ctg cat ggc gcg ggt gca gcg     1602
Gln Cys Arg Tyr Gly Asp Leu Ala Ser Leu His Gly Ala Gly Ala Ala
410                 415                 420                 425

gga ccc ggt tct ggg tca ccc tca gcc gcc gct tcc tca tcc tgg cac     1650
Gly Pro Gly Ser Gly Ser Pro Ser Ala Ala Ala Ser Ser Ser Trp His
                430                 435                 440

act ctc ttc aca gcc gaa gaa ggc cag ttg tat gga ccg tgt ggt ggt     1698
Thr Leu Phe Thr Ala Glu Glu Gly Gln Leu Tyr Gly Pro Cys Gly Gly
            445                 450                 455

ggt ggg ggt ggt ggc ggc ggc ggc ggc ggc ggc ggc ggc ggc ggc ggc     1746
Gly Gly Gly Gly Gly Gly Gly Gly Gly Gly Gly Gly Gly Gly Gly Gly
        460                 465                 470

ggc gag gcg gga gct gta gcc ccc tac ggc tac act cgg ccc cct cag     1794
Gly Glu Ala Gly Ala Val Ala Pro Tyr Gly Tyr Thr Arg Pro Pro Gln
    475                 480                 485

ggg ctg gcg ggc cag gaa agc gac ttc acc gca cct gat gtg tgg tac     1842
Gly Leu Ala Gly Gln Glu Ser Asp Phe Thr Ala Pro Asp Val Trp Tyr
490                 495                 500                 505

cct ggc ggc atg gtg agc aga gtg ccc tat ccc agt ccc act tgt gtc     1890
Pro Gly Gly Met Val Ser Arg Val Pro Tyr Pro Ser Pro Thr Cys Val
                510                 515                 520

aaa agc gaa atg ggc ccc tgg atg gat agc tac tcc gga cct tac ggg     1938
Lys Ser Glu Met Gly Pro Trp Met Asp Ser Tyr Ser Gly Pro Tyr Gly
            525                 530                 535

gac atg cgt ttg gag act gcc agg gac cat gtt ttg ccc att gac tat     1986
Asp Met Arg Leu Glu Thr Ala Arg Asp His Val Leu Pro Ile Asp Tyr
        540                 545                 550

tac ttt cca ccc cag aag acc tgc ctg atc tgt gga gat gaa gct tct     2034
```

```
Tyr Phe Pro Pro Gln Lys Thr Cys Leu Ile Cys Gly Asp Glu Ala Ser
    555                 560                 565

ggg tgt cac tat gga gct ctc aca tgt gga agc tgc aag gtc ttc ttc      2082
Gly Cys His Tyr Gly Ala Leu Thr Cys Gly Ser Cys Lys Val Phe Phe
570                 575                 580                 585

aaa aga gcc gct gaa ggg aaa cag aag tac ctg tgc gcc agc aga aat      2130
Lys Arg Ala Ala Glu Gly Lys Gln Lys Tyr Leu Cys Ala Ser Arg Asn
                590                 595                 600

gat tgc act att gat aaa ttc cga agg aaa aat tgt cca tct tgt cgt      2178
Asp Cys Thr Ile Asp Lys Phe Arg Arg Lys Asn Cys Pro Ser Cys Arg
            605                 610                 615

ctt cgg aaa tgt tat gaa gca ggg atg act ctg gga gaa aaa ttc cgg      2226
Leu Arg Lys Cys Tyr Glu Ala Gly Met Thr Leu Gly Glu Lys Phe Arg
        620                 625                 630

gtt ggc aat tgc aag cat ctc aaa atg acc aga ccc tga agaaaggctg      2275
Val Gly Asn Cys Lys His Leu Lys Met Thr Arg Pro
    635                 640                 645

acttgcctca ttcaaaatga gggctctaga gggctctagt ggatagtctg gagaaacctg   2335

gcgtctgagg cttaggagct taggtttttg ctcctcaaca cagactttga cgttggggtt   2395

gggggctact ctcttgattg ctgactccct ccagcgggac caatagtgtt ttcctacctc   2455

acagggatgt tgtgaggacg ggctgtagaa gtaatagtgg ttaccactca tgtagttgtg   2515

agtatcatga ttattgtttc ctgtaatgtg gcttggcatt ggcaaagtgc tttttgattg   2575

ttcttgatca catatgatgg gggccaggca ctgactcagg cggatgcagt gaagctctgg   2635

ctcagtcgct tgcttttcgt ggtgtgctgc caggaagaaa ctttgctgat gggactcaag   2695

gtgtcacctt ggacaagaag caactgtgtc tgtctgaggt tcctgtggcc atctttattt   2755

gtgtattagg caattcgtat ttccccctta ggttctagcc ttctggatcc cagccagtga   2815

cctagatctt agcctcaggc cctgtcactg agctgaaggt agtagctgat ccacagaagt   2875

tcagtaaaca aggaccagat ttctgcttct ccaggagaag aagccagcca acccctctct   2935

tcaaacacac tgagagacta cagtccgact ttccctctta catctagcct tactgtagcc   2995

acactccttg attgctctct cacatcacat gcttctcttc atcagttgta agcctctcat   3055

tcttctccca agccagactc aaatattgta ttgatgtcaa agaagaatca cttagagttt   3115

ggaatatctt gttctctctc tgctccatag cttccatatt gacaccagtt tctttctagt   3175

ggagaagtgg agtctgtgaa gccagggaaa cacacatgtg agagtcagaa ggactctccc   3235

tgacttgcct ggggcctgtc tttcccacct tctccagtct gtctaaacac acacacacac   3295

acacacacac acacacacac acacacacac gctctctctc tctctccccc cccaacacac   3355

acacactctc tctctcacac acacacacat acacacacac ttctttctct ttcccctgac   3415

tcagcaacat tctggagaaa agccaaggaa ggacttcagg aggggagttt ccccccttctc   3475

agggcagaat tttaatctcc agaccaacaa gaagttccct aatgtggatt gaaaggctaa   3535

tgaggtttat ttttaactac tttctatttg tttgaatgtt gcatatttct actagtgaaa   3595

ttttccctta ataaagccat taatacaccc aaaaaaaaaa aaaaaa                  3641


<210> SEQ ID NO 5
<211> LENGTH: 2430
<212> TYPE: DNA
<213> ORGANISM: Homo sapiens
<220> FEATURE:
<221> NAME/KEY: CDS
<222> LOCATION: (328)...(2274)

<400> SEQUENCE: 5
```

```
gacactgaat ttggaaggtg gaggattttg ttttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgcttttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
                               1               5

gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
            45                  50                  55

cag cag cag cag cag cag cag cag cag cag cag cag cag cag cag cag      546
Gln Gln Gln Gln Gln Gln Gln Gln Gln Gln Gln Gln Gln Gln Gln Gln
        60                  65                  70

cag cag cag cag cag cag cag cag cag cag caa gag act agc ccc agg      594
Gln Gln Gln Gln Gln Gln Gln Gln Gln Gln Gln Glu Thr Ser Pro Arg
     75                  80                  85

cag cag cag cag cag cag ggt gag gat ggt tct ccc caa gcc cat cgt      642
Gln Gln Gln Gln Gln Gln Gly Glu Asp Gly Ser Pro Gln Ala His Arg
 90                  95                 100                 105

aga ggc ccc aca ggc tac ctg gtc ctg gat gag gaa cag caa cct tca      690
Arg Gly Pro Thr Gly Tyr Leu Val Leu Asp Glu Glu Gln Gln Pro Ser
                110                 115                 120

cag ccg cag tcg gcc ctg gag tgc cac ccc gag aga ggt tgc gtc cca      738
Gln Pro Gln Ser Ala Leu Glu Cys His Pro Glu Arg Gly Cys Val Pro
            125                 130                 135

gag cct gga gcc gcc gtg gcc gcc agc aag ggg ctg ccg cag cag ctg      786
Glu Pro Gly Ala Ala Val Ala Ala Ser Lys Gly Leu Pro Gln Gln Leu
        140                 145                 150

cca gca cct ccg gac gag gat gac tca gct gcc cca tcc acg ttg tcc      834
Pro Ala Pro Pro Asp Glu Asp Asp Ser Ala Ala Pro Ser Thr Leu Ser
    155                 160                 165

ctg ctg ggc ccc act ttc ccc ggc tta agc agc tgc tcc gct gac ctt      882
Leu Leu Gly Pro Thr Phe Pro Gly Leu Ser Ser Cys Ser Ala Asp Leu
170                 175                 180                 185

aaa gac atc ctg agc gag gcc agc acc atg caa ctc ctt cag caa cag      930
Lys Asp Ile Leu Ser Glu Ala Ser Thr Met Gln Leu Leu Gln Gln Gln
                190                 195                 200

cag cag gaa gca gta tcc gaa ggc agc agc agc ggg aga gcg agg gag      978
Gln Gln Glu Ala Val Ser Glu Gly Ser Ser Ser Gly Arg Ala Arg Glu
            205                 210                 215

gcc tcg ggg gct ccc act tcc tcc aag gac aat tac tta ggg ggc act     1026
Ala Ser Gly Ala Pro Thr Ser Ser Lys Asp Asn Tyr Leu Gly Gly Thr
        220                 225                 230

tcg acc att tct gac aac gcc aag gag ttg tgt aag gca gtg tcg gtg     1074
Ser Thr Ile Ser Asp Asn Ala Lys Glu Leu Cys Lys Ala Val Ser Val
    235                 240                 245

tcc atg ggc ctg ggt gtg gag gcg ttg gag cat ctg agt cca ggg gaa     1122
Ser Met Gly Leu Gly Val Glu Ala Leu Glu His Leu Ser Pro Gly Glu
250                 255                 260                 265
```

-continued

```
cag ctt cgg ggg gat tgc atg tac gcc cca ctt ttg gga gtt cca ccc      1170
Gln Leu Arg Gly Asp Cys Met Tyr Ala Pro Leu Leu Gly Val Pro Pro
            270                 275                 280

gct gtg cgt ccc act cct tgt gcc cca ttg gcc gaa tgc aaa ggt tct      1218
Ala Val Arg Pro Thr Pro Cys Ala Pro Leu Ala Glu Cys Lys Gly Ser
        285                 290                 295

ctg cta gac gac agc gca ggc aag agc act gaa gat act gct gag tat      1266
Leu Leu Asp Asp Ser Ala Gly Lys Ser Thr Glu Asp Thr Ala Glu Tyr
    300                 305                 310

tcc cct ttc aag gga ggt tac acc aaa ggg cta gaa ggc gag agc cta      1314
Ser Pro Phe Lys Gly Gly Tyr Thr Lys Gly Leu Glu Gly Glu Ser Leu
315                 320                 325

ggc tgc tct ggc agc gct gca gca ggg agc tcc ggg aca ctt gaa ctg      1362
Gly Cys Ser Gly Ser Ala Ala Ala Gly Ser Ser Gly Thr Leu Glu Leu
330                 335                 340                 345

ccg tct acc ctg tct ctc tac aag tcc gga gca ctg gac gag gca gct      1410
Pro Ser Thr Leu Ser Leu Tyr Lys Ser Gly Ala Leu Asp Glu Ala Ala
                350                 355                 360

gcg tac cag agt cgc gac tac tac aac ttt cca ctg gct ctg gcc gga      1458
Ala Tyr Gln Ser Arg Asp Tyr Tyr Asn Phe Pro Leu Ala Leu Ala Gly
            365                 370                 375

ccg ccg ccc cct ccg ccg cct ccc cat ccc cac gct cgc atc aag ctg      1506
Pro Pro Pro Pro Pro Pro Pro Pro His Pro His Ala Arg Ile Lys Leu
        380                 385                 390

gag aac ccg ctg gac tac ggc agc gcc tgg gcg gct gcg gcg gcg cag      1554
Glu Asn Pro Leu Asp Tyr Gly Ser Ala Trp Ala Ala Ala Ala Ala Gln
    395                 400                 405

tgc cgc tat ggg gac ctg gcg agc ctg cat ggc gcg ggt gca gcg gga      1602
Cys Arg Tyr Gly Asp Leu Ala Ser Leu His Gly Ala Gly Ala Ala Gly
410                 415                 420                 425

ccc ggt tct ggg tca ccc tca gcc gcc gct tcc tca tcc tgg cac act      1650
Pro Gly Ser Gly Ser Pro Ser Ala Ala Ala Ser Ser Ser Trp His Thr
                430                 435                 440

ctc ttc aca gcc gaa gaa ggc cag ttg tat gga ccg tgt ggt ggt ggt      1698
Leu Phe Thr Ala Glu Glu Gly Gln Leu Tyr Gly Pro Cys Gly Gly Gly
            445                 450                 455

ggg ggt ggt ggc ggc ggc ggc ggc ggc ggc ggc ggc ggc ggc ggc ggc      1746
Gly Gly Gly Gly Gly Gly Gly Gly Gly Gly Gly Gly Gly Gly Gly Gly
        460                 465                 470

gag gcg gga gct gta gcc ccc tac ggc tac act cgg ccc cct cag ggg      1794
Glu Ala Gly Ala Val Ala Pro Tyr Gly Tyr Thr Arg Pro Pro Gln Gly
    475                 480                 485

ctg gcg ggc cag gaa agc gac ttc acc gca cct gat gtg tgg tac cct      1842
Leu Ala Gly Gln Glu Ser Asp Phe Thr Ala Pro Asp Val Trp Tyr Pro
490                 495                 500                 505

ggc ggc atg gtg agc aga gtg ccc tat ccc agt ccc act tgt gtc aaa      1890
Gly Gly Met Val Ser Arg Val Pro Tyr Pro Ser Pro Thr Cys Val Lys
                510                 515                 520

agc gaa atg ggc ccc tgg atg gat agc tac tcc gga cct tac ggg gac      1938
Ser Glu Met Gly Pro Trp Met Asp Ser Tyr Ser Gly Pro Tyr Gly Asp
            525                 530                 535

atg cgt ttg gag act gcc agg gac cat gtt ttg ccc att gac tat tac      1986
Met Arg Leu Glu Thr Ala Arg Asp His Val Leu Pro Ile Asp Tyr Tyr
        540                 545                 550

ttt cca ccc cag aag acc tgc ctg atc tgt gga gat gaa gct tct ggg      2034
Phe Pro Pro Gln Lys Thr Cys Leu Ile Cys Gly Asp Glu Ala Ser Gly
    555                 560                 565

tgt cac tat gga gct ctc aca tgt gga agc tgc aag gtc ttc ttc aaa      2082
Cys His Tyr Gly Ala Leu Thr Cys Gly Ser Cys Lys Val Phe Phe Lys
570                 575                 580                 585
```

```
aga gcc gct gaa ggg aaa cag aag tac ctg tgc gcc agc aga aat gat     2130
Arg Ala Ala Glu Gly Lys Gln Lys Tyr Leu Cys Ala Ser Arg Asn Asp
                590                 595                 600

tgc act att gat aaa ttc cga agg aaa aat tgt cca tct tgt cgt ctt     2178
Cys Thr Ile Asp Lys Phe Arg Arg Lys Asn Cys Pro Ser Cys Arg Leu
            605                 610                 615

cgg aaa tgt tat gaa gca ggg atg act ctg gga gca gct gtt gtt gtt     2226
Arg Lys Cys Tyr Glu Ala Gly Met Thr Leu Gly Ala Ala Val Val Val
        620                 625                 630

tct gaa aga atc ttg agg gtg ttt gga gtc tca gaa tgg ctt cct taa     2274
Ser Glu Arg Ile Leu Arg Val Phe Gly Val Ser Glu Trp Leu Pro
    635                 640                 645

agactacctt cagactctca gctgctcatc cacaacagag atcagccctt ctttgtagat   2334

gattcattcc tggctgcatt tgaaaaccac atattgttaa ttgcttgacg aatttaaatc   2394

ccttgactac ttttcatttc aaaaaaaaaa aaaaaa                             2430


<210> SEQ ID NO 6
<211> LENGTH: 2427
<212> TYPE: DNA
<213> ORGANISM: Homo sapiens
<220> FEATURE:
<221> NAME/KEY: CDS
<222> LOCATION: (328)...(2271)

<400> SEQUENCE: 6

gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                             Met Glu Val Gln Leu Gly Leu Gly Arg
                              1               5

gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55

cag cag cag cag cag cag cag cag cag cag cag cag cag cag cag cag      546
Gln Gln Gln Gln Gln Gln Gln Gln Gln Gln Gln Gln Gln Gln Gln Gln
         60                  65                  70

cag cag cag cag cag cag cag cag cag cag caa gag act agc ccc agg      594
Gln Gln Gln Gln Gln Gln Gln Gln Gln Gln Gln Glu Thr Ser Pro Arg
     75                  80                  85

cag cag cag cag cag cag ggt gag gat ggt tct ccc caa gcc cat cgt      642
Gln Gln Gln Gln Gln Gln Gly Glu Asp Gly Ser Pro Gln Ala His Arg
 90                  95                 100                 105

aga ggc ccc aca ggc tac ctg gtc ctg gat gag gaa cag caa cct tca      690
Arg Gly Pro Thr Gly Tyr Leu Val Leu Asp Glu Glu Gln Gln Pro Ser
                110                 115                 120

cag ccg cag tcg gcc ctg gag tgc cac ccc gag aga ggt tgc gtc cca      738
Gln Pro Gln Ser Ala Leu Glu Cys His Pro Glu Arg Gly Cys Val Pro
            125                 130                 135
```

```
gag cct gga gcc gcc gtg gcc gcc agc aag ggg ctg ccg cag cag ctg      786
Glu Pro Gly Ala Ala Val Ala Ala Ser Lys Gly Leu Pro Gln Gln Leu
        140                 145                 150

cca gca cct ccg gac gag gat gac tca gct gcc cca tcc acg ttg tcc      834
Pro Ala Pro Pro Asp Glu Asp Asp Ser Ala Ala Pro Ser Thr Leu Ser
    155                 160                 165

ctg ctg ggc ccc act ttc ccc ggc tta agc agc tgc tcc gct gac ctt      882
Leu Leu Gly Pro Thr Phe Pro Gly Leu Ser Ser Cys Ser Ala Asp Leu
170                 175                 180                 185

aaa gac atc ctg agc gag gcc agc acc atg caa ctc ctt cag caa cag      930
Lys Asp Ile Leu Ser Glu Ala Ser Thr Met Gln Leu Leu Gln Gln Gln
                190                 195                 200

cag cag gaa gca gta tcc gaa ggc agc agc agc ggg aga gcg agg gag      978
Gln Gln Glu Ala Val Ser Glu Gly Ser Ser Ser Gly Arg Ala Arg Glu
            205                 210                 215

gcc tcg ggg gct ccc act tcc tcc aag gac aat tac tta ggg ggc act     1026
Ala Ser Gly Ala Pro Thr Ser Ser Lys Asp Asn Tyr Leu Gly Gly Thr
        220                 225                 230

tcg acc att tct gac aac gcc aag gag ttg tgt aag gca gtg tcg gtg     1074
Ser Thr Ile Ser Asp Asn Ala Lys Glu Leu Cys Lys Ala Val Ser Val
    235                 240                 245

tcc atg ggc ctg ggt gtg gag gcg ttg gag cat ctg agt cca ggg gaa     1122
Ser Met Gly Leu Gly Val Glu Ala Leu Glu His Leu Ser Pro Gly Glu
250                 255                 260                 265

cag ctt cgg ggg gat tgc atg tac gcc cca ctt ttg gga gtt cca ccc     1170
Gln Leu Arg Gly Asp Cys Met Tyr Ala Pro Leu Leu Gly Val Pro Pro
                270                 275                 280

gct gtg cgt ccc act cct tgt gcc cca ttg gcc gaa tgc aaa ggt tct     1218
Ala Val Arg Pro Thr Pro Cys Ala Pro Leu Ala Glu Cys Lys Gly Ser
            285                 290                 295

ctg cta gac gac agc gca ggc aag agc act gaa gat act gct gag tat     1266
Leu Leu Asp Asp Ser Ala Gly Lys Ser Thr Glu Asp Thr Ala Glu Tyr
        300                 305                 310

tcc cct ttc aag gga ggt tac acc aaa ggg cta gaa ggc gag agc cta     1314
Ser Pro Phe Lys Gly Gly Tyr Thr Lys Gly Leu Glu Gly Glu Ser Leu
    315                 320                 325

ggc tgc tct ggc agc gct gca gca ggg agc tcc ggg aca ctt gaa ctg     1362
Gly Cys Ser Gly Ser Ala Ala Ala Gly Ser Ser Gly Thr Leu Glu Leu
330                 335                 340                 345

ccg tct acc ctg tct ctc tac aag tcc gga gca ctg gac gag gca gct     1410
Pro Ser Thr Leu Ser Leu Tyr Lys Ser Gly Ala Leu Asp Glu Ala Ala
                350                 355                 360

gcg tac cag agt cgc gac tac tac aac ttt cca ctg gct ctg gcc gga     1458
Ala Tyr Gln Ser Arg Asp Tyr Tyr Asn Phe Pro Leu Ala Leu Ala Gly
            365                 370                 375

ccg ccg ccc cct ccg ccg cct ccc cat ccc cac gct cgc atc aag ctg     1506
Pro Pro Pro Pro Pro Pro Pro Pro His Pro His Ala Arg Ile Lys Leu
        380                 385                 390

gag aac ccg ctg gac tac ggc agc gcc tgg gcg gct gcg gcg gcg cag     1554
Glu Asn Pro Leu Asp Tyr Gly Ser Ala Trp Ala Ala Ala Ala Ala Gln
    395                 400                 405

tgc cgc tat ggg gac ctg gcg agc ctg cat ggc gcg ggt gca gcg gga     1602
Cys Arg Tyr Gly Asp Leu Ala Ser Leu His Gly Ala Gly Ala Ala Gly
410                 415                 420                 425

ccc ggt tct ggg tca ccc tca gcc gcc gct tcc tca tcc tgg cac act     1650
Pro Gly Ser Gly Ser Pro Ser Ala Ala Ala Ser Ser Ser Trp His Thr
                430                 435                 440

ctc ttc aca gcc gaa gaa ggc cag ttg tat gga ccg tgt ggt ggt ggt     1698
Leu Phe Thr Ala Glu Glu Gly Gln Leu Tyr Gly Pro Cys Gly Gly Gly
```

```
            445                 450                 455

ggg ggt ggt ggc ggc ggc ggc ggc ggc ggc ggc ggc ggc ggc ggc ggc      1746
Gly Gly Gly Gly Gly Gly Gly Gly Gly Gly Gly Gly Gly Gly Gly Gly
        460                 465                 470

gag gcg gga gct gta gcc ccc tac ggc tac act cgg ccc cct cag ggg      1794
Glu Ala Gly Ala Val Ala Pro Tyr Gly Tyr Thr Arg Pro Pro Gln Gly
    475                 480                 485

ctg gcg ggc cag gaa agc gac ttc acc gca cct gat gtg tgg tac cct      1842
Leu Ala Gly Gln Glu Ser Asp Phe Thr Ala Pro Asp Val Trp Tyr Pro
490                 495                 500                 505

ggc ggc atg gtg agc aga gtg ccc tat ccc agt ccc act tgt gtc aaa      1890
Gly Gly Met Val Ser Arg Val Pro Tyr Pro Ser Pro Thr Cys Val Lys
                510                 515                 520

agc gaa atg ggc ccc tgg atg gat agc tac tcc gga cct tac ggg gac      1938
Ser Glu Met Gly Pro Trp Met Asp Ser Tyr Ser Gly Pro Tyr Gly Asp
            525                 530                 535

atg cgt ttg gag act gcc agg gac cat gtt ttg ccc att gac tat tac      1986
Met Arg Leu Glu Thr Ala Arg Asp His Val Leu Pro Ile Asp Tyr Tyr
        540                 545                 550

ttt cca ccc cag aag acc tgc ctg atc tgt gga gat gaa gct tct ggg      2034
Phe Pro Pro Gln Lys Thr Cys Leu Ile Cys Gly Asp Glu Ala Ser Gly
    555                 560                 565

tgt cac tat gga gct ctc aca tgt gga agc tgc aag gtc ttc ttc aaa      2082
Cys His Tyr Gly Ala Leu Thr Cys Gly Ser Cys Lys Val Phe Phe Lys
570                 575                 580                 585

aga gcc gct gaa ggg aaa cag aag tac ctg tgc gcc agc aga aat gat      2130
Arg Ala Ala Glu Gly Lys Gln Lys Tyr Leu Cys Ala Ser Arg Asn Asp
                590                 595                 600

tgc act att gat aaa ttc cga agg aaa aat tgt cca tct tgt cgt ctt      2178
Cys Thr Ile Asp Lys Phe Arg Arg Lys Asn Cys Pro Ser Cys Arg Leu
            605                 610                 615

cgg aaa tgt tat gaa gca ggg att ctg gga gca gct gtt gtt gtt tct      2226
Arg Lys Cys Tyr Glu Ala Gly Ile Leu Gly Ala Ala Val Val Val Ser
        620                 625                 630

gaa aga atc ttg agg gtg ttt gga gtc tca gaa tgg ctt cct taa          2271
Glu Arg Ile Leu Arg Val Phe Gly Val Ser Glu Trp Leu Pro
    635                 640                 645

agactacctt cagactctca gctgctcatc cacaacagag atcagccctt ctttgtagat   2331

gattcattcc tggctgcatt tgaaaaccac atattgttaa ttgcttgacg aatttaaatc   2391

ccttgactac ttttcatttc aaaaaaaaaa aaaaaa                             2427


<210> SEQ ID NO 7
<211> LENGTH: 4039
<212> TYPE: DNA
<213> ORGANISM: Homo sapiens
<220> FEATURE:
<221> NAME/KEY: CDS
<222> LOCATION: (328)...(2376)

<400> SEQUENCE: 7

gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
```

-continued 1 5 gtc tac cct cgg ccg ccg tcc aag acc tac cga gga gct ttc cag aat 402
Val Tyr Pro Arg Pro Pro Ser Lys Thr Tyr Arg Gly Ala Phe Gln Asn
10 15 20 25 ctg ttc cag agc gtg cgc gaa gtg atc cag aac ccg ggc ccc agg cac 450
Leu Phe Gln Ser Val Arg Glu Val Ile Gln Asn Pro Gly Pro Arg His
30 35 40 cca gag gcc gcg agc gca gca cct ccc ggc gcc agt ttg ctg ctg cag 498
Pro Glu Ala Ala Ser Ala Ala Pro Pro Gly Ala Ser Leu Leu Leu Gln
45 50 55 cag cag cag cag cag cag cag cag cag cag cag cag cag cag cag cag 546
Gln Gln Gln Gln Gln Gln Gln Gln Gln Gln Gln Gln Gln Gln Gln Gln
60 65 70 cag cag cag cag cag cag cag cag cag cag cag caa gag act agc ccc 594
Gln Gln Gln Gln Gln Gln Gln Gln Gln Gln Gln Gln Glu Thr Ser Pro
75 80 85 agg cag cag cag cag cag cag ggt gag gat ggt tct ccc caa gcc cat 642
Arg Gln Gln Gln Gln Gln Gln Gly Glu Asp Gly Ser Pro Gln Ala His
90 95 100 105 cgt aga ggc ccc aca ggc tac ctg gtc ctg gat gag gaa cag caa cct 690
Arg Arg Gly Pro Thr Gly Tyr Leu Val Leu Asp Glu Glu Gln Gln Pro
110 115 120 tca cag ccg cag tcg gcc ctg gag tgc cac ccc gag aga ggt tgc gtc 738
Ser Gln Pro Gln Ser Ala Leu Glu Cys His Pro Glu Arg Gly Cys Val
125 130 135 cca gag cct gga gcc gcc gtg gcc gcc agc aag ggg ctg ccg cag cag 786
Pro Glu Pro Gly Ala Ala Val Ala Ala Ser Lys Gly Leu Pro Gln Gln
140 145 150 ctg cca gca cct ccg gac gag gat gac tca gct gcc cca tcc acg ttg 834
Leu Pro Ala Pro Pro Asp Glu Asp Asp Ser Ala Ala Pro Ser Thr Leu
155 160 165 tcc ctg ctg ggc ccc act ttc ccc ggc tta agc agc tgc tcc gct gac 882
Ser Leu Leu Gly Pro Thr Phe Pro Gly Leu Ser Ser Cys Ser Ala Asp
170 175 180 185 ctt aaa gac atc ctg agc gag gcc agc acc atg caa ctc ctt cag caa 930
Leu Lys Asp Ile Leu Ser Glu Ala Ser Thr Met Gln Leu Leu Gln Gln
190 195 200 cag cag cag gaa gca gta tcc gaa ggc agc agc agc ggg aga gcg agg 978
Gln Gln Gln Glu Ala Val Ser Glu Gly Ser Ser Ser Gly Arg Ala Arg
205 210 215 gag gcc tcg ggg gct ccc act tcc tcc aag gac aat tac tta ggg ggc 1026
Glu Ala Ser Gly Ala Pro Thr Ser Ser Lys Asp Asn Tyr Leu Gly Gly
220 225 230 act tcg acc att tct gac aac gcc aag gag ttg tgt aag gca gtg tcg 1074
Thr Ser Thr Ile Ser Asp Asn Ala Lys Glu Leu Cys Lys Ala Val Ser
235 240 245 gtg tcc atg ggc ctg ggt gtg gag gcg ttg gag cat ctg agt cca ggg 1122
Val Ser Met Gly Leu Gly Val Glu Ala Leu Glu His Leu Ser Pro Gly
250 255 260 265 gaa cag ctt cgg ggg gat tgc atg tac gcc cca ctt ttg gga gtt cca 1170
Glu Gln Leu Arg Gly Asp Cys Met Tyr Ala Pro Leu Leu Gly Val Pro
270 275 280 ccc gct gtg cgt ccc act cct tgt gcc cca ttg gcc gaa tgc aaa ggt 1218
Pro Ala Val Arg Pro Thr Pro Cys Ala Pro Leu Ala Glu Cys Lys Gly
285 290 295 tct ctg cta gac gac agc gca ggc aag agc act gaa gat act gct gag 1266
Ser Leu Leu Asp Asp Ser Ala Gly Lys Ser Thr Glu Asp Thr Ala Glu
300 305 310 tat tcc cct ttc aag gga ggt tac acc aaa ggg cta gaa ggc gag agc 1314

-continued

```
Tyr Ser Pro Phe Lys Gly Gly Tyr Thr Lys Gly Leu Glu Gly Glu Ser
    315                 320                 325

cta ggc tgc tct ggc agc gct gca gca ggg agc tcc ggg aca ctt gaa      1362
Leu Gly Cys Ser Gly Ser Ala Ala Ala Gly Ser Ser Gly Thr Leu Glu
330                 335                 340                 345

ctg ccg tct acc ctg tct ctc tac aag tcc gga gca ctg gac gag gca      1410
Leu Pro Ser Thr Leu Ser Leu Tyr Lys Ser Gly Ala Leu Asp Glu Ala
                350                 355                 360

gct gcg tac cag agt cgc gac tac tac aac ttt cca ctg gct ctg gcc      1458
Ala Ala Tyr Gln Ser Arg Asp Tyr Tyr Asn Phe Pro Leu Ala Leu Ala
            365                 370                 375

gga ccg ccg ccc cct ccg ccg cct ccc cat ccc cac gct cgc atc aag      1506
Gly Pro Pro Pro Pro Pro Pro Pro Pro His Pro His Ala Arg Ile Lys
        380                 385                 390

ctg gag aac ccg ctg gac tac ggc agc gcc tgg gcg gct gcg gcg gcg      1554
Leu Glu Asn Pro Leu Asp Tyr Gly Ser Ala Trp Ala Ala Ala Ala Ala
    395                 400                 405

cag tgc cgc tat ggg gac ctg gcg agc ctg cat ggc gcg ggt gca gcg      1602
Gln Cys Arg Tyr Gly Asp Leu Ala Ser Leu His Gly Ala Gly Ala Ala
410                 415                 420                 425

gga ccc ggt tct ggg tca ccc tca gcc gcc gct tcc tca tcc tgg cac      1650
Gly Pro Gly Ser Gly Ser Pro Ser Ala Ala Ala Ser Ser Ser Trp His
                430                 435                 440

act ctc ttc aca gcc gaa gaa ggc cag ttg tat gga ccg tgt ggt ggt      1698
Thr Leu Phe Thr Ala Glu Glu Gly Gln Leu Tyr Gly Pro Cys Gly Gly
            445                 450                 455

ggt ggg ggt ggt ggc ggc ggc ggc ggc ggc ggc ggc ggc ggc ggc ggc      1746
Gly Gly Gly Gly Gly Gly Gly Gly Gly Gly Gly Gly Gly Gly Gly Gly
        460                 465                 470

ggc gag gcg gga gct gta gcc ccc tac ggc tac act cgg ccc cct cag      1794
Gly Glu Ala Gly Ala Val Ala Pro Tyr Gly Tyr Thr Arg Pro Pro Gln
    475                 480                 485

ggg ctg gcg ggc cag gaa agc gac ttc acc gca cct gat gtg tgg tac      1842
Gly Leu Ala Gly Gln Glu Ser Asp Phe Thr Ala Pro Asp Val Trp Tyr
490                 495                 500                 505

cct ggc ggc atg gtg agc aga gtg ccc tat ccc agt ccc act tgt gtc      1890
Pro Gly Gly Met Val Ser Arg Val Pro Tyr Pro Ser Pro Thr Cys Val
                510                 515                 520

aaa agc gaa atg ggc ccc tgg atg gat agc tac tcc gga cct tac ggg      1938
Lys Ser Glu Met Gly Pro Trp Met Asp Ser Tyr Ser Gly Pro Tyr Gly
            525                 530                 535

gac atg cgt ttg gag act gcc agg gac cat gtt ttg ccc att gac tat      1986
Asp Met Arg Leu Glu Thr Ala Arg Asp His Val Leu Pro Ile Asp Tyr
        540                 545                 550

tac ttt cca ccc cag aag acc tgc ctg atc tgt gga gat gaa gct tct      2034
Tyr Phe Pro Pro Gln Lys Thr Cys Leu Ile Cys Gly Asp Glu Ala Ser
    555                 560                 565

ggg tgt cac tat gga gct ctc aca tgt gga agc tgc aag gtc ttc ttc      2082
Gly Cys His Tyr Gly Ala Leu Thr Cys Gly Ser Cys Lys Val Phe Phe
570                 575                 580                 585

aaa aga gcc gct gaa ggg aaa cag aag tac ctg tgc gcc agc aga aat      2130
Lys Arg Ala Ala Glu Gly Lys Gln Lys Tyr Leu Cys Ala Ser Arg Asn
                590                 595                 600

gat tgc act att gat aaa ttc cga agg aaa aat tgt cca tct tgt cgt      2178
Asp Cys Thr Ile Asp Lys Phe Arg Arg Lys Asn Cys Pro Ser Cys Arg
            605                 610                 615

ctt cgg aaa tgt tat gaa gca ggg atg act ctg gga gga ttt ttc aga      2226
Leu Arg Lys Cys Tyr Glu Ala Gly Met Thr Leu Gly Gly Phe Phe Arg
        620                 625                 630
```

```
atg aac aaa tta aaa gaa tca tca gac act aac ccc aag cca tac tgc      2274
Met Asn Lys Leu Lys Glu Ser Ser Asp Thr Asn Pro Lys Pro Tyr Cys
    635                 640                 645

atg gca gca cca atg gga ctg aca gaa aac aac aga aat agg aag aaa      2322
Met Ala Ala Pro Met Gly Leu Thr Glu Asn Asn Arg Asn Arg Lys Lys
650                 655                 660                 665

tcc tac aga gaa aca aac ttg aaa gct gtc tca tgg cct ttg aat cat      2370
Ser Tyr Arg Glu Thr Asn Leu Lys Ala Val Ser Trp Pro Leu Asn His
                670                 675                 680

act taa gttttatgat ggaaggatac gactatgaag aaagacacag agcaacatca      2426
Thr

gacagtcaag aatttcagag ccagctggca tgcagtggac ctcatgccag cccattttat   2486

gactatttag ggaaacagaa gtacctgtgc gccagcagaa atgattgcac tattgataaa   2546

ttccgaagga aaaattgtcc atcttgtcgt cttcggaaat gttatgaagc agggatgact   2606

ctgggagaaa aattccgggt tggcaattgc aagcatctca aaatgaccag accctgaaga   2666

aaggctgact tgcctcattc aaaatgaggg ctctagaggg ctctagtgga tagtctggag   2726

aaacctggcg tctgaggctt aggagcttag gtttttgctc ctcaacacag actttgacgt   2786

tggggttggg ggctactctc ttgattgctg actccctcca gcgggaccaa tagtgttttc   2846

ctacctcaca gggatgttgt gaggacgggc tgtagaagta atagtggtta ccactcatgt   2906

agttgtgagt atcatgatta ttgtttcctg taatgtggct tggcattggc aaagtgcttt   2966

ttgattgttc ttgatcacat atgatggggg ccaggcactg actcaggcgg atgcagtgaa   3026

gctctggctc agtcgcttgc ttttcgtggt gtgctgccag gaagaaactt tgctgatggg   3086

actcaaggtg tcaccttgga caagaagcaa ctgtgtctgt ctgaggttcc tgtggccatc   3146

tttatttgtg tattaggcaa ttcgtatttc cccccttaggt tctagccttc tggatcccag  3206

ccagtgacct agatcttagc ctcaggccct gtcactgagc tgaaggtagt agctgatcca   3266

cagaagttca gtaaacaagg accagatttc tgcttctcca ggagaagaag ccagccaacc   3326

cctctcttca aacacactga gagactacag tccgactttc cctcttacat ctagccttac   3386

tgtagccaca ctccttgatt gctctctcac atcacatgct tctcttcatc agttgtaagc   3446

ctctcattct tctcccaagc cagactcaaa tattgtattg atgtcaaaga agaatcactt   3506

agagtttgga atatcttgtt ctctctctgc tccatagctt ccatattgac accagtttct   3566

ttctagtgga gaagtggagt ctgtgaagcc agggaaacac acatgtgaga gtcagaagga   3626

ctctccctga cttgcctggg gcctgtcttt cccaccttct ccagtctgtc taaacacaca   3686

cacacacaca cacacacaca cacacacaca cacacacgct ctctctctct ctccccccccc  3746

aacacacaca cactctctct ctcacacaca cacacataca cacacacttc tttctctttc   3806

ccctgactca gcaacattct ggagaaaagc caaggaagga cttcaggagg ggagtttccc   3866

ccttctcagg gcagaatttt aatctccaga ccaacaagaa gttccctaat gtggattgaa   3926

aggctaatga ggtttatttt taactacttt ctatttgttt gaatgttgca tatttctact   3986

agtgaaattt tcccttaata aagccattaa tacacccaaa aaaaaaaaaa aaa          4039


<210> SEQ ID NO 8
<211> LENGTH: 3922
<212> TYPE: DNA
<213> ORGANISM: Homo sapiens
<220> FEATURE:
<221> NAME/KEY: CDS
<222> LOCATION: (328)...(2259)

<400> SEQUENCE: 8
```

-continued

```
gacactgaat ttggaaggtg gaggattttg tttttttctt ttaagatctg ggcatctttt     60

gaatctaccc ttcaagtatt aagagacaga ctgtgagcct agcagggcag atcttgtcca    120

ccgtgtgtct tcttctgcac gagactttga ggctgtcaga gcgctttttg cgtggttgct    180

cccgcaagtt tccttctctg gagcttcccg caggtgggca gctagctgca gcgactaccg    240

catcatcaca gcctgttgaa ctcttctgag caagagaagg ggaggcgggg taagggaagt    300

aggtggaaga ttcagccaag ctcaagg atg gaa gtg cag tta ggg ctg gga agg    354
                              Met Glu Val Gln Leu Gly Leu Gly Arg
                               1               5

gtc tac cct cgg ccg ccg tcc aag acc tac cga gga gct ttc cag aat      402
Val Tyr Pro Arg Pro Pro Ser Lys Thr Tyr Arg Gly Ala Phe Gln Asn
 10                  15                  20                  25

ctg ttc cag agc gtg cgc gaa gtg atc cag aac ccg ggc ccc agg cac      450
Leu Phe Gln Ser Val Arg Glu Val Ile Gln Asn Pro Gly Pro Arg His
                 30                  35                  40

cca gag gcc gcg agc gca gca cct ccc ggc gcc agt ttg ctg ctg cag      498
Pro Glu Ala Ala Ser Ala Ala Pro Pro Gly Ala Ser Leu Leu Leu Gln
             45                  50                  55

cag cag cag cag cag cag cag cag cag cag cag cag cag cag cag cag      546
Gln Gln Gln Gln Gln Gln Gln Gln Gln Gln Gln Gln Gln Gln Gln Gln
         60                  65                  70

cag cag cag cag cag cag cag cag cag cag cag caa gag act agc ccc      594
Gln Gln Gln Gln Gln Gln Gln Gln Gln Gln Gln Gln Glu Thr Ser Pro
     75                  80                  85

agg cag cag cag cag cag cag ggt gag gat ggt tct ccc caa gcc cat      642
Arg Gln Gln Gln Gln Gln Gln Gly Glu Asp Gly Ser Pro Gln Ala His
 90                  95                 100                 105

cgt aga ggc ccc aca ggc tac ctg gtc ctg gat gag gaa cag caa cct      690
Arg Arg Gly Pro Thr Gly Tyr Leu Val Leu Asp Glu Glu Gln Gln Pro
                110                 115                 120

tca cag ccg cag tcg gcc ctg gag tgc cac ccc gag aga ggt tgc gtc      738
Ser Gln Pro Gln Ser Ala Leu Glu Cys His Pro Glu Arg Gly Cys Val
            125                 130                 135

cca gag cct gga gcc gcc gtg gcc gcc agc aag ggg ctg ccg cag cag      786
Pro Glu Pro Gly Ala Ala Val Ala Ala Ser Lys Gly Leu Pro Gln Gln
        140                 145                 150

ctg cca gca cct ccg gac gag gat gac tca gct gcc cca tcc acg ttg      834
Leu Pro Ala Pro Pro Asp Glu Asp Asp Ser Ala Ala Pro Ser Thr Leu
    155                 160                 165

tcc ctg ctg ggc ccc act ttc ccc ggc tta agc agc tgc tcc gct gac      882
Ser Leu Leu Gly Pro Thr Phe Pro Gly Leu Ser Ser Cys Ser Ala Asp
170                 175                 180                 185

ctt aaa gac atc ctg agc gag gcc agc acc atg caa ctc ctt cag caa      930
Leu Lys Asp Ile Leu Ser Glu Ala Ser Thr Met Gln Leu Leu Gln Gln
                190                 195                 200

cag cag cag gaa gca gta tcc gaa ggc agc agc agc ggg aga gcg agg      978
Gln Gln Gln Glu Ala Val Ser Glu Gly Ser Ser Ser Gly Arg Ala Arg
            205                 210                 215

gag gcc tcg ggg gct ccc act tcc tcc aag gac aat tac tta ggg ggc     1026
Glu Ala Ser Gly Ala Pro Thr Ser Ser Lys Asp Asn Tyr Leu Gly Gly
        220                 225                 230

act tcg acc att tct gac aac gcc aag gag ttg tgt aag gca gtg tcg     1074
Thr Ser Thr Ile Ser Asp Asn Ala Lys Glu Leu Cys Lys Ala Val Ser
    235                 240                 245

gtg tcc atg ggc ctg ggt gtg gag gcg ttg gag cat ctg agt cca ggg     1122
Val Ser Met Gly Leu Gly Val Glu Ala Leu Glu His Leu Ser Pro Gly
250                 255                 260                 265
```

-continued

```
gaa cag ctt cgg ggg gat tgc atg tac gcc cca ctt ttg gga gtt cca      1170
Glu Gln Leu Arg Gly Asp Cys Met Tyr Ala Pro Leu Leu Gly Val Pro
                270                 275                 280

ccc gct gtg cgt ccc act cct tgt gcc cca ttg gcc gaa tgc aaa ggt      1218
Pro Ala Val Arg Pro Thr Pro Cys Ala Pro Leu Ala Glu Cys Lys Gly
            285                 290                 295

tct ctg cta gac gac agc gca ggc aag agc act gaa gat act gct gag      1266
Ser Leu Leu Asp Asp Ser Ala Gly Lys Ser Thr Glu Asp Thr Ala Glu
        300                 305                 310

tat tcc cct ttc aag gga ggt tac acc aaa ggg cta gaa ggc gag agc      1314
Tyr Ser Pro Phe Lys Gly Gly Tyr Thr Lys Gly Leu Glu Gly Glu Ser
    315                 320                 325

cta ggc tgc tct ggc agc gct gca gca ggg agc tcc ggg aca ctt gaa      1362
Leu Gly Cys Ser Gly Ser Ala Ala Ala Gly Ser Ser Gly Thr Leu Glu
330                 335                 340                 345

ctg ccg tct acc ctg tct ctc tac aag tcc gga gca ctg gac gag gca      1410
Leu Pro Ser Thr Leu Ser Leu Tyr Lys Ser Gly Ala Leu Asp Glu Ala
                350                 355                 360

gct gcg tac cag agt cgc gac tac tac aac ttt cca ctg gct ctg gcc      1458
Ala Ala Tyr Gln Ser Arg Asp Tyr Tyr Asn Phe Pro Leu Ala Leu Ala
            365                 370                 375

gga ccg ccg ccc cct ccg ccg cct ccc cat ccc cac gct cgc atc aag      1506
Gly Pro Pro Pro Pro Pro Pro Pro Pro His Pro His Ala Arg Ile Lys
        380                 385                 390

ctg gag aac ccg ctg gac tac ggc agc gcc tgg gcg gct gcg gcg gcg      1554
Leu Glu Asn Pro Leu Asp Tyr Gly Ser Ala Trp Ala Ala Ala Ala Ala
    395                 400                 405

cag tgc cgc tat ggg gac ctg gcg agc ctg cat ggc gcg ggt gca gcg      1602
Gln Cys Arg Tyr Gly Asp Leu Ala Ser Leu His Gly Ala Gly Ala Ala
410                 415                 420                 425

gga ccc ggt tct ggg tca ccc tca gcc gcc gct tcc tca tcc tgg cac      1650
Gly Pro Gly Ser Gly Ser Pro Ser Ala Ala Ala Ser Ser Ser Trp His
                430                 435                 440

act ctc ttc aca gcc gaa gaa ggc cag ttg tat gga ccg tgt ggt ggt      1698
Thr Leu Phe Thr Ala Glu Glu Gly Gln Leu Tyr Gly Pro Cys Gly Gly
            445                 450                 455

ggt ggg ggt ggt ggc ggc ggc ggc ggc ggc ggc ggc ggc ggc ggc ggc      1746
Gly Gly Gly Gly Gly Gly Gly Gly Gly Gly Gly Gly Gly Gly Gly Gly
        460                 465                 470

ggc gag gcg gga gct gta gcc ccc tac ggc tac act cgg ccc cct cag      1794
Gly Glu Ala Gly Ala Val Ala Pro Tyr Gly Tyr Thr Arg Pro Pro Gln
    475                 480                 485

ggg ctg gcg ggc cag gaa agc gac ttc acc gca cct gat gtg tgg tac      1842
Gly Leu Ala Gly Gln Glu Ser Asp Phe Thr Ala Pro Asp Val Trp Tyr
490                 495                 500                 505

cct ggc ggc atg gtg agc aga gtg ccc tat ccc agt ccc act tgt gtc      1890
Pro Gly Gly Met Val Ser Arg Val Pro Tyr Pro Ser Pro Thr Cys Val
                510                 515                 520

aaa agc gaa atg ggc ccc tgg atg gat agc tac tcc gga cct tac ggg      1938
Lys Ser Glu Met Gly Pro Trp Met Asp Ser Tyr Ser Gly Pro Tyr Gly
            525                 530                 535

gac atg cgt ttg gag act gcc agg gac cat gtt ttg ccc att gac tat      1986
Asp Met Arg Leu Glu Thr Ala Arg Asp His Val Leu Pro Ile Asp Tyr
        540                 545                 550

tac ttt cca ccc cag aag acc tgc ctg atc tgt gga gac gaa gct tct      2034
Tyr Phe Pro Pro Gln Lys Thr Cys Leu Ile Cys Gly Asp Glu Ala Ser
    555                 560                 565

ggg tgt cac tat gga gct ctc aca tgt gga agc tgc aag gtc ttc ttc      2082
Gly Cys His Tyr Gly Ala Leu Thr Cys Gly Ser Cys Lys Val Phe Phe
570                 575                 580                 585
```

```
aaa aga gcc gct gaa gga ttt ttc aga atg aac aaa tta aaa gaa tca      2130
Lys Arg Ala Ala Glu Gly Phe Phe Arg Met Asn Lys Leu Lys Glu Ser
                590                 595                 600

tca gac act aac ccc aag cca tac tgc atg gca gca cca atg gga ctg      2178
Ser Asp Thr Asn Pro Lys Pro Tyr Cys Met Ala Ala Pro Met Gly Leu
            605                 610                 615

aca gaa aac aac aga aat agg aag aaa tcc tac aga gaa aca aac ttg      2226
Thr Glu Asn Asn Arg Asn Arg Lys Lys Ser Tyr Arg Glu Thr Asn Leu
        620                 625                 630

aaa gct gtc tca tgg cct ttg aat cat act taa gttttatgat ggaaggatac    2279
Lys Ala Val Ser Trp Pro Leu Asn His Thr
    635                 640

gactatgaag aaagacacag agcaacatca gacagtcaag aatttcagag ccagctggca    2339

tgcagtggac ctcatgccag cccattttat gactatttag ggagacagaa gtacctgtgc    2399

gccagcagaa atgattgcac tattgataaa ttccgaagga aaaattgtcc atcttgtcgt    2459

cttcggaaat gttatgaagc aggggtgact ctgggagaaa aattccgggt tggcaattgc    2519

aagcatctca aaatgaccag accctgaaga aaggctgact tgcctcattc aaaatgaggg    2579

ctctagaggg ctctagtgga tagtctggag aaacctggcg tctgaggctt aggagcttag    2639

gtttttgctc ctcaacacag actttgacgt tggggttggg ggctactctc ttgattgctg    2699

actccctcca gcgggaccaa tagtgttttc ctacctcaca gggatgttgt gaggacgggc    2759

tgtagaagta atagtggtta ccactcatgt agttgtgagt atcatgatta ttgtttcctg    2819

taatgtggct tggcattggc aaagtgcttt ttgattgttc ttgatcacat atgatggggg    2879

ccaggcactg actcaggcgg atgcagtgaa gctctggctc agtcgcttgc ttttcgtggt    2939

gtgctgccag gaagaaactt tgctgatggg actcaaggtg tcaccttgga caagaagcaa    2999

ctgtgtctgt ctgaggttcc tgtggccatc tttatttgtg tattaggcaa ttcgtatttc    3059

ccccttaggt tctagccttc tggatcccag ccagtgacct agatcttagc ctcaggccct    3119

gtcactgagc tgaaggtagt agctgatcca cagaagttca gtaaacaagg accagatttc    3179

tgcttctcca ggagaagaag ccagccaacc cctctcttca aacacactga gagactacag    3239

tccgactttc cctcttacat ctagccttac tgtagccaca ctccttgatt gctctctcac    3299

atcacatgct tctcttcatc agttgtaagc ctctcattct tctcccaagc cagactcaaa    3359

tattgtattg atgtcaaaga agaatcactt agagtttgga atatcttgtt ctctctctgc    3419

tccatagctt ccatattgac accagtttct ttctagtgga gaagtggagt ctgtgaagcc    3479

agggaaacac acatgtgaga gtcagaagga ctctccctga cttgcctggg gcctgtcttt    3539

cccaccttct ccagtctgtc taaacacaca cacacacaca cacacacaca cacacacaca    3599

cacacacgct ctctctctct ctcccccccc aacacacaca cactctctct ctcacacaca    3659

cacacataca cacacacttc tttctctttc ccctgactca gcaacattct ggagaaaagc    3719

caaggaagga cttcaggagg ggagtttccc ccttctcagg gcagaatttt aatctccaga    3779

ccaacaagaa gttccctaat gtggattgaa aggctaatga ggtttatttt taactacttt    3839

ctatttgttt gaatgttgca tatttctact agtgaaattt tcccttaata aagccattaa    3899

tacacccaaa aaaaaaaaaa aaa                                             3922
```

<210> SEQ ID NO 9
<211> LENGTH: 21
<212> TYPE: DNA
<213> ORGANISM: Artificial Sequence
<220> FEATURE:

-continued

<223> OTHER INFORMATION: Primer

<400> SEQUENCE: 9
tccttcacca atgtcaactc c 21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gagccatcca aactcttgag a 21

<210> SEQ ID NO 11
<211> LENGTH: 22
<212> TYPE: DNA
<213> ORGANISM: Artificial Sequence
<220> FEATURE:
<223> OTHER INFORMATION: Probe

<400> SEQUENCE: 11
agtaccgcat gcacaagtcc cg 22

<210> SEQ ID NO 12
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 12
gcgctctgac agcctc 16

<210> SEQ ID NO 13
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 13
cacctgcggg aagctc 16

<210> SEQ ID NO 14
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 14
ggctgtgatg atgcgg 16

<210> SEQ ID NO 15
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 15
cttcgcgcac gctctg 16

-continued

<210> SEQ ID NO 16
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 16
atggtgctgg cctcgc 16

<210> SEQ ID NO 17
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 17
ggtcgaagtg ccccct 16

<210> SEQ ID NO 18
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 18
gacaccgaca ctgcct 16

<210> SEQ ID NO 19
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 19
cccgaagctg ttcccc 16

<210> SEQ ID NO 20
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 20
cttgcctgcg ctgtcg 16

<210> SEQ ID NO 21
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 21
gttgtagtag tcgcga 16

<210> SEQ ID NO 22
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 22
aagttgtagt agtcgc 16

<210> SEQ ID NO 23
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 23
gcgctgccgt agtcca 16

<210> SEQ ID NO 24
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 24
aggatgagga agcggc 16

<210> SEQ ID NO 25
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 25
gctcccgcct cgccgc 16

<210> SEQ ID NO 26
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 26
cgctttcctg gcccgc 16

<210> SEQ ID NO 27
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 27
gccgccaggg taccac 16

<210> SEQ ID NO 28
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 28
ccaaacgcat gtcccc 16

<210> SEQ ID NO 29
<211> LENGTH: 16

<212> TYPE: DNA
<213> ORGANISM: Artificial Sequence
<220> FEATURE:
<223> OTHER INFORMATION: Synthetic Oligonucleotide

<400> SEQUENCE: 29
agcttcatct ccacag 16

<210> SEQ ID NO 30
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 30
tcccttcagc ggctct 16

<210> SEQ ID NO 31
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 31
tttctgctgg cgcaca 16

<210> SEQ ID NO 32
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 32
gttcattcga agttca 16

<210> SEQ ID NO 33
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 33
gaggatcatc acagat 16

<210> SEQ ID NO 34
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 34
ctaaacttcc cgtggc 16

<210> SEQ ID NO 35
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 35
ttgatttaat ggttgc 16

<210> SEQ ID NO 36
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 36
gttgatttaa tggttg 16

<210> SEQ ID NO 37
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 37
atggttgatt taatgg 16

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
tggttgattt aatggttgca 20

<210> SEQ ID NO 39
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 39
tgatttaatg gttgca 16

<210> SEQ ID NO 40
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 40
ggttgattta atggtt 16

<210> SEQ ID NO 41
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 41
tggttgattt aatggt 16

<210> SEQ ID NO 42
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 42
agttgtagta gtcgcg 16

<210> SEQ ID NO 43
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 43
gatttaatgg ttgcaa 16

<210> SEQ ID NO 44
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 44
acagcactgg agcggc 16

<210> SEQ ID NO 45
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 45
aacttcaccg aagagg 16

<210> SEQ ID NO 46
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 46
agtctttagc agcttt 16

<210> SEQ ID NO 47
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 47
gcttcctccg agtctt 16

<210> SEQ ID NO 48
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 48
ccttgcttcc tccgag 16

<210> SEQ ID NO 49
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 49
gcactttcct tgcttc 16

<210> SEQ ID NO 50
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 50
tcagtcctac caggca 16

<210> SEQ ID NO 51
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 51
gactgaggca gctgcg 16

<210> SEQ ID NO 52
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 52
ccgactgagg cagctg 16

<210> SEQ ID NO 53
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 53
gctagctcgc ccgctc 16

<210> SEQ ID NO 54
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 54
cagctagctc gcccgc 16

<210> SEQ ID NO 55
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 55
gcaatgtgca gctagc 16

<210> SEQ ID NO 56
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 56
gtcgcctggc tcctaa 16

<210> SEQ ID NO 57
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 57
ctggctccgc actcgg 16

<210> SEQ ID NO 58
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 58
atctctggct ccgcac 16

<210> SEQ ID NO 59
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 59
tgatctctgg ctccgc 16

<210> SEQ ID NO 60
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 60
agtgtccact gaagta 16

<210> SEQ ID NO 61
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 61
aggctcacag tctgtc 16

<210> SEQ ID NO 62

<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 62
gacacacggt ggacaa 16

<210> SEQ ID NO 63
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 63
agaagacaca cggtgg 16

<210> SEQ ID NO 64
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 64
cgctctgaca gcctca 16

<210> SEQ ID NO 65
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 65
gtcgctgcag ctagct 16

<210> SEQ ID NO 66
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 66
ggtagtcgct gcagct 16

<210> SEQ ID NO 67
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 67
gcggtagtcg ctgcag 16

<210> SEQ ID NO 68
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 68

-continued atgcggtagt cgctgc 16

<210> SEQ ID NO 69
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 69
gtgatgatgc ggtagt 16

<210> SEQ ID NO 70
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 70
ctgtgatgat gcggta 16

<210> SEQ ID NO 71
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 71
gaagagttca acaggc 16

<210> SEQ ID NO 72
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 72
gcttggctga atcttc 16

<210> SEQ ID NO 73
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 73
ccttgagctt ggctga 16

<210> SEQ ID NO 74
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 74
atccttgagc ttggct 16

<210> SEQ ID NO 75
<211> LENGTH: 16
<212> TYPE: DNA

```
<213> ORGANISM: Artificial Sequence
<220> FEATURE:
<223> OTHER INFORMATION: Synthetic Oligonucleotide

<400> SEQUENCE: 75

tccatccttg agcttg                                                      16


<210> SEQ ID NO 76
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 76

gtaggtcttg gacggc                                                      16


<210> SEQ ID NO 77
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 77

gattctggaa agctcc                                                      16


<210> SEQ ID NO 78
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 78

gctctggaac agattc                                                      16


<210> SEQ ID NO 79
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 79

cgcgcacgct ctggaa                                                      16


<210> SEQ ID NO 80
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 80

tcacttcgcg cacgct                                                      16


<210> SEQ ID NO 81
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 81

tggatcactt cgcgca                                                      16
```

<210> SEQ ID NO 82
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 82
gttctggatc acttcg 16

<210> SEQ ID NO 83
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 83
cgctcgcggc ctctgg 16

<210> SEQ ID NO 84
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 84
tgcgctcgcg gcctct 16

<210> SEQ ID NO 85
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 85
gctgcgctcg cggcct 16

<210> SEQ ID NO 86
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 86
aggtgctgcg ctcgcg 16

<210> SEQ ID NO 87
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 87
gctgttcctc atccag 16

<210> SEQ ID NO 88
<211> LENGTH: 16
<212> TYPE: DNA
<213> ORGANISM: Artificial Sequence
<220> FEATURE:

<223> OTHER INFORMATION: Synthetic Oligonucleotide

<400> SEQUENCE: 88
tgctgcggca gcccct 16

<210> SEQ ID NO 89
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 89
ggtgctggcc tcgctc 16

<210> SEQ ID NO 90
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 90
tgcatggtgc tggcct 16

<210> SEQ ID NO 91
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 91
gttgcatggt gctggc 16

<210> SEQ ID NO 92
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 92
tgctgttgct gaagga 16

<210> SEQ ID NO 93
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 93
ggatactgct tcctgc 16

<210> SEQ ID NO 94
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 94
tcggatactg cttcct 16

<210> SEQ ID NO 95
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 95
tgccttcgga tactgc 16

<210> SEQ ID NO 96
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 96
ctcgctctcc cgctgc 16

<210> SEQ ID NO 97
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 97
tgtccttgga ggaagt 16

<210> SEQ ID NO 98
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 98
tggtcgaagt gccccc 16

<210> SEQ ID NO 99
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 99
cagaaatggt cgaagt 16

<210> SEQ ID NO 100
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 100
tgttcccctg gactca 16

<210> SEQ ID NO 101
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 101
agctgttccc ctggac 16

<210> SEQ ID NO 102
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 102
gaagctgttc ccctgg 16

<210> SEQ ID NO 103
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 103
ccgaagctgt tcccct 16

<210> SEQ ID NO 104
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 104
gtacatgcaa tccccc 16

<210> SEQ ID NO 105
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 105
acagcgggtg gaactc 16

<210> SEQ ID NO 106
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 106
ggacgcacag cgggtg 16

<210> SEQ ID NO 107
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 107
gtgggacgca cagcgg 16

<210> SEQ ID NO 108
<211> LENGTH: 16

<212> TYPE: DNA
<213> ORGANISM: Artificial Sequence
<220> FEATURE:
<223> OTHER INFORMATION: Synthetic Oligonucleotide

<400> SEQUENCE: 108
tgcattcggc caatgg 16

<210> SEQ ID NO 109
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 109
cctttgcatt cggcca 16

<210> SEQ ID NO 110
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 110
aacctttgca ttcggc 16

<210> SEQ ID NO 111
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 111
gctcttgcct gcgctg 16

<210> SEQ ID NO 112
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 112
cagtgctctt gcctgc 16

<210> SEQ ID NO 113
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 113
ttcagtgctc ttgcct 16

<210> SEQ ID NO 114
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 114
tcttcagtgc tcttgc 16

<210> SEQ ID NO 115
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 115
actcagcagt atcttc 16

<210> SEQ ID NO 116
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 116
atactcagca gtatct 16

<210> SEQ ID NO 117
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 117
tttggtgtaa cctccc 16

<210> SEQ ID NO 118
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 118
cctttggtgt aacctc 16

<210> SEQ ID NO 119
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 119
ctaggctctc gccttc 16

<210> SEQ ID NO 120
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 120
cagcctaggc tctcgc 16

<210> SEQ ID NO 121
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 121
agcagcctag gctctc 16

<210> SEQ ID NO 122
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 122
ctgccagagc agccta 16

<210> SEQ ID NO 123
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 123
tcgcgactct ggtacg 16

<210> SEQ ID NO 124
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 124
agtcgcgact ctggta 16

<210> SEQ ID NO 125
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 125
gtagtcgcga ctctgg 16

<210> SEQ ID NO 126
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 126
tagtagtcgc gactct 16

<210> SEQ ID NO 127
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 127
tctccagctt gatgcg 16

<210> SEQ ID NO 128
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 128
cagcgggttc tccagc 16

<210> SEQ ID NO 129
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 129
ccttcttcgg ctgtga 16

<210> SEQ ID NO 130
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 130
ggtccataca actggc 16

<210> SEQ ID NO 131
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 131
acacatcagg tgcggt 16

<210> SEQ ID NO 132
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 132
cgccagggta ccacac 16

<210> SEQ ID NO 133
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 133
catgccgcca gggtac 16

<210> SEQ ID NO 134
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 134
accatgccgc cagggt 16

<210> SEQ ID NO 135
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 135
ctgctcacca tgccgc 16

<210> SEQ ID NO 136
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 136
acacaagtgg gactgg 16

<210> SEQ ID NO 137
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 137
cccttcagcg gctctt 16

<210> SEQ ID NO 138
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 138
cagagtcatc cctgct 16

<210> SEQ ID NO 139
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 139
caccctcaag attctt 16

<210> SEQ ID NO 140
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 140
aaggtagtct ttaagg 16

<210> SEQ ID NO 141

-continued

<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 141
gttttcaaat gcagcc 16

<210> SEQ ID NO 142
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 142
gccatgagac agcttt 16

<210> SEQ ID NO 143
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 143
attcttgact gtctga 16

<210> SEQ ID NO 144
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 144
gcatgccagc tggctc 16

<210> SEQ ID NO 145
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 145
cgcgcaggta ggagcc 16

<210> SEQ ID NO 146
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 146
tctaaacatg acggtt 16

<210> SEQ ID NO 147
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 147

-continued atgcaattgc ctgcca 16

<210> SEQ ID NO 148
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 148
atgggagtaa cttttg 16

<210> SEQ ID NO 149
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 149
catattattg tgctgc 16

<210> SEQ ID NO 150
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 150
gtcaatatca aagcac 16

<210> SEQ ID NO 151
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 151
gagttgtgat ttcagg 16

<210> SEQ ID NO 152
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 152
ttgatggaat gctgat 16

<210> SEQ ID NO 153
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 153
ggttaacttt ctctga 16

<210> SEQ ID NO 154
<211> LENGTH: 16
<212> TYPE: DNA

<213> ORGANISM: Artificial Sequence
<220> FEATURE:
<223> OTHER INFORMATION: Synthetic Oligonucleotide

<400> SEQUENCE: 154
tggattgtaa attacg 16

<210> SEQ ID NO 155
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 155
gaacattatt aggcta 16

<210> SEQ ID NO 156
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 156
tcaatctaga taccat 16

<210> SEQ ID NO 157
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 157
cacatcagaa ggagta 16

<210> SEQ ID NO 158
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 158
gagtgttaat gaagac 16

<210> SEQ ID NO 159
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 159
ctgattagct atgacc 16

<210> SEQ ID NO 160
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 160
atgagtcctc agaatc 16

<210> SEQ ID NO 161
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 161
gtagattcta gctttg 16

<210> SEQ ID NO 162
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 162
acaggctctg actagg 16

<210> SEQ ID NO 163
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 163
tgtgtgaccc ttggac 16

<210> SEQ ID NO 164
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 164
aagtatgagc atggtt 16

<210> SEQ ID NO 165
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 165
ggattctcta cacaca 16

<210> SEQ ID NO 166
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 166
ccatttgtgc caaacc 16

<210> SEQ ID NO 167
<211> LENGTH: 16
<212> TYPE: DNA
<213> ORGANISM: Artificial Sequence
<220> FEATURE:

-continued

<223> OTHER INFORMATION: Synthetic Oligonucleotide

<400> SEQUENCE: 167
aggttaggga gtaggc 16

<210> SEQ ID NO 168
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 168
tagggtttgg tcagaa 16

<210> SEQ ID NO 169
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 169
ccttatggat gctgct 16

<210> SEQ ID NO 170
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 170
gttatcttac tctccc 16

<210> SEQ ID NO 171
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 171
gattgtgtat agctgc 16

<210> SEQ ID NO 172
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 172
ggttatggtt ctgtct 16

<210> SEQ ID NO 173
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 173
cttcattgca ggtctg 16

<210> SEQ ID NO 174
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 174
tagccaactt tcttta 16

<210> SEQ ID NO 175
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 175
cattgtacta tgccag 16

<210> SEQ ID NO 176
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 176
tttggtaaca ttaggc 16

<210> SEQ ID NO 177
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 177
atggttgtcc tgtaca 16

<210> SEQ ID NO 178
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 178
accaagtttc ttcagc 16

<210> SEQ ID NO 179
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 179
tcttatgttt ccgaaccgtt 20

<210> SEQ ID NO 180
<211> LENGTH: 21
<212> TYPE: DNA
<213> ORGANISM: Artificial Sequence
<220> FEATURE:
<223> OTHER INFORMATION: Primer

<400> SEQUENCE: 180
gcccctggat ggatagctac t 21

<210> SEQ ID NO 181
<211> LENGTH: 21
<212> TYPE: DNA
<213> ORGANISM: Artificial Sequence
<220> FEATURE:
<223> OTHER INFORMATION: Primer

<400> SEQUENCE: 181
ccacagatca ggcaggtctt c 21

<210> SEQ ID NO 182
<211> LENGTH: 24
<212> TYPE: DNA
<213> ORGANISM: Artificial Sequence
<220> FEATURE:
<223> OTHER INFORMATION: Probe

<400> SEQUENCE: 182
actgccaggg accatgtttt gccc 24

<210> SEQ ID NO 183
<211> LENGTH: 18
<212> TYPE: DNA
<213> ORGANISM: Artificial Sequence
<220> FEATURE:
<223> OTHER INFORMATION: Primer

<400> SEQUENCE: 183
cttgcgcccc aggagtct 18

<210> SEQ ID NO 184
<211> LENGTH: 27
<212> TYPE: DNA
<213> ORGANISM: Artificial Sequence
<220> FEATURE:
<223> OTHER INFORMATION: Primer

<400> SEQUENCE: 184
ctcagagtaa gctctagcac acatgtc 27

<210> SEQ ID NO 185
<211> LENGTH: 28
<212> TYPE: DNA
<213> ORGANISM: Artificial Sequence
<220> FEATURE:
<223> OTHER INFORMATION: Probe

<400> SEQUENCE: 185
agtgtgtgag cctccatctc ctgtccaa 28

<210> SEQ ID NO 186
<211> LENGTH: 19
<212> TYPE: DNA
<213> ORGANISM: Artificial Sequence
<220> FEATURE:
<223> OTHER INFORMATION: Primer

<400> SEQUENCE: 186
gccaaggagg gagggtctt 19

<210> SEQ ID NO 187
<211> LENGTH: 21

```
<212> TYPE: DNA
<213> ORGANISM: Artificial Sequence
<220> FEATURE:
<223> OTHER INFORMATION: Primer

<400> SEQUENCE: 187

cccccatag tgaatcagct t                                              21


<210> SEQ ID NO 188
<211> LENGTH: 28
<212> TYPE: DNA
<213> ORGANISM: Artificial Sequence
<220> FEATURE:
<223> OTHER INFORMATION: Probe

<400> SEQUENCE: 188

atgaagtaag gagagggact ggaccccc                                      28


<210> SEQ ID NO 189
<211> LENGTH: 174000
<212> TYPE: DNA
<213> ORGANISM: Macaca mulatta
<220> FEATURE:
<221> NAME/KEY: misc_feature
<222> LOCATION: (1)...(174000)
<223> OTHER INFORMATION: n = A,T,C or G

<400> SEQUENCE: 189

aagttgtggt gggattaaat gttgcaatga gtattcaaat aaggttgaag tatctatgca     60

ttctacttac atatggttga ggtatattca aggaagcctg tagccattaa aatctcaggg    120

aacaattttt cacctcctca ggtgaaaggg tcttcaggcc tttgtgttct ggaaggttca    180

tttatagcca tttcccaaat aacattgaga cggatgagtc tagagtctag ctcaaatggc    240

aatgggctgg aagactagtt tagtttttac taatgtggaa catagaacaa aattatgtcc    300

ttgtttcagc ctgctcatct gtgaagtaga gcctatcata tccagtctcc cttgccttta    360

ggtttgagtt accttctttg gtcaaggtaa gtaaatgcct atgatgtttt gctgtgcaca    420

agataaagct acaacaaagc tacaacctgt cttttctctg tagaagacgg caaaaagcaa    480

aagagaccca ggcaaaaatc tcggaatgac ttttgaaaca gacagcctcc ctagaatcag    540

aagtcaaagg aatttaaaac atagggaggc ccagggtctc tactgacata aaagaaagct    600

gttttcgtta taggtttact tttacatttt ctctctcttt ccattcccac ctgcctctcc    660

acctttacac agggcttatg ggacctcctc cacaaaagag cagttgcaat aacccacatc    720

atcctccacg cctggctgtc catcaagagg cgaaaagcag ccctatatag gttctatcct    780

tggatagttc cggttggaaa gtttaaaata tgcaaaggca acttggaaaa gcaagcggct    840

gcatacaaca caaacctttg caaagctctg cacaaaattg agggcctatg cgtacatggc    900

aagtgttttt agtgtttgcg tgtttacctg cttgtctggg tggttttgcc tttgcaagtc    960

tggatgagaa atgcatggtt aaaggcaatt ccagacagga agaaaggcag agaagagggt   1020

agaaatgacc tctgattctt ggggctgagg gttcctagag caaatggcac aatgccagga   1080

ggcccgatct atccctatga cggaatctaa ggtttcagct agtatctgct ggcttggtca   1140

tggcttgctc ctcagtttgt aggagactct cccgtctgca cgctcttatc agtcctgaaa   1200

agaacccctg gcagccatta ggagcaggta ctcctatcgt ccttttcctc cctcctcctc   1260

tacaccccgt tggtttttta gattgggctt tggaaccaaa tttggtgagt gctggcctcc   1320

aggaaatctg gatctctggc gcttaaagct tggtttagca aagcaggagc tattcaggaa   1380
```

```
gcaggggtcc tccagggcta cagctagcct ctcctgccct cgcccacgct gcgccagcac   1440
ttgtttctcc aaagccacta ggcaggcgtt agcgcgcgat gaggggaggg gagaaaaaga   1500
aaggggaggg gagggaaaag gaggtgggaa ggcaaggagg ccggcccggc gggggcggga   1560
cccgactcgc aaactgttgc atttgctctc cacctcccag cgccccctcc gagatcccgg   1620
ggagccagct tgctgggaga gcgggacggt ccggagcaag cccagaggca gaggaggcga   1680
cagagggaaa aacggccgag ctagccgctc cagtgctgta caggagccga agggacgcac   1740
cacgacagcc ccagcccggc tccagcgaca gccaacgcct tttgcagcgc ggcgacttcg   1800
aagccgccgc cccggagctg ccctttcctc ttcggtgaag tttttaaaag ctgctaaaga   1860
ctcggaggaa gcaaggaaag tgcctggtag gactgacggc tgcctttgtc ctcctcctct   1920
ccaccccgcc tccccccacc ctgctccccc ccccgccccg cgtcttctct cccgcagctg   1980
cctcagtcgg ctactctccg ccaacccccc ttactgcccc tctccccacc ctccctcccc   2040
cgtcggccca gcgctgccag cccgagtttg cagagaggta actccctttg gctgcgagcg   2100
ggcgagctag ctgcacattg caaagaaggc tcttaggagc caggcgactg gggagcggct   2160
tcagcactgc agccacgacc tgcctggtta ggctgcacgc ggagagaacc ctccgtttcc   2220
ccccactctc tctctacttc ctcctgcttt ccccaccccg agtgcggagc cagagatcaa   2280
aagatgaaaa gacagtcagg gcttcagtag ccaaaaaata aaacaaacaa aaacaaaaca   2340
aaacaaaaaa acgaaataaa agaaaaagat aataactcag ttcttatttg cacctacttc   2400
agtggacact gaatttggaa ggtggaggat tttgtttttt cttttaagat tcgggcatct   2460
tttgaatcta cccttcaagt gttaagagac agactgtgag cctagcaggg cagatcttgt   2520
ccaccgtgtg tcttcttctg caggagactt tgaggctgtc agagcgcttt ttgcgtggtt   2580
gctcccgcaa gtttccttct ctggagcttc ccgcaggtgg gcagctagct gcagcgacta   2640
ccgcatcatc acagcctgtt gaactcttct gagcaagaga aggggaggcg gggtaaggga   2700
agtaggtgga agattcagcc aagctcaagg atggaggtgc agttagggct ggggagggtc   2760
taccctcggc cgccgtccaa gacctaccga ggagctttcc agaatctgtt ccagagcgtg   2820
cgcgaagtga tccagaaccc gggccccagg cacccagagg ccgcgagcgc agcacctccc   2880
ggcgccagtt tgcagcagca gcagcagcag cagcaagaaa ctagcccccg gcaacagcag   2940
cagcagcagc agggtgagga tggttctccc caagcccatc gtagaggccc cacaggctac   3000
ctggtcctgg atgaggaaca gcagccttca cagcctcagt cagccccgga gtgccacccc   3060
gagagaggtt gcgtcccaga gcctggagcc gccgtggccg ccggcaaggg gctgccgcag   3120
cagctgccag cacctccgga cgaggatgac tcagctgccc catccacgtt gtctctgctg   3180
ggccccactt tccccggctt aagcagctgc tccgccgacc ttaaagacat cctgagcgag   3240
gccagcacca tgcaactcct tcagcaacag cagcaggaag cagtatccga aggcagcagc   3300
agcgggagag cgagggaggc ctcgggggct cccacttcct ccaaggacaa ttacttaggg   3360
ggcacttcga ccatttctga cagcgccaag gagctgtgta aggcagtgtc ggtgtccatg   3420
ggcttgggtg tggaggcgtt ggagcatctg agtccagggg aacagcttcg gggggattgc   3480
atgtacgccc cagttttggg agttccaccc gctgtgcgtc ccactccgtg tgccccattg   3540
gccgaatgca aaggttctct gctagacgac agcgcaggca agagcactga agatactgct   3600
gagtattccc ctttcaaggg aggttacacc aaagggctag aaggcgagag cctaggctgc   3660
tctggcagcg ctgcagcagg gagctccggg acacttgaac tgccgtccac cctgtctctc   3720
tacaagtccg gagcactgga cgaggcagct gcgtaccaga gtcgcgacta ctacaacttt   3780
```

-continued

```
ccactggctc tggccgggcc gccgcccct ccaccgcctc cccatcccca cgctcgcatc   3840
aagctggaga acccgctgga ctatggcagc gcctgggcgg ctgcggcggc gcagtgccgc   3900
tatggggacc tggcgagcct gcatggcgcg ggtgcagcgg gacccggctc tgggtcaccc   3960
tcagcggccg cttcctcatc ctggcacact ctcttcacag ccgaagaagg ccagttgtat   4020
ggaccgtgtg gtggtggggg cggcggcggt ggcggcggcg gcggcggcgc aggcgaggcg   4080
ggagctgtag cccccctacgg ctacactcgg ccacctcagg ggctggcggg ccaggaaggc   4140
gacttcaccg cacctgatgt gtggtaccct ggcggcatgg tgagcagagt gccctatccc   4200
agtcccactt gtgtcaaaag cgagatgggc ccctggatgg atagctactc cggaccttac   4260
ggggacatgc ggtaagtttc tccttccaga aatgtcgcct ttcggcccag ggcacagagt   4320
cgctctgcat tctggggtgt ctagtggctc ctacctgcgc gaacactcag actgcccctg   4380
ggagagctca gcagggtaaa cctagagctc tccccgtgga ctcccggcct gccagaggtt   4440
taacctgagc tctcctaatt tctgctgcgt gtcctgggtg ctgattcctg ccctcccaga   4500
ttcttcaact cccccaacgg ccccaaattc tcgctacctc ctggtacccg agtcccaaac   4560
ttaaatccta ttgtacgggc caccttcaga gacaaagctc ataagccctc cactcttcct   4620
tttctcctgt cctcgaagtc tgagaacctc aatcagaaat ttgggcaatt tcttctcttc   4680
gggtctgtta ggacttccct ttcagcctgt gcagattaga gtcaaaaaga ctggcccaag   4740
agcttctcag cggatctcct ccaaagaggt aaaatgaaat tctcggttag ggaaagaaag   4800
tggtctctgg gtgctgaggt ctgctatgtg aaggagtgaa cttctttccc ggaagcaact   4860
ggggacttgc tccagggctg gaggtcagta gagataatct gaaccgtcat gtttagagta   4920
ggcagagggg caactttctt ggtaaagact ccacaggatt tgcattcaca gtttctcaac   4980
gttggttgac tatgttgaaa gtagttgctt gggtcggttt tctcttataa agtgtttatt   5040
ttctctgtgg attttaacag atccacaacc ccctacttca ggtttgcatc agatctataa   5100
agaggagaat attcttttaa tgtacaattt aattaggctt cagtctgact tacaaaagtg   5160
ttggaaaaca tatttttgtg aaacatttcc tgctatttca gtgtgcccca aaatctccac   5220
tggggaggga ggagtgaggt ttttcttatt atattccttc atttttagga catgttggca   5280
ttttagaata catgctgtta gctctaacaa attgagtaag aactcttagt gacctatgag   5340
ccataatctt accccagagt tttaattagc atatgagaaa agtggcaggc aattgcatcg   5400
tgcttattaa aaattattcc tcaccgcaat tgttgagctt cttggagacc atgctgaaga   5460
ttttctcccc cagcaaatta agatattagt ttatctagtg agggaggaca tactgaattg   5520
gggaattcac tcctcaggta gaccaggtgc tgatgtccct gtggacttat gtcttattct   5580
ttgtttctat ggctgttttc ttttatctgt gacttctccg aaatttcttt gttagcctta   5640
acatcttcgt ttggggactt aaatccagca atttgccttc tttcactgat gctttccttg   5700
ttacaaggta gagatagcac gctattagtg aagaaagaaa gaggagggta ggatttcata   5760
ttattttgtg ggctgttgaa gaaacagctt cttaccaggc tttacattcc attaggtttt   5820
taatgtttgg cttacaagat tttgaaaggg ttcatttgat atcgtcaaag tattttccag   5880
ttaatttaga ctctttattt ttgtaatggg tttatcctat gggacaaaaa aagtattctt   5940
cattttataa gaataaattt tcttggcagg gttaattttt tttctaagcc tgtcactaga   6000
cggtggagcc cttcttctac tgtaaacttt tcttgtggga aaatgtctaa ggtgcatttt   6060
gacctgccat gatactaaac ccagactctg gaaccttcca tcttctgcat gcctccccca   6120
```

-continued

```
caacttactt acttagcagg gaaaaaactg atggttccac atatttctta aaaaatgtgt   6180
gccttcaaag gcaaaaccaa aatttttagg gaataactat agagagcaaa agttactccc   6240
atcaggtaga caatgagctt ggtgatttta tttcaggtct taatgaaaaa agcttcttta   6300
tgaggaagat tatcatatct tggtgcctcc ttgacagtct gcttaaatta atgacataaa   6360
ctaatgagaa tttagcagtt cctgcagaaa gtacaagatt ttttttctg gtttttgatt   6420
gctgcactga ttatgaggag tctagttaaa aggaaaactg gtgttcctgt ctcgtaagtt   6480
gacgaagact ttccatttct aggatagaga aaatccttaa gtcagtttat tgaaaattaa   6540
tcaatttaat cagaatgcaa tcaattccaa tccaaaagtt gatattttct tactttctct   6600
ttttttcccc tcactttgta ggggtgcaat ttggtgaaag gcaagagatt tcttaagcca   6660
aatcaagagt gtcttccctt tctgtattgc atgcattatg tgccattttt tagctaaaaa   6720
tctcaaaatt gtgcaggctt ccagtgacct gttgggttcc tctcttttcc attcatgtgt   6780
gtgtttatgc acattagtta attttgtgaa gggatttttt taaaccttag taacatctgc   6840
actcactctg tgttcttaca catttacaat gtttctgctg agaggatggg agatgcaaag   6900
gtggtctctt ttacttaatt tagcatgtga tttaaacaga aggaaaaata aaaagtgatg   6960
ggacttgtgt gcaaccctga tgatattttg tggagttgtc tgtcttctct ctgagatcaa   7020
acaggactac aactttgtta attgaccact ggctcccttg gcagaggtag ggcttcttag   7080
attccagcag gcagcacaat aatatgacaa aaatttattc ttgggagttg ggttctaaga   7140
gagtctgcat gccagaatta gagtttgggg tttagagaaa ttatccagat gcaaaaagaa   7200
cattttaatt tttctcttgg taatttgttc tggtctccat agtaggtagt actttagcag   7260
tgctttgata ttgacaagtc ttgttccctt tttctattag attttacaaa ataaggcatt   7320
ttattaattc ctctttcctt ctcctctctc ctctcagtta ccaagcattt ttatgactat   7380
cttacaaggg acagtttgtc ttgtaaagca gaattttcct ttgaaaccaa gacagactat   7440
ttctccccat aggcttcaag aaccaatatt ttggcaagaa gcatcttttc cttgtggtca   7500
gcaaataggt agtgagttct gtctggattc caacaatcaa cacctgagga ccaaatagcc   7560
acactgggtg gcaccccatc tggaagtata cacaggatgt agccctcttt cttgtccaca   7620
gctcaagtca gccaaagatt aacactggtg agagatattt tcgaagaagt ttgcaggctt   7680
ccaattgcag ggtcgttttg gggtgctttc ttgcctgtgc taattttatc tcatcaggct   7740
tccattcttt gagctgtaaa ctttgaaata atatattaga ttcgctggta cgtttaattt   7800
tctttgtcaa gtgtttttca ttccaatagt aatttttcat ctggtgtaca tatatgcatt   7860
taaaacaaaa aattctttgg tctcctttcg cgtacatgca ctgtggcttg tacgtgtgca   7920
agccacttgg tgggattatg tgaattgggg ttagaaatgt ggacaatttt attatgatta   7980
tttttaatgg tgatatcaag atcaccagtt tcattcagaa ccttgcataa gcagggagca   8040
gaatgtggac tgggtgtggc aaagcaaggg cttattttat agccaaacct gaaatcacaa   8100
ctctgaaata taaaaaaaaa agcaaacaaa aaaatcaagt tttgtgagct tggtcagaga   8160
aggaaaagaa aatctctccc caccccccac ctccaccatt ttctctttgt ctgcagcttc   8220
ctcaagtgct gcctgtcccc gattttcttt tattccactc ctttcatgtt tttgacattg   8280
aaatacagac tcttctttcc acttctcagg gcattttttct cattacacct gtggcatgct   8340
cctaaataat ttcttaaaaa aaaaaaatct gtaaagtagc cgattagatc aaccccagca   8400
tctctccctt aagacctaga tgacatgagg ggattgcaaa atgaatagct gggttttttt   8460
taccttgagg ttaaagcctg gttcaacagt tgctgaggga gttaactaga tggcttgagg   8520
```

```
acttggcaat ttcataaagt attttgtctt atgctgtcgc tgtctctgtc tctgtcttga   8580
tctctgtctc tctctgtgta ctgtaatgtt ggccaccttc tctcagaacc tgagagagag   8640
ctctgagacc cttcccaggt cggttcggtt cagacctcgg tagcctggtc acaagcagta   8700
cctaatatgc atatgtgggt gcatgctgta agtgtcctgc tgggctaatc tgcttaagct   8760
acataaaaat taatcatatg aaaacaaaga aagatattaa agaaattatt ctacctccga   8820
cttctcatat cagcattcca tcaagttctg ggatgttaaa ttcagagaaa gttaacctca   8880
tcttaaacac aaagttgact tttaaacaaa attgcttata aagttccgta cagttaccag   8940
cattggttgc cctttgtcat acggaagaga attatgaaat ctcatattta catagcattc   9000
ttaaaaaaaa aaaaaagaca cagtgttttc cagtttattc actgcattca tgttagtttg   9060
agtaggccag gaggggtgct tagtgattac ccttttgcta ggtaaagaag tagaaagata   9120
gattttctat gatgtttgtt taccatgtag gggaatctct ttagagcaac actcccaggc   9180
tttttcttct tgaaatttcc cacctgacaa atactttaga ttgttactcc taaggacttc   9240
tctcagtagc tgctacatag agacgatagt ctatgaatta ttgcttgcac actcatgggt   9300
gatgccacac gctctctctc ctggcagttc ttgctgccaa cctgcaggcc acaccaggac   9360
tgaaggcagc tcatctagat aagtttatag cattaaagtg ctgggtcact tgagaatgtt   9420
gtcaatttag gttacttagt acctaagtgt tattttttaa ataatagctt tattgagacg   9480
taatttacaa tccatacaat tcactcttct aaagtgtaca gttccatgct tttcagtata   9540
ttcagagttg tgcaaccatt attgcaatca attttagaac attttaatca cccccaaagg   9600
aaacgctatg caccttttg ttcaatgcct tatgttccct cagtccttag caaccaataa   9660
tctacttcta tctatggatg tgcttattct aatattttgt atgaatgaaa tcatgtaata   9720
tgtggtcttt tgtgactagc ttctttcaca cagaatatgt tttcaaggtc atccatgctg   9780
aagcacgtat cagtacttcg ctatttttta tagcctaata atgttccact gtatgactat   9840
acaacatttt atctatccgt ttatcaggag atgagcatta gggttgtttc caccttttga   9900
ctattatgaa taatactgct gtgaacattc atgtacaagt ttattgtgga catattcagt   9960
ccacatattg tggacatttt caattctttt ggatacatac ataggattga aatctctgag  10020
tcatatggta cctctatgtt tatcctttga agaactgtca aactgttttc gaaagtgtct  10080
gcactgtttt acaatcccat cagcaacgta tgaggggtcc atttcttcca catccttgca  10140
aacacttgta attctctttt ttattacagc tatattagtg ggtgtgaagt ggtacctcat  10200
tgtggttttt atttctattt ccctaataac gaataatgtt cagtatctat tcatgttctt  10260
attggccatt tgtatatctt ctttttgag aaatatctat ttggattctt tgcccatttt  10320
ttagttgggt tttttattat tgagttttaa gagttttaaa aaatatattc tggatgcatg  10380
tcctttaata gattgtgatt tgtggatatt ttttcacatt ctgtgggttg tctttttac  10440
tttcctttt tttcttttg tgttcttaat ggtatctaga ttgaagcaca aaaaaagttt  10500
ttaagtttga tgaagtccaa ttcatctgtt ttttttttc tgttttggcg tatgattttg  10560
gcatcatatc taagaaggct ttgcctaatc caagattaca aagatttaca catatgtttc  10620
cttctaagag ttttatagtt ttcgctgttt acacttaggt ctttcatcag ttttgatgta  10680
atgtttatat atgattgagg taggggtccg acttcattct tttacacata gatactcatt  10740
tcttacaata ttcttgttga atttttcctc acttaactgt cttggcaccc tttgtgtaaa  10800
atcagttgac tgtaaatgtg agggtttatt tgtggactct caactgtatt cagttgatct  10860
```

```
atatgtttat tcctatgcca gtaccacatt atcttgatta ttgtaggttt ttagtgagtt  10920
ttgaaattag gaattttgtg ctctttgact ttggtcttgt ttttcaaggt tgttttggct  10980
cttgtgggtc ccttgagttt tcatatgaat tgggataagt ttgtcaattt ctacaaagaa  11040
gtcagctggg attctcacag gaactatatt acatctgtaa atcaatttgg ggagcattgc  11100
catctcaaca acgttaagtt ttttcatcca taaatatgag atgtcttccc atttatttag  11160
atcttccttt tgtcaacaat tttttattgt tttcagatga taagttttgc agttcttttt  11220
aaaatttagt cttaagtgat ttattttttg atactattat aaattgaact gttttgttga  11280
ttttcttttc agattattca ctgccaatgt atgaaaacat aattgttttg tgtattgatc  11340
ttgcatcctg caaccttgct gaaaatacct gagttttgaa tacttctggg acttatgggg  11400
aagagggctt ctgctgtttc actgaacgtt aaagcttatt tcatttcatc ctgtatgaag  11460
gctgcataca agccttctgt atgaagggga cactgttgtc atttttactc agctataaat  11520
ttgaactggt aatcccatcc cctttcagga tgaataggag agtgttttta aatgttcatc  11580
tctttagaga acagcgggaa agaagcctaa taaggtttgg gtcgtttata atcccttttt  11640
cagaatttgg atttgggaac tattagcaag ggagtgagta ataataataa tttctacata  11700
gaaaactaac atgtagaggt gacaaatgaa atcactagct atatttggct tatgtttagg  11760
tttttataag cagctaaaat cataattttg tgtttttatc tcttgtcctt tggacagagt  11820
aaattccaat actccttctg atgtgcattt ctagatgggg aaaggattcc tttactctca  11880
tataatttaa gcttcttttt agagatgtac tccatagcca tgaagcaaag ataaaattca  11940
tctatgtaga gattgaactt tgtcttcatt aacactctag gctaaaggtc atagctaatc  12000
agctacaact gtcatgtcct gataattgtg agttaactgc aggccaccca gcaaaaggtt  12060
tagttataat ctgatagctg tctgtagaga ttaccctaat aaagggaatt ttttaaaaaa  12120
gaatctggca ggggatagta gctcactcct gtaatcccag cactttggga ggccgaggtg  12180
ggcggatcat ctgaggtcag gagttcaaga ccagcctggc caacatggtg aaaccccatg  12240
tctactaaaa atacaaaaat tatccaggcg ttttggtggg cacccataat cccagctact  12300
tgggaggctg aggcaggagg atcacttgag cctaggaggc agatgttgca gcgagccgag  12360
atcatgccac tgcactccag gatccgtcaa aaaaaaaaaa aaaaaaaaaa aaaaaaaaaa  12420
aaaagactct atcaatcaac cacttttcat taagcacctg ctatgtgtcc agcatgtact  12480
aggaagagat aagataaaag gggacacaat tcagacagaa tcttcttgag gtaattgctt  12540
acaaggagct tatagccact gaaaacaaaa acaaacaaaa acaaataacc aaaacccaaa  12600
cagaaatgca gcaccatcat gccataatgc ctgtatgaga tcctggattg tacggtgtgg  12660
atctttttaa atgtagatat ttaaaaaaaa aaaaaaagag agagagagag agagaaatga  12720
atcaatagag gctgaagtgg tcaacaatgt tacctgtggc tgcttttaat cctttgtggc  12780
agtaagtagg agcatgtcta aactcaagca atagattaaa gatcctgatg tatattttaa  12840
ataacagaag ttggtacctc tggaaagaat taactggagg catgggttga aatctatttc  12900
tgcttattaa atagtgcacc ccagtcaagt tagttgccaa tttttttca gtttctttgg  12960
ctatatcatc gcacttgttg ggtacatgtt tttgatgtat ttatctgaac aagtccgcaa  13020
taatatgagt aataaattag aatagaaggt gattaatagc tctgaatttg atataagatg  13080
cccagtgtgg tggtcagatc aagagttgtt tttcggccgg gcgcggtggc tcaagcctgt  13140
aatcccagca ctttgggagg ccgaggcggg tggatcacga ggtcaggaga tcgagaccat  13200
cctggctaac atggtgaaac cccgtctcta ctaaaaatac aaaaaactag ccgggcgtgg  13260
```

tggcgggcgc ctgtagtccc agctactcgg aggctgaggc gggagaatgg cgtgaacccg 13320
ggaggcggag cttgcagtga gccgagatcg cgccactgca ctccagcctg ggcgacacag 13380
cgagactccg tctcaaaaaa aaaaaaaaaa gagttgtttt tctgccttct aagtttccat 13440
tgatcctgat ggattgcaca aatagaacaa ttcggggagt atgggggcac atgacgatct 13500
tataagagct ttgctgtaat agacaacgta acattctgaa acggcctacc acctaacatg 13560
ggctctggtt ctctgcaggt tgagtgagtt ccttgcttgt ggaactgtag tcccgctatc 13620
tggccgctag gggactgca agtgccccgt ggcaggattt ccctgggaat ggtgagcctc 13680
cattgacggt ttcaacacac agcccaaggcc ctatcgcagg ataacttcaa ccagaactgc 13740
ttagcaccag acaataaata agctactatg gtacttactg tttcatttgg gatgttcttt 13800
ctcgaagtgt caagcatttt aaagtaatat tttgactttt taatacctct ctttgcatat 13860
ggagcaggac acagcaaata tattcaagta gcactgtcca gtttatagag aagtttcata 13920
ttccattatt gcatttcatt cttgtttcta ccctgtacaa gtaactagag tttggagtat 13980
tataatagta ttcatactat tacaatactt ttattcccat tataaaaatt atgctaagag 14040
tggttaagtt acatgtttac aatcaaacag catcaaagtg acagatctgg gatttcagtc 14100
tcattctttc ttctccagat catgtgttcc ctgcttttat ctcacagctc tttttacctt 14160
atagatagga aacatgagag tcagagaggc aaaagaacca caagtggtgt caatactaga 14220
aatttatgaa gttcttaagg cttctaggtt tgttacccat ccaccagact gatggatttg 14280
gttgtgtgag agttctgggt gtcaataacc ttgccattct actttacaga ctgcatacat 14340
tcaataaatg cctattaagc atctactatg tgccaaattc tgtactaggc accaatgatg 14400
tagcagcgaa cagaacacac aaaaatatct gaatggagct gacagtttaa tgagaggaga 14460
catgtagtat acatctgagc atgaatagtg tcatgcagaa taacttcaga gtatagggta 14520
tagagattca tggtgagagg gaatatttta tatctgctgg ccagggaaaa ccttactgga 14580
aaggtaaatt ttgagcagtg acctgaagga aattaggaaa tgagctgcta tttggacatc 14640
tggagttaga atattccagg cccagggaac cacaggcaca aagggcctga ggcaggagag 14700
catgcttgct ttgatggagg acaaaaaggc tcatatggct ggtttaaata agtgaaggat 14760
ggtagacaat gagatcagag ttaatgaggt tgcatggtag gtcttcttta agactttgga 14820
ttttactcct aagcagggtg tattggaagg ttttgagcaa agtaacatga cctgacttac 14880
actttaacag gctccctcct cttcataaca tctgtcactc tgatatatta tacgtttgtt 14940
tgtttactta ctgtatgtgt ggagaagaga ctgtgggagc aaggagggaa gcagggagac 15000
aaggccactg cagtgatctg ggtgagaggt aaccatgtct cagactaagg tagtattggt 15060
ggagaagata ggaagtggct gaattctaga tgagttttga tggtagagcc aacagcattt 15120
actgacaggt tggatattca ctgtgaaaaa aatagaggag atgaggatga ttgccaaatt 15180
tttggtctga gtaactggaa aaatgagatt gccatttact aaaattgtga agactgtatg 15240
tagagcaggt gcatgggcag gatagaaatc aagagtttga ttttttactt ataaagtttg 15300
agttatctga tgagcatcct gatggcttct cagttttcat tcagtgccct cagctttgct 15360
gttcttcaag aagattaaaa aggaccttag agatcaccta ggctgtaggt accctctccc 15420
ttctttcctt ttactttata gaggtctata gaagggtagg gacttatcca aggtaaaaca 15480
gtgagctggt gacagaacta gggcacaaac ccagttctct tcgattctga ttcagtagat 15540
ttttgtgtgt gtgtgtgtga ttctgaggac tcatttgggc aagagtgagt tttttgtttg 15600

-continued

```
tttgtttgtt tgcgcaaacc taaaaccagg tgattaaact aaatagtgac taaaactgga  15660
aaactataca aattggttgc tctccccaat caaactgaaa tattattatt aggtttttac  15720
tgaactacat accaaaatat ttttttcctg taaaaacaca gtaagtgggc ttttaaaggc  15780
aattgagctt ttatcaaagc tagaatctac agggcacctg gacaaaaatg gcctaaaatc  15840
ctaagaaatt agagttcatg gaacctggaa gaccatcttg tccagctagc tcattttatt  15900
ggtagagtgc ctgaggcacc gagatggaaa gggacttggc taagctcata cagcaagcta  15960
gtgcctgacc tagtcagagc ctgttctaag tattagttgt atgttgtttt cttgaaaaaa  16020
gtctatattg gaaaaatgaa aattctttgt tccatactga gaacaaagaa ttatatataa  16080
tcatatataa taataatgat agcacttact gaatgtttgc tgtgtaaact tccgcacctt  16140
gcatgaactg attcatttaa ttctcatgtc aactttagga agcaggccta gagacgttaa  16200
ataacttgtc caagggtcac acagctagga agtagcagaa cttgtgtgca ctcccaggaa  16260
gtctggcttc taaccacaag gttctaacta ctgtgcaata tcagcagctt ctcagattac  16320
tcttcacctt caccatccca aaagactggc gacataggtg acttcattat gcactgcccc  16380
tattatagtc cactgatcct caccaaatag ctgggtggcc tagaggttaa agtaggggca  16440
cagtgatgga aaggggtggt tagaagaggt tgataactta tgatagggat tggaaaacag  16500
aactctagga attattgaaa agggcctaga gatcccaagg aggttgatct cagactgcta  16560
caaaccaggg caattcgatg cctgcttaaa taggagagtt aagataagaa aaataaaatt  16620
gccagttttt acagtcaggc attgttttat ttcttttaca tgtattaatt cgtttaatcc  16680
tcaaaataat ccatgaggta gctacaatta tcatttctat gttatagatg aagaaacagg  16740
cacagagcaa ttaagtaacc tgcccaagat tagagaacaa gtaagtgaaa gtgccaatat  16800
tagaatctag gtgattcagc tccacaactt atgttatttt ccaatacatt tatggaacga  16860
ggtaattttc atataacaga aagtgtttaa agtgcaaaaa cattgtgcct gaacttcaaa  16920
cattgaacaa ctcatatcct taatatacac cagctgcttt taaggactct tagaagtaag  16980
gatacttacc taaagtcata tgttgaacaa gtagcagaac cggaacttga atttgagact  17040
ccagactgcc agacctcttt ccactctatc acttgggctc ccttctaacg ttgatttgtc  17100
tctctccatt cttcctccgt attgctctgc ccttcacctt ttaattacct gtctccatca  17160
acaagattgg acagagaatt gggggagtga gcagagtcca tttccttcca gagactggac  17220
aaaaggaaca aaatgttggg aaaaaagtca gcatgtggat tttgtgggat ttacactaaa  17280
taagaacgga cacttgccag gactgacaag atgctacctc aatccctcta ggccccaatg  17340
tgttatgcag gatcccataa gaagtcatga atgtagttgt cagataatct ttttgttact  17400
gtggaaatgg aagcaggata ctgcaaaaat ctgtctctcc aggtttctt ttaaagaagg  17460
tacagtcttg ctaaatgata actgtttgga catttatttg aaaatgggca gtgcaggaga  17520
gaaagaattt ttccaagctt gtcacattgg gccatctctc tgaagcattg tccaacctct  17580
aattagatga ggagactgca ttaaccaaga gttgagagta aagatggaaa cacttgatgt  17640
ttggtgtttg ggtgcagaaa ggattccaaa acatgttctg agtttcttta ctctgcccat  17700
ccctccttcc ctttcatctt tgtttaaaaa ccatggttag caaatgtgtg tagtctgttt  17760
gcaattgttc atctgaaaaa tttgtttgat cagccttttg aaaaaaagat caaaatagac  17820
tgagatattt tagtcaccaa ctatctaata atagaccaaa aatttaaacc atgctcatac  17880
tttcatatgg tatgtggttt gttttagacg ctttctgggc ttcgctgagg tgctagattg  17940
actcaaagta tggcaggtca gatgtggaat tgagtagggt ggactcttct ctatgcctcc  18000
```

```
agattcagaa ttccccatca gagatgatct catagtgttt ggaaaaacca agctgaaggc  18060
tttgggaatt agggtggtga agggatatgt tgtttcccaa agccttctca gtcattcctt  18120
ctcccccaat tcagattctt aacacctctt gccgggatta gtgcagtgat cccacatcct  18180
ttctctctag ctctctctgc tactctctaa ttcctattgt atttgtgcca ccagatcttt  18240
ccaaagttta gctccaaccg tttctgtata ctgctttaaa tgtctattag tctttaagct  18300
ccataagggc aggagtcctg tcttattttt tccctattct tcatgcttaa tacaaaggaa  18360
gctttgtatg attaaaattt cagcttctcg ccattggctt atgggtaagt ccaaattatt  18420
taaatctggt gttcaagtcc ttttatgatc tgcttatttt tccagcctga attcctggag  18480
ttcccttaca aaactcttaa aacccagcca aatggatcta gtcaccgtca ctttaaacca  18540
tcctcactct cttgtttttt gaacatgtta cttttattat tatccctttg accttgaagg  18600
ctatcccaat ttcaatacta tccattcttc tataacagtc ccctacaaaa tgaatattat  18660
caacccccca acccaaggag aagtgatcta tatgacacaa catggttgaa agaatgttgg  18720
tttcactact ttatctgtaa accaggggct agaaatctct agtttataag attttgtgga  18780
gaggggatca catgtgatta tggatgttag gctcgagtca agagtgcata agactttttg  18840
gatttatccc tttcttcttt ctccatcaat atggtactta gtcccttaag tactcgtggt  18900
acttgtgtta atgactgata gcatccttct aaatatactt ctaaacatct gtctcttttt  18960
agggcaaagg ttggatatat ctgcaaagat tctctttgga tataagatat ccacagcaca  19020
taacttaaca gtgttgtaca tagtagatat tccataagta tttctttatt aaatgattca  19080
gagtcaatag tagtaagtga ctgccgaaga caactgatag attgtaagtt ccattaacag  19140
aaatacagtt agccctccac atccataggt tccatatcca cagatttaag caacagcaga  19200
tggaaaatat attttagaga cacagtaaaa ataacaattc aacagtaaaa aaaaaagtta  19260
tgtaaaacaa ctatttacat aacacattgt attggctatt acaagtaatc tagatataaa  19320
tgaaatatat gggggatgtg tataggttaa atacaaatgt gacaccattt tatatgtttt  19380
aggtaaggaa catgaatatt tttggatttt ggtattcctg ggagtggggg aatggaacca  19440
agccccttca aataccaagg gactattata tgggatacag aataaaggaa ttgattgtct  19500
tgctctgtta aattctggtc agacacattt gcaatgtgtt gttcagcccc aatattcatg  19560
gagcatctcc ttttgtaaag catggaggag ctatgagaga gacatggagc agtgaacata  19620
actattgttt caatgaacct gaaggattat catggaataa agaagttaga tgtttttctg  19680
tagcacccca aagggcaaac gcaatgagga cagattacaa ttcagtaaaa gaaagagttt  19740
tttttttttt gtttggtttg ttttgttttt gggttttttt gggttttttt tgtttgtttg  19800
tttgtttttg tttttttttt tttagatgga gtcttcactc ttgttgccca ggctggagtg  19860
caatggcgca atcttggctt actgcaacct ctgcctccct ggttcaagtg attctcctgc  19920
ctcaccctct ggagtagctg ggattacagg tgcacaccac caatcctggg caattttttt  19980
tttttttttt ttttagtaga gatggggatt tcaccatgtt ggccaagctg gtctcaaact  20040
cctgactgca ggtgatccgc ctgcctcggc ctcccaaagt gttgggatta caggcgtgaa  20100
tcaacgagac cagcctgaaa gatattttct tagaagggct tctttcatcc ttcatcagaa  20160
gttgttaaca tggaccatat gagttttgtt tggtctatat ggggtgtgtg tgtgtgtttg  20220
tgtgtgtgtg tgtgtgtgtg tgtgtgtgtg tgtattgaat tacttgctaa cattttactt  20280
caaaattcag atttccaccg tagggaatga agatctgaca atacagaact ttcattctta  20340
```

catggtaatg accagctgca ggtgaaaagc agctgatcct ctggatgggc catgcacttt 20400
gcagtttgcc caggcaccag tgacccactt tattcattta agttacctgc ttgactcttc 20460
tagtcattcg agtatgtcat ccctgtcaga tcagagacct aagcaaatct tgagtccctt 20520
gcttactcca agggctttca ctcctcgtat aggaggggct aaagaaatgt acaagcagca 20580
ccacaatagg atcagacctg actttcaatt ctagcacagc catgtaacat agttggatga 20640
cctcaggtca gtaatataac ccctctgagc ctctagatct tcattatctg tagaacactc 20700
tccttacaga gttattgtaa gaatgaaata aaacaactag gataaagggc attacactta 20760
gtaggtgctg aaatattggt tcccttcttc ttattcatca caccatttct gtctgtctat 20820
tggctgaatt acataaatag taaattcaca ttcactgaag acatttaaga agagtctgga 20880
ccctttggga accatgtata ggacaaagat ttggactcat agattatttt tacagtcact 20940
ttctaacaat ttaaaagcct atggatgact ccaaaatgcc catttggatg atttgaggca 21000
tactttgtgt agttaaggat tttaaataca taacagagag actgaagggc ctttgggaaa 21060
caagctgggg taagagtcaa aatgtaatat gttgactgat gttcaggaat aggctttggc 21120
atctgataga ttttgttttc agtactgccc ctgggtctta ctagcttcca gttctgggcc 21180
acttcacctc tcttgagttt tagtttcttt atttctaaaa tgaagatact aatgcttcct 21240
ttgttgggtt tttgtgaaga taagtgagat aataaatgta aaacatgtag cccagggcct 21300
ggtgcatagt aaaagcttca taaattgtac ctattattat tagtagtagt agtagtccag 21360
acaaacagag cttgggaaaa tgctagactc tggctgacat acatggactt ttccccaggc 21420
cactgctgcc tggcttcccc ttccacaaag ctttgagtct ccaaaatgct ttggctggaa 21480
tgtaagcgtg aggtcattgc agataacagg ggagcatgat ttgcttcggt aatgcaagtt 21540
attaagttac ttccctcagc ccagctaaaa tctcttattg gttgatgttt gcttcaaagt 21600
gtgagactga gctagtttga ggagagaggg agagtaagaa gattcctctt cttggccaga 21660
ggtcatggtc ttccacaagg aacagaatga ctcaacgcaa attatgggac ctctttgagt 21720
ttggggcccc tacatttaaa ccagtcactc cattgcacaa attggtaccc ttccccccaac 21780 aaaattactg ggcaggaatt ttcttgactc cttccatggc ctggaatgat ctcccttctc 21840
atccttgtga tccacacagc tggcaaatgg caggcagcag aacaaaaaca agcctcttag 21900
catagagaga gagagaaaga gtcacagcag tactgaattt gcttgggaac ctaatgttaa 21960
caaaggatct tcctctcaac accccaaaca gattaaaaca ttttttttta acagcaagtt 22020
gtgtctcaga gcagctcttt gcttgggtat atttaaagat ctgctgagtc atttaagagc 22080
aggctggcag atcgtaagag gcaaggacta taccccagtc tatgggggag taagttgaga 22140
ggtgaaatct gtttggcttt ctcccatgtg aaacaaacaa ggtgatccac ttccatctcc 22200
cacaactctg gagagcatct actaaggctt cttattctat caactttgaa ctcctcagag 22260
tataatagag taagggtgag agggaaggag cagttgtacc agtgtgtctg ctgtctgaaa 22320
ttgtaatgcc cctgcattgg tagctgagag tagcatggaa gtgtcaggtt gatgggttca 22380
tttcattctt ttcttttcag tttctggtca catgcattgt taccatggca tatgacagtt 22440
gctagaaagt gaaataattt tttctacttt attcttaatt gcacttctaa atttattaaa 22500
ggagaaatta gcagttagca actgttaact ataggtacac attggggttt ccttagagcc 22560
aattttcccc ctagttttca acttgtaaat ctgatagatt ttgtcctaaa agttggcaaa 22620
acctggagct tctctttggt cctggccttt ttgaaccctg ttccacagag cccaatcttc 22680
tttcttgttt gagacaacta tccttctctt tgcccactgc cattttcctt catctacttt 22740

-continued

```
tcccatctct agcacctcag actgtcttcc cacagtggca cagactccca ctccactttc  22800
actgtgccat cttcttgcta tcaaaaccat cctcacagac ccttactttg ctgaaaccac  22860
ttctaggaag ggaaatcaca gtggatccat gaaggatgct ttctggatga ctttaaaaga  22920
ttggtattaa gatattttat tagtggtggc aacactgact tactcaggca gccatgccca  22980
ggatctataa gaaatcagat aagctaaaag ttgcttgagc tggcaggaga cctagttctc  23040
tgttttcctt tccctcatgc attttgttta tcaatggttt tcagagggct tagaggctgg  23100
ctttgttata gttagttggt aagagaaatg gtggaggact ggaaaatggg agtggaacca  23160
ttgagcatgt tattacaatt cctaggatgt ataaatcgct tgaaagtcta ccaagtactt  23220
tcagacacat tatctttttt actcttcaaa atcaacttgg aggtaggcac aacagggatc  23280
aaatccttag ttcacagatg agtaaaacga gactggagga aattaaagga cattccaagg  23340
taactcagac aataagcaac agaactagga tttgattagt tttttggggg gtggggagga  23400
cagagtctca ctcaggctgg agtgcagtgg caaggtctcg tctcactgca acctctgcct  23460
cctgagttca agtgattctc atgcctcagc ctcctgagta gctgggatta cagacatacg  23520
ccacaatgcc tggcaaattt ttgtcttttt agtagagatg gggttttgtc atgttgccca  23580
ggctggtcct gaattcttgg tctcaagtga tccacccccca ttggccttcc aaagtgcgtg  23640
gaaccactgc tcccggcccc ggaccattaa tttttgatgg taggtccacg ttttttcaag  23700
ttcacagctc ggatttgcta tataatgaat gaatgagtat atatgtcatt tgggaacatt  23760
attccaactt tcggttgaag atttgtttta tcagttgtgg aacttttttt catttttagc  23820
attatcagtt tagttaaatg aacatttcgt tcatgaattc actaattaat tattttattc  23880
atcaatacat ttcctgagta ccaaactttc tatcaaatgc tgtgctggat tctgaggcta  23940
caaaaagaaa tacgacacca tctcatgact ctaaaatatc acagactggg gactgacatc  24000
tcagtagtaa acatatgaat agcaacttat gaaatgccat tagaaaaatc tcaagttata  24060
ttcctcagtg agtatggcca tcctaaaaat gagaagtctt ttattttggg tacatgaaaa  24120
tgaagcgttg tgagaaattg cattttaatc taatcttgtc ttactaagaa cagaagtgaa  24180
atgtttcagc ctctgtgtgt gtatttgtgt gagtgaaggt tgagtgtgtg atgatggatg  24240
gggctgcgag attgctaagt aggatctatg gggggcctta gatggtcctg gtgagtccca  24300
actttctggt tatgtatttg ggtgcagtat gggagtgaca aagattgttg tttaagagtt  24360
gattttagat tttttccaag taaatagtca gcagacttgg agcatcatca ttccacttgc  24420
tttgaaaacc taccacttaa ggctccttct tgtcataggt taactctttc tggtcaagta  24480
ttactctttt tgagcatttg cctgtcagtg acaggtgcaa tgttagatgt tgtctctctg  24540
ttttcttgtt taatctttac tttgatccta ggtagctctt attagttcca ctttataggt  24600
aagaaactga atttcagaga ctttaatgac ttgttcaaga tcacatagta agtaacttgg  24660
tagtttggga cttgaatttt gattgttcaa tttttttttcg tttcctggcc tcactgctgt  24720
tttcactatt ccacaccact tcagctttat ttttcacaga ggccgttaaa tgtaccctcc  24780
atcagccaaa gcctcttgcc tcccttcaac gtaactcttc tctagcgtgt tcctaataat  24840
cttctgaaaa ggttttacag cctttctggg tactgggacc cagagtctta atccaggctc  24900
ttaagtgcct tagttaactg taatatggat aatcaaagtc acagctaatt caggaaaaat  24960
gagtttggga tgtgaatttc ctgggcaaca tgtcatctct tttttactcc cttagcttca  25020
taaacttacc cacaatgttc cctgaggact aacagtaatg gagggtgatg aggaaaggct  25080
```

```
ttcctccctt cctggtttcc aagagtcctt tagccaaatg ccacacctcc tcctgtttcc  25140
ctagtctctg tgcagagatg gaggtgggag atagacatgg gttcttttca gccctgagtt  25200
catgccagag ttttttttt ccctctagct ggagtgaagt aggaagagag gttcaatgtc  25260
caccaagaag accatgagtg aagaagacta aagtacttga aagaacatca gacctatgcg  25320
taaaatacca gggtttgtgt ccagactttg tgggttacta tctgtataat tttgggcaag  25380
tcaacagttc tgagtcagag tttccttatc agcagattgg aagataaatt ctaattatat  25440
ggatgaaaca ttaagtctag aagtattttg taaattcaga aagggcttat agatttaaag  25500
tgtagctgtt ttatcacata ctaaatccta tacttcaggg ataaaacctt ctcctgtttt  25560
ttctaaaagc ctgtgcatgt gtggtgtaag ggatgggttt tgcccctgta ccagccactt  25620
agcaattgta gtaactgggg gctgagggca gtggcctgct tctgcactga gcaagtgtga  25680
aaagagggta atgcattcag gggtcagcag atgacaggca gagtagcccc tccaaatctc  25740
cctcccatac cgcaaagccc cttatttatt caaacttaac attggaaact catttcaagt  25800
aggtacgtct gtgtctgggc gtctattttc tttctttgta tatagcaggc atttgtcaac  25860
ttggtgaaaa gcattaccct tctttccatt tctgaggact aattgtgctt attcgctaga  25920
catgagttca aaacagtggg ttgaaagagg gcaagtttat gccaaagaat cagaagtagt  25980
cataatttag agagaattct agaggtcagt tccctttcgt gtggattggg caactgaaac  26040
ccagatagaa aagcggatta gaccaagttc acaagcacaa acacgttact ggcacattca  26100
gattggaagt tgagggcttc tgctcccagg tcagaactaa atgccctttc cagctagggc  26160
gttctttgat ctcagtgatt tggactcttt ctactacact ctggggacag tgggttctga  26220
gataccaact ccaattaaag taggaatatg taccagctcc tccccttggt ttttttctag  26280
aggcctggca ttcagaggca gtgtgatctc tatatgtaat attttcacac tattgttctt  26340
atttaaatca catttgaatt ttggcaatta acaaggcagt aattggcatc aggaaggtat  26400
gttagtttgc ttatctgccc catccccccct cttcccgacc cactgtgcat tgcagaatgt  26460
tttatcagct ctgatttgcc aagttgctct cttctccagt aggtgctgca agcagagagg  26520
gattcctcgg aggtcatctg ctccatcttc ttgcctatgc aaatgcctgc ctgaagctgc  26580
tggaggctgg ctttgtacca gactttgtac agggaaccag ggaaatgaat gcagagtgct  26640
cctgacattg cctatcactt tttcccatga tactctggct tcacacgtgg gaggttcttc  26700
agctgaaaac ttagaactca ttttctaggg tagtgagtgt tgtaaggttt ggactgtgac  26760
ctaatattat gcagccatga cattatctat taggcatcta gaccagcttg cttgaatatc  26820
ttagcatgtt gactaatttg gggcagacta cagtgtgggt ggaggattgt gtgtgtgtgt  26880
gtgtgtgtgt gtgtgtgtgt gtgtatgggg ttgagcaatt cattattatt aatatgcaaa  26940
aagcacttat ttcgctatga caaggttgcc tttttcatgc atattggcct acctgcaaga  27000
cccctagaga cagtaagcaa catacatggt gtcttccagt tttcagcctt tgtgcaagga  27060
acaactgtgg gtttttgcat gtgtgttgtg gtttgatgtt tgtgtgtgat tgtgtaccag  27120
ggtatgtgtg tctgttactg tgagttcact tctgagcagt tgtgacacac agagatccag  27180
aaacagtgtc ttactctgtg tgctctgcta gtgggaacgt gtcttctctt ttgtgctcgt  27240
atctctgtgt aatcaagtgt cttgctaagt cagtgtgcct ctgtctcttt ttaccagttc  27300
ttccgtcttt gtgtctctat gccttcttgc gtttctttcc cctgagtttg cacatgtctc  27360
tgtctatgtg gatatctctc actccaggcc actgtgtcac tgtgtctgta tttacagctg  27420
tttctttctg tcggtgtgtg gattctttct gtcggtgtgt ggatttctat gtctgttttc  27480
```

atcttaattt gtgtgtctaa gcaagaagac tgttttgggg tcactatttc cgtttatgtc 27540
atagccccga ttgtccccat ctccatgtct ctctgtgtgt atatgttcta atgtatctgc 27600
ctacttatct ttattcgtat ttctctgggc atatatccct ctcttgcagt tcttggcctt 27660
tgcagttttt ggcttatgtt tttgtatata tcgactagaa ttggcctcct tatgtttttt 27720
gtgcatgttt tagttttttg tatatatcca ctagaattga cctccttatc atttttgtgc 27780
atgtatgagt gagcatatcc aactctgtct ttgagaagca gaactgtcta tgtttgcagt 27840
caattgtgtt ggctgtccct gtgtttgtcc ctgtgtgtgc atttcattgt atgtgcaccc 27900
attcatgtat ctttctgctt ctgtatgacc atatacttct gtgtagctgt ctatgtatat 27960
tggcttctat ctgtgtctgt gttgttggct acatgtctgt gcatatgcac ccactgagtt 28020
cataaaaagc tcacctgctc tctaaggaat ctaccagatt gttttgtgaa ataactcaca 28080
tctcgttttt tacttgctta gttatcttct ggcttgccag atgctttggt acttaaaagt 28140
gtgttggtac gtaggggtgc ataatttatt catgtaggat gtcaaaagag tcagttaaaa 28200
attatacaca gtgtgtcttt attaacagga cagttgtgtg tagagaatcc ttgagaaatg 28260
agcggttaga tgataaatct tttcatatta atttcatgat ttgagtgaag taaatttgaa 28320
aggtacaggc tgcataagag ctatgtgctt tttaaaactc attgtattga tggtggagaa 28380
agcatttatt tgtactgcaa agtcttattt gtgatgttca ttactgggtt agaaggtgtt 28440
acttttctga ttttgtttgg ctttttgaag agttactaca aatgacatct tagagacaaa 28500
gagctctgaa ggtgacttag aacacatgga gtacagacaa aaaggagaat ggaaaataac 28560
agagagatgg gcatattcct catttgaatg gagtcagcca ggggctcagg atggggtgca 28620
caggaaatgg agaggtgacg gtcatagaga gaagcttagc aggaccagat ctttccttgt 28680
cctgggctgc tgtgaccata taaggaaggc agtaagggga ggggtaggga tgaggaagag 28740
accagctctc cctttctttc tgatggaagg ttaccacctc tatttaaaac ttctgttctt 28800
ttggttctct ttctttgttt gattatatta ttttctggtc ttgttctgcc atagcaagaa 28860
ggaaattcca catgtggctc actcatttat tatacttgtt tctttgcatg atattataga 28920
gagcttgtta agtgtcactg cgaacatcac acacactgat ccactgatat gggcagggtg 28980
gtctttatgc cagctctgct cccttcccag tgtatctgtg gtgcttaatg gggacaacca 29040
tgatttttct gatgtcagtc tgtgatgtca gttgtccagt gtgtatgcag actgcttaaa 29100
agtacataca gttcctttgt aattatggta gtccctgaga aggaagtgct cactaataaa 29160
agactaggtt cagtagaaac atgtaagttg tctaggtgtt ggaaattaat atagtactct 29220
gctaagggaa tatatatcta gaagttaact ggattatgct caataaaaag attacaaaag 29280
tttcataaat atttttaact aattctataa gattaggaga gggatatttc agatattcaa 29340
ataatttttt taattgacaa acaccttaga catattattt acatacaatt gacataataa 29400
ttaaatcatt atgtctgttt tatgataaaa caggatcttt tggcttagtt tgaattattg 29460
aatgtaaaat aatgaaaatt taaaaaaaac agaggaggaa tctatcctat tttataattc 29520
agaccgttga attgaatttt tcttttgttg tattgatttc aatgtagaga agtctgtggt 29580
gctggattcc agtcaaaaga taaacatttg tatgtgggct ctacattgca gccaatcttg 29640
ataatttcaa accttgattt tctcatctgt ataatggtaa taataaagac tgtctcagct 29700
accaaatgat tgcatatgac aaacctctca cttatgtaag ggaaaaaaga aaaagaagga 29760
caatggggtg gatttttcgt atagtaaaat ttattcagtt agggtaatat tctgagcttg 29820

```
tcttctgaag caaaccctgc aaactctggc cattctgttt tgtttaggaa agagttaatc  29880
agttctgatt ctgcgttttc tggggaagga ggctgagtat ggattgaaga ggagtcacta  29940
cttttctgag atgatatatc tgtgctaaaa attagtaatg ctttgcacat gcaacataca  30000
gtgttcaatt ttgttagtca acagatattt aagtggcagc tgttatgacc tcaggggtgt  30060
agtgacttcc ttatataatg tcctttaatt attgaaaaag aaatctacat cagaatatca  30120
ggtaaaatct tattacatca aatattataa caaagatact ttttatattc tctaaaaaaa  30180
gtggagatct cagatgttgg ttcatttatc aatataatat tggatttgaa aattccagta  30240
tacaaaggga aaaagacagc ttcttaaagt ttatagtgat tttctatgaa ctttcaattc  30300
aggatttttt ctgttttact ggtatgatag agctaaattt cgaattgtaa gtagtagatc  30360
attagactgc agggtaagcc ttgagattgc ttcttttcag gtaggaaact ctactgtgta  30420
tttggctagt tcaacatatc atgggtagtc aaaaatagtt acatatccaa gtcagcattt  30480
tttaagttgt tcagttgtgc ttaaagattg gtcctttcca ggaccaatcc agctttatca  30540
aaaagttatt atgtacatct aaagtgttct gacattttaa tgctcacagt agccgaatga  30600
tgtgagtagg aatctttgtc ttcattttat agatgaagag acacagagaa ataaactaac  30660
tgggccaggg tcctaccact agaatgtgac agatgacaat ttgagcccag catatagttg  30720
tttccctata atattcgttt tatgattgta tagatatctg ctgaccaacc ttaatctctg  30780
ctccctgaga ttaaccgttc tacaaagcag aaactggagg tcgttcaaat gaaaactcta  30840
cacttttaga gggccattaa caatgctcaa gttaaagaaa agcaatcaaa gacaactgaa  30900
atactggtac cttcagacag tacatatgga tttttttttt ttttttgta ttatacttta  30960
agttctaggg tacatgtgca caacatgcag gtttgttaca tatgccatgt tggtgtgctg  31020
cacccattaa ctcgtcattt acaataggta tgtctcctaa tgctatccct ccccccttccc  31080
cctgccccaa aacaggccct ggtgtgtcat gtttcccttc ctgtgtccaa gtgttctcat  31140
tgttcaattc ccacctgtga gtgagaacag gcggtgtttg gttttttttgt ccttgcgata  31200
ttttgctgag aatgatggtt tccagctgca tccatgtccc tacaaaggac atgaactcag  31260
cctttttttat ggctgcatag tattccatgg tgtatatgtg ccacattttc ttaatccagt  31320
ctatcattga tgtacatttg ggttggttcc aagtcttggc tattgtgaat actgccgcag  31380
taaacatacg tgtgcatgtg tctttatagc agcatgattt ataatccttt gggtatatac  31440
ccagtaatgg gatggctggg tcaaacggga tttctagttc tagatccttg aggaattgcc  31500
acactatctt ccacaatggt tgaactagtt tacactctga ccaacagtgt aaaagtgttc  31560
ctatttctcc acatcctctc cagcacctgt tgtttcctga ctttttaatg attgccattc  31620
taactggtgt gagatggtat ctcattgtgg ttttgatttg catttctctg atggccagtg  31680
atgatgagca tgttttcatg tatctgttgg ctgcataaat gtcttatttt gagaagtgtc  31740
tgttcatatc ctttgcccat tttttgatgg ggttgtttgt tttttcttg taaatttgtt  31800
tgagttcttt gtagattctt gatattagcc ctttgtcaga tgagcagatt gcaaaaattt  31860
tctcccattc tgtaggttgc ctgttcactc tgatggtagt ttcttttgct atacagaagc  31920
tctttagttt aattagatcc catttgccag ttttggcttt tgttaccatt gcttttggtg  31980
ttttagacat gaagtccttg cccatgccta tgtcctgaat ggtattgcct aggttttctt  32040
ctcgggtttt tatggtttta ggtcttacat ttaagtctct aatccatctt gaattaattt  32100
ttgtataagg tgtaaggaag ggatccagtt tcagctttct acatatggct agccagtttt  32160
cccagcacca tttattaaat aggaaatcct ttcccaattt cttgtttttg tcaggtttgt  32220
```

-continued

```
caaagatcgg atggttgtag atatgtggta ctgtttctga gggctctgtt ctgttccatt  32280
ggtctatatc tctgttttgg taccagtacc atgctgtttt ggttactgta gccttgtagt  32340
atagtttgaa gtcaggtagc acgatgcctc cagctttgtt cttttggctt aggattgtct  32400
tggcaatgcg ggctcttgtt tggttccata tgaactttaa agcaattttt tccaattctg  32460
tgaagaaact cattggtagc ttgatgggga tggcattgaa tctataaatt accttgggca  32520
gtatggccgt tctcattata ttgatacttc ctatccatga gcatggaatg ttcttgtttg  32580
tttgtgtcct cttttatttt gttgagcagt ggtttgtagt tctccttgaa gaggtccttc  32640
acatccattg taggttggat tcctaggtat tttattctct ttgaagcaat tgtgaatggg  32700
cgttcactca tgatttggct ctctgtttgt ctcttactgg tgtataagaa tgcttgtggg  32760
ttttgcacat tcattttgta tcctgagact ttgctgaagt ttcttatcag cttaaggaga  32820
ttttgggctg agacaatggg gttttctaaa tatacaatca tgtcatctgc aaacagggac  32880
aatttgactt catcttttcc taactgaata ccctttaatg aattatttaa ccttagataa  32940
tttggctttg agctagaaag gtagagaaag atggaggaac caattcttcc ctgggttggt  33000
acttatttat cttgctcttt tgaagtctag gtcaatcgtc ctatttgttc tgaatggccc  33060
attcatgttt atccatttag ggacagcagg tttggcacaa atggattggt tttctgaggt  33120
ctcatgtaga gggctgcact gactgacttc tgaaagtccc ctctaaccct tcaaatctcg  33180
ggatcatttg atctcaagcc ttcattcatg catacatttc tatttccttt ttgagtacca  33240
gcacaacact gcaggctgac ccactggatg gatagaatgg ggctcttgcc ctaccaccct  33300
ttggcaaaca atttgagggt ggcattgtca ctatctcatt gatatagggt ctcttgaggc  33360
ccagaatgac aaagtaattt tcccactctc acacagctag ttattgtcag agtaaatagc  33420
aattttgaat ttgtagaaca cgtggtttta cctctatcat ttctgtttat tatgaaaatt  33480
ttagaagtaa taattaatta gaagtagaaa tgatgattaa aataaatgcg taactactaa  33540
aaagtagttc attgcagcac cacctaaatt catctcacca ttctaccagt agtacacatt  33600
tcgccattgg gttaacattg ttttggatct tatagctgtt gaagaagaca aaattctttc  33660
cattctctag attatatttt ccccatttgt aaaacataat ggaagtgtat ggaaaatagg  33720
agttgataat ttttaaggcc cctgtcagca tattggcaca taggattctt gtaagtggtg  33780
gtttacttca cttcagctat ggaaggccta tgcgacacca cccatagagg atagtttgaa  33840
agaaactgct agtgactgcg tgtgtttcct tcctgacata tttgctagaa ggtgatgagt  33900
tccagctttt tttcagactt ggatctggct ttcattcccc ttctcctccc accctcttaa  33960
acaacagagg cagcaaccat ttatacactt tccagaagta agtaagactc tattccagaa  34020
acaccctatt tcaaaatgga aatatactca gtgccccaat gacccattgg gcgagtttga  34080
acgtgtgcat tctctgtgct ccccgtttta gcttaggcct actccctaac ctgtcatatg  34140
tcacccagcg atggagccta gggcaatgag tgccatcata tctgactttg tggcctctca  34200
gctttcaatg actagctttg tagcagaagt ttagcctctc atccccagac ctttggaagt  34260
agtgttgaga taaagagagg ttgaattgaa ggttgtgttt tctagatttc tttcaattgc  34320
tccttaggct ttagaagaca aattctccta aaagacaggt gctacaatta atccaagcaa  34380
agggaaagat gtcaatagag ctgccccttt tcgtagaggt gtggcaactg ctgggaagga  34440
agaaattagc tggaggccgt gtgatcacta ataaaactca aagcggtgtt tttttacttc  34500
tcaatatgag gttgaaacta taagcttaaa ttgctgactt tctggcagca ccaaacagta  34560
```

aggaaaccac aaagataaac ccaaataata gagccaattt tctttttttg tgggggtggg 34620
ggatgacttc taactggtga tatgaggaag gataagaaaa tgtttatttt aatctaaaaa 34680
aaatggatag cacatatgat ctttgctaag tgcactgaat gtatgtagag gagacaagtc 34740
tgctaaaggt atgagaattg ggccgagatt taacacattt tcaaagctcc atgaagaaac 34800
ctactgaaca gtgggagtgg agcaggttgg ggatagtgaa gtatttgtaa tttattttta 34860
aaaaggagag ggagagagag aaaaggaaaa actgggccac ccatcctttg aaaagaaacc 34920
ttgaaagagg tccaaatatc cttagaaatc cttgacttct taaaagtgat aagagtttgt 34980
tttttccccc tgacaattat agaggtcaga gagttttctt ttctattgca aaacattgag 35040
agtgtgtaga aataattgta ggtagcttag ccttggctgt agtcagaact tttgtactgt 35100
gactttagga tctgtataga attgtatgat atgaggatac accaaaaact ctatgggcta 35160
tcaaaatggg atagcattaa aagaaatagt gcttttgttt agaagaagaa atgaaatgct 35220
tgtgtccagg tgcttaaagg aaggcagtgc agactttcag aaactagact ttaagagcta 35280
tactcagata ctgagaaggt ctgatggctg aaggaggaac aatttaaaag aatagccatc 35340
tctcccttcc ctgtaaatta gacataaaag aatatcccat tcatctcaga aatgtaatac 35400
aacattttag cttgctagta actttacatg ctatttcctt tacctcttat atttgaggtg 35460
tctatttgga gtgggctgtg tttctagcta ttctgtttat ctggtttgtt tttgtttgca 35520
taggaaactg gtgtacattt tatttgggta aatatcacct caattttcaa ataaagcttt 35580
atttaagttt cacatgaaaa agacaaatga gacaaagaag agaataattg cattgtcaga 35640
attataagaa aaaaatcaaa taaacatatt tgaaatgtcc agaaaaccta gagttttatg 35700
tatattatac aggagagata ttctgtcatc tggttgccaa actatggagg gtgggagact 35760
tagaattttt gtccaaaagt attgcttcat tagaaagata catgggtgtg cttccacatc 35820
agcaacatga ctgcagaccg ggaagtcctc acggagagct ggaatatggg tattttggac 35880
tctctggtaa gatgcggctt ttacttcact tcctcagtgg tactactgta aattttcatt 35940
ttcctatgga ataccctatt tggttccatt gtatatagtt gacaactaga attcgttcgc 36000
tgttgcttga actcaactgt aacttcttgg cactatacat atcttctgat gcgcctgtgg 36060
aagagctacc ataatgactg tgtacatgga caaaaaaaaa aaaaagagag agagagagag 36120
aattaaatca tgagtttgtg ccttgggagc tacagtttaa acatttgctg gttttctcaa 36180
ttaatgaaaa atttatttga aaataacagc acagaaagga agaaagacag gccggcaagc 36240
atcctcctcc taatatactt atccactttt ggataccttg atctcagtct cagaggtcat 36300
atttttagta aaatggccac cagaagtaaa ggattttatt ttccagactt tggtgtttgg 36360
agctggtgtg ctgagagctg gtagagaaag cgctactcag gtagatgtac caaaggagga 36420
tggttgctgg tggatatggc agagtacctt ttatgtggtt atctcttcct tgtaactctt 36480
ggctgcataa ctcttatttt cttttctatt tttgttctct ctcttggaaa aaatttggtg 36540
gtaaattttc atatgagcca tattgtcttt ttaaatagtt ttattaatat aaaatgtaca 36600
taccataaag catacccatt taaactgtaa aattcaatgg gtctctctct ctctctctct 36660
ctcttttttt tttgtatact cagagttgtg caacaattat caaaatcaat tttgaaacat 36720
tttcattgcc ccaaaaggaa accctctgcc cattagcagt tactccccat ttcccccacc 36780
cccagtcccc ttcaacccta ggcaaccaca aatctacttt ctgtctctat agatttagct 36840
gttctggaca tttcatgtaa acggaatcat gcagcatgtc accctttgta tctggcttct 36900
ttcacttagc atgatgtttc caaggttcag ccgcattgta gcatctgcca atacttcatt 36960

```
ccttatttat gactgaataa tattccattg tattaatgta tcatatttgt tttttccaat  37020
catcagttga tggacacttg ggttgttttc atcctttgtt tttttcttgg ctattttaaa  37080
taatgctgct atgaatgttc atgtacaaat tttttaatga acatctgttt ttatttctcc  37140
ttggtataca cctaggagtg gaattgctgg gtaatatggt agcttaacat ttaacctttt  37200
gaggaactgc cagatttttc caaagcagca caatcatttt acattttgac cagaagtata  37260
tgggagtttt agtttctcca catcctcaac aacactcatt attgtcattg tccttttcag  37320
ctcttttgat aatagtaatc tcaatgggtg tgaattggga ccccattatg gttttaattt  37380
gcatttcctt gaagactaag gatattgatc atcttttcat gtgcttattg gccgtttgta  37440
tatttttga tcttttgctc atttccaaat tgtgttgtct tttcattatt gagttgtaag  37500
attttaaaat atattttgga tatgtttgtc attttaggga tgatacttca cagttacatg  37560
atgttttcta gcaagcattt gtgttgttct actggtgtta catatcttag ctgcattagc  37620
cacttcgttg ggtatgaatg ccagcagaat ctaaatgacc ttggcttcac tgctgagaat  37680
gcaacccaag aacagaaatt tgtcagaaat ttaacactta agccccccac ttcccaaact  37740
catctgggac aaggagaatc tacatttaaa gttctatatt ttgtgttgct gtggtttttt  37800
ttttttttt tttttacttt agcttggttg ggtttaggat cttttctttt tgttttgcct  37860
taggcatacc taagcagagg caagggagga aagggatatg aaactgatag aaaagtgagt  37920
aagctttatt cagatcagca tattcatctt aatatggttc aattggctga agaaatatct  37980
caactaaaac tctggaatac tttgaagtac caataaaatg tacctaatgt acattttatt  38040
tatgtttggt ctctatgtac ttgtgtgtga aacaatgagc acaaataatt ccctcctttt  38100
ttttaagcaa tttatattgg tgatttaaaa ataaaataaa tgcaagtggg aagtcatgaa  38160
accccatgta aaacgaataa gagcatatat taaaatccca cagactttag tttcaaatag  38220
tggttttgct gtttcttagc tgtgtgtcac tgtgcaagtt actttgcttc tctgagtctt  38280
tatttcttta ttggtgatgt atgtaaaaac ccaccttctc gaattattgt gaggacaaaa  38340
tgaattaatt aacataaagt tcctggtgta taataagtgg tcatattttg tatttgagca  38400
cagggcaact gagtttttga aactgcacat taatgttgca gtcaaatccg gcatgaaatt  38460
agagagtgca tagacagagt gggctgggaa aatgaaagga ctttgaacat ttatattctg  38520
ctttatttag gcatcagtgc ttaataatta ttgatagttt cttctggtta tctgacattt  38580
tgaagagact attacctagc agaaatttct tgtaataata atctcttaca cttatatagt  38640
gttttgtgcc tttagaagta cttaatgctc tttatttcac tatccataaa tattctctga  38700
agcaagcata cagtcagtat caattccatt tttcagatga gactgcaaga catagagtta  38760
cttgtttcaa ttcacatagt aaagtgacag tttgaaccag agcccaggtc ttctctctga  38820
acatagctct ttttctcctt cattatatca ggcatagcgg caatgtatta ttttactagc  38880
tttttatctt gaatatcctt ttagtgacct gcctttggtg ttagtgtgcc tataacattg  38940
tcgttgaata tcttaataca tttagtggtc ttagcaagca gttttgtctt cagaaggaca  39000
ctgaaatctg tggaaaggac tgcagaagat tgggtgggca gatacctatc actttctggg  39060
ctggtagact ttctgttgaa gctatttgca aggctagttt gtattatcga aaagcactac  39120
ttcagaagag ggttgtgatg tcaaagtagg cactttgagt gaagaaaggg ctgtaagcat  39180
gggtggaaaa tgtggtagat gattgtcttg agttattttc tttaatgtca agcaggcagt  39240
ccttggaatg ctatttcaaa aagtgttgta taatgttgaa gacacagtta cagatttcca  39300
```

-continued

```
acacgaagct cataaatctg caattccctg tcctcctagg cacatgaagg aaaatttatg  39360
agcttcaggt ttctatgcag ctattaaagc atatttaatc tgctttgagc tcaagctccc  39420
tctcatttgc tctcttcgtt tgttcctctt acatgagcaa actgcctttc tttttcttta  39480
aaagtagtaa gtagatttgt tttcctccag gtgtcatgaa tgcaaacatt gtaatacctc  39540
atctgttagt tcagtctttt gcaaaacaaa atggcagcac ccaggaggtt gaaagagtta  39600
aattgtttcc ttctctgagt ggtaccataa gttgttagtc tgctactctt tctcccagtt  39660
ggcacatgac gctaacatcc aatcgctagt gatgtggcca ttttttgcct tattttggcc  39720
tttcctcagc caccagtcat cagttttcat gcatatttgt cagaccctgc ttcctcaact  39780
ccacagttct tagttcatct taagcaaatc gctgtctttt ctctaaagat cctcaaggaa  39840
aataaaaagc atctccaggg ggaatttact gcctcatagc cctgacagag atttctgacc  39900
aaaccctaac caaaaaattt cttccctcca tttgtctttt attgttttta caggggagat  39960
atgtaacata ataacaatta tattgtacat aataattact tttacaaata ataatatctg  40020
tcatcaaaaa tatacagagc tttggatttc cttagtatgg cacttcatta agttgtggtt  40080
taagaatagc tatgattatt acttttgtga taattacgtt ccataatatg gaaacttata  40140
aaattacctt taaaatgtta ctcttattct ggccacagga tggaaagatg ttcgctagtt  40200
actcatttat aacctgaatg tactttttac tgaatctaaa ggtatcatct ttgcttggca  40260
attcccatga cttgtctttc tgactcttca gatctcagct taaaagctca ctcttcaaag  40320
aagccttccc ctgaccactc tggttttgtc ttcttnnnnn nnnnnnnnnn nnnnnnnnnn  40380
nnnnnnnnnn nnnnnnnnnn nnnnnnnnnn nnnnnnnnnn nnnnnnnnnn nnnnnnnnnn  40440
nnnnnnnnnn nnnnnnnnnn nnnnnnnnnn nnnnngagtt tatattttaa ctcttagttg  40500
aataatctaa gccaagaatt atcaaccttg ggttgcacat gagaatcacc aatgaagctt  40560
taaaacagtg acaaggctat cccaatctat tcattaatta tctccaggtc taaactttag  40620
catgtatata catttttaaa agctcataag tgattcttat gtatagccag tgctatctgt  40680
ctcttctcct gttctttccc ctcctctcct tactcctttc tcatagtttt aagataagca  40740
tggccccaca acaagccttt aattcgcatg gcagtttcta gggtttatca tggaaaatga  40800
gccaaattgc cttcaagaag tttttacgta cctcttatat agagtgtgac attttatatg  40860
tacctcttat aaaatgtgag cttttaagag tcatatctta ttgcaagaaa tttcaatgtc  40920
gaaaaaagta ttgaatattt ataaagtcac aaatacaaac ttttatatga ttctcaaacc  40980
tgtgaagtta tgtcatgttc aggccttctt taaagcatgt ggctctcagc cctggtactg  41040
tccttaacca taaacctcat ctttgccctc tatagggaga ggattgtgat tataattact  41100
cattttaaat aatgtatatt agtaatgtac cttattcata tatttgttga gcacctccta  41160
tgtgccaacc actatgctag aaatttttta atattcttca aaatcttcaa gatattaaca  41220
tatccccatt ttacaaatga ggaaactgct ctcaaagagc ttagtttaca cagccagtaa  41280
gctgctaagc ctagattgga tggagggtgt gtgagaaaaa aagcagcatc cataaggttt  41340
tcattctcct accctgtatg atagaggtac tagaaattat taaagaaaca atagaatttt  41400
acaagacttt aggaagggag aatgtgaagg gtacagttcc cagttgctgg aatgagtact  41460
ggagtaccaa tacatggctt gccatggggt ttggactacc tatcttaact cctttgctcc  41520
tcccaatctt gatctcattt gtttgaaaga tcatctgccc aacataaaaa tgcatttcta  41580
attctgtaat ttaagtcagt ggcaagatca gattcagtta aagtttactt tcctgacaac  41640
tatttaggat gatatctatt ttgcaaaact ctagtgataa atgtatgcac acttacacat  41700
```

catacagcgt ctcttctgat tctgactaag atgtgatgga gctgtgcaga tgtgatgggc 41760
tctttggaag aaaggtttga tatactacta atctaaggac tgaattttct ctctcatctt 41820
tgtttttgtc ccttttgaat gatgatgaga gcagcagcac ataacattct tttgtgctaa 41880
cagtatctct gcatcacatt gatcaggaga attggccctg gaatggtatc ttctcagttg 41940
attttcagga aagattaggt gattattttc tccataggaa gaggatgttt gatgtgtctt 42000
ggctttggca aaaggaagct tgtcgactca actgtaagta gatagaattg cctttgactt 42060
catctgtttc agtcgttgtt catactcagg tcctccagaa ggcctttaag catttttatt 42120
gactttgtgg tctattacac aaaactaaag atactgattc tcagtcgtga gtctgcttca 42180
aaattgccta gagaatcaaa aataattgta ccagttcctg ttcctggaca ttgtgattca 42240
tttggtctgg tatgaaggcc aggaatctgt atttttaaaa ttcactcaag taatttttgt 42300
atatagctat agttatgaaa ttataacaat aatgaaataa taataatgaa taatgaaata 42360
ataatgaaaa tctgtggctg aacttgtcca ctcccctatc ccctgcaata cttccccaag 42420
gtggcattta agatgggcct agaaggttat ataagatttg aatattaaaa catggattga 42480
cagtgaggac tttttgagag gtgacaatgt gctagcagcc ctggcttgct cttggcacct 42540
cctcgacctt ggcgtccact ctggccacac ttgaggagcc cttcagccta ccgctgcact 42600
gtgggagccc ctctctgggc tggctgaggc cagagccagc tccctctgct tgcagggagg 42660
tgtggaggga gaggcatgcg tgggaaccgg ggcacggggc tcatgggcca gctcgagttc 42720
ctggtgggca caggctccac cggccctgca ctcggagcag ctgactggcg ccgtgggccc 42780
tgggcagtga ggggcttagc acccgggcca ataactgcgg agggtgcacc aggtccccca 42840
gcagtgctgg cacaccaatg ccacgcttga attcttgcag ggcctcagct gccttcccgc 42900
ggggcagggc tcaggacctg cagcccgcta tgcccaagcc atccccctgt gggatcctgt 42960
gtgtgccaag cctccccaac gggcaccatc ccctgctcca cagtgcctgg tcccatctac 43020
tgcccaaggg ctgaggagtg tgggcacgta gtgcgggact ggtgggcagc tccacccaca 43080
gccgcagtgc cagatccact aggtgaagcc agctgagctc ctgagtaggg tggggacttg 43140
gagaactttt atgtctagct ggaggattgt aaatgtacca atcagcactc tgtgtctagc 43200
tccgggttcg tggatgcacc aatcagcact ctgtatctag ctaatctggt ggggacttgg 43260
agaactttta tgtctagctg gagaattgta aatgcaccaa tcagcacttt gtgtctagct 43320
caagtttgta aatgcaccaa taagcactct gtgtctagct caaggtttgt aaatgcacca 43380
atcagtgctc tgtgtctagc taatctatgg gaacttggag aacttttgtg tctagctaaa 43440
ggattgtaaa tgcaccaatc agcactctgt gtctggctca aggtttgtaa atgcaccaat 43500
cagcaccctg tcaaaacaga ccaatcagtt ctctgtaaaa tggaccaatc agcaggatgt 43560
gggcagggtc agataaggta ataaaagcag gctgcctgag ccagcagctg caaccactct 43620
ggtccacttc cacacagtgg aaggtctgtt ctttggctct ttgcagtaaa tcttgctgcc 43680
gctcactctt tgggtccaca atgccttcat gagctgtaac actcaccgtg aagatctgca 43740
acctcactcc tgaaatcagt gagaccacga acccactggg agggatgaac aactccaaac 43800
gcgccacctt aagagctgta acactcactg caaaggtctg cagcttccct cctgaagcca 43860
gtgagaccac aaactcacca gaaggaagaa actctggaca tgtatgaaca tctgaaggaa 43920
caaactctgg agataccatc gttaagaact gtaacaccta ccacaagcgt ctgcagcttt 43980
attcttgaag tcagtgagac caagaaccca ccaattccgg acacgttttc acatggagat 44040
aatttggaag aaaaacttgt aaaaatgtga gaacattgag aacttttatt ttccaaggaa 44100
agaagtggca gcttcatttt tggtcattgc aaacagcagt gccatacatg aaaggaaagt 44160
ggtggtgctc atcaacttag aacacttgag actcttttct gcttataaag aaaaagtgtc 44220
aactgtaaag ttgatttatt tatgaaccat aggctactat gaaatctctg ttcacagcta 44280
gaggcctggg agagtaagat aactacttgt ttattccatg aagccactta ctgtttcttt 44340
tctattgcac atacctcaaa tgaagcattt caatagaaga accacattct attcacttgc 44400
ttcattttat tctgatttct gtaaaaactc aaaaattcct caagcagtgt ttctttgcaa 44460
ggcaacaatc ttcagttctg ttgcaaaggt caggagtgat agaatgaaaa tggtactaga 44520
ttcaacagaa ctttggtatt tgcatggcta taacattgcc atggggctgc aagacttgtg 44580
agagcttgat attttgcttg ttgatgaatg agtctgtgtt ggtgctggtg gagtgatttg 44640
agaggtagtt ttccactgtc aatcaagagg ttggttttga aagctgattg ccagtagtca 44700
ttctgctaac cactctggtt ctcctttaga tagagaccta ctcagattca agtctcatgt 44760
actttgtggc ataaacattg tacacaccag atgtattgaa caaccacaaa gaaaactatt 44820
aggactcaag tagtatgtca gagagtagtc actgatgatg tataattctc cacttccaag 44880
aagatgtaag cgcactgttg agtggctaca tcctacatat gttggccaga atttaggaat 44940
acacatgtgc tctatacatt ttgaggtact gcctgacccc tagagaatcc tggtgaagtt 45000
tttctggtgt cagtttggtc ttaatgttta ggaaatgccc acagacgact cctgctttct 45060
gcttactcat gtagtaaaca caaagcacag gactagtttg tcttctggat caaggagaaa 45120
tgagttagca gatataaaac aaatcagaaa ggaagtagtt ctcacatatt taaccataaa 45180
tagttgctgg atgttcatta actctatagc aatatttact acttattggg gatcctggaa 45240
agaaaatata ctgtccatgt ccactgttca ctgagggccc cccgccaccg agaaactccc 45300
tgtcttcatc actcactctc cacattcatt gacctagagg aacagttcat ggatgagtga 45360
gagcttgagc tatatcttaa aggatggagt tggatttcaa ggcaagaggt ataagagaaa 45420
attcagagac aatattgacc atggtctttg cgaagaaaag tactttggga gataaggttg 45480
aggaaaagta cgtttgaatc ttcatccaga ggtagcccct aaatatgttg actctgttga 45540
aagagtactt gacttggatt cagacagatc tgcatttgac tcctgttttg ccatttataa 45600
gaacttgagt aattattgtt tctgaataag agtttattta gccaagcact cagtaaatgc 45660
ttgaatgtga aaatttactg ccctgttttt ctattgtcag atggtcccct tccttggata 45720
actttgtaat cgttgataac cttttctcag gaatcagaag gtagaaggat tgggaaaata 45780
taagaaacaa aaaggcatat tcttattttt attttcatat tgtcttccaa ctctccaagg 45840
catcttcgtt tgcaaggctg acttatctaa tacttgttgg gtagagcagg tctttctttg 45900
gttttcccct gtttggggtt aaactctgag taacgttatt ttctaggtct cagccaactt 45960
tgaagcgcat gaactcacag tagcctcacg agggtcactt cagcagtgag aagttacctt 46020
tcccatataa aagtgtaaga gtcgatggcg gccaggcgca atggctcatg cctgtaatcc 46080
cagcatttta ggaggccgag acgggtggat catctgaggt caggagttca agaccagcct 46140
gaccaacatg gtgaaactct gtgtctacta aaaatactaa aattagttgg gcgtggtggc 46200
acacacctgt aatcccagct actcagaagg ctgagacagg agaattgctt gaacccggaa 46260
ggcagaagtt ggaggttgca gtgagccgag actgcaccac tgcactccag cctgggtgac 46320
agaatgagac tctgtcaaaa aataataata ataataagag ttgatagcaa aataactatc 46380
tgtagcgtaa acctcagtat tctttatcat tcagtatcaa cattattacc aaaaaaacga 46440

-continued taagcaatag ggactgagtt tctgtggggt ggaaatgtga agtggatctt ggcatgatat 46500
aacttgtgat ttggcttcct ttataaacat tatcaactac ctcagctcta tcaatcactt 46560
ggcagtccat agtgaacatt ataactcaaa tgactagtcg agtctgttca ttgtccatgt 46620
aaaggcgtat acctgaagtg agaagtctga ggtaacttag caataagttt gcagtacagt 46680
gtttagtgaa gtctgaaaat tcaaggcttc gagtcatgcc agattgctcc ataaccatag 46740
cctatctctg tcacaagtaa gaaggtttaa aaatcacata ccattattgg tcacaatgtt 46800
tggagatggg gaagagtttg tggatggatc atggcagtgc atggacagtg attagcccac 46860
agcacagcca gtgagcactg ttgtacccaa agcacgtaaa tcaccacata tactatcaat 46920
atatttatgg atgacaacag acactatagt tttatgtcag tgctttctgc tgctgaaaac 46980
aaagttagtt aagggtacct tttgtatatt tgcaacatat ctccacacct gttcctttgt 47040
ctccttcttg caagttcttt ctttcagctg actatccgct gttcctacta tggctcccag 47100
tggcttttca agagggtgat tgttttttaa gagaagatcc ttgaaggaca gagaaagcct 47160
gaatcgttca aaataatgaa ttactcagga tgaaatttca ataatttgca agtttgtgga 47220
gacagatatt ttggggaagc ataattttct atgtacccct caaatcatgg ctggagatga 47280
cagcctcttc cacctccata taagaccatt tcatttcttt ctactttttt ctccctcctt 47340
ccccccaaaa cacaaacata cacatatcct gtgcttcagc cacccagaac ttcttactat 47400
gtcttttcaa ttctctgtgg ctttgcatgt tctgctcctt ctgcctagaa tgctcctttc 47460
cttttcttac ctggaaacac cccaattcaa atgtcacctt ccttatttat accaactttg 47520
tccataactc ctttatcaca cttcttcttg tgattagtct attcacttgt ctgctgttac 47580
acctgtatga gagatgaaaa ttccttcttc atctctggaa ctcacgccct tagcatatag 47640
tagacaatct gtaaatgttt gaaggttgag tgaattaatg aatgaccttc aacctttcag 47700
gcttccaatt ttctctctga aaaggacagc taaatgaaaa ctcataattt tagaagatga 47760
ggttagacgg ttggtaggtg catgcagaga ccaattatta tttaggcatt atagaagtgt 47820
atagttcttg tatgttgagt gcagtgtaag agtggcccca aatatagtta atgcccactc 47880
cagacccagt tattatagag ttggccccag ctgtattgct tctatttaag actgagataa 47940
gaaatgacac tttcctattt ttttacctta ttgaaagggt aggggctggc tgttatcaat 48000
ctcagttcac ttgttgattg cattggcttg ccaagtgaga atattagcac ccctgcacat 48060
ttctatagtt ctgccactta tgagatcctt ccttcccatt gtcatattta ataatcagga 48120
tagccctata aaatatgcat tcttatttcc cagatgagga tactaaggct caagtaggag 48180
aacttacttg tttagtaaga tcgtacaact aggaagtggg agaggcaaga gttgaaccca 48240
gatcttccta gctcccggta catcgctctg tctactgagt cacactggag cagccaggag 48300
gcaggaaaat catctgggga atgtggtgcc aacgtgtgat gtttgcctaa atgtgtgcat 48360
ccttgctgga agccagccat gattccatgc tgcataagta ttcattaatg ttcatttcat 48420
ttatttggct atccatatgc tttccagggc gaaggcaagc taggacaagg gcagacaagc 48480
agccttaaag tttgggtgct ttccttcaaa gctgggctgc ctgtttgaaa atcaaacatt 48540
tttggtgata gaagatggtt ccagtacaga ttttattcat tactgcatct acatggacag 48600
acattttcca aagcatagct gaaaatatgt gtaagtccca gaatatttcc tgatttagac 48660
acagactttg agcatgataa ccacatttag catgttagga aattctgtca gaatgcttct 48720
ggaaaggcta cctttccaga atgaaatgaa aaaaaaaaaa aaaaaaagga tggactttga 48780

-continued

```
aactgattag atttgggtta tactccctca cagtgtgacc ctggcaaatg atttaactta  48840
tccgagtttc acttttctta ttctttgaag tgaaatttta aaatgtcatc ttgcctgatt  48900
tttgtgagaa tgaaaatgag atcccacacc aggaatttag aagctactca gtaaatattg  48960
cttctctcct ttccccttcc cgagtcctgt cccccaagtc attcattagt tattcagagg  49020
catgcattct gaaatctgcc tactgctcca cgttgaaatg cactgctctt gcaaagactg  49080
attatctatt tttttgtctt ccaaggcccc ctgtgttcca ctccaccctc ccaattctgg  49140
gggcttccaa agtgggcagg tacagaatgt tctgtggagc atcggaggct gttactcaat  49200
atcctggcca gcactctcaa ctgctctttg cacatactcc atatgaaggc aaactccaga  49260
acttggagtc catgtttgtg tcatgcattg cactgcttct tttacccaaa tccatctcaa  49320
gggtgagtag accaagctca gacttgtctt tggagcagat ttctcaagct gcccatgtcc  49380
ccacactgct tgattaaaag gaggtgcttc aaactctttg gctttatata gactagaagc  49440
agaatgattg gtggtgcctc tgttctcaag gtatcccaaa gcactttgta aggaaatatg  49500
acaagcgctg aggccacgca ggctagtaca acagccgcca cccagcactt cacaattagt  49560
catgcccagc ctgggatcat caagcctgtt tttgttggaa gagcaagaga gggagggaat  49620
gctagctggc aatttccccc ggtacccttt atgaaagtgc ccttggctct tccaatttca  49680
cctgaataac cagctcaggc aaattttcct ctatcaaaaa gcagaacgtt atagtgacaa  49740
gctgatgcct ggctgatgcc ccaggacatt gaccaaatag gcttggcctc acaattggtt  49800
tttattcccc atatcctttc ttccctttg ttctttttct atgtttcttt cccccatcgc  49860
catctgcaga gtgtcctcag tcagaagtca gctgtggggt ggacagtttg tcatttaaaa  49920
tcatccctat tctgtctacc cttcttatcc ctcacataat tgcttttaga gcaaggacaa  49980
ttctggaagt gaaactacaa taacaccctg ggctcctttc cctctagtag tactcagcac  50040
acttgcaatt acatgttcaa atttgtcttt cttatttctg tttaggttca tgaaggcaag  50100
ggacatgcct gtgttgctta ctttctcttg gcaggcacat atagcaagtc ttcaaaaaat  50160
gcttgttaac tataaattaa gtgtttaaga agcccatcgt tagtatcttt gcccctgcct  50220
tatttgtaaa caaccggccc cttctatttg taagttacct tgttttgatt tccatatccc  50280
ccaaagcaaa ctttagctca tggccttaca gagtgtgtat attagtatgt taaaatgaaa  50340
tcaactctcc tcccccaagc cttctaattg acatgaattt gggagttgac ttgcattggc  50400
ctttgtcctg acagccaaca gagtcctctt ctggtgtatt cactgttggc ttccatgaag  50460
atgctatgga gaaagtttgc cattgacata cattttgagg gcagactcaa cctgagtaga  50520
ccggattgag ctttccccat ctgcctgcca gagatcacta cctgtgtgtt gctaaaaaga  50580
gaattatagg agtcctctca aggcagaaag acctaaaatt agacatggca gccatgcctt  50640
tggtgtgtat gggggtggga tacaggcagc cagtttcccc tctgttttct cccttgctta  50700
cacagccaag gagtggagcc aagcctcaaa gggaagagct gtatactgga gcatgccagt  50760
atacaggttc ctggccctgg ctgagttact attttatata ttccaataga gaagcataga  50820
agacttctag gttgccactg tcatttgaaa ttgggtattt ttaaaagaga aacttgaaga  50880
ctcaaagaaa gctttctttt gcctcccctt acagttgatt tttgagcttc ataaagctac  50940
ctagtccaaa gtacccacac tcttattatt tttgtctttc ctaccggttt tttttttttt  51000
tttttttttc atcttcccag gtgtttgatg atcactaaga gcttcaacat tgctcacctt  51060
gaccaggtat gaaaccaaga gttttgttta aggcataaaa gaatgtagga actcaaggat  51120
taggttgaga tggggaaggg ggatgaaggc ttctttttc ttgggttaaa cagaaatgac  51180
```

-continued

```
ttagatctca gagtgaaagc cttgaattgt cacatatatc actggcaaag actagttctt  51240
tgctatgata agaattgttc atcatctcgc ccctgaggat ttagggtcaa ggcctggcta  51300
caccttttga tgatctcagt catatgactt aacctcttta aagttaacct ttggtgagca  51360
ctgtgccccc tgcaacccca gtaaggccca acagggctct ccaaggaggc aaaattctga  51420
tgatacattt ctgtttagtg aaaatgggta gggaaaatta tgtcttagaa tcaattaacc  51480
aaacataaaa tcctccaagg ggcttggtag gatgcctagg gaagagcaac gagataaaaa  51540
ctccaggctg gaagggcatt gttgcagcac tgtcattctc cagtttctct tggagttgtc  51600
actaccctct cctttgttct cactgctgac atcatttgta aaataatttc ttcccataaa  51660
taaacaaaac gtacaatcct ctaaatgact aaagaacagt tatctagaag aacagtggaa  51720
agtattttct tcacctaagg gatgattctc tttacagagg tggagtaaag gatgtgcgag  51780
gaggcataat caagctaaga gatgcatgct gacttaaaag gcatgacatg tgtgaaacta  51840
agataatgtg ttcaagagtg atgctttgtt gatgcagaac ccactgaatt ccttactgtt  51900
atgtttgact gactatcagc ttattaataa agaaattgtg gtttgagtgt tcattgaaat  51960
tagccatgtt aggtttatgt ggggatgtga ggatctatgt ctaccaattg cagcttctga  52020
tgcagattgg aggcagaaat ctggcctgaa caataagtaa gagtgtcagc tctacagata  52080
tctcacatgc taagcaagca caatataggg caatccaggt ttacacaaag gattaatttg  52140
ggaacaatta tcctcatttt cactttctta aacgattttg aataaggtct tttaagtaag  52200
aagctccctg aatgcattta aaatatggtt tgattatgta catttaagat ttttctacct  52260
ttgtaggagt atctctgttg tataaaaaca caaaattccg gaacttttga aaggaagatg  52320
tgcctctctt catacatttg tcattcttga aagattgtaa aatgaagtga ctgcatatca  52380
tgtcgtgttc cctattgatt tcttttctca ttttaggaat attcccagaa taaaaaaaaa  52440
tttttttaa tctactaagc atgctaggta agactgaaga tgaatctatt taagttatgt  52500
caatatctat ttataaagat ttttgtgata ttctttttac tgtagaactt gaagcatatc  52560
ctaaagggaa tggttagcta tgtctgcaaa ctgtggcaat gacttactga gtaattgcta  52620
gcaactgatt tttggtgctt cttgttttga tagtatagca gtgcgagtag gttttagaaa  52680
agcaaaacta agaaaaatcca gggaaatgcc atttgagaat ttctaacttt aaaaaacaaa  52740
taaaatagtg tcaagaaaaa atattatcca actaacccca aagtctacaa tgtaactctt  52800
ttattttgat aatgctgttc taactctatc tacttcagtc cattgccatc cagctggttt  52860
aggaatcaaa ttcccaatgt ttcatcactg ttaacattac tgttttactc ttcagtttag  52920
ttcttaaatg gcatagtgtc ttaaattccc tcagcctctt tcacgtttga tttctttgga  52980
aactttttac cttttcattg aagcccatat gatcttttct gaaacagacc cttatcttta  53040
ccttcttctt tggagtcttt ctcctacttg aatttctgaa cttcttaaaa tggccgcttt  53100
ggattggtgt aataaatttt cttttctttc tttctttcct ttttttttt ttttttttt  53160
ttttttgag aaggagtctt gctttgtcac caggctgcag cctgtagtgc tgtggagcaa  53220
tcttggctca ctgcaacctc cacttcccag gttcaagcga ttctcctgcc tcagcctccc  53280
aagtagctgg tactacagga gtgcagcacc atgcccagct aatgtttgta tttttagtag  53340
agttggggtt ttaccatgtt ggccaggatg gtctcgatct cttgacctca tgatctgcca  53400
ggctcgccct cccaaagtgc tgggattaca ggcgcgtgcc actatgcctg gccagtaata  53460
agttttctta agtgctttct taatgttctg atattttaaa aaagatctgg actattttgt  53520
```

catacaggca acagaatgtt aaaccatttc ataaagcaat gacaaatata catgattttt 53580
catcagttat aaatgctttt cctttataac attgaacatg tttttgcaac tgaaataagt 53640
gtgattttca tttttagaag gtacatgata aagttaaggc agtggttaat taatttttttc 53700
agattaattt ttcagaaaag tgactgtttc tgtctgttca cttaacccca ggcatcaaac 53760
gactttaatc agaaagaact gaagagtaat ttggttattt tagtgccctt ttttgaggca 53820
aagtcttatt ctgtcaccca ggctggattg cagtagtgtg ctcatggttc actatagcct 53880
cgatctcctg ggttcaagtg atcctccaac ttcagtttcc cagataactg ggaccacagg 53940
tgggccccac actctctgct attttttttt ttttaatttt tcatagaaat ggggtctcac 54000
tatgttgcct tggctggtct caaaatccta ggttcaagca atccttccac ctcagcctcc 54060
taaattgctg tgattacagg cgtaagccac tacacttgcc ctattttaga gatttgtcaa 54120
gctttggaaa gagaaccatt tacaatataa taggtaaatt atggatattt gaggcagttt 54180
ttatcatagt atttgtagta aactacagcc ccccctttat aatatttgta tttaataaaa 54240
atgaaaatat tacttttatc ttgaacaaca aacataagtt ttaacaaagc aagcatattt 54300
agattagcac taataaccaa acgaaaacct ttataatgat agctgttttt aacatgatta 54360
caaaaaattc gctacacaaa tttttatcct aatcagtgtg aaaaacggaa aatattagct 54420
tatagggcca acttagtctt cagagtcctc ttcctaccta ctactgctaa taagccaatg 54480
aaaaactccc tgatgtgtgt ggtggctcag gcctgtaatc ccagcacttt gggaggccaa 54540
ggtgggtgga ttgcttgcac tcaggagttt aagaccaacc tgggcaacat ggtgaaactt 54600
tgtctctact aaaaatacaa aaaattagct aggtgttgtg gttcacacct gtagtctcag 54660
ctactcagga ggttgaggtg gggggatcgt ttgagcccag gtggtcgagg ttgcagtgag 54720
ccgagatcac aggactgcac tccagcctaa gctacaaagt gaaaccttgt caaaaagaaa 54780
gaaagagaga gagaaaaaga gagagagaaa gagagagagg caggcttctc cgctttttca 54840
gttcctgaat aattttccaa tctagaatgc aaaagattct gaaggaagac agttaccatt 54900
tcagattggc agaagttgtg actttaatct ggacttgaat atgttttaca tcaaagggtt 54960
gcctcaacag tgctcaaacc tgcctctctg aaaacatgct gagcgcaaag gttacttgaa 55020
gtcttagctt gagtacttaa gagaatgcta tggagggatt gttgaagaga gctgtgtcac 55080
agctaattct tctttagtaa ttaaaggttt agaaaactct tacactgcat attgacaaat 55140
ttagcaacaa aatgagcttg agaaaaaaat caaggcctgc tgtggaatct tttttttttt 55200
tctctaaaac aaacaaacaa acaaacgaaa cctttttaga aagattatgc aactgtatta 55260
tctgtaacta ctgcaatagt gtaaattctg atagtataat ttgcttttta aagctatctt 55320
tacttcagtg caacttagat taaatttatt ttaaatttaa acgatatttt tctctttgtt 55380
tattatttta tagtaagttt cccatagaat tcacaaaatt cattagaaag attttctttt 55440
ttttacttcc ttaggtcatt aagtttctga tttgtcagtg gatttcacag aaaccctgtc 55500
tttccaaaaa tatacaaaaa aaaaaaaaaa aaaaaaagcc aggtgtgatg gtgtgtgcct 55560
gtagtcccag ctactcagaa agccgagttg ggaggactgc ttgagcccag aagttgtggc 55620
tgcagtgagc tatggtcaca ccacttcact ccagcctggg caacaaagcg agaccccatc 55680
tccaataaat aaataaacaa ataagtaaaa agtttttcac cttgaaaagc ttataaacat 55740
atgaaacacc attagggtct ctgatatagt ttggatgtgt gtccccgccc aaatttggtt 55800
ttgaattgta atccccagtg ttggaggtgg ggcctgcggg gaagtaattg gatcatgagg 55860
gcagtttttt catgaatggt ttagcaccat ccccttggta ctgttgtcgt gatagtgagt 55920

```
aagttctcat gagatctggt tgtatagcac ctctcccctt gctctcttgt tcctgctttc  55980
accatgtgac atgcctgctc ccccttcacc ttctgccata attttaagtt gcctgaggcc  56040
tccccagaag ccgagcagat gccagcacca tgctttttgt acagcttgca taaccatgag  56100
ccaattaaac ctcattttta atataaatta cacagtctca ggtattcttt atagcaaggc  56160
aagaatggac ttacacagtc tcttttgtat cagggagaag gtctcctggg tgactccact  56220
tcttttcttg tttatgtatc cttccagatg atgtatttat ttcctttgtt tttcaattga  56280
tatttactct taaattaaac taatttatta ataaaaagca ttttaaagtc tcattttaga  56340
ttattttgac tatctgattt tttaaatgga gtaaaaaaaa tctaccttgg cctccatatg  56400
caatcaagca agaaacacat tttaagcata ttatttgcct tgtggattct gccttcctcg  56460
atgtgttcag tctgtatata ttcatttctc ccacactgta agaagctagt cagatgtata  56520
attggattat catgctacat gatcttagca cactcatttt aagcttacat agactagtga  56580
gcaccactca ttacatgtca tttctctaga gaaactagtt gggccgtggc tgcaggactc  56640
tcacttgaag agacacatgt ggtgatgttt tctcaggcag ttaagcaata aagtgtaccc  56700
tgatttgcac tgaaaataaa gattccttta aagggagcag ttctagttat ctctctcttt  56760
agataccata tgctaaacgt ttttctatgc actaaaacaa taactaggtt tttatactctg  56820
ccttacagcc tacttcacac ccatttcaca gggagaggaa cagagaggta agtgatttgc  56880
cccaacttac ataactagga agttatttac tcagtgtgga aacttgttca gacggtcatt  56940
tcattgaaat gtaggaagag tttctggcac ttctcttgag caggagtcaa aaacttcttt  57000
tttgcactag cccagatagt aaatatttta ggctttctgg gccatatggt ctctgtcaaa  57060
actcctctac tttgttgttg tagtgcataa gcagctatac acaatcctga aatgaatggg  57120
tgtggccgtg ttccagtaca accttacaga aaaggcaata ggctggattt ggctctgaga  57180
ctgtagtttg ctgacctcag ctcttgaact gagctcttta actgacctca gctctcgaac  57240
tatggtccaa gatcccgtgg tcctgtttgg tacctccatt tgccctcctt ttcactctct  57300
gggagcatag ctaagttcaa aattgaatta ggtacttgta gtaagagtac acttataatc  57360
ctgggatctt catgttgcca gatattaacc tcttgaagtt tatcaccaca gcctgggcac  57420
ttttctgatt tgctcacttc tagccccacg tttgggcccc ttcacaagca aacatgcaga  57480
ttttccagag agctgtatgc tactgaatgt agaaaatttg gctcatactg gcctatggac  57540
tatctgctca ctgccctgat aactattttc caagggagtg ggtgccctac ctttcctaca  57600
cagagttttt ttgctagtct cgccctaaaa attctaggta tcccttgctt ttaggataaa  57660
tatgtttcac taggaccagc cgaaaaatga aaaatagagt tatccaacta ccactttaaa  57720
actggacaag gatttttgtt gctgttgttg gagggggtgg taaacatcat tttggcagac  57780
caaatatact tttggtgtaa ggcagccttt tgcaaagaca gaacacttgg acaagatttt  57840
gaagtcctgg ttgcctttac tactgattta actacagtat ttgtggactt gggcaagtca  57900
cttcccttct gtgagcctca ggttattcat ctttgaaatg agtataatac ctgtgattat  57960
aattacttct ctggattctg cagagaactg aaggagataa tggatgtaaa agtactttag  58020
tgcccagcac tgctccttat gaaaatgagg aaataattga gatgagtgag ccattgagac  58080
aaccgtacaa aaagtgctga aaactcactg cttaaataag cacctcttac tgcttttgtg  58140
gcactttgta gcaatgtgtt tttattctga ttagaaagta atgtttggtt ttgtttggct  58200
ctttgctcag taaacccata ataaggatac ctatttgccc ttggaccatc agttcaaata  58260
```

ttattttact aatatggaat tatttggctc cagaagccac agttttctta gctgctcccc 58320
atccccactc tcacctcaaa ttttttttc actttatttt ttttttcttc tcagggaaag 58380
gtttgaggca aaaaaatgcc ttcttatgat ccaaaaccaa gcatggtggt gatttattca 58440
ccaagcgatt cctgagtacc tgtgtgatgg acatggtaga atctttgtcc tgatccatgc 58500
cttctgatat gcagccagta gccacttgtg gtaatggagc aacagaaaca tcactagttc 58560
aagtggaaat gtgagatgag aagtaggagg tggagagaac taaccagaag agggtaccca 58620
aataaaccag aaataggtat ttgttagaga aggggcctat tgagtgggtg gcagtggtat 58680
gtgtggcatt acttgctcct gtattctctg ctttttactt agttgtggct ttggtggtat 58740
agtctcagat ctctaagtta tgcaggtaat attgttatgt atcatgtttt ggcaatgtag 58800
actgaatact tgctcataag agtacaggac aatgaagata gtttggtttt atttactgca 58860
tggaaagtac aggatgttta gtaaacagat ccatggcata gtgagttcac cactaaaatc 58920
agactctgag aatgggtttg atttagatgg ctagtttaga atactggatt caggccactt 58980
gattaagaaa ggccattttg gctaattata agccaccaac attgtgtttt caatgttaaa 59040
gcttatattt gtcttccagt taccagaatg taagcttctt gaggaagaaa agaggagttt 59100
tcttaatctc tgaacctata cctgtctttc ttctgtgtct agcccagtgc ctggcaccaa 59160
acaggtgctc aatcaatgtt gattctatgc taccaacaaa aatgagttca tgatgtttac 59220
tattcgataa atgaatgcaa ttttagagtc aatttttact acttacacta catgtagatt 59280
ttctttttag agatttcaca atgctgattt ttttcaaaat aagcttgaag ctaagtgaca 59340
aagctgaatg atgatttgtt ttttattttt aattctaaac ttacaatttt ccatgtcatt 59400
gccagaaaaa tcattaaata aattatgata tactcatatg gaatactttg caaccattaa 59460
atcaaccatt aaatactatg caaccattaa atcagccatt aacgtattta atggctgatt 59520
taatggttgc atagtattta atggttgatt tgcacatttg catataccaa catattatat 59580
agttgagtga gaaaagttag tttcaaatga ctatgttaat atccccctgac tcttgcaaaa 59640
agaaaaccat acatttgaat gtacgtatac gcgtatgttt atacgtgcat agaaaaagct 59700
atggggggat atacctcaag ttgctaaaag tggctccacc tggagaggga catggaaagg 59760
agctggctaa aaactgaggt ttgttacgtt atacacccct gcacagtttg atttcttaaa 59820
agcgatgatt ataaattcct tttgttattt ataaaaatat tatttaaaac tttggtacta 59880
aaaacagagc tccatcaaca gatcaatgga taaagaaaat gtggtacgta tatacagtgg 59940
agtactattc ggccataaaa aatgagatcc tgtcattttt acaacaaaat ggatggaact 60000
ggaaattatt atattaagtg aaataaggca ggcacagaaa ggcagacatt gcatgttctc 60060
atttaatctg tggaatctaa aaatcaaaac aattgaactc atggatatag agagtagaat 60120
gatggtaacc aaaggctagg aaggatagtt ggtggggcag gggagggtga ggtgaggatg 60180
ttaaatgggc acaaaaaaat agaaagaatg ccattctaac tggtgtgaga tcaggaaaca 60240
acaggtgctg gagagaatgt ggagaaatag gaacactgtt tacactgttg gagggattgt 60300
aaactagttc aaccattatg gaaaacagta tggcaattcc tcaacgattt agaactagat 60360
gtaccatatg acccagccat cccattattg gggatatacc caaaggatta taagtcatgc 60420
tgctataaag acacatgcac acatatgttt attgtggcac tattcataat agcaaagact 60480
tggaatcaag ccaaatgtcc atcagtgaca gactggatta agaaaatgtg gcacatatac 60540
accatggaat actatgcagc cataaaaaag gatgagtttg tgtcctttgt agggacatgg 60600
atgcagctgg aaaccatcat tctcagcaaa ctatcactag aacagaaaac caaacaccgc 60660
atgttctcac tcataggtgg gaactgaaca atgagatcac ttggactcgg gaaggggaac 60720
atcatacact ggggcctatc acggggagag gggagagggg agggattgca ttgggagtta 60780
tacctgatgt aaatgacgag ttgatgggtg ctgacgagtt gatgggtgca gcacgccaac 60840
atgacacaag tatacatatg taacaaacct gcacgttatc cacatgtacc ctagaactta 60900
aagtataata ataaaaaaaa attaaaaaaa tagaaagaat gaataagacc tactatgtga 60960
taacacaata aggtgactat agttataatg atttaattgt acattttaaa ataactaaag 61020
gggtacaata ggattgattg taacacaaag aataaatgct tgagggatgt atacctcatt 61080
ctctataatg tgattagtac acattgcatg cttctatcaa aacatttcat ataccccata 61140
aatatataca cctattgtgt actcacaaaa atttaaaaaa aaactgtaca ttaaagaaaa 61200
acaaaaataa aaactgtagt tcaagttata aacaaaataa aagtaatttg gaggaaaact 61260
atcttcagtt atattggata tttgggggac atttttgtat gttagttagc aaaaatcact 61320
tgaaaaaaag gattcttcct tccatgattc aaaggagcat agcaaaaaat aaatgaaata 61380
aaataaaata ataaaaagag aaaaagaaaa ttattccata aattctactt acttatttct 61440
ggcaaacttg ttgacagcac atgtgacctt tttggtaaaa agacatattt ttatattttt 61500
agttaagttt caaatataaa ttgtttgtgt ttttaaaata aattaaatgg atgacttcag 61560
ccaggtcatc atgaaaacac atgagatatt gggttatgca atgactaaca gtgtgtacgt 61620
tttcttggta tttattcata aactggggaa taaaaatact ttttggctca tttactcccc 61680
aaataatttt atgtctccca aggagaattg taagttgttt gatagtaaat gctatgtatt 61740
ttgtatctta gtgtatgtat gggatttcag cgttagaaga gctcttaaat gccgtcttca 61800
tagtccaacc tgtcttctga tgcttgaaag ccccttgcaa taggaaatgc aaagtagaga 61860
gtagatactc aataatgtgg ttattgaatt atttagaaag aggcattttg agcccataat 61920
gtacaatagg tacttctaga tttattgttt tattctttgc agagctgcag aaaactaaga 61980
aaaaagttta tttcagattc atgtgtttat ttgattaatc tcttcataag tttcattttt 62040
cagctcctgt cagaaaatac agattcttat aaggttcacc tttacccata agaataatag 62100
tataaaaggg ttaatgtgaa atacaatcac ttcacagact gtttcaatta aataagagct 62160
cgtagataat tcagtccacc ccaccccatt ttacagatgt tgaaattgaa gcccccacca 62220
aaagtaaaag acttgctcaa agtcacacag caagtcagtg gtgagcctaa ttaggccccc 62280
tgccttccat tttggtgaga ttcctgtgct gatagtcata cccgtgtcaa atcctcttcg 62340
gcagttatgg cttgcccaca gtaatgtgtc ctgaaaaata tgacaataaa ttaagttgga 62400
gacagaacca taacctcttt ataaaaatgt tctggaaagt ttacatgaca gtacgtaata 62460
tataattaga aaggataatt cttatttcat atttatcttt ttgtttcaga ataataaact 62520
aagctatctc tactcagtcc attttaatac aaaaatattt ttaaccagat tgagttttta 62580
tgctttttag gaacttttttg tctacctcac ttaattaaaa tactagctgc actaatcact 62640
tactgtggta ggcagaattc tagaatgacc ctgattacct tgtccttgta tgattccttc 62700
ctctttaagt aaggatagaa actgtgaata tgatatcact cccatgatta agctttgtta 62760
catggcgcag ttaactttaa gaaaggacca gtcacacaag ccatttgaaa gcagagagtt 62820
tgggattttt ttaactggtg acagaaagcc acgcagagat ttgaacattg agggtaattt 62880
gaatttgata tgccagtact aacttgaaga tagaggaggc tgcacagaaa gtggccttta 62940
ggaatgatcc ctggctgaca gccatctaga aaatgagggc ctcagaccta cggccataaa 63000

```
gaattctgtc aacgaacttg aacttggaag tggattcttt ctccagaact tccatataag  63060
agtccagcct gattgacact gtgattttgg ccttgtgcga ccctgagtag agaatccagt  63120
tgacttctga cttaaaaaaa aagtaagata ataaatgagt attgttttaa actgctaatt  63180
ttgtgataat ttgttacgca gcaataaaaa ctaatatatt taccatacaa gtcaaggcat  63240
ttatcctttc atgattcagt ttctttttac ctgacataat ggaattaatt tatactgttg  63300
tgaaattgta gttgagaaac acgacttcca aagtaataaa atacatgtat tattaatttt  63360
aatagtatta atagtaatga tactgattct ccgaggccta tacaaatcct ttgatacaca  63420
aatgaatagt aaaggaacat aagttgtctc taggtaggct ttcccacaat gcaattttac  63480
gatacagaag tcatatgcct attattctac tatggcagag aaaataagga gcctggaaaa  63540
ctgttcattt gcatcacata catcttaaga gctcactctg aacctggtac cttaataagc  63600
tctgtagaca gtataaagaa gaaaggaatc agacatggtg tctgacctca ggtgtctcat  63660
aatggagtag aagaggtaaa atatgggtca cactaactct actgctaaat aggaagtgct  63720
cgttgccttg agattgacaa aatttgataa gagttcagag gacattttct gtgaactggg  63780
ccttgaaaaa taggatatga gtaggagaag atgaagaagg aaggcattcc agctagagag  63840
aagagcacaa gcaaaagaat agataacctt gaaagtcatc atatgggata attcaagagt  63900
tcagtataat ggaagtataa gatgcataaa aataagtgta gtaggaaacg agtttgaaag  63960
tacagattgg ggtttgtcat agaaggcctt gaatttcagg ctgaggagtt ttaatattaa  64020
catttgtttt tgaacaaagg ggttaactga tcacatctgt gatttagaaa gaaaattcta  64080
gcaatagtgt agataagggt tgatggtaaa gtttggaggg tggtgaggca gagactggag  64140
acagggaggg catttaggat agaaagatga tgaagagatg atttagaaga gttgttttgg  64200
aaaaggagga gagagaaaat gttttagatg tgtcacagag ataaaatggg catggcatgg  64260
tgcaaggagg taaagcccaa tagctttgta aggtgctgag atagattgaa atcacagagt  64320
taagaagttt tagaatcagg attagtacca agacagcttg gctctagatc tcatacttaa  64380
ccattatggt ataatcctga gagggtgggt aacagcaata gtcagaggaa agaacccttt  64440
tatacatgat ggtacaggaa cagcactgtc ttccaacccc acagctgctc tttaacagaa  64500
ggtcagaaac tggggagaaa ttgtgtgtgt gtgtgtgtgt gtgtgtgtgt ctgtgtgtgt  64560
gtgtgtgtgc catttctgga actaaggatg ggaagtagat tagatgaggc cactgcagtg  64620
gagtctgcaa gttactagca ctcacccgtt ccaagaggcc ttaagggtgt tgacctgttc  64680
cctgggcatc accacattct acaaatttat gttcctctga gagaataggg tgattcaatt  64740
tcactgtgct tgaaggttac ttttggggtt catgtttgtt tgttctaact ctatgctaat  64800
gatctgccaa ctgtttgtca ctttctctaa cccttaggat gtctaaactg atctgttggg  64860
aaatgtgtag catttacagg atggtaggat ttgtaacatg cgatcacagg gctgtctata  64920
tagagtcctt gggaagggga gagaagagta tttctgttac aaatgcagat tcctagggcc  64980
ctcctcaaac ttactgaggt tcaaggattg atatttataa taagcacata tccattttca  65040
ataagcatga aagtttcata ccctctttta atgtttgaaa tcctcaaata aattagtcat  65100
tgatgccaga gtattacata attatggtac agaatgtgtt tctctgaatg acactttctc  65160
ccagagattc tgatatatat tcctctgcac tcaccctgtt tgataattac cagtatatgg  65220
accatttacc tgaagaataa gagtagggtt ttctactatt gttgaaaatg ttctcgactc  65280
ttaacaactt gtgtgtgact gtaacaagat cacacagggt aaacagtatt agcttattca  65340
accactggct gaagaaattt aggaaagtga acacattttt ctttacattt ctctttgttc  65400
```

```
tgtgagcctt ttatgctgga atagttttca ctgcaggctg ttattgtctg cccccagagg  65460
agggagttga cctagcgatg gtaactggag agtgtttttt gaaacctctt tcctaggttg  65520
gttgccaatg gcatctttgg aacagtgtcc ttcactttag tccctcaggg accagtgtga  65580
gaatgggaac tttatgatct ggagctggtt aagtgaagtc caaaaataat taggaaagtg  65640
tttccttccc tgggaatgag ttcagtagga atctcaatat attgtagagc acgaaggact  65700
cagcatcagg catttgcaaa ggattcttcc agttgcctgt gttacagagg acacagttgg  65760
aatttccttt tagtgttgag gggagatgtg tacatgattg tgagatgact caccctttt   65820
gcttagatgg ttccactttc attgtggaca gactctttgg agggccagtt tggcatgcac  65880
gtgtgtgttc attccatcct ggagcattct ttatgagaaa gccatttgtt gagtggtttg  65940
ccattttgtt ttacagccac tctgtgggct atgaaatggt catctggccg ctttatttgt  66000
ccctaaaaaa gcagtttttt cctttcttat cttcaaggct gccaagcagc agaaagagta  66060
actcagggaa gccatgtgat agccttttat ctgtctgttc agaaactgat gatgtatcgg  66120
atttgataat tcatgaaatg tgaggtttac tggtttgcat ttgcctcaaa atgggcatgc  66180
aatattttgt caggtaacat aatagataat tggcattgct ttattgaagt gaattaattc  66240
aataagccta taagtgcctg acatgtgcca ggcactgtgc taggcattct gttaatagat  66300
gagacaaatc tctgtctttt aggtgttttt agtcaaccag gggagacaaa acacctttaa  66360
aaagacaaaa acacttttta aattgctatt ttaaaaaaaa ttcatagtgt acgtgaatat  66420
aaggtgctga atatgtgatt gattctgagg gaaaagagtg ataagggaaa attctcagag  66480
aaactcaagc tgagggaaga aaaggacccc agacagaggg actaggctag agctatgcta  66540
ctacattgca ttaaggggaa tggcacatac ttcactgttg cttcagcaga gagcaggcct  66600
gtgttaggtt acaaagggcc ttggatgaca tcctgtgggg ttttaaaatt ttatttaatt  66660
tttaattgac aaaatataat tatatatttc agtggggtac aatgtgatgt tatgatgtag  66720
gtatgcaatg tagaatgatt aaatcaagct aatttgcata tttatcactt cacatactta  66780
tggtttggtt acaacattta aaatttattc ttaacaattt tgaaatagac aacacattat  66840
tatcaactat agtcaccatg ttgtgcagat ttcaaaaact tctaacaaaa actttttgcc  66900
cttcgaagat attgaacttt gtcttatgaa catagtctta gaaggattta aaaaataatt  66960
tgctattcac tgagtacttc ttatgtacac tgtgcatgaa atgagtatta ctttttctaa  67020
tattagtttt cttgattgag gcttggcaat tattagtttg tatgcctgta gaaggattat  67080
aaacagaggt gtatcccagt aggatttgca ttttagaatg atgactgcga gtaaaataca  67140
gagaagtaaa accaaagata gtgggatcat tcaggagtct gtttcctaca ctgaacagta  67200
gttgagcaaa aaaaggatgg gcagaatgtg ttgcttctgg gtactgcaaa ttcatggcac  67260
ttgaatgaac aagtttaagc cttttattgg ctctttgtgc atatcttcaa catgtatgac  67320
tacaaagaga ccacacggtt ttgttgttgt tgttgttgtt gttgttgttg ttgttttatc  67380
tgaggtggag tttcactctt cttgcccagg ctggagtgca atggctcgaa tttggctcac  67440
tgcaacctcc gcctcctggg ttcaagcgat tctcctgcct aagcctcccg agtagctgga  67500
attagaatca tgtgccacca ctcccagcta attttgtatt tttagtagag acagggtttc  67560
catgttggtc gggctggtct tgaactccca acttcaggtg atcctcccgc ctcagcctcc  67620
caaagtactg ggattacagg tatgagccac cacggccggc ccacacggta tttttgaaag  67680
aacagtgagc ttggaattag aacactagtg tctgggccct ggtgctactg cataagtaat  67740
```

-continued

```
tatgaatcca tagccatctt gttgctcttc ttctctaagc cttggtttct ttagctataa  67800
aatggaaagt tgaaactttc tagctacttc tttgagttat gagtaacaag ttaggtaata  67860
cacttgaagg agaatgtgct atacaaatac tggttcttaa gacagctgtt gttaatgtac  67920
tgagtattat gcttacctca cagggttgtt gtgagcatca aatgggataa tggatttgaa  67980
agcattttgt ttaaagtgtg attcaaatgt taagaattag taaaaatagt aaaagagaac  68040
aattcattct ccatccagat gttccgtccc cacttatgtg ctcattcaga gttgtacaga  68100
aaaacctcca cgtaattttc acagactgga gttccacatg taacagaatc atatgggacc  68160
aaaaaagctc tctattgact tctttcctgc catattttgg ctctgggacc aacaagacac  68220
ctatttttca tgagctgcct gccaccaact ttgggctcac atctagttct gttgcccatg  68280
tgcatgctga atttgggccc atgtccccag atctaacatg aaactcaagt ttccttctgt  68340
tcaaactgtc caggcataat agtcttgaag tgtgatgccc aggagagctg tagatttttc  68400
actgtccaaa aatcaacatg aaaccagatg tatctgtaaa tctagtttca tgccactttg  68460
tagtcaatgg aaatacacta gcaggcagac aagaccagag tttactattt ccagcggaat  68520
taatagccac atggaaactt tgcctttggt atctgtgaga tggaagataa aggtgagaaa  68580
tcaaagcagt tcccacctca tcctctaaat tccaacataa agaggccttg aatatccttc  68640
tatcttattg tatatttcat taacagaagt atgttcctaa ttacttagtc attctatctc  68700
cattctcctt tgttttaact tcagtggtgc caggttaaga tgctctggct ttcagctttc  68760
atggagcatg gcatgttttt aaacttattt ttaaggacag gtatgttggg aagatcctag  68820
ttcctcatct ctttgctcct ggcaaggaaa tttagaattg cctaaagaaa agctgtattg  68880
gccaacataa taataaatca gtattagtga atctaaagcg tattggagaa ctttgtaaca  68940
tgagttgaaa ttcagacctg caatgaagtt tttttaaaag atttaaaatt gaaataataa  69000
aaaaaaagtt aaaaacaagt aaaacatatc agtagttaat cattctacca aaatttggtt  69060
ttacgtttgc atatttaacc atttttattt tctgtatttg tccatgaaca tgtgtttttg  69120
tatattgttt atattaaaca tggttttaat catggcttat ttcttttatg ttttacttct  69180
tttcctttga cataaaatat tgtattttta aaattttaac tgcttcttgg tataccattc  69240
caatataggt ggctacatag attgaagtta aaactaatta caatcagaga aaattaacaa  69300
ttcatccctt cagtctcatt agtcacaagt taaatactca atagccacat gtatctagtt  69360
gctaccgttt tgaatagaac agatataaga cattttcatc aacacagaaa attcagttgg  69420
aaagtattgc cctggagtaa atgtgccata ctgtactaaa tcatttttct cttgttggac  69480
atctaagtta tttcttattt ttttaatatt ttatataact tgacggtgaa tatacatacg  69540
tacatagcta tttgctttgc tgaattattt cttagaatca atttcaaaag tggagttatc  69600
aggtcaaaga gcctgagaag attttttgga acctgtagtg tattgccata gtcctttcac  69660
aaaagtttat gtcaacttaa agtacttcta gcagcaaatg attgtactaa tttcgctgca  69720
atctcaacaa cactggacat tataagtttt tattctaccc tattttccat taaaagataa  69780
cttatgcttg attgactttg cattttattt tattattaat aatgttgtgg tttccttttt  69840
ctgattttat ttttagttaa ggtatccttt aattttaacc tgatattttt ctctaaaaat  69900
tattctaaga aaagacaaag gtgatgtcaa atatatcctg agttttcatt ttttcttgca  69960
tggaatttgt atatttgcac ctttgcccat ttatattatg atttcttagt gtcttcccta  70020
tcaattttaa tgaagatttc atatatatca atttttccac aaatataatc tttttaaaaa  70080
tatatttttt ccacgatata attctaatgt attctccgaa atgttggaaa aacttaagta  70140
```

```
gtcatcaaag catttgaaga ttttttaaag gttgttttta taccagtctt aaatgttaat  70200
ttaagggtcg taaaaagagg tgaaaattaa atcatttttc agtaaggggt aagaccattt  70260
aactcttgga aaatacagga aacatgtaga tttctagagg ccaagaagga ggtagggatt  70320
aattattttg taactgcccc caaccttcta acctataatg aaagaaccac tgaaggccct  70380
taaatatttt taggcttaat tggctgtcct tgtacttagg gcacatctaa aaatcctgag  70440
gcaaccactt aagagaacat gcttttgtta attcacaggg agctgtccta agagtgtcca  70500
gaatcctctg tagtcttggg cctggtgctt gagagaccca aaggaaaggt caatggaatt  70560
gcagcttagt gttagagttt tcatggatca cactaattag ttaatgtcat aaaggtctct  70620
ctcctgttat gggaaaaagc agcaaatagg aacttctggt agggtgctta aagttggttt  70680
gatatttttc ttagtaattt taactaataa aagtaataca tgcttatggt agaatgataa  70740
acctgaacga aaaggtatga aaatgtagaa gttctcctac ttatgacctc accccttctt  70800
tgcactccca gtttcactcc tcagagggta accatagtga ctagtttctt gtgtttggtt  70860
cctgagattt tctgtgcata tatattgtta gatatatgca tattatattt tcaaaattcc  70920
tatcacatga caactactgt tctgtaactt aatttcttca cttaattaat agaccttata  70980
tatgcttttc catatcaata tatatagatc tatataagtt ttcctaaagg ttgcacaatt  71040
ttcaactgta tggctgtctt gtaatttact ttttgtttcg cctactaatg gatatttcat  71100
gttttcataa ctcttttgat attaaaagta gtgctgcaat taacatcctt gagaggcagt  71160
atatatggtg tttaaggtga atggctctgg agccagacta ctttggactg aatattgatg  71220
ccactaattc cttgctgtat gaccttaggc aagttgctta atttctttgc ctcagtgtcc  71280
ttgtgtgaaa aaatggaggc aataatggtc actatccagt agagttttta tgaggattta  71340
ataagttaat aatgcacatt aagaacttag ttatttttag attaagtagt gaaggactat  71400
ataattgtta gtataattgt atacctttat tagcatactt ttgcatgtat agcaataaga  71460
caaattctta gatgtttaac agttggacat aaggagtgta cacattttca gtactggtag  71520
atgttacctt ttccctgcca aaaattgcaa atatttgata ttaactttta aaatcttagt  71580
aaatctgata agtataaata acaatttatg atcattttaa gttgcctttc ttaattttgt  71640
gtgaaaatga gtatcttttc acatgttttt tggccattta tgtttctttc catgtgaact  71700
aactgttctt ggccgttgcc tattttttgt tcctgttact atatggcttt tcatctgttt  71760
ctcgttgggt tatggagctc tttgtatata aaaggattta gcctcttgtt atatgtgtga  71820
caaatacttt ttccaattta tatttcaact ttgcttatgt tttcctattc atcagtctaa  71880
aattatgtag ttaaattcat cattgttttt tcttacggct ttggagtttg gagatcatgc  71940
ttcaaaggtc tttctaggtg gggttgattt aaatcaagta ctggaagtat ttttgccaaa  72000
aagactcatg aattatagat gttagagcta aaagggacct tagagatttg ctagttcaac  72060
ctccttttct tcataccttt ttaattttttc tctgcagatg aaaagaagtt tagtcccaaa  72120
gaaagaaagg actctaaagg ttctccagta agctaatggc aaaaatgtag actggaactt  72180
ctagctcctg atgggtattt cagtgatcat tcaatttaac cagatggttt cacaaaagga  72240
gctttctact aaaaaataaa atacatattt aagcaactca gataaatatt ttttatttat  72300
cagattaatt tttacttaga gattcatcag catatgtact atatatgtac aaatcaccta  72360
tgtgttttgg atatttagtt gaacaaatgt gcaaatattt taaccaaagg agcatatcta  72420
ttttcatttt actttcttaa tggttttagt tatgaatgtg aaatgtgtac ttaccttaac  72480
```

-continued

```
agaaattaag tagatttttg gtctgacata tatgagaact gaaaagcatt ggcttggctg  72540
ctaactgcat tctcatcttt ctttccctgc tttggcaaag tctgggatta aatctaatac  72600
cttttaaact gtttgggact tcagccagag tgacctgtct tgaattcaga actgtgcaga  72660
tcattcccca ttctaaggtc ctctcatggc tcctcattgc ctgtaggatg agatccaagt  72720
accttagcat agcttacgca ctgcagtcac ttgacctcta gcacctatgc agtcttccag  72780
tcttatttcc acattccttt gcacatgctg tttccccatg tggggcaact tttttcttgc  72840
ctgtctgcct gcctaagcca acttaaataa acatgatttc tgtaacttct gtgaagcctt  72900
ttccaatctc tccattccaa gacgaaggtg tttctatagg catgacttct ggaatggcag  72960
atcaaggatc tggtggaccc tctactcagt gaaacaacca tttaactggt aaaaatgatt  73020
taactggtaa aaatgatcaa tcaaccattt aaaatcttca gaaaatatcc taagggcaca  73080
tagcaaaaag agaaatgttt attcaagaaa agctattaag cctcagtaaa aacagcaaga  73140
gtctatggca tttgagtcat gacctgttcc tattccttcc cttagctcca ttctacaggc  73200
aagtgcaacc aagaagacgt aggcttcctc tctttcaaaa tcttactcca tagttataat  73260
ttcaccctac aatggggcag gccacaagca tctctttccc cccccacccc agccctatat  73320
tacagaagca ctgttctagg aaggcatagc tgagaggatt ggagattcct tcctcaccca  73380
ctttctacat atgagggctt tgccccaggg atggtaaacc aagaatacag gggtcctgct  73440
tgtgcctgcc tcagctcatc tataaggtaa aacttccaca ctaggaaagg ctaattaaga  73500
ggactaggga acataccatt atccccaggg tccacttgta gaacagggga gttattctgg  73560
gagaagcagg tcactgcccc acttgtggaa caggggagtc actctgggag aagcagatca  73620
ccgtccctgc tcccaattct attgcagtga cagaagttct gtcccaggga aaggcattag  73680
gatggagaac tctatagttc tccctgaggt gactgacttt atttggaaca gagcatgaag  73740
aagcttatgc ctaagggcac tgtcaaaaat aatgcagatc ttggtggtaa gcaattaaga  73800
gtggattggt agctccatga taactagtag caacaagcaa aacagcagac caacatggag  73860
gataccagag aaccagacaa aggaatcact aagaagcgcc cttgtggaac tacactcact  73920
gctgggtgtg tggaaagtta tgcatgtgtg ctttactgta ccctctcaaa agcaacctaa  73980
acaggatgtg gcgtaggctc taaagcattc ctcaagccac acatggatcc atcagtaaaa  74040
tatggagggc ttaaggttaa aaaggcttaa gtacaatgtc tggccctaca ttttctacat  74100
gttatgccac cctgaccaag gggcaactcc tacaaagcca ggcataataa taaaatcata  74160
tttgtctctt ttggaatgga tgactgtgcc taaaactgtg ccctttgaaa agcaactaga  74220
gagataattt ctgaagtgtt tgtccctacc tgaatgcggg caaaattcta aactccctga  74280
agtgtgaaag tgttttccaa gtcacatgca catccagtag tggtaaaggg taaaaatcta  74340
actgactaag agggcttcac agcaacatta accaaaaagt ggtttatgta atctttgcct  74400
acctcataat tccctaggca ttctatgcta ttctgtactc agaaggctta aaagtcaggt  74460
tagggaaagg aggcctttga ggttactgtg cagaggcagt gctgggaaag gaatgaagtt  74520
caataaattt aggccatcat ggtttaaaga atggattatg tagataggaa ggataaagga  74580
aacccagagt caagaaaagt aaagcttttc attggtgcta tgccaaccca tatctgagcc  74640
tgaggcaaaa ggaaaaatgt gctccccaat atacatttat acaaaatatc aactaatttt  74700
atttgttgaa ctgaatttaa aaagtcaaca aaaattaaaa ataaaaaaat cgtgactata  74760
ttcttaataa gtggtttatg taaacccaga gttgaccaat gggatgccag tctcaaccat  74820
aaaaacaaac aaataatgtg agtagcaaca ccagaagttt caaagtgtca gggaaaccag  74880
```

```
tttcacagaa gtggttcagc caagtcacta aacaaagaaa tgactaagca aaaaacaaaa  74940
tgagtctcag agagggtcag gtcaatatcc agagttgtta caatatagta actaaaatat  75000
tgttttgaac taaaaatttt gaggcatgca aagaatgagg aaagtgtaac tcatacatgg  75060
tattatatga aaaaatcaac aaaaaactat ccatgaggaa acaaggatgt tgaacttaac  75120
taggcaaaaa ctttaaaaat cagctattta aacatattca aagaactgaa ggaactatgt  75180
ctaaaatact aaaataaagc gtaataacaa tttctcatca agtagagaat gctaataaag  75240
agatagaagt tatagaaaaa gaagaaaatg gaaaatctgg agttgaaaag tataactgaa  75300
atgaaaaata cactagaaaa ggtcacaaga agatataact tggcagaaga aacaatcagc  75360
aatttagaac atagatcaat atagattatt catttttaaa gatagaagga aaaaaagaat  75420
gaaccaaact gaagattccc aaagaaatgt aggacatctt aaaggcacat cattaggaga  75480
agaaaagaag aaaaagaaaa gagcagaaag aatatttttt aaaaatggat aaaatcttcc  75540
caaatttaat gaaaaacatc aatctacaca tcaaagaaga ttttttttta atttcaagga  75600
ggaaaatgta aagatattga tacttagata catcatagtc aaaatattgg agccaaatat  75660
aaagagaaaa ttttgaaatt agcaagagaa aaatgaaacg gaaccacaat aagattaaca  75720
actgattctc atcagaaata gcagagagca gaaggcagtg caatgccata ttctaaacat  75780
tgaaagaatg aaaaaactgt cagccaagaa tcatatattc aacaaaagta tctttaaagg  75840
taaaaatgaa atgaagacat tcctaggtaa acaaaggctg agaaaatttt ttgttagctg  75900
acatgccttg aaagaaatac taaaagcttc ctagacagta gcttgaatct gcatgaaaaa  75960
agcaattcca ataaagggaa atttgtaaat aataaaaagg tatcattata tattattttc  76020
cacttaactt acttaaaatc aatttcttaa agcactatct gtaaaaatgt attgttattt  76080
gataataaaa tgtaaaagag gggagtggga attaagctaa attggagtaa ggaaatggta  76140
tcatatggta aattgaattt acagaaagaa atgaaaaaaa ttaagtggca aatatgaaga  76200
ttaacaaaaa cttctataaa ttaattgtgt tctctttccc ttagcttctg taaaagacat  76260
aagactattc aaaatgacaa tagcttaaac gcattgtttt attggtaaca aatatagaca  76320
aattatgtac aacaattatt attatacaag gagagagaat ggagctatag aggattaaag  76380
tttttataac ctattggaac taagtcagta taaatctgat gtggattctg ttaatttaag  76440
atatatgtta gaagccccaa agtaatcact gagaaaatga tgcaaaaata cagttttaaa  76500
aagttaaaaa catagtttag cttatgtatg cctagtattc cattattttt tttttatac  76560
tttaagttct ggggtacatg tgcagaacgt gcaggtttgt tacataagta tacaagtgcc  76620
atggtagttt gcagatccca tcaacacgtc atctacatta ggtatttctc ctaatgctat  76680
ccctcccaca gtcccccacc cccctcgaca ggccctagtg tgtgatattc ccctccctgt  76740
gtccatgtgt tctcattgtt caactcccac ttacgagtga gaacatgcgg tattccgttt  76800
tctgttctgt gttagtttgc tgagaatgat ggtttccagc ttcatccatg tccctgcaga  76860
ggacatgaac tcatcctttt ttatggctgc atagtattcc atggtgtata tgtgccacat  76920
tttctttctg cttgttccta ggagaaagtg gctgaagctt ccagagagaa gctgagagta  76980
gtttaattct ttttgccata aacacggcaa cccagttttc tgcaagctgt gttagtttgc  77040
tctctccttg gttcatccat tcatttattc atagcttcca taaatgttta acaaacatta  77100
attaggggcc aagccatgtg ctaggcgcag gggataaaac tgtggacaaa acaagcccca  77160
gctactctta aggaactgat agacaaatgg accagcaaac aggctggtcc tgttttgaag  77220
```

```
gcaaagtgcc tggtgctcct gatctcatga gcacaaagca tttagcctaa atctcatcct  77280
cctaaggcct cagaaacaag gccttatttt aataactgca agtcagtcat ttgaagacta  77340
aatcatagaa tcctagaaaa ctagtactgg gagcaaaaca aaagaatggg atgagcatga  77400
aacatatatt cagaagttgt ggtgtgtagg tgtataagcc aagctctttt cttcacttgc  77460
ttgctaagtc acttagcttt tctgcctttt tctttgctct gtctggaaat tgagttaatg  77520
aaatatatct acatgataga gatattgaga tgattaaata agatgctgct gtcacccagt  77580
atgcccttac ctgctgtact tagaagtatc tgtaattcat tttctaaact ttttgtatga  77640
gtgcttcatg catgcccacc accatggaag ctaccttaag acagtgaggg cctttgttta  77700
acttgtttgt actgtatcct cagtctaatg gtgtctggct tatagtaggc accgaataca  77760
attttattga cagaatggat tataatgaat gtgaaggcat ttttaaattt atgaagtgtt  77820
gtgcatattg ttgttaattt taagctgttc agttaaagaa cccctaatcc aactctcttg  77880
agttttatag atatcataga agatatatct tcccttgaca cagaagcttt ccttgaagct  77940
tcccttgact catctatttg cctcacagag tgattgtgca gatcccacaa gataaattta  78000
tgtgaatgtg ctttatgtgt ttgaagcgct ccacaaatac gggtttttata agttgagaaa  78060
atagagtcag ggagaaaggt gactgatcca aggtcatgca gcgagttagt atcagaattt  78120
atgatggaat ttcaggctcc caatttccag tccagtatac taaggcagat tccagagaag  78180
aaacagtgga gagcaggcac tgacgaggga cgaagaaaag caggctccgt ctggctgcaa  78240
cttgtctctt catggcaaag agaaactagg acagtactat gccagagacc acatgataac  78300
tttgcagaat ggaaagagct tgtttaccaa attgaacact ttatctgtgt ttatctaaca  78360
atgacagttc caccagctcc ttaccagctc tcttttgcct agtttaacaa tataccaact  78420
atgacacatt ttccttctca gtttttattc tagattacat tttgttcaac ttcatcttaa  78480
tgtgtagtat agaaagagta aggtaagagt ataacaagtg gttattttcc atttctactg  78540
aggacagaga aataatctaa gggatttgta ttagatatga agaagttcat ggccgggaca  78600
tgagagatac tgtgatagaa tggatattgt taagtctttg gtagtttttg aggggaaaaa  78660
agagaaattt tttatttgtc tgataatagt ttagcaatgt cttaatttag gattcaaaag  78720
ttgttcaggg tccatcttgg ccttcaaatt aagatgcctg ttgagagata acgttgttgt  78780
tttcaaactc cattctgtga cttaagaatg agagaaggag gaagaaaaga ggagaaaatt  78840
ggagggaaaa gtgcccaggc agtgtcaagg ctagacactg gaaatttatc aatgaaagcc  78900
acatggtgga tgggaatcag atatgtgcat caattatttg tgttctaatc catagagaag  78960
taccgtataa tgcaccaaga tatgagatgc tttgaaagaa gaccatataa gtggagatgt  79020
gttcctattc tatctaggga tagagtcaga aagggcttca ttgaataagt ggcagcctct  79080
tgggctgaga cctgagttat gagatgatgt ggcaaaggag acagatgatt gggggcaagg  79140
tggggtcatt gaagttggag gcagtgacaa tataagcaaa gctacagggg catgaaacag  79200
caaggttaga ttagggaatt gcaacagggt ggtactgctg gaaggtcaca tggaaaagat  79260
tatgagagta ttgagataag aagctagaaa taagctttga atgccatcct agtgctttga  79320
atttgtatcc tgcaagccaa gtggttttca cttggtcatt taataaaatt gcagattctc  79380
aggtctcacc tgtaacttca gattcagaag agtctgtgct aactgaaggt ggaatcagtt  79440
tccatattgc taattagctc ctcagaggat tctaatatat cagtgagtta caaccactgc  79500
tgtaagccat aggtagttat tgaaagctgc tagggagagg agccacagaa gcagatgttt  79560
tagataggat ccctctgggg ttctgtgtaa tttatggact ggactggaga ggatcagaca  79620
```

-continued ggaaacagaa agacttgaat aaggcagttg cagttagttt ggaggcaaag attctctctc 79680
tctctctctc tctctctctc tctctctctc tctctgtgtg tgtgtgtgtg tgtgtgtgtg 79740
tgtgtgtaat tgtaggaact atttaggcag taaaattaac agatattagt cactgattga 79800
ctgattggat ggcagtgata ggtggggtgc attgagggaa ttgtattaca ttaagtccag 79860
gatgactcat ggttttctaa gttgagtcat tggggattgc cagccaatgt gagaaactat 79920
atcgtctaat agttgatctt ggagttagac ttgaattaaa atcttgaagc catcaattgc 79980
tgtatgtggt cttgggcaga acacttaagg tttctagacc tcagctcttt cttctataaa 80040
ataaggataa taatgcatac ctcatgcatt tgttgtaaag actaaatgag gttaaattat 80100
gtagagtgta gtatagtaac tagcacatac agtggcccag taaacgtcag ctgttattat 80160
tgtgctatat gttgtgatgt gtactggagt gagatggggt aggggatttt ttagtctctg 80220
acaatgactc ctctccccat gatcaaaatc agaaaatcag tctcttatgt gctgagaaga 80280
gagacacttc tcccaagtgt ttaaggctaa taccttgcct tgttttgcct tgggccagac 80340
ctcactacac atctgtttaa gagataaggg taagctctgt tcttggtgag tatctcagtg 80400
gggctgtttt tctagttctt gtagtttctt tgggccaaca tgaaatgtct aaccttggct 80460
tcttggttgt ggattctcgt caacatttca ctgctaccca agttgtgtct gctcacatga 80520
tgctatcttc cttcttttgg gtttccgaag ccctcagaca cttggctgaa cacttttttc 80580
acatttctta agctatatca tctgtgtttt ccctgccaca gacaaagtca caaaaggact 80640
ttaagatagg gtctttttcc ccccagggtt tttatacatt ttgagtaagg gcaagtggta 80700
aatgctgctt ttctgcctta accagtagtg tctgacagag gaggcagcat gatgattgca 80760
gagctcactg aactgaaagt cagatgcctt acccacctgg actctagtac caaggggaag 80820
atggagtggg atggggaaaa tggggataaa ttatcattta ttttgagtgt gccaggccct 80880
ttcccatgta ttgtctgatg catttgtcac aattctcttt gggtttgaaa tgtgattttc 80940
ttcattttat agataaggaa acttatggga agggagatta ggttcatctc gtgcccaact 81000
ttacatggct agtgatcaat aatagtgaga ttcaaactca ggtttctctg ttccaaaacc 81060
tttgcttttt catcttttga cactgtaact tattagaaga tgtctttgac tctgagtctc 81120
atttgcctca actgtaaaat ggagctctgt aacccttgct ctgtatgaca gtaaatctcc 81180
tgagaccaga tttatgatag gggacaagga tatttgtatc tttgggcccc taatgtattg 81240
aaagtgcctc tcagtgcctg gcacagagaa gggcactcaa taaatattta ctaatcattt 81300
tccagaaaga gggtagctcc ataatgagcg agattcattt tgatggctgc tgtagtgttt 81360
aatgttttta ccacctgtta aaatgatttt ggagtataga tggataactg atgatggttg 81420
ttatatagat tttttcatag gttgcctgtt ccaaattcta tgccctggaa gaagctaaat 81480
atccagaatt tgacaggaaa tattattcta caacagatcc ctggcataag aacagtaaca 81540
cctctgttct attctcagac ttgcctctga ataactgttt ctcctggtca attctctgtc 81600
tctatctggg attgaaactt ccccctggac aatgagggag ttgaactagt ttagtggggt 81660
tcagccttga gtggccatta caattatttg gggattgttg aaaaaaattg gatgcccaga 81720
tttttgtcgt tgttgttgtt gtttgttttt taattatact ttaagttctg ggatacatat 81780
gcagaatgtg caggttggct acataggtat acacgtgcca tggtggtttg ctgcacccat 81840
caacccgtca tctatattag gtatttctcc tgatgctatc cctccctagc cccctagccc 81900
cagacaggcc atagtgtgtg atgttcccct ccctgagtct atctgttctc attgttcaac 81960

```
tcccacttat gagtgagaac atgtggtgtt tggttttctg ttcctgtgtt agtttgctga  82020
gaatgatggt ttccagcttc atctgtgttc ctgcaaagga catgaactca tcctttttata  82080
tggttgccta atatttcatg gtgtattgaa ctgcttaccc cagttcaatc aaataagaat  82140
acagaatgtt gagaggagca tcagtatttt aagaaggcca cctagtgagt tcaatgtgca  82200
accaaggatg agaaacactg aactagatga ttggtaaggg ccatccaact ttgatagtcg  82260
acaagagaca atgctataga gtatggtgga cagagcatgg gctttagagt tagccaggca  82320
tgcattcaga ccctggctct gttacttact agttgtgtga tcttgaagaa atcaaaatgg  82380
agatacactt tgtccctggc agtaatagtt gtggggatta agcacctttg ccagtgctta  82440
ggacataata aacccccagt aaatagcttc tttagtatca gaagttcaga tggaagatgt  82500
gagaaaaata ttggttcagt aagatttaac atgtagatta aaatcaagta tttaaaaaaa  82560
ttttcctgtt tctttagcaa tggattccag aaacataatg tggaaatagc tctgagtcct  82620
aagatttgat gacattgcag aaagaaatct ggctagttgt cccatggctg attggctatg  82680
atggctaaga agccattgga aaaaaaaatt ggctcacaga agacagcaga tgtggcttgg  82740
gaaatgcaag gacatgactc taataaggat ttgtcccatt tatgagagtg attccaggag  82800
aaaaggacag atttgtattg tcagtgggat atgctgttaa aaaacacttt tgctaccacc  82860
actccagctg tcttggcatg tttgttggtg atgtaagcta cagaaaatgg aaatcaccaa  82920
aagggctata gcagcctgat gcatagtgac aagtaattgt tctattcatg gttatgtgtt  82980
gtacagagca cttgctgcat gtcaggtttg aggtttgagt atgcattagg gccatggata  83040
cccccatctt ctctctaagt agatttcaaa gtaaatattt gatgagtatg taaaatattt  83100
agtttggtca gtcataggac tgagaacgtg gtgggggtta cctcctagta tctgcaggca  83160
aaaaaacttt tttcttccta tagcaattgc catctcagcc ccttttgcag cgtttctctt  83220
gctacacttt gcattaacca tctgtgcact tgtcttagcc tcaaacaggc catgaaagct  83280
ccttgaggat aggggctatg tctttttcat ctttatatat gcatcattta gcagagctgc  83340
tcctttataa tgtactaatt actgaatgaa gggatccata gatgaataaa tgaatgcaaa  83400
gtaggagtga cctctcttct gtctttcttc atgatgggga ttagtgtgtg tgtataaggg  83460
aataatcgtg tcacataaaa tataacctta cttagaaggc aagacttcca gaatggtgga  83520
atgagaacca acccccgccc ccataaattc accctttcat gaaagcaatg aaaacactag  83580
gaaacgttgt gaaaattaac ttttccagaa ctctgggaag gaaacaaagg tttccaacaa  83640
tctgagaaga atgtattcaa gaaaaacttc ggtaagttct ctgatcacag tggaaataat  83700
aaacaattag taatagaagg atatttggga aattcaccat ttgtagaaca taaacagtgg  83760
atcaaagaag aaatcataag ggaaatgaga aaatactttg agattaatga aaatgaaaat  83820
acattatacc gaaacttaca ggatacagcc aagctaaagc agtacttaaa gggtaattta  83880
taactgtgaa tgcctacatc aacaaagaca aatgatctca aatcaagaac ctaactttcc  83940
accttaggaa actaggaaag gaacagcaaa ctacaaagaa agaaggaaga aagattaata  84000
aagactagaa gggaaataaa tgaaatatag aatagaaaaa cactagaatc aatgaaatta  84060
aaaattgttt ctttgaagag atcaacaaaa ttgaaaaaac tttagtcaga ttgaataaga  84120
aaaaaaagag agaagattca aattatcaaa atgagcagtg aaactggggc catcactacg  84180
taccttaaaa agaattctca aaggattaaa aggaaatacc attgcattag tttattctca  84240
tacagctata aaaacaacta cctgagactg ggtgtttatg aagaaaagcg ctttaattga  84300
ctcatagttc cacaggctgt acaggaggca tggatggtga agcctcaaga aacttacaat  84360
```

caggtggaag gctaaggggc atgaaagaca tgtcttcaca caatggcagg agagagagag 84420
agagcaaagg gggaagtgcc acaaactttt aaaccatcag atcttatgac aactcactca 84480
ctacaatgag aacagcaagg agaaaatctg cccacgtgat ccagttacct cctacgaggt 84540
cccttcccca acactggaaa ttacaattca acgtgagatt tgggtgggga cacagagcaa 84600
aaccatatca accatactgt atgccaaaaa cttagatgat ctagatgaaa tggacaaata 84660
ctcagagaaa cacaaactat ctgaagtgtc tgaagtgacc agtgaagaaa cagaaaatct 84720
gagtagtcct gtaacaagtc ttgtaacaaa actggattaa taattaagaa acttcccaca 84780
aataaaaacc caggttcaga tgtcttcact ggtgaatatt atcaaatatt taaggaaaat 84840
ttaatccttc acaaattctt tcaaaaattg gaagaggctg gaacccttcc cttcccaact 84900
aattctgcac agtcagcatt accctgatgc caaaaccaaa gatatgacac aaaaataaaa 84960
ctgcaggcta atatcacatt tgaatataga taactttcta aaaatcttaa caaaatgcta 85020
gcaaactgaa ttcaacaaca aataaaaagg tttataaagg gtgaccaggt aggatttatc 85080
tctgcaatgt aaattaatat tcaaaaagct aagaatagga ggaaactttc ttaactttgt 85140
aatggacatc tctgaaaaac acacagctaa catcatactt agtagtgaaa gactgaaatt 85200
tttccttgta agatcaggaa caagacaagg atgactgctg tcaccatttc aatttaccat 85260
tgtattgtag gtttattgta ggctcaagtc aagcaaaaaa aaaaaaaaaa gtaaaagaca 85320
cccatattgg aaaggaagag gtgaaattat ctatattcac agatgacatg atcttataca 85380
aagaaaaccc ctaaagaatc catgacaaac tattaaaatg agtaaacgag ttcagcaagg 85440
tttcagaata caagattaat gtgcaaaaat caattgtatt tctgtgcact agcaatgaac 85500
aatctgaaaa tgaaattaag agaacagttc actcacaata tcatcaaaat accagaatac 85560
ttaaaaataa atttaacaaa agaagtgtaa gacttgtatg ctacaaaccg taaaacactg 85620
tggaaagtaa ttaaaaatct aaataaatag aaaaacattc cttgttcatg tgccagagga 85680
ctcaatattg tcaagatgga aatactcccc aaaggttgaa ggaaatccct gtcaaaatcc 85740
tggctgtttt cttagcagaa aatgaaaatc tgaccctaaa attaatattt aaatacatag 85800
aatctaggat agccaaaata atattgagaa agaaaaacaa agtcagtgta cccacgcttc 85860
ctgattccaa accttactac aaagcagtgg taatcaagag cgtatggtat tggcatacgt 85920
acaaacagat caataaatgg aatactattg agaatccaaa aattaactct tacatttaag 85980
ggcaattgat cttcaaaagt gttgttaaga caatttaatg aggaaagaat agtcttttca 86040
ataaattgta ctggaaaaat tggatatcca catgaaaata aaagatgttg gaccacttca 86100
aacctgcaaa aaaaaaaaaa aatgatctaa tggtgtatca tggatctaaa tgctatagag 86160
ctaagatgat aaatctcaga agaaaatatc agagtaaatc tttatgacct tgaagtaggc 86220
aatgtttttt tggctgtaac accagaagca caagtagtaa gagaaaaaaa aaatggactt 86280
catcagattt gaaatttttg tgctgcaaat gatgccatca agaaagtgaa aatctcaccc 86340
acagaatgag agaaagtatt tgcaaatcat atatctgata agggtattga atttagaata 86400
tataaagaac tcttgcaact caatataaaa agacaaccca attttaaaat gggcaaagta 86460
tttgaatata aatttcttga tagaagatat acaaatttaa aactgctcaa cttcattagt 86520
cattagggaa atgcagatca aaaccaaatt gagataccgg tttacaccta ttaggatggc 86580
tatagtgaaa aagaacaaat aacaagtatt ggctttaatg tggaggaacc ttatacattg 86640
gtggtaaaat gtaaagtcgt gcagcccttt ggaaaacagt ctgaaagtct ttaaaaattt 86700

-continued

```
actatttgtt atttggtttt tcttcacttt taatttaggt tcagaggtac atatgcaggt  86760
ttgctatata gctaaattat gtgtcacagg ggtttagtgt acacattatt tcatcaccca  86820
ggtaataagc atggtaccca ataggtagtt tttggatctt caccctcctc ctaacctcca  86880
ccatcaagta ggccctggtg cctcttgctc tcttctttgt gttcatatgt actcaatatt  86940
tagcttccac ttatcagtga gaatatgcgg tatttggttt tctgttcctg ctttagtttg  87000
cttaggatat tggcctccag attcatccac gttgctgcaa aggacatgat ctcattcttt  87060
ttgcatagtg tactatggtg tacatgtatc aaaaatgtta ctgtttgacc tagtaattct  87120
attccaatat aactactcaa gagaaatgaa aacatgtcca cacaaaaact tgtacacaaa  87180
tgttcattgc agcattattt ataatagcca aagagtggaa gacaaatgtc ttccaaatgt  87240
gggctccaaa tgtccaccaa ctgataaatg gaaaaacaaa atgtggtata tccacgccat  87300
ggtttatctg tcaataataa gaaatgaagt aatgatacat gctacaatga accttgaaaa  87360
tattatgcta ggtgagagaa gcaactcaca aaagaccaca ctgtatgatt ttatttatat  87420
taaatgtcca taaaagaaaa atatttagag atagaaagga aattagtgtt tccagggtct  87480
gggaggagat ggtataagca atggctgcta atgggtacag gatttctttt tggggtgata  87540
taattgctct aaaattagtt tgaggtaata gatgtgaata tgctaaaatg ggtgaatttt  87600
ataatatgtg aaatataact cagtaagccc attaaaaaca acctaattaa attaaaagca  87660
agctataaca gaaatattat atagccttgg cagtttagaa tagtgggaaa atatggagtt  87720
ggggcaggga aatagtcgca agtataattc tggttttgtc actactagtg tatggacttg  87780
gatgagtcat ttcctttctc taagtctcag tttgcatata tgcaaaatag aggtaatgat  87840
acctacctca gtggtagctt ttcaaaacct tgttctccct catctctcct ctacaacttt  87900
ctcgtaagat tattacagta ataaccattt attaagcact gtgtcagcaa tggtgtggga  87960
ccacaacttc actgaatcct cattgcaatc ttgtggggtc tgtatttctt tgcctgtttt  88020
acatgtaaag aaattgacgt caaaagagtt gttcaaggtc attctgttag caagtggcag  88080
agatggacat gaaaactaga tgttctacct atatgtcttt ccacttcaac taaagaattt  88140
attaaagaga attaaaaagc tatgaactac ttttaatagt aaacattgct gtcctcgtga  88200
atgaacacac actaaatttc aaatctcacg atggcaggga ataaagatgc tacctgtctt  88260
aagccattac ttcaccaact tctccaccaa aatattcctt gtaaccacaa ataagtaagt  88320
acaatagatc tataaggaga gaataattga gaactctctg attttatctt aaaagtcatg  88380
tagggatgtc atgttccaca atgtaattaa taaaatatat tttgttacta aacataagga  88440
aaaattttat gttcaacata aagatgtttg gtggttgcct caacctcttt tagtttgaaa  88500
agtaggtatg tatgagaaag atacgtgttt acatgtctac ccttgccctc tctgtctctt  88560
cccctctctc tctctctctc cctccctccc cacccccctct gccctacacc ccccaacccc  88620
cacatgtatt tacctttctc taaaagctct gcataaccaa gaaaaatggt ctttttttatt  88680
tttaggatgt tagatatttc attttcttat ggtaagacaa aagattaagg caaccaagac  88740
ttacaatgta tctaccgtgt ggcaggcacg gaggcaaggg cttttacatg tgttatttaa  88800
tgtaattgta attctcacaa aagccgtcta gagttgaaaa tatttccagc tctaattgag  88860
gcaaatggag cacagagagc cttaattatt tcacccaaag ttcagtggta gaggcaggat  88920
tccaacccag gtctggtggg ctccaaagcc ttgttggttt gccattcctc tcgctaacaa  88980
atgaaactgg tctgtgactt ttgcatttca ccccacttcc acagtcactg gtgggactta  89040
tttaaattaa tcagatcctt caaagtatcc ccaagtcctc ctttaaaaag aaagttaggg  89100
```

ggcaggggga ggagcagagg agaggagata aaaaggaaag gagtcagaga gagagagaga 89160
gagagagaga gagagagaga gagagagaga cctggtggtc tcagctgggt gccaaggttt 89220
cctaagccca agttccccat ggttgagcct gcattagcag gccgacagct tctagtaatt 89280
cacttttatt taattaatag tgaaactgtt gaagaattgc aagtggtgtt ctagttcaga 89340
aaccttccat tctatggggc attgcttttg cctcagactc ataaaaccaa atgccctgcc 89400
tcaggataat aagtgaacat gtaacccacg agaggtaaga aaaaacacaa tgtcacgtgc 89460
aaattctgca cttgttctca aagcaaacct ctcctgtgtt tgcaattagg atgttatcta 89520
ggagcatatt caaaactttt gaggttttta ttttagtttt tcttttatta tgtgctgttt 89580
tagtaatatc aaagaataca tgtaatatat gttatatggc ataacaataa aattaatgtt 89640
tatgagccct gattaaagaa tcaacaacat taacatcatc attgcaacaa ccctattaga 89700
atggaagctc tgtgaaggca aggatttttt tctgttttgt tcactgctat atccccagga 89760
cctagaggag tgtcagccac ataataggag cttagtcaat attttttaaa taagagcata 89820
aatctactta tatcctcttt cctcttatca tcactcccag cctcccctca gaggtagcca 89880
ctatcctatt ttagggtttt aatattccct tgcattttgt taacttttca catgtgtatt 89940
cccaaataat atattgtttg cttttgcttc tttttgaact ttatataatg gaatcatatt 90000
gtatgtatcc aattgtgagt tatgactttt acgcaacatt agtatttgag attcaactat 90060
gtgtagctcg attccattcc ttttcattgc tgaattgtat tttattggat atgtgtgcca 90120
taaattattt ttctcctgtc agttgatgtt tatcttttat gcttttataa acaaaacggc 90180
tatgactgtt cctgcatgtg cctcctggta catatgtgcc caactttctc taggatataa 90240
gcctcagagg gggactgcac ttggaatttt catttccaga gcccaaagtt tagctcatga 90300
gtcagagctg caatgtgccc tttgtccaca ctaggtcagg atcagtggga gtgctaccca 90360
aaatattttc ctagtggggg aatcagggag aggcagagac tgacctagtg aggccaggag 90420
ttactatctc aggtctctag tcaaaatggg ttgcaattag taaaagttca gattctgaat 90480
ccccttcatt atttatcttc ttcttcctcc tttacagtta tttttgttca aggtgcactt 90540
tattaaactc atacctaaca aacaaaactc taatgaatat tttgtctttc attgattgta 90600
aattcaatta gattctttga aaaaatttta actgtatttt cactttagca tggatgaaaa 90660
tttcgatttc tttaaaaaac atttttaata ataacacaat aaggtctacc ctcataacaa 90720
aatttaaggg cacaacacca tattgttaac tataggcaca atgttgtaca gcagatgtct 90780
agaatttttt tcttcatgct taactgaaac tttatagcca ttgaacggca acagtccatt 90840
tctatttctt aaaagtcctt tacaaaatga gctttctaca tgtttccatt ttgtttatct 90900
gataattttt tttcgttttt tattatactt taagttctgg gatacatgtg cagaatgtgc 90960
aggtttgtta cataggtata cacgtgccag ggtggcttgc cacacccatc aacccgtcat 91020
ctacattaga tattactcct aaagctattc cctccgcttg cccctcaccc atcactggcc 91080
ccagtgtgtg atgttccctg tcctgtgtcc aagtgttctc attgttcaac tcccacttat 91140
gagtgagaac atgtagtgtt tggttttctt ttcttgtgtc agtttgctga gaatgatggt 91200
ttccagcttc atccatgccc ctgcaaagga catgaactca tctttttata tggctgcata 91260
gtattccatg gtgtatatgt gccacatttt ctttatccag tctatcattg atgggcattt 91320
gggttggttc caagtctttg ctattgtgaa tagtgcctct gtaaacatac gtgtgcatgt 91380
gtctttatag caccatgatt tataatcctt tgggtatata cccagtattg ggatggctag 91440

-continued gtcaaatggt atttctagtt ctagatcctt gaggaattgc cacactgtct tccacaatgg 91500
ttgaactaag ttacaacccc accaacaatg taaaagcatt cctatttctc cacatcctct 91560
ccagcatctg ttgtattctg actttttaat gatcatgatt ctaactggca tgtgatagtc 91620
tctcattatg gttttgattt gcatttctct aatgaccagt gttgatgacc ttttttttat 91680
atgtttgttg gttgcataaa tgtcttcttt tgagaagtgc ctgttaattt ccttcaccca 91740
ctttttgatg ggttgtttt tttcttgtaa atttgtttaa gttccttgta cattctggat 91800
attagccttt tgtcagatgg atacattgca aaaattttct ctcattctgt aggttttctg 91860
ttcactctga tgataattta ttttgccgtg cagaagctct ttagtttaat tagattccat 91920
ttgtcaattt tggcttttgt tgccgttgct tttggtgttt tagtcatgaa gtctttgacc 91980
atacttatgt cttgaatagt attacctagg ttttcttcta gggatttaat ggttttaggt 92040
cttacgttta agactcatct tgatttaatt tttgtataag gtgtaaggaa ggggtccagg 92100
ttcagttttc tgcatatggc tagccagttt tcccaacacc atttattaaa gagggaatcc 92160
tttccccatt gcttgctttt gtcaggtttg tcaaagatca gatggttgta gatgtgtggt 92220
gttatttatg agacctctgt tctgttccat tggtctgtat atctgttttg gtaccagtat 92280
catgctgttt tggttactgt agccttgtag tatagtttga agtcaggtag cgtgatgcct 92340
ccagttttgc tctttttgct tagaattgtc ttggctatgg gggctcttta ttggttccat 92400
atgaaattta aagtagtttt ttctaattct gtgaggaaag tcattggtag cttgatggga 92460
ttagcattga atctgtaaat tactttgggc agtatggcca ttttcatgat aatgattctt 92520
cctagccttc agcatggaat ggttttccag ttatttttgt cctctcttat ttacttgagc 92580
agtggtttgc aattctccat gaagaggtcc ttcacatccc ttgtaagttg tattcctaca 92640
tattttattc tgtttgtagc aattgtgaat gggagttcac tcatgatttg gttctctgtt 92700
tgtctgttat tggtgtatag gaatgcttgt gattttcaca cactgatttt gtatcctgag 92760
actttgctga agttgctgat aagcttaagg tgattttgga ctgagacgat ggggttttct 92820
gaatatacag tcatgtcatc tgcaaacaga gacaatttga cttcctgttt tcctatttga 92880
ataccccttta ttgatttctc ttgcctgatt gccctggctg gaacttccaa tgctatgttg 92940
aataggagtg gtgagagacg gcatccttgt cttgtgctgg ttttcaaagg gaatgcttcc 93000
agtttttgcc cattcagtat gatattgggt ctgagtttgt cataaatagc tcttattttg 93060
agatatattt cattaatacc tagtttattg agagttttag catgaagggg tgttgaattt 93120
tgtcaaaggc cttttctgca tctattgaga taatcatatg gtttttgtca ttggttctgt 93180
tgatgtgatg gattatgttt actgatttgc gtatgttgaa ccagccttgc attccaggga 93240
tgaaacccac ttgatcatgg tggataagct ttttgatgtg ctgctggatt cggtttgcca 93300
gtattttatt gaggattttc gcattgatgt tcatcagggt tattgtcctg acattttctt 93360
tttttgttgt gtctctgcca ggttttggtg tcaggatgat gctggcccat aaaatgagtt 93420
agggaggatt ccttcttttt ctattgattg gaatagtttc agaaggaata gtaccagctc 93480
ctctttgtac ctctggtaga attcggctgt gaatccatct ggtcctggac attttctggt 93540
tggtaggcta ttaattactg cctcaatttc agaacttgtt attggtctat tcagggattt 93600
ggaggtctat ttaggcttgg gagggtatat gtgttcagga atttttctat ttcttctaga 93660
ttttctattt tatgtgcccc agaggtgttt atagtattct ctgatggtaa tttatatttc 93720
tatgggatga gtggtgatat actctttatc attttttatt gcatctatga ttcttctctc 93780
tcttcttttt tattagtctg gctagtggtc tatctacaaa atagatagac tgtttatctg 93840
atatttattt tgtaattatc taataataat catcattatc atcagcatca tcattgtcat 93900
ctcctttacc catacataca tttgtgtctt tcaaataata atcccatctt tgaagtacat 93960
cctcatctgt agcagtcttc actctgcttt cttatatcat ttactatctt attttataat 94020
tatttacttc ccgtctttct tctctaacag atagtatttt tttagggcca aggaaatatc 94080
tcgatcacca ctatatcccc agcatctacc cctgtgcctg gtccataggg ctagatgcta 94140
agagttgagt tgaaccaatc tacctaatct taaccttcag tagcacaaca tggtttgtca 94200
gtggttaaga atctacactt tggagtcaga ctcacccagg atggaatcct ggcattacca 94260
cttattatta atagatacat gaccttgaac aagttcactt aattgttctt agcatcagtt 94320
tcctcttctg tgatataggg atgatacaga gctacctggt aggttgttgg aataattaaa 94380
tgagatgata tgtatgaaat ggcctggcac atagagtgcc taaatacacg ttgttctgat 94440
tttatttgga ctgtttgtgt tagtaacaga aatcaaaaag gtggagaaag gagaaaggta 94500
cttgggaaaa ttttctattt cttctccatg tttcattcaa gactgaggaa gggggcacag 94560
tttttaccca aggaaacgac atttttagcc aaaggaatta tgatcttagc atttagctga 94620
attgtatatt ggaagtaagc tccttccttg tggaacttat ggccttgcta gccttggttt 94680
gttggaagtg ctcttgctgg ctttctagtt agggtaggga aaggaaggct tgtggggagt 94740
gaagataggc catgatatca agccactgag tgtgcaaatc agtagaactt ttcgattgct 94800
ttctgttgta cttgggactt gaataaaggc tgatatttgt gtcttgctgg taaagtgctt 94860
gtaaagtgag tgaaagtttt ctttgttctt gtcctgccag agctgttcac ttggggctga 94920
ggggaggata acctttcatg tttttatttt tttttattct gatgactgtg ctgagcattt 94980
gaacgaaatg gccattggtg gaaagtaaag gtgaatggtg agaagacaat aggataatgg 95040
aaactgtgat ggacttggag tcaaattctt ctgaacttct cctctccaag tcttacttct 95100
ttcatctgta caatgaatat taaaatgaga aaataagctt gtcttcacag agttattgtt 95160
aggtgttgaa atcacccgac acagcaaaca ggctcccatt agggctcatt ttccttcatt 95220
ccttagtaag gaagaagtac ttataaaata cagcagttgt gctcttgtga atgatagcat 95280
gggcagttgt catctctctg aggcagatta acccagaatg ccacttgagt tttgtttaat 95340
gcttaggcat aagacatagg aaagacaaaa gttgaccttt gggtagtaag aacaatgttc 95400
cattttgttc aaacttgaat ttttttacta taggagactg agaattaacc ttccatgaag 95460
gttttaggat ttgctttctg actcttctct ttcatatcca cctgaaagag cttgggcaca 95520
gatgttcttg gagaaaggta gttaaacaag gtgacttctg aagctccatc cttgcccaaa 95580
gaacttatga gtcccttagt ggccaagtat tttgatggta gtagcctaaa agatgtccag 95640
gatcaccgtg catcattttt tcaacagaag cctcaggcat agggattatg cttggtactt 95700
tatgttgtgg aatggaatcc ggcagatgtc catgtgatct agagaaacac ctaaggaaag 95760
tgaagaaatg ggggaaaaaa taacaagact tgtatgataa tactaatcac tatccttgtg 95820
tatttattcc aaggacattt tctccattat ctgatttata ttaccactca cagcagcagc 95880
tcaataggat gggagatatt atccctattt tatagatgag atttgaggct cgaggagcta 95940
aaacaagaaa catcaaattc ctttgatatt tggtctgatt ttgttatagt tctccctttg 96000
gatgaggtaa agtcacaaaa ctgggttcat atcatttaat tagtctgaaa atgttgcctg 96060
aacaccacct taagttagat atcttaacct caggtttcct actttcattg ctgcctctta 96120
tagacataga ctatgagatt ggctaatccc agagaacttc cctaatccct tggcaagatc 96180
caaaaaggct cagtcacacc ctactaccac catctttagg agaagtctca gaaaattcag 96240
cttcacacta actcacttga gcatcaaata atagtagttt atgcatgcag gttaatcctg 96300
aagacctcag acttcacttg cctatttctg ccattctatg acatgtgttg cattggtttt 96360
ttgtgtcttt ccagtttgga gactgccagg gaccatgttt tgccaattga ctattacttt 96420
ccaccccaga agacctgcct gatctgtgga gatgaagctt ctgggtgtca ctatggagct 96480
ctcacatgtg gaagctgcaa ggtcttcttc aaaagagccg ctgaaggtaa agggacatgc 96540
acatgcactt ctgtttccct ttctccttta ccttccagag agagacacta acctttcagg 96600
gcccaggatt ttatcatctc agaaacagag tcattggcaa ggccctatca aataacttag 96660
gagcctaagg aagcaaattt ttgcacttgc tagttccctg gtttcagcag ccttgtttgt 96720
acaggcaatg taggcagtga aggtggtccc agctggggct tggggctcag tgggtcctag 96780
aaatgaagga aaaattaatg atttgaaaag atttaatttc ctcccttctt gttttctact 96840
ctgctggcta gtaaaggaaa aatttgtcct tattagagag gttagaagtg gagaaacccc 96900
aactgagtcc ccagcctgtt ccttgggatg aatatgagac tgtttcttag caaaggcttc 96960
ctggcctcgg ccccagaaag agagtgttct cactcttcag cagactatca gtctctgcac 97020
ctgctccctc ctgttgctgc ctccttggga cctgtctttg cgttaatagt tcctaggtag 97080
gtaagaactc agagtgaaga aacacattta ttctcctctc cagagacctg acctcaaagc 97140
ctgtccatta gtccctaacc ttaatctaag gtagcatctt atatctggct aaattggttc 97200
aagccctagc tccttagttt tatttagctt agaacaactc atgtctgctc aacccctaaa 97260
ggtgctcagc ctacattctg cagtagaaac tcccatttc aggcctctta tatatgataa 97320
tgtctcttcc tctaaccacc cagggcttaa gcttcctgct tatccacttc actctccacc 97380
ctgtatcgag ggctttcttc tcaaaaggac attgatgagg agcccctaga gagagatttt 97440
gtgctctggg accagacccg ttgttaaacg ccagtattca cctctgcccc gactttcccc 97500
aaagaggtac ttcccgccaa ggcctttctc tttcctctca ctggctggaa gtgttgagtt 97560
ccatgtcaga accagaatag agaacctttc cttctataag ggctataaac cttgagaaca 97620
gtcttaaaga taggtatgta ggccacacca ttcaccacaa atgtactgat actcatcaga 97680
ggatggaaga agcaccagag agtttgaagc atctagagaa aaggtagaaa gagaatgccc 97740
tttaactgac ctcctcgatg atagtcaatc acaatgatga gtgttgattc atcattttgg 97800
ctgggtggca gaaatatcta taaaacagaa gctgccgtgt tgtttacttc cagtcctcgg 97860
ggcccacaag aaggcagcta tcatttggta ttactaaaaa catgccccat gttcagctca 97920
tacccccaaa tgacccactg ctactgttta tgctgggcta gcatgaagcc cagggcccta 97980
gtgtctaggt ctggtcagtg aggcctagag cagagcctaa agagcctgag agcagtgcct 98040
tcctttcttc agagtactca tgaaaggatg gctgtcagaa aaggaagtga ggaggggctc 98100
cagagacttc agaccacccc aacttcccca atgagaccct ggcacttccc cataacctct 98160
cactcagcgg gccctgtcta tagagcagaa aatgaaacag agcagtcatc tagaggtagt 98220
gtatcagcaa gcccaggcac cacagtaata gcaaccatat cagatgggaa aggagttcaa 98280
gtgaacaaac aagcaaattc aatagtcaga taggttagat tatacttgat gctgtttctg 98340
ggttttacaa atctgggtta ccaaattgtt attttcagaa aacagaggaa atgctctatc 98400
acattgtgaa agggaagatt ttactgtcgt atcatatatc ctacatggga gctttctgca 98460
gaagttagag ctgaaggagg gagacaggca gaagggcagc tggcagggct gcctgggagg 98520
agctctgcta taaggtggat cctgtgccat ttgagaacag ggaagaaagc aatgaagttg 98580
tggggaggga atcactcaac tcacagaaca tacagaaatc cagcaaggtt tcaaaatgct 98640
ctacacccta gagtctctta agttagggaa actctctgag ctcatggggc caaatgctct 98700
tgcctgcttg aaatatgaaa aatcaacaat ggattccttg caaaaccagg aaaagggaac 98760
cttctgagcc ccttggttat tttgaaatac ggaccataaa tttcagtcct gagccctttg 98820
aaggtaggag aaggtggttt agaaaacaca gacacagaca catacacaca caccccccaa 98880
aataaagcaa aaaaaaaaat actggtgttt tctttctccc cacatctgta aagttgttgg 98940
attgatttta ctgccatcgt tatccctatt tgaaggcagg gggctgtctt attacccaaa 99000
gaggacattt attgatttga ttatcttttt ccatttttac agtgcatcat ctttttcacc 99060
catatggcct ttctggaggt ggttctcaat ctggcttgtt gaagcatcaa attacacctg 99120
tcttagagag agtagaaaca caaatctttc tcttcctcat ttacttgttg tagtcagtta 99180
actcagactg tgtattcaga ctcttgatta tcacttaatt catagtttca gaaatctctg 99240
gaatgggcac aagtacagga cttaaaagcc tggaatctca gacagaaata tatttctagc 99300
tttgatggtt tataacacat gggactttta ggctgtcatt gatgcagggc tcagcacaga 99360
gtcagttgta atctggccag gttttgttgt tgaggaagag tgggaagggg gagtcctaca 99420
ttttctcctt gtcagtaata ttggagaatt ggggtgagag tgaagctggg cagggaaagg 99480
tctgcataga aaaaagggtc tggcgagaaa aaatcatgct actaagccat gagggtaaaa 99540
tgaccaagtt atggttgaca gaaacttggt catagtgtgt ggggggaggg taggggggtga 99600
gggcagagag aaagttggtc taagtctgtg ttgggggaca gtgcttggtg ggatgaactc 99660
tgggttagaa acaggcatgt agggaaatag ttggtttatg gtgtgggtag gatgaatggg 99720
gcggtgaaag ggaaggcatt ttgaatgcta agagaccagg aagtcaaagc aaagcaatac 99780
ccataaacag aggtaagggc tcagagaggt tttagttgta tagtcttggg taagaaattt 99840
ccccttttga acctcagttt tccttgactg taaaacaacg gacttgaact agatatttca 99900
aaatgtgctt ccaacttaga cattttgtga tcgttctaca aattacaaac ataatcatca 99960
tcatttcagc aaactcacgt gtatttatac ctgcatatgt ttttggtctt gctttcctag 100020
aagatgacta atccaagatc ctaatcaatt aaagaagcaa tcttcagatg gggatagagc 100080
cagctgagag agtgtactat gtatggagtg ggttaaaact caggactctg agatttttac 100140
cttgtgatca ttgctgggta acttcctttc ttttctattt ctcatctgga aaatcaggat 100200
atgaatcccc atctctacct cattatgttt caaagagggt taattaatcc atcatgtgca 100260
ttatgtgctc aagaatttac tatttttcag atattttcta gtaaaacgtt ggagattata 100320
tgtccatttg ttttgtacac atggagtgct gtttggtaca catcataaaa ttgaaactgt 100380
agtttacatt ctgaactcaa agaattacac catcctcact gatgtttaca ataggtccca 100440
atttagtttc tttggcaaat tttatgtaag tatggctttg attctctctc tcaccccagg 100500
tttttgttag ggaagaaatg caagtgaacc ctcattgaac tctttctgtc ctttaaatcc 100560
attctttccc acctcaactc atgtggaatt gaatgttacc tctagtttgg agtctagcag 100620
agagtttttg gtgcatatca gtgtcccctt cactccctga ctttttgagt aacatttccc 100680
agaggcaaat taactctgct aagaggatct gcttgcagct tcaacagagc cttcatcagg 100740
tatctttggc caaggagttg actgatcctg actttgcgag tcctagagat cttttcacaa 100800
aactcctctc atgtttctgt ctctggtttt cttaaaagtc gcagacagac tttagattta 100860
ggggttggtt aactttttgt aaagggccat gtagtaaata ttttaggctt tgtagatcat 100920
atggtctctg tgtcaactac tcagctctgc ctttgcagga tgaaagcagc catggataat 100980
acttgaacta atgggagtag ctgtgttcca ataaaacttt atgggcactg aaatttgaat 101040
ttcacttaat tttcacatat catttaatat tatttttctt tttaaccatt taaaaattta 101100
gaaatcattc ttatctcgtt gggcctcaca aaaacagatg gtagagtaga tttggtttat 101160
gggctgcagt ttgttgacct ctgctttaga taatcacttc tgtacttata aatctgcaaa 101220
ggttttatgt tttcccatct cttggtattt tagtagctct ctagattatc taatttaaaa 101280 atttttctc agtaggccaa agtttgcaca tcttgttagc acagaatgcc tggcctagtg 101340
gcttcttggc cctgagcctt ttactaaaca ggagaaaaac taaatgtcta gaaatgctag 101400
aagaggatac tattttgttt taatgatcta gtagatcact cctccttgca atacccagag 101460
gagaaactga aaatatttca agcattttct agacttctgt gttgtaaatg tgtggataac 101520
tatgaactat acatgaaagc acttttctgg atgacacata tattccagat ggcaaaaagg 101580
aagcactttg gggactctct ggtaccaagt atcatggaaa aattgtgtgt ctcatagaaa 101640
gtagatccca ggaagccagc tgagttgtgg atctgccata tattacctca tgattctgtc 101700
ttcgcacact cactggctta attctgggcc tccccataac acgactagac cacaggcttg 101760
cagaagaaat aatttagctc tgtaactcat tgcagttggt gcccacccaa gtctctgtca 101820
gtgcccaatt cgggagccat gccaagaatt tgccattgct gcttcgtagt ggccctgtgc 101880
ctgcttattt atagcctgtg cattttatga aacagagatt aataagaagt tgccatagta 101940
cttgcaccat tatgtaaata tctgcaatgc ttacatagcc tttgtcactt gcaagatctt 102000
ttgagtccac tgccttctgc taccatgcct taccaatttc ctagtccctt attattattt 102060
tttaatttat tatatttaac ttttgtgata catgttcaga atgtgcaggt ttcttatata 102120
ggtatacacg tgctgtggtg gtgtgctgaa accaacaacc cgtcatctgc attagttatt 102180
tattctaatg ctatccctcc cctagcccag tgtgtgatgt tcccctccct gtgtccatgt 102240
tttctcattg ttcaactccc acttatgagt gagaacatgc agtgtttggt tttctgttcc 102300
tgtgtttgtt ttctgagaat gatggtttcc agcttcatct atgtccctgg aaaggacatg 102360
aactcatcct ttttgatggc tgtatagtat tccatggtgt atatgtgcca cattttcttt 102420
atccagtcta tcattgatgg gcatttcggt tgattccaag tctgtgctat tgtgaatagt 102480
gctgcaataa acatacgtat gcatgtatct ttatagaaga atgatttata atcctttggg 102540
tgtataccca gtaatgggat tgctgggtca aatgatattt caggttctag atccttaagg 102600
aatctccaca ctgtctttca taatggttga actaatttac acccccacca ccaatgtaaa 102660
agcattccta tttcttcaca tcctctccat catctgttgt ttcctgactt cttaatgatc 102720
accattctaa ctggcatgac atggtatctc attgtggttt tgatttgcat ttctctaatg 102780
accagtgatg atgagctttt tttcatatgt ttgctggccg cataaatgtc ttcttttgag 102840
aagtgcctgt tcatatcctt cacccatttt ctgatgtggt tgttttttc ttgtaaatat 102900 gtttaagttc cttgtagatt ctggatatta gccctttgtc agatggatgg attgcaaaaa 102960
tttctctcat tctgtagctt ggttgttcac tctgatgcta gtttcttttg ctatgtagaa 103020
gctctttagt ttaattagat ttcatttgtc atttttggct tttgttgcca ttacttttgg 103080
tattttagtc atgaagactt tgcccattca ctattgctac aaagagaaca aaatacctag 103140
gaatacaact tacaagggat gtgaaggacc tcttcgagga gaactacaaa ccactgctca 103200
aggcaataag agaggacaca aacaaatgga aaaacattcc atgctcatgg ataggaagaa 103260
tcaatatcgt gacaattgcc atactgccca aagtaaatta tagattcggt gctatcccca 103320
ttaagctacc attgactttc ttcacagaat tagaaaatac tactttaagt ttcatatgga 103380
accaaaaaga gcccatatac cctagacaat tctaagcaaa aagaataaag ctagaggtat 103440
caagttacct gacttcaaac tacagtacaa ggctacagta acccttatca attttgtatt 103500
gcctgtccat tttctgcagc cagaagcttc ttcagtcctt taagggaatt tctgggtgac 103560
tatcaaactc tggtagttca tttttgcagt tgactgctat tgtgaggata agtgtcagac 103620
tcactctctc ttcagagata gaaattatgt attaattatc tggattctag acccacagca 103680
aggagcaaac tgctcctcaa aataactgaa ttcttcgaga agtcatcatt gtaaaacaat 103740
atcttcagtt atagtagcca tgtgtgcatg cttctggaaa ctgtttttca gattttcatc 103800
ttccttccct gtctcttcat agcaaggcag ctgctttcag ccttgtacag atgctagtga 103860
gctttgtacc tacaaacctg agaaaattga actgagattt ggaggtgaat gactcttgat 103920
aaagggaaca aggtttagaa ttatcagtcc ctttgctccc aggctgtgtt gtgactactt 103980
aggcactcca gtgaaatcac tattcctcct atctagacta atgcctgtcc ctgcagagca 104040
cctcatgaga acaggcctgg tagtaatatc ctcatgcatt cagtcagtaa atatttacgg 104100
agtgcttact acatgtagga tattgggctg acatactcaa ggtacagggc ttgcttccag 104160
gaggttatag tttattaatc ataaaagtgg cattttttt gagacggagt cttgctctgc 104220
ctgtcgccca gactggagtg cagtggcatg atctcggctc actgcaagct ccgcctccca 104280
ggttcatgcg attctcctgc ctcaccctcc cgaacagctg ggactacagg ggtgcaccac 104340
cacacctagc tattttttct tttatatata tatatatata tatatatata tatatatata 104400
tatatttttt tttttttttt tttttcagta gagacagagt ttcaccatat aggccaggct 104460
ggtctcgaac tcttgacttc gtgatccacc cacctcagcg tcccaaagtg ctgagattac 104520
aggtgtgaaa atgtgacaat ctttaaagct cttcagtgga tgaaaggcca ccctatctac 104580
tgtccatttg aactttgcaa ctatcttggt acagagtgag aagttattct cttggttttc 104640
catatgagta aactgaggct ttgccagttc atcagcaggt aataaataat gtatctggaa 104700
tttgaaccca ggtcttctgg ggtcaaaggc agcattcact ctgttccatc acagcagctc 104760
ctcaaataag ccaacataga aaccaagtac tatgcctagg caacaagaaa ggcagcaatg 104820
aagagcaaca gcagagtgaa atatgagaga aggaagttaa gaaagatgtt aagtactgtg 104880
gggagtaacc aagaaaccac caagtatcgc taacatcaca gggagcttgt cttcctaaga 104940
aaactccaag cacttaaaac agctggtagt tcatcagcaa ctctctttat tagatgtatg 105000
agggacatgt gggccatagt ccttctacca acttatatgc ttcaggggga agttctgatt 105060
ctgatgagac ccagcatggt cgcttttaat tcactgttgt cacacaacta tagaacagga 105120
agcacaactt aacacctgtg ctcatgagaa ttttgctcct tatgaccaag ctaaagaaag 105180
agcttagaca ggatgtgagg atataaatgt agattcatgg ttccttggct ctttggtttg 105240
agccttctca gcagagcatg ccacagagtg ttttccatgg ggccagtagc aagagaaatc 105300
catttccctc ctcctcgatg tcagaaaaca gagaatattg tctttcagga tagaattaaa 105360
aagtcataga ggcagcaact tgttttccta tattagggtt ttaaaattct gtttttcctt 105420
cctctcctga gtcacatcat tgtgtggatg gaccttgatt tcactgtggt atctggatgt 105480
gggccctgaa ggccatggac ttctaacagt tccttaagtt acagaagcac attcctatag 105540
gtcacaagct catttactta caggatggtt gattcagtca caggttattt catgaaaata 105600
cttaaaagat ttgcagtgtt caaaactgca ggatctttaa acactaaaac ttgaaggaag 105660

-continued ggaatttgga aatcaaaaaa tctggtcaaa ccgtttcatg gaaaagtaaa gtgaggctca 105720
gagagaggaa attactttcc tgggtttcta tagcatataa atggcagaag tgagagcctc 105780
cctgccattt atagttttct gcctgagaga ccctcctgct tcacagctaa ttagcagagt 105840
tacagaggtc attaccttgc aattctcaag aattatgtga ggcagtatag taagcattta 105900
tggcccttgg ttcccagaag gagcttagtc cctgatagtc ctctctgcct ttgctgccat 105960
tgtgtgagac catcttctgt aactgtatgt cttcccccct agtaagttaa tgagtaataa 106020
aggtattccg tagtgagagg actctgtaag agaattcttg gtgtaaggat tgttgcaagg 106080
ttgttttgtg tgtatgtgca tgtataaact tttttaggga gtgtattcat agcttttaca 106140
tggatctcag aggctctgta acagaaaatt acagaatact ggtcttgtct ttggtaagga 106200
ttttatagac ccataaggga gtattctgac tacagtgata tccaacatgg ctatttaatg 106260
cctggcattt tccccacata acatacgttt attcaacagt cagtgcctac tgtgtacatg 106320
agacctatac caggcactgg gataagagac atgaaataac agctaaaact gtttattgag 106380
cagtcaatat gcattagatg ctttgtaggc attttcttat tcaatctgta taccctcaat 106440
ttacaaatga gggaaccgag acacaaaaga gttgagtgat ttgcccaaag tcatacaaat 106500
agtcagtggc tatgtggtga atagttacca acatgaaaga gtgagattac tgctgtacta 106560
aaagtaggca cataattccc tgagcagata gtatgagaga atgatttatt ttacctggaa 106620
agtttaggaa ggcttcacag aggagttaag ggttgatctg gatcttgagg gatggataag 106680
aatttgccag atacaaaaag gtagaaagag aacttcagga ggagggaaca ggttgagcaa 106740
agacaaggtg atatgaaagc gggaggcttg tttggggagc attatggaat ctcgaagtca 106800
ttgtggggaa tctcatcaga tgcagcaagc tgcttgacag gccttcaatt ggctctttgt 106860
accttgctcc ctccccatgc tgagctgtcc atagctgcct taggctggtg tctgggattt 106920
tcggaaggtt actatccagg tagtgtaaca agatgcagtg taagagcacc agatcggggc 106980
tctggctctg ctactgactt aacacctggc attaagcatg tctagttccc tctttgtaca 107040
ttaaaatctc cattggagca gtaacatggt tgtattaaat gatcttgaag attttaaaaa 107100
taaatatata acaatataaa tcgttaacaa taattttagt agtaaatctc taaaatttta 107160
cagataatcc agattcatcc attggccaat ggttcacttt gtatgcataa tttttgggga 107220
aacaggcaga ccgaatttca atccttagtt gtaagactta atacatatgt gacctcaagc 107280
aaattatatt gaatgcctct ataaggataa taatatctta cagaactatt gtaagaacta 107340
aatgatgtgt aataaagctc ctggtactca gtcagttttg gatccttttc ctagagtgag 107400
tcttggtcat aggcacgcat atacttgcag gggtccctga gtaggcagaa agaacaaatg 107460
agagatggta tctgtggtat tccccaggta aaggaggcct tgggttggtg taagatttca 107520
cttcacttta gagttactta attagggacc agaaaggcca tcgcatctgt atgagaatat 107580
aacaaaggtc aatttcttcc tctttacttt ttacgctgtg agtaacattc cccagccagc 107640
ccagccggca cgtgttcttt gcctctcctg acttccagac tttggtcttg aaggtgtcag 107700
agctctctgt gtatctttgc ccccaacagg ataagtctga cctccccagc aaattcaact 107760
cctaagccac tgtccaggag aagagctagc aaggtcataa attattctcc atattttcca 107820
gccattggtt tcccttgtcc agccagaggt gtgtcttaaa gtatgctgag gctagattca 107880
atagaaacct gagccagcac ctgtgtaact aatttttaaa actccctttc ctgaagctgg 107940
atgaatattt tttaaaacta agctggatta tcttttatct agcatgccgt ttcctacatt 108000
cctagtgcta tggacctctt ggaggaatgt agtttggtta tagtggtatt gtcttgcttg 108060
tctgttgtgg gggaggagga catttctttc aaaaacaagg taatacttcg gtctggacta 108120
tgactatttt gtttaaaatg aaactatggc actgtactgg tactcattct gcttcctata 108180
ggttagcttt acatccctct gtcttcaccc actctacagt tctgatcctt ttaaaaagca 108240
gccaaccaaa accagcaagt acatactgct tatctctgac ttctacctga atcaacttca 108300
gatcttgtcc aaagctccat ctgaagagag gggataaca ccctgccaag agccctcagg 108360
gcccatcagt aagtagacat cctgtccttg aggtctctta actctgctca gcttcagaat 108420
acagaagggg ttggttcttc atttgtgttg tttataacta aaagcctcct acttcccgct 108480
ttttttgcat agcttcttct gccatcccac ctgtgtagcc tcttcaactc ccctaaaact 108540
cctctgtagc ccgtgtcact tggaaagagt tttctttgtc tcttttgcaa cttgacaatg 108600
actagccagc aagtttaagt tcaaattatt gttccatggg aacagagata gatataggaa 108660
acaaaaaaag ggatatggag gtatggagta atttcccacc tacctagtga gcactactga 108720
gatattcaaa tgctctctac tcaagaattc tattgatata aacgtaaaaa acttgatctt 108780
aggtctaata tccattagta gtgtgacctt gggaaaacga taccactccc aaaggcttag 108840
tttttttaac tataaaatag gaataatgat gaccaccccc agaggattca taaggataac 108900
atgagataag gcaacttgaa atttcctagc atggcgatag acttttgaaa ataaaatgaa 108960
ccaaacactg ataacagtac ttcctagtgc acaaatgaga aatcagtccc tcatcaaatt 109020
acagcacatt tccaatgctc cgattatgtc actgtagaaa tgctaatgtg gattaaataa 109080
tttgtctgtt gctatttata tggataattt gatagtaatt atttttggac atggatagtt 109140
ttgaagcctt acagatgagt ccatccccaa gtacccaaaa ttaaagaaag ttggctagag 109200
tgatggcaag gtggcagcac agagctccct gggttctggg ccctgtcccc tagctaggga 109260
gaactccagg ctataagcat ttgtattctc atagtccaat ggcagggaaa agggttgaag 109320
gtgagtactt ttcactcatt tattttttca acaagcatgt atggtgtcag gccttgtatg 109380
catccacaga caaatgtgag ctagccctga cctcaaggag atttcagttg cagctttagc 109440
actgcaaaga gtatctacct gcggcagata caatgtgatg ggacatggcg gagaaaaaat 109500
ctataaacag agcctcccca tccccaggca tggaaacaat cctaacccag gctggcatag 109560
tacaatgggc ctgtctctat cagcaggttt ggaagcttta acaacaacaa aaaaaacaat 109620
aataatgatg atgataatca tagtgcctaa tgttaccaaa cattttccgt gtgttaagta 109680
ctatactaag tgcatactta atcctcacag caactctata aggtagtaga tactcttact 109740
actaccctga ttttacaaat atggaaactg aggcacagaa gactgagaga acaggaatac 109800
acctaattca cctcagttca acaaacacca agcatctgtt ttatgtcagg cctcgtgctg 109860
ggtgccaggg agagagaaat gagtaaagca tagtttcagt ccagtgggag caaatgacag 109920
cacacagtgg acacatatat tgcagccctt ctgctttatg ctaagaactc attgtcagtg 109980
atgaatcaaa cacagtcctt ctctcaaaga tcttcaagct tagtaggaga tatctgtgtg 110040
aaaacaaaaa ttaaagactg ctgtgataag tgtcataaga gataagtgga aaatgagaga 110100
gagatcactg tagcagttga ttggtttaaa tcaaagcccc ccaaaaaaca gtgttattga 110160
gaattataga acaactaatt gatttaaatc aaagcccaaa cagaacagtg tttgctaatt 110220
ttatttcagg ttggttgata gattttcatt ttttattcca tcccgacaat ggaagattag 110280
tgcttgtttc ccacccaagg ataccaggat atttcaggga ctgtattaca atatagttaa 110340
attattcctt tatctcaaag cacacccaca ctttctccta tcctttcctt tactcaggct 110400

-continued atctcttctg cctcaggtgc tttttctcca catttccata ttcttaagtc ctaccttcct 110460
tcaaggcctc actcgaatgc ctcctcctcc atgaagcatc caccccatcg aaaggtacct 110520
cgccatctcc tgtactccca catcacttca tgggtgtctc tctgtggttc ttaccacttc 110580
ctgctttatc tttcagtaat gcacttacag ttctctttcc tccactagac agagctcttc 110640
agacaaagat tcacttggct gaaaccatga ttttacttta aacacattga aaacctctac 110700
cggaatgcat tgtgtctggt gggcttcaac cttaattctt aagtatgtga aaatacatta 110760
cctatctgga ggtttacact ttctgctaat gactttattt ttaagtccac caccctaaca 110820
caacaaatgc ttaaaacatg tcttcatttc ctttaggtct ggccctcatg catgcatata 110880
atttatagag tcactgtttt gctcggttgt cctcatgcct ctatattatt ggaggtttag 110940
attgtttcca cacacttagg ttgtattcat gtacattttt ttttcttttt aaatttccct 111000
agcatccatt cccaccattg gaaattcagg gtcaaaacag gggttgggaa ttggagcatg 111060
tgtatcacag ataaccaatc atgtgttatg acttaagaat ttatgaaagg gccctctacc 111120
tgaagatatc ttgctactga tgctgtctca cagtgtctga aactcccatc atatgtggaa 111180
ttgttttgga agattttgcc tcctggggca cattcagcca taatcaggaa atagtattga 111240
gcattagact gtcagtatgt ccattagcaa gactgtggaa gaatggaatc accaatatta 111300
tattttatag gggatacaga attcaagaga agttctgaag agaaaatgct tatctagaat 111360
aggaaggctt agatacagca tgaaagctgc aggctttgag gagccagagg tcaaatgaaa 111420
gcactgagta tttgtttata tgaaagaaca gaaagggaaa agagaagcag aggaagggat 111480
agtagagaga aatgaataag ttttatccat ttaacttgga attgtgtttg gctatgggca 111540
caacagaagc agtgagatca ctttatttta ttttattctt catagacagg gtcttgctat 111600
gttgcgcagg ctggagtgtg cagctcttca caggtgtgat catagtgtac tacaccctcg 111660
aactcctgaa ctcaagcaat cctccaacct cagcctcctg agtagctggg acaagtgcac 111720
accaccacac ccaatgagat cacttaaaaa ctagggagag atgtgtgagt tctgggcaac 111780
cagtagttag aaaaccagga ggggtttgga aatcagaaaa ccagcagagg caggaaaact 111840
cagggcagca tggcagattt agtatataca agtaggttca caccagtcat cagacagaat 111900
tgtaactgct gatgtggagt agaggctagc tttgtctgct gtgtgatacc caaaccttta 111960
agaatagtag gtgtatacgg ggaattggag ggagataggt ggctgtattt actaattggt 112020
tgatttcact gagatggttt gggtattgtg gcttccagat gctcatattt tctttttttgg 112080 gtagagactc caacatcatt acagaactat aaattacata tggaaaagaa aggcctccta 112140
tgttagaata gaaaatagaa tgctgtgggg ttgagggaca gagggtctgt ctaggaagtc 112200
agatagcatt ttcccgttct gtccctcaga gttccttgtc cccattgaga ctcaatttct 112260
cttactttgg tttctagtgt taccacccac tgttcttttc catctcaacc ctgagtataa 112320
gtacagatca cattccttgg gttcttagaa cataatagaa atgaactctc attcatcaaa 112380
atgcccatta gtaaatactg agggagaaca aactagaaat ccagtataga aagtaaaaat 112440
aggattatat tccttgcaat ctcagaaaaa acaatgaaga gctttcttcg ggcattagac 112500
accttcccat aaggtggctg actctctttt agtcatgtca acttgaccaa atcttcactt 112560
ggtagcactt ctttcttgtt cattaaccca tctgctatgc tcctatgggg tcctagagaa 112620
atgccgctca tgtacacgca tatccaataa cacaaagatc actctcgact ggcaagccct 112680
tttatgatgc tgtgagcatt tgataccctt gttgctagta atatcagtga gtgacctgac 112740
ccatatttgg aacagaatat gatcagtata ttgcctcaaa gaggccctca ctgttctaaa 112800
aaatataatt ccagagtttg ctgactcaca ccgtggaata tgtgcaaaaa tgaatcctgc 112860
agataagcct ttctctgact agtttcagaa ttttttctg ggtaatttta aaattatttt 112920
tttatttttg taggtacaaa gtaggtgcat atatgtatga ggtacctgag gcattttgat 112980
acaagtatac agtgtgtaat aatcaccagc gtcaatgggg tatcccttac cacaagtatt 113040
tatcctttct ttgtgataca aacaatccaa ttatattctt ttagttattt taagatggac 113100
aatgttattg ttgactgcag tcaccttgtt gagctatcaa atactagatc tcattcattc 113160
taactatatt tttgtaccca gtagccatcc cacttcctcc cctcccacta ccctttccag 113220
cctctgataa ccatcattcc actctctatg tctatgagct caattgtttt aagttttagc 113280
tcccacaaat atgtgagaaa atgccaagtt tgtctttctg tgcctggctt atttcacgta 113340
atataatgtc ttctagtgcc atccatgtta ttgcaaatga caggatctct ttctttttta 113400
tggctgaata gtactttatt gtacgtatgt accacatttt cttcatccat ttgcctgttg 113460
atggacaaga gttgcttcca aatattggct attgtgaata gtgctgcaat aaatgtggga 113520
atgcagatat ctcttcaata tgctgatttt ctttctttag ggtgtatacc cagcagtggg 113580
attgctgggt catatgatag ctctattttt agtattttgt ggaacctcaa atctattctc 113640
cataatggtt ttactgactt acatatccac caacagtgta tgaggatact cttttctcca 113700
catcctcacc agcattcatt acttcctgtt ctttggatga aagccatttt aaccgtggtg 113760
aaatgagatc ccattgttgt tttgatgtgc acttctctga tgatcagtga ggttgaggac 113820
cttgtcatat atctgtttgt catttgtatg ttttattttg agagatatct acccagatct 113880
tttgcccatt ttgtaatcag attgttatat atttttttcc tatagagtta cttgagctcc 113940
ttatataccc tagttattaa tacttggtca gatgggtagt ttgcaaatag tttctctcat 114000
tctgtgcatt gtctcttcac tttgttgact gaatcctttg ctgtgcagaa gctttttaac 114060
ttgatgtgac ctcatttgtc catttttagt tgcctgtgct ggtatggtat tatccaagaa 114120
atttttggcc agattaatgt tttggagagt ttccccaatg ttttcttgaa gtcgtttcat 114180
ggattgatgt cttagattta agtctttaat atgttttgat tattatattt gtatttgctg 114240
agagataggg ctctagtttc cttctgcata tggatatcca gtttttccag caccatcttt 114300
tgaagagact atccattctt taatatacat ccttggtacc tttgttgaaa ataagttcac 114360
tgtagatgta tggacttgtt tctgggttct ctgttctgtt tcattcgtct atgtgtttgc 114420
tttcatatga ataccatgtt gttttggtta caatagctct gtattataat ttgaagtcag 114480
ataatgtgat tcttccagtt ttgcttggtt ctttttcctc aagatagctt tgcctatcct 114540
gggtctcttg tggttctata tacattttag gattattttt tctatttatg tgaagaatgt 114600
cattgatatt ttgatataaa ttgcattgaa tctgtagata gcttcaggta gtgtggacat 114660
tttaacaata tcaattcttg aaattcacga gcatggaata tcattctatt atttggatgt 114720
cttcaatttc ttatatatgt attatatata tattagtttt cattgtagag atatttaatt 114780
tatttaacta aatttattgc taggtatttt attttatttt tacctattgt caatgggatt 114840
gttgtcttga tttctttttt agattgttca ctgttggcat acagaaaagc tactgatttt 114900
tatatgttga ttttgtatcc tgcaacttta ctgaatttgt ttatcagttc taataggctt 114960
ttggtgcagt ctttaggttt ttccaaatat aagatcatat cgtctgcaaa caagaataat 115020
ttgacttctt tcttttcaat ttggatgccc ttcatttctt tctcttgtct gattgctcta 115080
gctaggactt ccagtactct gttgaataac agtggggaaa gttaacatcc ttgttttgtt 115140
tcagatctta tagccaatgc cttcagtttt tccaaattta gtatgatgct agctatgggt 115200
ctgtcatata tggcttttgt tatgctgaag tatgctccct agttttttga aagtttttgt 115260
cttttaagga agataaaaat tgaatgttat caaatgcttt tcatgtaaca attgaaatga 115320
tcaagtgctt tttgtccttc attctgttga tatgatatat cacattgatt gacttagatg 115380
tattttgagc catccttgca gcccttggta aatcccactt agtcatggtg aatgaacttt 115440
ttaatgtgtt gttgaattca gtttgctagt attttcttga ggatttttgc atcaatgttt 115500
atcagggata ttggcctata gttttccttt ttgtgtgtgt atattttgga ttttgttatc 115560
aggttaatac tggccttgta gattgagttt ggaatgattc tctcctctat tttttgaaat 115620
actttgaata ggattgatgt tactttttct taaaatgttt ggtaaaattc tgcactgaag 115680
ccactgggtc ctggactttt tactgctgag aagacttttt gttacagctt caatcttatt 115740
atttgttatt ggtctgttca agttttagat ttttttcgtg gttcaatctt cccaagttgt 115800
ctgtttctcg aaatttatca atttattcta ggttttccaa tgtattgtca tatagttgct 115860
catagtagcc tctaatgatc ccttgaattt ttgcagtaac cattgtaata tttccttttt 115920
ttaaatctct gattttattt gagcattctc tttttttctt agtctagcta aatatttgtc 115980
aatgttgttt cttcatccac aaaaccaact tttcgtttca ctgatgtttt ttgtattttt 116040
tccttttaat tttatttatt tctactctga tctttatcat ttcatttatt ccagttattt 116100
gagtttggtt tgctcttgct tttctagttc tttaatatgc attgttaggt tatttatttg 116160
aactttttga tgtaggtgca tattgctata aactttcgtt ataatattgc ttttgctgga 116220
tcccataggt tttagtatgc tgtttagtat gttttcaatt tggtacattt caataaattt 116280
ttaaattttc ttctttattt attgacatag tcattccaga gtatactgtt taatttccat 116340
gtggttggta tagtttccaa aattcctcgt gtttttgatt tctagtttta ttctattgtg 116400
gtcagagaat aagcttgata tgattgcaat ttttaatact tttttaaaaa cttgttttgt 116460
ggcctaagat atgatctgtc attgagaatg atctatatgc tgaggaaaga atgtatattc 116520
tgcagccatt ggataaaatg gtctttaaat atctattatg tccatttaag acataatgca 116580
ggccaggcgc ggtggctcaa gcctgtaatc ccagcacttt gggaggccga gacgggcgga 116640
tcacgaggtc aagagatcga gaccatcctg gccgacacgg tgaaaccccg tctctactaa 116700
aaaatacaga aaactagccg ggcgaggtgg cgggcgcctg tagtcccagc tactcgggag 116760
gctgaggcag gagaatggcg taaacccggg aggcggagct tgcagtgagc cgagatccgg 116820
ccactgcact ccagcctggg cgacagagcg agactccgtc tcaaaaaaaa aaaaaaaaag 116880
acataatgcg gattaaggcc aatgtttcat tgttcatttt tctgtctgga taatcttttc 116940
aatgctgaaa gtggggtgtt aaaatctcca aatgttattg tattgggatc tttctcttct 117000
ttcaactctg ataatatttg ctttagatat ctgggtgctc cagtgttggg tgcatatata 117060
cttaaaattg ttgtatcctc ctgatgaatt gaccctttta tcattatata atgaccttct 117120
ttttctcttt gtgtagtgtt ggtcttgaaa tctattttgt ctgatattag tatagctgct 117180
aatttttttg gtttccattt gcatgaaata tctttttcat tcctttattt tcaatcaatg 117240
tgtttcttta tatttaatag gtgaaatatg tttcttgtaa ataaaaatta ttattttaac 117300
atattttaaa aataatactt tttaaataat aacagttatt attatttttt aaattttcat 117360
tagttttggg agcccaggtg gattttgatt acatgagtga gttctttagt agtggatttt 117420
gagattttag tggagcagtc acctgagaag tgtacattac ccaacatgta gttgtatgta 117480
tattatatat acagtatata tataaagcat atatacacac tatatatagt atatatgtac 117540

-continued atatagtata aatatatata gtatatatgc tttatatata gtgtatatat gctttataat 117600
tgtatatata tgctttatat atgttgtgta tatctagtat atattgtata tatagtatat 117660
ataatatata atgctttatg tattgtattt atatattgta taatatataa agcatatata 117720
gtatatatac tatatataaa gcatatattt tgtatatata ttatatatgt tgtgtatata 117780
tattatatat ataattaaat tctgggatac atgtgcagaa cttgcagttt tcttacatag 117840
gtatacatgt gccatggtgg tttgctgcac ccatcaacct gccatataca ttaggtattt 117900
ctcctaatgc tatccctccc ctagccccac cctactccct gacaggcccc agtgtgtgat 117960
gtccccctcc ctgtgtccat gtgatctcat tgttcaactg ccacttatga gtgagaatat 118020
gcggtgtttg gttttctgtt cttgtgttca ctgagaatga tggtttccag cttcatccat 118080
gtccctgcaa aggacatgaa ctcatccttt tttatggcta catagtattc catggtgtat 118140
aggtgccaca ttttctatat ccagtctatc actgatgggc atttcggttg gttccaagtc 118200
catgctattg tgaatagtgc tgcaataaac atatgcgtgc atttgtcttt atagaagaat 118260
ggtttataat cctttgggta tatacccagt aatgggattg ctgagtcaaa tggtatttct 118320
ggttctagat ccttaaggaa ttgccacact gtcttccaca atggttgaac taatttatgc 118380
tcccaccaac aatgtaaaaa cgttcctatt tcttcaaatc ctcactaaca tctgttattt 118440
cctgactttt taatgatcac cattctaact ggcatgagat ggtatgtcat tgtggttttg 118500
ctttgcattt ctctaatgac cagtgatgat gagcttttttt tcatgtgtgt tggcagcata 118560
aatgtcaaga agtgtctgtt catattcttc acccactttt ggatggggtt gtttggtttt 118620 tttttcttg taaatttgtt taagttcctt gtagattctg gatattaccc ctttgtcaga 118680
tggatagatt gcaaaaattt tctcccattc tgtaggttgc ctcttcattc tgctgatagt 118740
ttcttctgct gtgcagaagc tttttagttt aattagatcc catttgtcaa ttttggcttt 118800
tgttgccatt gcttttggtg ttttagtcat gaagtctttg cccatgccca tgtcctgaat 118860
ggtattgcct tggttttctt ctatggtttt tatggtttta ggtcttgcat ttaagtcttt 118920
aatccatctt gagttaattt ttgtataaca tgtaaggaag ggtccagtt tcagttctct 118980 gcgtgaggtt agccagtttt cccaacacca tttattaaat agagaatcct ttccccattg 119040
cttgtttttg tcaagtttgt caaagatcag gtggttgtag atgtgtggtg ttatttctga 119100
ggcctctcct gtgttccact tgtctatata tctgttttgg taccagtacc atgtggtttt 119160
gggtaatgta cccttgtagt atggtttgaa gtcaggtagc gtgatgcctt cggctttggt 119220
ctttttgttt aggattgtct tgactatatg agctcttttt tggttccata tgaaatttga 119280
aaagtaaaca gtacaataag atgtaaatag aaacaacaaa gtgataacaa gcagagagat 119340
gaattagaaa aaaatatttt ttttctaatt ctgtgaagaa agtcaatgat agcttattgg 119400
ggatagcatt gaatctataa gttgctttgg gcagtgtggc cattttcatg ataatgattc 119460
ttcctatcca tgagtatgga atgtttttcc atttgtttgt gtcctctctt atttccttga 119520
gcaatggttt gtagttctcc ttaaagaggt atttcacatc cttgtgaatt gtattcctag 119580
gtattttatt ctctttgtag caattgtgaa tggcggttca ttcatgattt gattctctgt 119640
ctgttattgc tgtataggaa tgcttgtgat ttttgcaaat tgattttgta tactgagatt 119700
ttgataaagt tgcttatcag ctttaaggat atttttgggt gaggtgatgg ggtttctaa 119760 atatatggtc atgtcatctg caaacggaga caatttgact tcctctcttc ctatttgaat 119820
acctttattt ctttctcttg cttgattgcc ctcactgtaa ctttcaatac tatgttgaat 119880
aggattggtg aaagagagct tccttgtctt gcactggttt tcaaagggaa tgcttcagct 119940
tttgcccatt cagtatgacc aatatgtagt cttttattcc tcaccttctc tcaacccccta 120000 ccccaacgga gtcctcaagt cctttacatc actgtgtgtt attgcatcct catagcttag 120060
ctcccactta taaatgagaa aatgcagtat ttggttttct attctttgct tacttaatta 120120
gaataatggc ctccagctcc atccaggtgt cttgtttttc attcattcag ccagtctaca 120180
tgttttgctt ggagagtttc gtccatttag attcagtgtt atgactgata actaaggact 120240
tactcctgcc atttggttgt tttctggttg ttctgtggtc ttctcttcct tttttccttc 120300
cttcctgtct gccttttagt gaaagtgatt ttctctggtg gtgtatttta ttttattttc 120360
ttccttttta tttttatttt ttgtgtgtgt atttgttgta cgttattgat ttgaggttac 120420
cgtgaggctt gcgcataata ttttctaact cattatttta aactgatgac aacttaacac 120480
tctattgtgt aaaaaatcat ggaaagagaa aactaataaa aactgtacat tttaacttta 120540
tcgctctgct tgttatcact ttgtcatttc tatttacatc ttactgtact gtttatgtct 120600
tgaaaagtag tttcagttat tattttttat tggtccatct catagtcttt ctactcaaga 120660
tatgagtagt tcacatacca caattacagt gttacaatat tctgtgtttt tctctgtact 120720
tttaattacc agtgagtttt gtattttcag ataatttgtt attgctcact aacattctat 120780
tctttcagat taaagaggtc cctttagcat tacttatagg aaaagtctgg tgttaatgaa 120840
ttccttcagc ttttgtttgt ctgtgaaagt ctttattttt ccttcatgtt tcataggtat 120900
tttcactgga tattctattc tattctaagg taaaaggttt ttttgtttgt ttgtttgttt 120960
gttttcttca gccctttagg tatgtcatgc cactctctcc tgacctataa ggctaccact 121020
gaaaagtctg ctgccagaca tatatgagct ccattttatg ttacttgttt cttttctctt 121080
gttactttta ggatcctttc tttatccttg gacctttggg agtttgatta ttaaatgcct 121140
tgaggtggtc ttttttggat taaatcttct tggtgttctg taactttctt gtacttggat 121200
gttaatatct ttctctaggt ttgggaagtt ctctgttatt atccctttga ataaactttc 121260
taccaagatg tctctctctc tctctccctc tctctctcat tcttaaggcc aataactctt 121320
agatttgccc ttttgaggct attttctaga tctcgtaggt gtgcttcatt gtttgttatt 121380 ctttttgtc tcttctgact acattttcaa atagcctgtt ttaaaactca ctaattcttt 121440
cttctgcctg atcaattatg ttgttaagag actctgaggc attcttcagt gtgtcagttg 121500
catttttcag caccagaatg tctgcttatt tttcttaatt atttccatct ctttgttaaa 121560
tatatctgac agaattttga attctttctg tgttatcttt aatttccttg aatttcctca 121620
acacatctat tttgaattat ctgtctgaaa ggtcacatat ctctattttt ccaggatggt 121680
tatctggtgc tttatttagt tcattttgtg aggtcatgtt ttcctggatg gtgttaatgc 121740
cagatgtttt tcagtgtctg agcattcaaa agttaggtgt ttattgtagt cttcacagtc 121800
tgggcttgtt catacctgcc cttcttggga gactttccaa gtattccaag ggatttggat 121860
tctgtgatct tagtctttgg tcactacagc catatctgct ttatggagca tcccatgctc 121920
agtaatgctg tggctctttc agactcatag agttactgcc tgcatgctct tgggtaagag 121980
ccaggaaaat tccctggatt accaagcaga gactcttgtt ctcttccctt acttcccccc 122040
aaacagagta tctgtcgcat tctctttttc tctctttctc tctctctctc tctctctctc 122100
gctcattctc tgccgacctg cctggatctg ggtagggat gacataatca catttgtagt 122160
caccaccaat gggactgtgc taggtcagac ccaaagccag cacagcactg agtctcgccc 122220
aaagcccaca gagaccactc cctgggtact gtccgtgctt gctcaaggcc caagggctgt 122280

```
acaagctggt gaggccagcc tgtcttatgt ccttcccttc agggtgatga gttcttcaag 122340

caggtcaagg gatggtgtcc aggagccaag gcctcgagct gtgactgagc tggcacccaa 122400

tccataagac aacgattttt tccacacttt ccttcctttt tctcaagcaa aggagtctct 122460

ccctgtggcc accaccaccc ccatgttcat ggcaagtatt gtctggctac caccaatctt 122520

cactcaaggc ccaagcgttc tttagtcaac ttaaggtgaa tgctaccagg gctgggtctc 122580

taccttcagg gaagtgggct cctctctggc ccagggcagg tccagaaata ccatccaaga 122640

gccaaggcct gaaatcaggt tccccaagag cccatttggt gctctacccc cactgtggca 122700

gaaccagtac ccaagctgca agacaaagtc ctctttactc ttccttctcc tttacagaga 122760

ctctccctat agccaccaca gctaggaata tgctgggtca ctcttgaagc aagaacagct 122820

ctgagtctca ctcaaaactc ctggcaagtg ctgcctggct accacactga ttattcaggg 122880

cccaagggct ctttagtcag caggagttgc atcctgccag tactggttcc ttcccttcaa 122940

ggcagccgat taccttctgg cccagtgtgt atctagaaat atcgtttggg agctagggcc 123000

tggcatggtg acctcaggac tctgcctggt gcccttttct actgtggctg atgtagtgtc 123060

caaattgtaa gacaaagtcc tctgtactct cccctctccc atctttaagc agaaggaaag 123120

agtccaccct ggagttggga catgcattgc ctgagattgg aggaggggtg gcacaagcac 123180

tctcttggtc acctcagctg gtgtttcact aggtcacatg ttccccaagt ccactggctc 123240

tgagcccagc acaacaccag gagttgacca agaattgcaa ttcttgtggt ttagactgcc 123300

tttcaagttt atttgggact gcagaccact ttagcccaca gtgacagggc ttgccagaat 123360

ttagtttctg actgctgaga tgggcaattt gcctctgatt aggacggatc taagtgctcc 123420

ttctgtgggc actggctgag ttctgctcca tgttgctttc tgctgtgaca gggcaacatt 123480

gagtgccaat gcaagtccca caatcactgt aatcttcctc tcccaagcct actctgaaca 123540

ccatgtggtt gctgctggga gattggcgag ggatgttgta ggcaattcaa gaatgtcttt 123600

cctacccttt tcagtgcttc tttccttagt atgatgttaa aaccagttac tgtgattgct 123660

catctgattt ttggttctta ggaaggtgct ttttgtgtgg atcactgttc aatttgttgt 123720

gcctgcaggc aggggtgggg gacaattgct ggaggcttct ctttagccat cttgctccac 123780

ctcttcccta gtattagaaa tttcaaagca gttaggatga gggtagaagg aaagggtgct 123840

tggaatcaga aaatccatgt cttagctttg agccttagga aattcatttg acccttgtaa 123900

gcctctgttg cttcatctgt aaaagagaaa taatatagtg actgaaaata tcaaaggtga 123960

taatgctgtt gaaagcacta tagaaaatga tgaaatatca catgagtatt attttctagt 124020

ttctaggagt ctccttacca ttgtacagga caaccatgtc tattttttaaa taaattatta 124080

tttgcctctg agcacccctg caaagagttg cctataggag aaacagctta acttgcaaat 124140

cactccactg ttttctttgt gtacagttta ttaatacata aggcacatgt cctccagtct 124200

gtagtaacat tggaatgatt acctctttgg agtacctacc agagcttctc aaagtgaatt 124260

ttgtatatca ccaccaaaaa tagtctgttg cagagataac ctccaaattc aatgacaata 124320

tttccaatca cttttgcatg atacagaaat agacaaatat ataattttgg ttatacagat 124380

aattattgtc tcccaacaag tgattagtag tcagaaaatg gccaagaaat accatggggt 124440

gtgccttccc ataacaactt atctttgggt tttagttgca aggttactaa aagcctgtgt 124500

agggttcatg gcaaaagtaa aacttgctcc aagagcaagc ccttgtttca ttgtctaatg 124560

ttcttaatcc ccagcagaca tgatttggat ctggcatttg gcaacaggac agtttccaaa 124620
```

gttgctgtat gcaacttgag gaagagaggt gatattattg gaatgaattt atttgttgta 124680
agttataaat atatgggctt ttccaatccc atcaccctta aaaatttttc tgcagtaagg 124740
gtgtctctct tgtctttaat atgcttgctt tgagttcatg gatgaacatt cttgcttggc 124800
tgacatgtgg actctctgaa attgttctaa ggtctttttc tttgtttttt tcttgattcc 124860
caagctgcca agggtagtac tggtagtggt gggcagacaa ggaggtgata gcaagctgaa 124920
ctttgtcctc tggcttccct tgacccattg cattcattat ctaagggact ccaagtcagc 124980
attccacaga atggccttac caaactcact gagactgaaa gagaaccaag attccaaaca 125040
gccaatatga aaggaaagag agagagactt agggtttgca gaatgggata ctctgttgat 125100
tatttttatt ccatacagat actaatattc tttaggaaaa cattaaaatc acatgatctt 125160
ccaggacctg ggctgcttct ttaagaagca tgttacagag agctctcttg gccaacaaca 125220
tattgaaaga taaattaatc aatcattcat tcaaataagg tatattcaga attgaggtat 125280
attgtagcca gacagtgaga ctataaaaat gaatgcacct tacccttgtc tcttgcacaa 125340
tctaatgagg gagataacca ctcttccaat ttatagtgac ctataacatt tcatacgctg 125400
ctgaatatct ttacatgata atgacacaat agaaagattg caaaatagac agaggctggg 125460
ggaagaagga ttgagtgtga atatagcctc tcataaatcg agggggaatg gtctgcatct 125520
cctgatcatg cagaggtaat aaatacagaa atgatttcaa actaacaaac caaatgtgca 125580
gaaaatactg agaatatagt gggcaggata cctgagtttt agttctatct ctgttattga 125640
ctcattgtgt aatctgggtc aggtctgttc tgctctctgg atctcaccct ttcctatctg 125700
taaaatgaga ttattgaatt agacgatatc tatagaggtt ctcgcctatt ctgacattca 125760
aggagttttt ctttaagtaa taatatatgt gatctgtata gtgctttaca cttgacatga 125820
tatttttgca tctattatct catgtgagaa aatcactgga ctgctggact gggaatgagg 125880
acacctggat tcttgtccct attttgacac tgattcatgg tgtgaccttt aagcaaattc 125940
tctgagtttc agtttctcaa tctgtaaaat agggaggtat gaggattgga ctaaatcagt 126000
aggtctctaa aatgttccac aaagccctgg ggttggggac tcctacagag tttcactaag 126060
gcaaaccaca aggctaggcc tgcatagaag aggagaaaaa gagtgacctg gcaagagaag 126120
ttccaagttt cctatgccaa ccccaggcag attaggttta attttatctg ttttataaac 126180
agagcttcta tgtaatgttt tattggtaaa aagactttac tataaaaaac tcaactagtt 126240
tgatttttta aaattgcaca tttaagtgag atcatacagt cagtatttgt ctttctgtgg 126300
ctggcttatt tcacttagca taatgtcctc cagcatcatc tatgttgctg caaatgacac 126360
actcttcttt tcattaaagg cgatatagca ttccattgtg tatgcacacc acattttctg 126420
ttttgtaact ttcattttag gttcaggggt tcatgagcat gtttgataca taggtaaact 126480
gcatgtcaga gaggtttctt gtacagatta tttcatcacc caggtaataa gcatggtagc 126540
atagtaccta atggattttt tttttctgat cctctccctt ctcccaccct ccaacctcag 126600
gtaagccctg gtgtctgttg ttcccctctt tgtgtccatt acaccagatt ttctttatcc 126660
acttatccat ccatggacac ttagtttgct tccatatgtt ggctattgtg aataatgacg 126720
aaaaaagtca aactcataga agcagagagt agaatggtgg ttaccaggga ctgggaggca 126780
gttcagtgag ctaggaaaag agagctaata aaagggtaca atgtgtgagt tatatagaag 126840
gaataagtta tattgatcta ttgcccagca tcgtgaccat agttaaaaat aatgtattat 126900
atgtcttagt attgctaaaa gagtagattt taaatattct aaccacaaaa aattataagt 126960
aggtgaggtg atggatatgt taatttactt gatttaatct ttctacaatg catacatata 127020
tcaaaatatc ccactgtatc ccataaatat atactattat tatttgtcaa ttaaaaaatt 127080
taaaaacttg atttagatga gctctaaggc cttaagtatt aaaatattat taaagtgata 127140
tgtaaccaag tatattgctt ggtaacttca tttttgttgt tgttttaaca aaccaatata 127200
ttgtgaatat acttccaagt gaaaagaaaa aaagacatta cagtcatcat taattactgc 127260
aaaatattcc tttgcatgaa tatggaataa ttcatttaat cattccctta atgttagaca 127320
ttcaaatgtt tccaactttt tctgtttaaa taatgctaca ataaacttct attttgtgct 127380
tattgtatta ttttcttata acacatccct agaagtggaa tttctagaag tttatagaca 127440
tttccaattt ttttccaaat atgtgggaaa atttctctct aaagtattta tgttcctacc 127500
agaaatacct ctttaccaac acacagtgtt taatctgtac caatctggct tgagaaaatg 127560
atatttactt tgtatttctg tgatttctag ctaaattaaa taatcttcac atgcttattg 127620
gtcattttta tttctttgaa ttgcctcttc ctgtctgttg cccatttttc tattgtgctg 127680
tttattttta tatatcaaat atattgacca ttgattttac atacttgatg ctaataatta 127740
gtnnnnnnnn nnnnnnnnnn nnnnnnnnnn nnnnnnnnnn nnnnnnnnnn nnnnnnnnnn 127800
nnnnnnnnnn nnnnnnnnnn nnnnnnnnnn nnnnnnnnnn nnnnnnnnnn nnnnnnnnnn 127860
nnnnnnnnnn nnnnnnnnnn nnnnnnnnnn nnnnnntttt gattttaact agtaatttaa 127920
ctttattttc ttctccaaat gattcactag ttgttctgac attatttagt gaataattca 127980
tcctttttttc actgaattgg aatggcatat tccatatact gtgtctggtt ttggcttttc 128040
tgttctcttc cactgatcaa cctaagctgg agccagtatc aaactgttat aatcattatg 128100
gctttagata ctttaaatgt acagcaggga atgtcttatt actcttattt ttcacaaata 128160
tcttgacact gtctcatgtt ttattccttc gataaatttt gggattcatt tgtgatgatt 128220
ttgtctgagt tgttttaaat ttttagattt cactggggaa gaactgaaat ccttgaaata 128280
ctgcttctta ttagccagga atatggtaca actttgcatt taattcaggt ctttccttaa 128340
ataccacaat gaagtttttt gttttgttca tataggtcct gcattaacac tgtttatata 128400
aagtgtaaga aagactatag tcctcaggct tctctatagg ttaacaatga agatgatgac 128460
tcaacctttt ctttatttgc ataatgtgat gccactaata gtgggcaact tccctgtctt 128520
acctcctctg ttccaaacag gattttttgg aatgaacaag ttaaaagaat cgtaatcaga 128580
cactaacccc aagccatact gcatggcagc accaacggga ctgacagaaa acaacagaaa 128640
taggaaggaa gcctgcagaa aaacaaactt gaaagctgtc tcatggcctt tgttcctgct 128700
ggagctttga gtcatactta agttttatga tggaagaata ggagtgtgaa gaaagataca 128760
gagcaccatc agacagtcaa gaatttcaga gccagctggc atgcagtgga cctcatgcca 128820
gcccatttg ttactattta ggtagtcaag gatttaagat tcttctaata agacagtttt 128880
tatgcattta aatgagtgac ttctttgcag ctctagcgtg tggccttacc tacttcaaca 128940
tgagaagatt tttgtatttt gtcactcatt tcacaatgac ttatagtgag cccttcatta 129000
tacactgtgg atacaacttt gctgttggaa attaacagtg tcaaaaaact gggtataatg 129060
tttgtagtat ctgaggaggg agagctgcct aggaagttgt attccctgtg ttaatttttc 129120
agtctcttag gttatagaag accttctaga accaccttac agcaggccta gatctcattt 129180
acacacttct tctgtcactt gaatacagag aagggatcca caaggtcata tacttcctag 129240
acaaagagca aagatttcta ccacactcag aagactttgt cttcagactg taatcaccca 129300
caccatattt cctttggatc cagtttccag atttttgtgc tggcactaac accaacttgc 129360

-continued

```
tgtggcttgg ggcatgtaat ttcaatattt tgtgcccatt ttcttaactg aagagtcagg 129420
catcacactg ggcattttaa gattctttac agcccaatga ttctgtgttt ctaattaggc 129480
ccaatgggtt agagctataa ggaaacagtg agtttcctgg aaggaaagga cacataacac 129540
agtccagaga taaaacgggc tgcattcaag aaaagattgg gcaatacttt gcagggatgc 129600
tacagagaca attcaagcct tgtatggagg aatggatgtg atacaaccaa aaagtcttta 129660
aaaattcttt ccaactaatc tgggattcat aaccttatgg actgtgattt gcagcaaacc 129720
aaggatgtga tgccaggcag aacaatatct ctgatcaaca tcaatgcaag gttcctcaac 129780
aaaagactag tattgtttct ggaatgcaag gatggttcaa catatgcaaa tcaataatat 129840
taacagaatg aaggacaaaa actatatgat catctcaata gatgcagaaa aataatttga 129900
caaaattcaa catcatttta tgatgaaatc tttcaagaaa ttgggtatta gaaggaatgt 129960
ttctcaacac aataaaggcc atatcagaca agcccacagc taacattata ttcaatgacc 130020
aggaatgaga taaggatgct cactctcatc acttctattt aacatagtac tggaagtcct 130080
agccaatttc atattaatga gtctcatttt cttcatcata gaatgaagta tgtaataatc 130140
cctattatac ttactttgca caattattat tattttatta ttattttgag acagggtctc 130200
actctgtcac ccaggctgga gtgcagtacc acaatcacag cttacttaaa ccacgacctc 130260
ccaggcacaa aggatccagc ccctcagcct cctgagtagc tgggacttca ggtgcacacc 130320
accatgccta actaatttc tttttttcat ttttttatag agacggagtc tcactatgtt 130380
acccaggctg gtctcaaact cctgtgctca agcaatcttt ccaccttggt ctcccaaagt 130440
gctggtatta caggagtgag ccactgcacc tggccttgca gattattatt aaactttgta 130500
aactaatcaa atgagagtga ttattgttac tgttaagaac tctaatagcc tcattcatat 130560
atttggagaa attgaataaa taggaaagaa ataatagcag accaatgatt ttaccttggc 130620
tctatcatca tttggggaag tgataattca gataggagaa gtgacttgta agcagtcttg 130680
agagattacc tgttccatcc cctatatttg tccttaaacc aaattgtaca gataaataag 130740
gtcttatttt taggacttac agaaaaaaag attcctttca tatccatctt tggaatcctc 130800
agccacttct gtcactatta aatgtcattt taaacgttaa attcatcatt ctgctttgaa 130860
ggaacacatg tgtcatgtgt acctatttgt atgttttggt gtgttttatg ctttatatga 130920
tcacccacat atgcacagat aattagtgtg caggtgttgt attccctgtg ttaattattc 130980
agtcacacac tctcacacac ctatgcactc acacatacat gaatacacac atgttcatta 131040
gaatgtttat gcttatgttg catgtgactg gcaacatcag tgcctttcta aggcaatatt 131100
aaccactttg agttttggga gagctttaga aaacaaagac aagagactaa atgattctag 131160
atgtaagaga caatgttgca ataagttact atcctaaaaa gacagaatac aaggacaaga 131220
gattattatt ttggataatt tcttgcttac cagtaatact taagtccttt acattaaaaa 131280
aaaaaaaaca actctaaata tattacagaa gacatccaga tgtccttcaa gattcttaga 131340
gttggaaaag attttaatga ctttccagtc caatctattt catgtaatca gtgggatcag 131400
agaggcaaaa ggacttgtcc aaggtcatat agtgagttag tgataaggct gaacaaggat 131460
tcagatgttg gggcttccag cccactgatc tgtctctcat ctgggacttg tatatttttg 131520
ttcattagag attttcctct gtaacctcaa tatccaatgc agggccttgc acataataga 131580
ttaccagtaa atgttaaatt aatatgtcat ggctttggtt ttactgggct ttgcacttac 131640
tcctgagtaa attgtaaata atatctatgt tttaggtctc cttgttttag accaagatgt 131700
acccagagaa aaggtatgaa ctatgctaag aaaattatct gagtcccaaa ttgaaaaaaa 131760
```

aaaaaaaaaa tcatgctttt ccactatgac ctctctcatt cacagagtga ttctctttca 131820
aaagggcaat gtagaaccat tctggcattc tgggagccat attccattgg ctgtgcaatc 131880
atttattggc aaactggggt ccaggaaagt attttcctgg ggaagatgag atttctcaaa 131940
gaagtcatgc actttctaac ctaagcttat ttcagtaatc agtgtagcaa actggtcttg 132000
aggattgcag cagtaccaat actgtgggag tgtaccagtt ctagaacagc tacagcattg 132060
gaattgaacg cactagaatt ggatacagga cctgtttttg aggagctaac acccaaaggc 132120
tgaaagcact cgtagcactg tcctttctgt gcacatatcg tagtcctcag tttgcagcag 132180
aaaaaaaagc tgttagcaaa ttatgtgctc tgtttatgca aataaaatcc tgtggtatac 132240
tagaaagagc accggcctag aggccttagt tttctcatat gttaaaaaac cctaacacag 132300
gcctggttca tagtaggcac ccaataaata ctagagtttt tcctttgggg gcctctgatt 132360
cagtgtgctt cttcaggtaa ttcacttccc tggaactcct ccttgtaatg agagttgttc 132420
tgttgtgatt tttaacagtt ccttcaagcc aagcattttg gaatcctttc ataaagggag 132480
aaaggaagga aaggagaaag gaaaattaaa ggaaaaaaaa ggaaataaaa agttaaaaag 132540
gaggaaagga aaaagaatcc tttactacaa taaatctaat ctcatgctct tgcaagtagc 132600
actttaagta aaagaagttc tttgctgacc tggttactac tgaacctact acataaaata 132660
gcctactgta acacatgcat ttctgtgcct aatcttcacc ttttagcctt agtaaatgta 132720
gaggaatgct gatgtatagt taaatttatg tttttagttg cttttttttt ctactctcaa 132780
atgtcaatca ctctttagtt tctctttctt tttccgaccg caagtattct tcctctgcct 132840
aaagaagctt ccctaaaatc ccagtctatc cagtaaatca aagcacagca ataaatttga 132900
ggaaacaata ccagagacaa aaaggagtga ggggatgcag aagctcaagc tggagcagga 132960
ttgtaagcat gagaagttct gcgtgcttca gagcagcgaa ggatgtattt ttgcttattc 133020
ctgctggtga ctctttgtct atgcatccat ctgctgcaat tgcatgttta gtcagtcaat 133080
ccacgtttgt tgagagactg ctgtgtgcca ggattgtgct agcataaagg agcgaagtat 133140
tgagcaaaat atgtttgagc agctgtaatt ctgaggatct ctaggtctga gcatgtgtat 133200
gtgtatgcac ttctgtgtat ctgtgacaac tccaggtgtg catgacagtg atctttgtta 133260
ctctgttggc ttcatcaaac ttccttttag ttgctgtgat tcactacata gagtgggctt 133320
tatctctgat ttttataacc tgcatgacta ggggtatgat caccagaaat ctaaaaacag 133380
ttagaaatcc catggagtta tcttttatag aagttttcct gtactaatat tatgaaaaat 133440
aagcatcttg ttaacttgag tgtaattcta tgcatgatta caggtgtcaa taggaagaaa 133500
cattgactga gttcagatct cttctacgcc atgctaaagg ggtgacaagt tccacaatgg 133560
atcattttct catgggcatt tctggctttt ggtaaaagta gggcatctta ttttaaaaac 133620
cagtgagtag tcctaataat ggagatatca tcaggatctg aattgttcat ccctaaaaaa 133680
aaacaaaaaa aacaaaaaaa caaaaacaaa acaaaaaaaa aaaaaccaat ggaaatcaaa 133740
taatatagtg ccaaattaaa ctgctttaat atttaggttc tgtaggatca aattgtttgg 133800
tgccatactc tgtccacttt tctgtccact tttctcatgt gataggatat aattttatat 133860
cttttctgtt ctagaaatac ccaaagaaag agactctgga aactcattaa caggtctgtc 133920
cactcttgta tttgttatcc cagggaaaca gaagtacctg tgtgccagca gaaatgattg 133980
cactattgat aaattccgaa ggaaaaattg tccatcttgc cgtcttcgga aatgttatga 134040
agcagggatg actctgggag gtaagatact tttctttctc ttcttcctcc tccttcctgt 134100

-continued ctccccttt cctccctcat tttctagtct ctctttaaac cagattttct tctttgatgc 134160
ttccaagggg accagccatg ctccagacac aggcggaccc tttcatagcc aacgtggcca 134220
tcagccagct ggtgcctttt tttttttaat ccttaactat accaatcccc attctggggc 134280
tcagcattag agcaggaggt gtgaagcagg gataaggagc caacagaggg tgagtgagga 134340
tgcatgtgac tgggcagggt ccccagggga cttaatggta ctgacctgat gttgttcaat 134400
ggtagctagg atgagagaac taagaaatcc agaacagtca caggtgcagg atgacccagg 134460
cataggtaca ggatgaccca ggcacagtct gaccctgaac acctgggaat atccctcagc 134520
taactgctgc ctatgttgta gggccagcca cctggaatga gaagctgctt ctctttggag 134580
cctgtgacta ggctgacaaa cagtgccaat ttcctatcct atctctccca aagatgaaca 134640
ggtgttttaa tcatttcctt ttctttgcaa agctattgat catttccaaa agcatttttt 134700
tttcagtagg acagtaacat tacagaagga agatacagct ctttcaaggg tgttcctcta 134760
tcataaggct ctctgtccca tgaacctgtc tgccatgagt gttgtcatca ttccagaaag 134820
gcttgacatc agttgattga catttatatt ttccctctcc aaactccccc atctctccat 134880
gtttacatct gcccaatgcc agggtcatca ctgcagcctg ctgcttccaa aaatatgtgt 134940
ctttccttag aaaaacaaga tcattaatct acttcaattt ggaaatggaa tttgaagaaa 135000
ggcaagccta tttctgagtg cctgcaactg tagcctcata tccgattatt cattattagc 135060
ctggaaaacc caagtgccta gaatccaacc ctttccccta tcctcttaag gctaatttag 135120
accagttgtc tatcactggc tttctgtgag ttgttcaata ccttgtctgc ctatgtgcac 135180
atctatagac aacaactagt gctcttatcc tggaacaggg ccatgtgtga atctatatgt 135240
agataactat atccttccca tcctcacagg gcagtggtat tatttaaaca gaacaaagta 135300
cctcaaatga attgacccag gctggatgag agacaatttc aaaagaatca tctcaagtag 135360
catccagtac tcccaaacat cacaggtaga tattctgtga gtggctttcc aagcatccct 135420
atcaaatgag aatcagatat ctgagaaaac tcaaccttgt tttggtttgc ttagtgtacc 135480
ccaaagaaat ccaacaattg aggtctacag tggagaagaa gtaggactgg ggtcagggag 135540
tacagaggca aaggcaggaa gggtgacaaa gtgattgaca agagaaaatg ttctccatat 135600
gaatgttgca gccccatgtt gagggttctt atacactcag ctttcaatta tttagccttc 135660
tgcgaattat gtatagtata agagatagag actctcaggt agggaacctc ttggctggtc 135720
atctggcaat atgaattgca agtccacttt gatgcaggta aagtttaatg gtaacaaaag 135780
tcctcataat atttggatac aaatcttaac attaattcca tgtctcagcc aacattctcc 135840
attataaatc aggctgtgat atgattacag tgacccactt ttgaaaagga gcctgtgtat 135900
aacagataat ttcactatac tatatagtac tcagatgcag gtttgtaaat taatttattg 135960
gtgagaatgg ttcagtacat tttcaaattg atttattagt agagtactca aatttgagtg 136020
ggcttggtga acacaatgaa gacaagctga gaagtgttgt gactggcctt catttcagtt 136080
gcaggcccat gatattttga gcatcttcca tgtacaaggc accatgctag tcattagagc 136140
ttgaggctgg caaacttcag gaaatgttca caagatacca gcattcttga tgttgtgtaa 136200
atggccttgc ctttagagtc aggcagatct agtttaaagg ctcagctcct ttatttaatg 136260
tgtgcccctc tgagcttcaa gatcttcgtc tgtgatttag aaataccatc ctcatagaat 136320
tataatgaag atcagatgac atgatgaatg tgaacatcct tgataaatag caaaatgcta 136380
gacaaatgtg gggcttaat atgtcattga ggtcactagt aatttagctg gaaaggctgt 136440
aacacagcac ttcccgatgg cttttaccct aagtaacttg gtatgccata taatatgtaa 136500
cagatccaac aggcagagca tcgccagaaa acagtcttga ttacctcaaa ccaaaaagtt 136560
ccaccaggat cctgttcaga agctaatttt agtaattaag ggaatcatat gctatgttca 136620
agtaccatgc cagtaaaaac ccaattgtgt accttcttaa atcactgctt gaagagcaaa 136680
tctttccact ttggtgaatg aacttatctc cacattccct gccctactga cacaactccc 136740
tcccacgttt attgttaact tacacattca atgcacagca cacctttact caaacaacgg 136800
aaaagaaagt gtcaatacaa agtggccctt gtctattcct taaggagtag acttccattt 136860
tcatgagatg tggatttagc atagacatat tgattacctt gaagaagaat tcatataatt 136920
ttatcttctg attctcatca ctcaaatcaa aattatataa tatatcccaa aatgacaact 136980
agaaatgtgg ccttgggcaa gtcccttctc ttctctgatg cttggttttc ccatcataga 137040
attggaattg tgggcttcac caaggacctt tctggtgcta acattttgtg attctgtgta 137100
aaaagccacg cagaaaggat tgtttttcag ccctttctta gattgtctgt tccctgctcc 137160
cagaagtata gataatgaga cttgagtgct ttgatacatc gtaattgtat ctacctccat 137220
tcatacctac ttaagatatc tgtctaaaag tagactagac agattattga gagagtggag 137280
ggcagaaggg ctgtctctgt atcttaaaga agctggcact tttcagctga tggctgcttg 137340
gtcttgaggc ctcaagatct ctaatctggc tttctctata gtgtttcatt cactgtttgg 137400
tgatggaatc tcttcagctc agagatactt aatagatata gctttttatt tcctgcttcc 137460
aggcctacct acctgttcct tgcttttttt tttttttttt tttttttat actagttgct 137520
gttgtttctg aaagaatctt gagggtggtt ggagtctcag aatggcttcc ttaaagacta 137580
ccttcaggct ctcagctgct catccacaac aaagataagc ctttatttgt agatgattca 137640
ttcctggctg catttgaaaa ccacatattg ctaattgctt gaagaattta aatcccttga 137700
ctacttttca tttcagaaaa cccttacaaa aaaagtccaa atgaggacct tccctccagt 137760
gaattagctg tggctttctc acagtccata gttaggatta atgtaaagcc atctctcatt 137820
tttctggaca cttcccaagg atacactcct tgtttccaaa atggaatgag aaagaaagaa 137880
gtgcccttcc tgccatcttc tcccatgacc cttttctcct tcccactttc cctcctattc 137940
ctcctcaaac atgatttatt tctgtgtttt gcaactcttg agttctcatc atttagtaaa 138000
tggtgttggc ccctattgat tccttcctgt cctggaccat ggagagtagt aggcctttca 138060
gaaatttcag gtagcagcca aaccctggaa gaagagaagg aacacggagt cctagaccat 138120
gtgagaacct gaggtgtgca gcatttcctt cacagattcg tctagcatat ttgagaagta 138180
tctttcccac taggagactg aactctgcat ctgagaaaaa aaaaaactta acatatctac 138240
aggttttgac aacctctatg aattacctag ttgagaggat ggctcaagga gcctatggcc 138300
atggtctgat gtcattatgg acactatgaa catccttgag gtttccattg ttgaagacag 138360
ccctgatgcc agctgtctca tcattcccca tgttcaagag catcccagca tcgctacctc 138420
aggatcccat gtcctgaatg caacagagtg atttcgctgc tgaattacta ttcatggcac 138480
ggctcttcac agcatttatt catccatgtc catccgtcct tccagccagc caagaagctc 138540
atgctttcat cttttcatcc tgagtaccaa ctatgtgcca gacactctgc taggcatttt 138600
ggggaagcag aactgaataa gatatcattc ctttcctgaa aaatttaagc aagaggagaa 138660
aggtagtgat aaggaatata ccttagccat aaaggaaaaa taataaatca cttagaagaa 138720
gttgagtgag atggaaggaa aaggacatcc aaagcaaagg gtacagtttg aataaaggca 138780
gagagacatg aacaaaatgc attgagggtt tgaggaacag caattggttt aacatggcca 138840

-continued gagctgggga aatggtaaag gcaagctgaa agcacattga aagcaaactt cgttactata 138900
ctaggtagtt tagacttcaa agagttgaaa atctatgacc atgggacagg tatgatgaca 138960 tattatttg tttattttct ttttttttt ttttttttt tgagacggag tctcgctctg 139020
tcgcccaggc tggagtgcag tggccggatc tcagctcact gcaagctctg cctcccgggt 139080
ttacgccatt ctcttgcctc agcctcccga gtagctggga ctacaggcgc ctgccacctc 139140
gcccggctaa ttttttttt tgtattttt agtagagacg gggtttcact gtgttagcca 139200
ggatggtctc aatctcccga cctcgtgatc cgcccgtctc ggcctcccaa agtgctggga 139260
ttacaggctt gagccaccgc gccgggcctt taatttgttt attttcatgt ttctttaaag 139320
aaaactggca gcagcacaaa tgttttgttg atgagggctt aaattttaga aagtgagaca 139380
attttagaaa ggccagctag agagaaattt ttagcatcaa gttttgctaa acacctagaa 139440
tttattcctg gagctagtta cctccatttg ggttgttacc tgcaagtact gaccacgtat 139500
atgaagaaat actggtttag accaaggcaa ttggctgtat aagaggccta ccctcatacc 139560
aaaagccagt ttccttggtc taggccagtg tttaccagta tgtgttctga gaaaactagt 139620
tccatgacat gttccatgaa aaatacgatt tctattctca aataagtgag agaaacttgc 139680
atattatggt cctgctcagg aagatttaca gtccttatta gcatatcgca ggtcctggtg 139740
aatactgcaa taaagtaacc tgaggagctt tgtaactcag gattcccaaa gttgattcaa 139800
ccacagaacc tcatttattc acataacacc tgttatccta caaaaccact gttctctaga 139860
atacactttc gaaaacttgg gtatagataa aaactctatc ctataggcag agaatacctc 139920
tagctcaggt catcattttg cagatgtgtg tgtcattaag aatcaatcca taatgcatta 139980
atgatcaaaa gcagaccatc cttaccacat ggtgcataag attatgctat tagctactaa 140040
agccactgaa gttaatcatg ttgggtctgt aatattgttg ttatgcacaa aggataggct 140100
gcaaaagtgt cctaggccaa agcatggcta ttgcccaagt tatctaatgt ctgcaggtac 140160
atattcctga cctaaggatt gtgctaaaga agttatttct aagaaatata gtgacttcca 140220
gcatcatgca gaatgatcat ttaatatttt gaatatctag acattttgct gtagaattta 140280
atagtccttt tatacactgt ctgaccaaca ttttgacatt tactcagaat cccatcacag 140340
tgctaccaca taacctcatt actaaagtag gaggcctaga aatcacagat ttgtagaaac 140400
catccaatga ttgaatcccc tctacctcct gttcagcagg cagcagagtg tcataaataa 140460
ttaacaatgt ggaactcagt tactgggatt tcttccattc tcctttggct ctctagacta 140520
gattctaaag accctcaggc tggtaatgca agtggtaagt ctcatttctg agaaatgctg 140580
cttcctacac acagttctct gatacctgag tgctttgact gatctgcata actgaggcat 140640
gcaccaagga gcagaattac tctataaatt ttggcatcaa tatgtacaac gtgtgactca 140700
gcactttgaa actctgggga tttttttgtt cggttggttt ttgttttaag aggtcctgtg 140760
gtatagtgga aatcgtatgg tagactcaga tacagagagg ccttgtttct agtcttggtt 140820
ctgtcactta ctatcttgat gaccttgggc aaatgactag aactctctga gcctcagttt 140880
ctccaaccac actgtaggaa taataaaatc ttgtttacgg catttttgta aatacgtaga 140940
gaaactggta cacagtaggc acacagtaaa tgtcaccata cccttcagtc cttcttttgt 141000
ggatgaaaaa tggtctttct ttgtgctccc agtaaccact ggggtctgtt ctctctctct 141060
gctggacagt gtggcttctg gttcttgttt ctttgttctt tggtctctaa attacccttg 141120
aaacaaccct tgaaatttcc actcgatgac ctaaattgtc atccctaagt tggttacatg 141180
catatttggt gacactttgg aggggaaaag ctttatgtct ctctaactgt agttcttaag 141240

-continued ggaatttgca tatggaaaaa caagagactc catctcttaa ttcctccaaa ccaaattatc 141300
tgggatagta catatatgtt gtactctgtc tcttagcatt tgctcttaga gaaatatggt 141360
tagagagaag taattttttc taatcataaa aattaatgat actgcatatc tgatacttga 141420
atgagtacct ccttgtaaaa tttctactta aatccttgag tttttaaagt gtaatagcaa 141480
tagaaagatt ttattattgt ttacttttgc tatgagtgct ccaaaatccc tcagtagctc 141540
ttgagagagc aagatgatgt cataggcaat attttccaaa ggtagtaggc agaaaactaa 141600
gtacacagca cacaataggc catatataca aaggcaagta ttttacaaat atagtaattc 141660
aagaaaaaag tttcatttc actggtaacc tgactgtttg tttaaaaaca ttttattatt 141720
tattatttaa aaagagtgtc acttgttaca gattgtggga tgtgttcctt aagatcacaa 141780
aaatgtaaaa tattttcttt ttatattgaa cacatacata gacaactaac ctgagcaagc 141840
tgctttttag agacatttgc acatcttttg ggatcacgtt gttaagaagt agaactaagg 141900
gaaaaagaca cagccaccca gaaaccggta gagctttcag ttcatctgtt attaatattt 141960
ccatgacaca gatatctagg aagtaaacag aaaatagcat cgctatcctg cgtcaccttt 142020
tttggaatca ggttccattc ttctcagtcc agttcatcct tctgatactt ttaagatctc 142080
aaccaagaca tagaaatatc atattttccc ttgcttaata ccccatggaa ccaatgcccc 142140
tgtggctgaa gtaaaaatta attgttgagg gacatttcag ccctctagca gtcaacaatt 142200
aaaaacatgt aagcaccgag cacctgcaga aaacttgcac tggcatttgg atctaagaag 142260
aaaatctgca tcttaaacaa catgaaaagt cgccagccca agcttgtgca gtgaagtgtc 142320
atgctggcca caatgaaacc gaaagagact gatgactctc ctcagggtgg aaaacgaggc 142380
atggaagctt tgattagtga gctgttaggc acacagacat taatttcaaa gcattctcat 142440
ctccagtctg agtaataatt cttgtagtat tatgcaattg tttggctgct gcaagaaatt 142500
cagcagactc caacaagtag tctttcttgg tctctgagtg actgtaactt aaattctacc 142560
tcccttctct tctcctacat cttcccactc cccacccgac ctcaccccac acacacacac 142620
aattcttgta cactgtgttc agagagatgc acacacacat atatatgtat atatatagta 142680
tatttgtcaa taaagcagaa aagaagaaag aactccaatt aacaattttc catttcccca 142740
tctcacctct gtcttacaag tagataggaa aagagaaaac cccagtaaaa aatggcaacc 142800
acccgcctcc ccaactttac atgctgcttc ctatgttaga ggacttggct taggcatctg 142860
attgtggagc ctgctagata caagcccata tttagactgc tacattcaac aatgtctctc 142920
tttcatatta gaaaaattcc gggttggcaa ttacaagcat ctcaaaatga ccagaacctg 142980
aagaaaggct gacttgcctc gttcaaaatg agggctctgc tctagtggat agtccggaga 143040
aacctggagt ctgaggctta ggagcttagg tttttgctcc tcaacacaga ctttgacgtt 143100
ggggttgggg gctactctct tggttgctga ctccttccaa cgggaccaat agtgttttcc 143160
tacctcacag ggatgttgtg aggacgggct atagaagtaa tagtggttac cattcatgta 143220
gttatgagta tcatgattat tgtttcctgt aatgcggctt ggcattggca aagtgctttt 143280
tgattgttct tgatcatata tgatggtggc caggcactga ctcaggcaga tgcagtgaag 143340
ctctggctca gtcacttgct tttcgtggta tgttgctggg aagaaacttt gctgatggga 143400
ctcaaggtgt caccttggac aagaaacaac tgtgtctgtc tgaggttcct gtggccatct 143460
ttttttgttt attaggcaat tcgtatttcc cccttcggtt ctagccttcc agatccctgc 143520
caaggaccta gatcttagcc tcaggcccca tcactgagct gaaggtagta gctgatccac 143580

-continued agaagttcag taaacaagga ccagatttct gcttctcccg gagaagaagc cagccaaccc 143640
ctctcttcaa acacactggg atactagagt cagactttcc ctcttacatc tagccttact 143700
gtagccacac tccctgattg ctctttcaca tcacatgctt ctcttcgtca gttgtgaggc 143760
cctctcattc ttctcccaag ccagactcaa acattatatt gatgtcaaag aagaatcact 143820
tagagtttgg aataccttgt tctctctctg ctccatagct tccatattga aaccagtttc 143880
tttctcgtgg agaagtggag tctgtgaagc cagagacagg cacatacgag agtcagaagc 143940
actctccctg acttgcctgg ggcctgtctt tcccaccttc ttctccagtt tgtctaaact 144000
ctctctctct ctctctctct ctctctctct ctctctcttt ctctccccccc cctacacaca 144060
cacacacaca cacacacaca cactttttttc tctttcccct gactcagcaa cattctggag 144120
aaaagccaag gaaggacttc aggaggggag tttctccttt ctcagggcag aattttaatc 144180
tccagaccaa caagaaattc cctaatgtgg attgaaaggc taatgaggtt tatttttaac 144240
tgctttctat ttgtttgaat gttgcatatt tctgctagtg aaattttccc ttaataaagc 144300
cattaataca ccaatcgtat tttcttattt acaacagact gagagaatta atgctgttaa 144360
cattggacct tttttctttt tttctgtttt cctttttttt ttttttcctt tttttctctc 144420
ttgtttgctt tccaggtcat gctgacctgt tcagcttgga ctgtttcaca tttgtttttta 144480
atgtcagttt aaatgtaatt gtaaaagcat gtatgctcta aattcatgta gttacttttt 144540
tcagtggaaa agcctggtat tcgaaagcat ttccaggctc cgcaatttca tatgagcagg 144600
ttttcggtaa aatcttttgt ccctcactca ggatggtatc tggacagtga gcccctttct 144660
tctggctcag tagtcagaga gaggagactt ggagacagtt tctgccggat cctgtgcttt 144720
ggcaaggatg tgcagcattg catatcattc tatcattaat tacgtttact cctccatgaa 144780
ctaaaaacca ttagactaaa tagtccaaca taaaccttga aagataaaat ttgatattct 144840
ttcgcctggc catttctctg acccagaatt ggggctggga ggggaatgga gacttggggg 144900
agagaatcaa ggaggcttct tgcctggggg aatttggcat gcacttatta atcccatttg 144960
gttgtactcc ctactaatcc ctcactccat acctgccaag gattggcttt gctccctgct 145020
tctcatcccg gtcctagttc ttcctcaacc atctccattt cccaccactg atccttctct 145080
ccagtaagat gctattcaac ctgatgaaat ataaagagta gcaccaccct ggaagtcagg 145140
ataccttagt tttagctcct gctctaccat tatctaactg tgtgaacttg ggtatgagtt 145200
aacctttgcc ctttaatctg aacagtcttt aagaattggt ttataggaga aaggaaggga 145260
tagacaagat ccaaggcctt tgaacccttt tttggaaatg aatccttttc ttcaaacaaa 145320
atttgactca gagtcccaaa tataggtaca gaataaaatg ctgctgttct tgtttgaaag 145380
gtggtggggt gcttggagcc acatgctcag gcccactttg ccacctctca ggaaccctcg 145440
aaaaaactta taggactctt ggggctctac cattgtacta gactgatgtc tggggagtct 145500
tctaactcca attttctctt ctgttacatt tcagtccttg tgaaaactct atatgtttca 145560
tcagttcact ttttcagaaa gttcacctgc ttggggtaaa gggcatgcag tggagaatgt 145620
ggggctcagt aactagcaat agtaaaaaac atcattggct ggcttacata atttactctg 145680
ttctaagcat cttaaacaca tactcatctg aaaaatcaca acaaccttgt gaggtagatc 145740
ctgttattat cttaggattc tgaaacctgc cagcttgact ctcaaccttt gacttgagac 145800
cagtcgccca agatggaaag ttatactttt cacagtttac caccgtaagc agtttttcag 145860
agtgacttct agctagagat ccattcttag aaaaagtcag aacctgccca ttagcatgca 145920
ctatcaccgg gcgcagagta ccttcactgg gttcatccca tttcctccta aaaatagtcc 145980

```
tatgcagtag tcaagtcata tcatcaccat tatataggtg agaaagctga ggtgtaggag 146040
aaatcaagag atctgttcaa ggttacacat cccataagac tctgaatacc accatcaaga 146100
ataataagcc ttttatgtga aaagcatttt agaacttcag tgtcattatt gcattctgcc 146160
tcctggagtt cagtgcactt tttcaccatg ctttaatctt ggagtcctgg tggtacagaa 146220
tctgccttct actctcaggc aacaccatag tgtctttatc cctcataaca aacatatgat 146280
ttaagtaatg atattatccc cattttacaa attagttaac tgagataccg agaggctaag 146340
tcttgcccaa agtcacaaag ctagtcagcg atagagccgg agttacaaat gaggcagcct 146400
gactccagaa tatttgctct taactactac tctttataca tatgtaagga aactaaaagc 146460
caaagaggga aagacgtccc tgaggtccca cattgagttc cccgactcat ccagtattct 146520
tctgaccttc taatcctaaa gttatacagt aagatccctt gactctaatc ctcgtagatg 146580
gaaagatggc tggcatgatt taagctacag gccacaaact ggctttcccg gagccagaaa 146640
tcacctgcag aattctgttt gtccagcaca gtgtttgttt agaaaattga catagactgc 146700
ccctaggcag ggcatcaatc actgtcactg tccccagccc tccctattta tgtttgccaa 146760
gctttttttt tttttctca tttatgtgtc tgcctgactt gtgaaggtat ttgagtttat 146820
gacttttaga tttaagcatt ggaatatata agcactgcac atacacacat actcacatgc 146880
attcacaaaa gtatagccta gtctagcttc acaaagaatt tgtagcccta caccaaacac 146940
acctttatgt ttacttaaca tttagaatta gatttaagat ctgaatttag tttcacaggc 147000
attcaagtgt ggaagaatct cggttattat tttttgtttc atactgtttc actcttgctt 147060
tccctgctgt gtctggaccc ctgtcagtcc tgctttctgc cattctccat gcctgagtta 147120
gggcccctgc aagccactca ctcattaatc tttaggaata gatggagagt ggaaaccagt 147180
ttggagggtt caccatgtgc caggcatcct ctcatttagt tctcataagt gtcctaagag 147240
acaggtggca gcacattcgt tttataaatg aggaaactaa atcttagaga agctcaacaa 147300
agacctcaaa gtcattaagg tactaattaa cggagctggg atttgaatgc aagattgtcg 147360
gactccagag cctattcttt tgccctatac cacagttcct tacaaggaag atgtattcgt 147420
tttctattac tgcataacac attgccacaa atttagcagc ttcaaacatt tatcagctca 147480
gttttgtaag tcagaagtct ggcacagcat ggctagattc tcagttcagg gtctctgaag 147540
gatgaaggtg tttaccagga tgcattctaa tctgaagctc agggttctct tccaaactca 147600
tgtaattatt gcaggattca gttatttgtg gttgtaggac taaggttccc acttcctttc 147660
tggctaccag ccaagggcca ttcttagctc ctggaggctg ccctctttcc ttttcatgtg 147720
gaccccaaca ccttcaaagc cagcaacaga gactcttcct tgtgttgaat gtttctcact 147780
ctacggatgt ctttccagga gaatcccagt cctgtgaggg ctcacctgac gaggtcaggt 147840
acatcaagaa taaccacact tcaaattcaa ctgaattagc accttaatta catctgccta 147900
gtttttcaa cagcacctag gttagtgctt gactgaatga ctggaaggaa ggatgtgtat 147960
gctcaggcct cagaatcttg ggggccatct tagaagtcag cctaccacag acgttgattg 148020
ctttcatgtg tcaaatttca tagtgagaca gggagaacag aaatatcctt gaccttagat 148080
agagcgattc aaactttcta agactttgga aacttcacat cactttcacc tttcccttga 148140
tcatggttga gaaggcctat gtcttggagt ggcaaggagt gagactggaa cagtacctaa 148200
aggttaagga gactaaagaa gttacagatt ggtcacatct gctcctccct aggaatgagc 148260
catggaacct gatttgaatt ttttttttct ctggtgctat agagatagct cccacagggg 148320
```

-continued

```
tctaatgccc caaggctgaa aagttcgttc cccataggat ccaggcatga tatcagacca 148380
ggtgttacaa tctcctaaag aggaggtatg gacaggaaag ccccttgcca atgacccttt 148440
cttgtcactg ctctgactca agactaatag ggcagagata gtgagcaact cacatactac 148500
taaaactatc cacttatact gccccctttc tccttgcttt atcactccat ttaagtaagc 148560
cagtgagtct ctgccttgac acagtggcaa gctgatctgt atcttatatg gaagaattag 148620
atttgactct ggggctcagg tgcagagggc aggaggggca taggggtggc cctcatggaa 148680
gaaaacaagt ccttggatac tgagtaacag ctgagactag caagccttat tgtccaggat 148740
tccaagtcgt ctagcaacat ccttgcctct gctgcagaga gaacagagga tcccccggca 148800
gaatgaatgg agtctgattt caattacgtt cagtnnnnnn nnnnnnnnnn nnnnnnnnnn 148860
nnnnnnnnnn nnnnnnnnnn nnnnnnnnnn nnnnnnnnnn nnnnnnnnnn nnnnnnnnnn 148920
nnnnnnnnnn nnnnnnnnnn nnnnnnnnnn nnnnnnnnnn nnnnnnnnnn nnnnnnnnnn 148980
nnnnnnnnnn nnnnnnnnnn nnnnnnnnnn nnnnnnnnnn nnnnnnnnnn nnnnnnnnnn 149040
nnnnnnnnnn nnnnnnnnnn nnnnnnnnnn nnnnnnnnnn nnnnnnnnnn ngggtcctgg 149100
aggcaagtgg gaatgcagct tctcttcctt aagcagatgc catataggcc tggggaggag 149160
aatgtgagaa taccagccaa gttctcattg gcactatacg gagaaagggg aattatttca 149220
tcttgatgga ttctccccac agtctctgca catattgatc ttacttgtaa tgagtttgtt 149280
cagattcacg agtcatcatc ccagggagat ctgagtcatt ggtgggaaag tcgaggtgac 149340
agattatatc tcgctgatct cactgtcacc aattgctctg tgtgtccctc caccttttga 149400
aaaagcccat ggaatcattt gtgtataatt aatttggatt tatttcttat ttatcaatag 149460
ctttagtggg gtattgtaaa tggaaagct accccagaga acagtgtaca ttcacagtat 149520
tattcaatag aactttctga gatgatgaaa atcttctata tcttatgttg tccagtataa 149580
tacagccgct aactacatgt agcttttgaa cactgaacat gtggctagtg agactgaggg 149640
attctatttt taatttttta atgttgtaat taatttaatt ttttaaaagt tttgctttct 149700
attttatagc ttaataatta aactaaactt acatagccca catgtggcta gttggccact 149760
atactggaca gtacaagtct agaaagatct cagagagaca catgctgaga tacagcagga 149820
ataggttagt cagaaagaga gccaatgtaa catagggaat tctggattgg gaattagagc 149880
cctggctcta atctcagctc tgccactagg tgaccttgcc ctctctggct tcagtctccc 149940
catctttaac ttgaaaggtt aaactaacta acgtcaaaag tcccaaaatc gtggctatgg 150000
actgaattca atttgggata cataagtttc aggaattttt ttaaaaatct attaatgcct 150060
tctaggtgtg tgtatgcacg cttacaggca tgtacccatg cacaagcatg ggacggcagt 150120
aaggcattca ttccagttca ccagtgtact aaccattcac acatacacac acacacacac 150180
acacagacac atacacacac acgcatgcat acacacccta ctgtattgcc tatgtagacc 150240
ctgaaggtct ttgaatctgt caccattgga taagataatt tctaacgacc cttcccgttt 150300
tgtcctgctg aaaatcttta agccactata gtgtccccaa tctatttcaa tttgggcaga 150360
tgactggagt attctcatag cttcctgtct cttcccctct gaatttgata ctagttatga 150420
agtttggcgt caaggatgaa gaagggaggc agggaggata taaccccagc cccactcctt 150480
aactccgctt ttggattaga agtagcgttc agggcttcag attccttggg gaggaagtag 150540
agataatatg ggctttgtaa tcagaagatg gggttcagat gattgggttc tcactttttc 150600
gatagctgtg ttacctcagt ttattcattt gtaaaatagg gataagaaat atctttaacc 150660
tcctaagatc atgtggaatt aagtgatgta acgtgatgaa gcgaggcatg cagaaggccc 150720
```

-continued

```
tgaaaaaata atagttaccc ttaagggaac taaatggtct ggcaacttgt gagctcaaag 150780
ctagaaaggc ccggtgatgg ggaagatggg gtctttctgc aggaactaca gcaggggagc 150840
agaacctgta agccaccagt ctgtggagct gtgtccaaga actcatgttt gcaacaagtt 150900
caccaaatta caagatactg tggggtccag gcctctaact caagaagatg gtcttggccc 150960
agatcatacc ttgcagcctg tgcctttggt gggatgtgag tgttggcagt ggctatgcat 151020
atctccttat tactggctgt gcccaagccc tgcagaaatg attgttggac aaggtcatct 151080
tgcactcagg gttggttttc caggcttcct tgttattttc cccttagttc ttctgtgctc 151140
ctcttgcaac accaacccca ccatttccct cttccctacc ttagttgttg gtccaaacat 151200
gtaatccatt cttgcagtga tttattgagt gataccgtaa ctggagtttg cattgaagga 151260
cttatttttc taattagaac taaaagtcag ttccaggctg ggtgtagtgg ctcacgcctg 151320
taatcccagc actttgggag gccgagatgg aaggattgct taaggccagg agtttgagtc 151380
cagcctgggc aacatagtga gatcccatct ctacaaaaaa acatgttagc caggagtggt 151440
agtgtacacc tctggtccca gctacttggg agactgagga gggagaattg cttgagccca 151500
ggaagttgag gctacagtga gcttttatca tgccactgcc ctccagcttg ggtgacagag 151560
ggagatcctc cctcaaaaaa taaataaaaa ctacaaaaaa aaatgtcact tccaggttgt 151620
atcttttttc acaggggcca gacacagatg aggagtaggt tttgttgtat ttatccattt 151680
aaattgagca atcagcttct ctctttggtt tataccttto ttatttatta ttattatttt 151740
aaaaggatta gagataaagt gctttatggt ctttctcagt gcaactgctt atgctagacc 151800
tcagaattat gacctcttca attatttata tttccgtctt tataaatact ggaaaaaata 151860
gtacaaagta aacatcggga tgcctaagga cctctaaatt gtgtgtgagc acctggggaa 151920
gatggttctt aaggtttgag ttttggatta ttgtggttgt cttaaataat gttatttcta 151980
tcattccttc caatggctgt ctcctagcat ggttcccatt ttacagactg atggtagagg 152040
cagaaagatt ctctcacttc tttgatagta ttgaggattt cagcctttca ccgctcctct 152100
ccccttttgct aaaaaagaaa aaaatcaata tgtatgttat agtgtatgtt caactatgag 152160
caactatgtg tattcaatga gaaatggaat accataaaat taccatagtt gaaccaaaat 152220
gataggatag aattcgatag tctgaggatg gaagggaact tcaaggccac tttaaaaaac 152280
cccattccta tataatgctt gaattcttaa ccactgtgca tctagtattt gatcatttcc 152340
agtgatatgt gtgcctggca acttttccat ctcccagcgc tttaactatc aaaatgtatg 152400
tatgtgtgtg tgtgcatgta tgtgtgtgtg tttagagaca gagagagaca gaaagagaaa 152460
gagagattaa aatccaagtc actgttcttt ctgggaccca aaaaacaagt ctagtcattc 152520
tccatttcta gtctctttcc ctagcaatcg gctagacatg ctagacatag acacatgtac 152580
atcactcctt tgatttacag cattcagtat ttgtctatca cttataagat aaaacccata 152640
cttacttttt atttttattt ttttagagac agtgttttac tatgtcaccc aggctagagc 152700
atcagtggca caatcatagc tcactgcagc ctagaactgc tgggctcaag caatccttcc 152760
acctctgcct cctgagtagc agagactaca gatgtgcacc accagacctg gctaatttag 152820
ttttttacta attttgtgga gatggtgtag tgtcttgcta tgttgctcag gctgatattg 152880
aggtcctggc ctcaagcact cctcccatct cagccttcca aaatgctggg attacaggta 152940
tgaaccacct tactcagcca gatttcttaa tatgatatac atgctccttt aaaatcaagc 153000
accatctttg ctttcaaccc cattattaac cactttccca tatacgcaac atatgcttca 153060
```

-continued

```
gtcatactag tctctggttg ttccccaaac actcctcagt gcttttgttt atgccctttc 153120
tgcccacctt tgcctggtga aatcctcatc aatcttcaaa ttctaggtca aatactatct 153180
ttcatataaa gcattttcta aacccacctg tgtaaaaaga ttagtggttt cctattttgt 153240
tgatgcctcc attgcagcat tttccagtct gactttttct agaattgact gtggcaaggc 153300
taccagcctg ggccagggcc tgtgtctttt ctgtcaccca gaagcaaagg tctaacaatg 153360
gatatctgct gaatgaatga atgaaaatga atcattaata tagtagtaaa tgagttaatt 153420
aaaggttcca ggtatgaata ctgaagcctg cattgaggca gagctgaatc caagactatg 153480
ttaggttggt ctggcacaag aatcagagtt ttcctctgca agctatgaaa aatttgggtt 153540
tagcacggat ttgggatgac gaattataca ttcaaccagt gttgaatgag cacttgtcct 153600
taaggagttt agagtctgtg accagggaga atgatgattt tcttagctcg ggcagttttt 153660
ctaacaaggt agttgcattg tgtgtttttg aacactgatg ataaattcaa gtttctcttc 153720
ctgccccata gcccggaagc tgaagaaact tggtaatctg aaactacagg aggaaggaga 153780
ggcttccagc accaccagcc ccactgagga gacagcccag aagctgacag tgtcacacat 153840
tgaaggctat gaatgtcagc ccatctttct gaatgtcctg gaggccattg agccaggtgt 153900
ggtgtgtgct ggacatgaca acaaccagcc cgactccttc gcagccttgc tctctagcct 153960
caatgaactg ggagagagac agcttgtaca tgtggtcaag tgggccaagg ccttgcctgg 154020
taaggaaaag ggaagtggga gcatgagata agggggatca tatttagtga acgctcctat 154080
gggccagcca ccacgtctgg tgcttttctg cccattaact caggtagtct tcgtcgtaac 154140
cctatgggag agggattgtt ataaatctca ctttaaacat acagggattg agactcagaa 154200
agcaaagaga aagataatat tataaggtgt cctatgtggc ccacattgat gcacagcagt 154260
catgctttca catttaactc acagaaatgg tcagcaaaat ttcccttaat cacaaaatca 154320
catagacata tccatatatg ccttaggata ctcttctata tttgcacaca caggctcacc 154380
ccaaagataa tctccagcct gactgacatt ctgtcttcag tgtcaccttt aggaactata 154440
tcatgggaac tctcataata tgatatggta gaaagaacat gaggttggga atcagaacac 154500
ttcagatcta cttttagttc tgctagtaac ttattgtgtg attccttccc cttctgggtc 154560
tcagtttctc tatctgtata atgtataagg catggtttgt accaaattga tggttttcaa 154620
attttgcttc gagaaatgct ttgtgcactt taaactacct aaggaatcat aataggagga 154680
aagattaggt gatagtgaaa gaattatcaa ctgttggtct aacagaagtt ggataacaga 154740
agttccccag tgatggggaa ctcacttctt tcttatgtca tctgttgctt aaacaagtct 154800
ggttattaaa atattacagc ttaaggaatt cttagagatc ctctatccaa tgattcacaa 154860
actttcattt aacagccaag tgctttattt ctcaaaagaa ttgtacacag atatgagtgg 154920
agctagttta tttaaagcca gagtctgtgg cttgggcctc accagttcag cctctttctc 154980
tctatcccag ggaagccccc aggtcactct tgcaaaatct tagggctccg aggaacacag 155040
tttgaaaacc agtgaagtat atgctcttta aaggttctcc taatcttgca attatgattt 155100
aaagactctt ttggaataat aacaactaaa ccttctcttg tggagtcaaa gattaaccgg 155160
cctttcaata ataactgcca ttcaggtaga aatgtatagt gaacagagca attttgtata 155220
tattacctga attgattctt ataggaatcc tataaaatga gattctttct cctgttttac 155280
agaccaaata gggaagctgt gagaataatg tgattgacct atagttacat agtcagaaaa 155340
tagcaggacc agaacttgag cccaggttct ctcctgattc caaatcctcc ctttattcca 155400
ctccacctgt aggctgcagc accactgcag ttctgtaact ctgggcttta cagtgagggg 155460
```

ccaaggcttc actgaaggcc acttgggtca tactgtgggc ttgctgcatt tgaagacatt 155520
gcatgttggc tgtcaagtct tagatttgta tttccaactc acaggttagg cctggtcaca 155580
gccctaacca tctcttgcac cttctcagct tgggaagctg aggttgacta ggcaataaga 155640
tcactgggaa ggaaacccaa ggactctgat tggatatgtt ctgtgccaaa gcagagggtt 155700
cacacagaga ggaaaaatat aaaaaagaaa aaggagaaag ctgctttaat tcttatcact 155760
ttttcatctg gatattttga tatcatgtgt ttgacaaaga ttcaaagttt aatcttccca 155820
agcagtttcc aaacacttat ctcattttat aagttacaga gctttttcat atatatgatc 155880
ccagttaatc ctcacaacaa ttctatgaat catagagact attatttcca tttcacatgc 155940
caaggctcaa agaggataac taacttgctc catttggtca cttaacacat ggaaccagaa 156000
cttgacctag accttcaggt ttctaaattg gttatcttga caataaccta gtgcaaaact 156060
ctatagcaga atttgtatga cttgggatca ctggggcttt ccttggccca gccaccagga 156120
tggaaagtcc cctcccctta cattaacaaa tctgcaaacc aatatcagtt caccatctag 156180
cttgccagac taagtgatct ctgactccga atcttttaaa agaatagctt caaaagaaag 156240
ccaattacca cattcataag aactgttctt catattatct ataattacct acaagttcaa 156300
gtaattcact aattcaatag attgagttct tgacctgtaa aatgaactgt gctaggcctc 156360
taataagata aattttgttg taagttttct acgacagtaa tgatgtatgg aaattgccta 156420
gtagagtacc tggcacatta ataaatgata actattaatt tagagtgggt gagtagactg 156480
ggtgtgcaca gtatatttag aatctaattt atctggtttg gaatcctagc tatggactat 156540
ttctgtgacc ttgagtaaat cacatgtctt ctctgtgctt ctgtgtcctc atttgtaaga 156600
tgatagaata atcgctacct ttcaaattgt cgtcaacaaa gagattatgt ataaagagca 156660
cctagtaagg tagcctgaaa catagtaaat gctctgtaaa tggtggttta ttattatgag 156720
acttgagtgc taagccactg ctttaatgaa actcaatttt agctaccact tgccttgcct 156780
gctcatgcat ggaccacaag gtgaaattgt cttctctgaa gaccttggca ggcagatgca 156840
ctacagcagc aaagatttcc aaactggcct ttctttgagc ctattctccc agaccagaca 156900
tgagactaca agtttctgct gcacatgaaa aaaatatgat gtcagttgga ttctagtgag 156960
aaaacagagt gtctaataaa ctgcttctgc tccctagcct gtttaatgtg tttcaaaacc 157020
tgagaatgac tcctctctgt ttctccagaa cagcctaaca caatggcaaa tgggcattga 157080
gtgaatgcat acttaaggaa atctgtaggg ctgcggctac tctttcctca agtaatccct 157140
tgatagtcat gcaggctact tcagagattg ggcattagag aacagagtca ggtattataa 157200
tcagattaga ctctagggag attagccagc catattgctg atatgtgcac agttactggg 157260
cttccgtgct aagcagctct cattaagcac agttaattaa tattatggcc aacttaagct 157320
ttccctttc tctcctgttt gttagttcgg cagcatttta gggagaaaaa aataagcatc 157380
agtatggaca atttgcttca tacctgtacg atttaattct catccttcca tgggccttca 157440
cattcacaca ctccactaga agaccaaggt tcaccagcca aagacttttc ttgctcccca 157500
ctgcctccta cccaagatat tcagggttca acctcccagg cctcttctct aagagatccc 157560
tggttgctac atgcctagac cctgcttctt atttcctact gagaagggtc agtccaaggc 157620
attctgtgct acagaagggt tccagacagg aactactctg ggatctgagg ctccagccag 157680
tctgtcagtg tgtcattacg gtgaaggtgg gaagcacagg cctgggagct aagactgcca 157740
agatgaggta ctctagaatc cctgatatct ggaaggctta ggatctaaag gaaaagaaca 157800

-continued gtgaaatggg gctatatgag tggacaggga ccaaccaagc agaacaatgt atctggataa 157860
tgtagacttc agacctgatc ctatggctga caaaagttgg tgaccttggt ggttcctgag 157920
ctgtaacctt cagcagtgga gtagaaaaaa cactggagaa cagaatcaga acacctgggt 157980
tctagtatta gttcagccac atataaacca tatgaccttg ggcaagtcaa tttatttctc 158040
tggccctcat gttccttgtt ggtaaaataa gtgtcacatc acctaacctc tgggattatt 158100
gtgagagtta aattaggtca tcaacaggaa agtgagaagt ttggtctaca tttggggaag 158160
cattcctaat gaggtatgat gacaaaattt cagataattc tggatttgtt agtgagaaga 158220
gagagtgttg gtagggatga gctctgaggt gatgccttta taactttaag catccaactg 158280
tttcagaacc tccaggagaa catggccatg tctgtactac ctgtgtgtta ttgtagaggt 158340
agcatctggg agcctctgct ctctgagctt aagggaggta atttggagat catttaattc 158400
tcattttata aaaggaaaac aaattgagga tctttaggcc atttgtttag gtttcttaag 158460
tgcccactca aatacgtgga ctgtactaag tactagggag gtaaacttga atatgaagat 158520
atggtccctg tcttcaagaa gctctaagtc ttgtggggga gacagacatg tatgtacata 158580
gatttcaatg ctgtgtaatg agtgctataa ctgtgtgagg ctacacaagg agcaatgaga 158640
atgtaaaata agaatcttta agccttcttc ttggatgagt tggaaaagcc ttcacagaag 158700
aggtagcctt tgagtgaaga cttgaaagat gagtaggtgt ttaaccggat gaaagacctg 158760
agaaggagga atgcattcta ggcaaaagca actgcctgtg cagagataac agagatatag 158820
aggcatgtga gagggcaagt ggcaacagat cagtctaggc agcaggtcat aaagggcctg 158880
ttcatatata atgatggcag taagatgggg atggcagtaa ggtgggaaac tagtagggcc 158940
aggctaccta ttgagtagaa aagaatggag aggaactgcc aggcagaaag tgggatggac 159000
gcaagaaagg gaacatgaaa gtggtcaaca ggaggcagtg gctgtcaaga catctctcca 159060
tacactgtac actgtatgta atatccgtct cccagggttg ttagaagggt caaaccagct 159120
catagctgga aaagagcttt gtgaagtgaa aactgtttat gtgggagaaa tgatgttatc 159180
ctgcatcttc ggaaaggtag agtgatcaag agcacagacc ttggaatctg actgctttgc 159240
tttggaactt ggtctaccaa ttactagctg tatgatcttg gacaagttcc ttaatctctc 159300
tctgactcac ttgtactggt tcacagaatg gagataataa tagtacctac tttactaatt 159360
gttgtgaata ttaaatgaga taatataagt aaagtgctta gaaaagagtt aaatgtgccc 159420
cataaataca tacaactatc atatacccaa aatatttttt aagttttttt aaaaaagcaa 159480
tccaatggaa atcaaaagaa aaaaagtttg ctcgtatatg cagtcaataa gtgttagatt 159540
atttttctct tacaactgac aatgcccttt ttttctccat catcatctca tttgagcagc 159600
tcagtgatgt agggaggaca acgaatatta tcctcaccat atagtttgtg cttttcccca 159660
ccacccctca gtggccagtc tggatggtcc ctggggatcc ttaggggatg tccaaatgcc 159720
agagcatctc tacccagcag gggctcagac ttagctcagc ccgtcagtac ccagattgac 159780
cactgcctct gcctcttctt ctccaggctt ccgcaactta cacgtggacg accagatggc 159840
tgtcattcag tactcctgga tggggctcat ggtgtttgcc atgggctggc gatccttcac 159900
caatgtcaac tccaggatgc tctactttgc ccctgatctg gttttcaatg agtaagtgct 159960
cctggggccc agacctcact aaaatacagc agcttggcca gacccagttg gtggtgatgg 160020
tgatggagtg acagtgaagc ttacctcatt tgacctgcag gtgtggcatt ggatgcccca 160080
gccagccaac tcggtatgag gcagctttgc cctggctttc agccaactgg taggagctga 160140
ggaggatggt gctgagacta cccctttcac acccaagaac caatcctggt cgtgtttctg 160200
gtctccttta cagcttatct cagaaccaca tggaaagatt cctccccttc actttgagca 160260
acatataaaa gaggcagaaa gactctggct ttaagggctg aagtttcttg ggttctgttg 160320
ctaccaccaa aggctactgc tagtcaccac ttgctgagca attagtttgt gccaagaata 160380
tgctagatac tttctaaatc ctatctcatt gagtcctcat ggtgacctga cctccccttt 160440
ttatagataa ctctattttt tttatggacg gggaaagtca ggctcagcaa agtaaagtga 160500
ctcacccaaa gtcacagagc tagtgcctgt tggagagaag attcaaatgt atttccgtgt 160560
gaatcccagc tcttctgcgt catggtggta actgatgggg aggagtacct ctaccactct 160620
ctgtctgtgt gaccttggta ctgccatttt ctttctctta aacagcttta attaatacct 160680
gccctgccac tagctctata taacatcatg aatttggcca gtggctcaga ttttggaatt 160740
acatttttct ccactaaaat ctcagttcta ttattttctt aatcagcatc tttgggaaag 160800
acccttaact tttctgaccc ccaatttctt catcaattaa tgataataga accttcataa 160860
gtaatttctt atgataacta aatgggaact gacagatgtg gaatgtctgg cccatagtgg 160920
gcaagaagaa aaaaaaaaaa gtccctttct gatccaccat tccctaagag tgatattttt 160980
ttccccccaa gatggagttt ggcgctgcca cccaggctgg agggtggtgg tgcaatgatc 161040
tcggcccact gcaacctcca cctctctggt tcaagcaatt ctcctgcctc agcttcccga 161100
gtagctgggc ttatagatgc cagccagcaa tgtccagcta atttttgtat ttttggtaga 161160
gatgggattt caccatgtta gccaggctgg tcttgaactc ctgacctcat tatctgccca 161220
cctcagccag gcatgataat cttttctatg tctgctgtat gaggtccctc gatggcataa 161280
tgaatggagc tggccagaga aatcttccca aggaccttga gctagtctcc ccacagagaa 161340
tccttccagt caggacagga attgaccttc ccccctcttc agccctctaa cccagaagag 161400
tcttaaaata aaatctacag gccagtggtt ccttccagta cagcactgca atgtgaggga 161460
gagtgagcgt ccccagctgc cctctcccaa ccctgccagc ctggtagcca gaagctaaga 161520
ataaccacta ggcttttggc acaaactgct ttgtggtttt cagacctcca aaaagttgcc 161580
tatgatgcca tcttctgggg caggccttga aaagccccct aactgttcat ctcccatcct 161640
caaacccctg ctgcccttaa gcaattgaat caactccatg agcacctgct ctaccttccc 161700
cagagctctg agacctttgg agctttgaaa agtgataatt ggctgttctc taaatcctca 161760
tttccttttc tacctctgag taagcatgtg gcatcccacc tcagcttcct ggtccagtct 161820
tgttcagctt ataaaaaggc ctccccacag ggtcagaggc ctagacccat caaatcccag 161880
ggctcctgaa acaataggac ccctattcct cctgtaggaa gccactatgt tagaactctc 161940
agggtgtcta caaacatcta gataagtgtt tctcaacatg gattattttg acatattggg 162000
aaaaataatt ttgtcaatat gtagaatatg gttgacatac ctggcaccag cctactttat 162060
accaaagagg attccagtca ttctgacagc ccaaactgct cccacgcatt tctaacaccc 162120
actgaagaag cagtactctc cagttgagag tgactaattg ctgccagcct ccctaaggtg 162180
ctaatgggga gcctcagacc caaagaggga gataagaact tgttcaaagt aggtcaaccc 162240
atttgctgat ctcttcaaca ccaaactcta ttatcagccc tgttttttcc tttccttctg 162300
tctttgtaga gatcacatgt tgtgaggata atgagcctga actttagctg tgtgaccttg 162360
ggcaaattac tgaacttcta tatgcctcaa attttatctg gagactgctg aagagtatta 162420
taatagcacc tttctacatg tcatttatgg aacacctgct atgtgtcagg cactgtgctt 162480
agtgttttcc aatcttcatt tctcatctta ttttctctct tgcactccca ccaaccctgc 162540

-continued tctcctccta aattccattc ctgcctcatt tttataccct ccattctcct ctctcttcct 162600
tcctttaact gtctccctag tattttttcc ctttttcccc ctttcttgtc cccttcccct 162660
atgaatttcc tccctttcct ttccccttct ctttcctcca ttccccactt tttctgcccc 162720
gaggcctgca gcaatgttaa aggaatcctc attccagcat tgtgatttca atggtaaaaa 162780
aagattgcag cactgtcatc aacagaggtg ggaaagtaca ttggagactg gagcagggcc 162840
agacctcagg gtcagccaat cttactaaaa aattctctat agtgaaagag cttggagcaa 162900
cactgttctg ctcaattgat ttgtgatacc atctaaacac ttcctctttc cagttgggct 162960
tcagcctgag ttgaataatt ctacaccatc tgccccttc tctctttctc caggacagcc 163020
aagatctctc tgagatagga tgctgagttt ccacccagac aataccaggc cttctcatcc 163080
tgtggagtag gctagtggct tggaaaccaa aatgtcaaac catagccttt aggctccatc 163140
tgggaggtct ttgtcctcac cacttaagtg ggtgtcagat ttccttccct ttctgcacat 163200
gctgcacaat caatttctgt cttacacaca cacacacaca cacacacaca cacacacaca 163260
caatttttga agtgctgaaa actagaaagc ctactagcat gaggatgctg tgtcttctct 163320
tagaggtatg ccatggtcag ccatggaacc aagagggtgc tcttccttga aaagttggcc 163380
aagcattggc cacctccccg tataatttat aggtgataat gtggtgatct gttcagaagt 163440
aactataata aatgcagctc acatatgtct acagtttcca aactgtggta aggagcagcc 163500
agcatatgag ggaatgggct cccccttcagc aggggacatt taaattagac attcaaaaac 163560
actccctggc agatttaaca ttgaaactca ttttgaaaga acaatgtgga atctccttca 163620
ctggaagttt ttgaagaaat attaaatttc tagtattcca ggccagaggc aaaggggtca 163680
acaggatgac caaacacttc gggtcacttg caaatcctgg tgtcctgatg ttaagagctg 163740
actactgggg cttctcctaa aaatccttca tgttgagctg cctgggaggc aggttcttgt 163800
tctggctgta gatgggatat tagaactgta gtcagggaga ccatgtgcct gccccattgt 163860
gttcatttgg ttaggctttc ttgtccccga ctcagaaaac agaaggggca cagagacctg 163920
gaaattccat gtgctaaccc atatcctggc cagggaagat agtagtaatc aggatgtcag 163980
gattttggaa aagagagaga taaaaaaaaa acaaaaaaac aaaaaaaaaa acagaccaac 164040
aaacaaacaa aaacctcatc ctgatccctg aagcaccagc aggagaaaca gcaagctctt 164100
cttggagaac ctggggagga agggcaatca gagacattcc ctctgggctt attgcaagcc 164160
tcccctcatt ccttttttcct ctatgtatct ccttcccagg taccgcatgc acaaatcccg 164220
gatgtacagc cagtgtgtcc gaatgaggca cctctctcaa gagtttggat ggctccaaat 164280
caccccccag gaattcctgt gcatgaaagc gctgctactc ttcagcatta gtaagtgcct 164340
agaggtgcag ggaatgcccc tgagggcaca gagactcaga gaggaccact tttgacatta 164400
aaacgttatt agggagaagc cagctccttg acatttccct tcttcatttc ccctccccat 164460
ccccactgta ctctccctca gtatcattct tctaacaaga aacaatttca tgactagaag 164520
ccaatgtatt tgctagaagt cagcttccat cagattcccc acctatccct agtctatctt 164580
tgggacaagg cctttttgac tggttatagc aggtctgtga atttctccac agcttctgct 164640
atagaaacaa acatgggcca ccttgtattc cttgcagggc agtaaagcag gaggcatttc 164700
ctcctggaaa gatttcctct tctgccaaca ggaggaggtc tatgtaagca actcaggtag 164760
gatttatttg gcagccaagg aacttttctt taatatcttt tctaacaaga gccctttctt 164820
agcctctgtt gagggagaaa ggcaaaattt gatattcaaa gctatgtgtt ttagttgtct 164880
aaatcagggt ttgactgtaa atgacataaa agcttaggtc ctaaaaaatg agtatatgag 164940

-continued aagagtagaa aaagaaaaga ttcaggaaat ttgatttact tgactccctt cagattggat 165000
ccagctatcc tttcccctga gatctccctg acagactgaa gtccccaagc ccacagactt 165060
caactaacag gaagccaagt agatggttcc ctgtgggggt gggggtcaag tttgtggtca 165120
gaaaacttgg tgctttgtct aatgttcctt cgtgggcatg cttcccctcc ccattctgtc 165180
ttcatcccac atcagttcca gtggatgggc tgaaaaatca aaaattcttt gatgaacttc 165240
gaatgaacta catcaaggaa ctcgatcgta tcattgcatg caaaagaaaa aatcccacat 165300
cctgctcaag gcgtttctac cagctcacca agctcctgga ctccgtgcag cctgtaagca 165360
aacgatggag ggtgctttat cagggagaac agcctgatag agccaatgat aatatgcttc 165420
tctagggtct ggcaccacct gttgggaggt gcttccattc ccctctggct ttgagtgtgg 165480
tccaggaaga aaatgtggtg aagaaaggaa cacgggtcac agtgtcccag ctggatattg 165540
tgaaaggggt ggaggagttg agaacagagc agttgggact cagggaaggg acttacagca 165600
gatgaattct ctaggcagac aaaacagacc tggatgtttc tcccctcttc tttgagtcat 165660
gttcatgtga gtttgtgtgt gtgtgtgcgc gcgcgtgtgt gtgtgtgtgt gtgtgtgaca 165720
gagagagaga ggagagaggg agagagagag agagagagag agatggagtg cagaggctgg 165780
ggtgagagca caagctggag aagtcttgag tcagaaagct tacaatggta taagacatcg 165840
cttgggagcc ctcagtgact cnnnnnnnnn nnnnnnnnnn nctctctctc tctctctctc 165900
tctctctctc tcactcacac acacacacac acacacacac acacacacac acacacacac 165960
gacctcatgg gggaggacca aggaaggaca gggaaggggg aggaaacaaa agactgaaag 166020
accaaaaatc aaaggttagg gaagagtcta gcagagccca cctccttgtc aaccctgttt 166080
ttctctctct tattgttccc tacagattgc gagagagctg catcagttca cttttgacct 166140
gctaatcaag tcacacatgg tgagcgtgga ctttccggaa atgatggcag agatcatctc 166200
tgtgcaagtg cccaagatcc tttctgggaa agtcaagccc atctatttcc acacccagtg 166260
aagcattgga aatccctatt tcctcacccc agctcatgcc ccctttcaga tgtcttctgc 166320
ctgttataac tctgcactac tcctctgcag tgccttgggg aatttcctct attgatgtac 166380
agtctgtcat gaacatgttc ctgagttcta tttgctgggc tttttttttc tctttctctc 166440
ctttcgtttt cttcttccct ccctatctaa tcctcccatg gcaacttcag actttgctcc 166500
ccattgtgac tcctatctgt gttttgaatg gtgttgtatg cctttaaatc tgtgatgatc 166560
ctcatgtggc ccagtatcaa gttgtgcttg tttacagcac tactctctgc cagccacaca 166620
aacgtttact tatcttatgc cacgggaagt ttagagagct aagattatct ggggaaatca 166680
aaacaaaagc aagcaaaaaa aaaaaaaaag gcaaaaacaa aacgaaaaat aagccaaaaa 166740
accttgctag tgtttttcc tcaaaaataa ataaataaat aaataattac acacatacaa 166800
acaaatatat agaaatcccc aaagaggcca atagtgacta gaaggtgaaa attgcaggcc 166860
cctgggaagt tactgatttt ttcatctcct ccctccatgg gagactttat tttctgccaa 166920
tggctgttgc cattagaggg cagagtgacc ccagagctga gttgggcagg gggctggaca 166980
gagagagagg agaggacaag gagggcagat ggaacatcag tacctgccca cagccttggc 167040
ccctgggggc tagactgctc aactgtagag caattcatta tactgaaaat gtgcttgttg 167100
ttgaaaattt gtctgcatgt taatgcctca cccccaaacc cttttctttc tcactctctg 167160
cctccaacct caaattgact ttcaatagtt tttctaagac ctttgaactg aatgttctct 167220
ttagccaaaa cttggtgact tccacagaaa agtcagacca ctgagaagaa ggggagcaga 167280

-continued

```
gatttaaccc tttgtaaggc cccatttgga tccaggtctg ctttctcatg tgtgagtcag 167340
agaggagctg gagccagagg agaagaaagt gatagcttga ctgttctcct gcttaggaca 167400
ctgactgaat agttaaactt tcactgccac tacattttcc ccacctttaa aagacctgaa 167460
tgaagttttc tgccaaactc cgtgaagcca caagcacctt atgtcctcca ttcagtgttt 167520
tgtaggcccg aacttcatca cactgcattt cagccatggt ggtcaagcct gtttgcttct 167580
tttgggcatg ttcacagatt ctctgctaag agctcccccc atcaagaagg ttagcaggcc 167640
aacagctctg acatctatct gtagatgcca gtagtcacaa agatttctta ccaactgtca 167700
gatcgctgga gcccttagac aaactggaaa gaaggcatca aagggatcag acaaactggg 167760
tgtcttgtcc ttgtccccca gagatgacac ccttccagca agtggagaag ttctcacttc 167820
cttctttaga gcagctaaag ggctgcccca gatcagggtt gaagagaaaa ctcaattacc 167880
agggtgggaa gaatgaaggc actagaacca gaaaccctgc aaatgctctt cttgccaccc 167940
agcatatcca cctgcagaag tcatgagaag agagaaggaa caaagaggag actttgacta 168000
ctgaattaaa atcttcagcg gcaaagccta aagtcagatg aacaccatct ggtgagttca 168060
ctcatcatcc tcctctgctg ctgattctgg gctctgacat tgcccatact cactcagatt 168120
ccccaccttt gttgctgcct cttagtcaga gggaggccaa accattgaga ctttctatag 168180
aaccatggtt tcttccggaa aggtctggtt ggtgtggctc caatacattg ccacccatga 168240
actcaaggtg tgccctggga cactggtttc atctagtctt ttggcacgcc tgtgttctgt 168300
tgacttcatt ctccaacccc aagtgcaagg caaaatgtcc acctactttc tcatcttggc 168360
cactgcctcc ttacttagct cttaatctca tctgttgaac tcaagaaatc aagggccagt 168420
catcaagctg cccattttaa ttggttcact ctgtttgttg agaggatagt ttctgagtga 168480
catgatatga tccacaaggg tttccttccc tgatttctgc attgatatta atagccaaac 168540
gaacttgcaa aacagcttct ttaaataaca agggagaggg gaacctaaga tgagtaatat 168600
gccaatccaa gactgctgga caaaactaaa gctaacaggt tccctttctg ggatgggata 168660
gacacattct ggttttcttt attactacac catctggctc atgtacagga tcacttttag 168720
ctgttttaaa cagaaaaaaa ttccaccact cttttcagtt acactaggtt acattttaat 168780
aggtccttta catctgtttt ggaatgattt tcatcttttg tgatacatgg attgaattat 168840
atcattctca tatctctcct tgtaaatact agaagctctc ctttacattt ctctatcaaa 168900
tgtttcatct ttatgggttt cccagttgtg actcttgtct ctatgaatat atgtttttca 168960
tttgcaaaag ccaaaaatca gtgaaacagc agtgtaatta aaagcaacaa ctggattact 169020
ccaaatttcc aaatgacaag actagggaaa aatagcctac acaaggcttt aggccttctc 169080
tttctgtgct tggatttgag tgaacaaagg aggttttagc ttggctctgt tctcccatgg 169140
atgaaaggag gaggattatt ttttttttct tttggccatt gatgttctag ccaatgtaat 169200
tgacagaagt ctcattttgc atgcactctg ctctacaaac agagttggta tggttggtat 169260
actgtactca cctgtgaagg actggccact cagacccact taactggcga gctagaagat 169320
gaggatcact caccggaaaa gtcacgagga ccatctccaa acaagttggc agtgcttgat 169380
gtggatgaag agtgaggaag agaaaaagaa ggagcaccag ggaaaagacc tcgtctgtgc 169440
caggcagcag actgctgcca ggatcacgaa ctctgtagtc aaagaaaaga gtcgtgtggc 169500
ggtttcagct ctcgttcatt gggcagctcg cctgggccca gcctctgtgt tgacatggga 169560
gttgttggat tctttgtttc atagcttttt ctatgccaca ggcaatgttg ttgttcttgg 169620
aaagtttatt attttttta attcccttac tctgagaaag ggatattttg aaggactgtc 169680
```

atatatcttt gaaaaaagaa aatctgtaat acatatattt ttatgtatgt tcactggcac 169740
taaaaaaata tagagagctt cattctgtcc tttgggtagt tgctgaggta attgtccagg 169800
ttgaaaaaca atgtgctgat gctagagtcc ctctctgtcc atactctact tccaaatgga 169860
tataggcata cataataagt tttattcgac ttgtacttta agagaaaata tgtccaccat 169920
ccacatgata ctgacacaaa tgagctaaca ttgagcttca agtagcttct aagtgttcat 169980
ttcactaggc acagcacaga tgtggccttt cccccttct ctcccttgat atctggcagg 170040
gcataaaggc ccaggccact tcctctgccc cttcccagcc ctgcaccaaa gctgcatttc 170100
aggagactct ctcgagacag tccagtaact accggagcat ggcccctgca tagccctgga 170160
aaaataagag gctggctgtc tacgaatcat cttgtgccag ttgcccaggt gagagggcac 170220
tgggccaagg gagtggtttt catgtttgac ccactacaag gggtcatggg aatcaggaat 170280
gccaaagtac cagatcaaat ccaaaactta aagtcaaaat aagccattca gcatgttcag 170340
tttcttggaa aaggaagttt ctacccctga tgcctttgta ggcagatctg ttctcaccat 170400
taatcttttt gaaaatcttt taaagcagtt tttaaaaaga aagatgaaag catcacatta 170460
tgtaaccaaa gattacattg tatctgctaa gataccaaaa ttcacaaggg cagggaggga 170520
gcaagcatta gtgcctcttt gataagctgt ccaaagacag actaaaggac tttgctggtg 170580
actgacttat aagagttttg tggggttttt tttccctaat aatatacatg tttggaagag 170640
ttgaaaataa ttttgggaaa atgggtttat gggtccttca ctaagtgatt ttataagtag 170700
aactggcttt ccttttcttt agtagttgct gagcaaattc ttgaagctcc atcattgcat 170760
ggttggaaat ggagctattc ttagccactg tgtttgctag tgcccatgtt agcttatctg 170820
aagatgtgaa acccttgctg ataaggaatc atttaaagta ctagattttg cactagaggg 170880
acagcaggca gaaatcctta tttctgccca ctttggatgg cacaagaagt tatctgcagt 170940
tgaaggcaga aagttgaaat atattgtaaa tgaatatttg tattcatgtt tcaaaattga 171000
aatatatata tatatatttt atatatatat atatacacac acacacatat atagtgtgtg 171060
tgtgtgtgtg tgcgcgcgcg cgcgcgtgtg tgtgttctga tagctttacc tttctctgga 171120
tctttatact tggttccaga tcacacctga tgccatgtac ttgtgagaga ggatgcagtt 171180
atgttatgga agctctctca gaacagacaa gacatgtaga ttaatcagat aactgaaagt 171240
tttctcccct attgggtctg acccacaggt cctgtgaagg agcagagggg taaaaagagt 171300
agaggacatg atacattgta ctttactagt tcaagacaga tgaatgtgga aagtgtaaaa 171360
actcaatgga actgattgag atttaccaca gggaaggccc aaacttgggg ccaaaagcct 171420
actcaagtga ttgaccagtg gcgccctaat gggacctgag ctattgggag aagagaactg 171480
ttctttggtc ttcaccatcc ttgtgagaga aggacagttt cctgcattgg aacctggagc 171540
aagcgctcca tctttcacac aaattccctc acctgagatt gaggtgctcc tgttaatggg 171600
tgtctgtgtg ctgtaattct ggttttggat atgttctgta aagattttga caaatgaaaa 171660
tatgttttta tctgttaaaa cttgtcagag tactagaagt tgtatctctg taggtgcagg 171720
tccatttctg cccacgggta gggtgttttt ctttgactaa gagattgaca ccgggatctg 171780
ttgcccaggg cctcccaact caaccatttc taggtgaagg cagaaaaatc cacattagtc 171840
actcctcttc agacatttca gctgagataa caaatcattt ggaatttctt cacccataga 171900
aagagtggta gatatttgaa tttagtaggt ggagttttat agaaaaaaca gcttttgcct 171960
cagttttgat ttatcctcat ttgatttggc cagaacgtag gtaatatgca tcgattggct 172020

-continued tctgattcca attcagtata gcagggtgct gggtttttc ttttccccac ccgtctctta 172080
gcctagggaa ttaaataaga agccttagaa tgggtggccc ttgtgacctg aaacacttcc 172140
tacataagct acttaacaag attgtcatgt agctgcagat tcctttgccc accaaagact 172200
agaacacacg catatccata aaccaaagga aagacaactc tgaaatgctg tttctctggt 172260
ggttccctct ctggctgttg cttcacagta tgggaacctg tactctgcat aggtgacagg 172320
ccagatttgc attctcttac aaccttagcc cttggtgtta actgtcctac agtgaagtgc 172380
ctgtggagtt gtcctatccc agaagccact tggatgctga gagcagccac catcagaacg 172440
acccacgcga aaaaaaaaaa attaaaaagt cccctcacaa cccagtgaca cctttctgct 172500
ttcctctaga ctggaacatt gattagggag tgcctcagac atgacattct tgtgctgtcc 172560
ttggaattaa tctgacagca ggagggcgca gactatgtaa acagagataa gaattaattt 172620
tcaaagttga aggggaaaaa aagaaagaaa aaagaagaga gagagaaaga aagcatcgta 172680
caaagatttt cttaaaaaaa acaattttgc ttgaaatttc tttagatggg gctcagttgt 172740
cacagtggca cttggcctcc actgggcagc aggaccagct ccaagcgcta gtgttctgtt 172800
ctctttttgt aatcttggaa tcttttgttg ctctaaatac aattaaaaat ggtagaaact 172860
tgtttgttgg actaaatgtg tgactttggg tctgtctctg cctctgcttt cagaaatgtc 172920
atccattgtg taaaatattg gcttgctggt ctgccagcta aaacttggcc acatcccctg 172980
ttgtggctgc aggatcgagt tattgttaac aaagagaccc aagaaaagct gctaatgtcc 173040
tcttatcatt gttgttaatt tgttaaaaca taaagaaatc taaaatttca gatgaatgtc 173100
atcagagttc ttttaattag ctctttttat tggctgtttt tattgaagtc aagagttggt 173160
atcatgccca gttgtgtttt atgctatttt gattttcata tatttttaaa agtctttgca 173220
caaggcttac aaatttgccc tgtggtggcc ttagcataag ctgacctggg accaccaaaa 173280
taacaaggaa tttgggctag aaagcacaga tggacactgg cggcccatca caacttctct 173340
tgaaaaacac caaacttgtc agctggggaa aagccacaca aagcccagtt gcctactttc 173400
acaaccttat ccatgtggga gcataaaatg gtggcatcac tgcccagttc taaccaagct 173460
tcagttaaag aatgggtacc ttcacatcct cactattttt caggggcctt accatcctca 173520
accacccaag taaaatctaa atcagccttc ttttgggttc ttcagttcaa gtaaggcctc 173580
ttcttgtggc ctctcagtgt gaatacttac gaggttccag attgaatttt tgggcctgag 173640
atacaaggca tcaatgaggt gtgacaaaac atgtcaacga ataataagaa aattctctat 173700
tcttccatat cctcccctgt aataagggtt gtcagaatgc cttctttctc ggctgagttg 173760
aagattcagt gagaacatat gtgacacagc tggtgggcta ttaagctctg gctttgctcc 173820
ctgttaaaat gccagaaccc ttgagaggga tcccacattc agccatgttt atcattgacc 173880
accttagaat ggatggattt ctcagatttt tcctgagatc agtgcttgat ggagaggaga 173940
ggagaacaat agattcttgg gatgtgtgct ttgcatgtgt ttaagtaaga gacagagagt 174000

<210> SEQ ID NO 190
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 190
gcgtttgctc ttcttcttgc gtttttt 27

<210> SEQ ID NO 191
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 191
tctggaacag attctg 16

<210> SEQ ID NO 192
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 192
gcttcatctc cacaga 16

<210> SEQ ID NO 193
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 193
ggctactacg ccgtca 16

<210> SEQ ID NO 194
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 194
gagaaccatc ctcacc 16

<210> SEQ ID NO 195
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 195
ggaccaggta gcctgt 16

<210> SEQ ID NO 196
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 196
cccctggact cagatg 16

<210> SEQ ID NO 197
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 197
gcacaaggag tgggac 16

<210> SEQ ID NO 198
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 198
gctgtgaaga gagtgt 16

<210> SEQ ID NO 199
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 199
tttgacacaa gtggga 16

<210> SEQ ID NO 200
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 200
gtgacaccca gaagct 16

<210> SEQ ID NO 201
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 201
catccctgct tcataa 16

<210> SEQ ID NO 202
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 202
tggggagaac catcctcacc ctgc 24

<210> SEQ ID NO 203
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 203
tccaggacca ggtagcctgt gggg 24

<210> SEQ ID NO 204
<211> LENGTH: 24

<212> TYPE: DNA
<213> ORGANISM: Artificial Sequence
<220> FEATURE:
<223> OTHER INFORMATION: Synthetic oligonucleotide

<400> SEQUENCE: 204
tgttcccctg gactcagatg ctcc 24

<210> SEQ ID NO 205
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 205
tggggcacaa ggagtgggac gcac 24

<210> SEQ ID NO 206
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 206
ttcggctgtg aagagagtgt gcca 24

<210> SEQ ID NO 207
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 207
cgcttttgac acaagtggga ctgg 24

<210> SEQ ID NO 208
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 208
catagtgaca cccagaagct tcat 24

<210> SEQ ID NO 209
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 209
gagtcatccc tgcttcataa catt 24

<210> SEQ ID NO 210
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 210

-continued

```
ctgtgaagag agtg                                                       14


<210> SEQ ID NO 211
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 211

tgtgaagaga gt                                                         12


<210> SEQ ID NO 212
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 212

ttgacacaag tggg                                                       14


<210> SEQ ID NO 213
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 213

tgacacaagt gg                                                         12


<210> SEQ ID NO 214
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 214

tgacacccag aagc                                                       14


<210> SEQ ID NO 215
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 215

gacacccaga ag                                                         12
```